(12) United States Patent
Blain et al.

(10) Patent No.: US 12,318,311 B2
(45) Date of Patent: Jun. 3, 2025

(54) SPINAL IMPLANT DEVICE

(71) Applicant: Spinal Elements, Inc., Carlsbad, CA (US)

(72) Inventors: Jason Blain, Encinitas, CA (US); David Hart, Oceanside, CA (US); Dean Johnson, Solana Beach, CA (US); Gregory Martin, Carlsbad, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 234 days.

(21) Appl. No.: 17/746,234

(22) Filed: May 17, 2022

(65) Prior Publication Data

US 2022/0387189 A1 Dec. 8, 2022

Related U.S. Application Data

(63) Continuation of application No. 16/577,511, filed on Sep. 20, 2019, now Pat. No. 11,382,769.
(Continued)

(51) Int. Cl.
*A61F 2/44* (2006.01)
*A61F 2/46* (2006.01)
*A61F 2/28* (2006.01)

(52) U.S. Cl.
CPC .......... *A61F 2/4611* (2013.01); *A61F 2/4455* (2013.01); *A61F 2/4601* (2013.01); *A61F 2002/2835* (2013.01)

(58) Field of Classification Search
CPC .. A61F 2/44; A61F 2/441; A61F 2/442–4425; A61F 2/4455; A61F 2/447; A61F 2002/443
See application file for complete search history.

(56) References Cited

U.S. PATENT DOCUMENTS 1,845,428 A 2/1932 Llewellyn
2,440,123 A 4/1948 Smith
(Continued)

FOREIGN PATENT DOCUMENTS

CA 1 329 525 5/1994
CA 2 521 526 11/2004
(Continued)

OTHER PUBLICATIONS

Official Communication in Australian Application No. 2006227755, dated Dec. 8, 2010.
(Continued)

*Primary Examiner* — Eduardo C Robert
*Assistant Examiner* — Michelle C Eckman
(74) *Attorney, Agent, or Firm* — Knobbe, Martens, Olson & Bear, LLP

(57) ABSTRACT

A spinal implant device is provided comprising a body structure with a central cavity and a movable lid configured to cover the central cavity. The movable lid is configured to be opened to pack a material in the central cavity. The movable lid can be connected to the body structure with a moveable joint. The spinal implant device can include a compressible feature. A method for treating the spine is provided comprising opening a movable lid of a spinal implant device, packing a material in a central cavity of a spinal implant device, closing the movable lid, and inserting the spinal implant device between vertebrae.

19 Claims, 174 Drawing Sheets

Related U.S. Application Data

(60) Provisional application No. 62/790,866, filed on Jan. 10, 2019, provisional application No. 62/734,148, filed on Sep. 20, 2018.

(56) References Cited

U.S. PATENT DOCUMENTS

| | | |
|---|---|---|
| 2,500,993 A | 3/1950 | Christopher |
| 2,677,369 A | 5/1954 | Knowles |
| 3,426,364 A | 2/1969 | Lumb |
| 3,574,381 A | 4/1971 | Ocheltree et al. |
| 3,848,601 A | 11/1974 | Ma et al. |
| 3,867,728 A | 2/1975 | Stubstad et al. |
| 3,893,196 A | 7/1975 | Hochman |
| 3,953,140 A | 4/1976 | Carlstrom |
| 3,987,499 A | 10/1976 | Scharbach et al. |
| 4,013,071 A | 3/1977 | Rosenberg |
| 4,309,777 A | 1/1982 | Patil |
| 4,349,921 A | 9/1982 | Kuntz |
| 4,388,921 A | 6/1983 | Sutter et al. |
| 4,401,112 A | 8/1983 | Rezaian |
| 4,464,090 A | 8/1984 | Duran |
| 4,484,570 A | 11/1984 | Sutter et al. |
| 4,554,914 A | 11/1985 | Kapp et al. |
| 4,599,086 A | 7/1986 | Doty |
| 4,834,757 A | 5/1989 | Brantigan |
| 4,892,545 A | 1/1990 | Day et al. |
| 4,904,261 A | 2/1990 | Dove et al. |
| 4,917,704 A | 4/1990 | Frey et al. |
| 4,955,908 A | 9/1990 | Frey et al. |
| 4,961,740 A | 10/1990 | Ray et al. |
| 5,002,576 A | 3/1991 | Fuhrmann et al. |
| 5,053,036 A | 10/1991 | Perren et al. |
| 5,057,111 A | 10/1991 | Park |
| 5,085,660 A | 2/1992 | Lin |
| 5,147,361 A | 9/1992 | Ojima et al. |
| 5,147,402 A | 9/1992 | Bohler et al. |
| 5,176,709 A | 1/1993 | Branemark |
| 5,192,327 A | 3/1993 | Brantigan |
| 5,269,784 A | 12/1993 | Mast |
| 5,275,601 A | 1/1994 | Gogolewski et al. |
| 5,304,179 A | 4/1994 | Wagner |
| 5,306,307 A | 4/1994 | Senter et al. |
| 5,364,399 A | 11/1994 | Lowery et al. |
| 5,397,364 A | 3/1995 | Kozak et al. |
| 5,458,641 A | 10/1995 | Ramirez Jimenez |
| 5,474,555 A | 12/1995 | Puno et al. |
| 5,501,684 A | 3/1996 | Schlapfer et al. |
| 5,520,690 A | 5/1996 | Errico et al. |
| 5,522,899 A | 6/1996 | Michelson |
| 5,534,027 A | 7/1996 | Hodorek |
| 5,558,674 A | 9/1996 | Heggeness et al. |
| 5,578,034 A | 11/1996 | Estes |
| 5,607,426 A | 3/1997 | Ralph et al. |
| 5,607,428 A | 3/1997 | Lin |
| 5,609,635 A | 3/1997 | Michelson |
| 5,616,144 A | 4/1997 | Yapp et al. |
| 5,643,265 A | 7/1997 | Errico et al. |
| 5,665,089 A | 9/1997 | Dall et al. |
| 5,676,666 A | 10/1997 | Oxland et al. |
| 5,676,702 A | 10/1997 | Ratron |
| 5,681,311 A | 10/1997 | Foley et al. |
| 5,713,900 A | 2/1998 | Benzel et al. |
| 5,735,853 A | 4/1998 | Olerud |
| 5,743,914 A | 4/1998 | Skiba |
| 5,749,916 A | 5/1998 | Richelsoph |
| 5,755,796 A | 5/1998 | Ibo et al. |
| 5,766,252 A | 6/1998 | Henry et al. |
| 5,776,199 A | 7/1998 | Michelson |
| 5,807,396 A | 9/1998 | Raveh |
| 5,810,823 A | 9/1998 | Klaue et al. |
| 5,849,004 A | 12/1998 | Bramlet |
| 5,851,207 A | 12/1998 | Cesarone |
| 5,876,402 A | 3/1999 | Errico et al. |
| 5,888,223 A | 3/1999 | Bray |
| 5,888,227 A | 3/1999 | Cottle |
| 5,902,303 A | 5/1999 | Eckhof et al. |
| 5,904,683 A | 5/1999 | Pohndorf et al. |
| 5,925,048 A | 7/1999 | Ahmad et al. |
| 5,931,838 A | 8/1999 | Vito |
| 5,951,558 A | 9/1999 | Fiz |
| 5,954,722 A | 9/1999 | Bono |
| 6,001,130 A | 12/1999 | Bryan et al. |
| 6,030,389 A | 2/2000 | Wagner et al. |
| 6,066,175 A | 5/2000 | Henderson et al. |
| 6,082,568 A | 7/2000 | Flanagan |
| 6,086,613 A | 7/2000 | Camino et al. |
| 6,117,173 A | 9/2000 | Taddia et al. |
| 6,136,031 A | 10/2000 | Middleton |
| 6,139,550 A | 10/2000 | Michelson |
| 6,152,927 A | 11/2000 | Farris et al. |
| 6,156,037 A | 12/2000 | Le Huec et al. |
| 6,176,882 B1 | 1/2001 | Biedermann et al. |
| 6,193,721 B1 | 2/2001 | Michelson |
| 6,206,881 B1 | 3/2001 | Frigg et al. |
| 6,206,924 B1 | 3/2001 | Timm |
| 6,215,093 B1 | 4/2001 | Meiners et al. |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,245,108 B1 | 6/2001 | Biscup |
| 6,261,291 B1 | 7/2001 | Talaber et al. |
| 6,273,889 B1 | 8/2001 | Richelsoph |
| 6,287,309 B1 | 9/2001 | Baccelli et al. |
| 6,302,883 B1 | 10/2001 | Bono |
| 6,306,136 B1 | 10/2001 | Baccelli |
| 6,306,139 B1 | 10/2001 | Fuentes |
| 6,306,170 B2 | 10/2001 | Rau |
| 6,331,179 B1 | 12/2001 | Freid et al. |
| 6,342,055 B1 | 1/2002 | Eisermann et al. |
| 6,383,186 B1 | 5/2002 | Michelson |
| 6,395,035 B2 | 5/2002 | Bresina et al. |
| 6,402,755 B1 | 6/2002 | Pisharodi |
| 6,413,259 B1 | 7/2002 | Lyons et al. |
| 6,428,542 B1 | 8/2002 | Michelson |
| 6,432,106 B1 | 8/2002 | Fraser |
| 6,447,544 B1 | 9/2002 | Michelson |
| 6,447,547 B1 | 9/2002 | Michelson |
| 6,454,769 B2 | 9/2002 | Wagner et al. |
| 6,461,359 B1 | 10/2002 | Tribus et al. |
| 6,478,823 B1 | 11/2002 | Michelson |
| 6,491,724 B1 | 12/2002 | Ferree |
| 6,503,250 B2 | 1/2003 | Paul |
| 6,508,818 B2 | 1/2003 | Steiner et al. |
| 6,537,320 B1 | 3/2003 | Michelson |
| 6,565,570 B2 | 5/2003 | Sterett et al. |
| 6,569,168 B2 | 5/2003 | Lin |
| 6,575,975 B2 | 6/2003 | Brace et al. |
| 6,579,290 B1 | 6/2003 | Hardcastle et al. |
| 6,582,432 B1 | 6/2003 | Michelson |
| 6,599,290 B2 | 7/2003 | Bailey et al. |
| 6,602,255 B1 | 8/2003 | Campbell et al. |
| 6,602,256 B1 | 8/2003 | Hayes |
| 6,613,053 B1 | 9/2003 | Collins et al. |
| 6,623,486 B1 | 9/2003 | Weaver et al. |
| 6,626,907 B2 | 9/2003 | Campbell et al. |
| 6,626,911 B1 | 9/2003 | Engman et al. |
| 6,645,208 B2 | 11/2003 | Apfelbaum et al. |
| 6,645,209 B2 | 11/2003 | Hall, IV et al. |
| 6,652,525 B1 | 11/2003 | Assaker et al. |
| 6,656,181 B2 | 12/2003 | Dixon et al. |
| 6,656,224 B2 | 12/2003 | Middleton |
| 6,660,038 B2 | 12/2003 | Boyer, II et al. |
| 6,669,700 B1 | 12/2003 | Farris et al. |
| 6,676,892 B2 | 1/2004 | Das et al. |
| 6,682,561 B2 | 1/2004 | Songer et al. |
| 6,682,563 B2 | 1/2004 | Scharf |
| 6,695,845 B2 | 2/2004 | Dixon et al. |
| 6,695,846 B2 | 2/2004 | Richelsoph et al. |
| 6,702,817 B2 | 3/2004 | Beger et al. |
| 6,719,794 B2 | 4/2004 | Gerber et al. |
| 6,730,127 B2 | 5/2004 | Michelson |

(56) References Cited

U.S. PATENT DOCUMENTS

| | | |
|---|---|---|
| 6,740,087 B2 | 5/2004 | Knox |
| 6,743,255 B2 | 6/2004 | Ferree |
| 6,746,450 B1 | 6/2004 | Wall et al. |
| 6,755,833 B1 | 6/2004 | Paul et al. |
| 6,758,849 B1 | 7/2004 | Michelson |
| 6,767,369 B2 | 7/2004 | Boyer, II et al. |
| 6,776,798 B2 | 8/2004 | Camino et al. |
| 6,780,186 B2 | 8/2004 | Errico et al. |
| 6,808,537 B2 | 10/2004 | Michelson |
| 6,830,570 B1 | 12/2004 | Frey et al. |
| 6,833,006 B2 | 12/2004 | Foley et al. |
| 6,835,208 B2 | 12/2004 | Marchosky |
| 6,884,242 B2 | 4/2005 | LeHuec et al. |
| 6,890,334 B2 | 5/2005 | Brace et al. |
| 6,890,335 B2 | 5/2005 | Grabowski et al. |
| 6,890,355 B2 | 5/2005 | Michelson |
| 6,932,610 B2 | 8/2005 | Ono et al. |
| 6,962,606 B2 | 11/2005 | Michelson |
| 6,964,664 B2 | 11/2005 | Freid et al. |
| 6,974,480 B2 | 12/2005 | Messerli et al. |
| 6,984,234 B2 | 1/2006 | Bray |
| 7,001,389 B1 | 2/2006 | Navarro et al. |
| 7,001,672 B2 | 2/2006 | Justin et al. |
| 7,025,769 B1 | 4/2006 | Ferree |
| 7,048,739 B2 | 5/2006 | Konieczynski et al. |
| 7,063,701 B2 | 6/2006 | Michelson |
| 7,077,844 B2 | 7/2006 | Michelson |
| 7,112,222 B2 | 9/2006 | Fraser et al. |
| 7,128,761 B2 | 10/2006 | Kuras |
| 7,135,024 B2 | 11/2006 | Cook et al. |
| 7,141,068 B2 | 11/2006 | Ross et al. |
| 7,172,627 B2 | 2/2007 | Fiere et al. |
| 7,182,782 B2 | 2/2007 | Kirschman |
| 7,186,254 B2 | 3/2007 | Dinh et al. |
| 7,217,291 B2 | 5/2007 | Zucherman et al. |
| 7,220,263 B2 | 5/2007 | Cordaro |
| 7,232,463 B2 | 6/2007 | Falahee |
| 7,232,464 B2 | 6/2007 | Mathieu et al. |
| 7,235,082 B2 | 6/2007 | Bartish et al. |
| 7,273,481 B2 | 9/2007 | Lombardo et al. |
| 7,306,605 B2 | 12/2007 | Ross |
| 7,309,340 B2 | 12/2007 | Fallin et al. |
| 7,473,277 B2 | 1/2009 | Boyer, II et al. |
| 7,481,829 B2 | 1/2009 | Baynham et al. |
| 7,481,830 B2 | 1/2009 | Wall et al. |
| 7,503,933 B2 | 3/2009 | Michelson |
| 7,521,017 B2 | 4/2009 | Kunze et al. |
| 7,524,325 B2 | 4/2009 | Khalili |
| 7,537,664 B2 | 5/2009 | O'Neill et al. |
| 7,540,882 B2 | 6/2009 | Michelson |
| 7,547,324 B2 | 6/2009 | Cragg et al. |
| 7,621,943 B2 | 11/2009 | Michelson |
| 7,628,816 B2 | 12/2009 | Magerl et al. |
| 7,641,665 B2 | 1/2010 | Zubok et al. |
| 7,641,690 B2 | 1/2010 | Abdou |
| 7,651,517 B2 | 1/2010 | Konieczynski et al. |
| 7,658,766 B2 | 2/2010 | Melkent et al. |
| 7,674,294 B2 | 3/2010 | Karahalios et al. |
| 7,674,297 B2 | 3/2010 | Falahee |
| 7,693,981 B2 | 4/2010 | Clubb et al. |
| 7,708,778 B2 | 5/2010 | Gordon et al. |
| 7,708,779 B2 | 5/2010 | Edie et al. |
| 7,718,109 B2 | 5/2010 | Robb et al. |
| 7,806,932 B2 | 10/2010 | Webb et al. |
| 7,815,682 B1 | 10/2010 | Peterson |
| 7,819,903 B2 | 10/2010 | Fraser et al. |
| 7,837,734 B2 | 11/2010 | Zucherman et al. |
| 7,857,839 B2 | 12/2010 | Duong et al. |
| 7,892,239 B2 | 2/2011 | Warnick et al. |
| 7,914,561 B2 | 3/2011 | Konieczynski et al. |
| 7,931,840 B2 | 4/2011 | Michelson |
| 7,935,137 B2 | 5/2011 | Gorhan et al. |
| 7,959,675 B2 | 6/2011 | Gately |
| 7,963,981 B2 | 6/2011 | Binder et al. |
| 7,972,366 B2 | 7/2011 | Richelsoph et al. |
| 7,985,255 B2 | 7/2011 | Bray et al. |
| 7,998,212 B2 | 8/2011 | Schwab et al. |
| 8,025,697 B2 | 9/2011 | McClellan, III et al. |
| 8,043,293 B2 | 10/2011 | Warnick |
| 8,062,375 B2 | 11/2011 | Glerum et al. |
| 8,088,163 B1 | 1/2012 | Kleiner |
| 8,100,955 B2 | 1/2012 | Blain et al. |
| 8,142,886 B2 | 3/2012 | Noble et al. |
| 8,147,554 B2 | 4/2012 | Hansell et al. |
| 8,157,845 B2 | 4/2012 | Warnick et al. |
| 8,231,661 B2 | 7/2012 | Carls |
| 8,252,060 B2 | 8/2012 | Hansell et al. |
| 8,267,966 B2 | 9/2012 | McCormack et al. |
| 8,268,001 B2 | 9/2012 | Butler et al. |
| 8,277,510 B2 | 10/2012 | Kleiner |
| 8,282,675 B2 | 10/2012 | Maguire et al. |
| 8,282,682 B2 | 10/2012 | Kirschman |
| 8,292,960 B2 | 10/2012 | Kleiner |
| 8,343,224 B2 | 1/2013 | Lynn et al. |
| 8,366,777 B2 | 2/2013 | Matthis et al. |
| 8,382,842 B2 | 2/2013 | Greenhalgh et al. |
| 8,394,125 B2 | 3/2013 | Assell |
| 8,409,290 B2 | 4/2013 | Zamani et al. |
| 8,414,590 B2 | 4/2013 | Oh et al. |
| 8,425,529 B2 | 4/2013 | Milz et al. |
| 8,430,930 B2 | 4/2013 | Hunt |
| 8,435,298 B2 | 5/2013 | Weiman |
| 8,444,650 B2 | 5/2013 | Warnick et al. |
| 8,470,039 B2 | 6/2013 | Blain |
| 8,480,745 B2 | 7/2013 | Liu et al. |
| 8,491,658 B1 | 7/2013 | Etminan |
| 8,496,691 B2 | 7/2013 | Blain |
| 8,496,708 B2 | 7/2013 | Blain |
| 8,506,636 B2 | 8/2013 | Dye |
| 8,518,120 B2 | 8/2013 | Glerum et al. |
| 8,545,566 B2 | 10/2013 | Niemiec et al. |
| 8,556,979 B2 | 10/2013 | Glerum et al. |
| 8,579,904 B2 | 11/2013 | Siccardi et al. |
| 8,603,175 B2 | 12/2013 | Thibodeau |
| 8,617,246 B2 | 12/2013 | Malone |
| 8,628,578 B2 | 1/2014 | Miller et al. |
| 8,632,595 B2 | 1/2014 | Weiman |
| 8,652,137 B2 | 2/2014 | Blain et al. |
| 8,652,143 B2 | 2/2014 | McClellan, III et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,690,949 B2 | 4/2014 | Messerli et al. |
| 8,696,721 B2 | 4/2014 | Blain |
| 8,702,798 B2 | 4/2014 | Matthis et al. |
| 8,709,086 B2 | 4/2014 | Glerum |
| 8,715,355 B2 | 5/2014 | Kleiner |
| 8,728,387 B2 | 5/2014 | Jones et al. |
| 8,740,942 B2 | 6/2014 | Blain |
| 8,758,443 B2 | 6/2014 | Ullrich, Jr. et al. |
| 8,795,366 B2 | 8/2014 | Varela |
| 8,795,370 B2 | 8/2014 | Kirschman |
| 8,801,785 B2 | 8/2014 | Brittan et al. |
| 8,801,791 B2 | 8/2014 | Soo et al. |
| 8,801,793 B2 | 8/2014 | McKay |
| 8,801,794 B2 | 8/2014 | Blain |
| 8,840,668 B1 | 9/2014 | Donahoe et al. |
| 8,843,229 B2 | 9/2014 | Vanasse et al. |
| 8,845,731 B2 | 9/2014 | Weiman |
| 8,852,279 B2 | 10/2014 | Weiman |
| 8,888,853 B2 | 11/2014 | Glerum et al. |
| 8,888,854 B2 | 11/2014 | Glerum et al. |
| 8,926,704 B2 | 1/2015 | Glerum et al. |
| 8,986,307 B2 | 3/2015 | Kirschman |
| 8,986,383 B2 | 3/2015 | Castro |
| 8,992,703 B2 | 3/2015 | O'Neill et al. |
| 8,998,924 B2 | 4/2015 | Simpson et al. |
| 9,060,873 B2 | 6/2015 | Abdou |
| 9,078,706 B2 | 7/2015 | Kirschman |
| 9,095,385 B2 | 8/2015 | Wallenstein et al. |
| 9,101,410 B1 | 8/2015 | Urrea |
| 9,138,327 B1 | 9/2015 | McClellan, III |
| 9,138,330 B2 | 9/2015 | Hansell et al. |
| 9,198,772 B2 | 12/2015 | Weiman |

(56) References Cited

U.S. PATENT DOCUMENTS

| | | |
|---|---|---|
| 9,204,974 B2 | 12/2015 | Glerum et al. |
| 9,220,542 B2 | 12/2015 | Kerboul et al. |
| 9,220,547 B2 | 12/2015 | Blain et al. |
| 9,226,836 B2 | 1/2016 | Glerum |
| 9,237,957 B2 | 1/2016 | Klimek et al. |
| 9,259,327 B2 | 2/2016 | Niemiec et al. |
| 9,265,546 B2 | 2/2016 | Blain |
| 9,271,765 B2 | 3/2016 | Blain |
| 9,271,845 B2 | 3/2016 | Hunt et al. |
| 9,320,610 B2 | 4/2016 | Alheidt et al. |
| 9,358,126 B2 | 6/2016 | Glerum et al. |
| 9,399,086 B2 | 7/2016 | Melkent et al. |
| 9,402,736 B2 | 8/2016 | Etminan |
| 9,415,137 B2 | 8/2016 | Meridew et al. |
| 9,421,108 B2 | 8/2016 | Hunt |
| 9,427,328 B2 | 8/2016 | Drochner et al. |
| 9,433,707 B2 | 9/2016 | Swords et al. |
| 9,439,778 B2 | 9/2016 | Biedermann et al. |
| 9,456,901 B2 | 10/2016 | Jones et al. |
| 9,463,099 B2 | 10/2016 | Levy et al. |
| 9,545,317 B2 | 1/2017 | Hunt |
| 9,549,823 B2 | 1/2017 | Hunt et al. |
| 9,554,918 B2 | 1/2017 | Weiman |
| 9,572,669 B2 | 2/2017 | Hunt et al. |
| 9,585,707 B2 | 3/2017 | Blain |
| 9,615,934 B2 | 4/2017 | Khurana |
| 9,636,226 B2 | 5/2017 | Hunt |
| 9,662,223 B2 | 5/2017 | Matthis et al. |
| 9,662,226 B2 | 5/2017 | Wickham |
| 9,668,876 B2 | 6/2017 | Blain et al. |
| 9,700,428 B2 | 7/2017 | Niemiec et al. |
| 9,707,317 B2 | 7/2017 | Hunter et al. |
| 9,757,235 B2 | 9/2017 | Hunt et al. |
| 9,757,247 B2 | 9/2017 | Mantri |
| 9,770,343 B2 | 9/2017 | Weiman |
| 9,782,269 B2 | 10/2017 | Hansell et al. |
| RE46,647 E | 12/2017 | Messerli et al. |
| 9,867,713 B2 | 1/2018 | Milz et al. |
| 9,889,020 B2 | 2/2018 | Baynham |
| 9,936,984 B2 | 4/2018 | Blain |
| 9,949,841 B2 | 4/2018 | Glerum et al. |
| 9,962,271 B2 | 5/2018 | Glerum |
| 9,968,462 B2 | 5/2018 | Weiman |
| 9,980,823 B2 | 5/2018 | Matthis et al. |
| 9,980,825 B2 | 5/2018 | Nichols et al. |
| 9,987,051 B2 | 6/2018 | Nunley et al. |
| 9,987,149 B2 | 6/2018 | Simpson et al. |
| 10,004,607 B2 | 6/2018 | Weiman et al. |
| 10,022,245 B2 | 7/2018 | Frasier et al. |
| 10,028,841 B2 | 7/2018 | Moore et al. |
| 10,034,770 B2 | 7/2018 | Etminan |
| 10,064,737 B2 | 9/2018 | Tsai et al. |
| 10,092,412 B2 | 10/2018 | Drochner et al. |
| 10,130,490 B2 | 11/2018 | Hansell et al. |
| 10,154,912 B2 | 12/2018 | Glerum |
| 10,245,152 B2 | 4/2019 | Kloss |
| 10,271,957 B2 | 4/2019 | Niemiec et al. |
| 10,299,938 B1 | 5/2019 | Ehteshami |
| 10,369,009 B2 | 8/2019 | Joly et al. |
| 10,470,892 B2 | 11/2019 | Abdou |
| 10,478,313 B1 | 11/2019 | Sweeney, III |
| 10,512,545 B2 | 12/2019 | Arnone |
| 10,517,740 B2 | 12/2019 | Ball et al. |
| 10,524,929 B2 | 1/2020 | Shoshtaev |
| 10,555,819 B2 | 2/2020 | Miccio |
| 10,568,664 B2 | 2/2020 | Blain et al. |
| 10,610,373 B2 | 4/2020 | Jang et al. |
| 10,624,757 B2 | 4/2020 | Bost |
| 10,660,763 B2 | 5/2020 | Wilson et al. |
| 10,667,927 B2 | 6/2020 | Lamborne et al. |
| 10,687,876 B2 | 6/2020 | Vrionis et al. |
| 10,702,397 B2 | 7/2020 | Simpson et al. |
| 10,709,575 B2 | 7/2020 | Robinson |
| 10,758,361 B2 | 9/2020 | Blain |
| 10,765,525 B2 | 9/2020 | Sansur et al. |
| 10,905,567 B2 | 2/2021 | Kuyler et al. |
| 10,993,810 B2 | 5/2021 | Magagnoli |
| 11,026,801 B2 | 6/2021 | Suh et al. |
| 11,147,682 B2 | 10/2021 | Trudeau et al. |
| 11,147,687 B2 | 10/2021 | Hyeon et al. |
| 11,173,047 B2 | 11/2021 | Milz et al. |
| 11,179,247 B2 | 11/2021 | Jebsen et al. |
| 11,213,404 B2 | 1/2022 | Foley et al. |
| 11,285,014 B1 | 3/2022 | Josse et al. |
| 11,364,057 B2 | 6/2022 | Blain et al. |
| 11,382,769 B2 | 7/2022 | Blain et al. |
| 11,654,030 B2 | 5/2023 | Valkoun et al. |
| 11,696,837 B2 | 7/2023 | Messerli |
| 11,911,284 B2 | 2/2024 | Huh et al. |
| 2001/0007941 A1 | 7/2001 | Steiner et al. |
| 2001/0014807 A1 | 8/2001 | Wagner et al. |
| 2001/0047207 A1 | 11/2001 | Michelson |
| 2002/0004683 A1 | 1/2002 | Michelson |
| 2002/0016595 A1 | 2/2002 | Michelson |
| 2002/0022843 A1 | 2/2002 | Michelson |
| 2002/0045898 A1 | 4/2002 | Freid et al. |
| 2002/0116064 A1 | 8/2002 | Middleton |
| 2002/0147450 A1 | 10/2002 | LeHuec et al. |
| 2002/0151895 A1 | 10/2002 | Soboleski et al. |
| 2002/0169507 A1 | 11/2002 | Malone |
| 2002/0169508 A1 | 11/2002 | Songer et al. |
| 2003/0040798 A1 | 2/2003 | Michelson |
| 2003/0060828 A1 | 3/2003 | Michelson |
| 2003/0093082 A1 | 5/2003 | Campbell et al. |
| 2003/0135279 A1 | 7/2003 | Michelson |
| 2003/0139812 A1 | 7/2003 | Garcia et al. |
| 2003/0167091 A1 | 9/2003 | Scharf |
| 2003/0171753 A1 | 9/2003 | Collins et al. |
| 2003/0187442 A1 | 10/2003 | Richelsoph et al. |
| 2003/0212399 A1 | 11/2003 | Dinh et al. |
| 2004/0010254 A1 | 1/2004 | Cook et al. |
| 2004/0068319 A1 | 4/2004 | Cordaro |
| 2004/0087951 A1 | 5/2004 | Khalili |
| 2004/0097935 A1 | 5/2004 | Richelsoph et al. |
| 2004/0127900 A1 | 7/2004 | Konieczynski et al. |
| 2004/0127904 A1 | 7/2004 | Konieczynski et al. |
| 2004/0176778 A1 | 9/2004 | Zubok et al. |
| 2004/0181227 A1 | 9/2004 | Khalili |
| 2004/0210219 A1 | 10/2004 | Bray |
| 2004/0220570 A1 | 11/2004 | Frigg et al. |
| 2004/0230192 A1 | 11/2004 | Graf |
| 2004/0260306 A1 | 12/2004 | Fallin et al. |
| 2005/0027296 A1 | 2/2005 | Thramann et al. |
| 2005/0027360 A1 | 2/2005 | Webb et al. |
| 2005/0033433 A1 | 2/2005 | Michelson |
| 2005/0049593 A1 | 3/2005 | Duong et al. |
| 2005/0085913 A1 | 4/2005 | Fraser et al. |
| 2005/0101960 A1 | 5/2005 | Fiere et al. |
| 2005/0149191 A1 | 7/2005 | Cragg et al. |
| 2005/0159746 A1 | 7/2005 | Grab et al. |
| 2005/0177237 A1 | 8/2005 | Shappley et al. |
| 2005/0177245 A1 | 8/2005 | Leatherbury et al. |
| 2005/0192576 A1 | 9/2005 | Michelson |
| 2005/0277933 A1 | 12/2005 | Wall et al. |
| 2006/0074488 A1 | 4/2006 | Abdou |
| 2006/0122604 A1 | 6/2006 | Gorhan et al. |
| 2006/0200147 A1 | 9/2006 | Ensign et al. |
| 2006/0224241 A1 | 10/2006 | Butler et al. |
| 2006/0235403 A1 | 10/2006 | Blain |
| 2006/0235409 A1 | 10/2006 | Blain |
| 2006/0235418 A1 | 10/2006 | Gil et al. |
| 2006/0241597 A1 | 10/2006 | Mitchell et al. |
| 2006/0241616 A1 | 10/2006 | Konieczynski et al. |
| 2006/0247650 A1 | 11/2006 | Yerby et al. |
| 2007/0055252 A1 | 3/2007 | Blain et al. |
| 2007/0055373 A1 | 3/2007 | Hudgins et al. |
| 2007/0093897 A1 | 4/2007 | Gerbec et al. |
| 2007/0123863 A1 | 5/2007 | Winslow et al. |
| 2007/0135814 A1 | 6/2007 | Farris |
| 2007/0213820 A1 | 9/2007 | Magerl et al. |
| 2007/0250166 A1 | 10/2007 | McKay |
| 2007/0255414 A1* | 11/2007 | Melkent ............... A61F 2/4465 623/17.11 |
| 2007/0255416 A1 | 11/2007 | Melkent et al. |

(56) References Cited

U.S. PATENT DOCUMENTS

| | | |
|---|---|---|
| 2007/0282441 A1 | 12/2007 | Stream |
| 2007/0282446 A1 | 12/2007 | Li |
| 2008/0103598 A1 | 5/2008 | Trudeau et al. |
| 2008/0140207 A1 | 6/2008 | Olmos |
| 2008/0161925 A1 | 7/2008 | Brittan et al. |
| 2008/0167686 A1 | 7/2008 | Trieu et al. |
| 2008/0177390 A1 | 7/2008 | Mitchell et al. |
| 2008/0249569 A1 | 10/2008 | Waugh |
| 2008/0294260 A1 | 11/2008 | Gray |
| 2009/0072006 A1 | 3/2009 | Clauson et al. |
| 2009/0082819 A1 | 3/2009 | Blain et al. |
| 2009/0182430 A1 | 7/2009 | Tyber et al. |
| 2009/0198339 A1 | 8/2009 | Kleiner et al. |
| 2009/0270929 A1 | 10/2009 | Suddaby |
| 2010/0069960 A1 | 3/2010 | Chaput |
| 2010/0070037 A1 | 3/2010 | Parry et al. |
| 2010/0145459 A1 | 6/2010 | McDonough et al. |
| 2010/0211176 A1 | 8/2010 | Greenhalgh |
| 2011/0015744 A1 | 1/2011 | Squires et al. |
| 2011/0015745 A1 | 1/2011 | Bucci |
| 2011/0040384 A1 | 2/2011 | Junn et al. |
| 2011/0106259 A1 | 5/2011 | Lindenmann et al. |
| 2011/0153020 A1 | 6/2011 | Abdelgany et al. |
| 2011/0172775 A1 | 7/2011 | Flickinger et al. |
| 2011/0184522 A1 | 7/2011 | Melkent et al. |
| 2011/0224796 A1 | 9/2011 | Weiland et al. |
| 2011/0264218 A1 | 10/2011 | Asaad |
| 2011/0282453 A1 | 11/2011 | Greenhalgh et al. |
| 2012/0016480 A1 | 1/2012 | Gerber et al. |
| 2012/0029636 A1 | 2/2012 | Ragab et al. |
| 2012/0046749 A1 | 2/2012 | Tatsumi |
| 2012/0197402 A1 | 8/2012 | Blackwell et al. |
| 2012/0277801 A1 | 11/2012 | Marik et al. |
| 2013/0006357 A1 | 1/2013 | Kruger |
| 2013/0030529 A1 | 1/2013 | Hunt |
| 2013/0110238 A1 | 5/2013 | Lindemann et al. |
| 2013/0110248 A1 | 5/2013 | Zipnick |
| 2013/0123923 A1 | 5/2013 | Pavlov et al. |
| 2013/0158667 A1 | 6/2013 | Tabor et al. |
| 2013/0158669 A1 | 6/2013 | Sungarian et al. |
| 2013/0173003 A1 | 7/2013 | Matthis et al. |
| 2013/0181015 A1 | 7/2013 | Cason |
| 2013/0197643 A1 | 8/2013 | Greenberg et al. |
| 2013/0218276 A1 | 8/2013 | Fiechter |
| 2013/0268078 A1 | 10/2013 | Richelsoph |
| 2013/0297024 A1 | 11/2013 | Khurana |
| 2013/0325129 A1 | 12/2013 | Huang |
| 2014/0012318 A1 | 1/2014 | Goel |
| 2014/0066758 A1 | 3/2014 | Marik et al. |
| 2014/0094922 A1 | 4/2014 | Abdou |
| 2014/0180422 A1 | 6/2014 | Klimek |
| 2014/0236296 A1 | 8/2014 | Wagner et al. |
| 2014/0309741 A1 | 10/2014 | Ganter et al. |
| 2014/0324173 A1 | 10/2014 | Kirschman |
| 2015/0173917 A1 | 6/2015 | Radcliffe et al. |
| 2015/0190242 A1 | 7/2015 | Blain et al. |
| 2015/0320568 A1 | 11/2015 | Ameil et al. |
| 2015/0342648 A1 | 12/2015 | McCormack et al. |
| 2016/0000576 A1 | 1/2016 | Kirschman |
| 2016/0022438 A1 | 1/2016 | Lamborne et al. |
| 2016/0058481 A1 | 3/2016 | Blain et al. |
| 2016/0120660 A1 | 5/2016 | Melkent et al. |
| 2016/0151171 A1 | 6/2016 | Mozelski et al. |
| 2016/0213481 A1 | 7/2016 | Blain |
| 2016/0213485 A1 | 7/2016 | Schaufler et al. |
| 2016/0296338 A1 | 10/2016 | Kim et al. |
| 2017/0056201 A1* | 3/2017 | Liang .............. A61F 2/447 |
| 2017/0095342 A9 | 4/2017 | Waugh |
| 2017/0105844 A1 | 4/2017 | Kuyler et al. |
| 2017/0119439 A1 | 5/2017 | Ozdil |
| 2017/0119538 A1* | 5/2017 | Baynham .............. A61F 2/447 |
| 2017/0231782 A1 | 8/2017 | Perez-Cruet et al. |
| 2017/0333205 A1* | 11/2017 | Joly .............. A61F 2/30771 |
| 2018/0014947 A1 | 1/2018 | Baynham |
| 2018/0042732 A1 | 2/2018 | Seifert et al. |
| 2018/0104063 A1 | 4/2018 | Asaad |
| 2018/0214279 A1 | 8/2018 | Etminan et al. |
| 2018/0235769 A1 | 8/2018 | Levy et al. |
| 2018/0250051 A1 | 9/2018 | Vrionis et al. |
| 2018/0256336 A1 | 9/2018 | Mueller |
| 2018/0289508 A1 | 10/2018 | Glerum |
| 2018/0303623 A1 | 10/2018 | Shoshtaev |
| 2018/0325693 A1 | 11/2018 | Weiman et al. |
| 2019/0046333 A1 | 2/2019 | Hansell et al. |
| 2019/0053910 A1 | 2/2019 | Sansur et al. |
| 2019/0091036 A1 | 3/2019 | Levy et al. |
| 2019/0133785 A1 | 5/2019 | Georges |
| 2019/0175357 A1 | 6/2019 | Sharabani |
| 2019/0254840 A1 | 8/2019 | Gray et al. |
| 2020/0085586 A1 | 3/2020 | Ludwig et al. |
| 2020/0093612 A1 | 3/2020 | Blain et al. |
| 2020/0146729 A1 | 5/2020 | Blain et al. |
| 2020/0197149 A1 | 6/2020 | Folger et al. |
| 2020/0229943 A1 | 7/2020 | Abdou |
| 2020/0246157 A1* | 8/2020 | Berry .............. A61F 2/447 |
| 2020/0315679 A1 | 10/2020 | Vrionis et al. |
| 2020/0345503 A1 | 11/2020 | Sansur et al. |
| 2020/0345505 A1 | 11/2020 | Etminan et al. |
| 2021/0000608 A1 | 1/2021 | Blain et al. |
| 2021/0137702 A1 | 5/2021 | Neubardt |
| 2021/0145600 A1 | 5/2021 | Sharifi-Mehr et al. |
| 2021/0145607 A1 | 5/2021 | Kuyler et al. |
| 2021/0154021 A1 | 5/2021 | Bae et al. |
| 2022/0015919 A1 | 1/2022 | Reah et al. |
| 2022/0031469 A1 | 2/2022 | Suh et al. |
| 2022/0151800 A1 | 5/2022 | Huh et al. |
| 2022/0192841 A1 | 6/2022 | Blain et al. |
| 2022/0241089 A1 | 8/2022 | Clauss et al. |
| 2022/0346843 A1 | 11/2022 | Blain et al. |
| 2022/0387189 A1 | 12/2022 | Blain et al. |
| 2023/0165690 A1 | 6/2023 | Blain et al. |
| 2024/0225851 A1 | 7/2024 | Huh |

FOREIGN PATENT DOCUMENTS

| | | |
|---|---|---|
| DE | 30 27 138 | 12/1981 |
| DE | 30 27 148 | 12/1981 |
| DE | 297 01 099 | 4/1997 |
| DE | 197 02 201 | 8/1998 |
| DE | 20 2004 015 912 | 12/2004 |
| EP | 0 242 842 | 10/1987 |
| EP | 0 974 319 | 1/2000 |
| EP | 1 029 510 | 8/2000 |
| EP | 1 346 697 | 9/2003 |
| EP | 1 470 803 | 10/2004 |
| EP | 2 719 360 | 5/2016 |
| EP | 2 967 904 | 5/2019 |
| FR | 2 766 353 | 1/1999 |
| FR | 2 813 519 | 3/2002 |
| FR | 2 859 904 | 3/2005 |
| FR | 2 923 155 | 5/2009 |
| JP | 2002-515287 | 5/2002 |
| JP | 2003-518977 | 6/2003 |
| JP | 2004-500156 | 1/2004 |
| JP | 2008-522787 | 7/2008 |
| JP | 2008-537498 | 9/2008 |
| JP | 2010-510852 | 4/2010 |
| JP | 2014-523751 | 9/2014 |
| JP | 2015-500701 | 1/2015 |
| WO | WO 88/003781 | 6/1988 |
| WO | WO 89/004150 | 5/1989 |
| WO | WO 93/010725 | 6/1993 |
| WO | WO 94/000066 | 1/1994 |
| WO | WO 95/035067 | 12/1995 |
| WO | WO 00/024343 | 5/2000 |
| WO | WO 01/003570 | 1/2001 |
| WO | WO 01/049191 | 7/2001 |
| WO | WO 01/078615 | 10/2001 |
| WO | WO 01/089428 | 11/2001 |
| WO | WO 03/017856 | 3/2003 |
| WO | WO 03/071966 | 9/2003 |
| WO | WO 2004/006792 | 1/2004 |
| WO | WO 2005/027760 | 3/2005 |
| WO | WO 2006/020464 | 2/2006 |

(56) References Cited

FOREIGN PATENT DOCUMENTS

| | | |
|---|---|---|
| WO | WO 2013/184946 | 12/2013 |
| WO | WO 2017/075079 | 5/2017 |
| WO | WO 2020/061487 | 3/2020 |
| WO | WO 2020/219789 | 10/2020 |
| WO | WO 2021/055363 | 3/2021 |

OTHER PUBLICATIONS

Official Communication in Australian Application No. 2012211502, dated Jul. 17, 2013.
Notice of Acceptance in Australian Application No. 2012211502, dated Sep. 10, 2014.
Official Communication in Australian Application No. 2014274519, dated Sep. 17, 2015.
Official Communication in Australian Application No. 2014274519, dated Jun. 17, 2016.
Official Communication in Australian Application No. 2014274519, dated Aug. 26, 2016.
Notice of Acceptance in Australian Application No. 2014274519, dated Sep. 22, 2016.
Official Communication in Australian Application No. 2016277588, dated Sep. 7, 2017.
Official Communication in Australian Application No. 2018271345, dated Jul. 31, 2019.
Official Communication in European Application No. 06738204.4, dated Mar. 26, 2009.
Official Communication in European Application No. 06738204.4, dated Apr. 6, 2010.
Official Communication in European Application No. 06738204.4, dated Apr. 5, 2011.
Official Communication in European Application No. 06738204.4, dated Oct. 28, 2011.
Official Communication in European Application No. 06738204.4, dated Jul. 18, 2012.
Official Communication in European Application No. 06738204.4, dated Oct. 14, 2013.
Extended European Search Report for European Application No. 11160061.5, dated Nov. 2, 2011.
Official Communication in European Application No. 11160061.5, dated Jul. 9, 2012.
Extended European Search Report for European Application No. 11160063.1, dated Nov. 2, 2011.
Official Communication in European Application No. 11160063.1, dated Jul. 12, 2012.
Official Communication in European Application No. 11160063.1, dated Nov. 27, 2012.
Official Communication in European Application No. 11160063.1, dated Oct. 14, 2013.
Official Communication in European Application No. 14190344.3, dated Feb. 10, 2015.
Official Communication in European Application No. 14190344.3, dated Jan. 4, 2016.
Official Communication in European Application No. 14190344.3, dated Sep. 8, 2016.
Official Communication in European Application No. 18150661.9, dated May 25, 2018.
Official Communication in European Application No. 18150661.9, dated Aug. 23, 2019.
Official Communication in Japanese Application No. 2008-501962, dated May 10, 2011.
Official Communication in Japanese Application No. 2008-501962, dated Nov. 13, 2012.
Official Communication in Japanese Application No. 2011-210533, dated Mar. 5, 2013.
Official Communication in Japanese Application No. 2011-210533, dated Dec. 3, 2013.
Notice of Allowance in Japanese Application No. 2011-210533, dated May 7, 2014.
Notice of Allowance in Japanese Application No. 2013-117602, dated May 7, 2014.
Notice of Allowance in Japanese Application No. 2013-117602, dated Feb. 2, 2015.
International Search Report and Written Opinion in International Application No. PCT/US2006/009120, dated Oct. 20, 2006.
International Preliminary Report on Patentability and Written Opinion in International Application No. PCT/US2006/009120, dated Sep. 18, 2007.
Official Communication in Australian Application No. 2016212009, dated Sep. 6, 2019.
Official Communication in Australian Application No. 2016212009, dated May 26, 2020.
Official Communication in Australian Application No. 2016212009, dated Jul. 14, 2020.
Official Communication in Australian Application No. 2016212009, dated Nov. 24, 2021.
Official Communication in Canadian Application No. 2,972,788, dated Jan. 31, 2022.
Official Communication in European Application No. 16743832.4, dated Jul. 24, 2018.
Official Communication in Japanese Application No. 2017-557269, dated Oct. 21, 2019.
Official Communication in Japanese Application No. 2017-557269, dated Jul. 13, 2020.
Official Communication in Japanese Application No. 2017-557269, dated Nov. 1, 2021.
Official Communication in Japanese Application No. 2020-181320, Sep. 21, 2021.
International Search Report and Written Opinion in International Application No. PCT/US2016/013062, dated Mar. 16, 2016.
International Preliminary Report on Patentability and Written Opinion in International Application No. PCT/US2016/013062, dated Aug. 10, 2017.
Invitation to Pay Additional Search Fees in International Application No. PCT/US2019/052211, dated Nov. 14, 2019.
International Search Report and Written Opinion in International Application No. PCT/US2019/052211, dated Feb. 3, 2020.
International Preliminary Report on Patentability and Written Opinion in International Application No. PCT/US2019/052211, dated Apr. 1, 2021.
International Search Report and Written Opinion in International Application No. PCT/US2021/072934, dated Feb. 24, 2022.
Invitation to Pay Additional Search Fees in International Application No. PCT/US2021/072334, dated Jan. 13, 2022.
International Search Report and Written Opinion in International Application No. PCT/US2021/072334, dated Mar. 18, 2022.
Official Communication in Australian Application No. 2020257035, dated Jun. 24, 2021.
Official Communication in Australian Application No. 2022201902, dated May 10, 2023.
Official Communication in European Application No. 18150661.9, dated Jan. 18, 2023.
Official Communication in Australian Application No. 2020281016, dated Aug. 26, 2022.
Official Communication in Australian Application No. 2020281016, dated Oct. 7, 2022.
Official Communication in Australian Application No. 2020281016, dated Nov. 16, 2022.
Official Communication in Australian Application No. 2020281016, dated Nov. 23, 2022.
Official Communication in Canadian Application No. 2,972,788, dated Oct. 31, 2022.
Official Communication in European Application No. 16743832.4, dated Jan. 26, 2023.
Official Communication in Japanese Application No. 2020-181320, Feb. 13, 2023.
Official Communication in Brazilian Application No. BR112021005206-2, dated Jun. 5, 2023.
Official Communication in European Application No. 19862906.5, dated Sep. 23, 2022.

(56) References Cited

OTHER PUBLICATIONS

International Preliminary Report on Patentability and Written Opinion in International Application No. PCT/US2021/072934, dated Jun. 29, 2023.
International Preliminary Report on Patentability in International Application No. PCT/US2021/072334, dated Jun. 1, 2023.
International Search Report and Written Opinion in International Application No. PCT/US2022/050050, dated Feb. 22, 2023.
International Preliminary Report on Patentability and Written Opinion in International Application No. PCT/US2022/050050, dated Jun. 13, 2024.

* cited by examiner

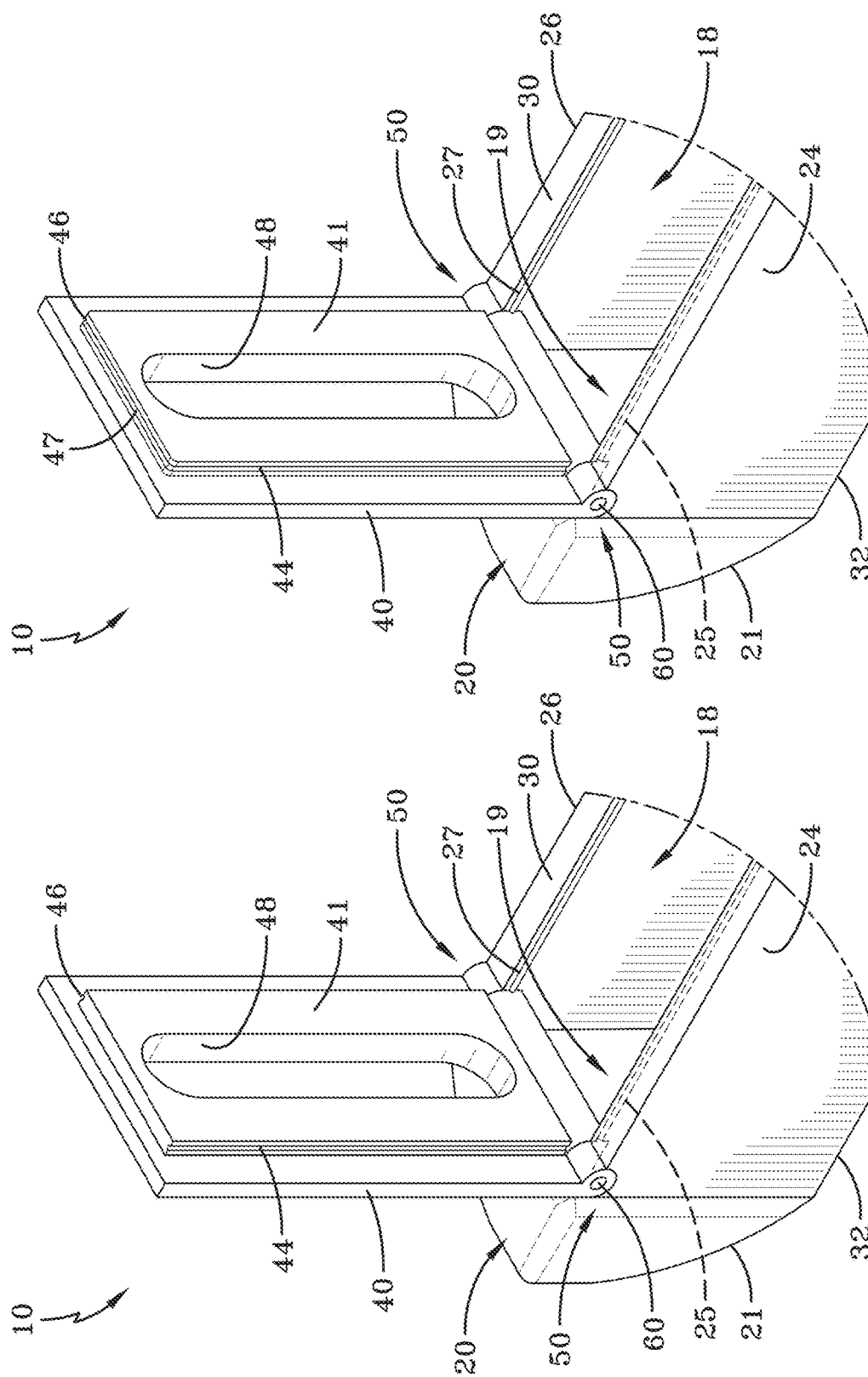

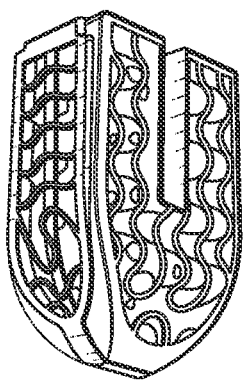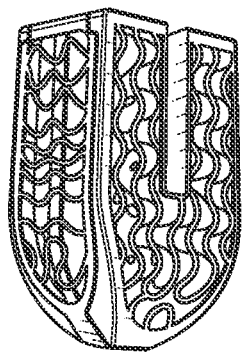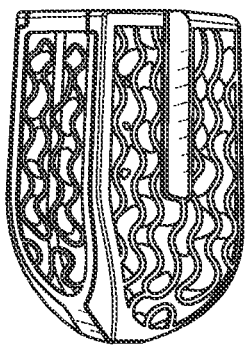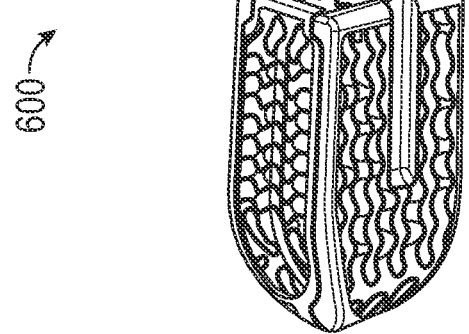
FIG. 53

SPINAL IMPLANT DEVICE

CROSS-REFERENCE TO RELATED APPLICATIONS

This application is a continuation of U.S. patent application Ser. No. 16/577,511, filed Sep. 20, 2019, which claims priority benefit to U.S. Provisional Patent Application No. 62/734,148, filed Sep. 20, 2018, and U.S. Provisional Patent Application No. 62/790,866, filed Jan. 10, 2019, the disclosures of each are incorporated by reference herein in their entireties.

BACKGROUND

Field

Some embodiments described herein relate generally to systems and methods for stabilizing bone, for example, stabilizing vertebrae by fusing adjacent vertebrae. Some embodiments relate to spinal implant devices, for example spinal implant devices with a structure to enhance rapid bone growth.

Description of the Related Art

Advancing age, as well as injury, can lead to degenerative changes in the bones, discs, joints, and ligaments of the spine. These degenerative changes can produce pain and spinal instability. Under certain circumstances, spinal fusion can alleviate these degenerative changes. Spinal fusion is a surgical technique in which two or more vertebrae of the spinal column are fused together to reduce or limit the motion between the vertebrae. Spinal fusion is used to treat various conditions including fracture, scoliosis, and spondylolisthesis. Spinal fusion with discectomy is used to treat herniation of the discs by removal of the affected disc and fusion of the adjacent vertebrae. There are several procedures available to patients with degenerative spine conditions.

One technique is called Posterior Lumbar Interbody Fusion ("PLIF"). In the PLIF method, the spine is typically accessed through a three-inch to six-inch long incision in the midline of the back. In this method, the left and right lower back muscles are stripped to provide access to the nerve roots. In some methods, the lamina and spinous process are removed to allow visualization of the nerve roots. In some methods, the facet joints, which are directly over the nerve roots, can be undercut. The nerve roots are then retracted to one side and the disc space is cleaned of the disc material.

In some methods, an interbody implant is then inserted into the disc space to promote bone growth between adjacent vertebrae. The interbody implant is positioned between adjacent vertebrae in the disc space. In some methods, the interbody implant can be secured to one or more vertebrae by bone screws or other similar fasteners inserted through holes in the interbody implant. The size of the interbody implant is typically selected such that the interbody implant forces the vertebrae apart to cause tensing of the vertebral annulus and other soft tissue structures surrounding the joint space. Tensing the soft tissues surrounding the joint space can result in the vertebrae exerting compressive forces on the interbody implant to maintain the interbody implant in place.

The current standard of care to address the degenerative changes of the spine is to fuse vertebrae. The relative motion between the two adjacent vertebrae is limited or reduced in some methods of use.

SUMMARY

In some embodiments, a spinal implant device is provided. The spinal implant device can include a distal end, a proximal end, two opposing side walls extending between the distal end and the proximal end, an upper wall, and a lower wall forming a lower surface of the spinal implant device. The spinal implant device can include a central cavity. The spinal implant device can include a movable lid. In some embodiments, the movable lid is configured to open to provide access to the central cavity to allow the central cavity to be packed with a material. In some embodiments, the movable lid is configured to close to form at least a portion of an upper surface of spinal implant device after the central cavity is packed.

In some embodiments, the movable lid comprises a hinge. In some embodiments, the movable lid comprises a movable joint. In some embodiments, the movable lid comprises a ball and socket joint. In some embodiments, the movable lid comprises one or more tapered articulations. In some embodiments, the movable lid is coupled to the distal end. In some embodiments, the movable lid comprises one or more ridges. In some embodiments, the one or more ridges are directionally oriented. In some embodiments, the central cavity comprises at least 50% of the volume of the spinal implant device. In some embodiments, the movable lid comprises an articulation and the distal end comprises a socket. In some embodiments, the movable lid comprises an opening. In some embodiments, the movable lid is at least partially surrounded by a portion of the upper wall. In some embodiments, the movable lid and the upper wall form the upper surface of the spinal implant device. In some embodiments, an exterior surface of the movable lid is configured to lie flush with a portion of an adjacent exterior surface. In some embodiments, the lower wall and the movable lid are curved to mimic the shape of the end plates. In some embodiments, the movable lid is configured to interlock with the two opposing side walls or the proximal end. In some embodiments, at least one of the two opposing side walls comprises a thin framework configured to support a porous body. In some embodiments, at least one of the moveable lid, the upper wall, or the lower wall comprises a thin framework configured to support a porous body In some embodiments, the two opposing side walls have a thin wall thickness adjacent the central cavity. In some embodiments, the distal end has a thick wall thickness adjacent the central cavity. In some embodiments, the distal end has a hollow internal volume open to the central cavity. In some embodiments, the central cavity is enclosed when the movable lid is closed. In some embodiments, a side wall of the two opposing side walls comprises one or more openings.

In some embodiments, a method is provided. The method can include providing a spinal implant device comprising a distal end, a proximal end, two opposing side walls extending between the distal end and the proximal end, an upper wall, a lower wall, and a central cavity. The method can include pivoting a lid to provide access to the central cavity. The method can include packing the central cavity with a material. The method can include pivoting the lid to cover the central cavity after the central cavity is packed. In some embodiments, the material is an osteoinductive material. In some embodiments, the material is a graft material.

In some embodiments, a spinal implant device is provided. The spinal implant device can include a body structure having a distal end, a proximal end and two opposing side walls extending between the distal end and the proximal end. The spinal implant device can include an upper wall and a lower wall configured for abutting end plates of two adjacent vertebrae. The spinal implant device can include a central cavity internal of the body structure. The spinal implant device can include a movable lid for covering the central cavity. In some embodiments, the movable lid can form part of the upper wall. In some embodiments, the movable lid is configured to open exposing the central cavity to be filled and packed with an osteoinductive material and closed to cover the central cavity when filled.

In some embodiments, the movable lid is hinged to the upper wall. In some embodiments, the movable lid is integral to the upper wall and connected to the upper wall by a flexible living hinge. In some embodiments, the movable lid is connected to the upper wall by a hinge pin. In some embodiments, each side wall has a recess for receiving and supporting the movable lid and wherein an exterior surface of the lid lies flush with an adjacent exterior surface at the proximal and distal end. In some embodiments, the distal end is convexly curved from a leading end toward the opposing side walls. In some embodiments, the convexly curved distal end is substantially frustoconical to facilitate insertion. In some embodiments, the proximal end has a means for receiving an insertion rod or tool. In some embodiments, the means for receiving an insertion tool is a threaded opening. In some embodiments, the two opposing side walls have a thin wall thickness adjacent the central cavity. In some embodiments, the proximal end has a thin wall thickness adjacent the central cavity. In some embodiments, the distal end has a hollow internal volume open to the central cavity. In some embodiments, the distal end has a thin wall thickness. In some embodiments, the upper wall and lower wall have a large load supporting area for abutting the end plates. In some embodiments, the upper and lower walls having a width between the opposing side walls greater than a height of the opposing side walls. In some embodiments, the upper and lower walls including the movable lid are curved to mimic the shape of the end plates. In some embodiments, the movable lid has a pair of grooves on an inner surface extending along lateral sides, one groove receiving a protrusion near a top edge of each side wall to interlock the side walls and the movable lid together under compressive load. In some embodiments, the pair of grooves extends to a proximal end groove forming a "U" shape to interlock with a protrusion near a top edge of the proximal end wall. In some embodiments, the interlocking grooves form features to prevent bowing of the side walls.

In some embodiments, the combination of thin walls increases the volume available for packing material into the internal cavity. In some embodiments, the upper wall and lower wall have a large load supporting area for abutting the end plates of the adjacent vertebral bodies when the spinal implant device is positioned. In some embodiments, the upper and lower walls have a width between the opposing side walls greater than a height of the opposing side walls forming a stable support. In some embodiments, the upper and lower walls including the movable lid can be curved to mimic the shape of the end plates.

In some embodiments, the movable lid has a pair of grooves on an inner surface extending along the lateral sides. In some embodiments, the one groove receives a protrusion near a top edge of each side wall to interlock the side walls and movable lid together under compressive loads. In some embodiments, the groove can extend to a proximal end groove forming a "U" shape to also lock a protrusion adjacent the top edge of the proximal wall. In some embodiments, these interlocking grooves on the interior of the lid form features to assist to prevent bowing of the thin walls. The above embodiments and methods of use are explained in more detail below.

In some embodiments, a spinal implant device is provided. The spinal implant device can include a distal end and a proximal end defining a length therebetween. The spinal implant device can include two opposing side walls extending between the distal end and the proximal end. The spinal implant device can include an upper surface and a lower surface defining a height therebetween. The spinal implant device can include a central cavity. The spinal implant device can include a feature configured to compress along the height of the spinal implant device.

In some embodiments, the upper surface comprises a movable lid. In some embodiments, the spinal implant device can include a hinge. In some embodiments, the spinal implant device can include a living hinge. In some embodiments, at least one side wall comprises an opening configured to be compressed. In some embodiments, at least one side wall comprises a longitudinally extending slot. In some embodiments, a movable lid and an upper wall form the upper surface of the spinal implant device. In some embodiments, at least one of the two opposing side walls comprises a thin framework configured to support a porous body. In some embodiments, at least one of the two opposing side walls comprises one or more openings.

In some embodiments, a method is provided. The method can include providing a spinal implant device comprising a distal end and a proximal end defining a length therebetween, two opposing side walls extending between the distal end and the proximal end, an upper surface and a lower surface defining a height therebetween, a central cavity, and a compressible feature. The method can include packing the central cavity with a material. The method can include inserting the spinal implant device between vertebrae, wherein the vertebra compress the feature.

In some embodiments, the height of the spinal implant device is reduced by a force applied by the vertebrae. In some embodiments, the compressible feature is a living hinge. In some embodiments, the compressible feature is a longitudinally extending slot. In some embodiments, the compressible feature is flexible. In some embodiments, the compressible feature is an opening in at least one of the two opposing side walls. In some embodiments, the spinal implant device compresses in height within a range from 0.1 mm to 1 mm. In some embodiments, the spinal implant device compresses in height within a range from 1% to 10% of the total height.

In some embodiments, a spinal implant device is provided. The spinal implant device can include a distal end, a proximal end, two opposing side walls extending between the distal end and the proximal end, an upper wall, and a lower wall forming a lower surface of the spinal implant device. The spinal implant device can include a central cavity. The spinal implant device can include a movable lid. In some embodiments, the movable lid is configured to open to provide access to the central cavity to allow the central cavity to be packed with a material. In some embodiments, the movable lid is configured to close to form at least a portion of an upper surface of the spinal implant device after the central cavity is packed.

In some embodiments, the movable lid comprises a hinge. In some embodiments, the movable lid comprises one or more tapered articulations. In some embodiments, the movable lid is coupled to the distal end. In some embodiments, the movable lid comprises one or more ridges. In some embodiments, the central cavity comprises at least 50% of the volume of the spinal implant device. In some embodiments, the movable lid comprises an articulation and the distal end comprises a socket. In some embodiments, the movable lid comprises an opening. In some embodiments, the movable lid is at least partially surrounded by a portion of the upper wall. In some embodiments, the movable lid and the upper wall form the upper surface of the spinal implant device. In some embodiments, an exterior surface of the movable lid is configured to lie flush with a portion of an adjacent exterior surface. In some embodiments, the lower wall and the movable lid are curved to mimic the shape of the end plates. In some embodiments, the movable lid is configured to interlock with the two opposing side walls or the proximal end. In some embodiments, at least one of the two opposing side walls comprises a thin framework configured to support a porous body. In some embodiments, at least one of the moveable lid, the upper wall, or the lower wall comprises a thin framework configured to support a porous body. In some embodiments, the central cavity is enclosed when the movable lid is closed. In some embodiments, a side wall of the two opposing side walls comprises one or more openings.

In some embodiments, a method is provided. The method can include providing a spinal implant device comprising a distal end, a proximal end, two opposing side walls extending between the distal end and the proximal end, an upper wall, a lower wall, and a central cavity. The method can include pivoting a lid to provide access to the central cavity. The method can include packing the central cavity with a material. The method can include pivoting the lid to cover the central cavity after the central cavity is packed.

In some embodiments, the material is an osteoinductive material. In some embodiments, the material is a graft material.

In some embodiments, a spinal implant device is provided. The spinal implant device can include a distal end and a proximal end defining a length therebetween. The spinal implant device can include two opposing side walls extending between the distal end and the proximal end. The spinal implant device can include an upper surface and a lower surface defining a height therebetween. The spinal implant device can include a central cavity. The spinal implant device can include a feature configured to compress along the height of the spinal implant device.

In some embodiments, the upper surface comprises a movable lid. In some embodiments, the spinal implant device can include a hinge. In some embodiments, the spinal implant device can include a living hinge. In some embodiments, at least one side wall comprises an opening configured to be compressed. In some embodiments, at least one side wall comprises a longitudinally extending slot. In some embodiments, wherein a movable lid and an upper wall form the upper surface of the spinal implant device. In some embodiments, at least one of the two opposing side walls comprises a thin framework configured to support a porous body. In some embodiments, at least one of the two opposing side walls comprises one or more openings. In some embodiments, the spinal implant device is configured to compress in height within a range from 0.1 mm to 1 mm. In some embodiments, the spinal implant device is configured to compress in height within a range from 1% to 10% of the total height. In some embodiments, the spinal implant device comprises a movable lid, wherein the movable lid is configured to hover above a ledge of the spinal implant device under normal anatomical loads. In some embodiments, the movable lid is configured to contact the ledge of the spinal implant device under greater than normal anatomical loads.

In some embodiments, a method is provided. The method can include providing a spinal implant device comprising a distal end and a proximal end defining a length therebetween, two opposing side walls extending between the distal end and the proximal end, an upper surface and a lower surface defining a height therebetween, a central cavity, and a compressible feature. The method can include packing the central cavity with a material. The method can include inserting the spinal implant device between vertebrae, wherein the vertebra compress the feature.

In some embodiments, the height of the spinal implant device is reduced by a force applied by the vertebrae. In some embodiments, the compressible feature is a living hinge. In some embodiments, the compressible feature is a longitudinally extending slot. In some embodiments, the compressible feature is flexible. In some embodiments, the compressible feature is an opening in at least one of the two opposing side walls. In some embodiments, the spinal implant device compresses in height within a range from 0.1 mm to 1 mm. In some embodiments, the spinal implant device compresses in height within a range from 1% to 10% of the total height. In some embodiments, the spinal implant device comprises a movable lid, wherein the movable lid hovers above a ledge of the spinal implant device under normal anatomical loads. In some embodiments, the movable lid contacts the ledge of the spinal implant device under greater than normal anatomical loads.

Accordingly, a need exists for a spinal implant device to quickly and/or easily stabilize and/or fixate a bone by enhancing the formation of new bone growth to fuse the spinal implant device.

BRIEF DESCRIPTION OF THE DRAWINGS

The structure and method of use will be better understood with the following detailed description of embodiments, along with the accompanying illustrations, in which:

FIG. 7A is a view of an embodiment of a spinal implant device with a movable lid shown in an opened position.

FIG. 7B is a view of an embodiment of a spinal implant device with a movable lid shown in an opened position.

FIG. 53 are views of embodiments of the spinal implant device of FIG. 45.

FIG. 117 is a top view of the spinal implant device of FIG. 113.

FIG. 118 is a top perspective view of the spinal implant device of FIG. 113 with the movable lid shown in an opened position.

FIG. 119 is a bottom perspective view of the spinal implant device of FIG. 113.

FIG. 120 is an exploded perspective view of the spinal implant device of FIG. 113.

FIG. 121 is a perspective view of an embodiment of a spinal implant device with a movable lid shown in a closed position.

FIG. 122 is a distal view of the spinal implant device of FIG. 121.

FIG. 123 is a proximal view of the spinal implant device of FIG. 121.

FIG. 124 is a side view of the spinal implant device of FIG. 121.

FIG. 125 is a top view of the spinal implant device of FIG. 121.

FIG. 126 is a top perspective view of the spinal implant device of FIG. 121 with the movable lid shown in an opened position.

FIG. 127 is a bottom perspective view of the spinal implant device of FIG. 121.

FIG. 128 is an exploded perspective view of the spinal implant device of FIG. 121.

Figure 129:
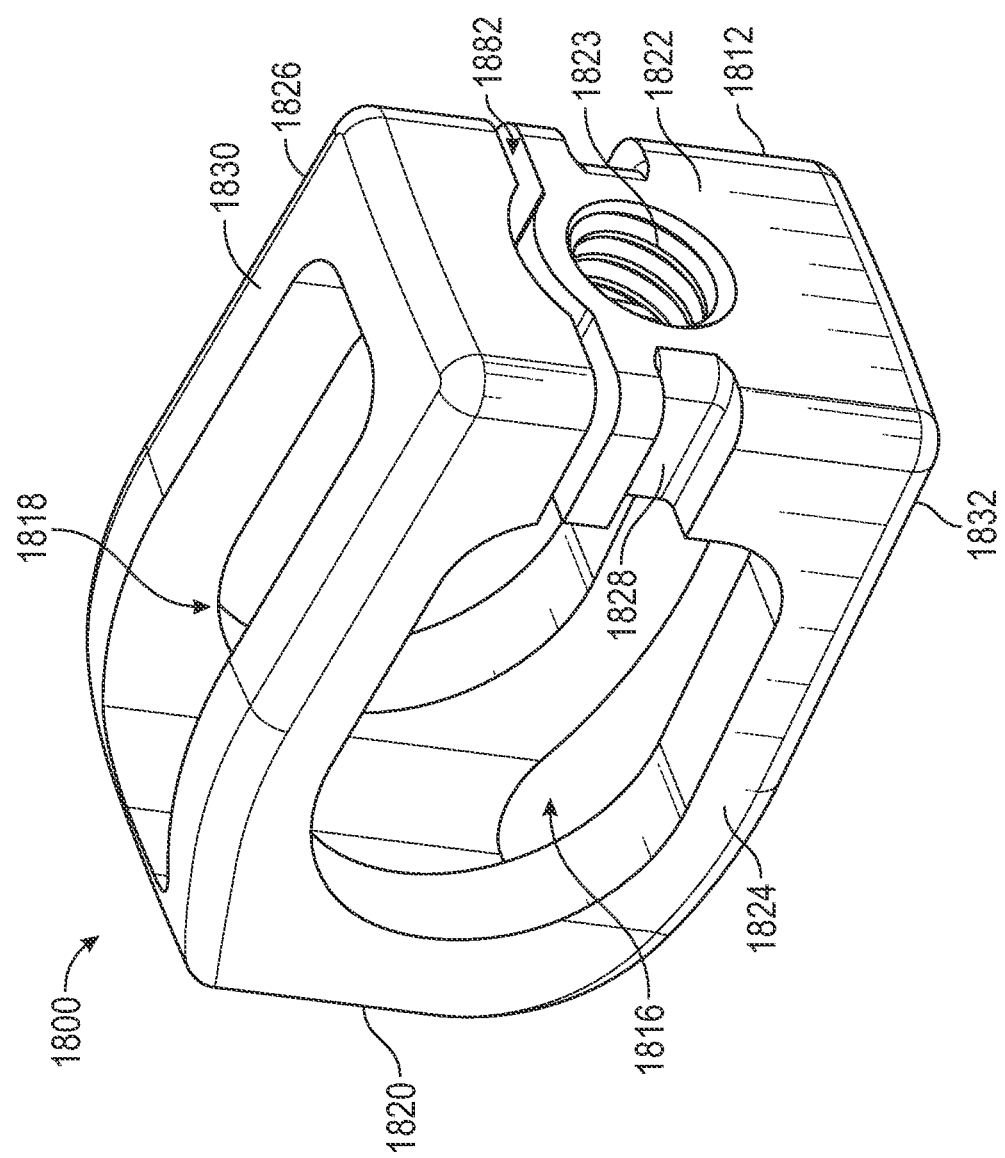

FIG. 129 is a perspective view of an embodiment of a spinal implant device.

Figure 130:
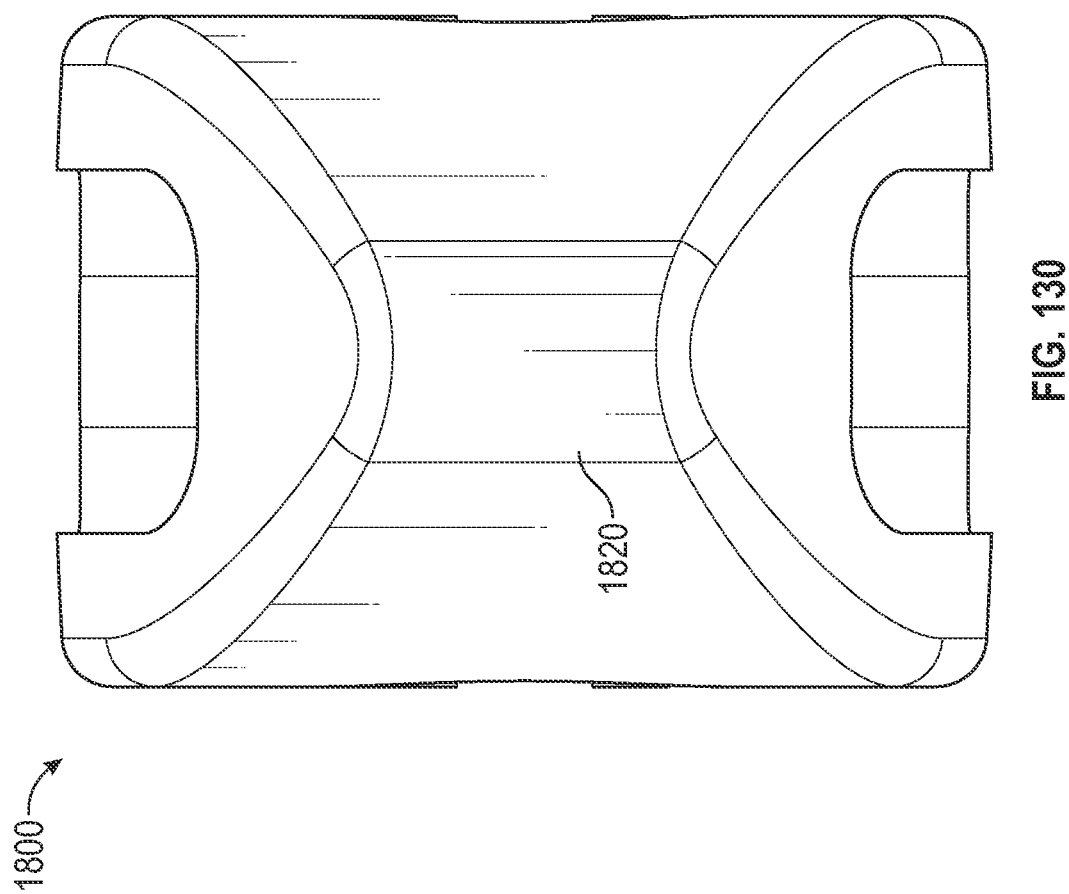

FIG. 130 is a distal view of the spinal implant device of FIG. 129.

Figure 131:
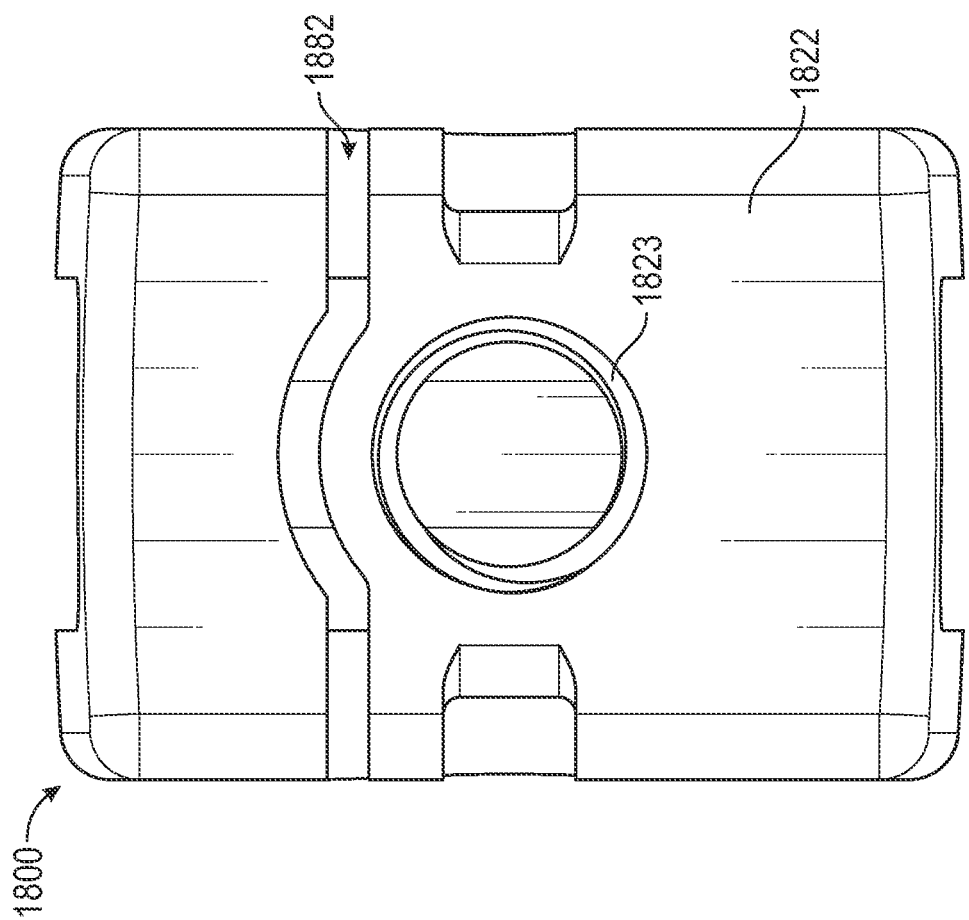

FIG. 131 is a proximal view of the spinal implant device of FIG. 129.

Figure 132:
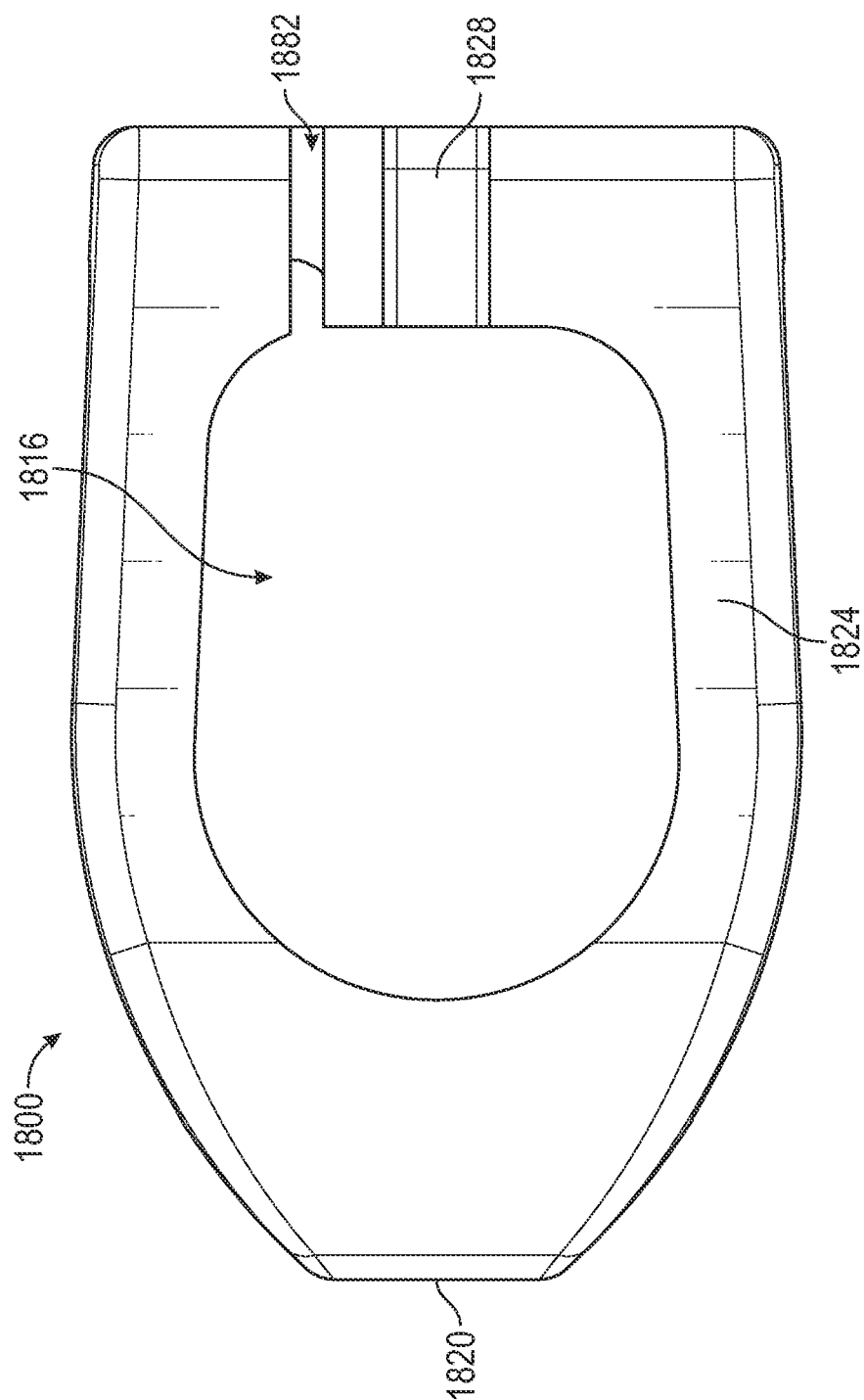

FIG. 132 is a side view of the spinal implant device of FIG. 129.

Figure 133:
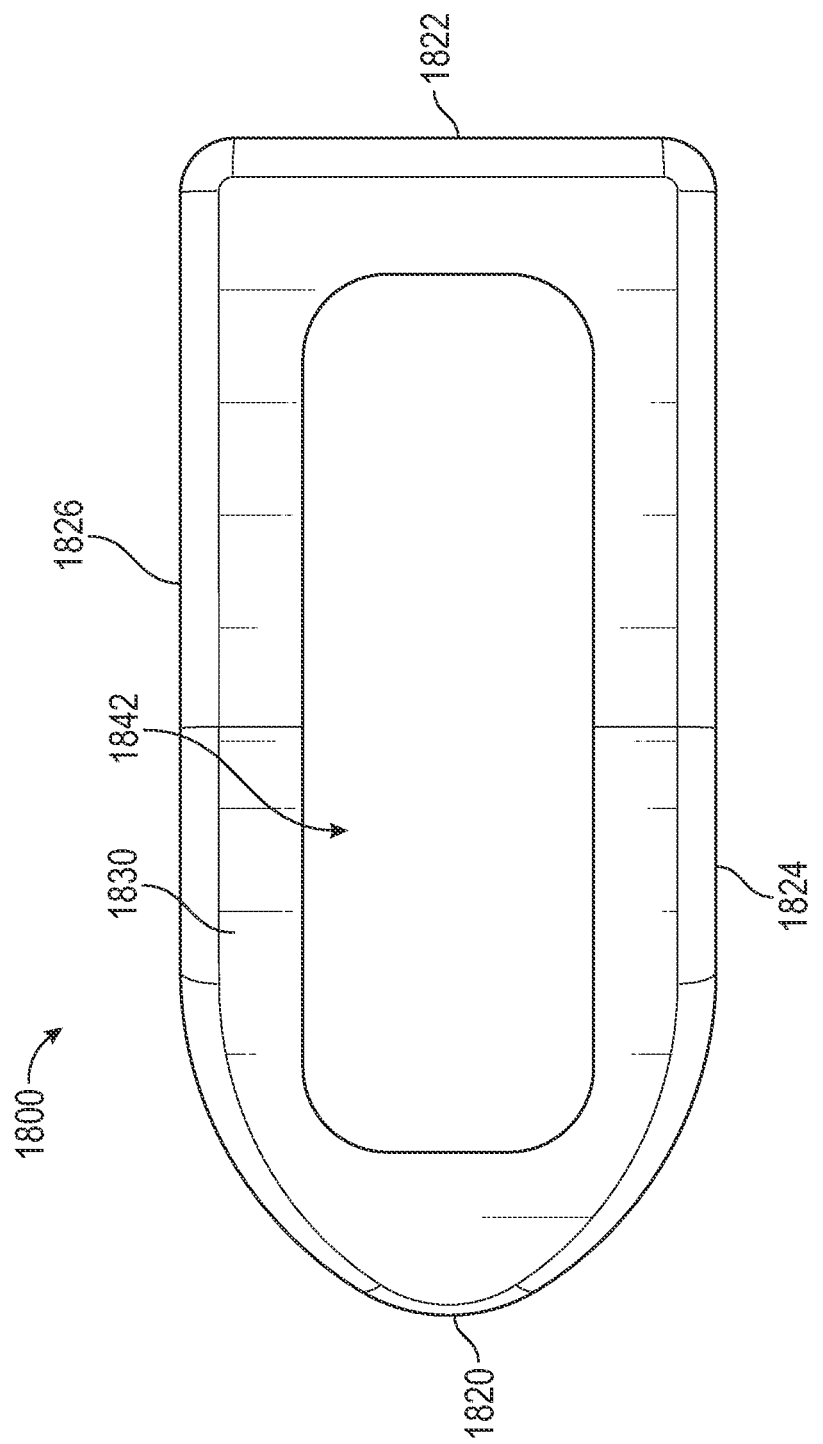

FIG. 133 is a top view of the spinal implant device of FIG. 129.

Figure 134:
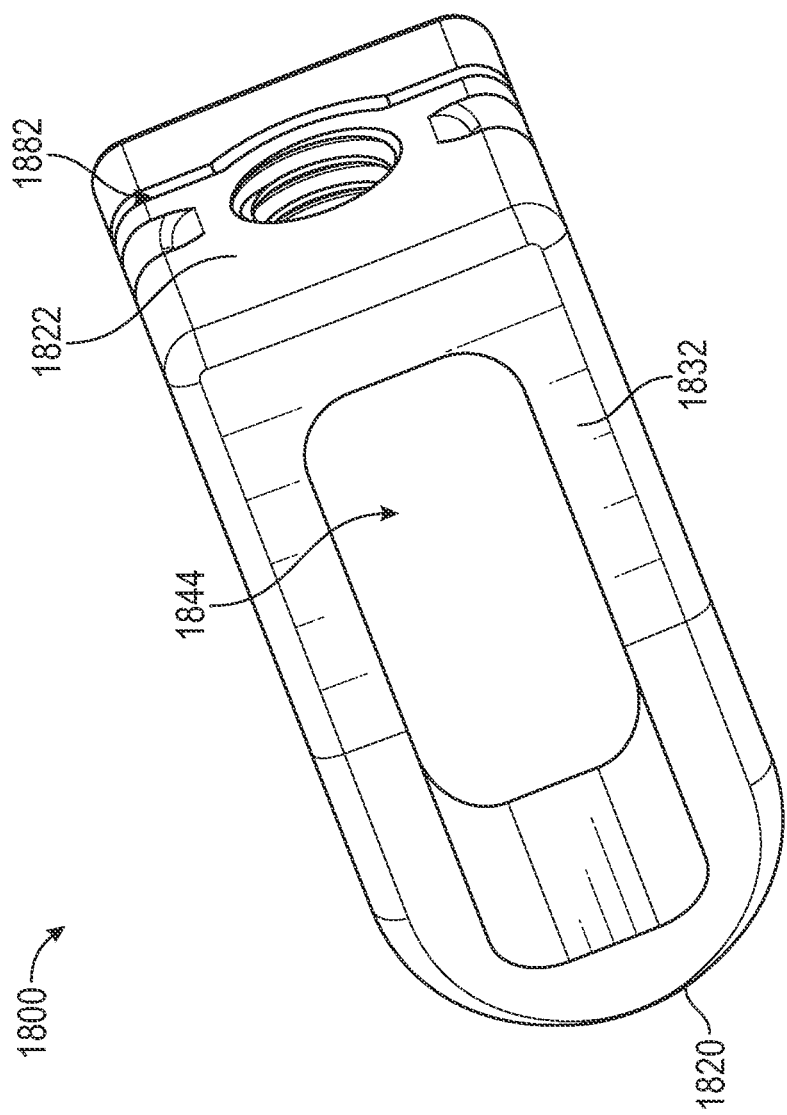

FIG. 134 is a bottom perspective view of the spinal implant device of FIG. 129.

Figure 135:
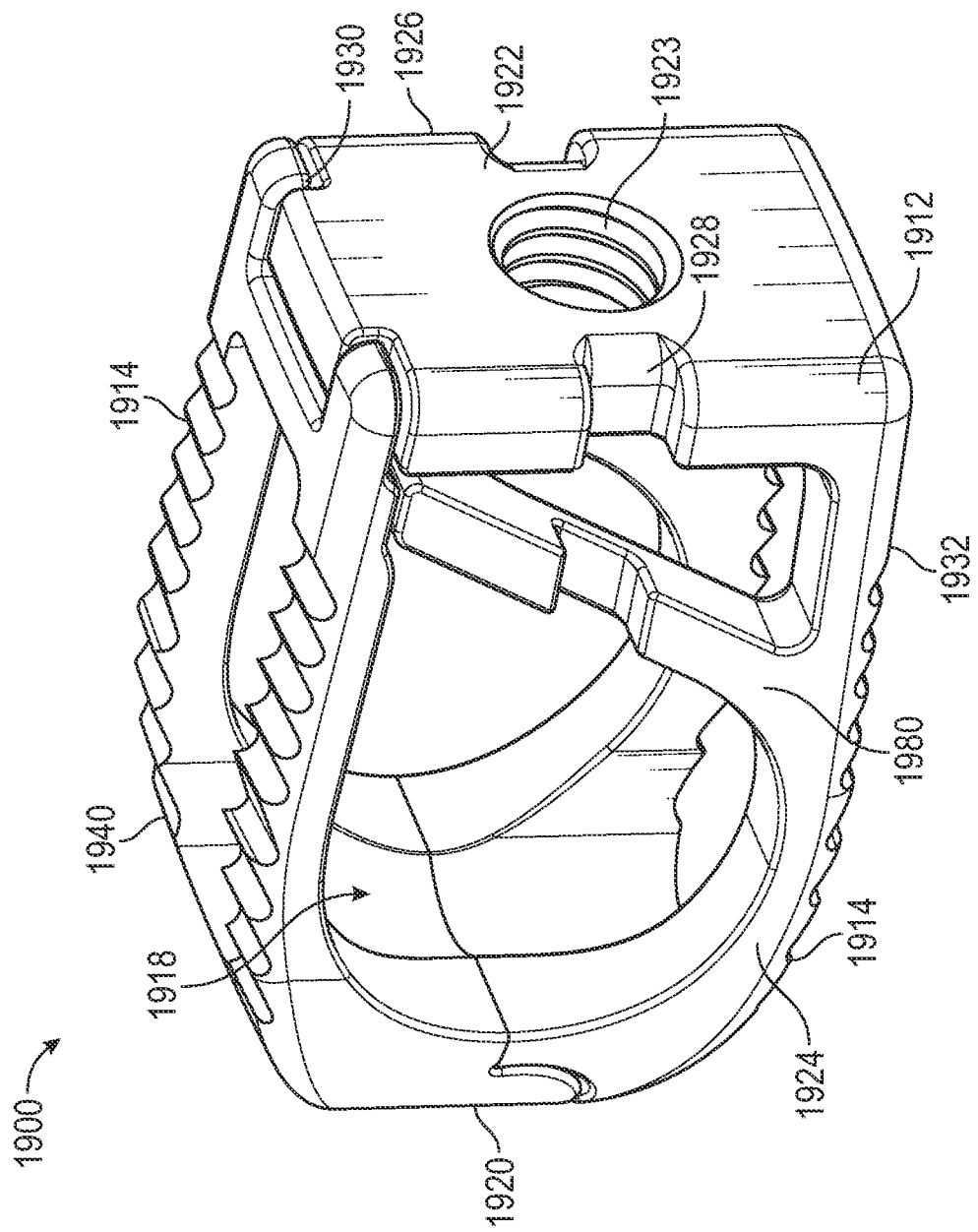

FIG. 135 is a perspective view of an embodiment of a spinal implant device with a movable lid shown in a closed position.

Figure 136:
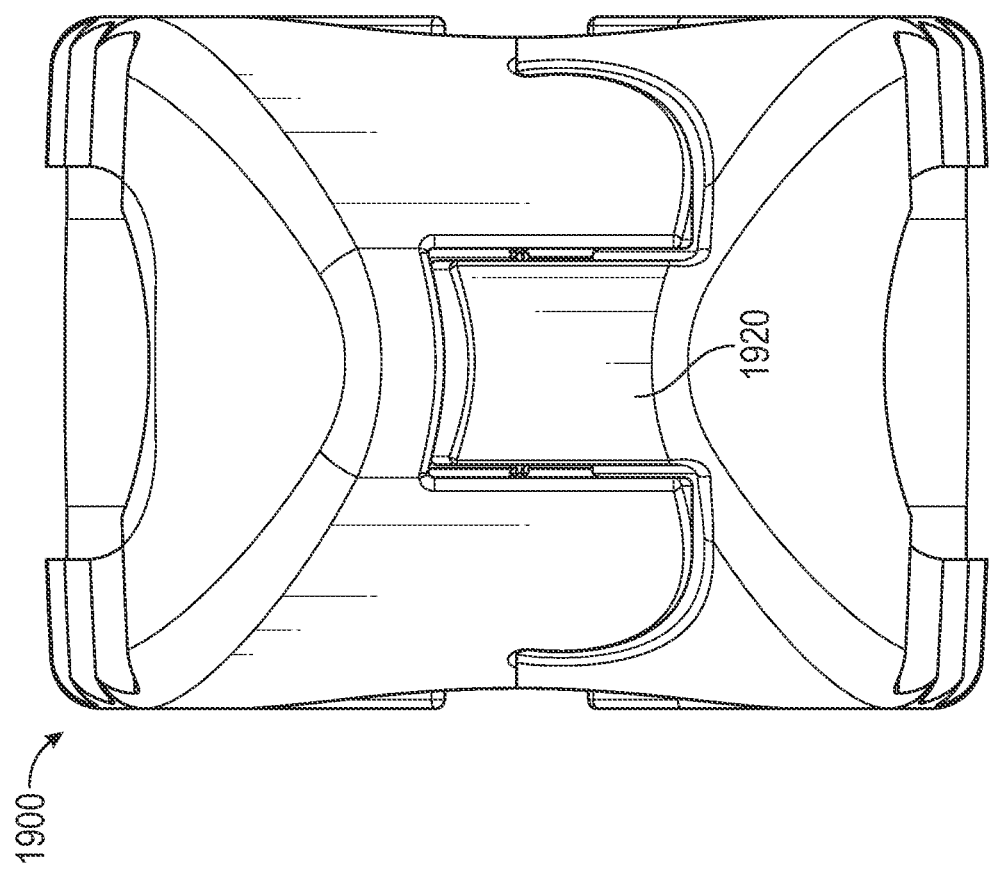

FIG. 136 is a distal view of the spinal implant device of FIG. 135.

Figure 137:
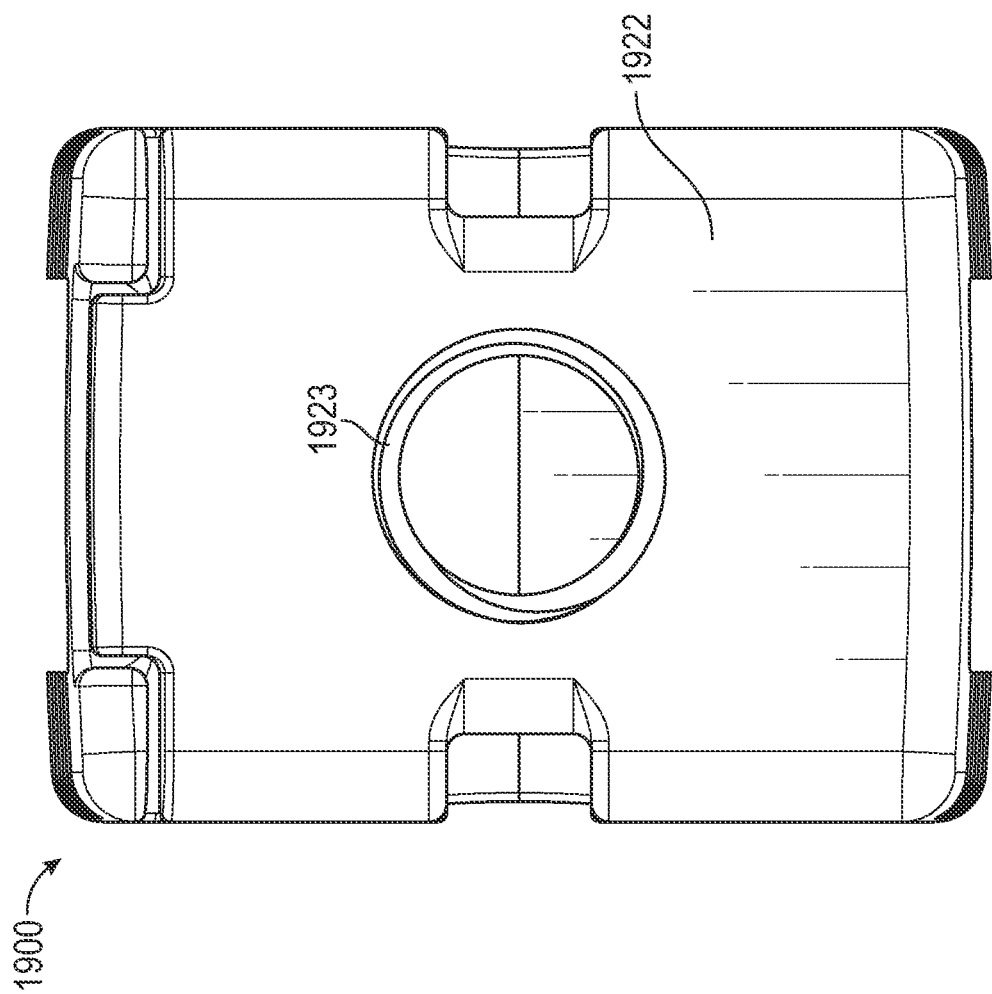

FIG. 137 is a proximal view of the spinal implant device of FIG. 135.

Figure 138:
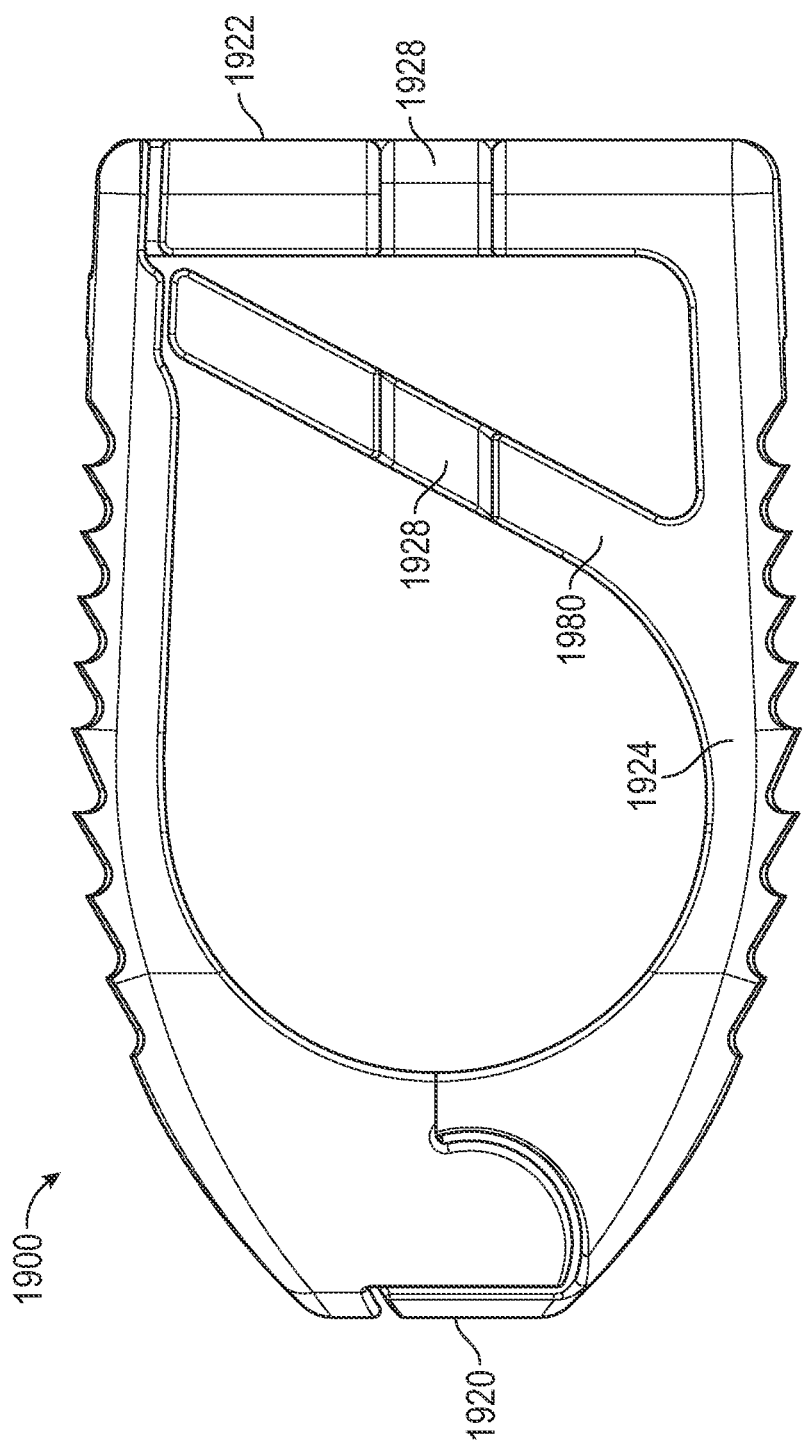

FIG. 138 is a side view of the spinal implant device of FIG. 135.

Figure 139:
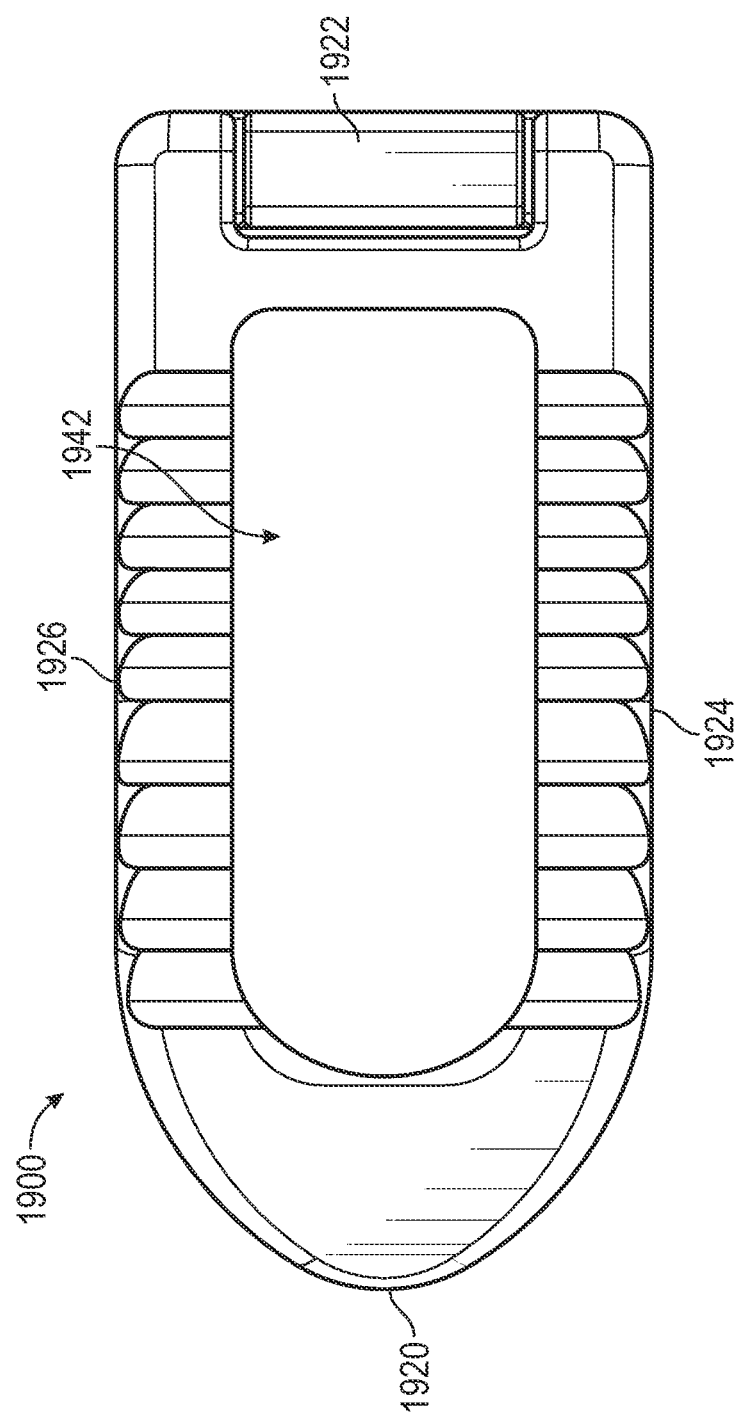

FIG. 139 is a top view of the spinal implant device of FIG. 135.

Figure 140:
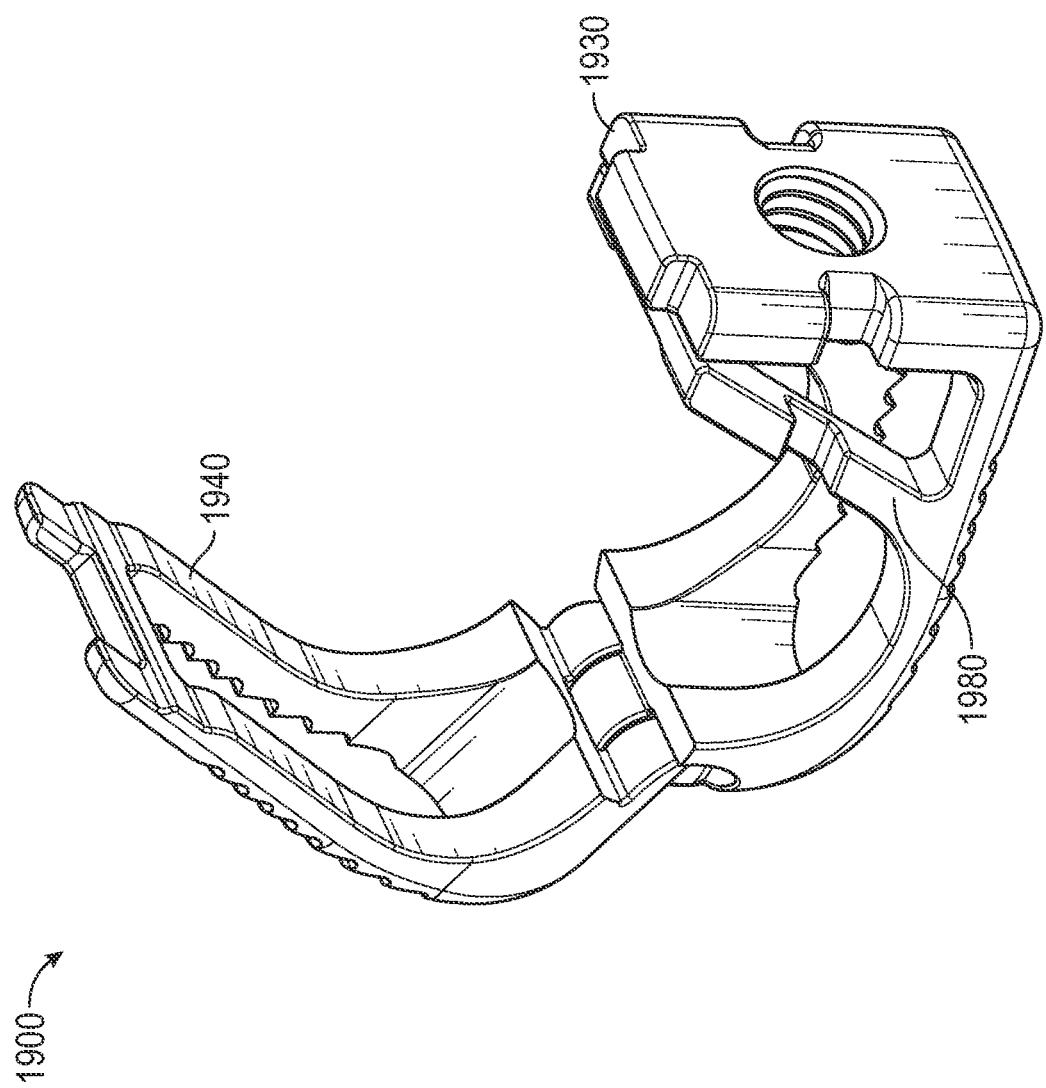

FIG. 140 is a top perspective view of the spinal implant device of FIG. 135 with the movable lid shown in an opened position.

Figure 141:
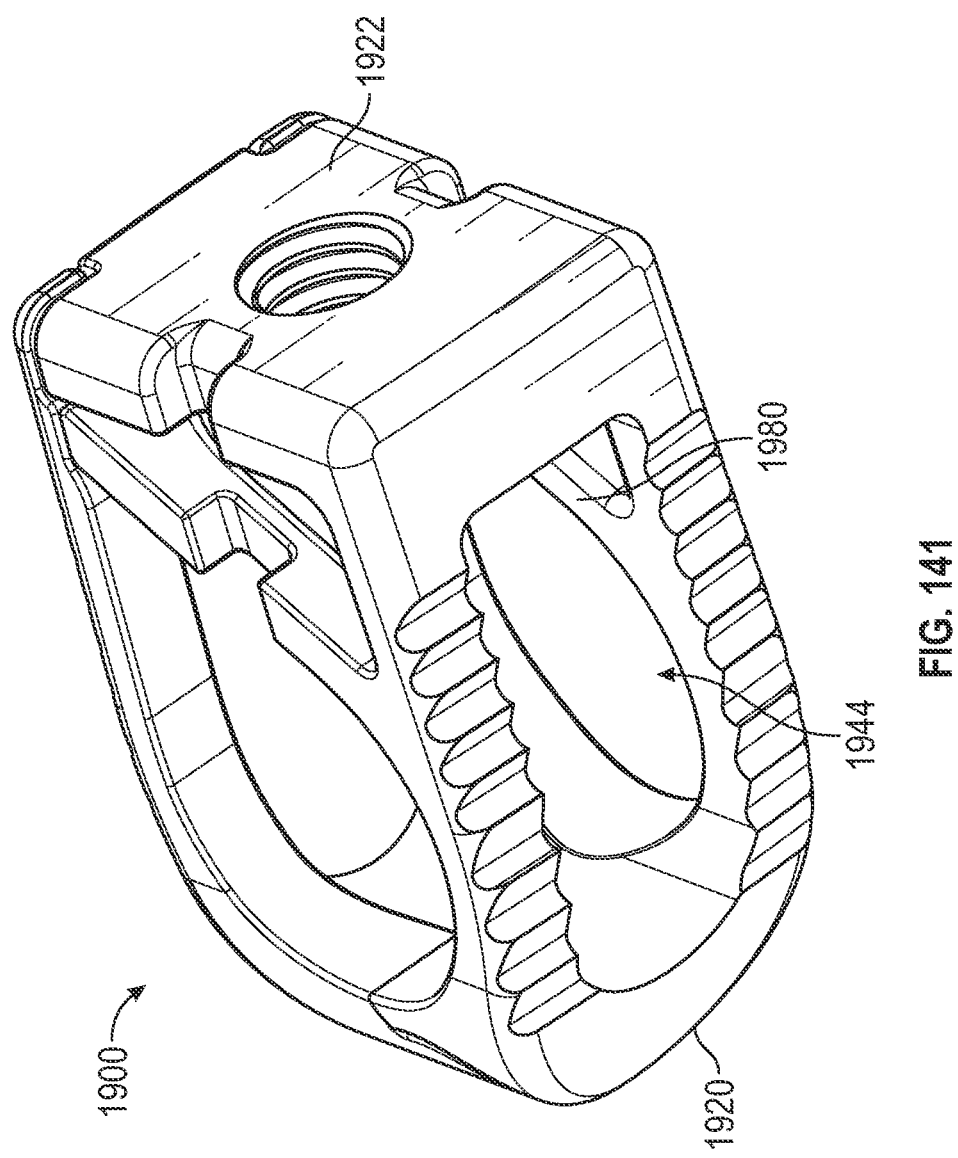

FIG. 141 is a bottom perspective view of the spinal implant device of FIG. 135.

Figure 142:
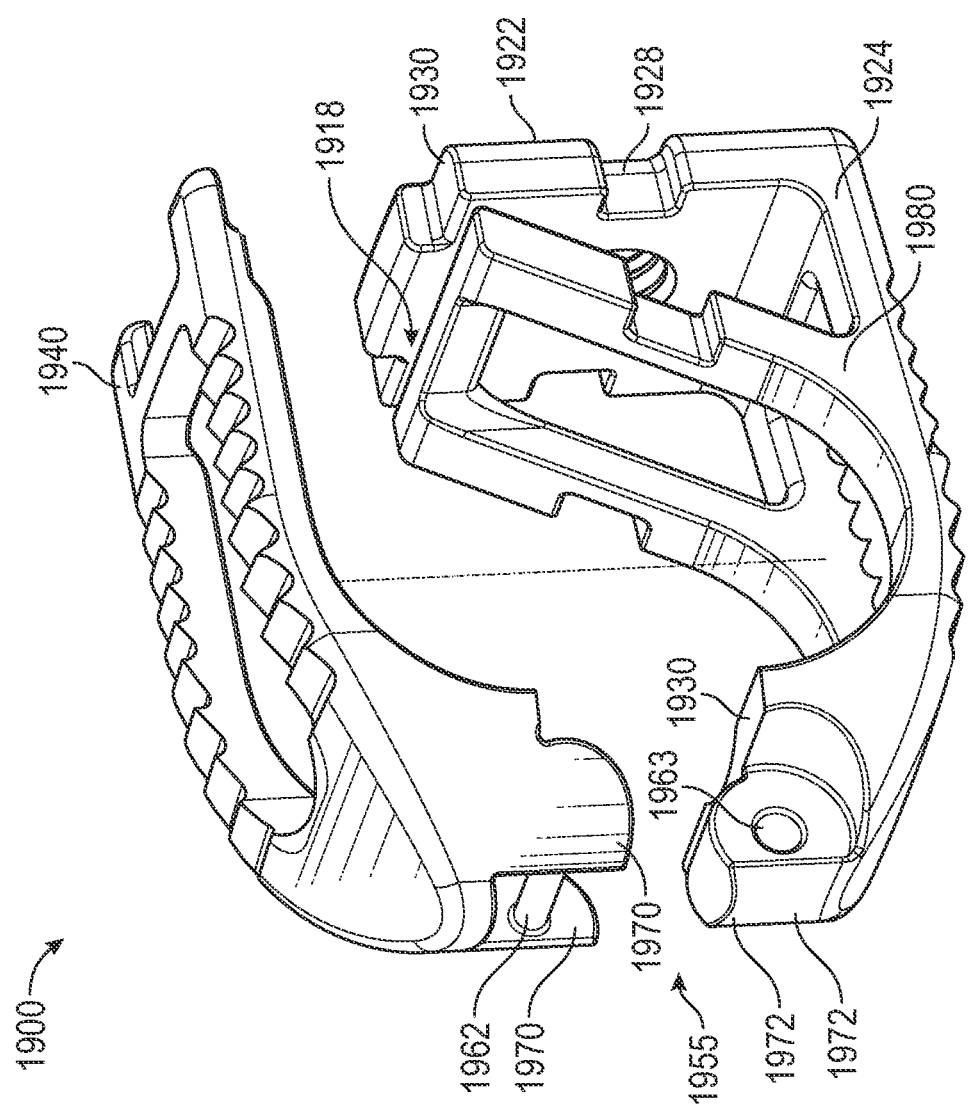

FIG. 142 is an exploded perspective view of the spinal implant device of FIG. 135.

Figure 143:
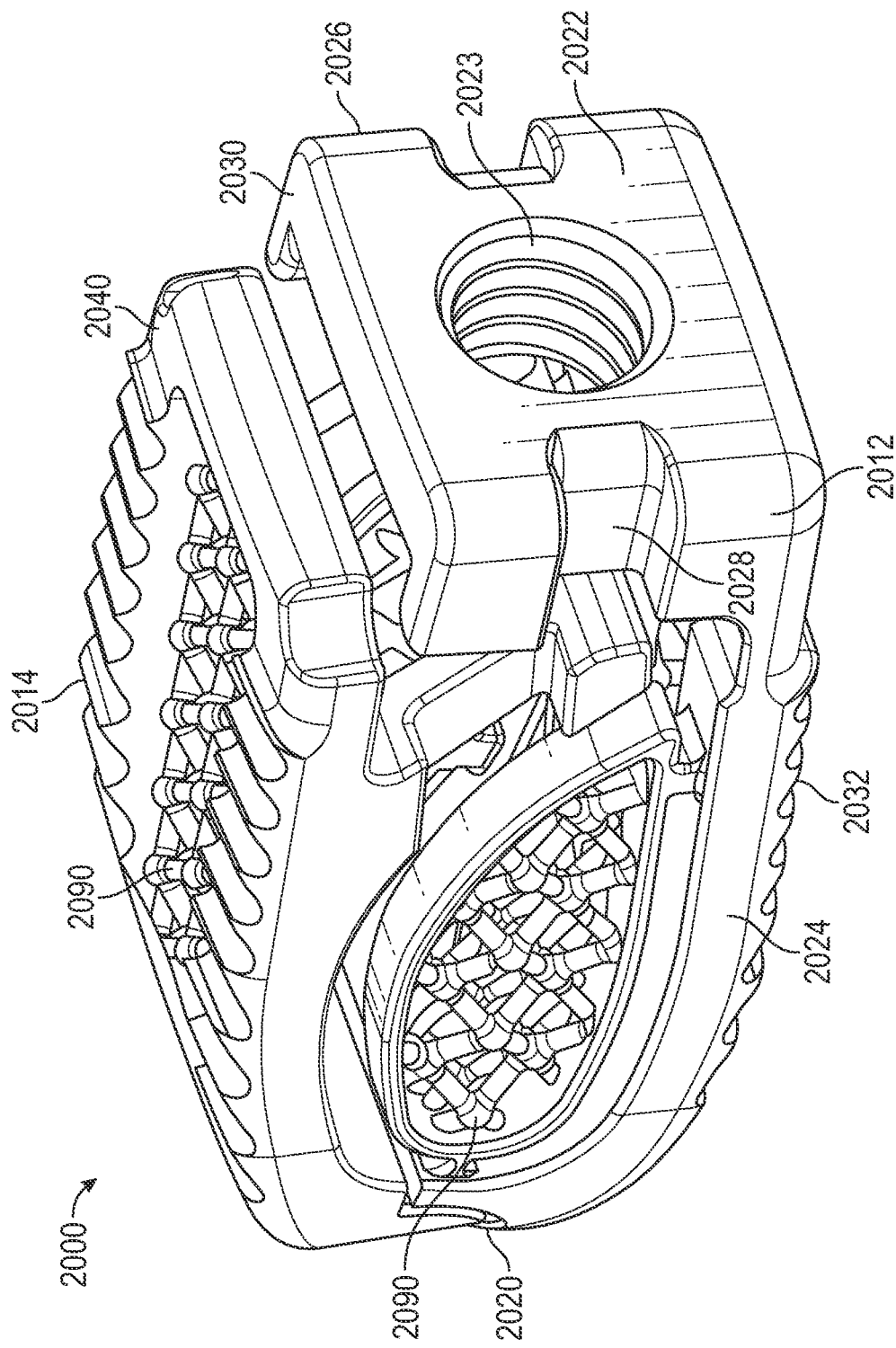

FIG. 143 is a perspective view of an embodiment of a spinal implant device with a movable lid shown in a closed position.

Figure 144:
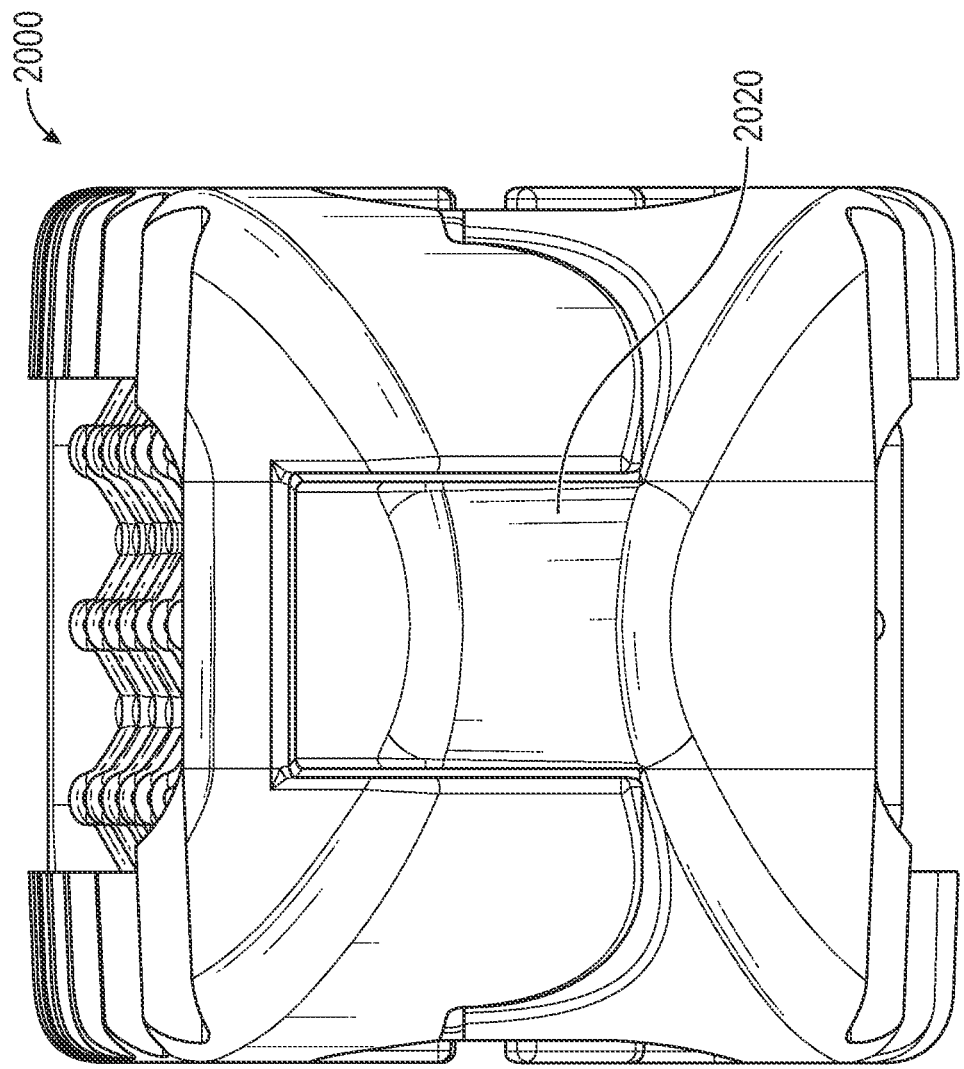

FIG. 144 is a distal view of the spinal implant device of FIG. 143.

Figure 145:
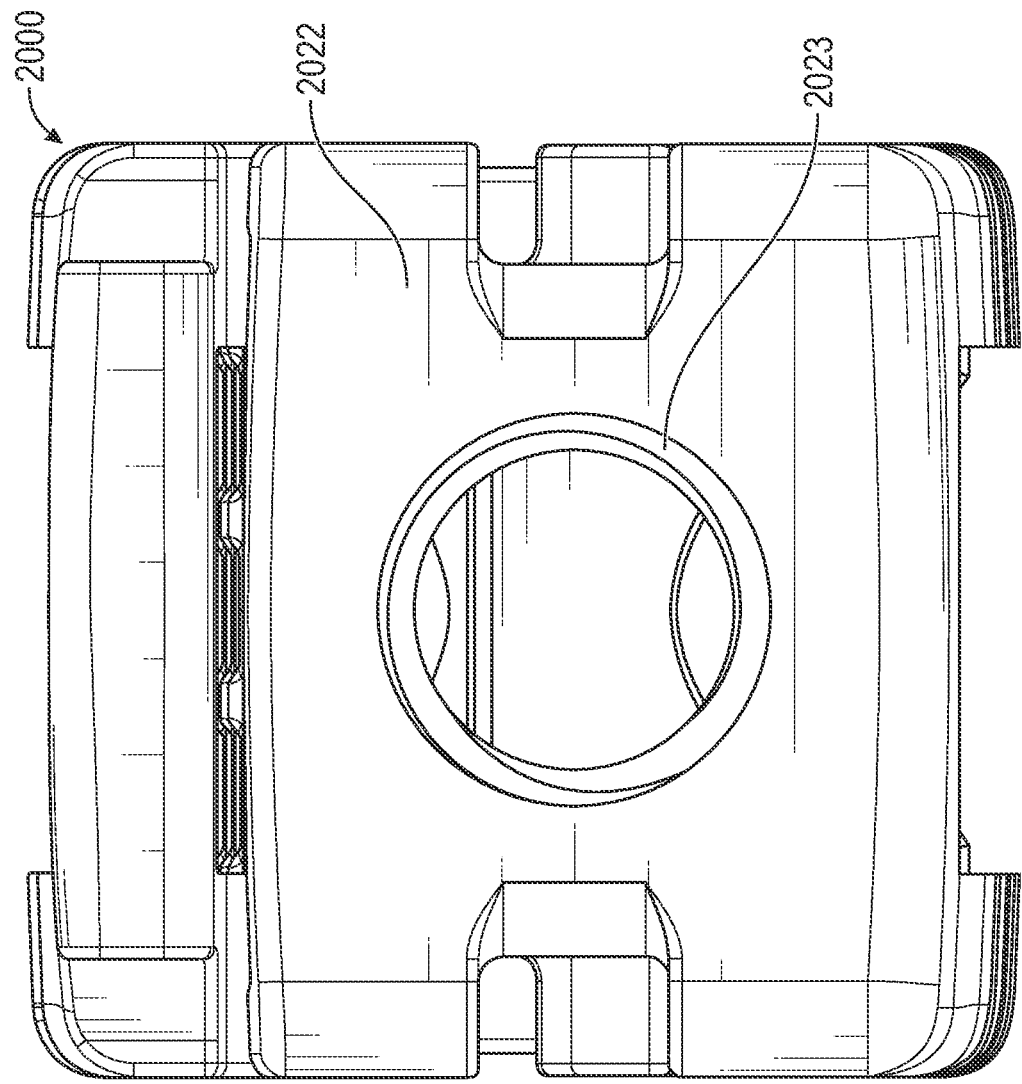

FIG. 145 is a proximal view of the spinal implant device of FIG. 143.

Figure 146:
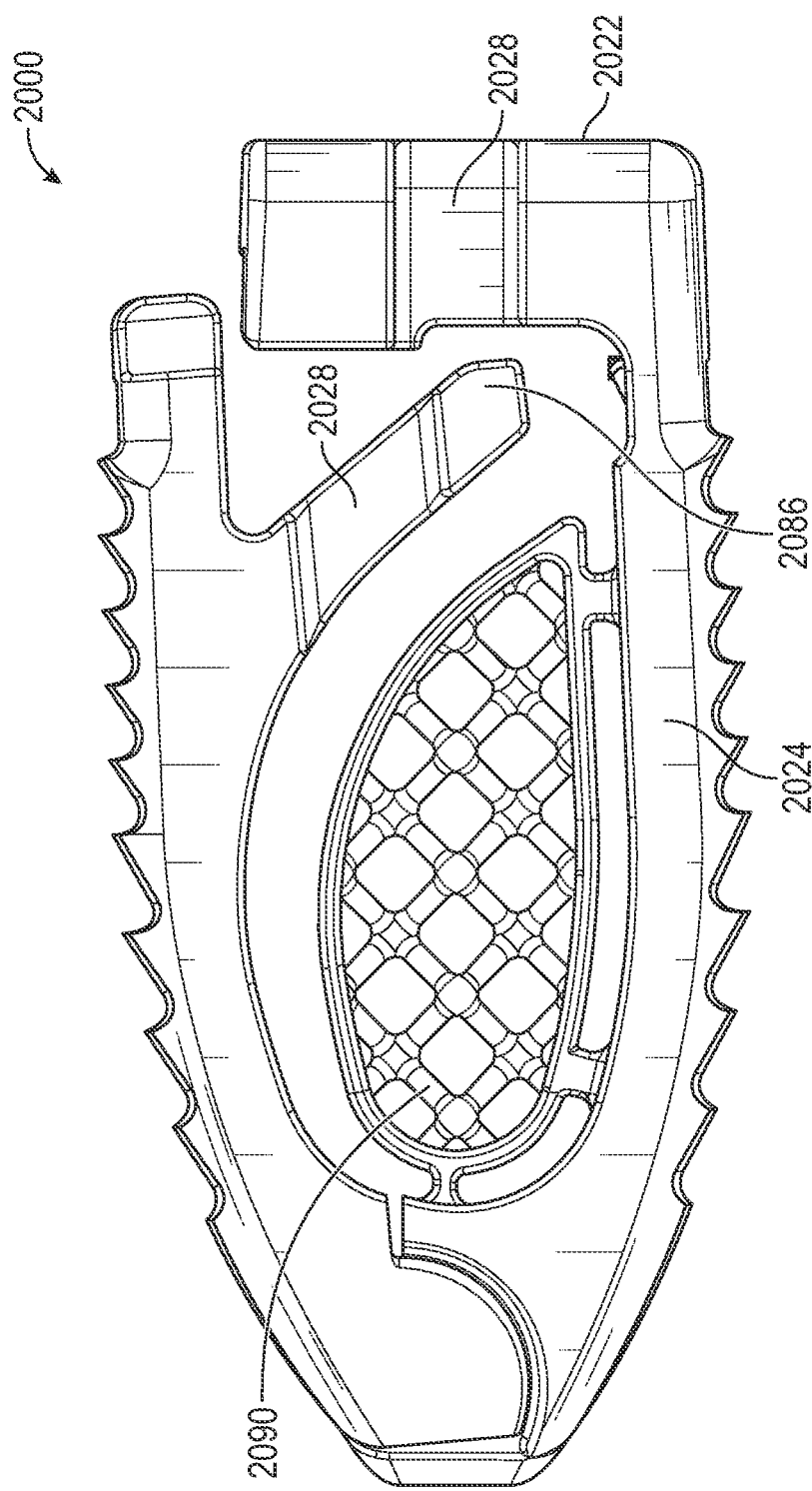

FIG. 146 is a side view of the spinal implant device of FIG. 143.

Figure 147:
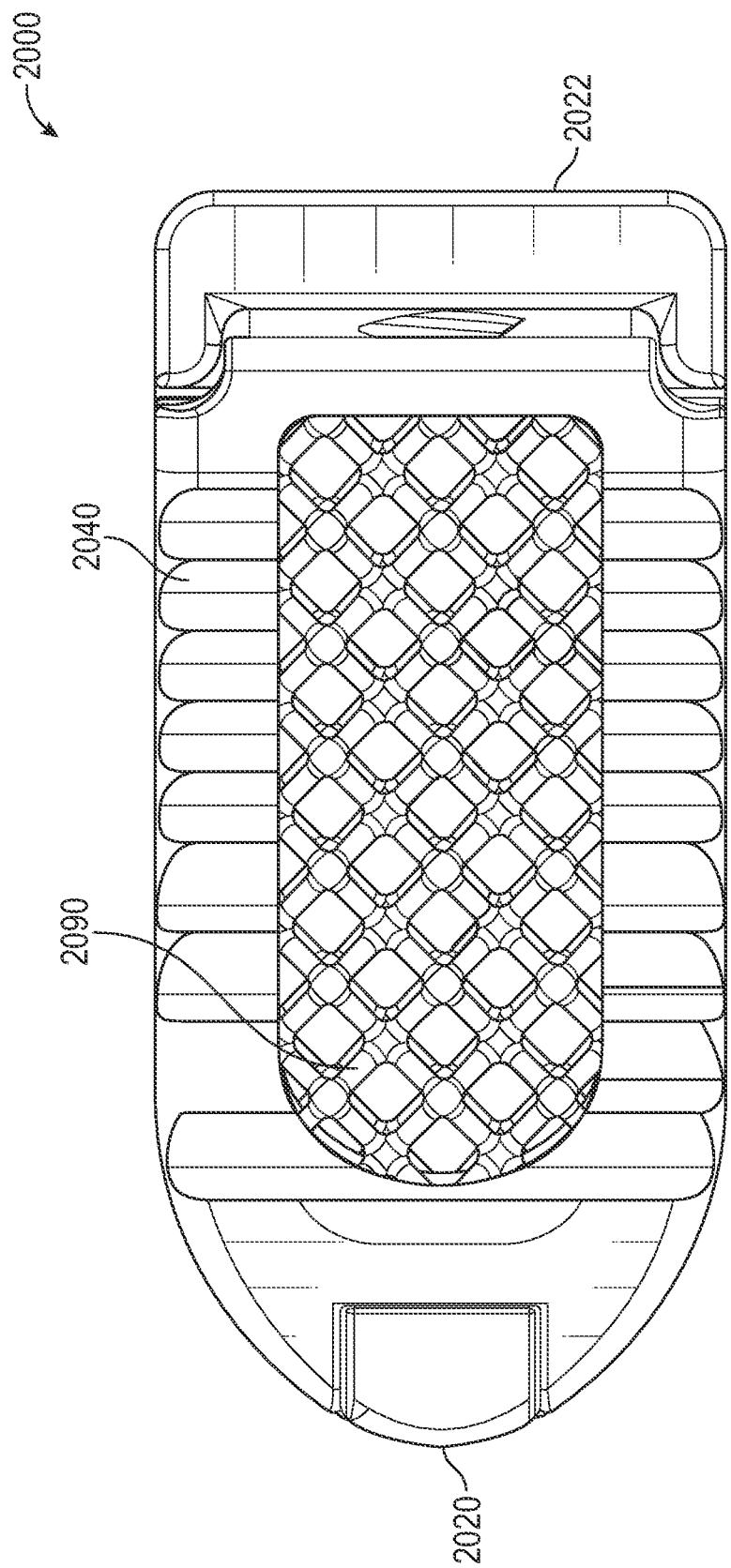

FIG. 147 is a top view of the spinal implant device of FIG. 143.

Figure 148:
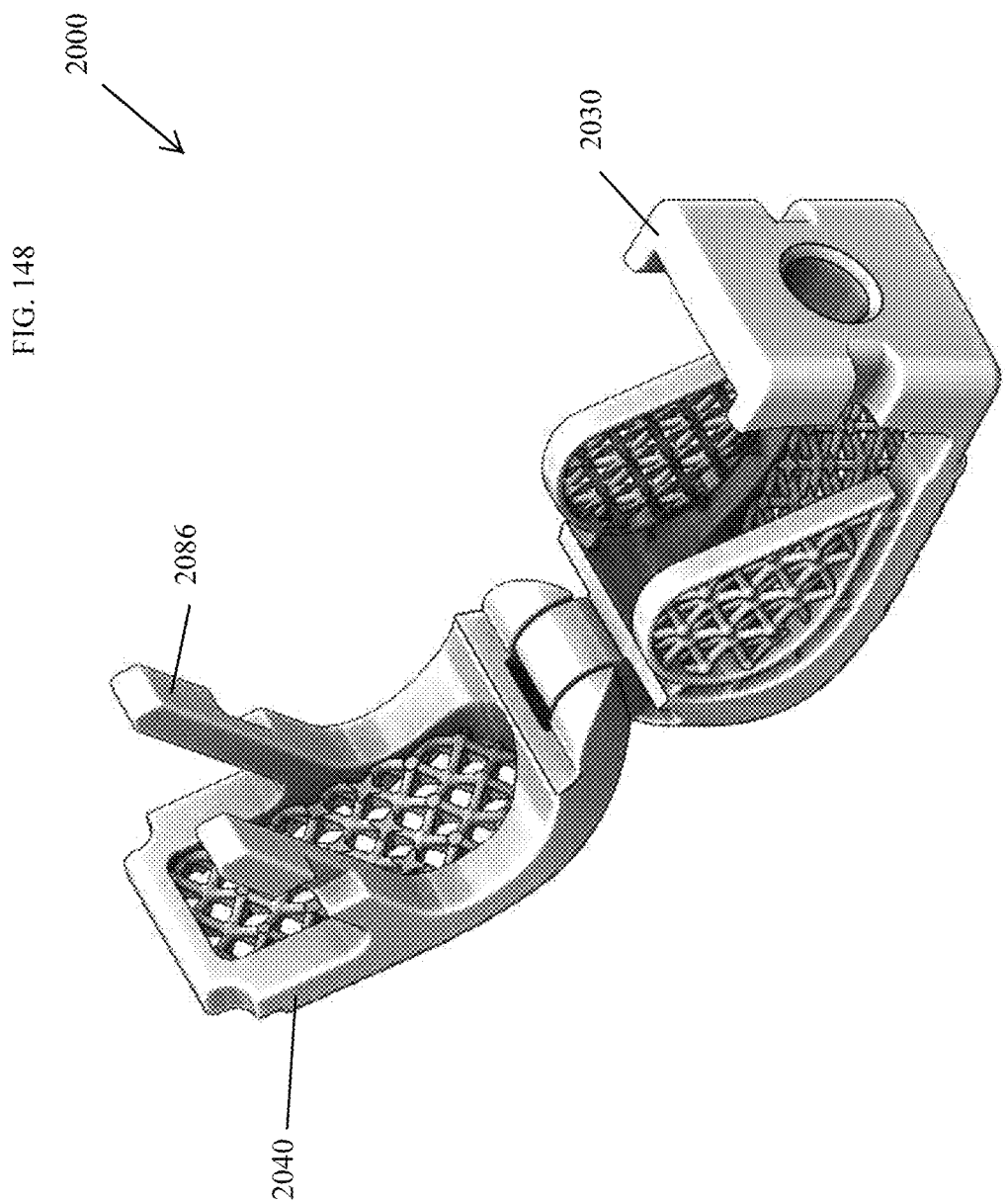

FIG. 148 is a top perspective view of the spinal implant device of FIG. 143 with the movable lid shown in an opened position.

Figure 149:
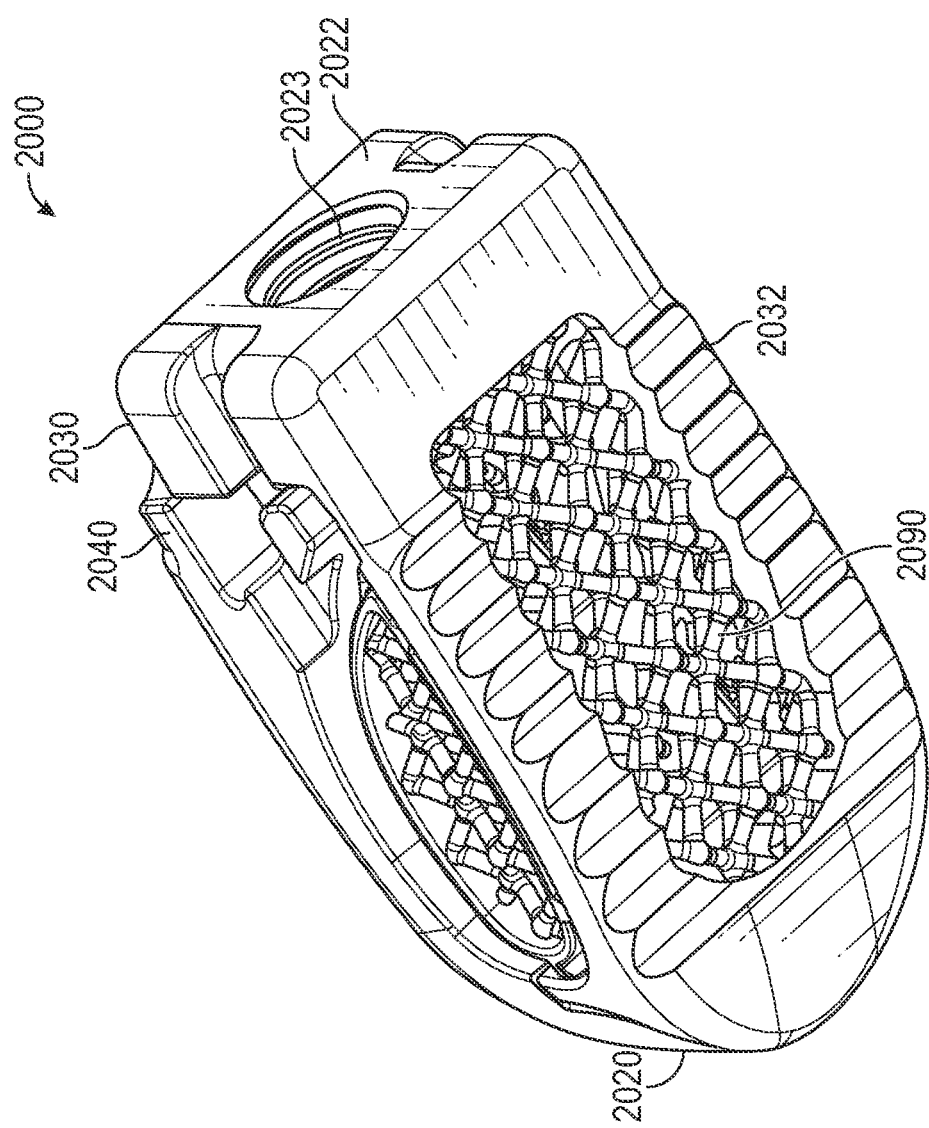

FIG. 149 is a bottom perspective view of the spinal implant device of FIG. 143.

Figure 150:
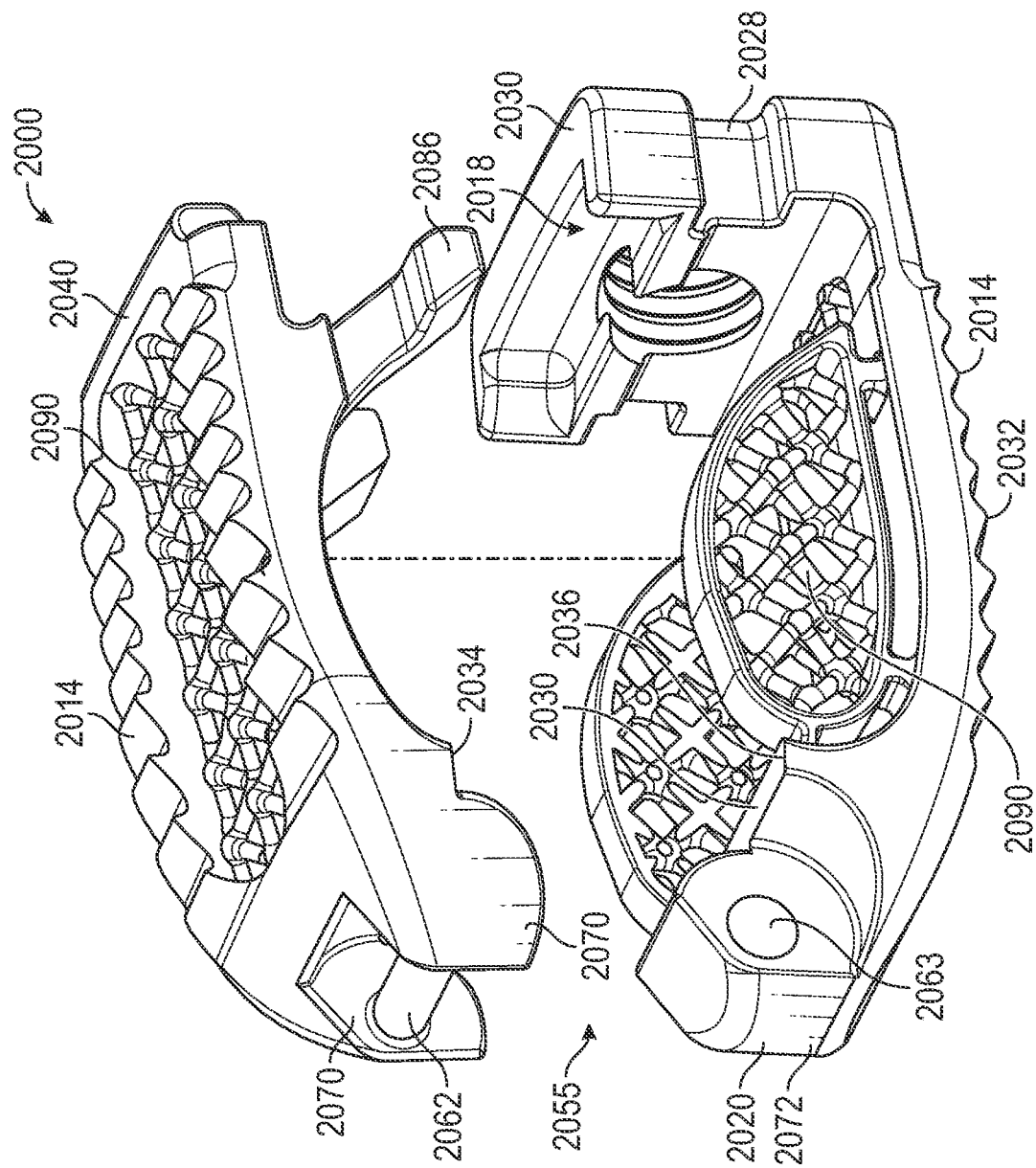

FIG. 150 is an exploded perspective view of the spinal implant device of FIG. 143.

Figure 151:
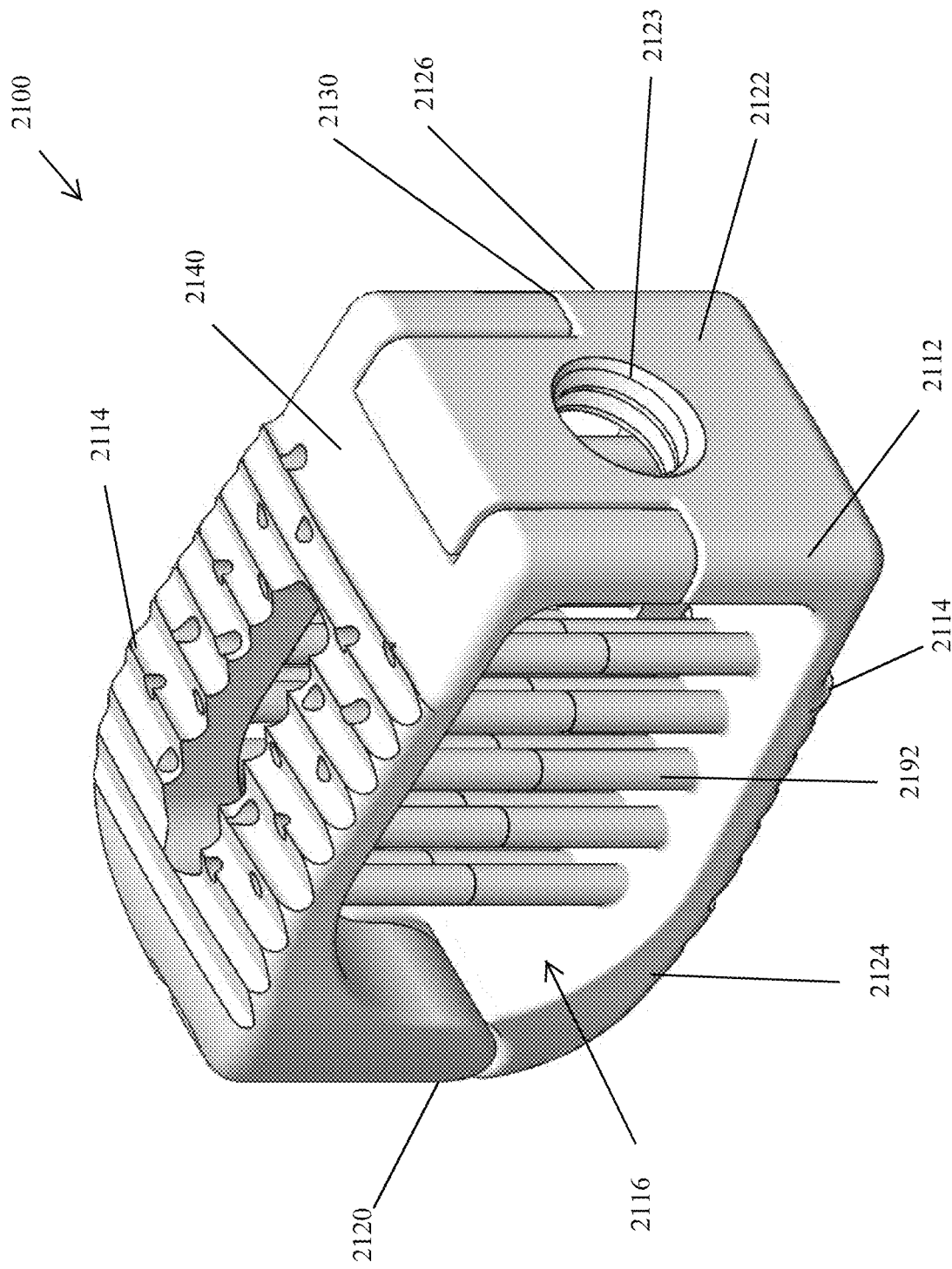

FIG. 151 is a perspective view of an embodiment of a spinal implant device with a movable lid shown in a closed position.

Figure 152:
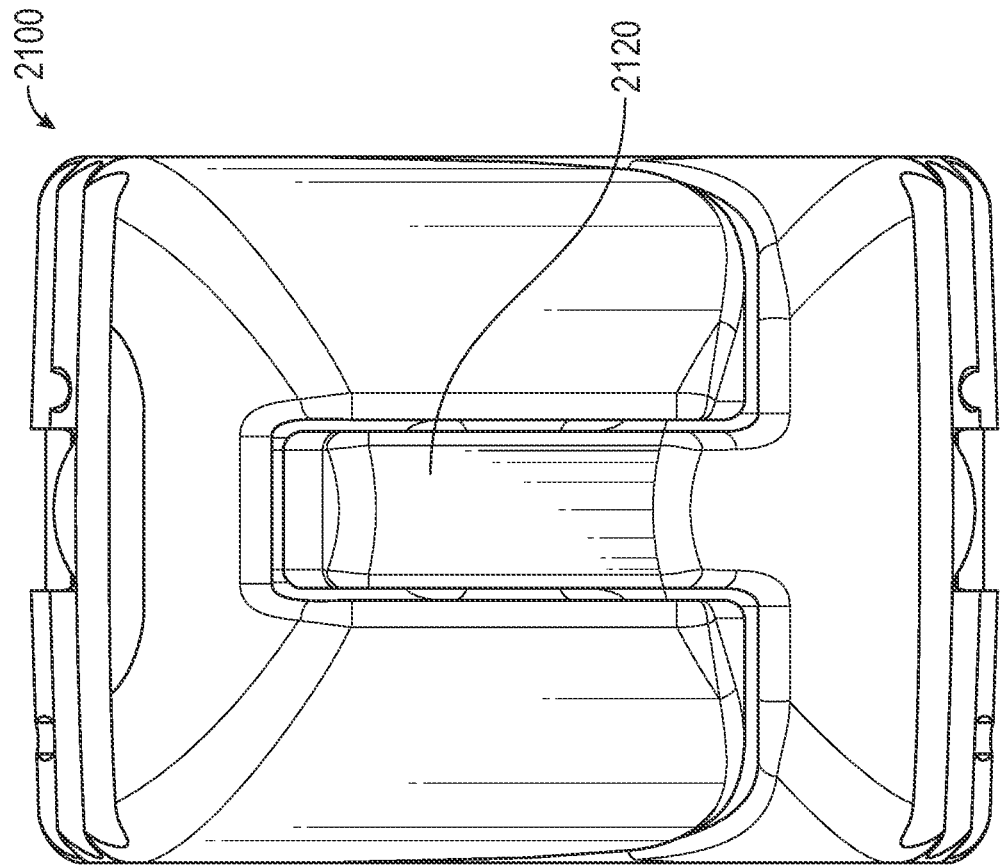

FIG. 152 is a distal view of the spinal implant device of FIG. 151.

Figure 153:
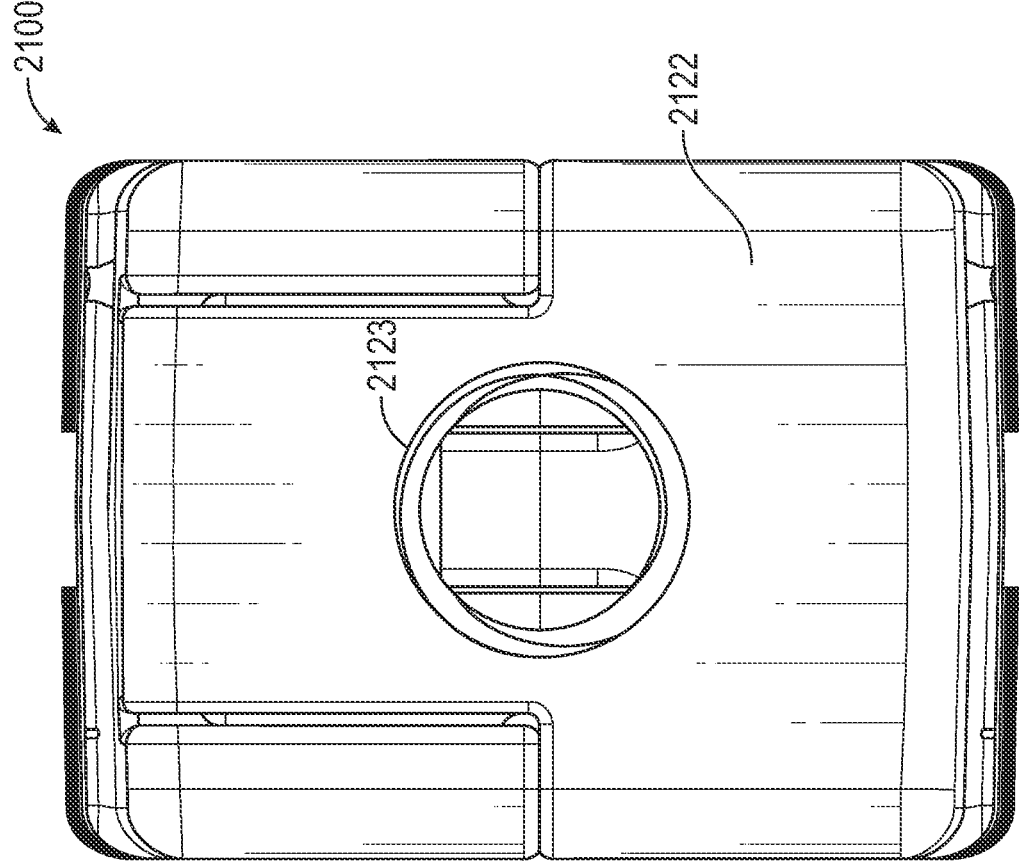

FIG. 153 is a proximal view of the spinal implant device of FIG. 151.

Figure 154:
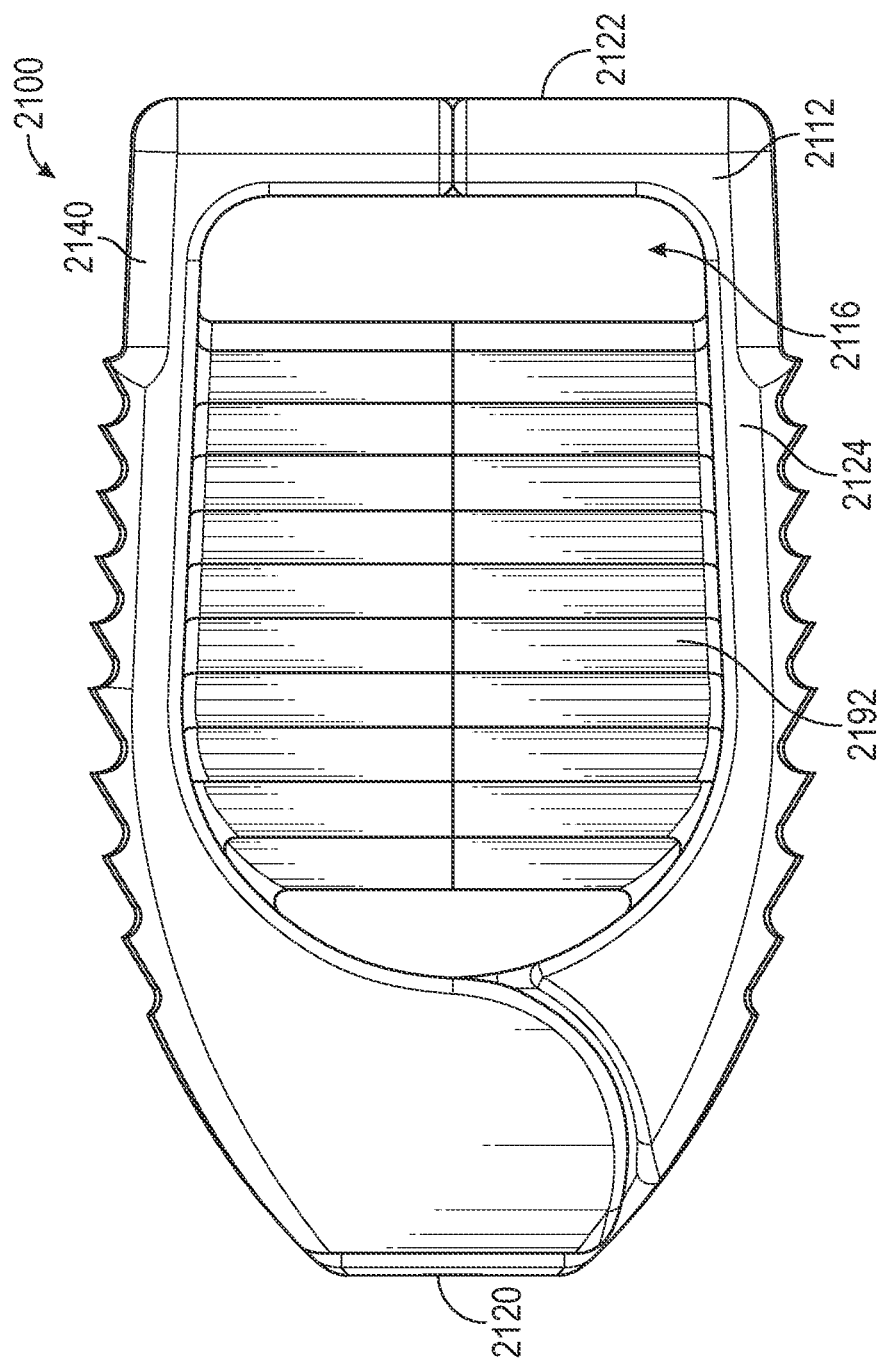

FIG. 154 is a side view of the spinal implant device of FIG. 151.

Figure 155:
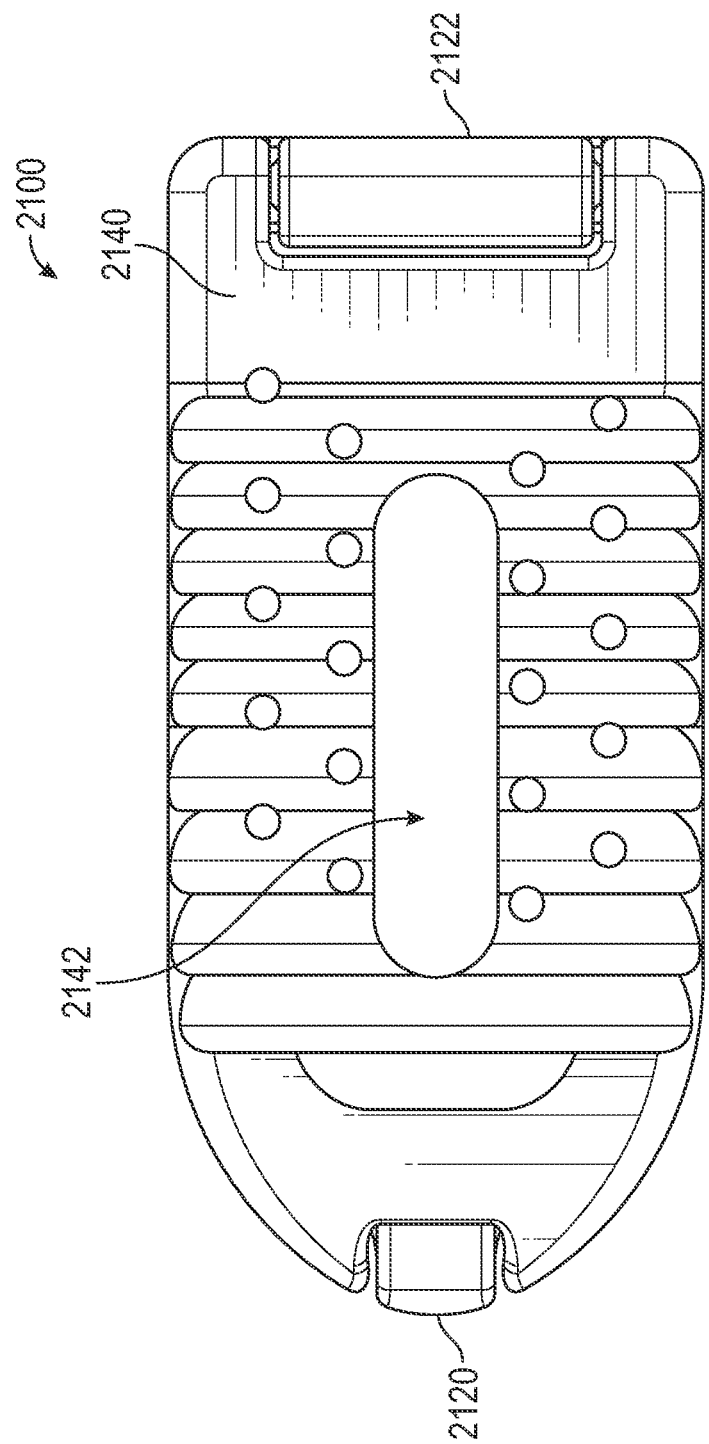

FIG. 155 is a top view of the spinal implant device of FIG. 151.

Figure 156:
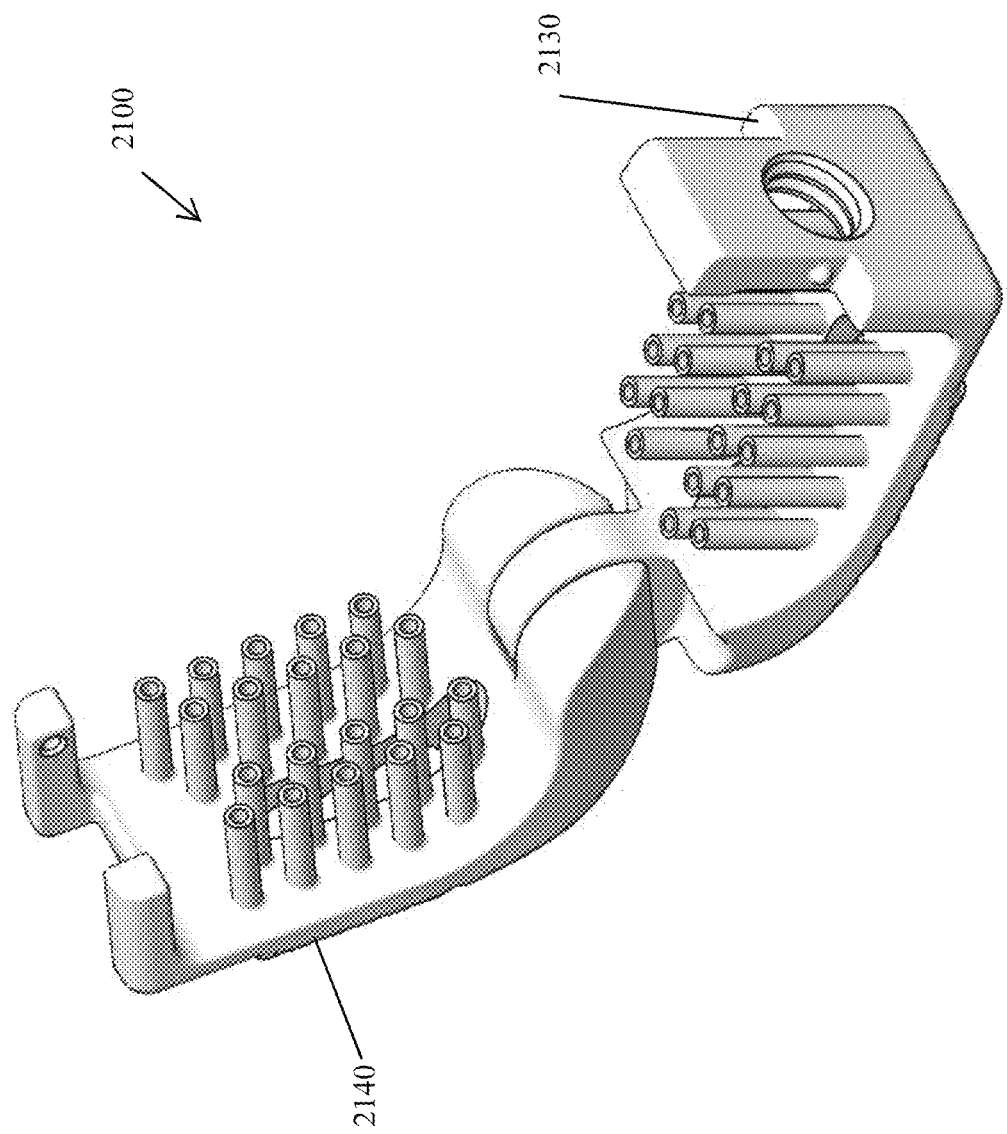

FIG. 156 is a top perspective view of the spinal implant device of FIG. 151 with the movable lid shown in an opened position.

Figure 157:
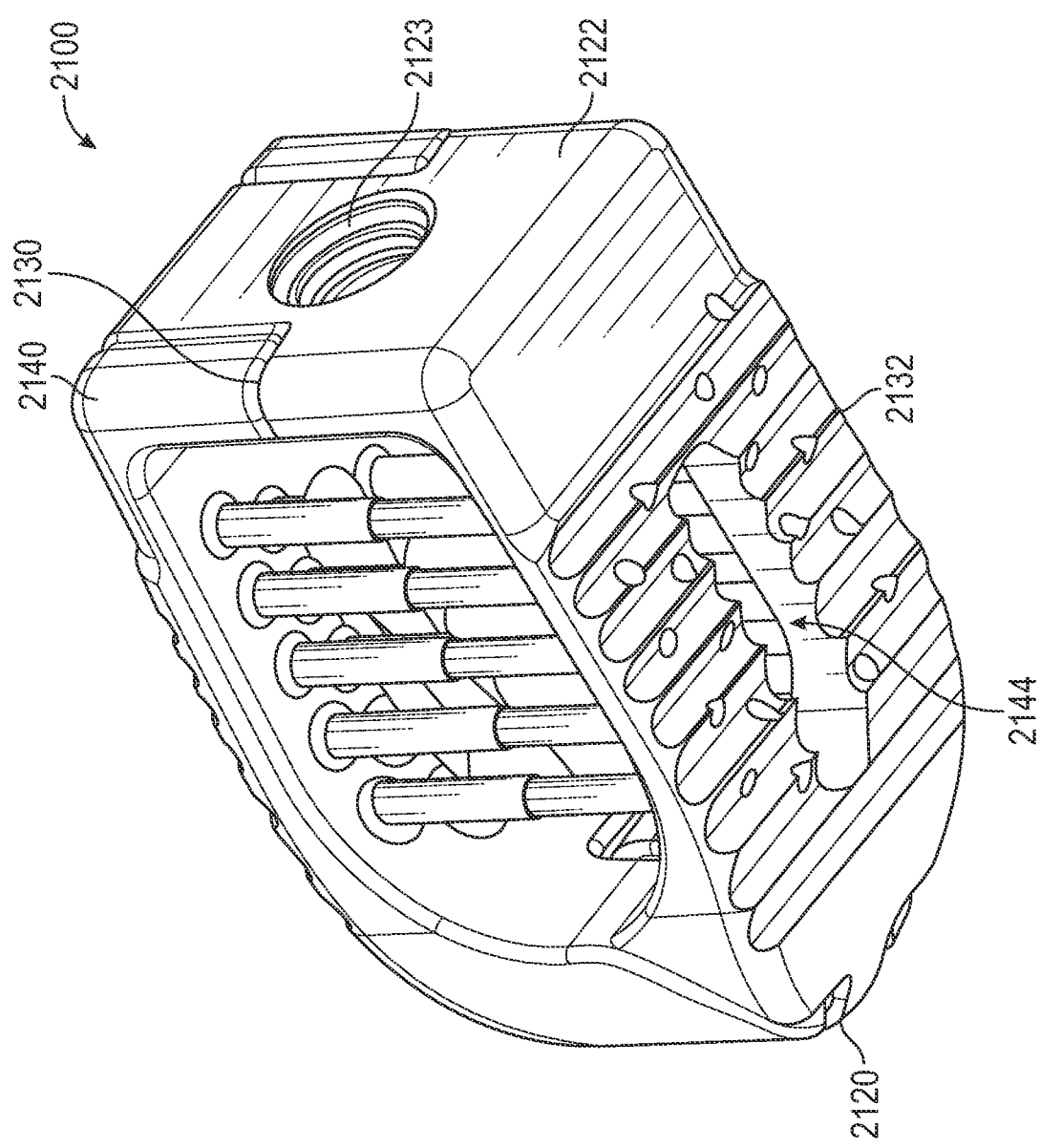

FIG. 157 is a bottom perspective view of the spinal implant device of FIG. 151

Figure 158:
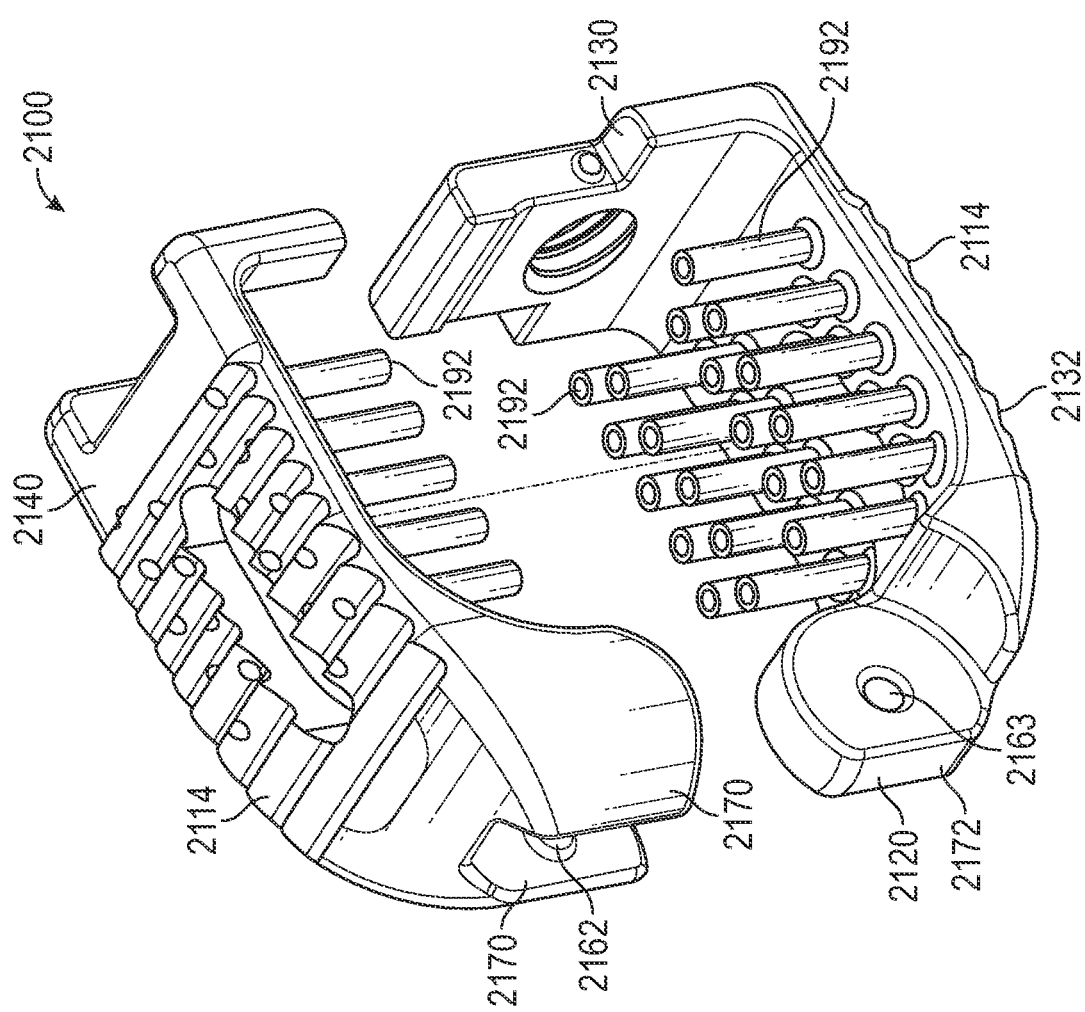

FIG. 158 is an exploded perspective view of the spinal implant device of FIG. 151.

Figure 159:
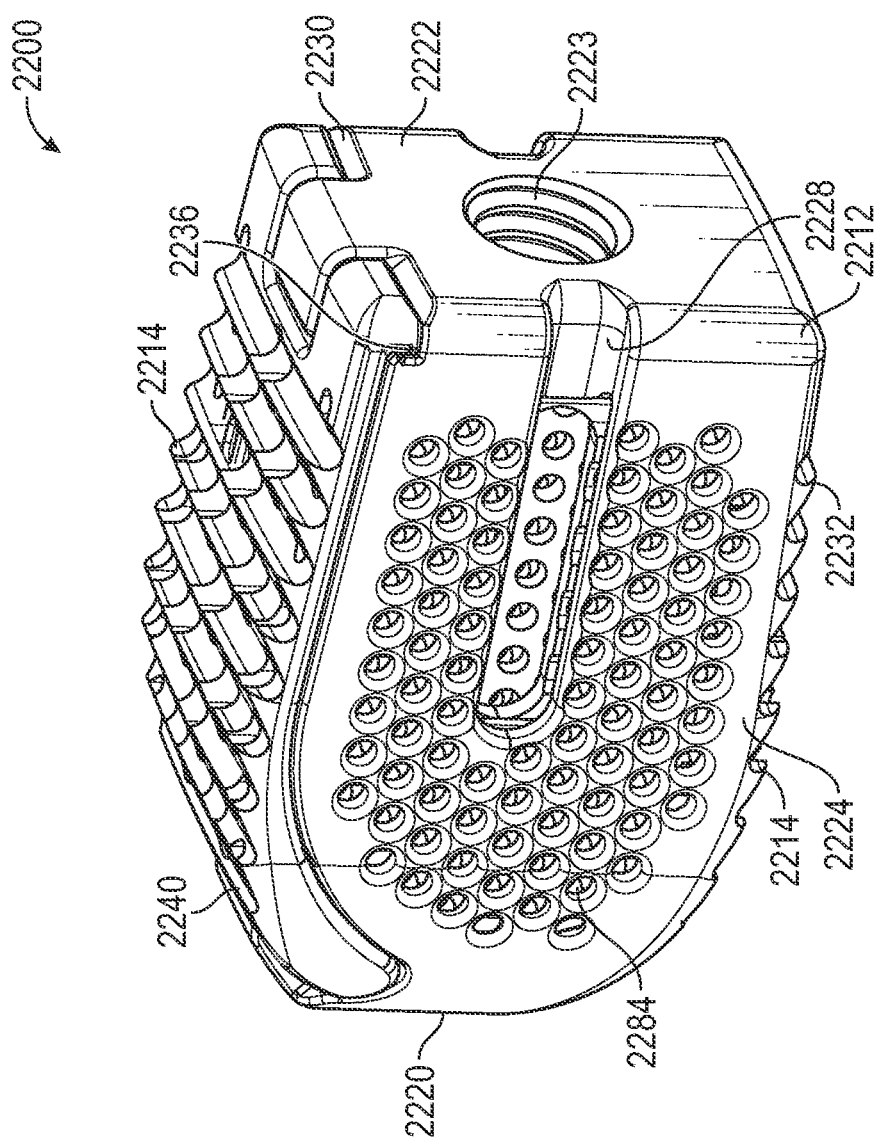

FIG. 159 is a perspective view of an embodiment of a spinal implant device with a movable lid shown in a closed position.

Figure 160:
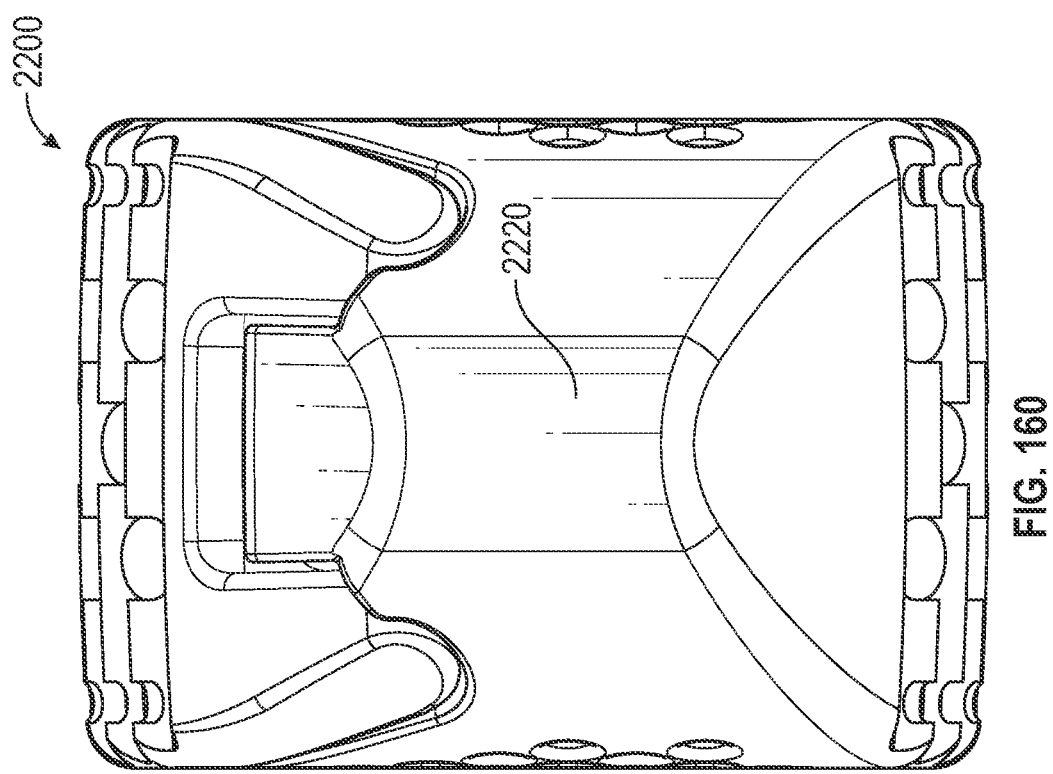

FIG. 160 is a distal view of the spinal implant device of FIG. 159.

Figure 161:
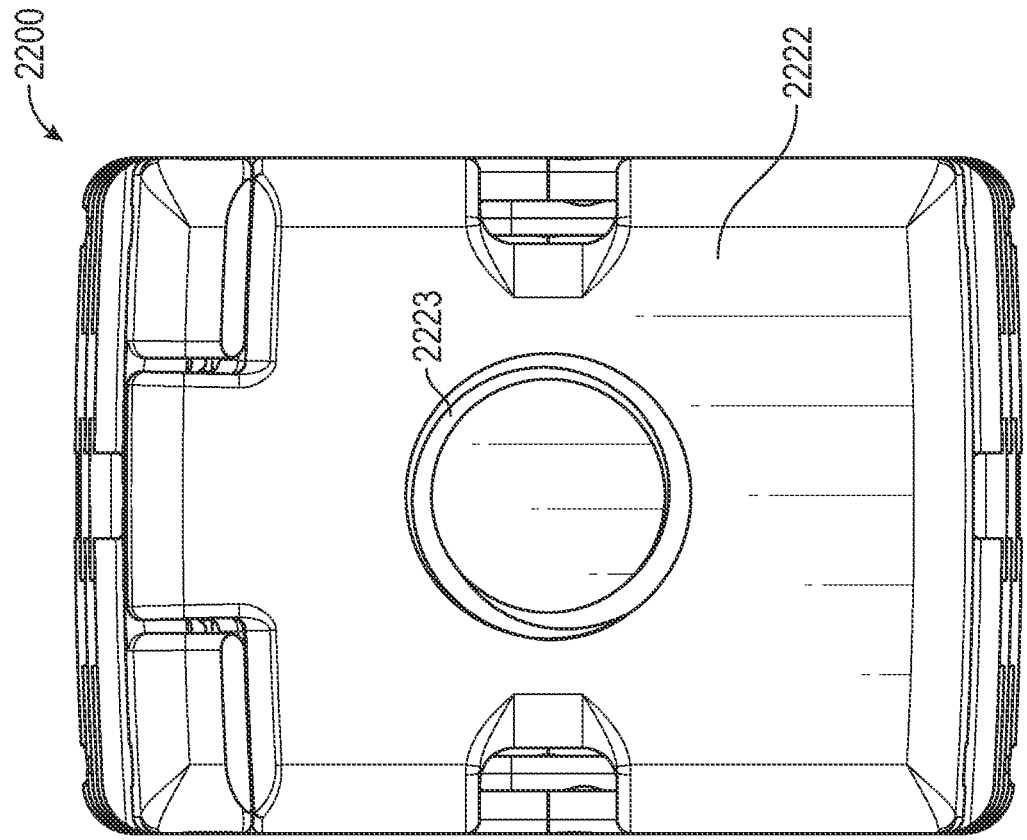

FIG. 161 is a proximal view of the spinal implant device of FIG. 159.

Figure 162:
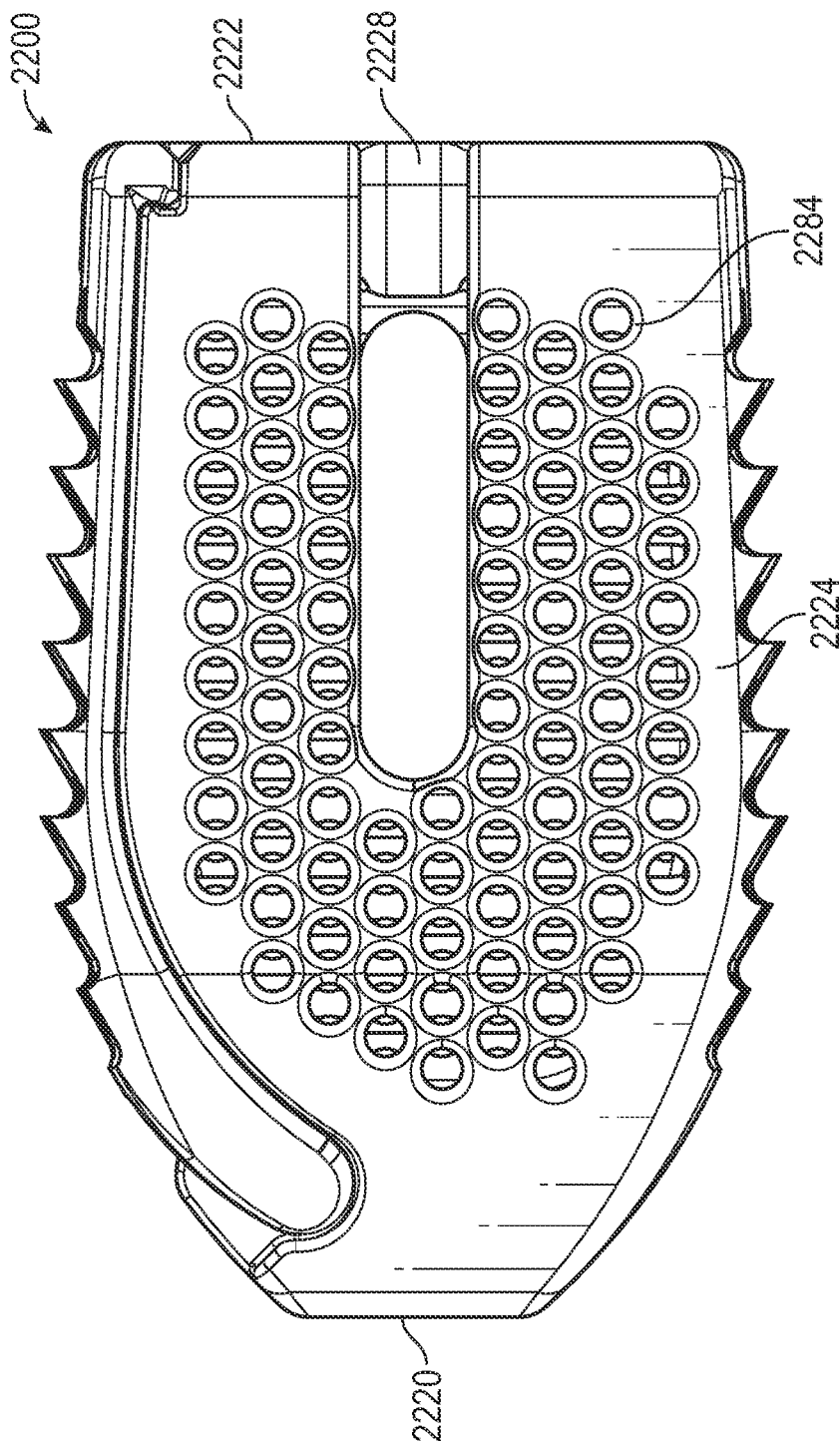

FIG. 162 is a side view of the spinal implant device of FIG. 159.

Figure 163:
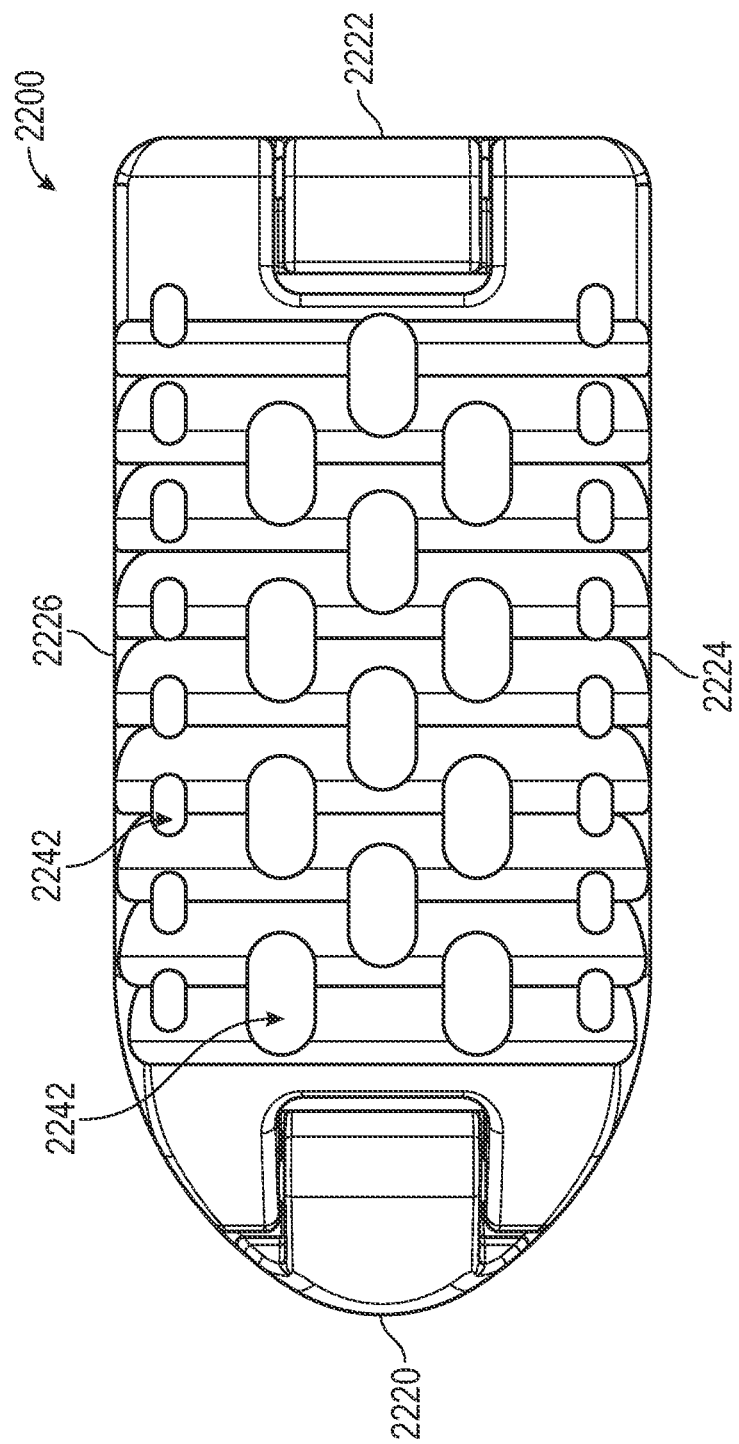

FIG. 163 is a top view of the spinal implant device of FIG. 159.

Figure 164:
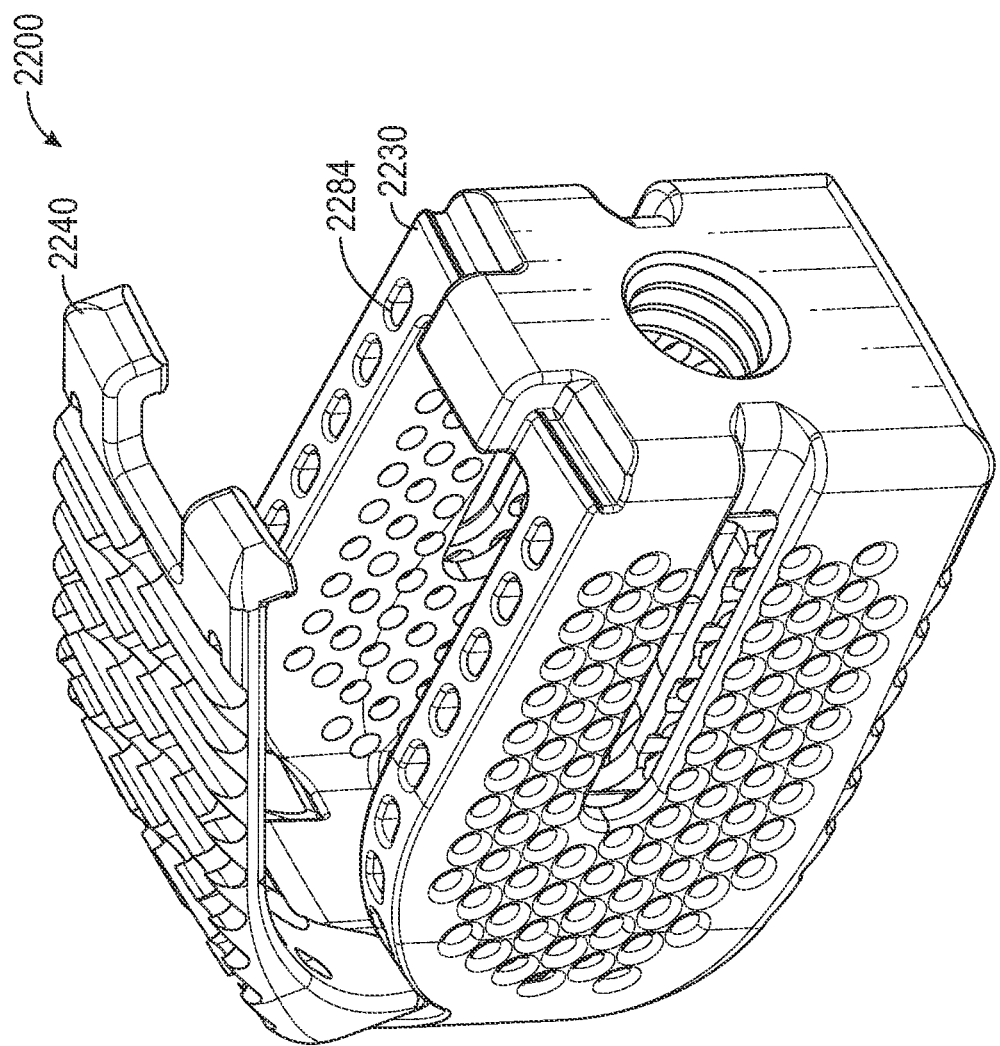

FIG. 164 is a top perspective view of the spinal implant device of FIG. 159 with the movable lid shown in an opened position.

Figure 165:
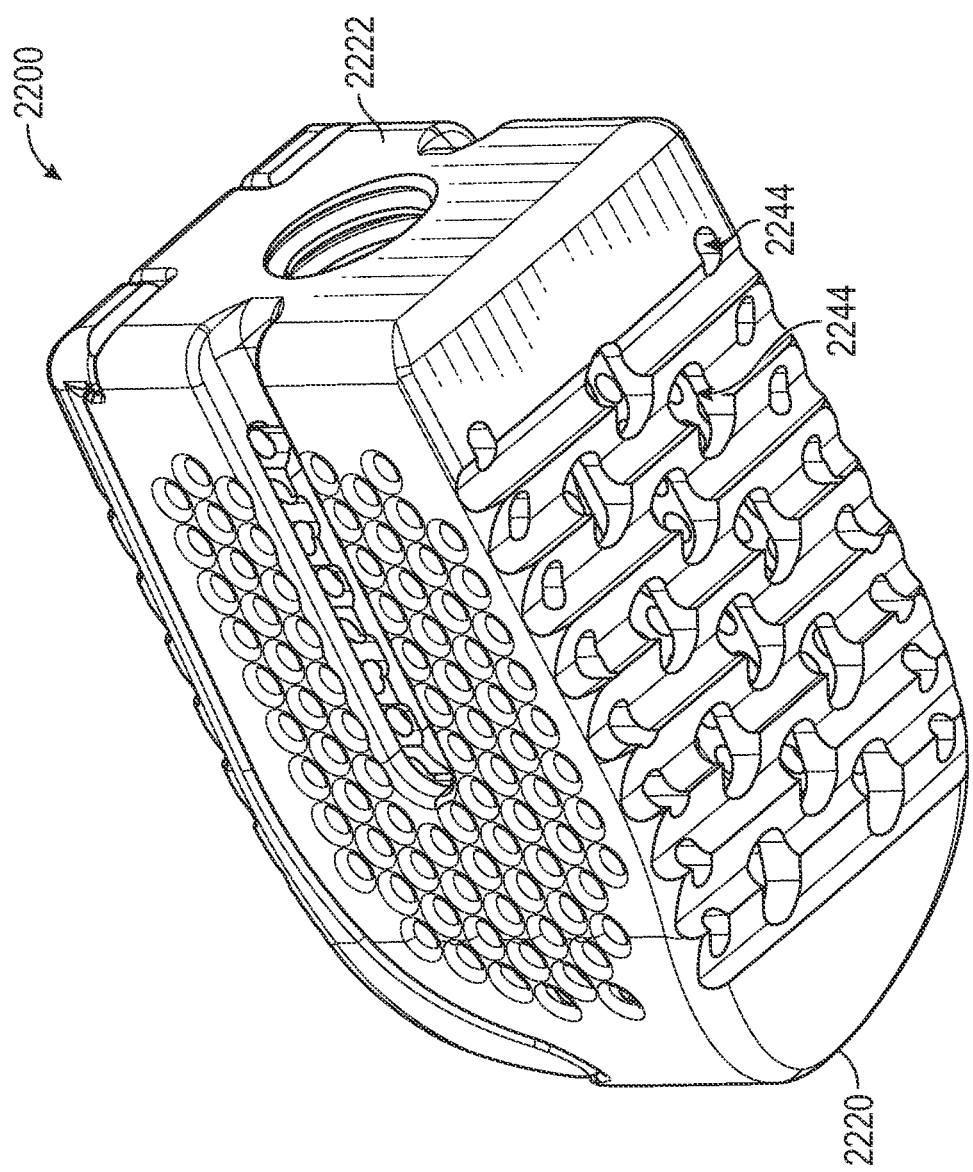

FIG. 165 is a bottom perspective view of the spinal implant device of FIG. 159.

Figure 166:
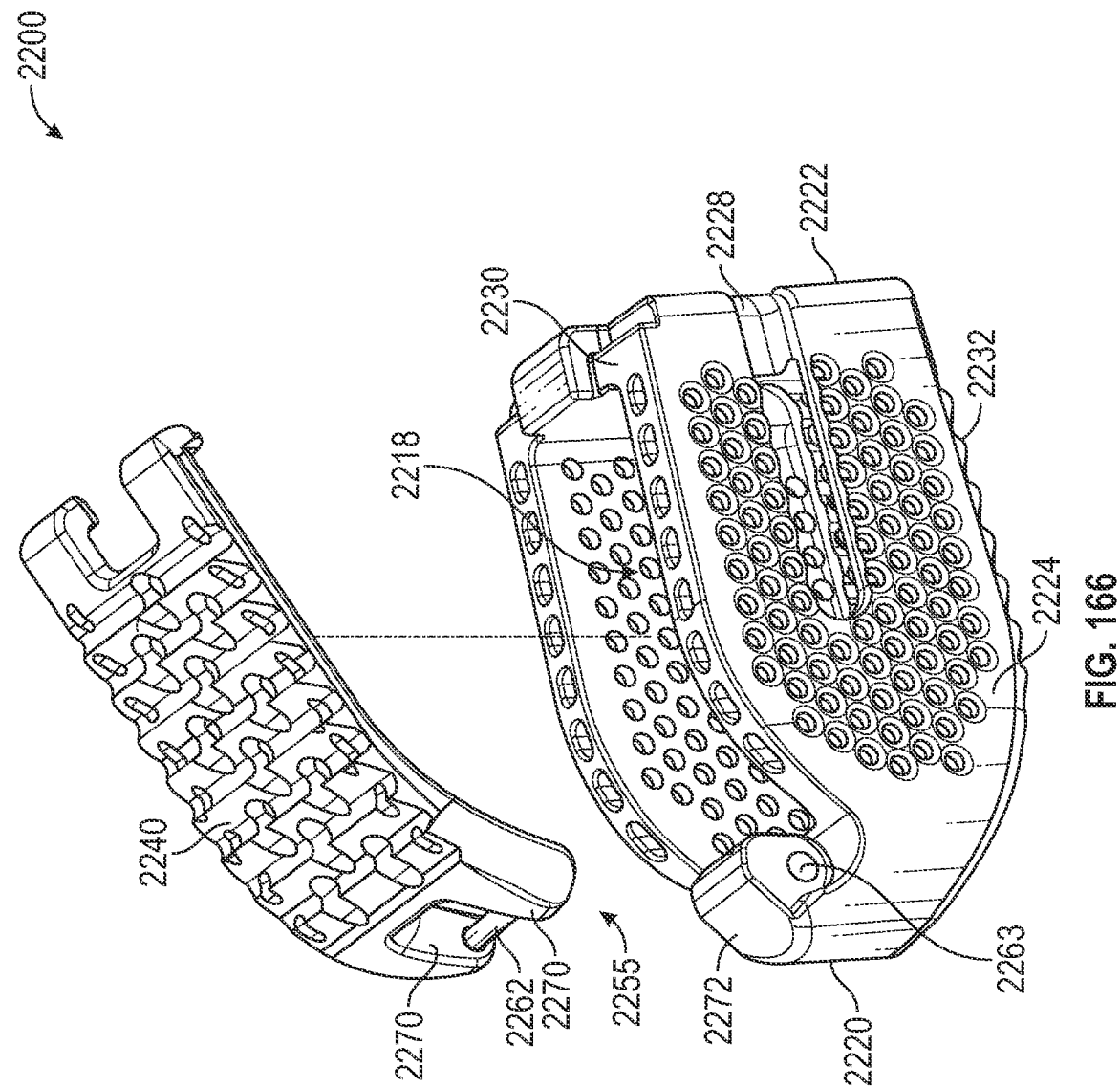

FIG. 166 is an exploded perspective view of the spinal implant device of FIG. 159.

Figure 167:
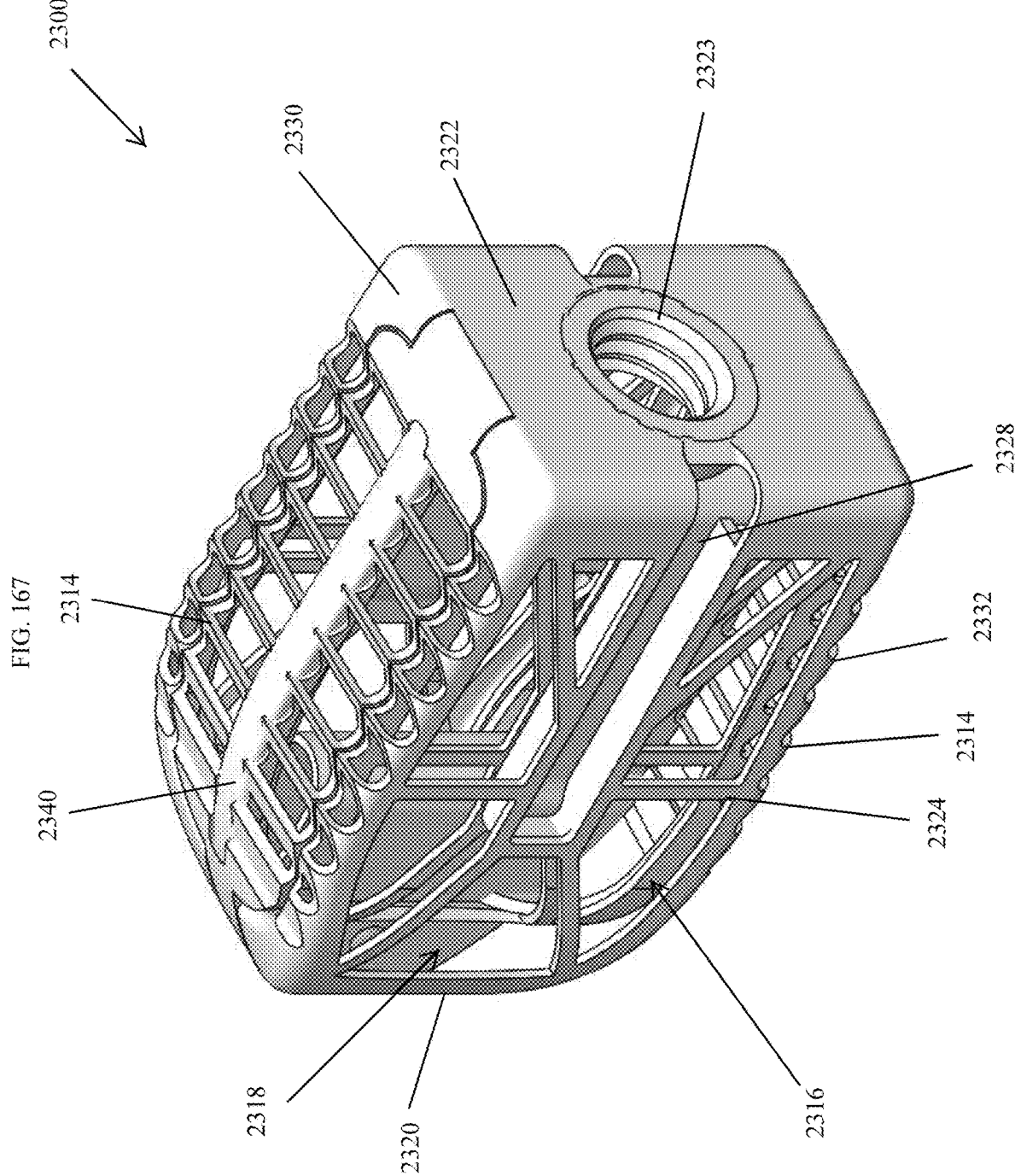

FIG. 167 is a perspective view of an embodiment of a spinal implant device with a movable lid shown in a closed position.

Figure 168:
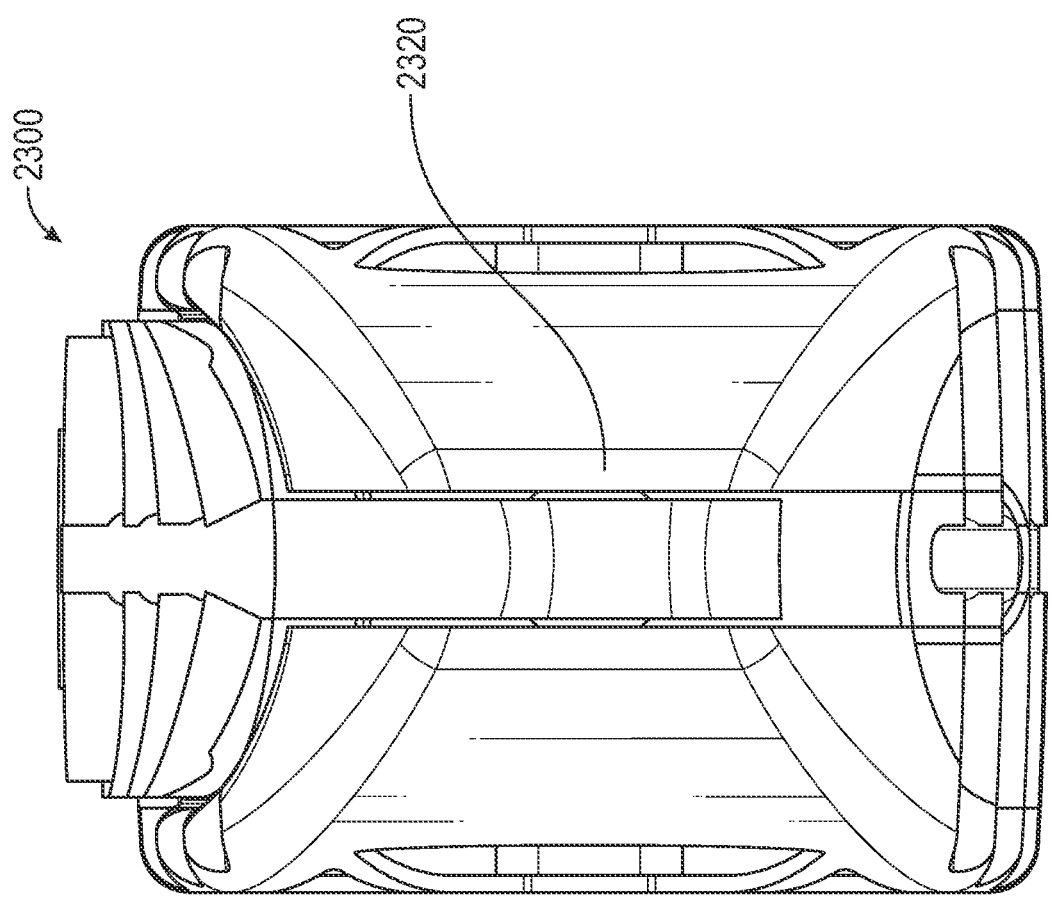

FIG. 168 is a distal view of the spinal implant device of FIG. 167.

Figure 169:
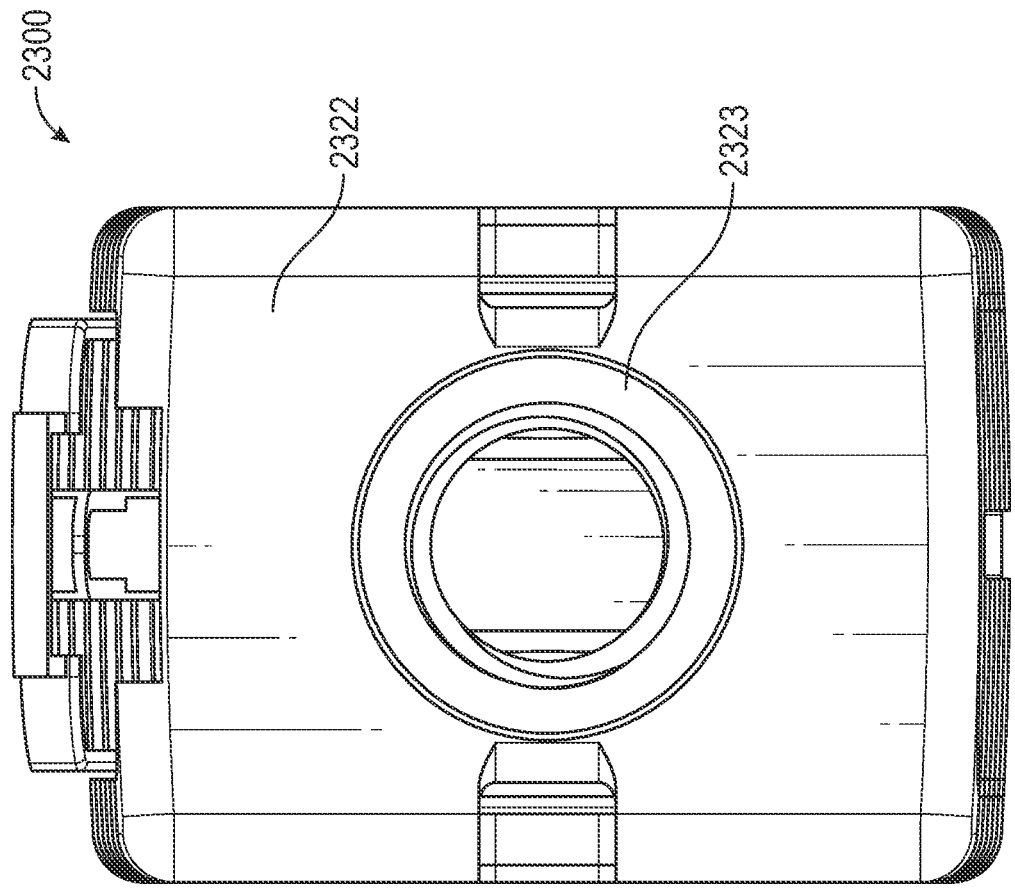

FIG. 169 is a proximal view of the spinal implant device of FIG. 167.

Figure 170:
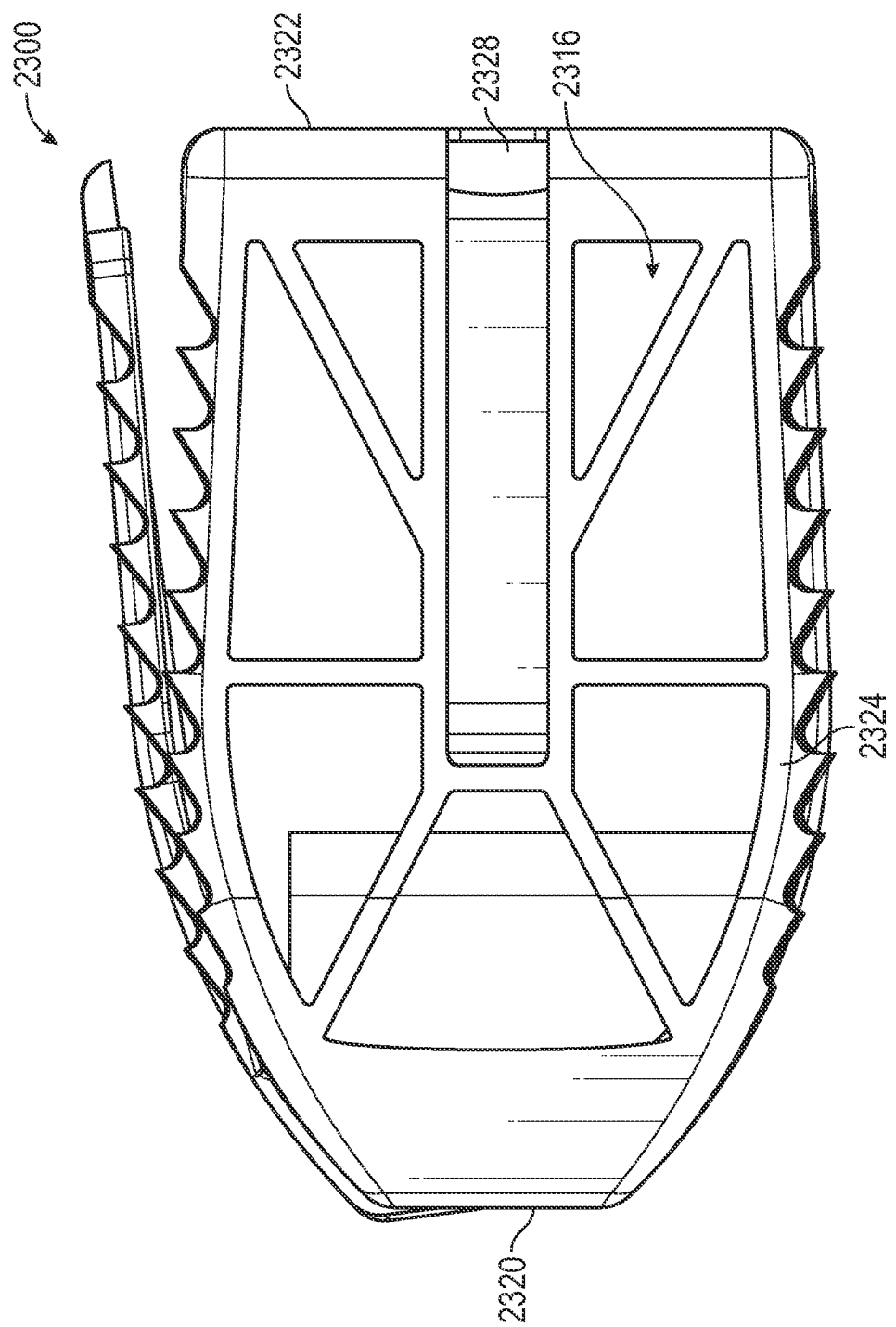

FIG. 170 is a side view of the spinal implant device of FIG. 167.

Figure 171:
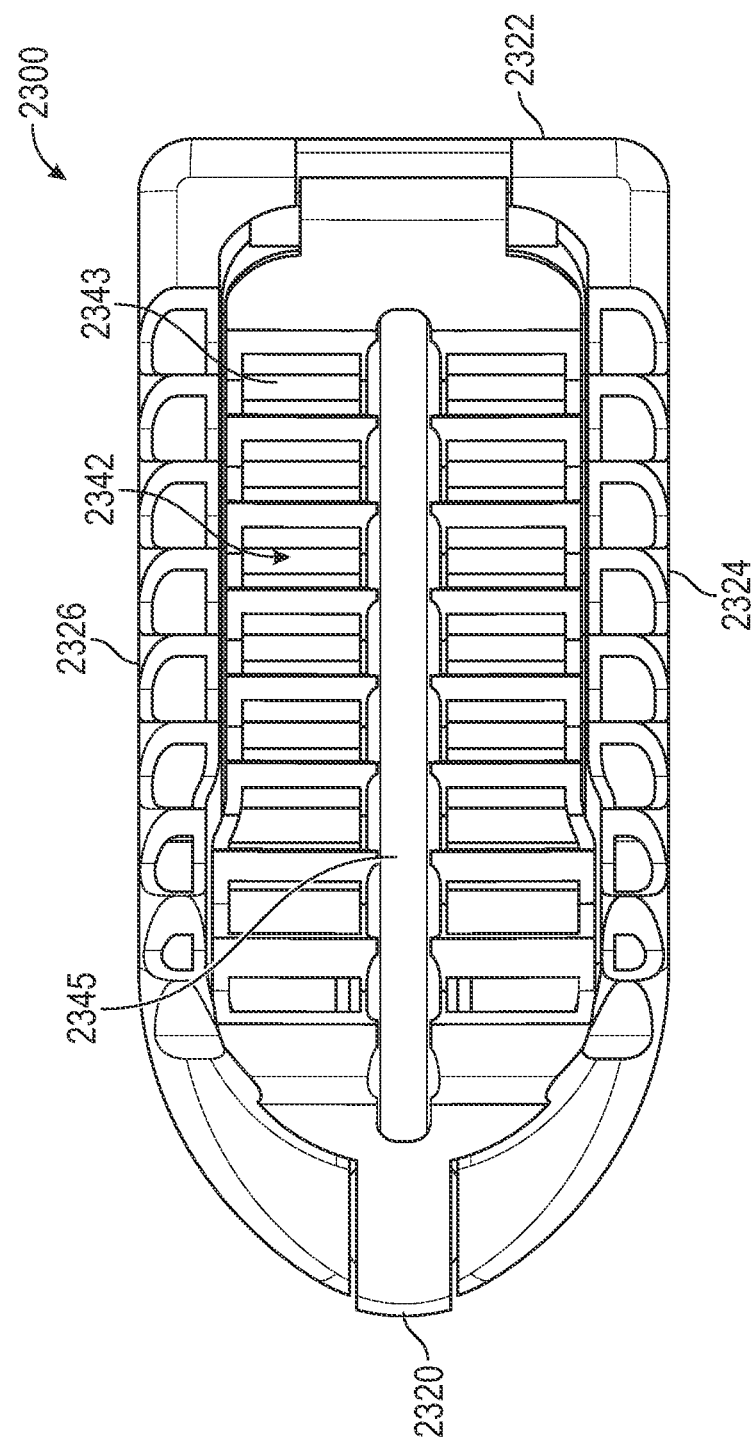

FIG. 171 is a top view of the spinal implant device of FIG. 167.

Figure 172:
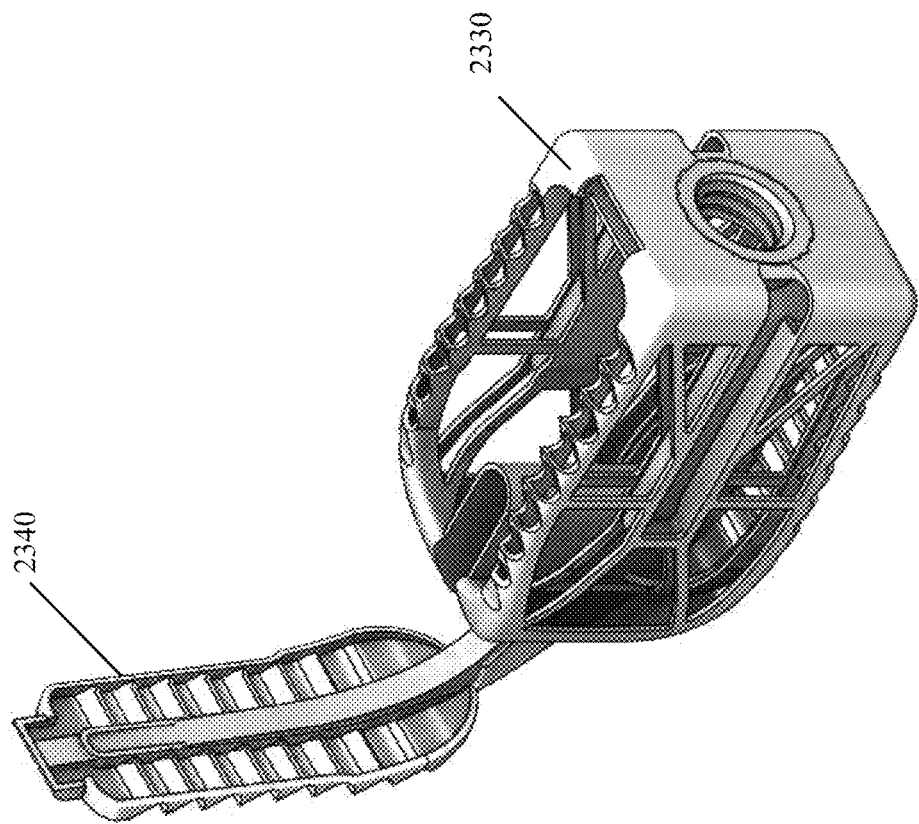

FIG. 172 is a top perspective view of the spinal implant device of FIG. 167 with the movable lid shown in an opened position.

Figure 173:
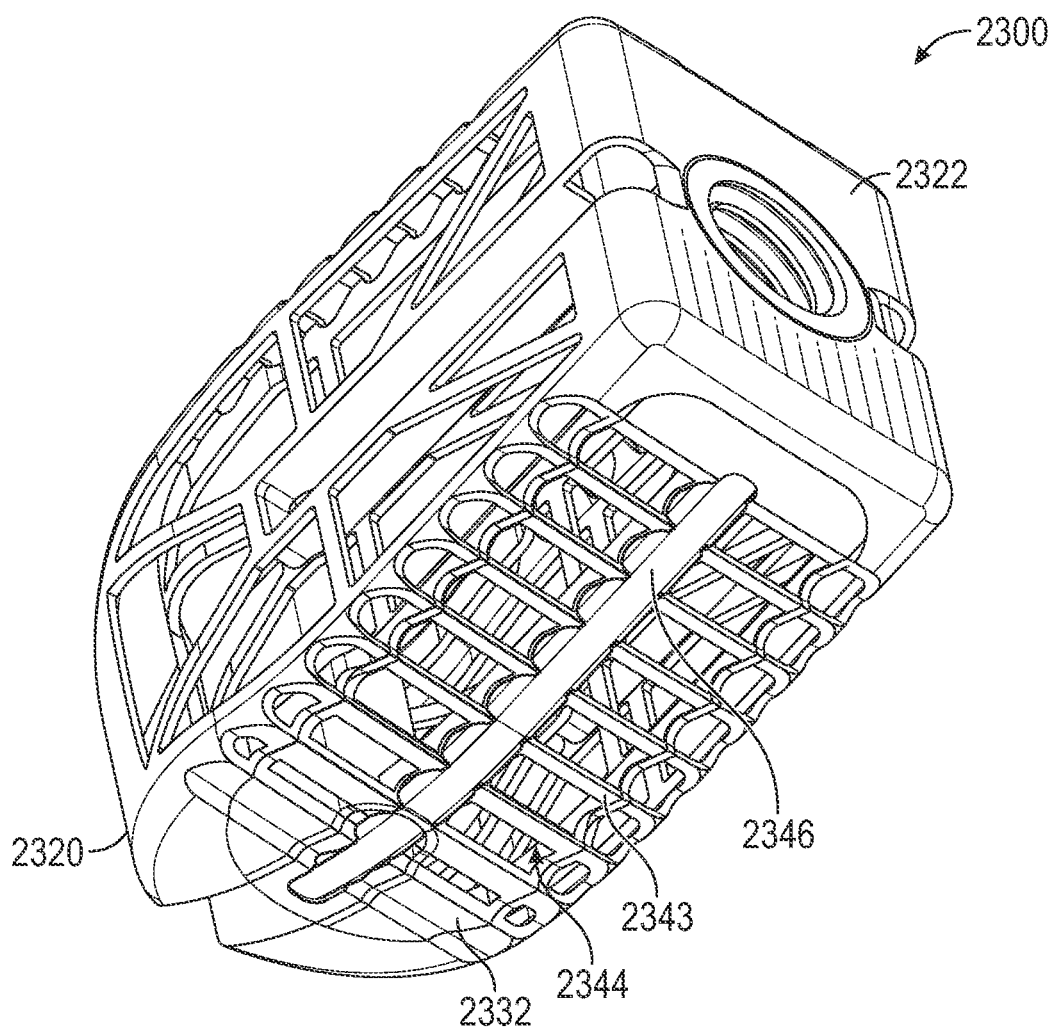

FIG. 173 is a bottom perspective view of the spinal implant device of FIG. 167.

Figure 174:
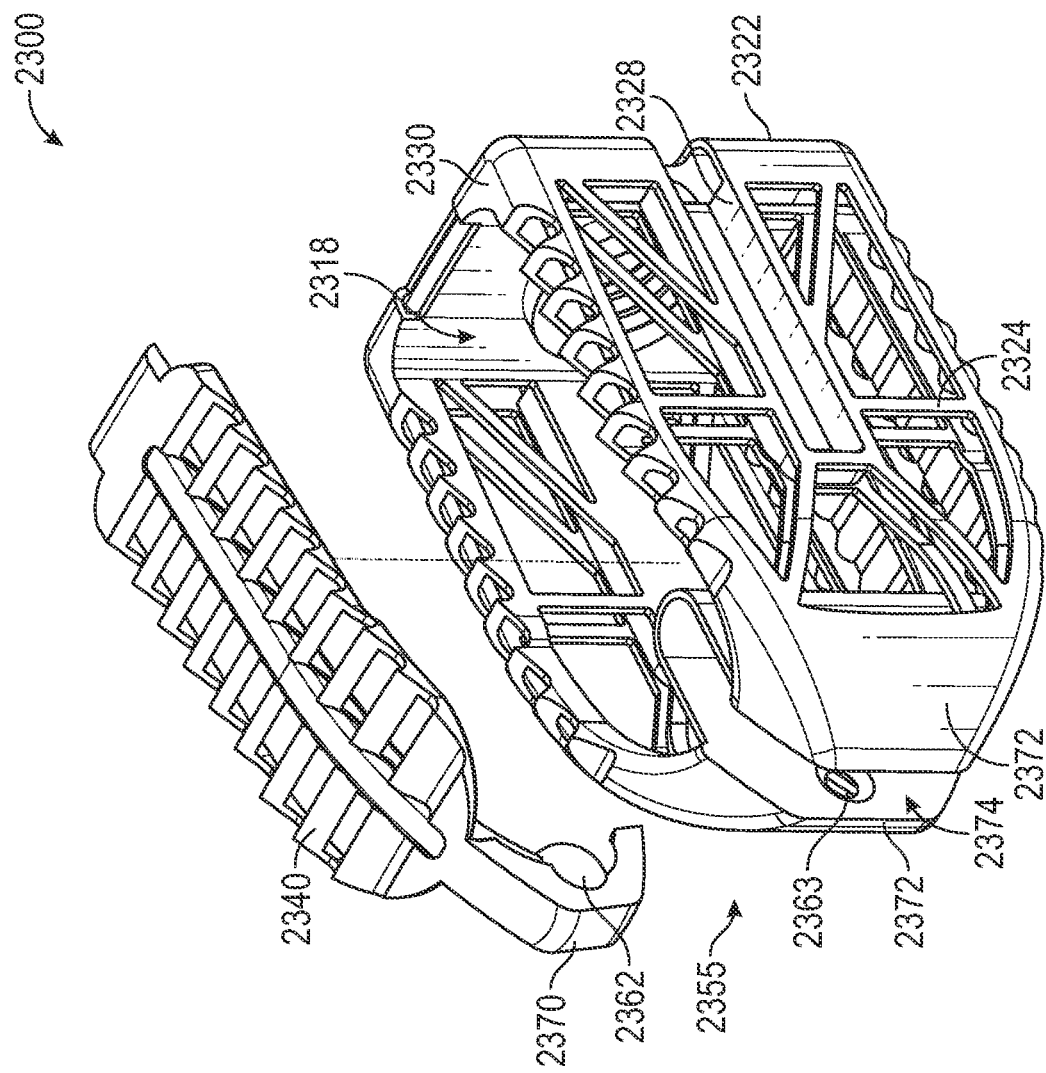

FIG. 174 is an exploded perspective view of the spinal implant device of FIG. 167.

Figure 175:
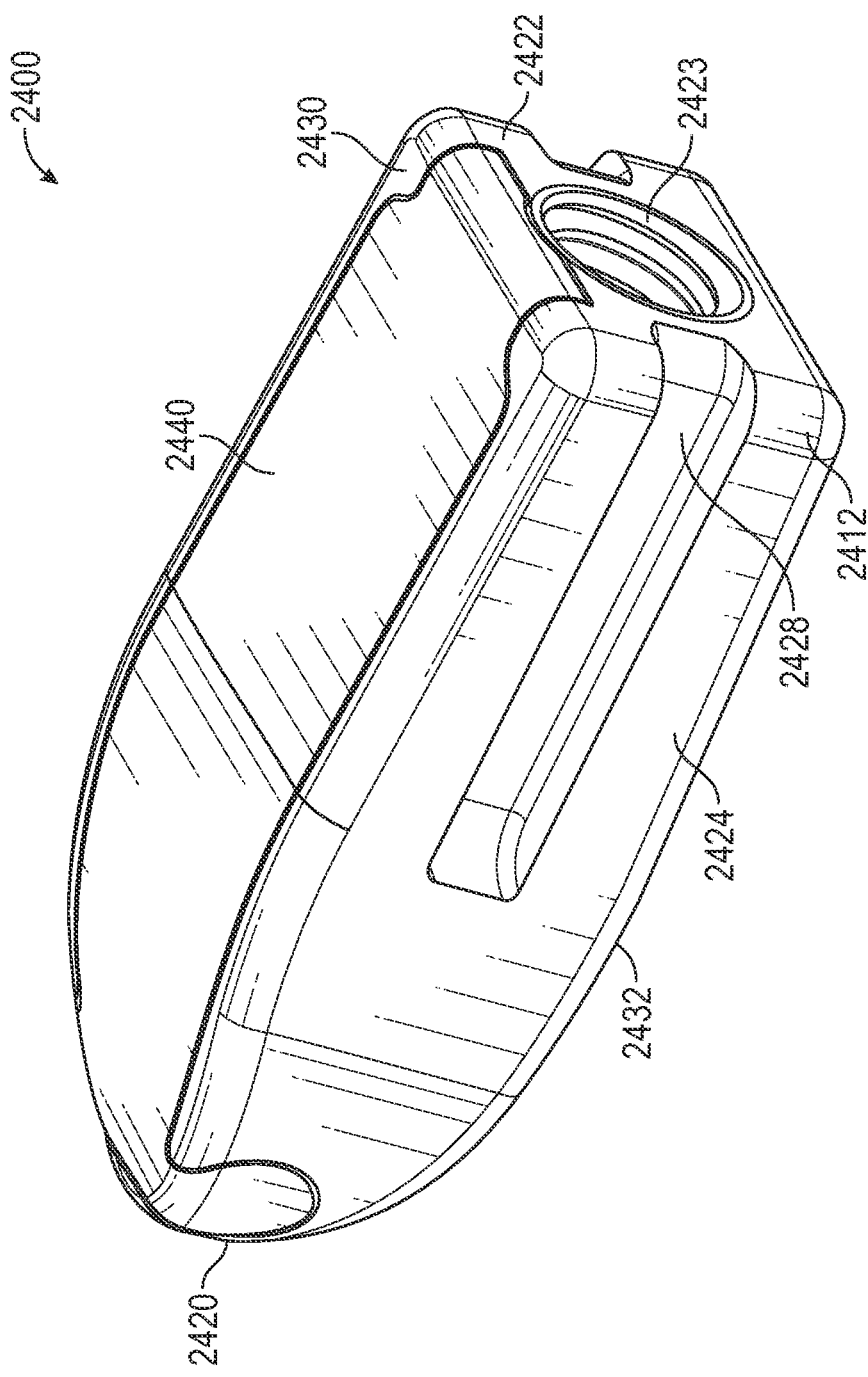

FIG. 175 is a perspective view of an embodiment of a spinal implant device with a movable lid shown in a closed position.

Figure 176:
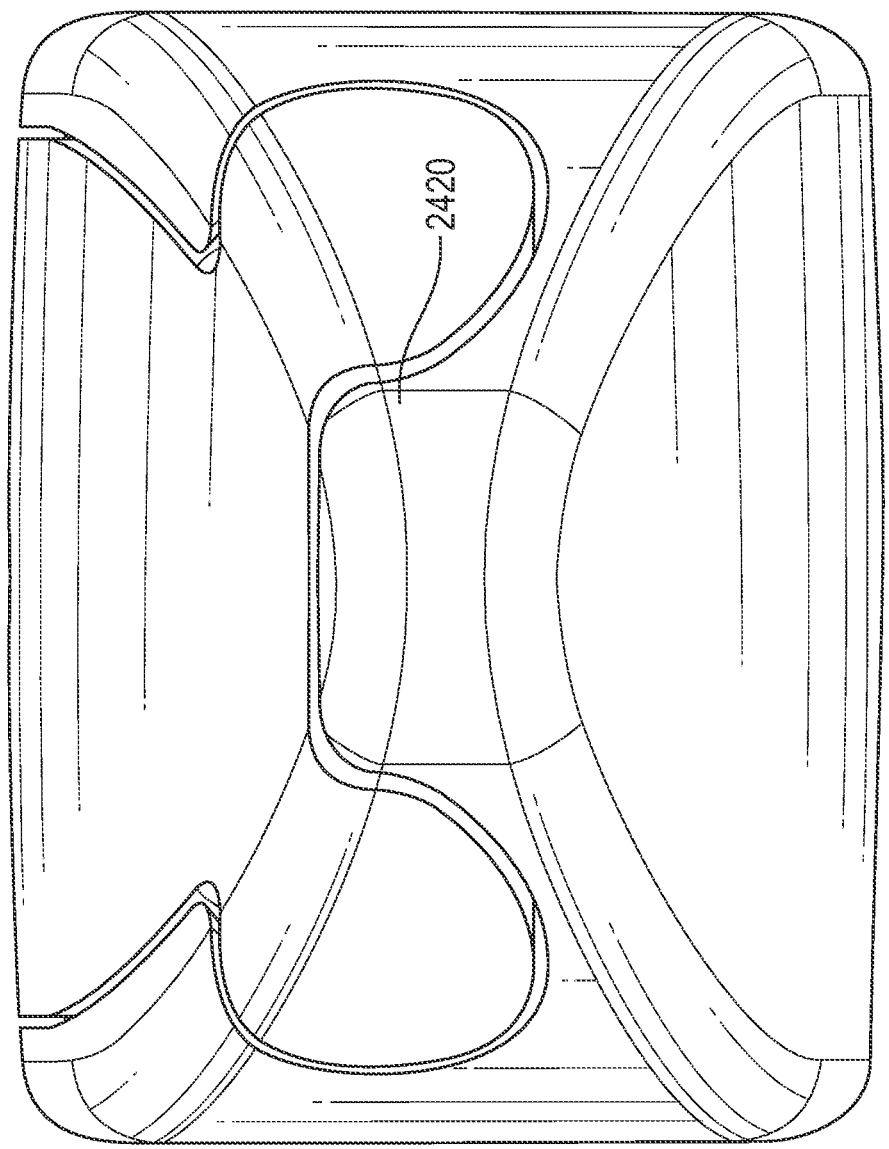

FIG. 176 is a distal view of the spinal implant device of FIG. 175.

Figure 177:
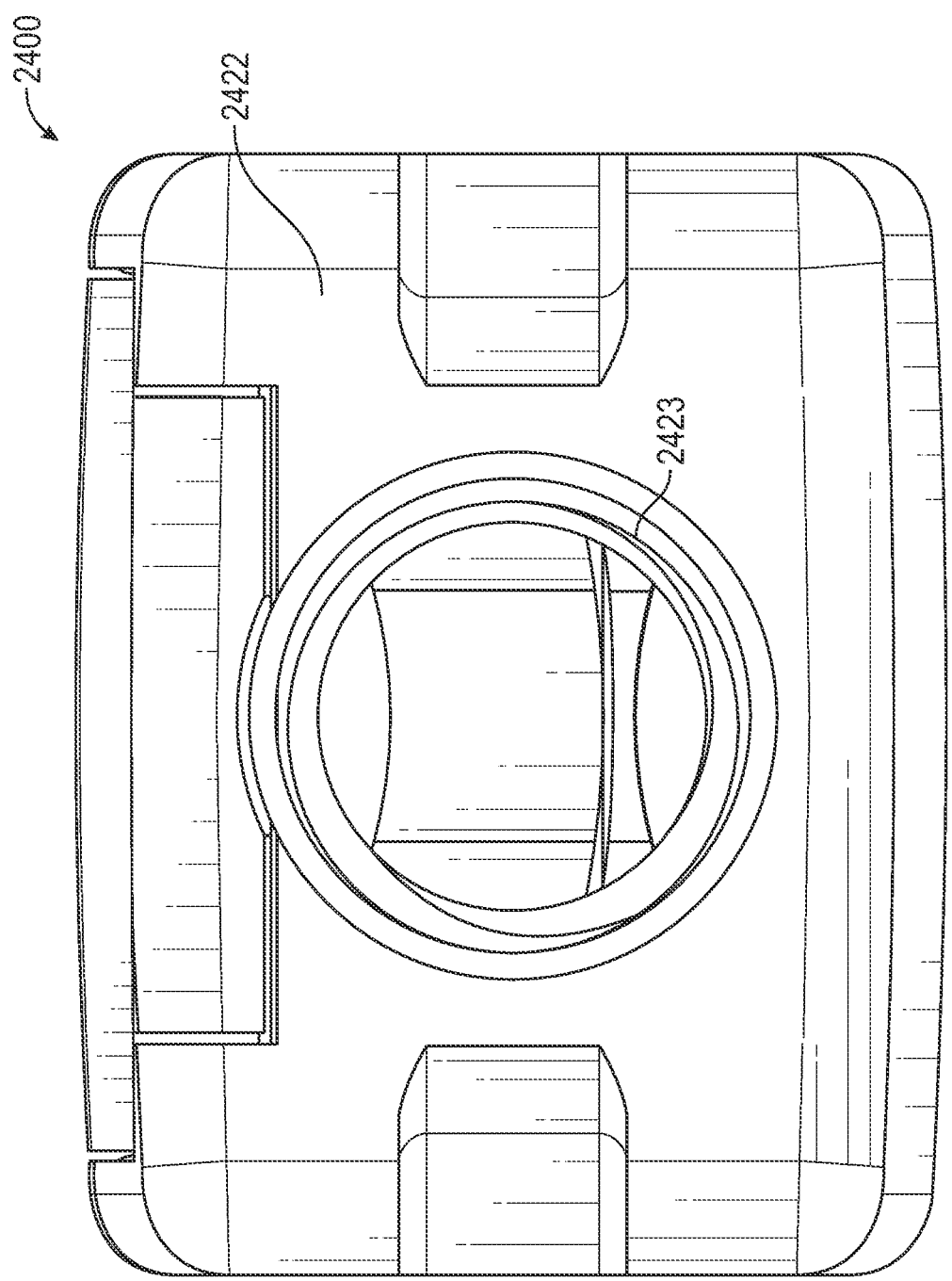

FIG. 177 is a proximal view of the spinal implant device of FIG. 175.

Figure 178:
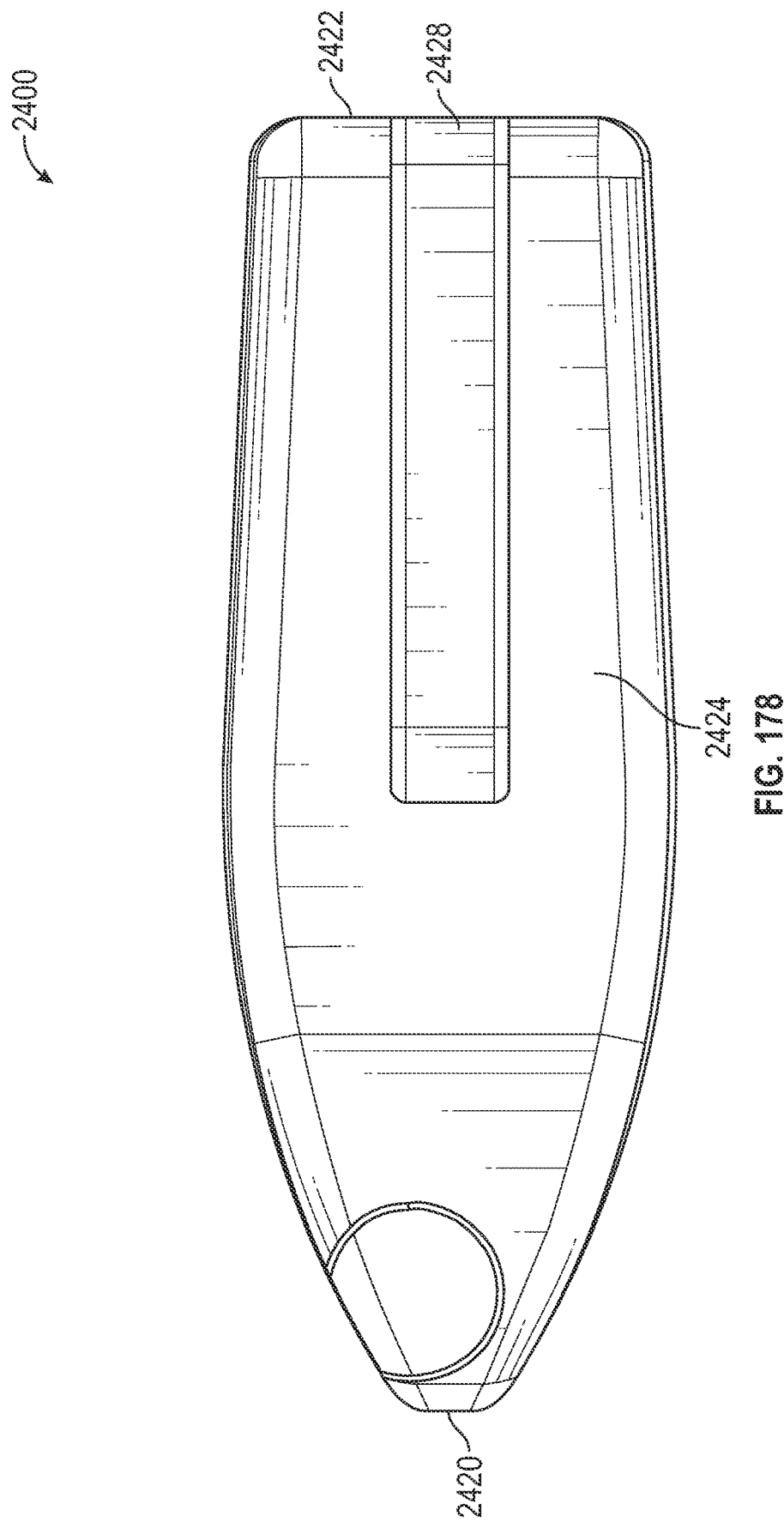

FIG. 178 is a side view of the spinal implant device of FIG. 175.

Figure 179:
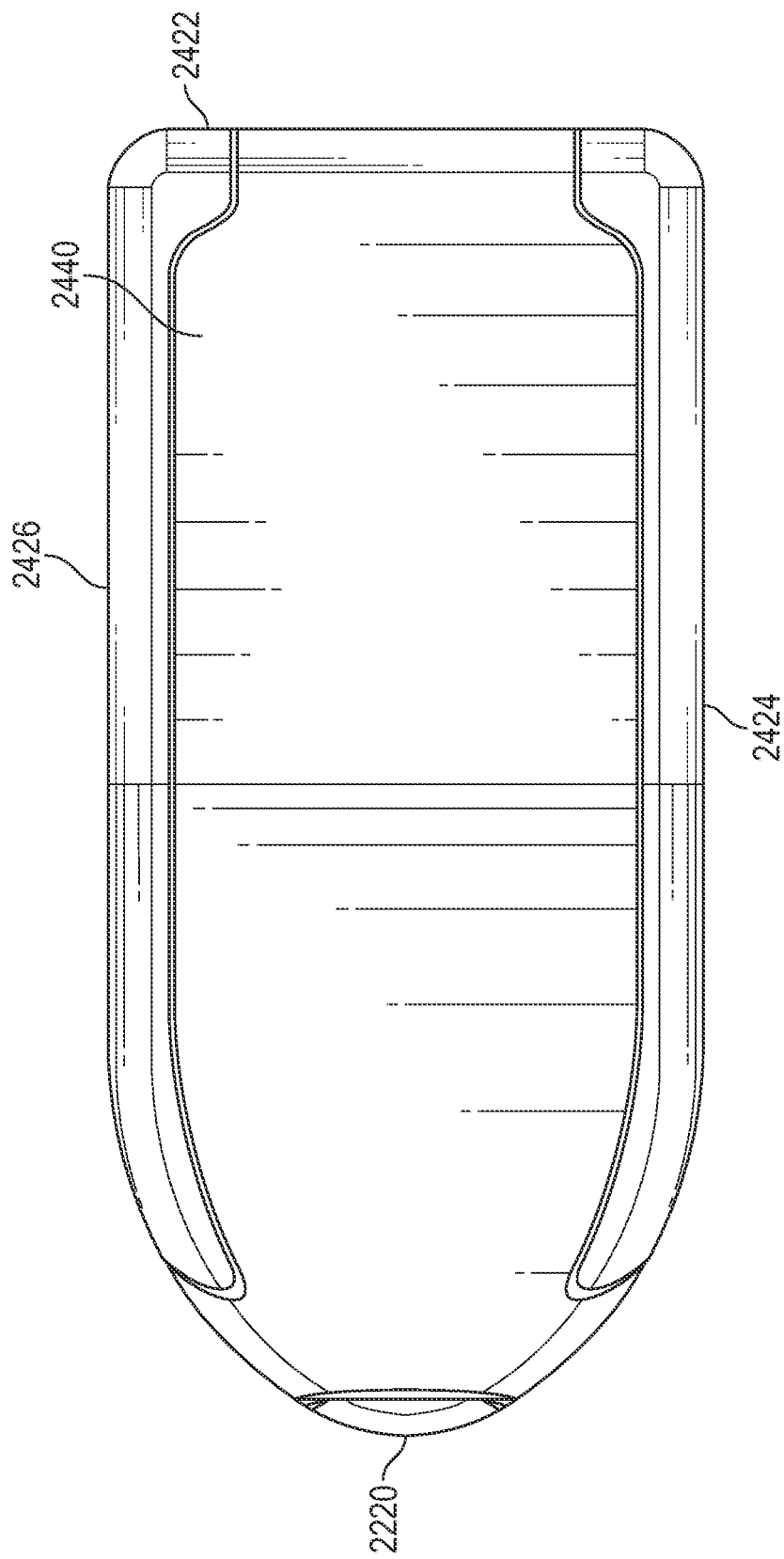

FIG. 179 is a top view of the spinal implant device of FIG. 175.

Figure 180:
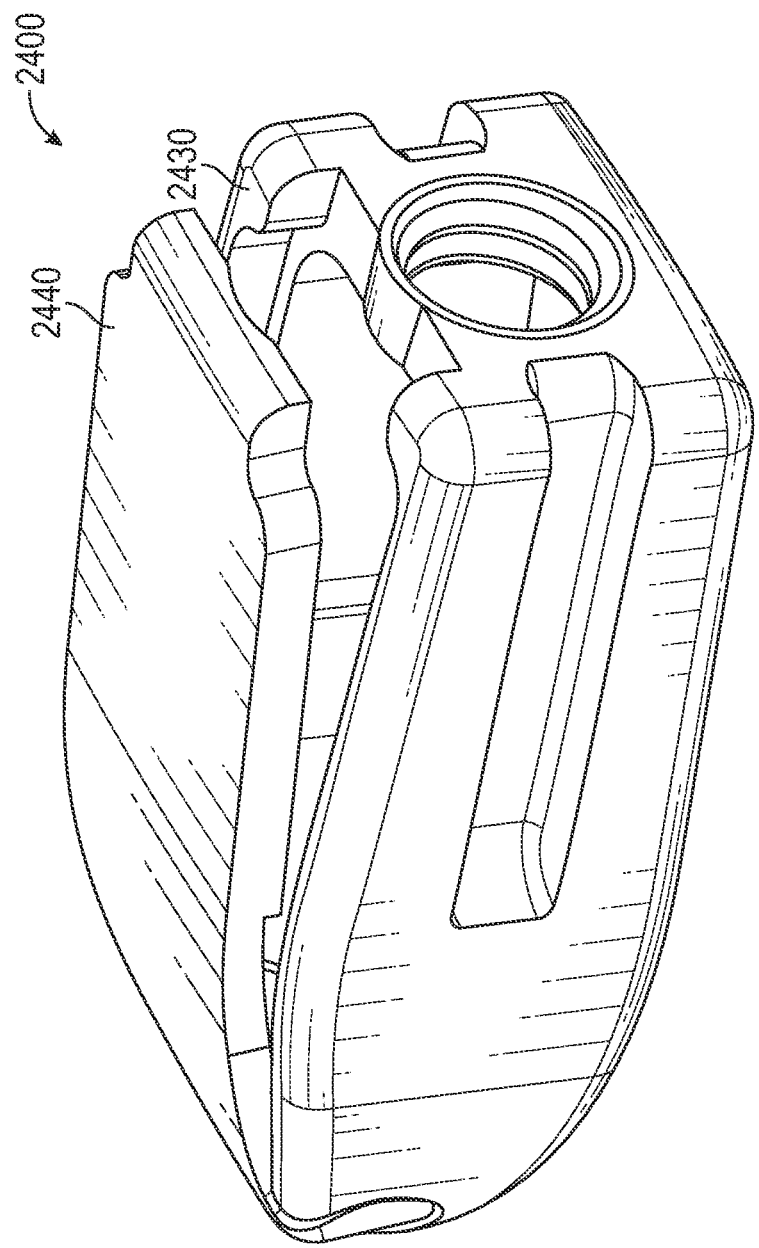

FIG. 180 is a top perspective view of the spinal implant device of FIG. 175 with the movable lid shown in an opened position.

Figure 181:
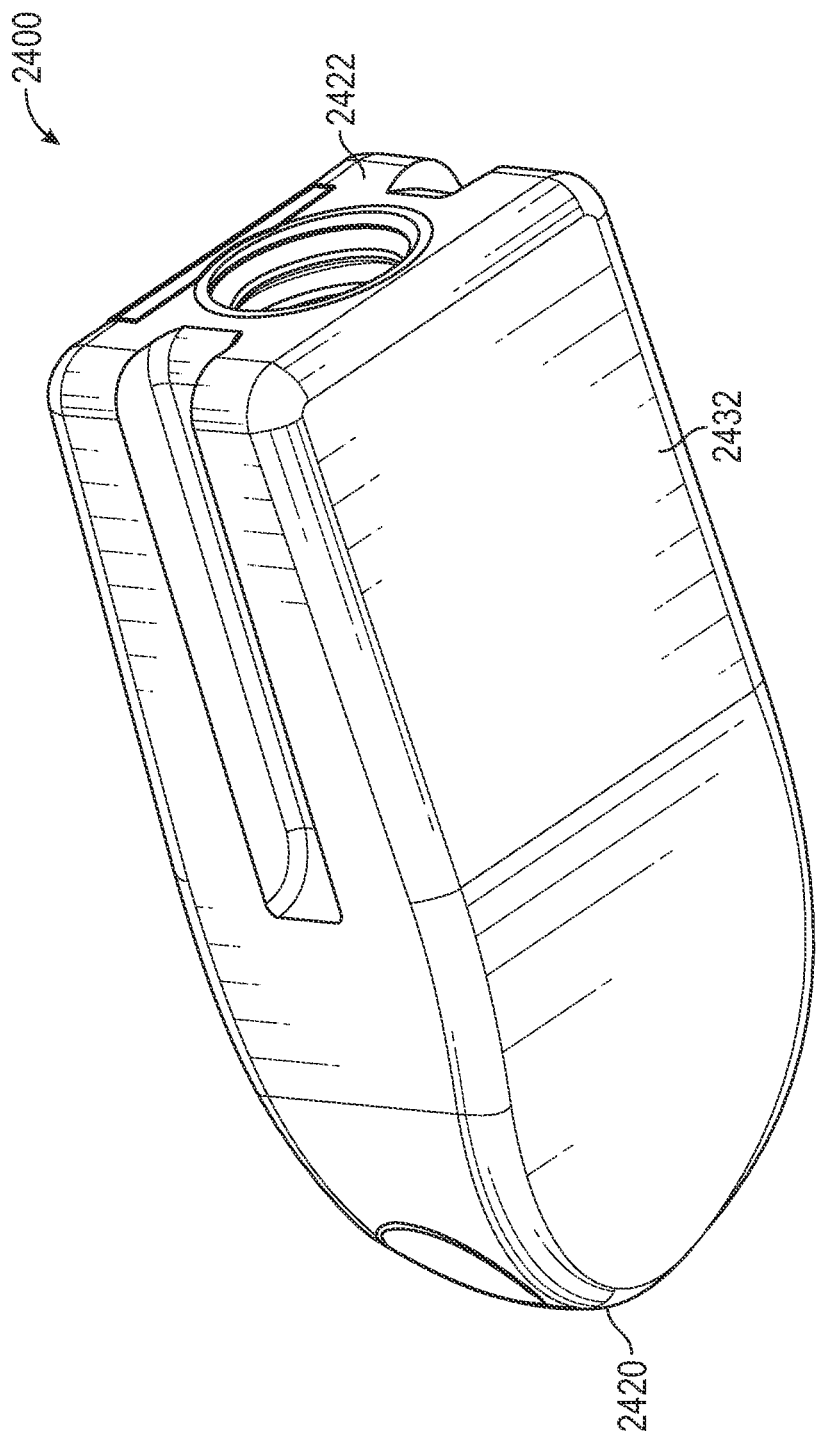

FIG. 181 is a bottom perspective view of the spinal implant device of FIG. 175.

Figure 182:
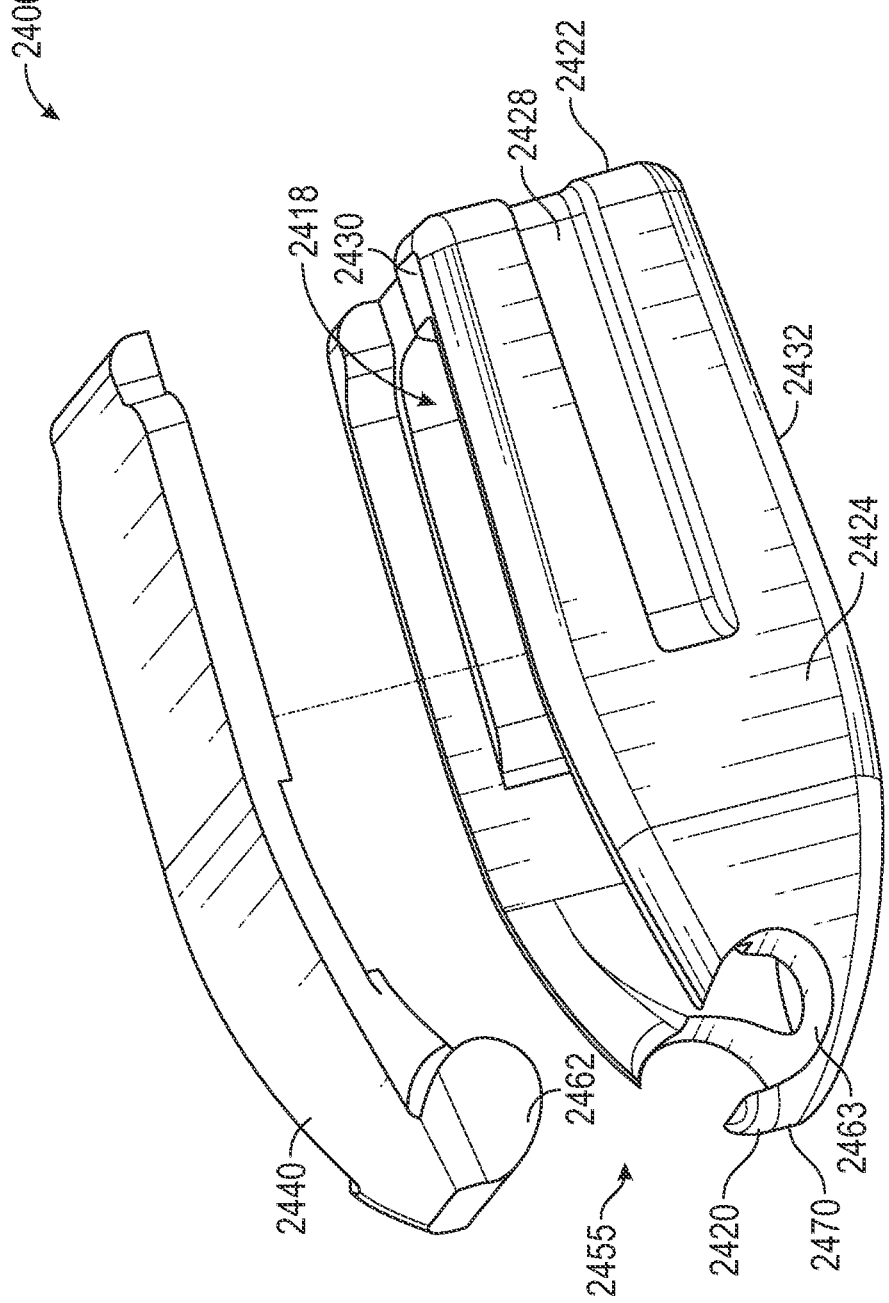

FIG. 182 is an exploded perspective view of the spinal implant device of FIG. 175.

DETAILED DESCRIPTION

Figure 1:
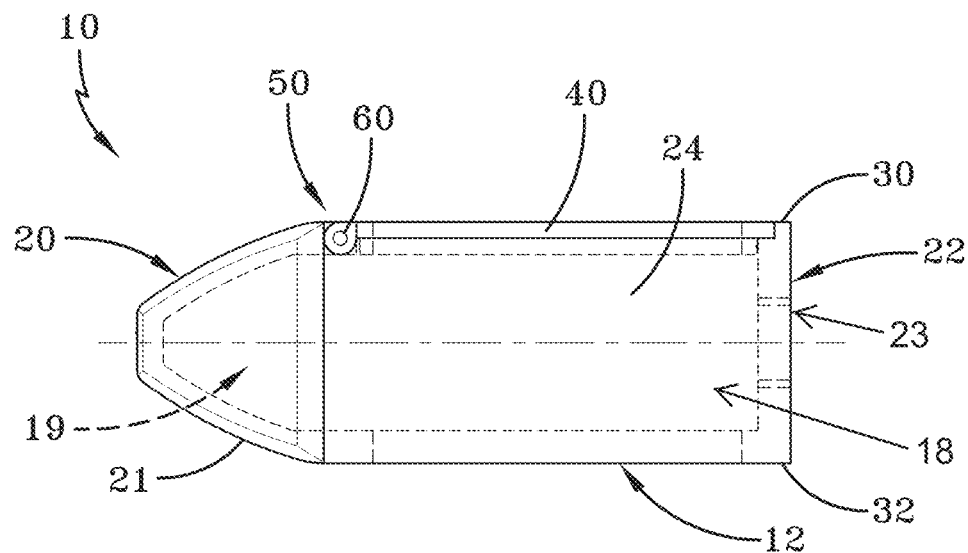
FIG. 1 is a cross-sectional side view of an embodiment of a spinal implant device with a movable lid shown in a closed position.

FIG. 1 illustrates a cross-sectional view of a spinal implant device 10. The spinal implant device 10 can include a body structure 12. The body structure 12 can be placed between adjacent vertebrae, such as a superior vertebra and an inferior vertebra. The orientation of the body structure 12 between the vertebrae can depend on the insertion direction and the methods of use of the spinal implant device 10. The spinal implant device 10 can be placed at any level of the vertebral column, between any adjacent vertebrae. The spinal implant device 10 can be designed to restore or maintain the spacing between adjacent vertebrae. The body structure 12 can include one or more walls which provide strength and stability to the spinal implant device 10.

The spinal implant device 10 can include a distal end 20. In some methods of use, the distal end 20 is the leading end which is inserted first into the intervertebral space. In some embodiments, the distal end 20 is tapered. The distal end 20 can form a frustoconical or convex curved shape 21 for facilitating insertion. The distal end 20 can be truncated slightly, as illustrated, leaving a flat or blunt portion of the distal end 20. The spinal implant device 10 can become progressively smaller toward the distal end 20. The taper can be straight, concave, or convex. The taper can extend to a point (not shown) or a distal end surface as shown. In some embodiments, two surfaces of the distal end 20 can taper, for instance, an upper surface and a lower surface of the distal end 20 can taper such as a triangular prism. In some embodiments, four surfaces of the distal end 20 can taper such as a square pyramid. Other three-dimensional shapes are contemplated for the distal end 20 including conical, cube, cuboid, spherical, hemispherical, square pyramid, triangular pyramid, polygonal pyramid, dodecahedron, triangular prism, hexagonal prism, or polygonal prism. In some embodiments, the upper surface and the lower surface of the distal end 20 equally taper. In some embodiments, one of the upper surface and the lower surface of the distal end 20 form a taper.

The spinal implant device 10 can include a proximal end 22. The distal end 20 and the proximal end 22 can form opposite ends of the spinal implant device 10. In some embodiments, the proximal end 22 forms a flat surface but other shapes are contemplated. In some embodiments, the proximal end 22 can be tapered. The distance between the distal end 20 and the proximal end 22 can form the length or depth of the spinal implant device 10.

The proximal end 22 can be configured to be coupled to an insertion tool or driver (not shown). In some embodiments, the proximal end 22 can include an opening 23 to accept the insertion tool. While one opening is illustrated, the proximal end 22 can include one or more openings (e.g., one, two, three, four, five, or six). In some embodiments, the opening 23 can be threaded to engage a threaded tip of the insertion tool. In some embodiments, the opening 23 can be adapted to provide an attachment location so that the insertion tool can be connected to the spinal implant device 10. The insertion tool can be used to position the spinal implant device 10 between the vertebrae. The insertion tool can be threaded tightly against the spinal implant device 10. The insertion tool can utilize any connection means including catch/release type mechanism, pin, detent, bayonet connection, or any other connection such that the insertion tool can hold the spinal implant device 10 in a fixed orientation during insertion.

The spinal implant device 10 can include two opposing side walls including a first side wall 24 and a second side wall 26. The side walls 24, 26 can connect the distal end 20 and the proximal end 22. The side walls 24, 26 can extend from the taper of the distal end 20 to the flat surface of the proximal end 22. While two opposing side walls 24, 26 are illustrated, the spinal implant device 10 can include two or more side walls, for example each side wall 24, 26 can include one or more side wall portions (e.g., one, two, three, four, five, or six). In some embodiments, each side wall 24, 26 can form a flat surface but other shapes are contemplated. In some embodiments, each side wall 24, 26 can be tapered. In some embodiments, the opposing side walls 24, 26 are separated the same distance along the length of the spinal implant device 10. In some embodiments, the opposing side walls 24, 26 are parallel. In some embodiments, the opposing side walls 24, 26 are closer near the distal end 20 and farther apart near the proximal end 22. In some embodiments, the opposing side walls 24, 26 are closer near the proximal end 22 and farther apart near the distal end 20. In some embodiments, the opposing side walls 24, 26 are skewed relative to each other. In some embodiments, the first side wall 24 and the second side wall 26 are the same shape, for example rectangular. In some embodiments, the first side wall 24 and the second side wall 26 are different shapes. In some embodiments, the two opposing side walls 24, 26 can form the height of the spinal implant device 10. In some embodiments, the distance between the two opposing side walls 24, 26 can form the width of the spinal implant device 10. In some embodiments, the two opposing side walls 24, 26 extend along a portion of the length of the spinal implant device 10 (e.g., 50% of the length, 60% of the length, 70% of the length, 80% of the length, 90% of the length, or 100% of the length, or any range of the foregoing values).

The spinal implant device 10 can include two more opposing walls including an upper wall 30 and a lower wall 32. The upper wall 30 and the lower wall 32 can connect the distal end 20 and the proximal end 22. The upper wall 30 and the lower wall 32 can extend from the taper of the distal end 20 to the flat surface of the proximal end 22. While two walls 30, 32 are illustrated, each of the upper wall 30 and the lower wall 32 can include one or more wall portions (e.g., one, two, three, four, five, or six). In some embodiments, the upper wall 30 forms a stepped surface as described herein but other shapes are contemplated. In some embodiments, the lower wall 32 forms a flat surface but other shapes are contemplated. In some embodiments, the upper wall 30 and the lower wall 32 are separated by the same distance along the length of the spinal implant device 10. In some embodiments, the upper wall 30 and the lower wall 32 are parallel. In some embodiments, the upper wall 30 and the lower wall 32 are the same shape. In some embodiments, the upper wall 30 and the lower wall 32 are different shapes. In some embodiments, the distance between the upper wall 30 and the lower wall 32 can form the height of the spinal implant device 10. In some embodiments, the upper wall 30 and the lower wall 32 can form the width of the spinal implant device 10. In some embodiments, the upper wall 30 and the lower wall 32 extend along a portion of the length of the spinal implant device 10 (e.g., 50% of the length, 60% of the length, 70% of the length, 80% of the length, 90% of the length, or 100% of the length, or any range of the foregoing values).

The upper wall 30 and the lower wall 32 can provide load supporting surfaces. In some methods, the upper wall 30 can be positioned adjacent to a vertebral end plate of an upper vertebra. In some methods, the lower wall 32 can be positioned adjacent to a vertebral end plate of a lower vertebra. In some embodiments, the distance between the upper wall 30 and the lower wall 32 corresponds to the height of the intervertebral space where the spinal implant device 10 is to be positioned. In some embodiments, the distance between the upper wall 30 and the lower wall 32 can restore the spacing between adjacent vertebrae. In some methods, when the spinal implant device 10 is positioned between two adjacent vertebrae, the load supporting surfaces of the upper wall 30 and the lower wall 32 contact the vertebral end plates of the adjacent vertebrae. The upper wall 30 and the lower wall 32 are designed to separate the adjacent vertebrae by a distance substantially equal to the total height of the spinal implant device 10.

The spinal implant device 10 can include a movable lid 40. In the illustrated embodiment, the movable lid 40 can be coupled to the upper wall 30 of the spinal implant device 10. In some embodiments, the movable lid 40 can be coupled to the lower wall 32 of the spinal implant device 10. In some embodiments, the movable lid 40 can be coupled to the first side wall 24 of the spinal implant device 10. In some embodiments, the movable lid 40 can be coupled to the second side wall 26 of the spinal implant device 10. In some embodiments, the movable lid 40 can be coupled to the distal end 20 of the spinal implant device 10. In some embodiments, the movable lid 40 can be coupled to the proximal end 22 of the spinal implant device 10. The moveable lid 40 can be coupled to the spinal implant device 10 at any location to facilitate packing the spinal implant device 10 as described herein.

Figure 6A:
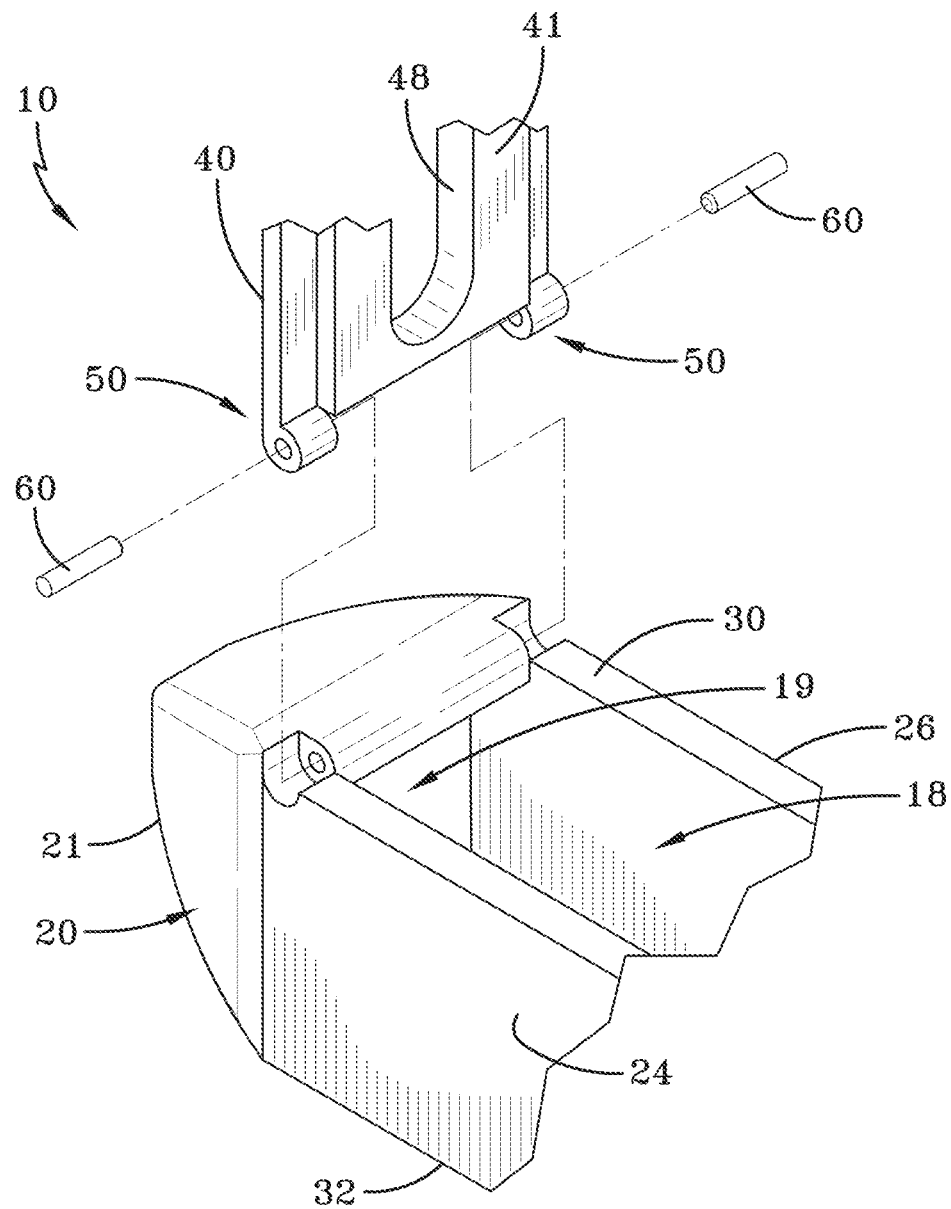
FIG. 6A is a partial exploded view showing the mechanical hinge of FIG. 1.

In the illustrated embodiment, the movable lid 40 and the upper wall 30 together form the upper surface of the spinal implant device 10. In the illustrated embodiment, the movable lid 40 and the upper wall 30 are flush. The two opposing side walls 24, 26 can have a slight recess along the upper surface relative to the distal end 22, as shown in FIG. 6A. The two opposing side walls 24, 26 can have a smaller height than the total height of the spinal implant device 10. This reduced height of the two opposing side walls 24, 26 can allow the movable lid 40, when in the closed position, to be flush with an upper surface of the spinal implant device 10 formed by one or more of the distal end 20, the proximal end 22, or the upper wall 30. In some embodiments, the movable lid 40 is flush with the opposing side walls 24, 26. In some embodiments, the movable lid 40 lies flush with an adjacent exterior surface near the proximal and distal end of the movable lid 40. In some embodiments, the movable lid 40 lies flush with an adjacent exterior surface near the side surfaces of the movable lid 40. In some embodiments, it is advantageous that the spinal implant device 10 has an upper surface which is generally flush in order to facilitate insertion of the spinal implant device 10. Other configurations are contemplated.

In some embodiments, the movable lid 40 can provide a load supporting surface. In some methods, the upper wall 30 and the movable lid 40 are positioned adjacent to a vertebral end plate of an upper vertebra. In some methods, when the spinal implant device 10 is positioned between two adjacent vertebrae, the load supporting surfaces of the upper wall 30, the movable lid 40, and the lower wall 32 contact the vertebral end plates of the adjacent vertebrae. The upper wall 30, the movable lid 40, and the lower wall 32 can be designed to separate the adjacent vertebrae.

The movable lid 40 is shown in a closed position in FIG. 1. In some embodiments, the movable lid 40 abuts a portion of the body structure 12 in a closed position. In some embodiments, the movable lid 40 abuts the upper wall 30 near the proximal end 22 in a closed position. In some embodiments, the movable lid 40 is separated in height from a portion of the body structure 12 in a closed position. In some embodiments, the movable lid 40 is separated in height from the upper wall 30 near the proximal end 22 in a closed position. The spinal implant device 10 can have one or more closed positions. The movable lid 40 is shown in an opened position in FIG. 2. The spinal implant device 10 can have one or more opened positions. In some embodiments, the movable lid 40 can include a mechanical hinge 50. In some embodiments, the mechanical hinge 50 can be positioned towards the distal end 20 of the spinal implant device 10. In some embodiments, the mechanical hinge 50 can be positioned towards the proximal end 22 of the spinal implant device 10. The mechanical hinge 50 can connect the movable lid 40 to the body structure 12. In the illustrated embodiment, the mechanical hinge 50 can connect the movable lid 40 to the upper wall 30. The mechanical hinge 50 can allow for pivoting motion of the movable lid 40 relative to the upper wall 30. The mechanical hinge 50 can allow the movable lid 40 to move in an arc relative to the upper wall 30, for instance 15°, 30°, 45°, 60°, 75°, 90°, 105°, 120°, 135°, 150°, 165°, 180°, 195°, 210°, 225°, or 240°, or any range of the foregoing values. In the illustrated embodiment, the movable lid 40 is designed to move in an arc relative to the upper wall 30 approximately 90°.

In some embodiments, the mechanical hinge 50 can include a pin 60. The pin 60 can extend the distance between the side walls 24, 26, or a portion thereof. The pin 60 can extend along the width of the spinal implant device 10, or a portion thereof. The pin 60 can be perpendicular to the longitudinal axis of the spinal implant device 10. In some embodiments, the mechanical hinge 50 can include one or more pins 60 (e.g., one pin, two pins, three pins, four pins, five pins, or six pins). The mechanical hinge 50 can include a pair of pins 60. The mechanical hinge 50 can be formed in a number of ways including one or more pins.

The spinal implant device 10 can include a cavity 18. In some embodiments, the proximal end 22 can define the back inner surface of the cavity 18. In some embodiments, the distal end 20 can define the front inner surface of the cavity 18. In some embodiments, the two opposing side walls 24, 26 can define the side inner surfaces of the cavity 18. In some embodiments, the movable lid 40 can define the top inner surface of the cavity 18, or a portion thereof. In some embodiments, the upper wall 30 can define the top inner surface of the cavity 18, or a portion thereof. In some embodiments, the cavity 18 is partially enclosed. The cavity 18 can be a large, central chamber inside the spinal implant device 10. In some embodiments, when the movable lid 40 is closed, the contents of the cavity 18 can be retained within the cavity 18. In some embodiments, access is provided to the cavity 18 through the movable lid 40 as described herein.

In some embodiments, the spinal implant device 10 can include a distal end cavity 19. In some embodiments, the distal end 20 defines the inner surface of the distal end cavity 19. In some embodiments, the internal space of the spinal implant device 10 includes only the cavity 18. The distal end 20 can form a solid structure such that the distal end 20 defines the front inner surface of the cavity 18. In some embodiments, the distal end 20 defines the inner surface of the cavity 18. In some embodiments, the internal space of the spinal implant device 10 includes both the cavity 18 and the distal end cavity 19. The cavities 18, 19 can be a large, central chamber inside the spinal implant device 10. In some embodiments, when the movable lid 40 is closed, the cavities 18, 19 can retain a material within. In some embodiments, access is provided to the cavities 18, 19 through the movable lid 40 as described herein. In some embodiments, the cavity 18 can be cube or rectangular prism or other similar shapes. In some embodiments, the cavity 19 can be a cone, a triangular prism, or a triangular pyramid or other similar shapes. The distal end 20 of the spinal implant device 10 can have the frustoconical or convex curved shape 21 for facilitating insertion. The distal end 20 can taper outwardly as the distal end 20 extends back towards the proximal end 22. The distal end 20 can be truncated slightly with the flat or blunt portion of the distal end 20. The cavity 19 can also have a frustoconical or convex curved shape with a flat or blunt portion. The cavity 19 can match the external shape of the distal end 20. The distal end 20 can form the cavity 19 in communication with the cavity 18. In some embodiments, the distal end 20 can form the tapered shape of the cavity 19. In some embodiments, the body structure 12 can form the rectangular shape of the cavity 18.

FIG. 1 illustrates the cavities 18, 19 of the spinal implant device 10 with the movable lid 40 in the closed position. FIG. 1 illustrates an example of the shapes of the cavities 18, 19 but other shapes are contemplated. The internal volume of the central cavity 18 can be fully unobstructed between the two opposing side walls 24, 26 of the spinal implant device 10. The internal volume of the central cavity 18 can be fully unobstructed between the upper wall 30 and the lower wall 32. The internal volume of the central cavity 18 can be fully unobstructed between the distal end 20 and the proximal end 22.

The spinal implant device 10 can include one or more walls as described herein. The one or more walls can be thinner than another portion of the spinal implant device 10. The one or more walls can include a thinned portion, for example a thinned portion near the central cavity 18. The one or more walls can be thicker than another portion of the spinal implant device 10, for example near the corners or distal end 20. The one or more walls can be thinner than the walls of commercially available interbody implants.

In some embodiments, the upper wall 30, or a portion thereof, is thin to maximize the volume of the cavity 18. In some embodiments, the lower wall 32, or a portion thereof, is thin to maximize the volume of the cavity 18. In some embodiments, the two opposing side walls 24, 26 are thin to maximize the volume of the cavity 18. In some embodiments, the distal end 20 is thin to maximize the volume of the cavity 19. In some embodiments, the proximal end 22 is thin to maximize the volume of the cavity 18. In some embodiments, the distal end 20 is thicker than another portion of the spinal implant device 10. In some embodiments, the proximal end 22 is thicker than another portion of the spinal implant device 10.

In some embodiments, one or more walls can have a uniform thickness. In some embodiments, the upper wall 30 and the movable lid 40 together can have a uniform thickness. In some embodiments, the lower wall 32 can have a uniform thickness. In some embodiments, each of the two opposing side walls 24, 26 can have a uniform thickness. In some embodiments, the distal end 20 can have a uniform thickness. In some embodiments, the proximal end can have a uniform thickness. In some embodiments, the distal end 20 provides structural stiffening of the spinal implant device 10. The distal end 20 can include a stiffer wall thickness than another portion of the spinal implant device 10. In some embodiments, the distal end 20 is solid or thick walled to facilitate insertion. Other configurations of the thickness of the walls are contemplated.

The spinal implant device 10 can comprise at least one material selected from the group consisting of polymers, polyetheretherketone (PEEK), polyetherketoneketone (PEKK), polyethylene, fluoropolymers, hydrogels, elastomers, ceramics, zirconia, alumina, silicon nitride, metal(s), titanium, titanium alloy, cobalt chromium, stainless steel, and combinations of these materials. In some embodiments, the spinal implant device 10 can include a coating. In some embodiments, the spinal implant device 10 can include a porous coating. In some embodiments, the spinal implant device 10 can include a body of a first material and a coating of a second material, different than the first material. In some embodiments, the spinal implant device 10 can include a body of polymer such as PEEK and a coating of metal such as titanium. In some embodiments, the spinal implant device 10 comprises a material which is radiolucent. In some embodiments, the spinal implant device 10 comprises a material with an elastic modulus similar to bone. In some embodiments, the spinal implant device 10 comprises a hydrophilic material. In some embodiments, the spinal implant device 10 comprises a hydrophobic material. In some embodiments, the spinal implant device 10 comprises a hydrophobic material and a hydrophilic coating on at least one surface.

The spinal implant device 10 can be manufactured by rapid prototyping. The spinal implant device 10 can be manufactured using three-dimensional CAD data or other three-dimensional modeling software. The spinal implant device 10 can be manufactured through 3D printing. The spinal implant device 10 can be manufactured using additive layer manufacturing. The spinal implant device 10 can be produced using any computer aided manufacturing method. The spinal implant device 10 can be produced through one or more of the following techniques: ballistic particle manufacturing, fused deposition modeling, direct shell production casting, laminated object manufacturing, laminated resin printing, shape deposition manufacturing, mold shape deposition manufacturing, directed light fabrication, solid ground curing, selective laser sintering, selective laser melting, or stereolithography.

The spinal implant device 10 can include, be made of, treated, coated, filled, used in combination with, or contain artificial or naturally occurring materials suitable for implantation in the human spine. These materials can include any source of osteogenesis, bone growth-promoting materials, bone derived substances, bone morphogenetic proteins, hydroxyapatite, genes coding for the production of bone, and bone including, but not limited to, cancellous or cortical bone. The spinal implant device 10 can be formed of material such as metal including, but not limited to, titanium and its alloys, surgical grade plastics, plastic composites, ceramics, or other materials suitable for use as a spinal fusion implant. In some embodiments, the spinal implant device 10 can comprise a radiolucent material, a radioopaque material, or a combination thereof. In some embodiments, the spinal implant device 10 can be partially or completely radiolucent, which can be advantageous when evaluating the effect of the spinal implant device 10 post-implantation. The spinal implant device 10 can include at least in part materials that are bioabsorbable in the body of the patient. The spinal implant device 10 can be formed of a porous material or can be formed of a material that intrinsically participates in the growth of bone from one of adjacent vertebral bodies to the other of adjacent vertebral bodies. The spinal implant device 10 can be treated with, coated with, or used in combination with substances to inhibit scar tissue formation. The spinal implant device 10 can be modified, or used in combination with materials to provide antibacterial properties, such as, but not limited to, electroplating or plasma spraying with silver ions or other substance. The antibacterial properties can include bactericidal and/or bacteriostatic characteristics. Similarly, antifungal characteristics can also be provided.

In some embodiments, at least one surface of the spinal implant device 10 can comprise a highly polished surface, for example the distal end 20 to facilitate insertion. In some embodiments, at least one surface of the spinal implant device 10 can comprise a roughened surface. For example, the upper surface or the lower surface of the spinal implant device 10, or a portion thereof, can comprise ridges as described herein. In some embodiments, at least one surface of the spinal implant device 10 can comprise a porous surface. In some embodiments, at least one surface of the spinal implant device 10 can be malleable to be capable of generally conforming to the shape of an adjacent surface or structure under normal anatomical loads.

In some embodiments, the spinal implant device 10 can be dimensioned to substantially fit in the disc space between two adjacent vertebrae. In some embodiments, the spinal implant device 10 can have a thickness generally equal to the normal anatomic spacing between two vertebrae. In some embodiments, the spinal implant device 10 can have a curvature designed to match the natural shape of a vertebral end plate. In some embodiments, the spinal implant device 10 can have a size adapted to fit substantially within a disc space. In some embodiments, the spinal implant device 10 can have an average height within the range of about 5 mm to about 20 mm (e.g., 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or between 7 and 14 mm, or any range of the foregoing values). In some embodiments, the spinal implant device 10 can have an average width within the range of about 5 mm to about 20 mm (e.g., 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or between 8 and 12 mm, or any range of the foregoing values). In some embodiments, the spinal implant device 10 can have an average length or depth within the range of about 15 mm to about 40 mm (e.g., 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, approximately 22 mm, between 20 and 25 mm, between 25 and 40 mm, between 27 and 37 mm, between 25 and 35 mm, or between 27 and 32 mm, or any range of the foregoing values). In some embodiments, the spinal implant device 10 can include a curve. In some embodiments, the spinal implant device 10 can be straight or substantially straight.

Figure 2:
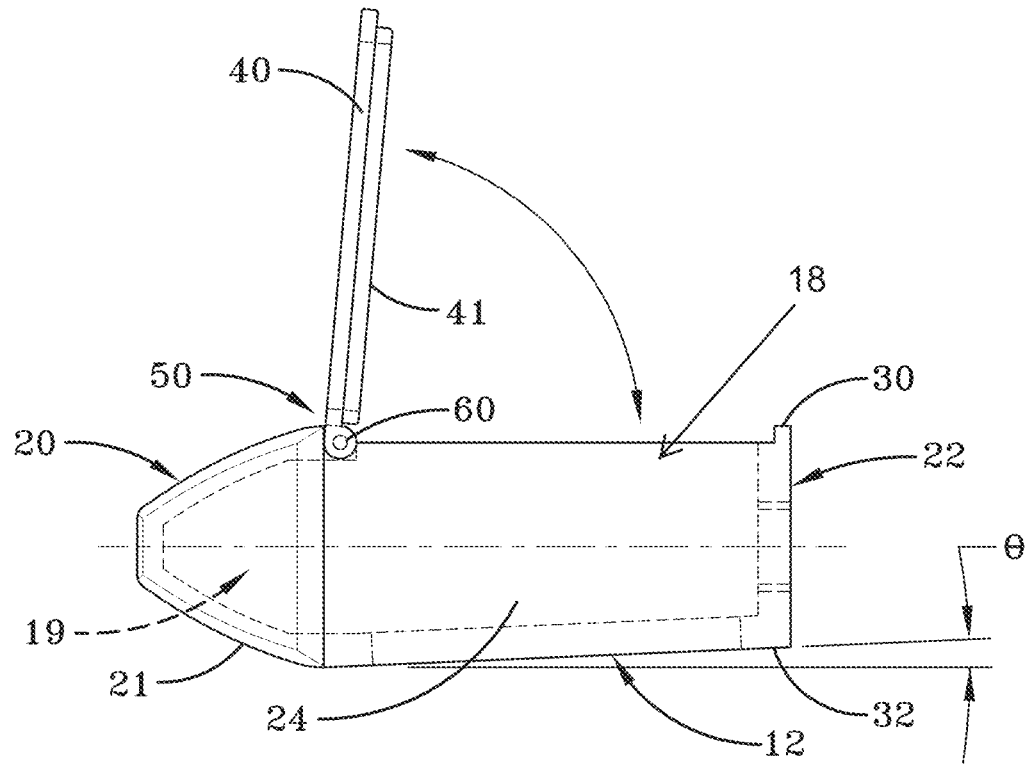
FIG. 2 is a cross-sectional view of the spinal implant device of FIG. 1 with the movable lid shown in an opened position.

FIG. 2 illustrates a cross-sectional view of the spinal implant device 10 with the movable lid 40 in an opened position. In some embodiments, the movable lid 40 can include a stepped inner surface 41. The upper wall 30 can include a corresponding stepped surface. The stepped inner surface 41 of the movable lid 40 can form a mechanical interfit with the upper wall 30. The stepped inner surface 41 of the movable lid 40 can distribute load bearing forces to the upper wall 30. The upper wall 30 can provide structural support to the stepped inner surface 41 of the movable lid 40. In some embodiments, the two opposing side walls 24, 26 can include a corresponding stepped surface. The stepped inner surface 41 of the movable lid 40 can form a mechanical interfit with the two opposing side walls 24, 26. The stepped inner surface 41 of the movable lid 40 can distribute load bearing forces to the two opposing side walls 24, 26. The two opposing side walls 24, 26 can provide structural support to the stepped inner surface 41 of the movable lid 40. In some embodiments, the opposing side walls 24, 26 have a recess or stepped configuration which allows the movable lid 40, when in the closed position, to be flush with an upper surface of the spinal implant device 10. In some embodiments, the spinal implant body 10 can have upper and lower surfaces that are generally aligned. In some embodiments, the upper surface can be a combination of one or more of the distal end 20, the movable lid 40, the two opposing side walls 24, 26, the upper wall 30, and/or the proximal end 22. In some embodiments, the upper surface can be a combination of the movable lid 40 and the upper wall 30. In some embodiments, the upper surface is curved to match the curvature of the adjacent vertebral end plate. In some embodiments, the lower surface can be a combination of one or more of the distal end 20, the two opposing side walls 24, 26, the lower wall 32, and/or the proximal end 22. In some embodiments, the lower surface is the lower wall 32. In some embodiments, the lower surface is curved to match the curvature of the adjacent vertebral end plate. In some methods, the aligned upper and lower surfaces are advantageous so that upon insertion, the spinal implant device 10 can be easily be inserted between the two adjacent vertebrae. In some methods, the aligned upper and lower surfaces are advantageous to facilitate load bearing. In some methods, the aligned upper and lower surfaces are advantageous to match the anatomical structure of the vertebral end plates.

In some embodiments, the spinal implant device 10 can have a slight inclination, called a lordosis angle θ. In some embodiments, the lordosis angle decreases the height of the spinal implant device 10. In some embodiments, the height of the spinal implant device 10 decreases near the proximal end 22 compared to the distal end 20. In some embodiments, the lordosis angle is approximately 5°. Other configurations are contemplated, for example 1°, 2°, 3°, 4°, 5°, 6°, 7°, 8°, 9°, 10°, 11°, 12°, 13°, 14°, 15°, 16°, 17°, 18°, 19°, 20°, between 4° and 6°, between 0° and 5°, between 3° and 5°, or any range of the foregoing values. In some embodiments, the spinal implant device 10 can be slightly enlarged at the leading or distal end 20. The distal end 20 can be the maximum height of the spinal implant device 10. The spinal implant device 10 can taper slightly inward by the lordosis angle toward the proximal end 22. In some embodiments, the lower wall 32 of the spinal implant device 10 can be tapered by the lordosis angle. In some embodiments, the upper wall 30 of the spinal implant device 10 can be tapered by the lordosis angle. In some embodiments, the upper surface of the spinal implant device 10 is tapered by the lordosis angle. In some embodiments, both the upper and the lower surface of the spinal implant device 10 taper inward. FIG. 1 illustrates the spinal implant device 10 without a lordosis angle and FIG. 2 illustrates the spinal implant device 10 with a lordosis angle.

In some embodiments, the spinal implant device 10 can have a slight inclination, called a kyphosis angle. In some embodiments, the kyphosis angle is approximately 5°. Other configurations are contemplated, for example 1°, 2°, 3°, 4°, 5°, 6°, 7°, 8°, 9°, 10°, 11°, 12°, 13°, 14°, 15°, 16°, 17°, 18°, 19°, 20°, between 4° and 6°, between 0° and 5°, between 3° and 5°, or any range of the foregoing values. In some embodiments, the spinal implant device 10 can be slightly enlarged at the leading or distal end 20 to correct kyphosis. In some embodiments, the spinal implant device 10 can be slightly enlarged at the trailing or proximal end 22 to correct kyphosis. In some embodiments, the spinal implant device 10 can be wedge shaped. In some embodiments, the upper wall 30 of the spinal implant device 10 can be tapered by the kyphosis angle. In some embodiments, the lower wall 32 of the spinal implant device 10 can be tapered by the kyphosis angle. In some embodiments, the upper surface of the spinal implant device 10 is tapered by the kyphosis angle.

The spinal implant device 10 can be designed to mimic the space between adjacent vertebrae. In some embodiments, the spinal implant device 10 can help to restore the normal angles between adjacent vertebrae to correct for spinal deformities. If a neutral vertical alignment is desired between two vertebrae, the upper and lower walls 30, 32 can have generally parallel and planar orientations. If a non-neutral alignment is desired, for instance to maintain a specific spinal curvature, the upper and lower walls 30, 32 can have a wedge-like relationship. In some embodiments, the non-neutral alignment with respect to the anterior-posterior direction can be used to compensate for excessive lordosis or kyphosis in portions of the vertebral column. The height of the spinal implant device 10 at any section between the upper and lower walls 30, 32 can accommodate degenerative changes or anatomical anomalies. The height of the spinal implant device 10 at any section between the upper and lower walls 30, 32 can provide load bearing support to the adjacent vertebrae.

Figure 3:
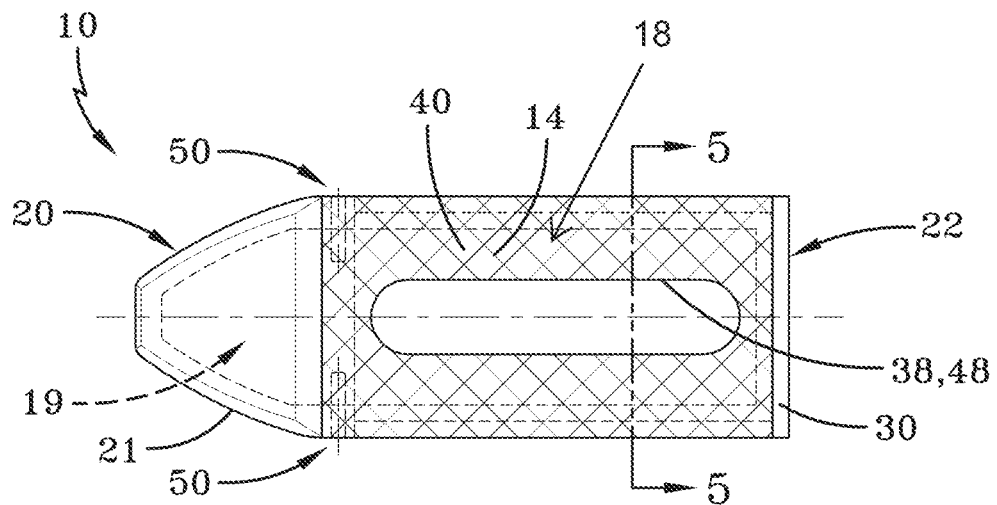
FIG. 3 is a top view of the spinal implant device of FIG. 1.

FIG. 3 illustrates a top view of the spinal implant device 10 with the movable lid 40 in a closed position. In some embodiments, the spinal implant device 10 can include features to facilitate holding the spinal implant device 10 in position between the vertebrae. FIG. 3 illustrates a plurality of facets or ridges 14. The ridges 14 are illustrated on the movable lid 40. In some embodiments, the ridges 14 are positioned on the upper surface of the spinal implant device 10, the lower surface of the spinal implant device 10, or both the upper surface and the lower surface of the spinal implant device 10. The upper surface of the spinal implant device 10 and the lower surface of the spinal implant device 10 can include the same ridges or different ridges. In some embodiments, the ridges 14 can extend over the entire upper surface of the spinal implant device 10 or the entire lower surface of the spinal implant device 10, or portions thereof. The ridges 14 can be positioned on any exterior surface configured to contact the anatomy of the patient. In some embodiments, the ridges 14 on the upper surface of the spinal implant device 10 and/or the lower surface of the spinal implant device 10 are directionally oriented such that the spinal implant device 10 can slide easily in between the vertebrae. In some embodiments, the ridges 14 on the upper surface of the spinal implant device 10 and/or the lower surface of the spinal implant device 10 are directionally oriented such that the spinal implant device 10 can directionally resist being pulled out from between the vertebrae. In some embodiments, the directionally oriented ridges 14 can limit or prevent the spinal implant device 10 from backing out once the spinal implant device 10 is positioned between the adjacent vertebrae.

In some embodiments, the spinal implant device 10 can have surface projections, indentations, or holes or pores that can alter the characteristics of a surface of the spinal implant device 10. Referring to FIG. 3, in some embodiments, angled projections, barbs, teeth, or ramped surfaces can incline outwardly from one or more exterior surfaces. In some embodiments, these features can allow insertion of the spinal implant device 10 in one direction but resist movement in the opposite direction. These ridges 14 can be advantageous in reducing the migration of the spinal implant device 10 out of the intervertebral space. In some methods, improved fixation of the spinal implant device 10 can maintain the position of the spinal implant device 10 during initial placement between vertebral bodies, thereby reducing the risk of back out. The ridges 14 can be provided on the upper and lower surfaces, or a portion thereof, of the spinal implant device 10, but other surfaces can also have other tissue or bone engagement structures.

Figure 4:
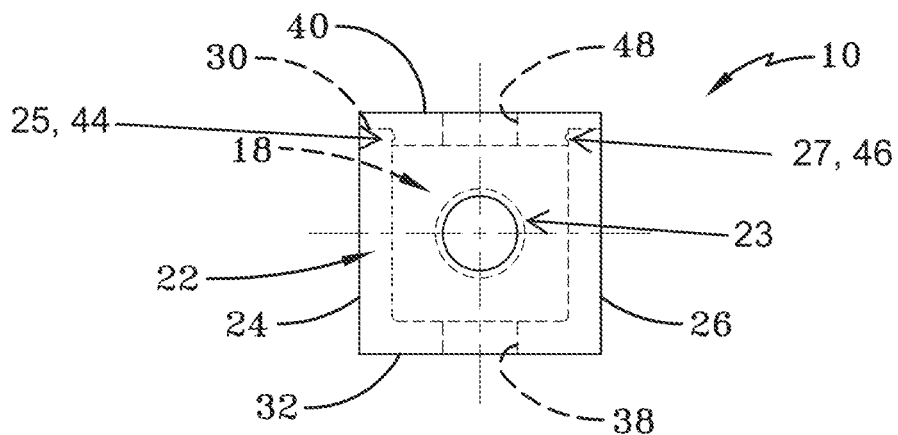
FIG. 4 is a proximal end view of the spinal implant device of FIG. 1.
Figure 5:
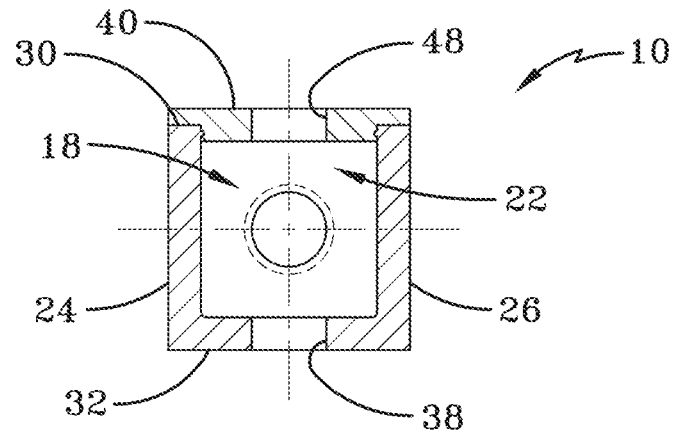
FIG. 5 is a cross-sectional view taken along line 5-5 of FIG. 3.

FIGS. 4 and 5 illustrate a cross-sectional view of the spinal implant device 10 with the movable lid 40 in a closed position. Referring to FIGS. 3-5, the spinal implant device 10 can include an opening 38 extending through the lower surface. The opening 38 can extend through the lower wall 32. The opening 38 can be elongate. The opening 38 can extend along the length of the spinal implant device 10. While one opening 38 is illustrated, the lower surface can include one or more openings (e.g., one, two, three, four, five, or six). The spinal implant device 10 can include an opening 48 extending through the upper surface. In some embodiments, the opening 48 can extend through the movable lid 40. In some embodiments, the opening 48 can extend through the upper wall 30. The opening 48 can be elongate. The opening 48 can extend along the length of the spinal implant device 10. While one opening 48 is illustrated, the upper surface can include one or more openings (e.g., one, two, three, four, five, or six). The openings 38, 48 can be located on opposed surfaces of the spinal implant device 10. The openings 38, 48 can be parallel. The openings 38, 48 can be offset. The openings 38, 48 can be the same size, shape, and/or configuration. The openings 38, 48 can be different sizes, shapes, and/or configurations. While the openings 38, 48 are illustrated as elongate shapes with rounded corners, any shape is contemplated, for example, oval, circular, ellipse, crescent, triangular, square, rectangular, rhombus, or polygonal. In some embodiments, each opening 38, 48 extends along a portion of the length of the spinal implant device 10 (e.g., 10% of the length, 20% of the length, 30% of the length, 40% of the length, 50% of the length, 60% of the length, 70% of the length, 80% of the length, 90% of the length, or 100% of the length, or any range of the foregoing values).

FIGS. 4 and 5 illustrate the openings 38, 48 extending from the cavity 18 to the outer surfaces. In some embodiments, the openings 38, 48 extend from the cavity 19 to the outer surfaces. In some embodiments, there may be one or more of the openings 38, 48 from the cavity 18 and/or from the cavity 19 to the outer surfaces. These openings 38, 48 can allow bony growth into the openings 38, 48. The cavity 18, and optionally cavity 19, within the spinal implant device 10 can also be filled with one or more materials. The cavity 18, and optionally cavity 19, within the spinal implant device 10 can also be designed to retain at least a portion of the one or more materials. In some embodiments, the material can be any material which is osteoconductive. The material can serve as a scaffold for new bone graft, for instance through the openings 38, 48. The material promotes new bone growth by the vertebral end plates. In some embodiments, the material can be any material which is osteoinductive. The material can stimulate cells to begin new bone formation. In some embodiments, the material comprises bone morphogenetic proteins. In some embodiments, the material comprises other osteoinductive cell mediators. In some embodiments, the material facilitates in forming new osteoblasts, thereby promoting faster integration of the new bone growth. In some embodiments, the material can be any material which allows for osteogenesis. The material itself can stimulate new bone growth by originating osteoblasts.

In some embodiments, the material is graft material. In some embodiments, the graft material can be an autograft, allograft, xenograft or synthetic material. In some embodiments, the graft material is limited to bone graft material which is osteoinductive. In some embodiments, the graft material is limited to bone graft material which is osteogenic. In some embodiments, the synthetic graft material can be ceramic-based, silicon-based or calcium-based. In some embodiments, the graft material can include osteoinductive factors to promote bone ingrowth. In some embodiments, the spinal implant device 10 can be packed with an allogeneic bone scaffold. In some embodiments, the spinal implant device 10 can be packed with allograft or allograft granules. In some embodiments, the spinal implant device 10 can be packed with cancellous or cortical bone. In some embodiments, the spinal implant device 10 can be packed with bone mixed with saline, blood, and/or bone marrow. In some embodiments, the spinal implant device 10 can be packed with demineralized cancellous sponge.

In some embodiments, the spinal implant device 10 can be packed with a solid material. In some embodiments, the spinal implant device 10 can be packed a mineral and collagen composite. In some embodiments, the spinal implant device 10 can be packed with a composite of carbonate apatite. In some embodiments, the spinal implant device 10 can be packed with demineralized bone matrix. In some embodiments, the spinal implant device 10 can be packed with bone putty comprising cancellous bone chips and demineralized bone matrix.

In some embodiments, the spinal implant device 10 can be packed with a fluid material. In some embodiments, the spinal implant device 10 can be filled with amniotic fluid that supports cell growth. In some embodiments, the spinal implant device 10 can be filled with growth factor, cytokines, extracellular matrix molecules, or proteoglycans.

The cavity 18 can be designed to be packed with one or more materials. When present, the cavity 19 can also be packed with one or more materials. The spinal implant device 10 can be designed such that a large volume of material can be filled into the cavity 18, and optionally 19. The spinal implant device 10 can be designed such that a large volume of material can be retained within the spinal implant device 10. In some embodiments, the cavity 18, together with the cavity 19 if provided, comprises a portion of the volume of the spinal implant device 10 (e.g., 50% of the volume, 60% of the volume, 70% of the volume, 80% of the volume, 90% of the volume, or 100% of the volume, or any range of the foregoing values). In some embodiments, the one or more materials fill a portion of the volume of the spinal implant device 10 (e.g., 50% of the volume, 60% of the volume, 70% of the volume, 80% of the volume, 90% of the volume, or 100% of the volume, or any range of the foregoing values).

Referring to FIGS. 3-5, the spinal implant device 10 can provide an open access area between the adjacent vertebrae. The spinal implant device 10 can provide an open access area through the elongated opening 48 in the movable lid 40 and the elongated opening 38 of the lower wall 32. FIG. 3 illustrates the openings 38, 48 are aligned to provide a vertical flow path between adjacent vertebrae when the spinal implant device 10 is positioned. FIG. 4 illustrates a proximal end view of the spinal implant device 10. The proximal end view of the spinal implant device 10 illustrates the opening 23 that can be adapted to provide an attachment location for the insertion tool. FIG. 5 illustrates the cross-sectional view of FIG. 3 taken along the line 5-5. This view is directionally looking toward the proximal end 22 of the spinal implant device 10. The movable lid 40 is in a closed position in FIGS. 3-5. In some embodiments, the central cavity 18 is fully unobstructed in the internal volume such that a large volume of osteoinductive material can be filled into the cavity 18.

FIG. 6A is a partial exploded view showing the mechanical hinge 50. The mechanical hinge 50 can couple the movable lid 40 to the upper wall 30. The movable lid 40 and the upper wall 30 can include corresponding openings to accept one or more pins 60. In some embodiments, the mechanical hinge 50 can include a pair of pins 60, but a single pin 60 is contemplated. In some embodiments, the mechanical hinge 50 can be located near the distal end 20. The mechanical hinge 50 can couple the movable lid 40 to the upper wall 30 near the distal end 20. In some embodiments, the mechanical hinge 50 can be located near the proximal end 22. The mechanical hinge 50 can couple the movable lid 40 to the upper wall 30 near the proximal end 22. In some embodiments, the mechanical hinge 50 can be located near the side wall 24. The mechanical hinge 50 can couple the movable lid 40 to the upper wall 30 near the side wall 24. In some embodiments, the mechanical hinge 50 can be located near the side wall 26. The mechanical hinge 50 can couple the movable lid 40 to the upper wall 30 near the side wall 26.

In some embodiments, the movable lid 40 can include the stepped inner surface 41. In some embodiments, a portion of the stepped inner surface 41 can abut the upper surface of the two opposing side walls 24, 26. In some embodiments, a portion of the stepped inner surface 41 can extend into the cavity 18. In some embodiments, a portion of the stepped inner surface 41 can extend along the inner surface of the two opposing side walls 24, 26. The stepped inner surface 41 can be designed to engage with the upper wall 30. The stepped inner surface 41 of the movable lid 40 can distribute load bearing forces to the upper wall 30. The stepped inner surface 41 of the movable lid 40 can distribute load bearing forces to the two opposing side walls 24, 26. The upper wall 30 can provide support to the movable lid 40 in a closed position. In some embodiments, the movable lid 40 interlocks with the upper wall 30 and the two opposing side walls 24, 26. In some embodiments, the movable lid 40 forms a frictional fit with the upper wall 30 and the two opposing side walls 24, 26. In some embodiments, the movable lid 40 forms an interference fit with the upper wall 30 and the two opposing side walls 24, 26. In some embodiments, the movable lid 40 rests against the upper wall 30 and the two opposing side walls 24, 26.

Figure 6B:
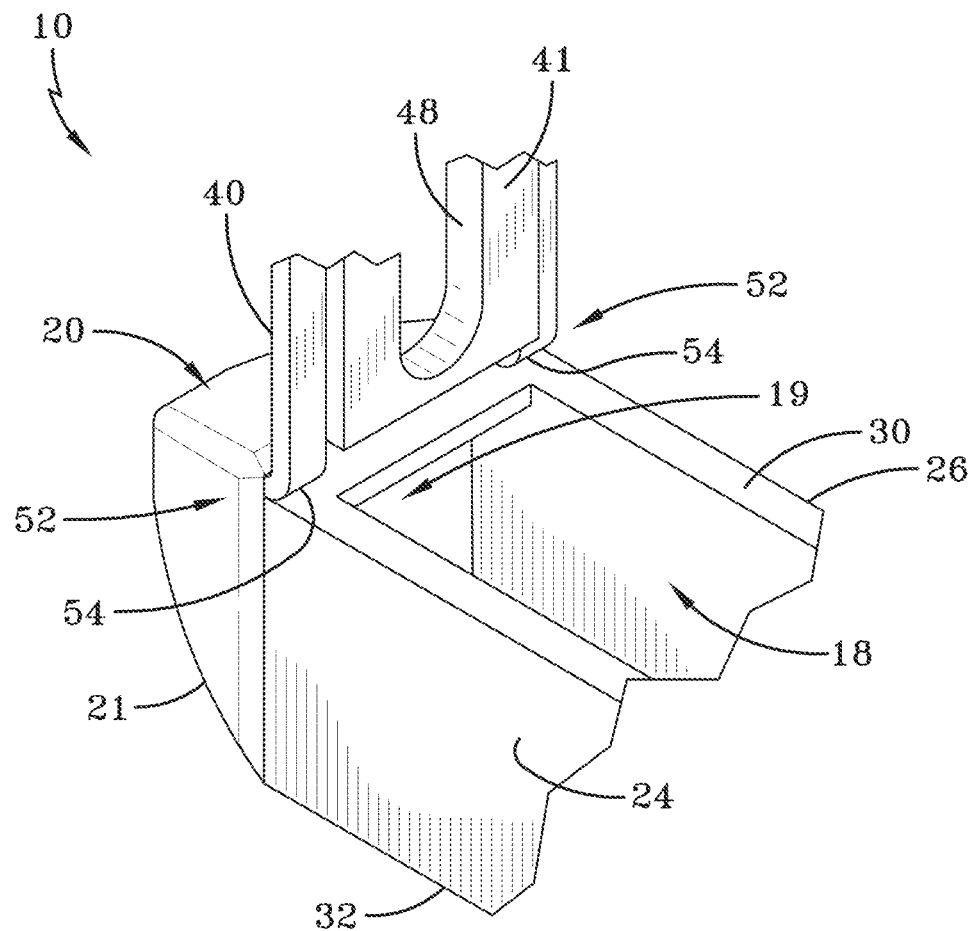
FIG. 6B is a partial view showing a living hinge.

FIG. 6B is a partial view showing an embodiment of a living hinge 52. In some embodiments, the living hinge 52 can connect the movable lid 40 to the upper wall 30. In some embodiments, the living hinge 52 can be integral with one or more walls of the spinal implant device 10. In some embodiments, the living hinge 52 can be integral with the distal end 20. In some embodiments, the living hinge 52 can be integral with the side wall 24. In some embodiments, the mechanical hinge living hinge 52 can be integral with the side wall 26. In some embodiments, the living hinge 52 can be integral with the proximal end 22. In some embodiments, the living hinge 52 can be integral to the upper wall 30 near the distal end 20 of the spinal implant device 10. In some embodiments, the movable lid 40 is integrally formed with the distal end 20. In some embodiments, the movable lid 40 can be monolithically formed with the distal end 20. The living hinge 52 can be formed by overlapping curved features.

In some embodiments, the movable lid 40 can be integrally connected to the spinal implant device 10 by employing a living hinge 52. The living hinge 52 can be formed as a thin flexible web 54 connecting a portion of the body structure 12 directly to the movable lid 40. The movable lid 40 can pivot or rotate back and forth between a closed position and an opened position by flexing the thin flexible web 54. In some embodiments, the movable lid 40 can include the stepped inner surface 41. In some embodiments, a portion of the stepped inner surface 41 can abut the upper wall 30. In some embodiments, the living hinge 52 extends from this portion. A portion of the stepped inner surface 41 can extend into the cavity 18 and along the inner surface of the two opposing side walls 24, 26. The upper wall 30 can provide support to the movable lid 40 in a closed position.

FIGS. 7A and 7B illustrates partial views of the stepped inner surface 41 of the movable lid 40. In some embodiments, the spinal implant device 10 can include features to facilitate holding the movable lid 40 in a closed position. FIG. 7A illustrates a pair of side grooves 44, 46 on the movable lid 40. The side grooves 44, 46 can be located on opposed sides of the stepped inner surface 41. The side grooves 44, 46 can be the same size, shape, or configuration. The side grooves 44, 46 can have different sizes, shapes, or configurations. While two side grooves 44, 46 are illustrated, the movable lid 40 can include one or more grooves (e.g., one groove, two grooves, three grooves, four grooves, five grooves, or six grooves). The grooves 44, 46 can be positioned on any surface of the movable lid 40 designed to engage a portion or wall of the spinal implant device 10.

The two side grooves 44, 46 are designed to be adjacent to the two opposing side walls 24, 26. The two opposing side walls 24, 26 can include a corresponding feature to interlock with the side grooves 44, 46. The two opposing side walls 24, 26 can include a pair of protrusions 25, 27. The protrusion 25 can be located on the side wall 24 and the protrusion 27 can be located on the side wall 26. The protrusions 25, 27 can be located along upper edges of the two opposing side walls 24, 26. The side grooves 44, 46 can be designed to fit over protrusions 25, 27. The side grooves 44, 46 can be designed to interlock with the protrusions 25, 27 of the two opposing side walls 24, 26 when the movable lid 40 is in a closed position. The interlock between the side grooves 44, 46 and the protrusions 25, 27 can structurally enhance the spinal implant device 10 to assist in preventing the two opposing side walls 24, 26 from buckling or bowing under the loads when the spinal implant device 10 is implanted between the adjacent vertebrae. In some embodiments, the movable lid 40 includes one or more protrusions and the two opposing side walls 24, 26 include one or more grooves. Other means to interlock the movable lid 40 and the side walls 24, 26 are contemplated including frictional fits, interference fits, snap fit, taper fit, hooks, detents, bayonet connections, ball and sockets, traps, annular fits, cantilever hooks, or compressive hooks, or other connection means. In some embodiments, the movable lid 40 is reversible between an opened position and a closed position. In some embodiments, the movable lid 40 is irreversible once closed. Referring back to FIG. 4, the movable lid 40 is shown in a closed position. The interlock between the side grooves 44, 46 and the protrusions 25, 27 is illustrated.

FIG. 7B illustrates an end groove 47 on the movable lid 40. In some embodiments, the end groove 47 can be continuous with the side grooves 44, 46. The end groove 47 and the side grooves 44, 46 can form a "U" shaped groove. The end groove 47 and the side grooves 44, 46 can extend along a portion of the stepped inner surface 41 of the movable lid 40. In some embodiments, the end groove 47 can be separate from the side grooves 44, 46. The end groove 47 and the side grooves 44, 46 can be the same size, shape, or configuration. The end groove 47 and the side grooves 44, 46 can have different sizes, shapes, or configurations. While one end groove 47 is illustrated, the movable lid 40 can include one or more grooves (e.g., one groove, two grooves, three grooves, four grooves, five grooves, or six grooves). The end groove 47 can be positioned on any surface of the movable lid 40 designed to engage a portion or wall of the spinal implant device 10.

The end groove 47 is designed to be adjacent to the proximal end 22. The proximal end 22 can include a corresponding feature to interlock with the end groove 47. The proximal end 22 can include a protrusion. The protrusion can be located along upper edge of the proximal end 22. The end groove 47 can be designed to interlock with the protrusion of the proximal end 22 when the movable lid 40 is in a closed position. The interlock between the end groove 47 and the proximal end 22 can structurally enhance the spinal implant device 10, for instance, to prevent buckling or bowing of one or more walls. Other means to interlock the movable lid 40 and the proximal end 22 are contemplated. In some embodiments, the spinal implant device 10 can include only one side groove. In some embodiments, the spinal implant device 10 can include two or more side grooves. In some embodiments, the spinal implant device 10 can include only one end groove. In some embodiments, the spinal implant device 10 can include two or more end grooves. In some embodiments, the spinal implant device 10 can include one or more side grooves and one or more end grooves. The end groove 47 can be an additional or alternative interlock between the movable lid 10 and one or more walls of the spinal implant device 10.

The spinal implant device 10 can include many advantageous features. The spinal implant device 10 can include large graft windows 38, 48. The spinal implant device 10 can be straight or curved depending on the intended approach. The spinal implant device 10 can include convex surfaces to match the general shape of the end plates. The spinal implant device 10 can include lordosis configurations. The spinal implant device 10 can include kyphosis configurations. The spinal implant device 10 can include serrated ridges 14. The spinal implant device 10 can include a tapered leading edge at the distal end 20. The spinal implant device 10 can comprise a strong, durable construction. The spinal implant device 10 can comprise a biocompatible material, such as PEEK.

The spinal implant device 10 can be packed with a material such as a bone graft material. The spinal implant device 10 can include the movable lid 40 that allows access to the full cavity of the spinal implant device 10. The spinal implant device 10 can have relatively thin walls in order to maximize the internal volume for the material. The upper surface including the movable lid 40 and lower surface of the spinal implant device 10 can have a high surface area for contact with the end plates and distribution of load.

The spinal implant device 10 can include the mechanical hinge 50. The mechanical hinge 50 can be located on one side of the spinal implant device 10. The mechanical hinge 50 can allow the movable lid 40 to be opened and closed. The mechanical hinge 50 can allow the movable lid 40 to provide access to the internal space of the spinal implant device 10. The spinal implant device 10 can allow access to the bone graft chamber by means of a hinged movable lid 40. The spinal implant device 10 can allow a greater volume of material to be packed into the spinal implant device 10. The spinal implant device 10 can include a high surface area of the upper and lower surfaces of the spinal implant device 10 that come in contact with the vertebral bodies. This high surface area can reduce the stress on the spinal implant device 10 and the vertebral body, ideally lowering the incidence of subsidence. Subsidence occurs when a spinal implant device migrates into surrounding bone. The vertebral bodies can surround a portion of the movable lid 40, the upper surface 30 and/or the lower surface 32 during subsidence.

The spinal implant device 10 can be advantageous over conventional devices. Conventional devices can include a cage with relatively thick walls. In some embodiments, the spinal implant device 10 can include one or more thin walls. In some embodiments, the spinal implant device 10 can provide a greater volume of material that can be used in a fusion. In some embodiments, the spinal implant device 10 can deliver a larger volume of material to the disc space. In some embodiments, the spinal implant device 10 can provide higher surface contact with the endplates, and therefore lower stress to the endplates. In some embodiments, the spinal implant device 10 can provide better fusion and less subsidence.

Figure 8:
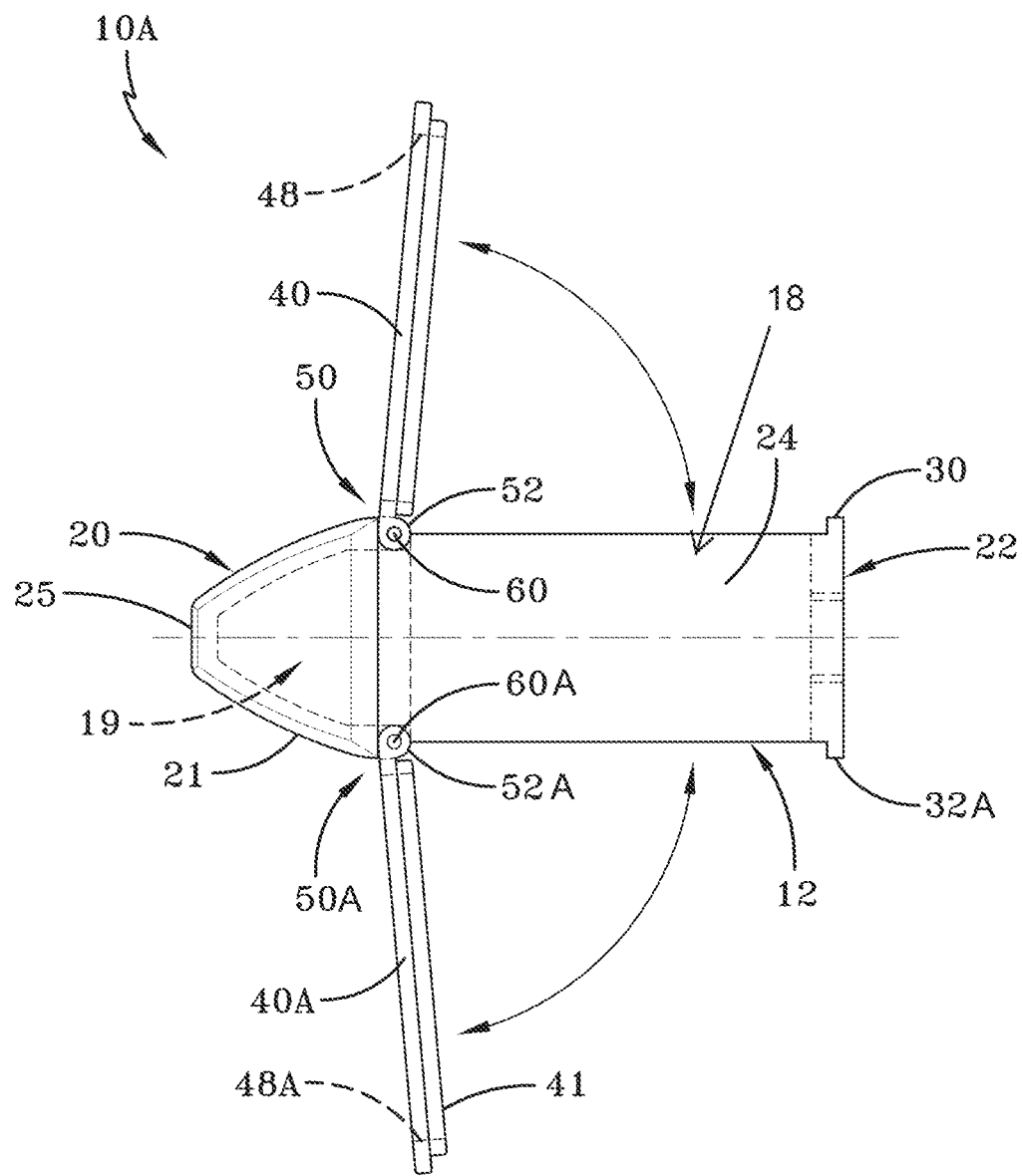
FIG. 8 is a view of an embodiment of a spinal implant device with movable lids shown in opened positions.

FIG. 8 illustrates a cross-sectional view of a spinal implant device 10A. The spinal implant device 10 can include a body structure 12, a distal end 20 including a frustoconical or convex curved shape 21 and a flat or blunt portion of the distal end 20. The spinal implant device 10A can include two opposing side 24, 26, an upper wall 30, and a lower wall 32A.

The spinal implant device 10 can include a movable lid 40 and a movable lid 40A. In the illustrated embodiment, the movable lid 40 can be coupled to the upper wall 30 of the spinal implant device 10A. In some embodiments, the movable lid 40A can be coupled to the lower wall 32A of the spinal implant device 10. In the illustrated embodiment, the movable lid 40 and the upper wall 30 together form the upper surface of the spinal implant device 10. In the illustrated embodiment, the movable lid 40 and the upper wall 30 are flush when the movable lid 40 is in a closed position. In the illustrated embodiment, the movable lid 40A and the lower wall 32A together form the lower surface of the spinal implant device 10. In the illustrated embodiment, the movable lid 40A and the lower wall 32A are flush when the movable lid 40A is in a closed position. The movable lids 40, 40A are shown in opened positions in FIG. 8.

In some embodiments, each movable lid 40, 40A can include a mechanical hinge 50, 50A. In some embodiments, the mechanical hinges 50, 50A can be positioned towards the distal end 20 of the spinal implant device 10A. In the illustrated embodiment, a first mechanical hinge 50 can connect the movable lid 40 to the upper wall 30. The first mechanical hinge 50 can allow for pivoting motion of the movable lid 40 relative to the upper wall 30. In the illustrated embodiment, the second mechanical hinge 50A can connect the movable lid 40A to the lower wall 32A. The second mechanical hinge 50A can allow for pivoting motion of the movable lid 40A relative to the lower wall 32. In some embodiments, each mechanical hinge 50, 50A can include one or more pins 60, 60A. In some embodiments, the movable lid 40 can be connected near the distal end 20. The movable lid 40 can be connected to the upper wall 30 at a hinged location 52. In some embodiments, the movable lid 40A can be connected near the distal end 20. The movable lid 40A can be connected to the lower wall 32A at a hinged location 52A.

The spinal implant device 10A can include a cavity 18 and a distal end cavity 19. The cavity 18 can be designed to be filled with a material. When present, the cavity 19 can also be filled with a material. In some methods, the material is an osteoinductive material. The spinal implant device 10A can be designed such that a large volume of material can be filled into the cavity 18. The spinal implant device 10A can be designed to allow material to be filled from the upper surface of the spinal implant device 10A, the lower surface of the spinal implant device 10A, or both the upper and lower surface of the spinal implant device 10A. The movable lid 40 can be considered a movable upper lid. The movable lid 40A can be considered a movable lower lid. The movable lid 40 can include an opening 48. The movable lid 40A can include an opening 48A. The movable lids 40, 40A can be connected to the respective one of the upper and lower walls 30, 32A.

In some embodiments, the spinal implant device 10A can be symmetrical along at least one axis of symmetry. In some embodiments, the upper wall 30 and the lower wall 32 are identical or substantially similar. In some embodiments, the spinal implant device 10A can be inserted directionally with either the upper wall 30 facing upward or the lower wall 32A facing upward. The spinal implant device 10A can be rotated 180°. In some embodiments, the spinal implant device 10A is symmetrical relative to the top and the bottom. In some embodiments, the movable lids 40, 40A are the same in size, shape, or configuration. In some embodiments, the movable lids 40, 40A are different in size, shape, or configuration. Variations in the hinged connection can be made. In some embodiments, one or more of the movable lids 40, 40A can be connected to one of the two opposing side walls 24, 26. The movable lid 40, 40A can be designed to pivot about a lateral pivot to open and close. One or more of the movable lids 40, 40A can be connected near the proximal end 22. In some embodiments, the movable lid 40, 40A can be hinged to open and close relative to the spinal implant device 10A regardless of the location of the hinge 50, 50A.

In some embodiments, the movable lid 40A can be designed such that the movable lid 40A is normally closed. In some embodiments, the movable lid 40A can be designed such that the movable lid 40A is normally opened. In some embodiments, each movable lid 40, 40A can be designed to pivot about the body structure 12 so that each movable lid 40, 40A can provide access to pack bone growth material into one or more internal cavities 18, 19. The user can pack the spinal implant device 10A, including filling the cavity 18 and the distal end cavity 19 if provided. The spinal implant device 10A can be filled with any material including allograft bone material or autograft bone material or any other osteoinductive material. In some methods, the user can pack the internal cavity 18, 19 full. In some methods, the user can close the movable lid 40, 40A by interlocking each lid 40, 40A in position prior to inserting the spinal implant device 10A between the vertebral bodies. In some methods, each movable lid 40, 40A can interlock with a portion of a wall, as described herein.

As described herein, the spinal implant device 10 can include openings 38, 48. The openings 38, 48 can allow bone in growth through the spinal implant device 10. The openings 38, 48 can allow the material retained within to flow outward. The openings 38, 48 can facilitate fusion of adjacent vertebrae. The openings 38, 48 can provide adequate space for bone growth between the end plates of the vertebrae which the spinal implant device 10 is supporting. As described herein, the spinal implant device 10A can include openings 48, 48A. The openings 48, 48A can extend through the movable lid 40, 40A. The openings 48, 48A can allow fusion through the spinal implant device 10A. The openings 48, 48A can allow the material to bridge between the vertebral endplates. The openings 48, 48A can provide a vertical flow path between adjacent vertebrae. The openings 48, 48A can provide adequate space for bone ingrowth and fusion between end plates.

The spinal implant device 10, 10A can be advantageous over conventional devices. In conventional devices, osteoinductive material can extrude out of the device without the ability to retain the packed material inside the device. In some methods, the spinal implant device 10, 10A can retain material within the spinal implant device 10, 10A. In conventional devices, osteoinductive material is packed after the device has been inserted between the vertebrae. Trying to pack material after a conventional device has been inserted between the vertebrae is both cumbersome and difficult. The methods of use of conventional devices often waste material and obstruct an otherwise clean surgical site between the adjacent vertebrae. In some methods, the spinal implant device 10, 10A can be packed prior to inserting the spinal implant device 10, 10A. In some embodiments, the spinal implant device 10, 10A provides a very compact and clean way to provide a fully packed spinal implant device between adjacent vertebrae.

The spinal implant device 10, 10A can be utilized in any surgical technique. Common fusion surgical techniques include PLIF, ALIF, and TLIF. As described herein PLIF stands for Posterior Lumbar Interbody Fusion ("PLIF"). In the PLIF approach, the vertebrae can be approached posteriorly. The spinal muscles can be retracted to provide access to the disc. In some methods, the lamina is removed to access the nerve roots. In some methods, the facet joints can be removed, trimmed, or replaced. In some methods, the disc can be removed. In some methods, the bone surfaces can be prepared such as by decortication.

The spinal implant device 10, 10A can be prepared. In some methods, the movable lid 40 is opened by pivoting motion. In some methods, the central cavity 18 is packed with one or more materials. In some methods, the distal cavity 19 is packed with one or more materials. In some methods, the distal cavity 19 is packed with one or more materials before the cavity 18 is packed. In some methods, the movable lid 40 is closed by pivoting motion. In some methods, the movable lid 40 is closed by interlocking the movable lid with one or more walls. In some methods, the movable lid 40 is closed by interlocking the movable lid with the two opposing side walls 24, 26. In some methods, the movable lid 40 is closed by interlocking the movable lid 40 with the proximal end 22. In some methods, the movable lid 40 is closed to be flush with an exterior surface of the spinal implant device 10, 10A. In some methods, the movable lid 40A is closed prior to filling the spinal implant device 10A. In some methods, the movable lid 40A is closed after filling the spinal implant device 10A.

The spinal implant device 10, 10A can be inserted. In some methods, the spinal implant device 10, 10A can be inserted after being filled. In some methods, the spinal implant device 10, 10A can be inserted before being filled. In some methods, the spinal implant device 10, 10A can be partially inserted, then filled, and then fully inserted. Once inserted, the spinal implant device 10, 10A can promote fusion between the vertebrae. Bone growth can be facilitated by the openings 38, 48 in the spinal implant device 10 and openings 48, 48A in the spinal implant device 10A. In some methods, two or more spinal implant device 10, 10A can be inserted. In some methods, two or more spinal implant device 10, 10A are parallel within the disc space. In some methods, two or more spinal implant device 10, 10A extend in a posterior/anterior direction.

In the Transforaminal Lumbar Interbody Fusion ("TLIF") approach, access is provided from the side of the spinal canal through a midline incision. In some methods, the spinal implant device 10, 10A is inserted through a TLIF approach. In some embodiments, the spinal implant device 10, 10A is straight along the length for use with the TLIF approach. In some embodiments, the spinal implant device 10, 10A is curved along the length for use with the TLIF approach. In some embodiments, the spinal implant device 10, 10A is placed anteriorly. In some embodiments, the spinal implant device 10, 10A is placed at an oblique angle. In some embodiments, the spinal implant device 10, 10A has a longer length for use with the TLIF approach than the spinal implant device 10, 10A for use with the PLIF approach.

In the Anterior Lumbar Interbody Fusion ("ALIF") approach, access is provided through an anterior approach. In some methods, an incision is made in the lower abdominal area or on the side of the patient. In some methods, the muscles in the lower abdominal area are separated. In some methods, the spinal implant device 10, 10A is inserted through an ALIF approach.

In some embodiments, the spinal implant device 10 can be designed to allow compression. The body 12 can compress. The movable lid 40 can compress. One or more sidewalls 24, 26 can compress. The distal end 20 can compress. The proximal end 22 can compress. Any side or surface of the spinal implant device 10 can compress.

The spinal implant device can comprise a rigid, sturdy material. In some embodiments, compression occurs due to the structure of the spinal implant device. In some embodiments, compression does not occur due to material selection. In some embodiments, compression occurs due to material selection. In some embodiments, the rigidity and/or dimensions of the material can be selected to accommodate individual anatomy and/or physiologic requirements. The spinal implant device can include one or more features that facilitate compression.

Compression includes the gradual downward settling of the spinal implant device between the vertebrae. Compression can decrease the height of the spinal implant device. In some embodiments, compression can occur with little or no horizontal motion. In some embodiments, compression occurs with lengthening of the spinal implant device. In some embodiments, compression occurs with widening of the spinal implant device. In some embodiments, compression occurs with bowing of the spinal implant device.

The spinal implant device can include one or more features to facilitate compression. The feature can allow compressibility of the spinal implant device, or a portion thereof. The compressibility of the spinal implant device can be greatest at an apex of the spinal implant device. The feature can allow the height to decrease. The feature can allow the top surface to draw closer to the bottom surface. The feature can allow the bottom surface to draw closer to the top surface. The feature can allow the top surface and the bottom surface to draw together. The feature can compress under a load. The feature can compress under the forces from the vertebrae. The feature can compress under motion of the vertebrae.

In some embodiments, the feature is a hinge. The feature can be a living hinge. The feature can be a thin flexible hinge. The feature can be a flexure bearing. The feature can be any flexure. The feature can be any compliant mechanism. The feature can be engineered to be compliant to allow compression. The feature can allow pivoting motion. The feature can be any thinned section. The feature can be cut or machined into the spinal implant device. The feature can be positioned to allow the spinal implant device to compress. In some embodiments, the feature is positioned at or near the distal end of the spinal implant device. In some embodiments, the feature is positioned at or near the proximal end of the spinal implant device. In some embodiments, the feature is positioned at or near one or more side walls of the spinal implant device.

The feature can be made of the same material as adjacent or other sections of the spinal implant device. The feature can be made of a different material than adjacent sections of the spinal implant device. The feature can be made of the same material as the two pieces the hinge connects. The spinal implant device can comprise at least one material selected from the group consisting of polymers, polyetheretherketone (PEEK), polyetherketoneketone (PEKK), polyethylene, fluoropolymers, hydrogels, elastomers, ceramics, zirconia, alumina, silicon nitride, metal(s), titanium, titanium alloy, Nitinol, cobalt chromium, stainless steel, and combinations of these materials. In some embodiments, the preferred material can be selected from the group consisting of titanium, titanium alloy, Nitinol, and combinations of these materials. In some embodiments, the feature is configured to flex without fatigue. In some embodiments, the feature comprises a material that allows for bending without fracture.

The feature can allow one or more rigid sections of the spinal implant device to bend or flex. The feature can allow the top portion or the bottom portion of the spinal implant device to bend or flex. The feature can allow the upper wall of the spinal implant device to bend or flex. The feature can allow the movable lid, if present, of the spinal implant device to bend or flex. The feature can pivot a top surface downward. The feature can pivot the upper wall downward. The feature can pivot the movable lid, if present, downward. In some embodiments, the feature is configured to only pivot.

In some embodiments, the feature can have a limited range of motion. The feature can be configured to pivot 1 degree, 2 degrees, 3 degrees, 4 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 120 degrees, 150 degrees, 180 degrees, 210 degrees, 240 degrees, 270 degrees, or any range including and between any of the foregoing values. The feature can be configured to pivot between 180 degrees and 210 degrees. The feature can allow a portion of the movable lid, if present, to rest on the same horizontal surface when opened as the bottom surface of the spinal implant device. The feature can be configured to compress 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.5 mm, 6 mm, 6.5 mm, 7 mm, 7.5 mm, 8 mm, 8.5 mm, 9 mm, 9.5 mm, 10 mm, between 1 mm and 3 mm, between 1 mm and 5 mm, between 1 mm and 10 mm, less than 1 mm, less than 3 mm, less than 5 mm, less than 10 mm, greater than 1 mm, greater than 3 mm, greater than 5 mm, or any range including and between any of the foregoing values. The feature can be configured to compress a percentage of the total height including 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or any range including and between any of the foregoing values. In some embodiments, the spinal implant device 10 can have an average height within the range of about 5 mm to about 20 mm (e.g., 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or between 7 and 14 mm, or any range including and between any of the foregoing values).

In some embodiments, this compression occurs under normal anatomical loads. In some embodiments, normal anatomical loads can include forces at which the spinal implant device remains elastic. In some embodiments, the mechanical properties of the spinal implant device could be similar to bone. In some embodiments, the mechanical properties of the spinal implant device could be similar to vertebral bodies. The feature can be configured to compress at 100N, 200 N, 300 N, 400 N, 500 N, 600 N, 700 N, 800 N, 900 N, 1000 N, 1100 N, 1200 N, 1300 N, 1400 N, 1500 N, 1600 N, 1700 N, 1800 N, 1900 N, 2000 N, 2100 N, 2200 N, 2300 N, 2400 N, 2500 N, 2600 N, 2700 N, 2800 N, 2900 N, 3000 N, 3100 N, 3200 N, 3300 N, 3400 N, 3500 N, over 100 N, over 300 N, over 500 N, over 700 N, between 700 N and 800 N, between 500 N and 1000 N, between 300 N and 500 N, or any range including and between any of the foregoing values. The feature can be configured to compress within the ranges mentioned above at normal anatomical loads and in some embodiments at 100N, 200 N, 300 N, 400 N, 500 N, 600 N, 700 N, 800 N, 900 N, 1000 N, 1100 N, 1200 N, 1300 N, 1400 N, 1500 N, 1600 N, 1700 N, 1800 N, 1900 N, 2000 N, 2100 N, 2200 N, 2300 N, 2400 N, 2500 N, 2600 N, 2700 N, 2800 N, 2900 N, 3000 N, 3100 N, 3200 N, 3300 N, 3400 N, 3500 N, over 100 N, over 300 N, over 500 N, over 700 N, between 700 N and 800 N, between 500 N and 1000 N, between 300 N and 500 N, or any range including and between any of the foregoing values. The spinal implant device can be configured to have a stiffness with the range of 2500 N/mm to 15000 N/mm.

In some embodiments, the spinal implant device reduces in height only. In some embodiments, the spinal implant device doesn't translate in any other direction. In some embodiments, the spinal implant device compresses a side wall. In some embodiments, the spinal implant device compresses a proximal end. In some embodiments, the spinal implant device compresses a distal end. In some embodiments, the spinal implant device compresses an internal feature. In some embodiments, the spinal implant device compresses an external feature. In some embodiments, the spinal implant device allows for compression to a desired height. The spinal implant device can allow for compression to a pre-determined height. The pre-determined height can be determined based on the interaction of two or more components or surfaces. The pre-determined height can be determined based on two surfaces abutting. The pre-determined height can be determined based on interference.

As described herein, the spinal implant device can be packed with material. In some embodiments, the material comprise one or more graft materials. In some embodiments, the material comprises an autograft, allograft, xenograft or synthetic material. In some embodiments, the material comprises bone graft material which is osteoinductive. In some embodiments, the material comprises bone graft material which is osteogenic. In some embodiments, the material comprises synthetic graft material that is ceramic-based, silicon-based or calcium-based. In some embodiments, the material comprises osteoinductive factors to promote bone ingrowth. In some embodiments, the material comprises an allogeneic bone scaffold. In some embodiments, the material comprises allograft or allograft granules. In some embodiments, the material comprises cancellous or cortical bone. In some embodiments, the material comprises bone mixed with saline, blood, and/or bone marrow. In some embodiments, the material comprises demineralized cancellous sponge.

In some embodiments, applying a force or load to the packed material can promote fusion. The effect of load on packed material can be to promote fusion. The spinal implant device can be designed to transfer a force or load from the vertebral end plates to the packed material. In some embodiments, the compression of the spinal implant device, or a portion thereof, can increase the load transferred to the packed material. In some embodiments, the compression of the spinal implant device can distribute the load transferred to the packed material. The load can be distributed more evenly across the surface of the packed material. The load can cause compression of the packed material. In some methods of use, the compression of the spinal implant device, and the resulting load on the packed material, can lead to better clinical outcomes. The compression of the spinal implant device can allow for increased load on the corresponding material disposed within the spinal implant device. In some embodiments, increased load can promote fusion.

Figure 9:
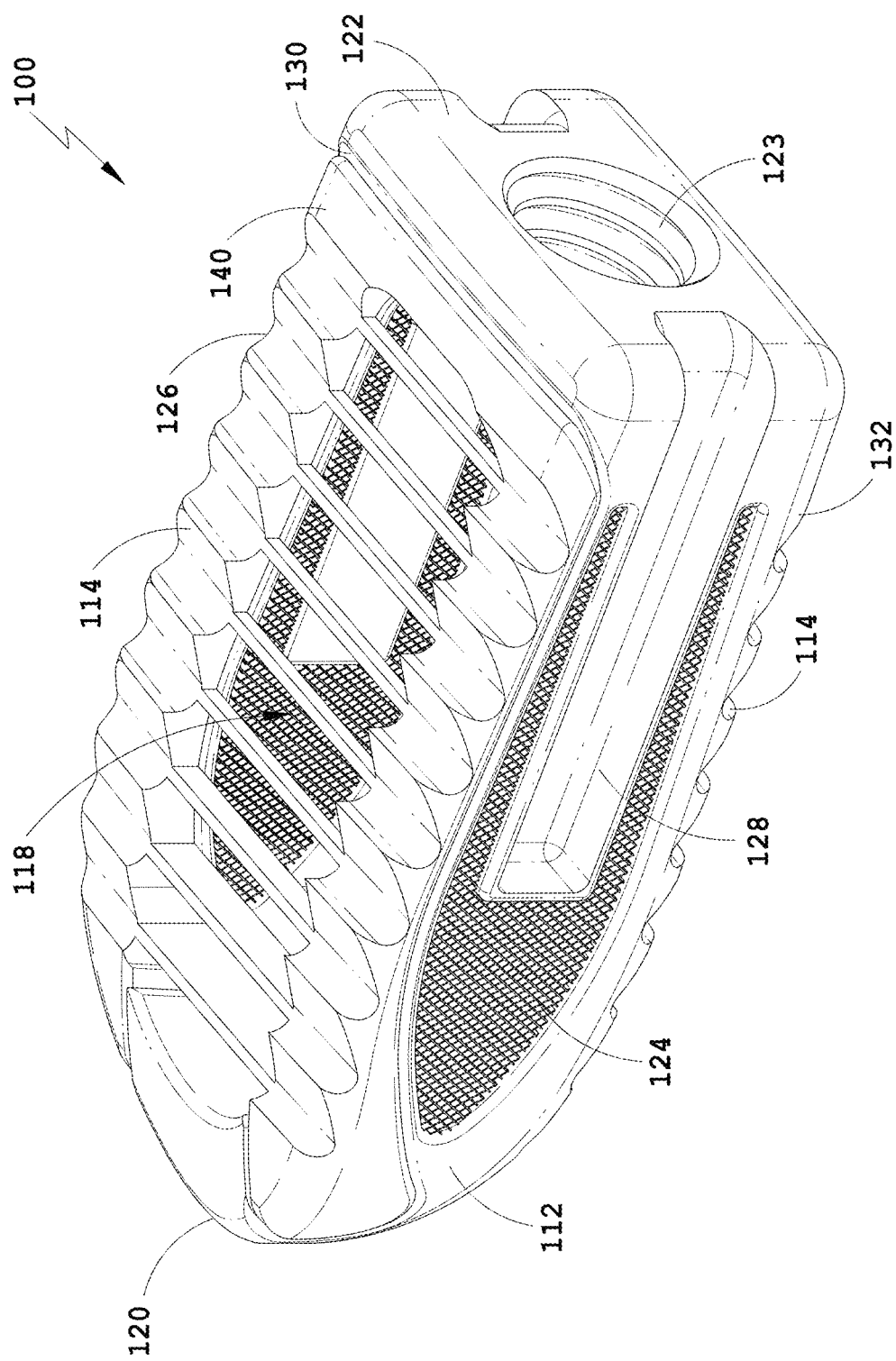
FIG. 9 is a perspective view of an embodiment of a spinal implant device with a movable lid shown in a closed position.

FIG. 9 illustrates a perspective view of a spinal implant device 100. The spinal implant 100 can include any of the features of the spinal implant device 10, 10A as described herein and can be used in any method or method step described herein. The spinal implant device 100 can include a body structure 112. The body structure 112 can be placed between adjacent vertebrae, such as a superior vertebra and an inferior vertebra. In some embodiments, the material selection of the spinal implant device 100, or a portion thereof, can facilitate compression of the spinal implant device 100. In some embodiments, the structure of the spinal implant device 100, or a portion thereof, can facilitate compression of the spinal implant device 100.

Figure 10:
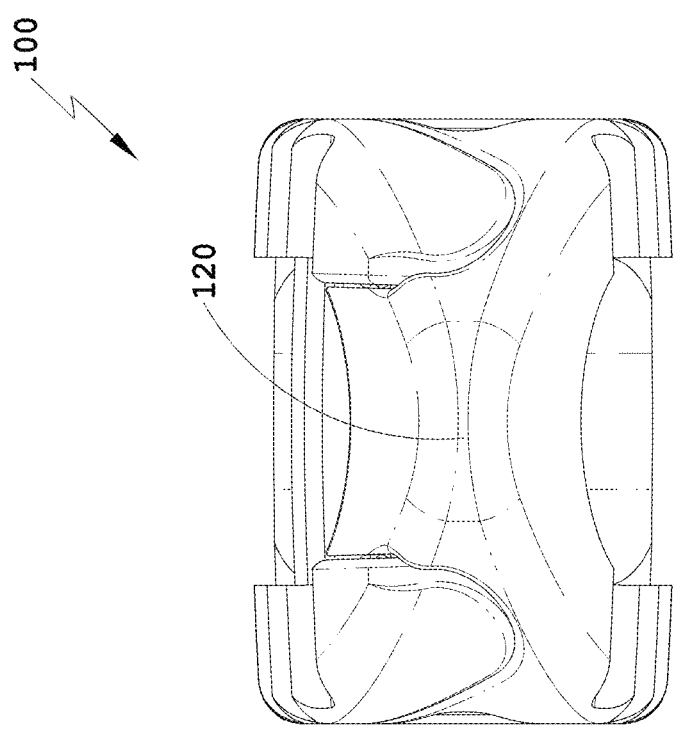
FIG. 10 is a distal view of the spinal implant device of FIG. 9.

FIG. 10 is a distal view of the spinal implant device 100. The spinal implant device 100 can include the distal end 120. In some methods of use, the distal end 120 can be the leading end which is inserted first into the intervertebral space. In some embodiments, the distal end 120 is tapered. The spinal implant device 100 can become progressively smaller toward the distal end 120. The upper and lower surfaces of the taper can be straight. The side surfaces of the taper can be convex. In some embodiments, two surfaces of the distal end 120 can taper, for instance, an upper surface and a lower surface of the distal end 120 can taper, forming a triangular prism or similar shape. In some embodiments, the upper surface and the lower surface of the distal end 120 equally taper. In some embodiments, the distal end 120 can include rounded corners or edges.

Figure 11:
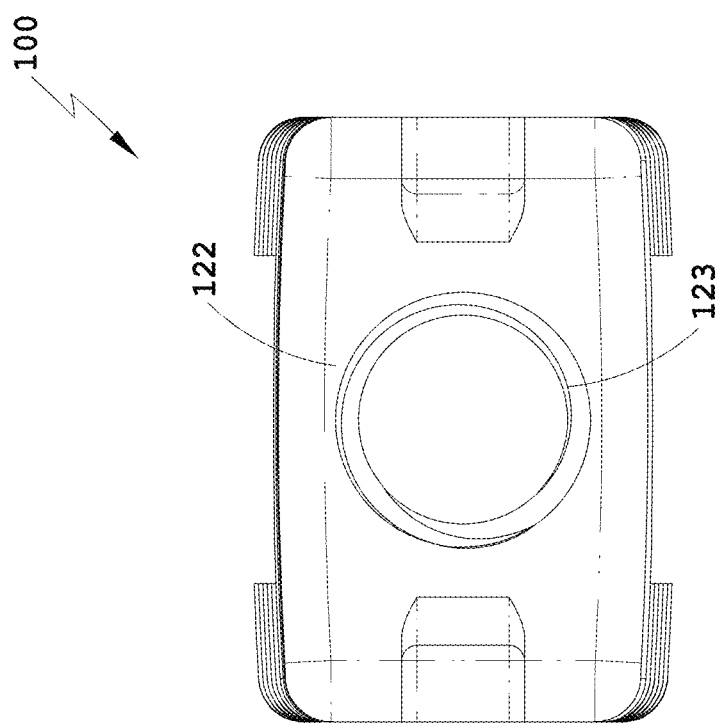
FIG. 11 is a proximal view of the spinal implant device of FIG. 9.

FIG. 11 is a proximal view of the spinal implant device 100. The spinal implant device 100 can include a proximal end 122. In some embodiments, the proximal end 122 forms a flat surface. In some embodiments, the proximal end 122 can include rounded corners or edges. In some embodiments, the proximal end 122 can include an opening 123 to accept an insertion tool. In some embodiments, the opening 123 can be threaded to engage a threaded tip of the insertion tool.

Figure 12:
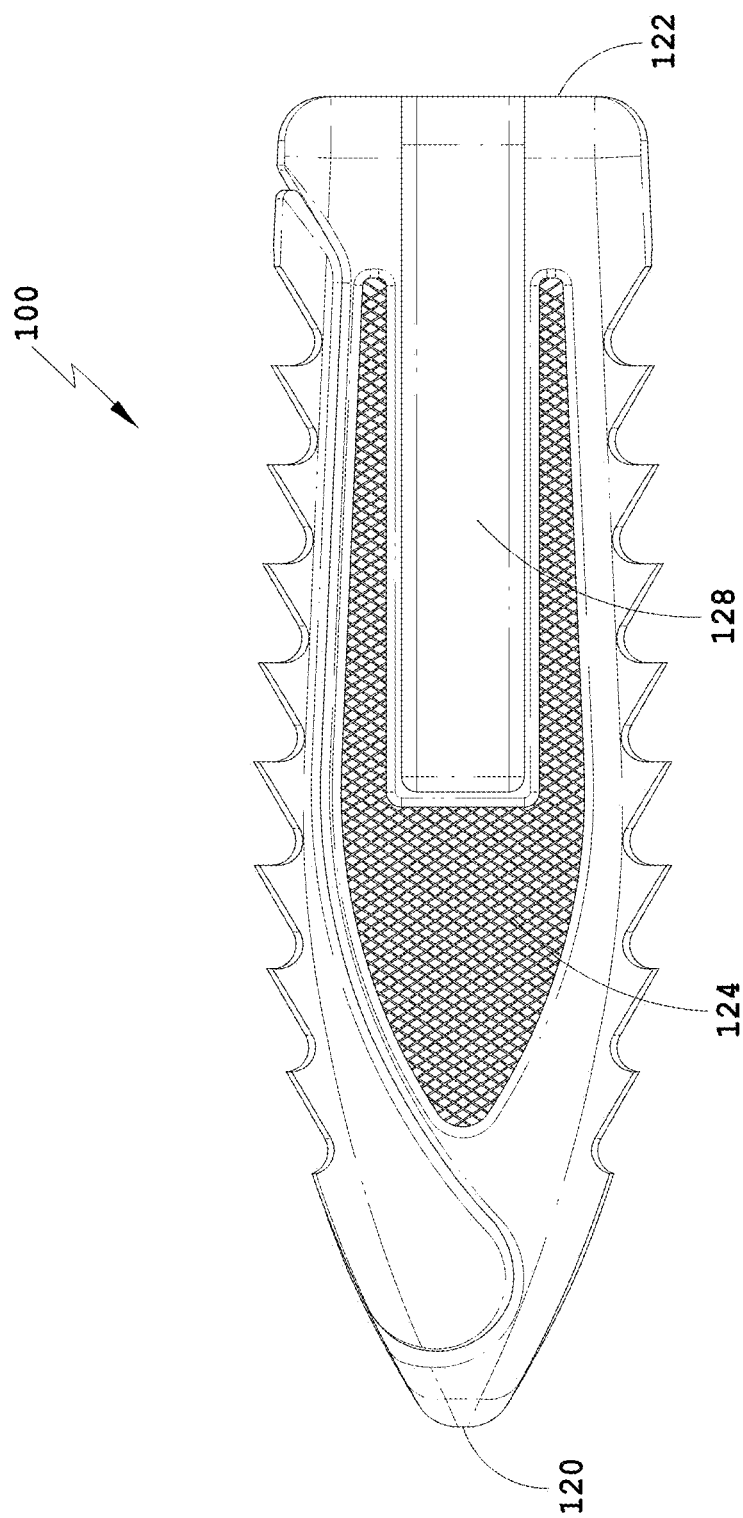
FIG. 12 is a side view of the spinal implant device of FIG. 9.

FIG. 12 is a side view of the spinal implant device 100. The distance between the distal end 120 and the proximal end 122 can form the length or depth of the spinal implant device 100. The distal end 120 and the proximal end 122 can form opposite ends of the spinal implant device 100. The spinal implant device 100 can include two opposing side walls including a first side wall 124 and a second side wall 126. FIG. 12 illustrates the first side wall 124. The second side wall 126 can be substantially similar to the first side wall 124. The second side wall 126 can be a mirror image of the first side wall 124. The second side wall 126 can include any of the features or elements described below.

Figure 13:
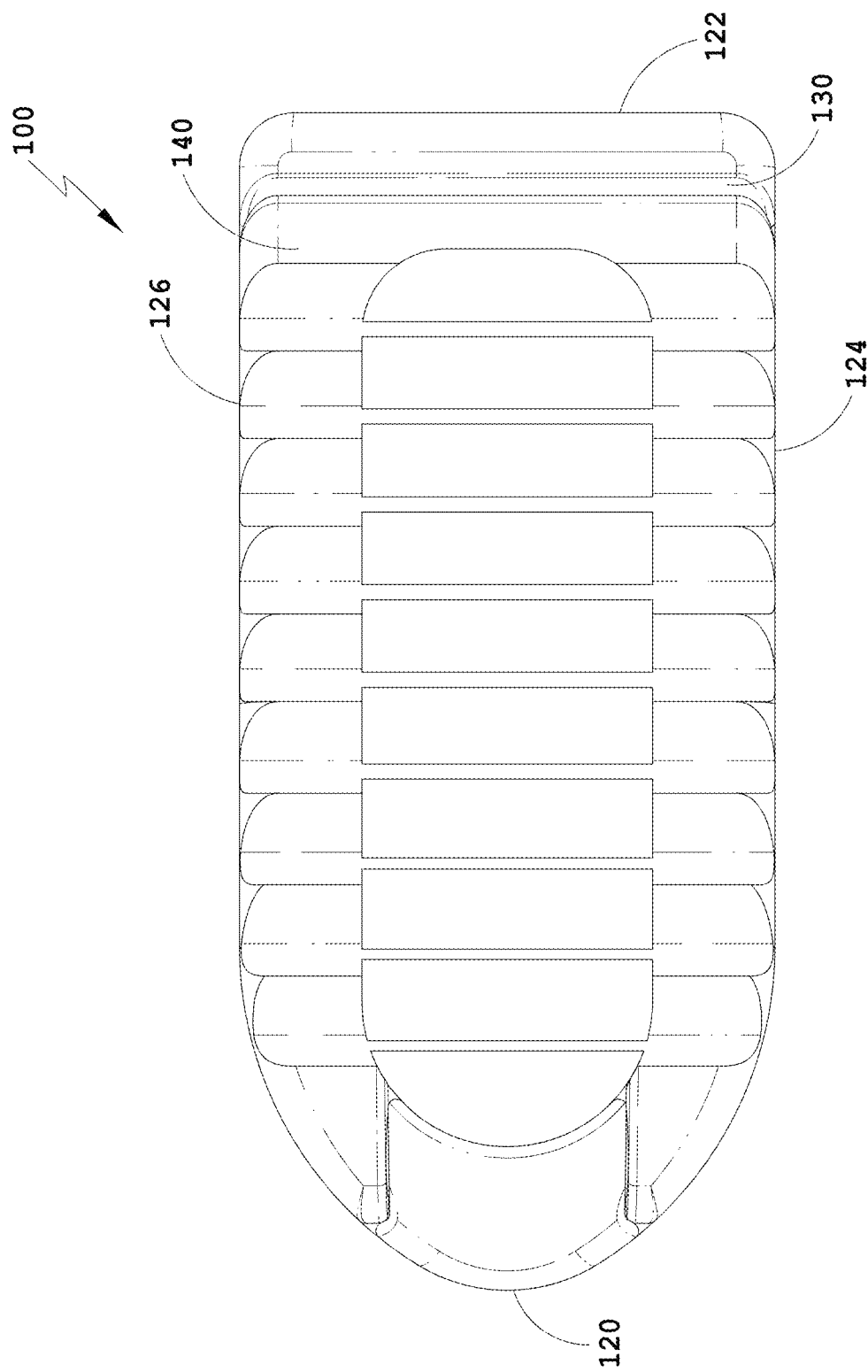
FIG. 13 is a top view of the spinal implant device of FIG. 9.

FIG. 13 is a top view of the spinal implant device 100. The two opposing side walls 124, 126 can connect the distal end 120 and the proximal end 122. In some embodiments, the two opposing side walls 124, 126 are separated the same distance along the length of the spinal implant device 100. In some embodiments, the two opposing side walls 124, 126 are parallel. In some embodiments, the first side wall 124 and the second side wall 126 are the same shape. In some embodiments, the distance between the two opposing side walls 124, 126 can form the width of the spinal implant device 100.

Referring to FIGS. 12 and 13, the two opposing side walls 124, 126, or a portion thereof, can be formed of a porous material. The two opposing side walls 124, 126, or a portion thereof, can be open or include through openings. The two opposing side walls 124, 126, or a portion thereof, can be formed of a mesh. The two opposing side walls 124, 126, or a portion thereof, can be formed of a material that intrinsically participates in the growth of bone. The two opposing side walls 124, 126, or a portion thereof, can be formed of a material that allows a material to flow outward from the spinal implant device 100. The two opposing side walls 124, 126, or a portion thereof, can be formed of a material that allows the transfer of material in or out of the spinal implant device 100. In some embodiments, the porous surface of the two opposing side walls 124, 126 can extend along a portion of the length of the spinal implant device 100 (e.g., 10% of the length, 20% of the length, 30% of the length, 40% of the length, 50% of the length, 60% of the length, 70% of the length, 80% of the length, 90% of the length, or 100% of the length, or any range of the foregoing values). The porous material of the two opposing side walls 124, 126 can facilitate compression of the spinal implant device 100.

The two opposing side walls 124, 126 can include a feature 128 to facilitate insertion of the spinal implant device 100. In some embodiments, the feature 128 can include a groove to accept the insertion tool. In some embodiments, the feature 128 can extend from the proximal end 122 of the spinal implant device 100 toward the distal end 120. In some embodiments, the feature 128 can extend inward for a portion of the width of the side walls 124, 126. In some embodiments, the feature 128 can extend along a portion of the length of the spinal implant device 100 (e.g., 10% of the length, 20% of the length, 30% of the length, 40% of the length, 50% of the length, 60% of the length, 70% of the length, 80% of the length, 90% of the length, or 100% of the length, or any range of the foregoing values). In some embodiments, the feature 128 can include a slot. The slot can be considered an opening.

Figure 14:
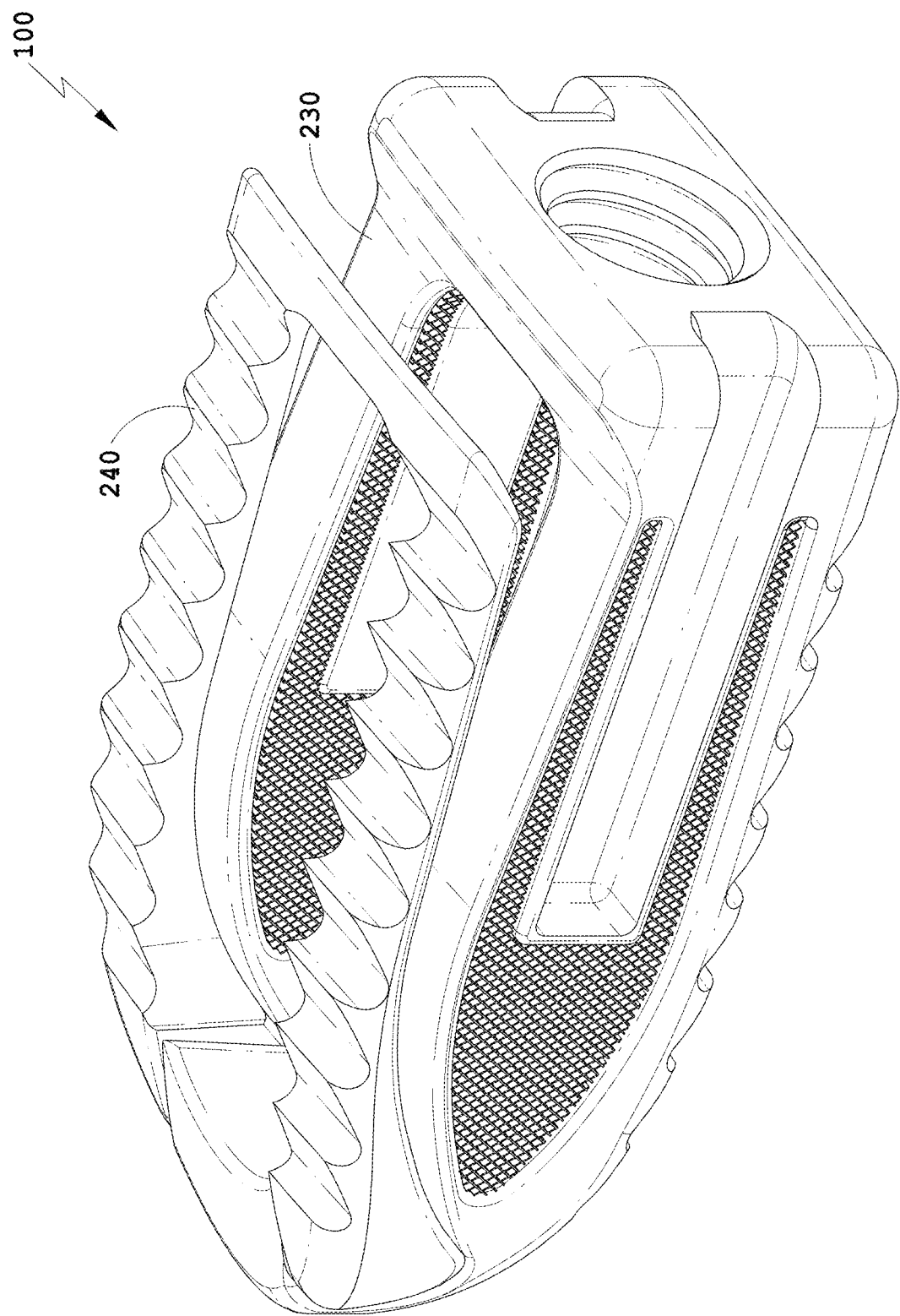
FIG. 14 is a top perspective view of the spinal implant device of FIG. 9 with the movable lid shown in an opened position.

The spinal implant device 100 can include a movable lid 140. FIG. 13 is a top view of the spinal implant device 100 with the movable lid 140 closed. FIG. 14 is a top perspective view of the spinal implant device 100 with the movable lid 140 opened.

The spinal implant device 100 can include an upper wall 130. The upper wall 130 can connect the distal end 120 and the proximal end 122. In some embodiments, the upper wall 130 is curved. In some embodiments, the upper wall 130 is convex. In some embodiments, the upper wall 130 is curved inward near the distal end 120 and curved inward toward the proximal end 122. In some embodiments, the upper wall 130 forms a recessed ledge to accommodate the movable lid 140. In some embodiments, the upper wall 130 forms a ledge for the movable lid 140. In some embodiments, the upper wall 130 allows for compression of the moveable lid 140. In some methods of use, the compression of the moveable lid 140 can promote fusion.

In some embodiments, the movable lid 140 forms the upper surface of the spinal implant device 100. In some embodiments, the movable lid 140 and a portion of the upper wall 130 form the upper surface of the spinal implant device 100, for instance the portion of the upper wall near the proximal end 122. In some embodiments, the movable lid 140 and the upper wall 130 are flush when the lid is closed. The movable lid 140 can be sized to rest against or abut the upper wall 130. The movable lid 140 can match the curvature of the upper wall 130. In some embodiments, the movable lid 140 and the upper wall 130 fit together. In some embodiments, the movable lid 140 can provide a load supporting surface. In some methods, the movable lid 140 can be positioned adjacent to a vertebral end plate of an upper vertebra.

Figure 15:
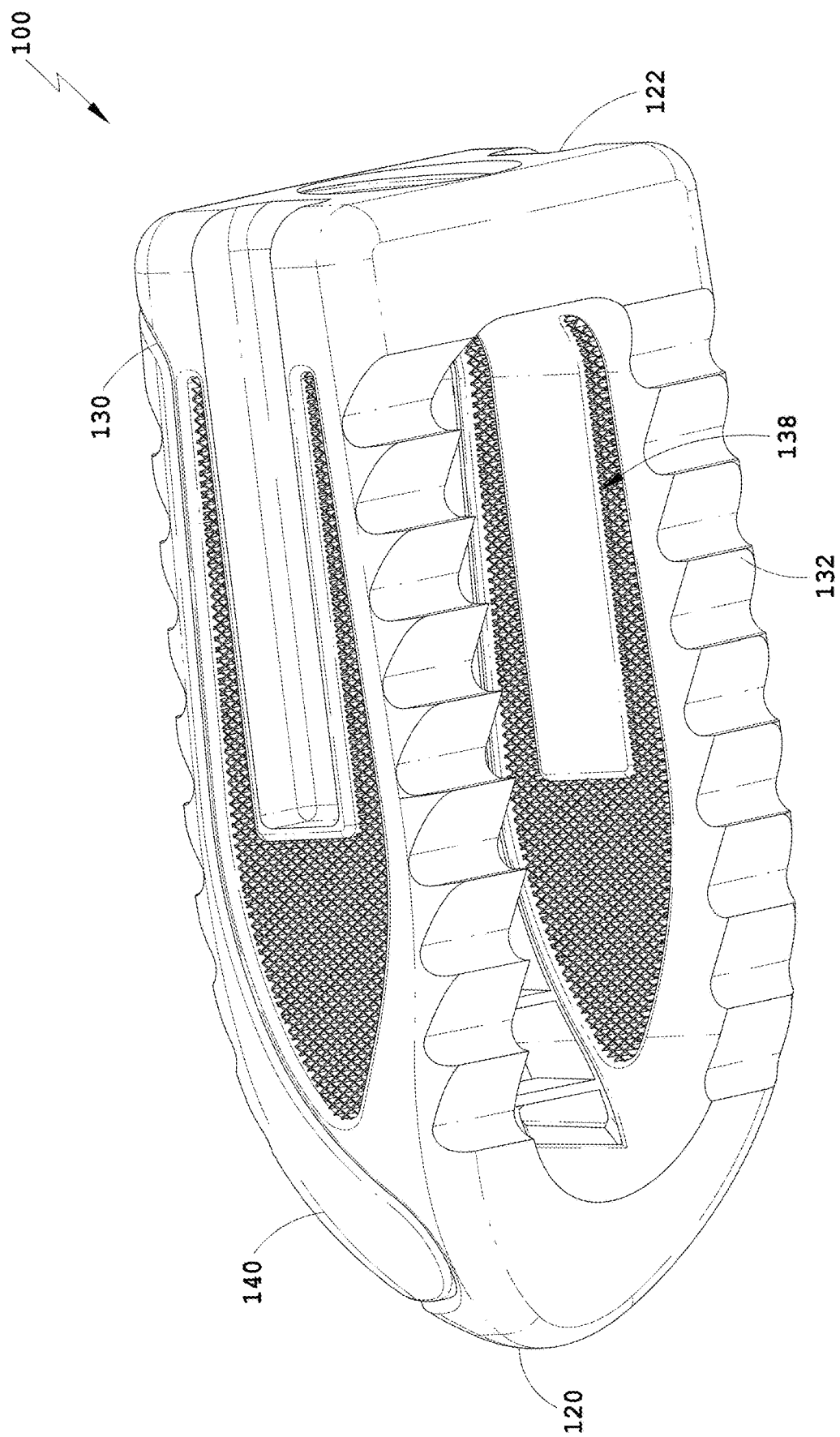
FIG. 15 is a bottom perspective view of the spinal implant device of FIG. 9.

FIG. 15 is a bottom perspective view of the spinal implant device 100. The spinal implant device 100 can include a lower wall 132. The lower wall 132 can connect the distal end 120 and the proximal end 122. In some embodiments, the lower wall 132 is curved. In some embodiments, the lower wall 132 is convex. In some embodiments, the lower wall 132 is curved inward near the distal end 120 and curved inward toward the proximal end 122. In some embodiments, the lower wall 132 forms a substantially flat surface. The lower wall 132 can provide a load supporting surface. In some methods, the lower wall 132 can be positioned adjacent to a vertebral end plate of a lower vertebra. In some methods, when the spinal implant device 100 is positioned between two adjacent vertebrae, the load supporting surfaces of the movable lid 140 and the lower wall 132 contact the vertebral end plates of the adjacent vertebrae. In some embodiments, the distance between the movable lid 140 and the lower wall 132 can form the height of the spinal implant device 100.

In some embodiments, the upper wall 130 and the lower wall 132 are separated by approximately the same distance along a substantial portion of the length of the spinal implant device 100. In some embodiments, the upper wall 130 and the lower wall 132 are substantially parallel. In some embodiments, the upper wall 130 and the lower wall 132 are bowed outward. In some embodiments, the upper wall 130 and the lower wall 132 are shaped to match the vertebral end plates.

Figure 16:
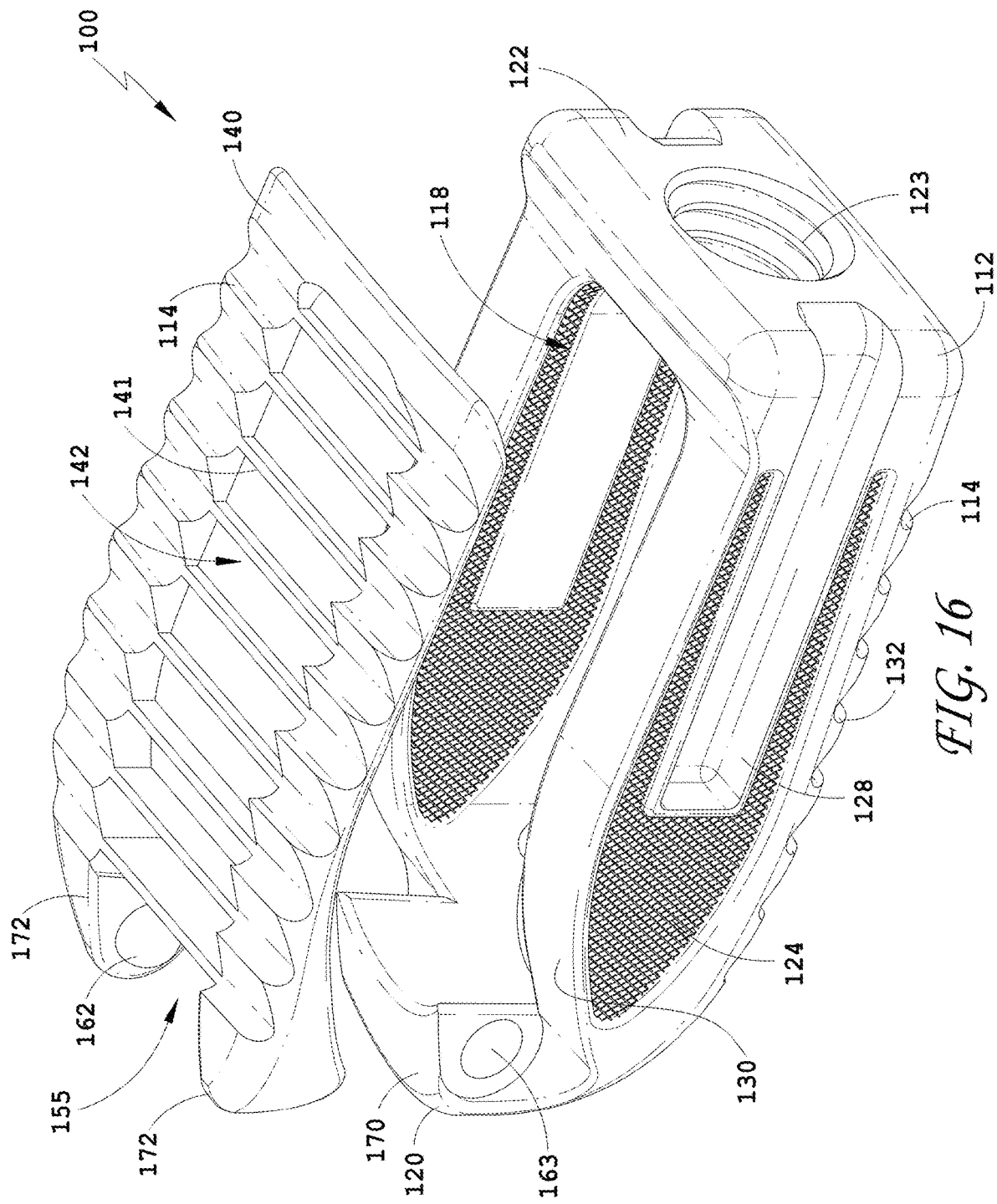
FIG. 16 is an exploded perspective view of the spinal implant device of FIG. 9.

FIG. 16 is an exploded view of the movable lid 140 of the spinal implant device 100. In some embodiments, the movable lid 140 can be coupled to the spinal implant device 100. In some embodiments, the movable lid 140 can be coupled to the distal end 120. The distal end 120 can include a central post 170. The central post 170 can extend between portions of the upper wall 130. In some embodiments, the upper wall 130 is recessed relative to the central post 170 to accommodate the movable lid 140. The central post 170 can extend along a portion of the width of the spinal implant device 100. While the central post 170 is illustrated as centrally located along the longitudinal axis of the spinal implant device 100, other positions of the central post 170 are contemplated.

In some embodiments, the spinal implant device 100 can include a movable joint 155. In some embodiments, the movable joint 155 can be positioned towards the distal end 120 of the spinal implant device 100. The movable joint 155 can couple the movable lid 140 with another portion of the spinal implant device 100. The movable joint 155 can allow for pivoting motion of the movable lid 140 relative to another portion of the spinal implant device 100. In some embodiments, the movable joint 155 can allow for pivoting motion of the movable lid 140 relative to the distal end 120. In some embodiments, the movable joint 155 can allow for one degree of motion of the movable lid 140 (e.g., one axis of rotation). In some embodiments, the movable joint 155 can allow for more than one degree of motion of the movable lid 140 (e.g., more than one axis of rotation).

In some embodiments, the movable joint 155 can include a pair of articulations 162. The pair of articulations 162 can be located on the movable lid 140. The pair of articulations 162 can extend from two opposing lateral posts 172 of the movable lid 140. The two opposing lateral posts 172 can be located near a distal end of the movable lid 140. The pair of articulations 162 can extend inward from the two opposing lateral posts 172. The two opposing lateral posts 172 of the movable lid 140 can be sized to accommodate the central post 170 of the distal end 120. The two opposing lateral posts 172 of the movable lid 140 can interlock with the central post 170 of the distal end 120 as described herein.

The central post 170 can include a pair of sockets 163 configured to engage the pair of articulations 162. The pair of sockets 163 can be perpendicular to the longitudinal axis of the spinal implant device 100. The pair of sockets 163 can extend inward from the side surfaces of the central post 170. In some embodiments, the orientation is reversed and the pair of articulations 162 can be located on the central post 170 and the pair of sockets 163 can be located on the movable lid 140. In some embodiments, the movable joint 155 can form a ball and socket joint.

In some embodiments, each articulation 162 is hemispherical and each socket 163 is hemispherical. In some embodiments, each articulation 162 is rounded and each socket 163 is rounded. In some embodiments, each articulation 162 is convex and each socket 163 is concave. In some embodiments, the movable joint 155 can include one or more articulations 162 (e.g., one, two, three, four, five, or six). In some embodiments, the movable joint 155 can include a corresponding number of articulations and sockets. In some embodiments, the movable joint 155 can allow the movable lid 140 to be easily removed from the spinal implant device 100. In some embodiments, the movable joint 155 can allow the movable lid 140 to be snapped onto the central post 170. The moveable lid 140 can be coupled to the spinal implant device 100 at any location to facilitate packing the spinal implant device 100 as described herein.

The spinal implant device 100 can include a cavity 118. In some embodiments, the proximal end 122 can define the back inner surface of the cavity 118. In some embodiments, the distal end 120 can define the front inner surface of the cavity 118. In some embodiments, the two opposing side walls 124, 126 can define the side inner surfaces of the cavity 118. In some embodiments, the movable lid 140 can define the top inner surface of the cavity 118. In some embodiments, the cavity 118 is partially enclosed. The cavity 118 can be a large, central chamber inside the spinal implant device 100. In some embodiments, the cavity 118 comprises a portion of the volume of the spinal implant device 100 (e.g., 50% of the volume, 60% of the volume, 70% of the volume, 80% of the volume, 90% of the volume, or 100% of the volume, or any range of the foregoing values).

In some embodiments, the spinal implant device 100 can include features to facilitate maintaining the position of the spinal implant device 100 between the vertebrae. The spinal implant device 100 can include a plurality of ridges 114. The ridges 114 can be located on the movable lid 140. The ridges 114 can be located on the lower wall 132. In some embodiments, the ridges 114 are positioned on the upper surface of the spinal implant device 100, the lower surface of the spinal implant device 100, or both the upper surface and the lower surface of the spinal implant device 100.

In some embodiments, the ridges 114 on the upper surface of the spinal implant device 100 and/or the lower surface of the spinal implant device 100 are directionally oriented. The ridges 114 can form a triangular surface sloping upward closer to the proximal end 122. The ridges 114 can be directionally oriented such that the spinal implant device 100 can slide easily in between the vertebrae. The ridges 114 can be directionally oriented such that the spinal implant device 100 can directionally resist being pulled out from between the vertebrae.

The movable lid 140 can include one or more crossbars 141. While nine crossbars 141 are illustrated, the movable lid 140 can include any number of crossbars 141 (e.g., one, two, three, four, five, or six). In some embodiments, each crossbar 141 extends perpendicular to the longitudinal axis of the spinal implant device 100. In some embodiments, each crossbar 141 extends parallel to the longitudinal axis of the spinal implant device 100. Each crossbar 141 can extend between opposed ridges 114. Each crossbar 141 can extend across the width of the spinal implant device 100. The spinal implant device 100 can include one or more openings 142 extending through the movable lid 140. The openings 142 can be separated by the crossbars 141. The crossbars 141 can form a grated framework. In some embodiments, the one or more openings 142 comprises a portion of the upper surface area of the spinal implant device 100 (e.g., 50% of the surface area, 60% of the surface area, 70% of the surface area, 80% of the surface area, 90% of the surface area, or 100% of the surface area, or any range of the foregoing values). In some embodiments, the spinal implant device 100 does not include one or more openings 142 extending through the movable lid 140. In some embodiments, cavity 118 is fully enclosed by movable lid 140.

The spinal implant device 100 can include an opening 138 extending through the lower wall 132 as illustrated in FIG. 15. The opening 138 can be elongate. The opening 138 can extend along the length of the spinal implant device 100. While one opening 138 is illustrated, the lower surface 132 can include one or more openings (e.g., one, two, three, four, five, or six). In some embodiments, the opening 138 comprises a portion of the lower surface area of the spinal implant device 100 (e.g., 50% of the surface area, 60% of the surface area, 70% of the surface area, 80% of the surface area, 90% of the surface area, or 100% of the surface area, or any range of the foregoing values).

The openings 138, 142 can be located on opposed surfaces of the spinal implant device 100. In some embodiments, the openings 138, 142 can include different shapes. In some embodiments, the openings 138 and the one or more openings 142 can include the same perimeter. The spinal implant device 100 can provide an open access area between the adjacent vertebrae. The spinal implant device 100 can provide an open access area through the one or more openings 142 in the movable lid 140 and the elongated opening 138 of the lower wall 132.

Figure 17:
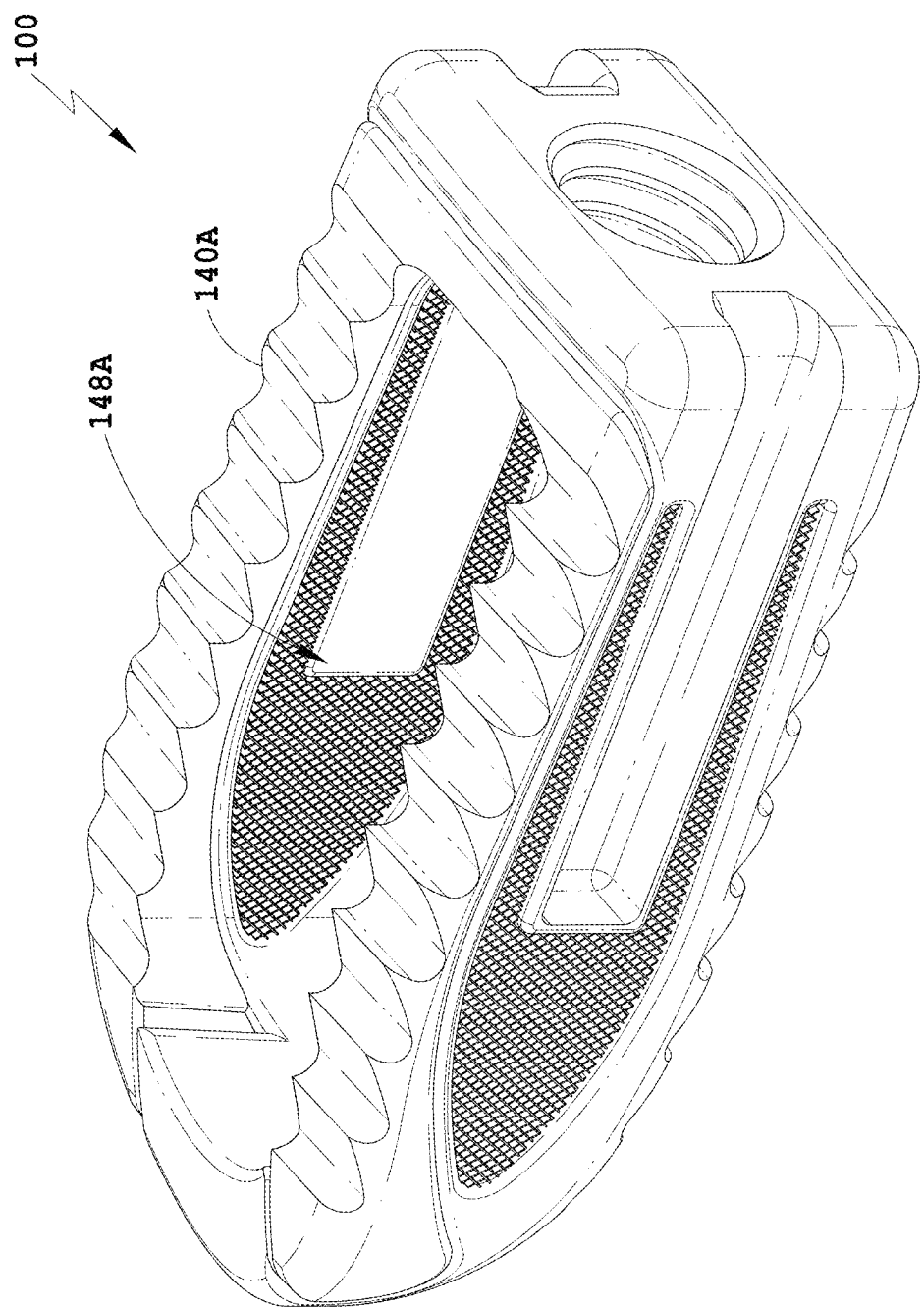
FIG. 17 is a perspective view of an embodiment of a movable lid.

FIG. 17 is a view of a movable lid 140A of the spinal implant device 100. The movable lid 140A can include an opening 148A. In some embodiments, the openings 138, 148A can include the same perimeter or shape. The openings 138, 148A can be located on opposed surfaces of the spinal implant device 100.

The spinal implant 100 can include a side wall width. The side wall width can be defined, in part, by the openings 138, 148A which span the spinal implant device 100. The first side wall width can extend from the movable lid 140A, along the first side wall 124, and to the lower wall 132. The second side wall width can extend from the movable lid 140A, along the second side wall 126, and to the lower wall 132. In some embodiments, the two opposing side walls 124, 126 have the same width. In some embodiments, the two opposing side walls 124, 126 have different widths.

The spinal implant device 100 can be shaped and configured for the TLIF method. The spinal implant device 100 can have a greater length or depth than the spinal implant 10, 10A. In some embodiments, the spinal implant device 100 can have an average length or depth within the range of about 27 mm to about 37 mm (e.g., 27 mm, 28 mm, 29 mm, 30 mm, 31 mm, 32 mm, 33 mm, 34 mm, 35 mm, 36 mm, 37 mm, between 27 and 37 mm, or between 27 and 32 mm, or any range of the foregoing values). In some embodiments, the spinal implant device 10 can have an average length or depth approximately 22 mm. In some embodiments, the spinal implant devices 10, 10A, 100 can have the same height. In some embodiments, the spinal implant devices 10, 10A, 100 can have the same lordosis. In some embodiments, the spinal implant devices 10, 10A, 100 can have the same kyphosis. In some embodiments, the spinal implant devices 10, 10A, 100 can have approximately the same width within the range of 8 mm to 12 mm. In some embodiments, the spinal implant devices 10, 10A, 100 can include a curve. In some embodiments, the spinal implant devices 10, 10A, 100 can be straight or substantially straight.

Figure 18:
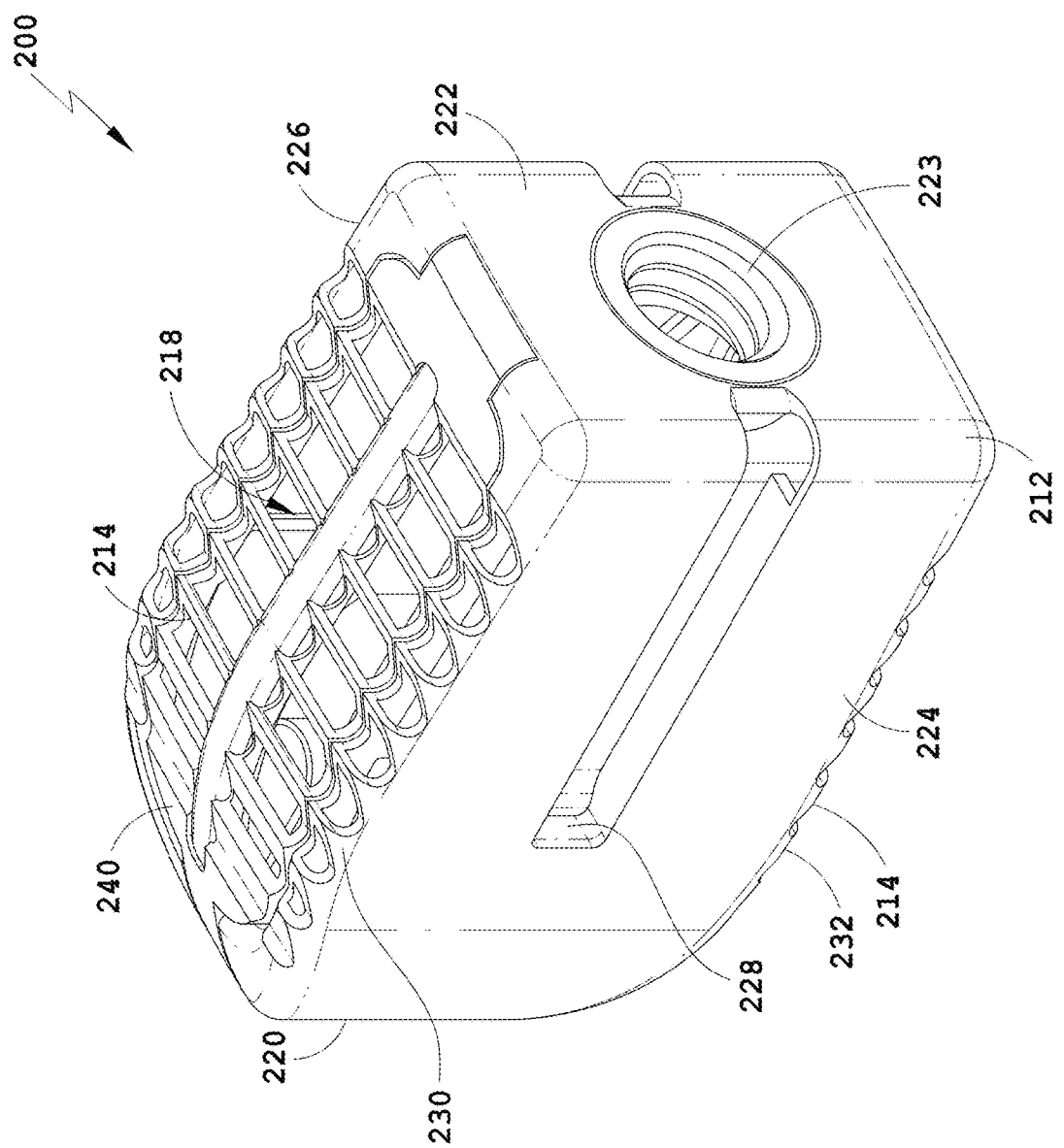
FIG. 18 is a perspective view of an embodiment of a spinal implant device with a movable lid shown in a closed position.

FIG. 18 illustrates a perspective view of a spinal implant device 200. The spinal implant device 200 can include any of the features of the spinal implant device 10, 10A, 100 as described herein and can be used in any method or method step described herein. The spinal implant device 200 can include a body structure 212. The body structure 212 can be placed between adjacent vertebrae.

Figure 19:
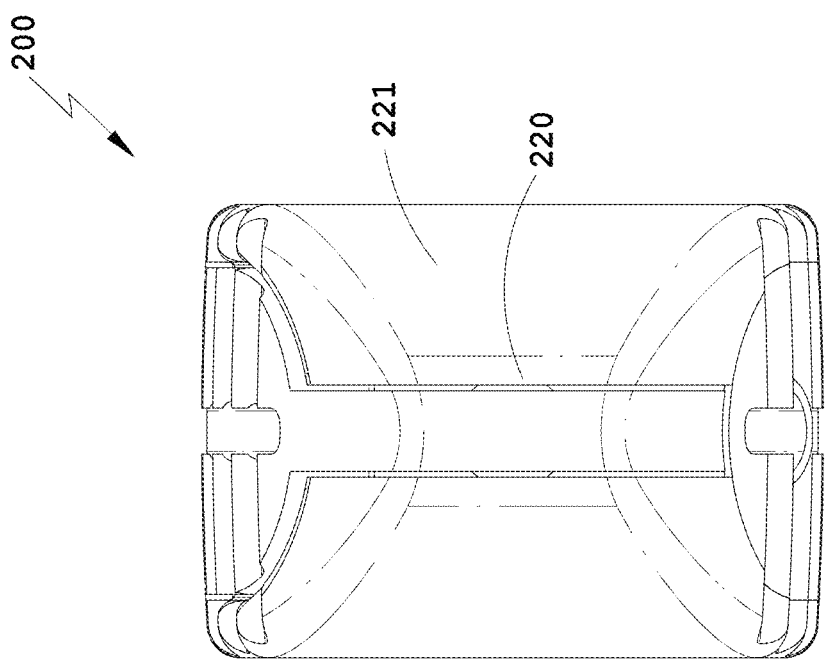
FIG. 19 is a distal view of the spinal implant device of FIG. 18.

FIG. 19 is a distal view of the spinal implant device 200. The spinal implant device 200 can include a distal end 220. In some methods of use, the distal end 220 can be the insertion end. In some embodiments, the distal end 220 is tapered inward. In some embodiments, the four surfaces of the distal end 220 can taper to from a square pyramid or similar shape. In some embodiments, the upper surface and the lower surface of the distal end 220 equally taper. In some embodiments, the side surfaces of the distal end 220 equally taper. In some embodiments, the distal end 220 can include rounded corners or edges. The distal end 220 can form a frustoconical or convex curved shape 221. The distal end 220 can include a cavity to accommodate a movable lid as described herein.

Figure 20:
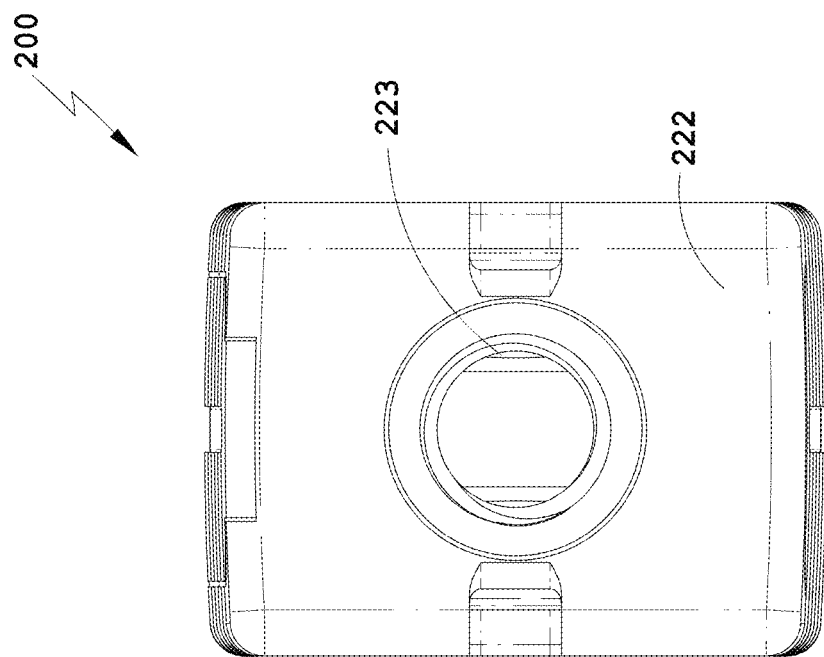
FIG. 20 is a proximal view of the spinal implant device of FIG. 18.

FIG. 20 is a proximal view of the spinal implant device 200. The spinal implant device 200 can include a proximal end 222. In some embodiments, the proximal end 222 can be flat. In some embodiments, the proximal end 222 can include one or more rounded corners, and in the illustrated embodiment, the proximal end 222 includes four rounded corners. The proximal end 222 can be substantially square or rectangular. In some embodiments, the proximal end 222 can include an opening 223 to couple to an insertion tool. In some embodiments, the opening 223 can be threaded.

Figure 21:
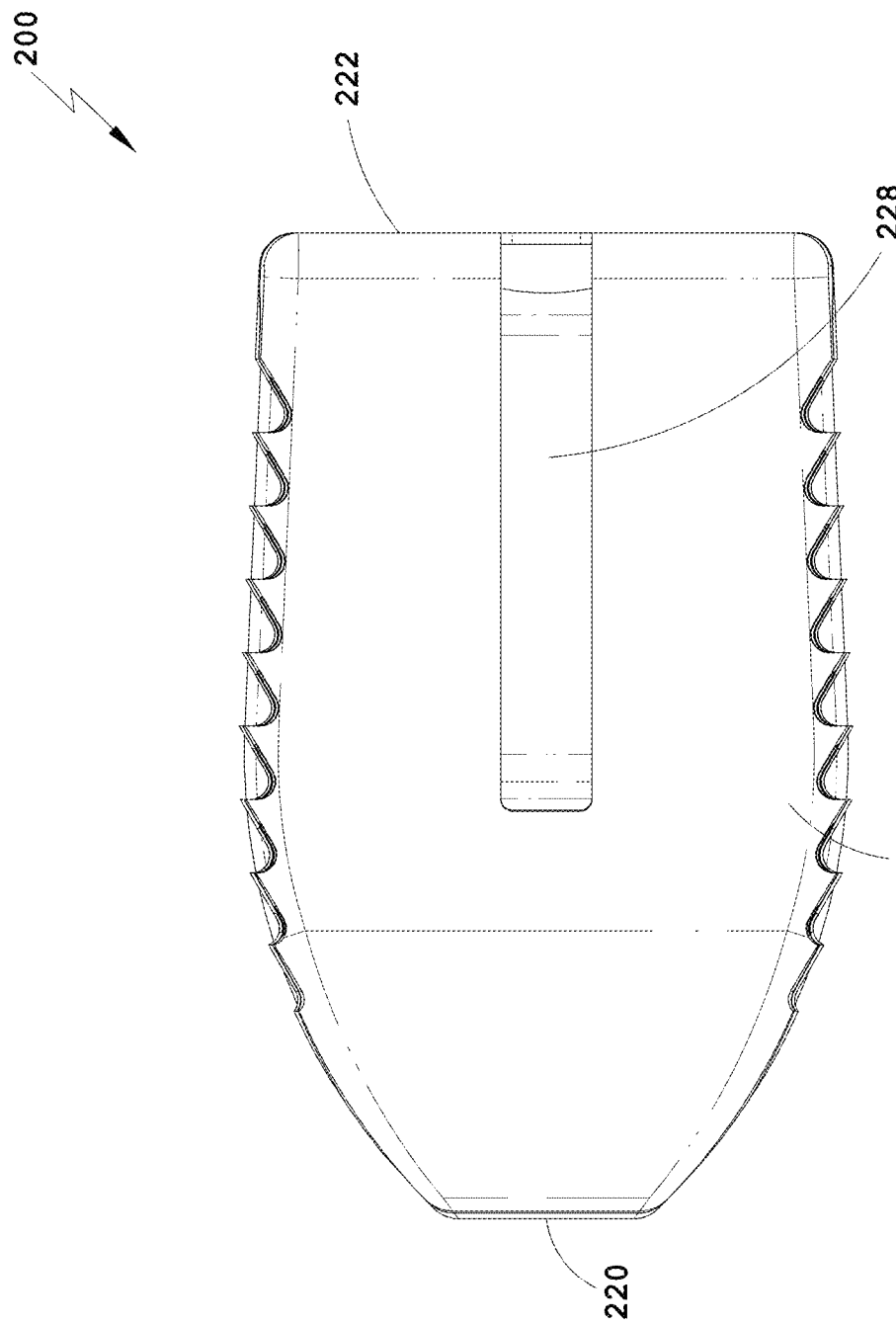
FIG. 21 is a side view of the spinal implant device of FIG. 18.

FIG. 21 is a side view of the spinal implant device 200. The length or depth of the spinal implant device 200 can be the distance between the distal end 220 and the proximal end 222. The distal end 220 and the proximal end 222 can form the leading and trailing end, respectively. The spinal implant device 200 can include two opposing side walls including a first side wall 224 and a second side wall 226. FIG. 21 illustrates the first side wall 224, but the second side wall 226 can include the same or similar features. The first side wall 224 and the second side wall 226 can be mirror images.

In some embodiments, each of the two opposing side walls 224, 226 can include a feature 228 to facilitate placement of the spinal implant device 200. In some embodiments, the feature 228 can include a channel to accept an insertion tool. In some embodiments, the feature 228 can extend from the proximal end 222 of the spinal implant device 200 toward the distal end 220. In some embodiments, the feature 228 can extend inward for a portion of the width of the side walls 224, 226. In some embodiments, the feature 228 can extend along a portion of the length of the spinal implant device 200 (e.g., 10% of the length, 20% of the length, 30% of the length, 40% of the length, 50% of the length, 60% of the length, 70% of the length, 80% of the length, 90% of the length, or 100% of the length, or any range of the foregoing values). In some embodiments, the material selection of the side walls 224, 226 can facilitate compression of the spinal implant device 200. In some embodiments, the feature 228 can include a slot. The slot can be considered an opening.

Figure 22:
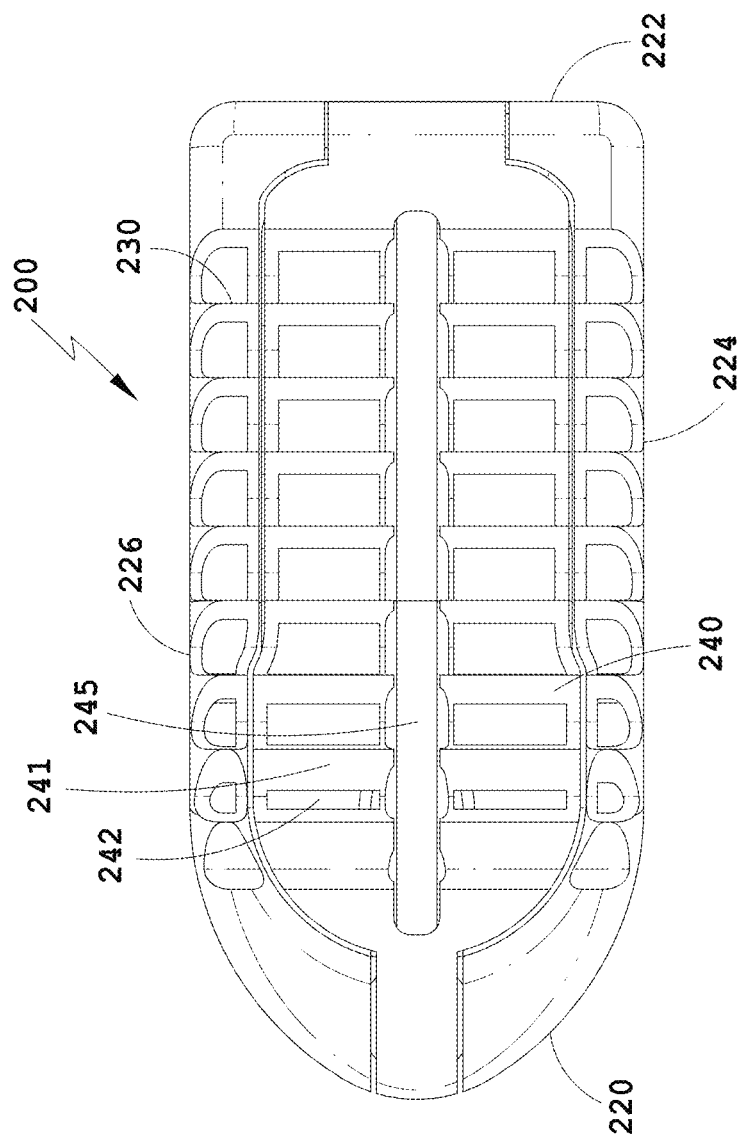
FIG. 22 is a top view of the spinal implant device of FIG. 18.

FIG. 22 is a top view of the spinal implant device 200. The two opposing side walls 224, 226 can extend between the distal end 220 and the proximal end 222. In some embodiments, the two opposing side walls 224, 226 are separated the same width along the length of the two opposing side walls 224, 226. In some embodiments, the two opposing side walls 224, 226 are parallel or substantially parallel. In some embodiments, the two opposing side walls 224, 226 are the same shape. In some embodiments, the distance between the two opposing side walls 224, 226 can form the width of the spinal implant device 200.

Figure 23:
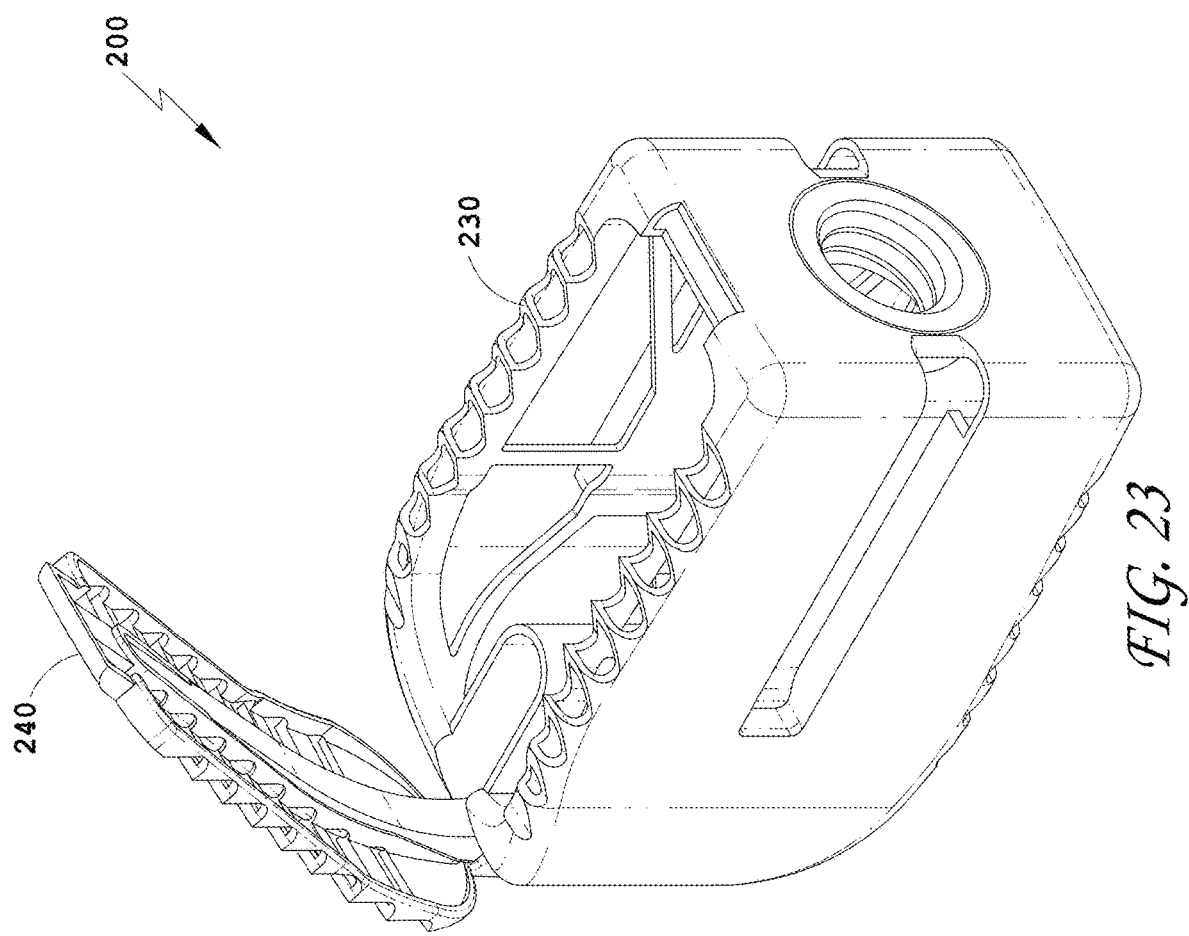
FIG. 23 is a top perspective view of the spinal implant device of FIG. 18 with the movable lid shown in an opened position.

The spinal implant device 200 can include a movable lid 240. FIG. 22 is a top view of the spinal implant device 200 with the movable lid 240 closed. FIG. 23 is a top perspective view of the spinal implant device 200 with the movable lid 240 opened.

The spinal implant device 200 can include an upper wall 230. The upper wall 230 can extend between the distal end 220 and the proximal end 222. In some embodiments, the upper wall 230 is curved to mimic the shape of the vertebral endplates. The curvature can be slight for the upper wall 230. In some embodiments, the upper wall 230 is tapered inward by the lordosis angle as described herein. In some embodiments, the upper wall 230 is tapered outward by the kyphosis angle as described herein. In some embodiments, the upper wall 230 forms an opening to accommodate the movable lid 240. In some embodiments, the upper wall 230 does not form a ledge for the movable lid 240. Instead, the moveable lid 240 is received between edges of the upper wall 230. The moveable lid 240 can be unsupported along the sidewalls 224, 226, or a portion thereof. The moveable lid 240 can be supported at the distal end 220 via a movable hinge, as described herein. The moveable lid 240 can be supported at the proximal end 222 by a ledge formed by the proximal end 222. In some embodiments, the upper wall 230 allows for compression of the moveable lid 240 to a desired depth. In some embodiments, the upper wall 230 allows for compression of the moveable lid 240 relative to the upper wall 230. The compression of the moveable lid 240 can allow for increased load on the corresponding graft material to promote fusion.

In some embodiments, the movable lid 240 and the upper wall 230 together form the upper surface of the spinal implant device 200. In some embodiments, the movable lid 240 and the upper wall 230 are laterally adjacent when the lid 240 is closed. The movable lid 240 can be sized to be located within the upper wall 230. The movable lid 240 can be sized to be surrounded, at least partially, by the upper wall 230. The movable lid 240 can match the curvature of the upper wall 230. The movable lid 240 can match the lordosis angle of the upper wall 230. The movable lid 240 can match the kyphosis angle of the upper wall 230. In some embodiments, the movable lid 240 and the upper wall 230 interlock together. In some embodiments, the movable lid 240 and the upper wall 230 can provide a load supporting surface. In some methods, the movable lid 240 and the upper wall 230 can be positioned adjacent to a vertebral end plate of a superior vertebra.

Figure 24:
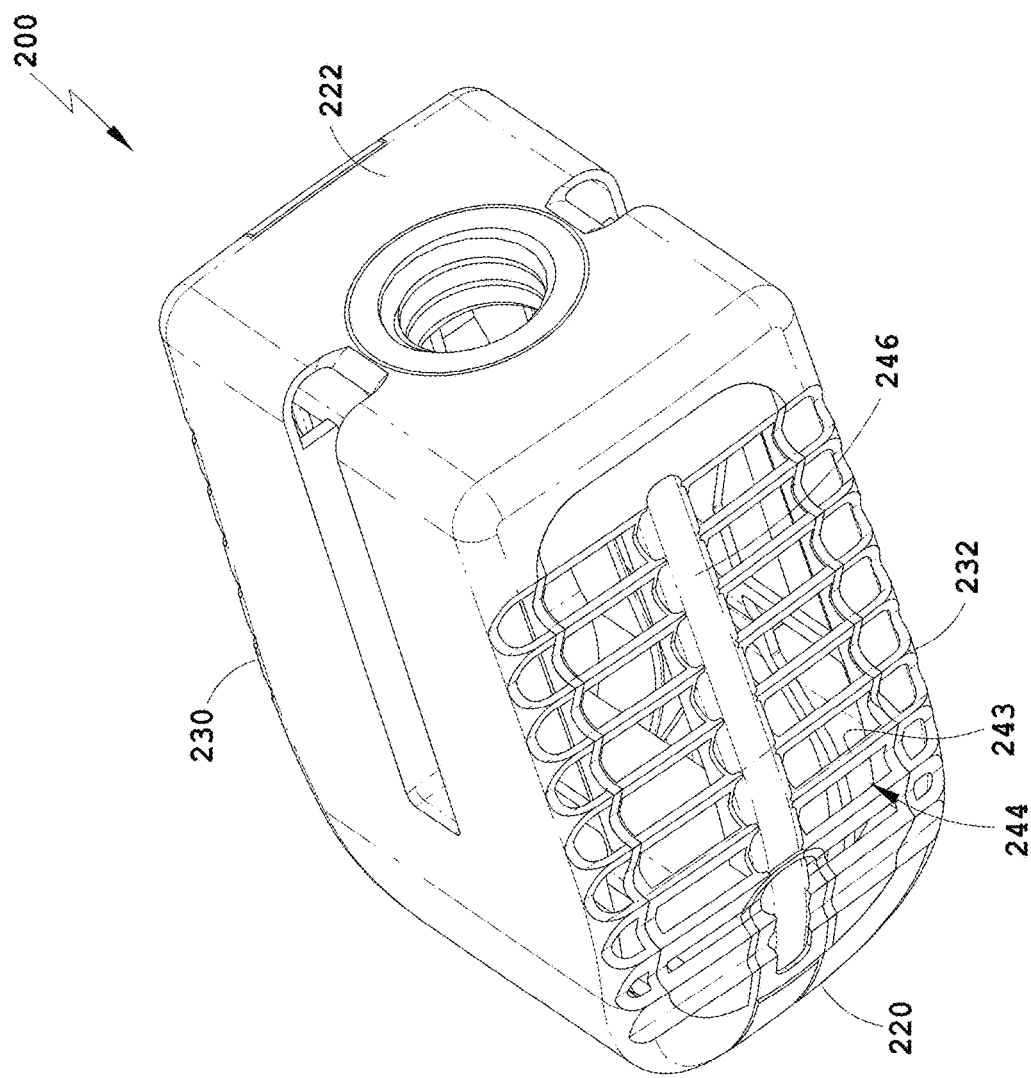
FIG. 24 is a bottom perspective view of the spinal implant device of FIG. 18.

FIG. 24 is a bottom perspective view of the spinal implant device 200. The spinal implant device 200 can include a lower wall 232. The lower wall 232 can extend between the distal end 220 and the proximal end 222. In some embodiments, the lower wall 232 is curved to mimic the shape of the vertebral endplates. The curvature can be slight for the lower wall 232. In some embodiments, the lower wall 232 is tapered inward by the lordosis angle as described herein. In some embodiments, the lower wall 232 is tapered outward by the kyphosis angle as described herein. The lower wall 232 can provide a load supporting surface. In some methods, the lower wall 232 can be positioned adjacent to a vertebral end plate of an inferior vertebra. In some methods, when the spinal implant device 200 is positioned between two adjacent vertebrae, the load supporting surfaces of the movable lid 240, the upper wall 230, and the lower wall 232 contact the vertebral end plates of the adjacent vertebrae.

In some embodiments, the distance between the movable lid 240 and the lower wall 232 can form the height of the spinal implant device 200. In some embodiments, the upper wall 230 and the lower wall 232 are separated by approximately the same distance along a substantial portion of the length of the spinal implant device 200. In some embodiments, the upper wall 230 and the lower wall 232 are substantially parallel along a portion of the length of the spinal implant device 200. In some embodiments, the upper wall 230 and the lower wall 232 are bowed outward along a portion of the length of the spinal implant device 200. In some embodiments, the upper wall 230 and the lower wall 232 are tapered inward along a portion of the length of the spinal implant device 200.

Figure 25:
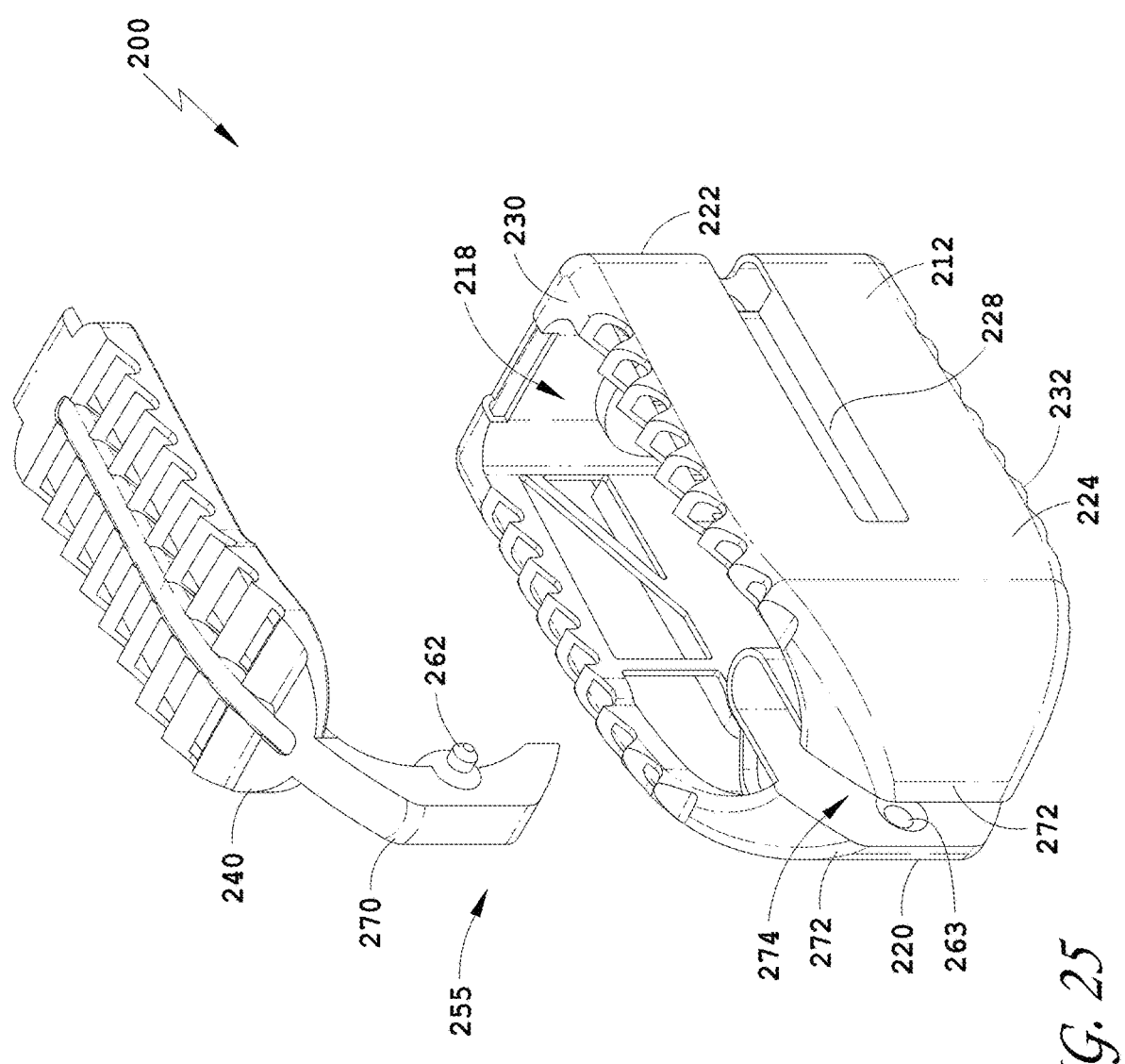
FIG. 25 is an exploded perspective view of the spinal implant device of FIG. 18.

FIG. 25 is an exploded view of the movable lid 240 and the body structure 212. In some embodiments, the movable lid 240 can be coupled to the body structure 212. In some embodiments, the movable lid 240 can be coupled to the distal end 220. The distal end 220 can include two opposing lateral posts 272. The two opposing lateral posts 272 can extend from portions of the upper wall 230. In some embodiments, the two opposing lateral posts 272 are connected with a recessed channel 274. The recessed channel 274 can accommodate the movable lid 240. The two opposing lateral posts 272 can extend along a portion of the width of the spinal implant device 200. While the two opposing lateral posts 272 are illustrated bilaterally, along each side of the spinal implant device 200, other positons of the two opposing lateral posts 272 are contemplated.

In some embodiments, the spinal implant device 200 can include a movable joint 255. In some embodiments, the movable joint 255 can be positioned distally. The movable joint 255 can couple the movable lid 240 with the body structure 212. The movable joint 255 can allow for pivoting motion of the movable lid 240 relative to the body structure 212. In some embodiments, the movable joint 255 can allow for pivoting motion of the movable lid 240 relative to the distal end 220. In some embodiments, the movable joint 255 can allow for one degree of motion of the movable lid 240. In some embodiments, the movable joint 255 can include one axis of rotation. In some embodiments, the movable joint 255 can allow for more than one degree of motion of the movable lid 240. In some embodiments, the movable joint 255 can include more than one axis of rotation.

In some embodiments, the movable joint 255 can include a pair of articulations 262. The pair of articulations 262 can be located on the movable lid 240. The pair of articulations 262 can extend from a central post 270 of the movable lid 240. The central post 270 can be located near a distal end of the movable lid 240. The pair of articulations 262 can extend outward from the central post 270. The two opposing lateral posts 272 of the distal end 220 can be sized to accommodate the central post 270 of the movable lid 240. The two opposing lateral posts 272 can allow motion with the central post 270 as described herein. The central post 270 can match the convex curved shape 221 of the distal end 220 (shown in FIG. 19). The central post 270 can be truncated slightly with a flatter or blunter portion. In some embodiments, the upper surface and the lower surface of the central post 270 equally taper. In some embodiments, the side surfaces of the central post 270 are flat.

The two opposing lateral posts 272 can include a pair of sockets 263 configured to engage the pair of articulations 262. The pair of sockets 263 can be perpendicular to the longitudinal axis of the spinal implant device 200. The pair of sockets 263 can extend inward from the inside surface of the two opposing lateral posts 272. In some embodiments, the orientation is reversed and the pair of articulations 262 can be located on the distal end 220 and the pair of sockets 263 can be located on the movable lid 240.

In some embodiments, each articulation 262 is conical, at least in part. In some embodiments, each articulation 262 forms a truncated cone. In some embodiments, each articulation 262 includes an elongate post. In some embodiments, each socket 263 is conical, at least in part. In some embodiments, each socket 263 forms a truncated cone shaped recess. In some embodiments, each socket 263 forms an elongate post shaped recess.

In some embodiments, each articulation 262 is a convex frustum and each socket 263 is concave frustum. In some embodiments, the movable joint 255 can include one or more articulations 262 (e.g., one, two, three, four, five, or six). In some embodiments, the movable joint 255 can include a corresponding number of articulations and sockets. In some embodiments, the movable joint 255 can allow the movable lid 240 to be snapped onto the body structure 212.

The spinal implant device 200 can include a cavity 218. In some embodiments, the proximal end 222 can form the back inner surface of the cavity 218. In some embodiments, the distal end 220 can form the front inner surface of the cavity 218. In some embodiments, the two opposing side walls 224, 226 can form the side inner surfaces of the cavity 218. In some embodiments, the movable lid 240 can form the top inner surface of the cavity 218. In some embodiments, the lower wall 232 can form the bottom inner surface of the cavity 218.

In some embodiments, the cavity 218 is partially enclosed on at least six sides. In some embodiments, the cavity 218 is fully enclosed on at least two sides. In some embodiments, the cavity 218 is fully enclosed on at least three sides. The cavity 218 can be a centrally located space within the spinal implant device 200. In some embodiments, the cavity 218 comprises a portion of the volume of the spinal implant device 200 (e.g., 50% of the volume, 60% of the volume, 70% of the volume, 80% of the volume, 90% of the volume, or 100% of the volume, or any range of the foregoing values).

In some embodiments, the spinal implant device 200 can include features to facilitate maintaining the position of the spinal implant device 200 between the vertebrae. The spinal implant device 200 can include a plurality of ridges 214. The ridges 214 can be formed on the movable lid 240. The ridges 214 can be formed on the upper wall 230. The ridges 214 can be formed on the lower wall 232. In some embodiments, the ridges 214 on the movable lid 240 and the upper wall 230 align to form substantially continuous ridges 214.

In some embodiments, the ridges 214 on the movable lid 240 and the upper wall 230 are directionally oriented. In some embodiments, the ridges 214 on the lower wall 232 are directionally oriented. The ridges 214 can form a sloping surface which increases toward the proximal end 222. The ridges 214 can be directionally oriented to prevent the spinal implant device 200 from backing out.

The movable lid 240 can include one or more crossbars 241 shown in FIG. 22. While seven crossbars 241 are illustrated, the movable lid 240 can include any number of crossbars 241 (e.g., one, two, three, four, five, six, seven, eight, nine, or ten). In some embodiments, the one or more crossbars 241 extend perpendicular to the longitudinal axis of the spinal implant device 200. Each crossbar 241 can extend along a surface of a ridge 214. Each crossbar 241 can extend across the width of the movable lid 240. The spinal implant device 200 can include one or more openings 242 extending through the movable lid 240. The openings 242 can be formed by the crossbars 241. The crossbars 241 can form a grated framework. In some embodiments, the one or more openings 242 cover a portion of the surface area of the movable lid 240 (e.g., 50% of the surface area, 60% of the surface area, 70% of the surface area, 80% of the surface area, 90% of the surface area, or 100% of the surface area, or any range of the foregoing values). In some embodiments, the spinal implant device 200 does not include one or more openings 242 extending through the movable lid 240. In some embodiments, cavity 218 is fully enclosed by movable lid 240.

The lower wall 232 can include one or more crossbars 243. While seven crossbars 243 are illustrated, the lower wall 232 can include any number of crossbars 243 (e.g., one, two, three, four, five, six, seven, eight, nine, or ten). In some embodiments, each crossbar 243 extends perpendicular to the longitudinal axis of the spinal implant device 200. Each crossbar 243 can extend along a surface of a ridge 214. Each crossbar 243 can extend across the width of the lower wall 232. The spinal implant device 200 can include one or more openings 244 extending through the lower wall 232. The openings 244 can be formed by the crossbars 243. The crossbars 243 can form a grated framework. In some embodiments, the one or more openings 243 cover a portion of the surface area of the lower wall 232 (e.g., 50% of the surface area, 60% of the surface area, 70% of the surface area, 80% of the surface area, 90% of the surface area, or 100% of the surface area, or any range of the foregoing values).

The openings 242, 244 can be elongate. The openings 242, 244 can extend along the length of the spinal implant device 200. While eight openings 242, 244 are illustrated, the spinal implant device 200 can include any number of openings. The openings 242, 244 can be parallel. The openings 242, 244 can be aligned to define a vertical flow path between the upper and lower surface of the spinal implant device 200.

The openings 242, 244 can be located on opposed surfaces of the spinal implant device 200. In some embodiments, the openings 242, 244 can include different shapes. In some embodiments, the openings 242, 244 can include the same perimeter. The spinal implant device 200 can provide access between the adjacent vertebrae. The spinal implant device 200 can provide access through one or more opening 242 in the movable lid 240 and one or more opening 244 of the lower wall 232.

The spinal implant device 200 can include a longitudinal bar 245 located on the movable lid 240 shown in FIG. 22. While one longitudinal bar 245 is illustrated, the movable lid 240 can include any number of longitudinal bars 245 (e.g., one, two, three, four, five, or six). The spinal implant device 200 can include a longitudinal bar 246 located on the lower wall 232. While one longitudinal bar 246 is illustrated, the lower wall 232 can include any number of longitudinal bars 246 (e.g., one, two, three, four, five, or six). In some embodiments, the one or more longitudinal bars 245, 246 extend parallel to the longitudinal axis of the spinal implant device 200. The one or more openings 242, 244 can be divided by the one or more longitudinal bars 245, 256. The one or more crossbars 241, 243 and the longitudinal bar 245, 246 can form a grated framework. In some embodiments, the longitudinal bar 245, 246 can extend across the ridges 214. In some embodiments, the longitudinal bar 245, 246 can be flat or substantially flat. In some embodiments, the spinal implant device 200 does not include a longitudinal bar 245 located on the movable lid 240.

Figure 26:
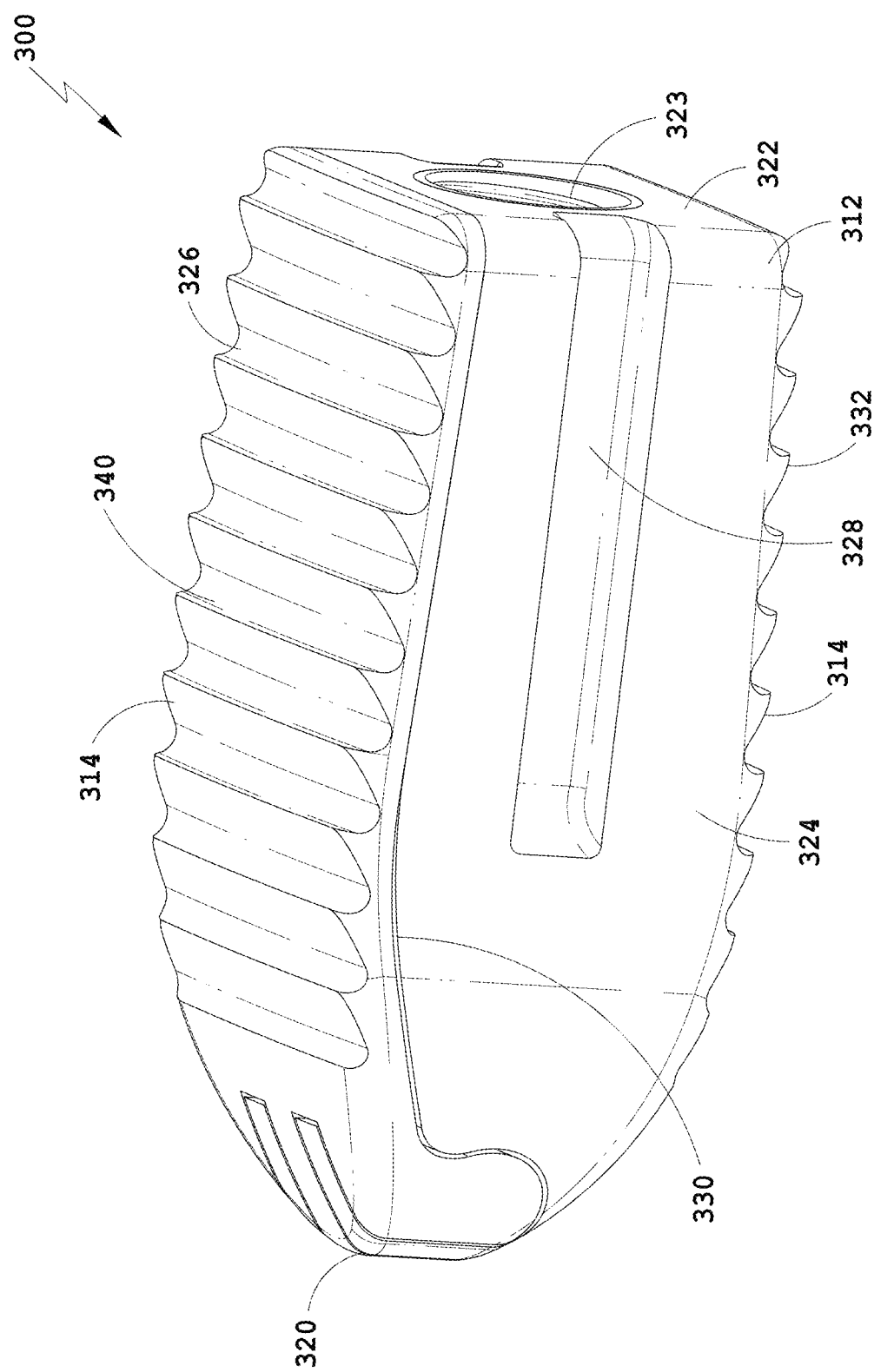
FIG. 26 is a perspective view of an embodiment of a spinal implant device with a movable lid shown in a closed position.

FIG. 26 illustrates a perspective view of a spinal implant device 300. The spinal implant 300 can include any of the features of the spinal implant device 10, 10A, 100, 200 as described herein and can be used in any method or method step described herein. The spinal implant device 300 can include a body structure 312.

Figure 27:
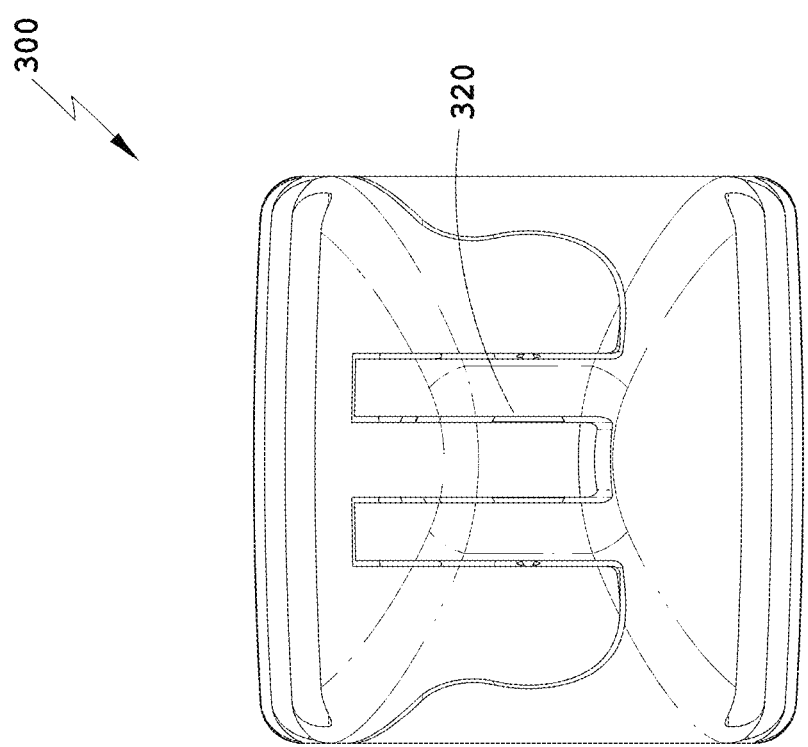
FIG. 27 is a distal view of the spinal implant device of FIG. 26.

FIG. 27 is a distal view of the spinal implant device 300. The spinal implant device 300 can include a distal end 320. In some methods of use, the distal end 320 can facilitate insertion of the spinal implant device 300. In some embodiments, the distal end 320 is tapered inward. In some embodiments, a portion of the four major surfaces of the distal end 320 can taper. In some embodiments, the upper surface and the lower surface of the distal end 320, or a portion thereof, equally taper. In some embodiments, the side surfaces of the distal end 320, or a portion thereof, equally taper. In some embodiments, the distal end 320 can include rounded corners or edges.

Figure 28:
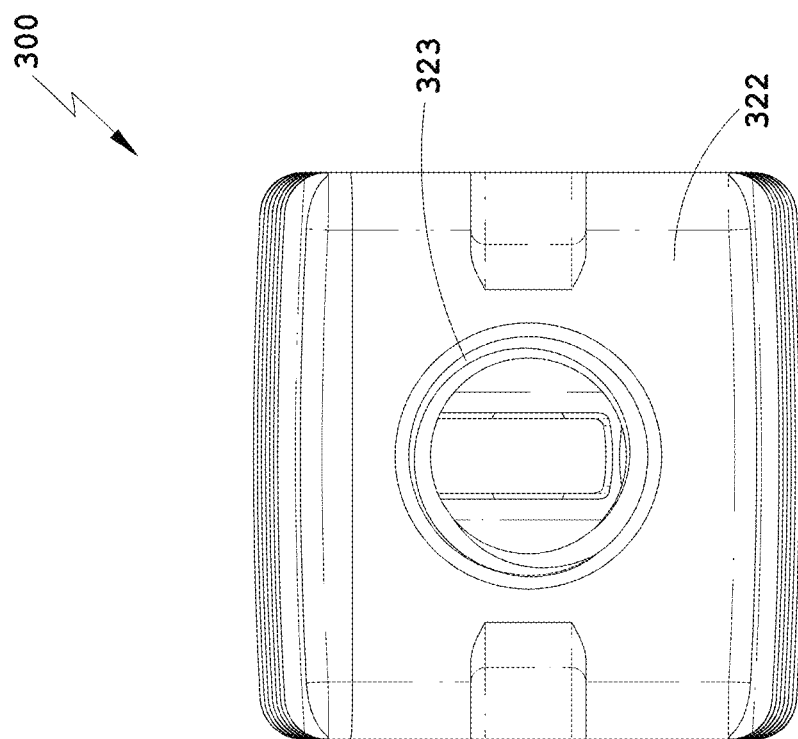
FIG. 28 is a proximal view of the spinal implant device of FIG. 26.

FIG. 28 is a proximal view of the spinal implant device 300. The spinal implant device 300 can include a proximal end 322. In some embodiments, the proximal end 322 can be planar or substantially planar. In some embodiments, the proximal end 322 can include one or more rounded corners or edges, for instance the bottom corners can be rounded. In some embodiments, the proximal end 322 can include an opening 323. In some embodiments, the opening 323 can be threaded or have another feature to engage an insertion tool.

Figure 29:
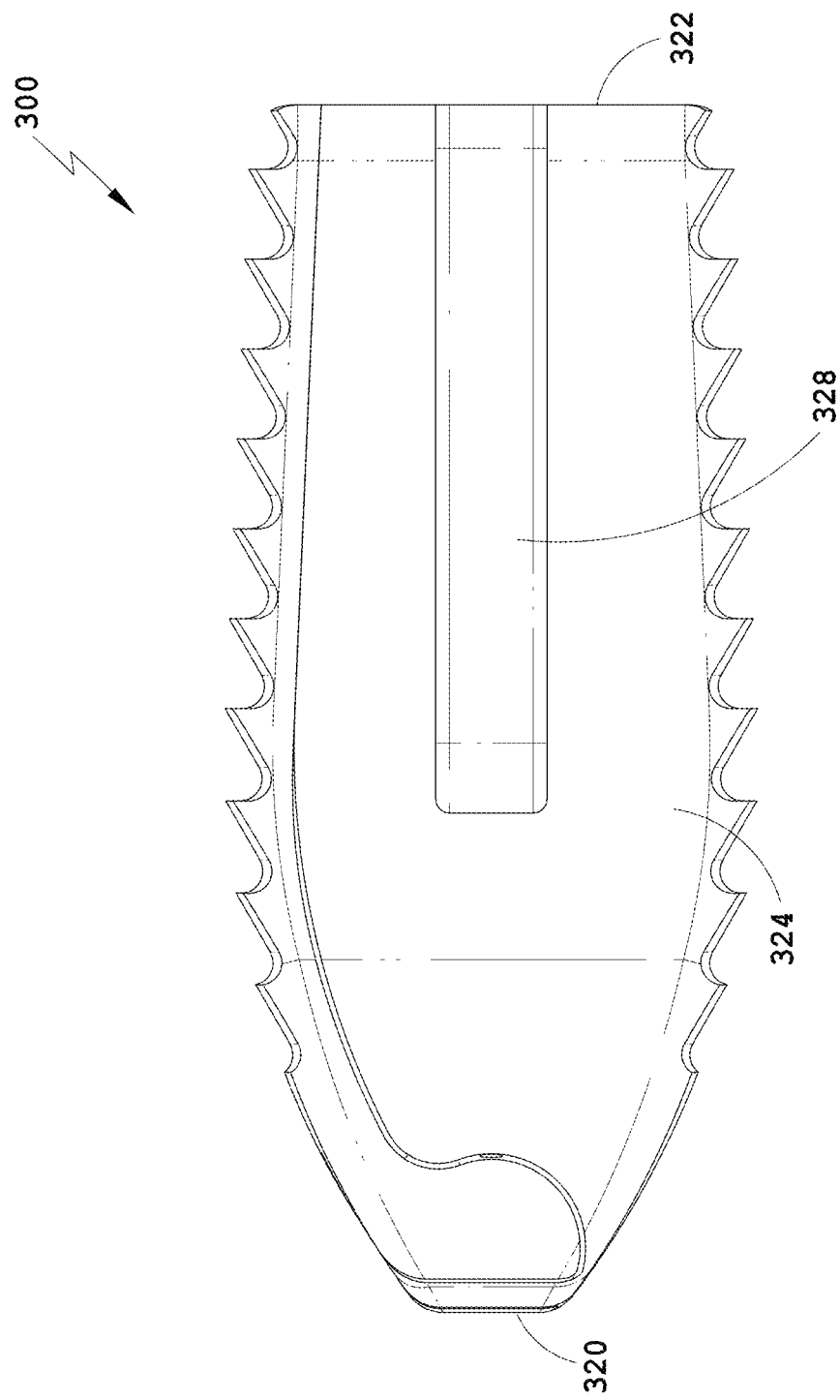
FIG. 29 is a side view of the spinal implant device of FIG. 26.

FIG. 29 is a side view of the spinal implant device 300 which illustrates the length between the distal end 320 and the proximal end 322. The spinal implant device 300 can include two opposing side walls 324, 326. FIG. 12 illustrates the first side wall 324. The second side wall 326 can be rotated 180° relative to the first side wall 324. The second side wall 326 can include any of the features or elements described below.

The two opposing side walls 324, 326 can span between distal end 320 and the proximal end 322. In some embodiments, the two opposing side walls 324, 326 are separated the same distance defining a substantially rectangular shape. In some embodiments, the two opposing side walls 324, 326 are parallel along at least a portion of the length of the spinal implant device 300. In some embodiments, the distance between the two opposing side walls 324, 326 can form the width of the spinal implant device 300.

The two opposing side walls 324, 326 can include a feature 328 to facilitate manipulation and control of the spinal implant device 300. In some embodiments, the feature 328 can include a channel to accept an insertion tool. In some embodiments, the feature 328 can extend from the proximal end 322 of the spinal implant device 300 toward the distal end 320. In some embodiments, the feature 328 can extend inward for a portion of the width of the side walls 324, 326. In some embodiments, the feature 328 can extend along a portion of the length of the spinal implant device 300 (e.g., 10% of the length, 20% of the length, 30% of the length, 40% of the length, 50% of the length, 60% of the length, 70% of the length, 80% of the length, 90% of the length, or 100% of the length, or any range of the foregoing values).

Figure 30:
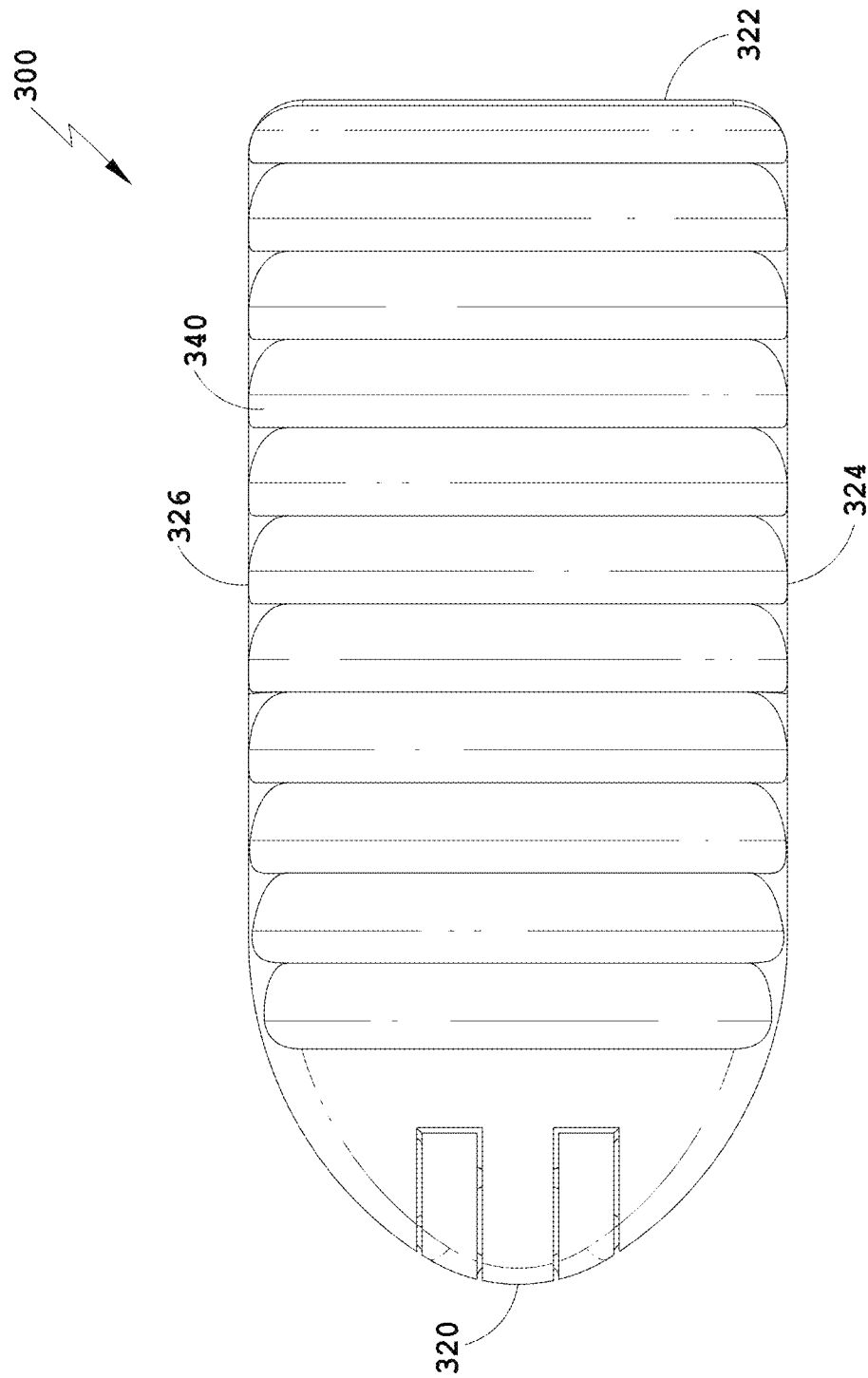
FIG. 30 is a top view of the spinal implant device of FIG. 26.
Figure 31:
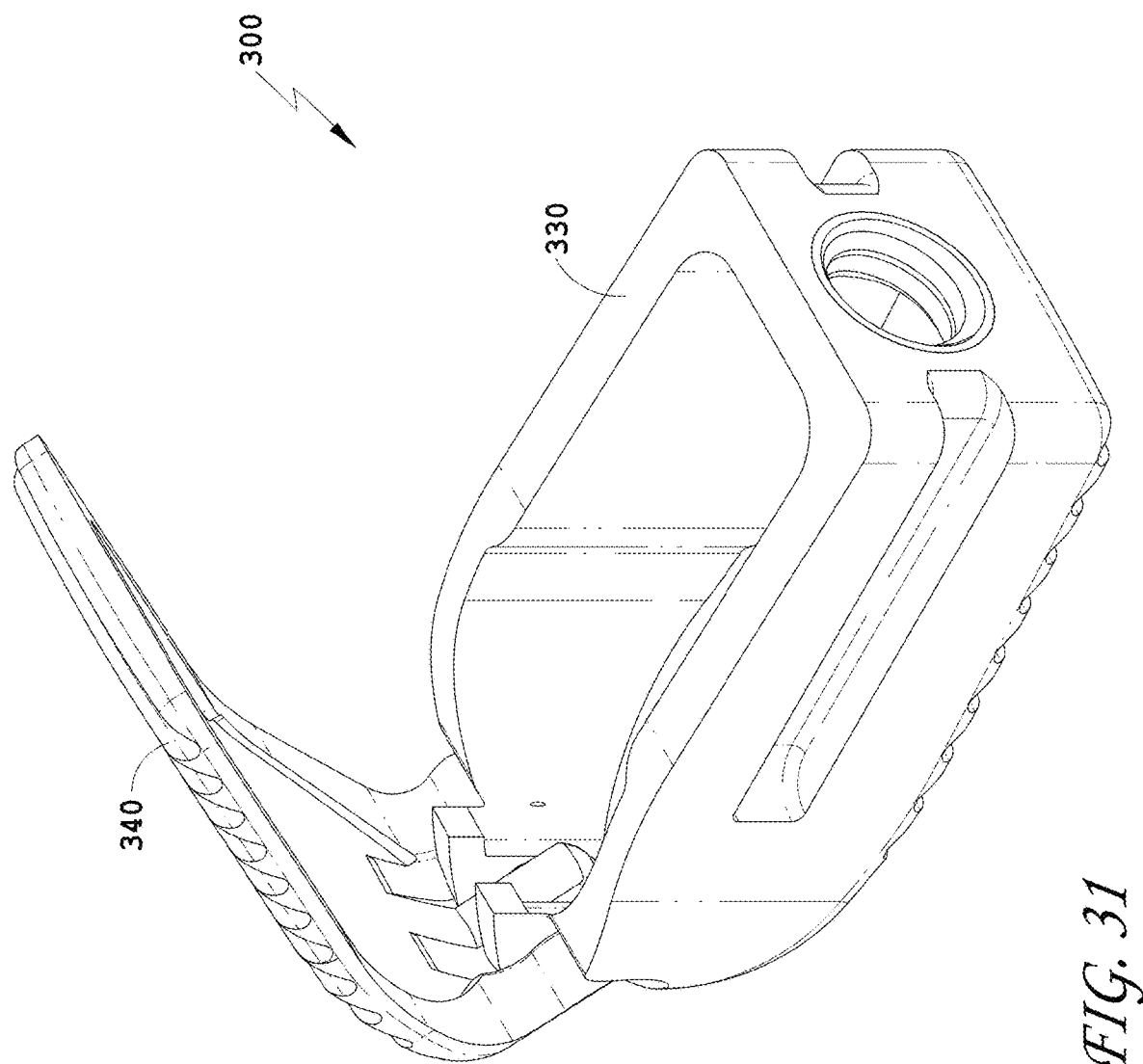
FIG. 31 is a top perspective view of the spinal implant device of FIG. 26 with the movable lid shown in an opened position.

FIG. 30 is a top view of the spinal implant device 300 with a movable lid 340 closed. FIG. 31 is a top perspective view of the spinal implant device 300 with the movable lid 340 opened. The spinal implant device 300 can include the movable lid 340.

The spinal implant device 300 can include an upper wall 330. The upper wall 330 can span between the distal end 320 and the proximal end 322. In some embodiments, a portion of the upper wall 330 is tapered inward. In some embodiments, a portion of the upper wall 330 is tapered toward the distal end 320. In some embodiments, a portion of the upper wall 330 is planar. In some embodiments, the upper wall 330 forms a ledge to support the movable lid 340. In some embodiments, the upper wall 330 forms a support surface for the movable lid 340. In some embodiments, the upper wall 330 allows for compression of the moveable lid 340. In some methods of use, the compression of the moveable lid 340 may promote fusion. In some embodiments, the upper wall 330 supports the movable lid 340 along the side walls 324, 326. In some embodiments, the upper wall 330 supports the movable lid 340 along the proximal end 322. In some embodiments, the upper wall 330 supports the movable lid 340 along the distal end 320.

In some embodiments, the movable lid 340 can form the upper surface of the spinal implant device 300 configured to contact the vertebral end plate. In some embodiments, the movable lid 340 and the upper wall 330 can correspond in shape. The movable lid 340 can match the curvature of the upper wall 330. The movable lid 340 can abut the upper wall 330 when the lid 340 is closed. In some embodiments, the movable lid 340 can provide a load supporting surface for the adjacent vertebrae. In some methods, the load can be transferred from the movable lid 340 to the upper wall 330. In some methods, the movable lid 340 can be positioned adjacent to a vertebral end plate of a superior vertebra.

Figure 32:
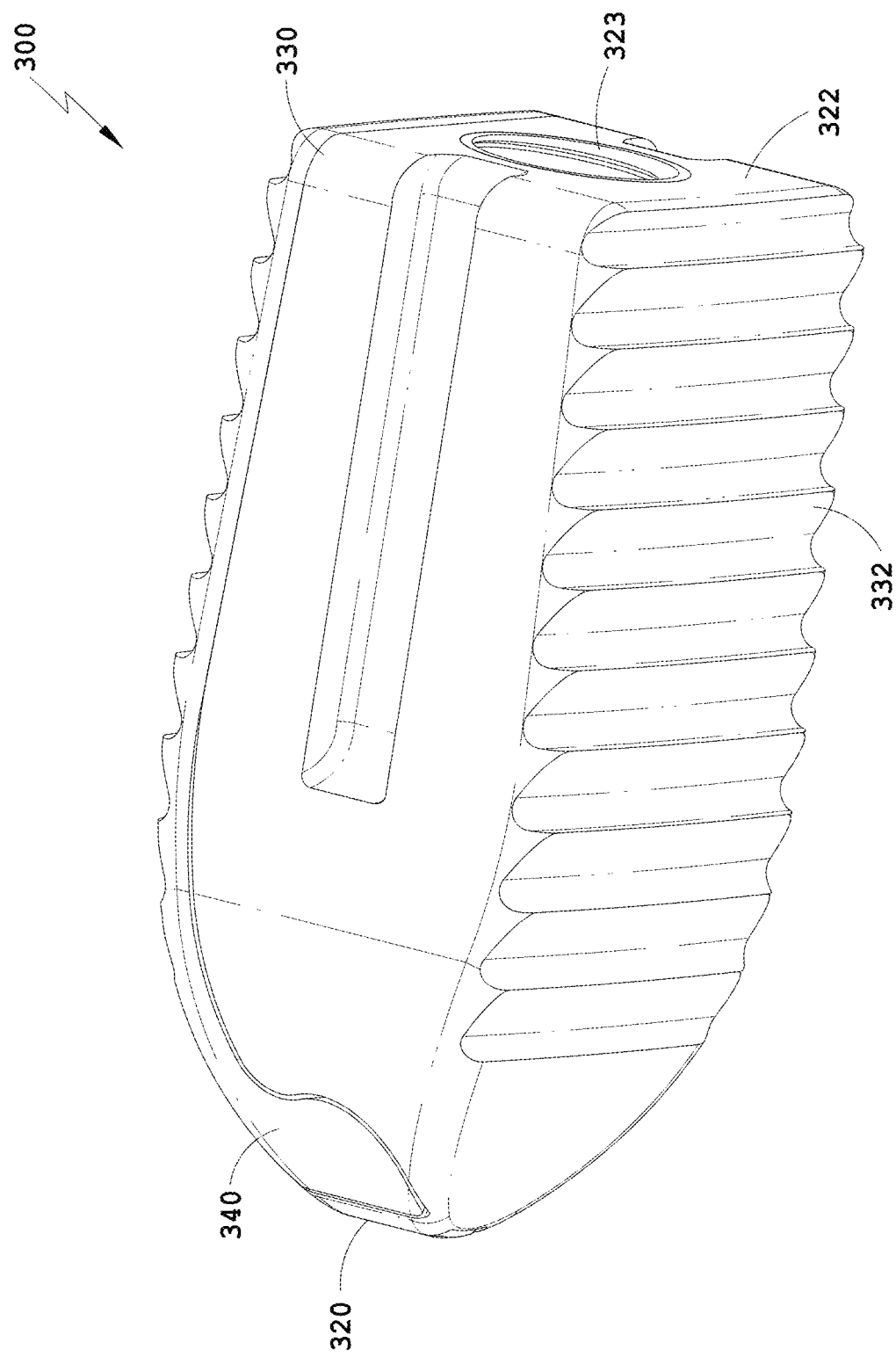
FIG. 32 is a bottom perspective view of the spinal implant device of FIG. 26.

FIG. 32 is a bottom perspective view of the spinal implant device 300. The spinal implant device 300 can include a lower wall 332. The lower wall 332 can span between the distal end 320 and the proximal end 322. In some embodiments, a portion of the lower wall 332 is tapered inward. In some embodiments, a portion of the lower wall 332 is tapered toward the distal end 320. In some embodiments, a portion of the lower wall 332 is planar or substantially planar. In some embodiments, a portion of the lower wall 332 is convex. In some embodiments, a portion of the lower wall 332 is bowed outward.

The lower wall 332 can provide a load supporting surface. In some methods, the lower wall 332 can be positioned adjacent to a vertebral end plate of an inferior vertebra. In some methods, when the spinal implant device 300 is positioned between two adjacent vertebrae, the load supporting surfaces of the movable lid 340 and the lower wall 332 contact the vertebral end plates of the adjacent vertebrae. In some embodiments, the distance between the movable lid 340 and the lower wall 332 can form the height of the spinal implant device 300. In some embodiments, the upper wall 330 and the lower wall 332 have the same or similar shape. In some embodiments, the upper wall 330 and the lower wall 332 are bowed outward. In some embodiments, the upper wall 330 and the lower wall 332 are shaped to match the vertebral end plates.

Figure 33:
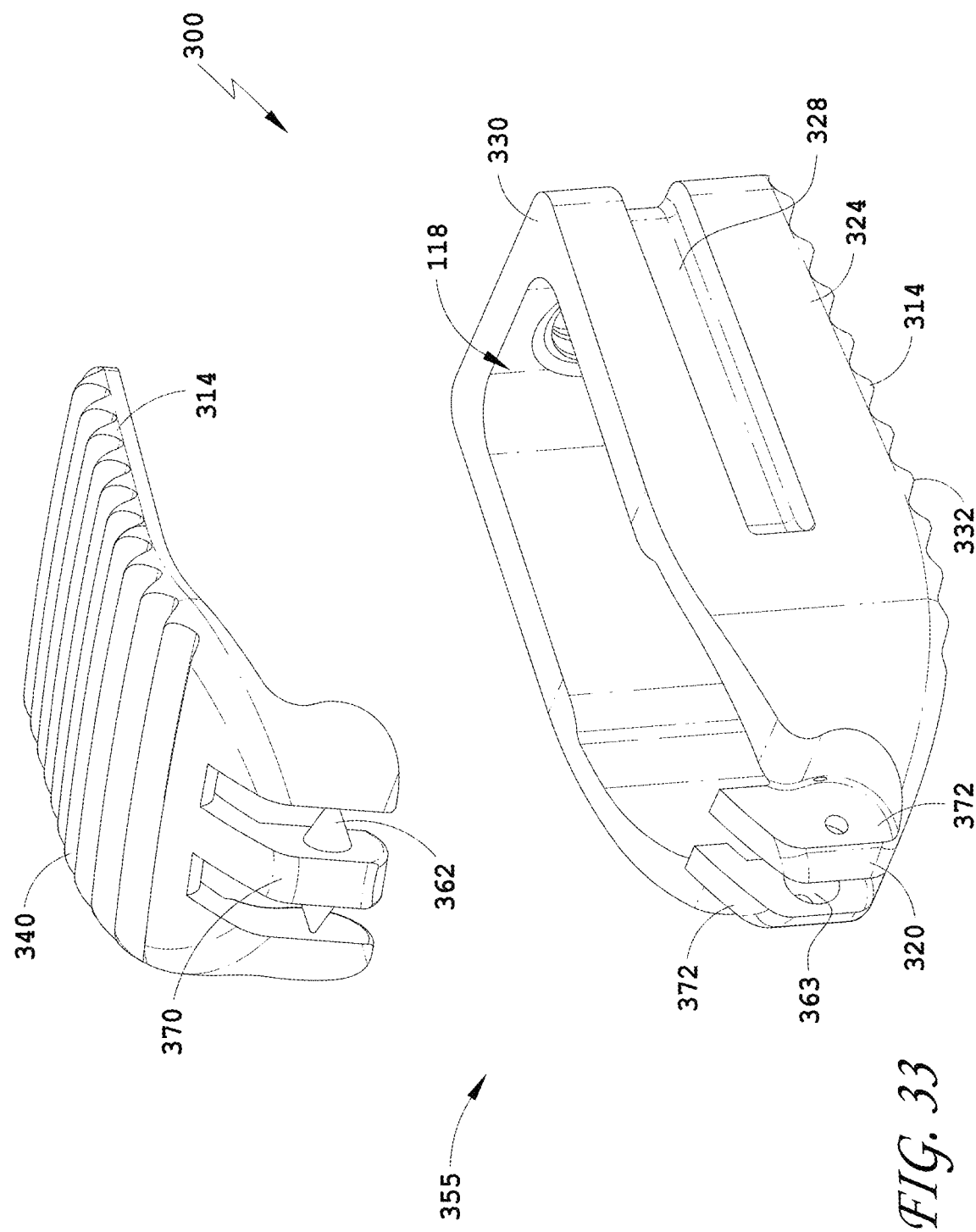
FIG. 33 is an exploded perspective view of the spinal implant device of FIG. 26.

FIG. 33 is an exploded view of the movable lid 340 of the spinal implant device 300. In some embodiments, the movable lid 340 can be coupled to the distal end 320. The distal end 320 can include two opposing lateral posts 372. The two opposing lateral posts 372 can extend between portions of the upper wall 330. In some embodiments, the upper wall 330 is recessed relative to the two opposing lateral posts 372 to accommodate the movable lid 340. The two opposing lateral posts 372 can extend along a portion of the width of the spinal implant device 300. While the two opposing lateral posts 372 are diametrically located along the longitudinal axis of the spinal implant device 300, other positions of the two opposing lateral posts 372 are contemplated.

In some embodiments, the spinal implant device 300 can include a movable joint 355. In some embodiments, the movable joint 355 can couple the movable lid 340 to the distal end 320. The movable joint 355 can couple the movable lid 340 with any portion of the body structure 312. The movable joint 355 can allow for pivoting motion of the movable lid 340. In some embodiments, the movable joint 355 can include one axis of rotation. In some embodiments, the movable joint 355 can include more than one axis of rotation.

In some embodiments, the movable joint 355 can include a pair of articulations 362. The pair of articulations 362 can be located on the movable lid 340. The pair of articulations 362 can extend from a central post 370 of the movable lid 340. The central post 370 can be located near a distal end of the movable lid 340. The pair of articulations 362 can extend outward from the central post 370. The two opposing lateral posts 372 of the distal end 320 can be sized to accommodate the central post 370 of the movable lid 340. The two opposing lateral posts 372 of the distal end 320 can interact with the central post 370 of the movable lid 340 to allow for pivoting motion.

The two opposing lateral posts 372 can include a pair of sockets 363 configured to engage the pair of articulations 362. The pair of sockets 363 can extend perpendicular to the longitudinal axis of the spinal implant device 300. The pair of sockets 363 can extend outward from the inner surfaces of the two opposing lateral posts 372. In some embodiments, the orientation is reversed and the pair of articulations 362 can be located on the distal end 320 and the pair of sockets 363 can be located on the movable lid 340.

In some embodiments, each articulation 362 is conical and each socket 363 is conical. In some embodiments, the movable joint 355 can include one or more articulations 362 (e.g., one, two, three, four, five, or six). In some embodiments, the movable joint 355 can include a corresponding number of articulations and sockets. The moveable lid 340 can be coupled to the spinal implant device 300 at any location to facilitate packing the spinal implant device 300.

The spinal implant device 300 can include a cavity 318. In some embodiments, the proximal end 322 can define the back inner surface of the cavity 318. In some embodiments, the distal end 320 can define the front inner surface of the cavity 318. In some embodiments, the two opposing side walls 324, 326 can define the side inner surfaces of the cavity 318. In some embodiments, the movable lid 340 can define the top inner surface of the cavity 318. In some embodiments, the lower wall 342 can define the bottom inner surface of the cavity 318. In some embodiments, the cavity 318 is partially enclosed. In some embodiments, the cavity 318 is fully enclosed. The cavity 318 can be a contained space within the spinal implant device 300. In some embodiments, the cavity 318 comprises a portion of the volume of the spinal implant device 300 (e.g., 50% of the volume, 60% of the volume, 70% of the volume, 80% of the volume, 90% of the volume, or 100% of the volume, or any range of the foregoing values).

In some embodiments, the spinal implant device 300 can include features to limit or reduce movement of the spinal implant device 300 between the vertebrae. The spinal implant device 300 can include a plurality of ridges 314. The ridges 314 can form a portion of the movable lid 340. The ridges 314 can form a portion of the lower wall 332. In some embodiments, the ridges 314 are positioned on the upper surface of the spinal implant device 300, the lower surface of the spinal implant device 300, or both the upper surface and the lower surface of the spinal implant device 300. In some embodiments, the ridges 314 can be directionally oriented as described herein.

Figure 34:
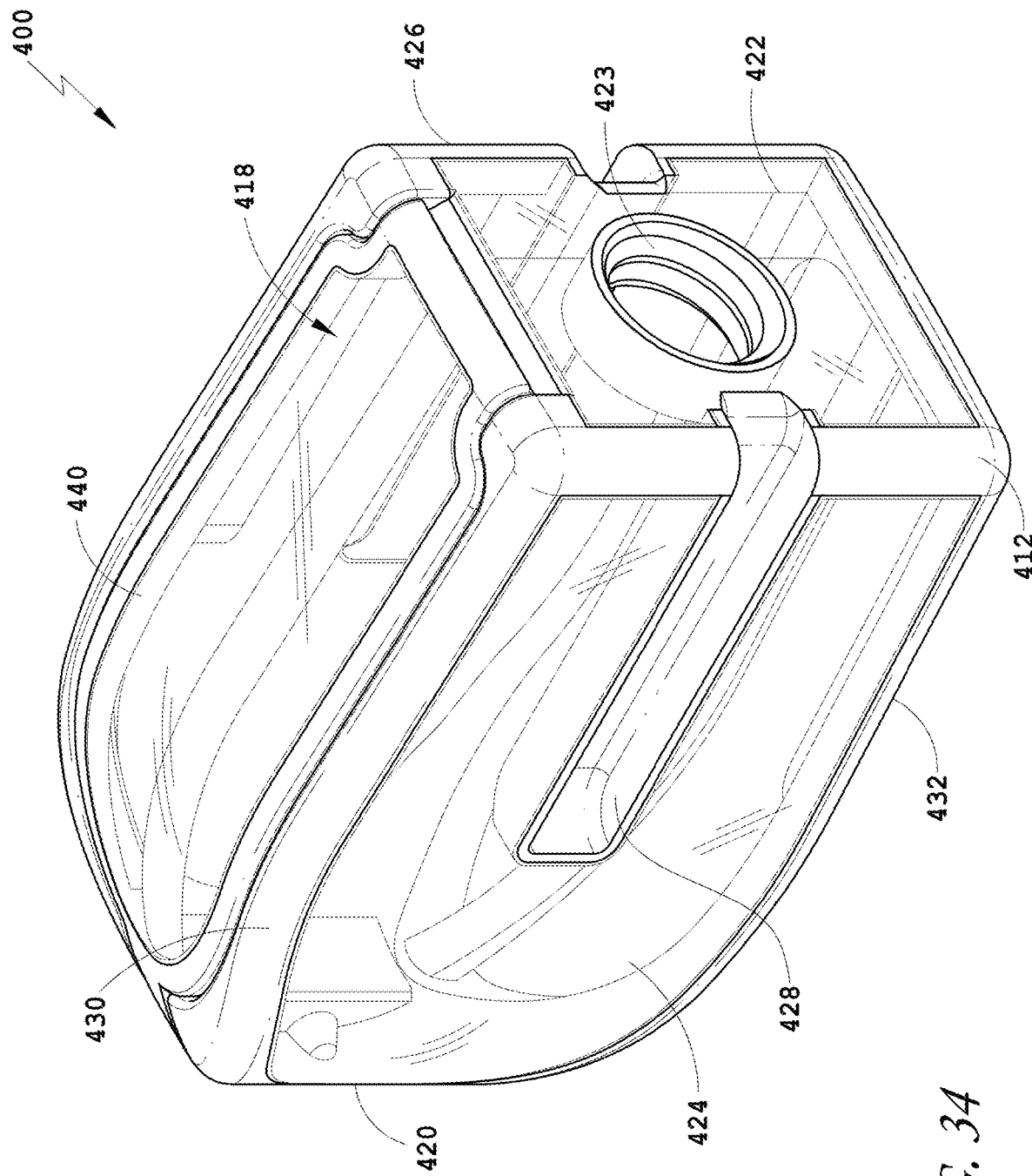
FIG. 34 is a perspective view of an embodiment of a spinal implant device with a movable lid shown in a closed position.

FIG. 34 illustrates a perspective view of a spinal implant device 400. The spinal implant device 400 can include any of the features of the spinal implant device 10, 10A, 100, 200, 300 as described herein and can be used in any method or method step described herein. The spinal implant device 400 can include a body structure 412. The body structure 412 can include a thin framework supported by thicker edges. In some embodiments, the thin framework is solid. In some embodiments, the thin framework is porous or a mesh. In some embodiments, the thin framework allows bony ingrowth therethrough. In some embodiments, the thin framework allows the fusion of material therethrough. In some embodiments, a porous body is applied to the thin framework. The porous bodies arranged on one or more sides can allow material to flow outwardly from the spinal implant device 400 to promote fusion. The porous bodies can include any porous material. The porous bodies can be formed of any material that intrinsically participates in the growth of bone.

In some embodiments, at least a portion of one surface of the spinal implant device 400 can have a porous body. The porous body can be created in any a variety of ways, such as by applying sintered beads or spraying plasma onto the thin framework or by 3D printing. The porous body can allow bone to grow into or attach to the surface of the spinal implant device 400, thus securing the spinal implant device 400 to the bone. In some embodiments, an adhesive or sealant, such as a cyanoacrylate, polymethylmethacrylate, or other adhesive, can be used to bond the porous material to the spinal implant device 400.

Figure 35:
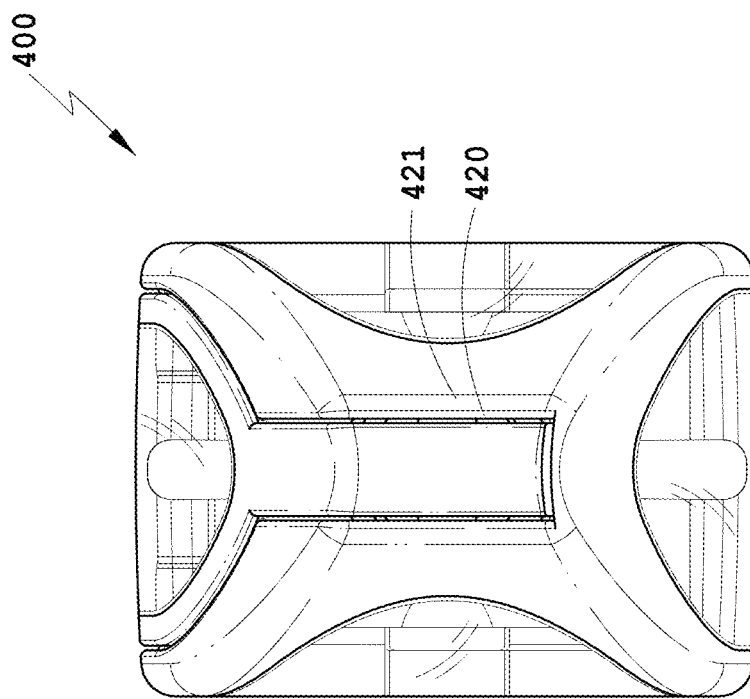
FIG. 35 is a distal view of the spinal implant device of FIG. 34.

FIG. 35 is a distal view of the spinal implant device 400. The spinal implant device 400 can include a distal end 420. The distal end 420 can include thicker edges which facilitates insertion of the distal end 420. The distal end 420 can be inserted between vertebrae. The distal end 420 can be more rigid than another portion of the spinal implant device 400. The distal end 420 can be tapered. In some embodiments, the four surfaces of the distal end 420 can taper to from a square pyramid or similar shape. The distal end 420 can form an X-shape. The distal end 420 can be formed from four thicker edges which come together. In some embodiments, the upper edges and the lower edges of the distal end 420 equally taper. In some embodiments, the distal end 420 can include rounded corners to facilitate insertion. The distal end 420 can form a frustoconical or convex curved shape 421.

Figure 36:
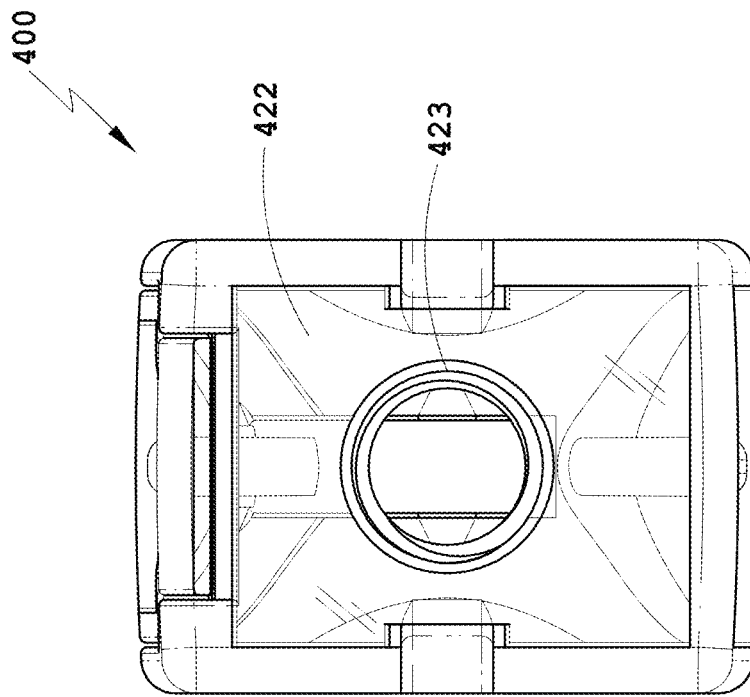
FIG. 36 is a proximal view of the spinal implant device of FIG. 34.

FIG. 36 is a proximal view of the spinal implant device 400. The spinal implant device 400 can include a proximal end 422. In some embodiments, the proximal end 422 can include a thin framework supported by thicker edges. The proximal end 422 can include four thicker edges surrounding a thin framework. The thin framework can be square, rectangular, quadrilateral, or other polygonal shape. The thin framework can support a porous body, such as a porous body applied thereto. The thicker edges can be rounded to facilitate insertion of the spinal implant device 400. The proximal end 422 can be substantially square or rectangular. In some embodiments, the proximal end 422 can include an opening 423 such as a threaded opening to couple with an insertion tool.

Figure 37:
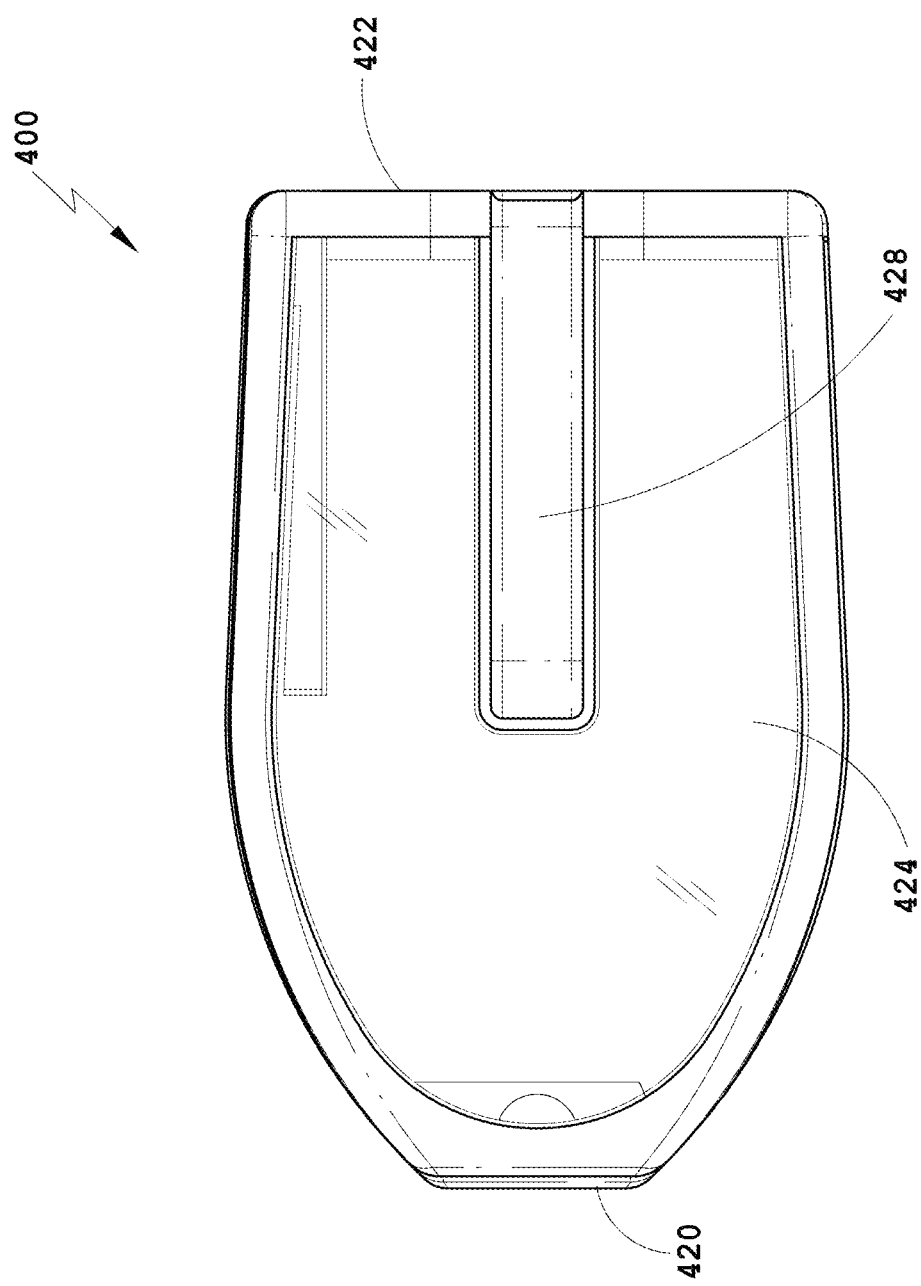
FIG. 37 is a side view of the spinal implant device of FIG. 34.

FIG. 37 is a side view of the spinal implant device 400. The length or depth of the spinal implant device 400 can be the distance between the distal end 420 and the proximal end 422. The spinal implant device 400 can include two opposing side walls including a first side wall 424 and a second side wall 426. FIG. 37 illustrates the first side wall 424, but the second side wall 426 can include the same or similar features. In some embodiments, each side wall 424, 426 can include a thin framework supported by thicker edges. Each side wall 424, 426 can include four thicker edges surrounding a thin framework. The thin framework can have a rounded edge near the distal end 420. The thin framework can have a flat edge near the proximal end 422. The thin framework can span the height of the spinal implant device 400 or a portion thereof. The thin framework can follow the shape of the side wall 424, 426. The thin framework can support a porous body. The porous body can be coupled to the side wall 424, 426. The porous body, once coupled, can be flush with the thicker edges. The porous body, once coupled, can be less than the thickness of the edges. The porous body, once coupled, can be greater than the thickness of the edges. The thicker edges can be rounded to facilitate insertion of the spinal implant device 400. In some embodiments, the thin framework of the spinal implant device 400, or a portion thereof, can facilitate compression of the spinal implant device 400.

In some embodiments, each of the two opposing side walls 424, 426 can include a feature 428. The feature 428 can be designed to facilitate placement of the spinal implant device 400 by coupling with an insertion tool. In some embodiments, the feature 428 can include a channel or groove that originates at the proximal end 422. In some embodiments, the feature 428 can extend from the proximal end 422 along a portion of one of the side walls 424, 426. In some embodiments, the feature 428 extends inward from one of the side walls 424, 426. In some embodiments, the feature 428 can extend inward greater than the width of one of the side walls 424, 426. In some embodiments, the feature 428 is formed from the same material as the thicker edges. In some embodiments, the feature 428 is stronger or more rigid than the adjacent thin framework. In some embodiments, the feature 428 can include a slot. The slot can be considered an opening.

Figure 38:
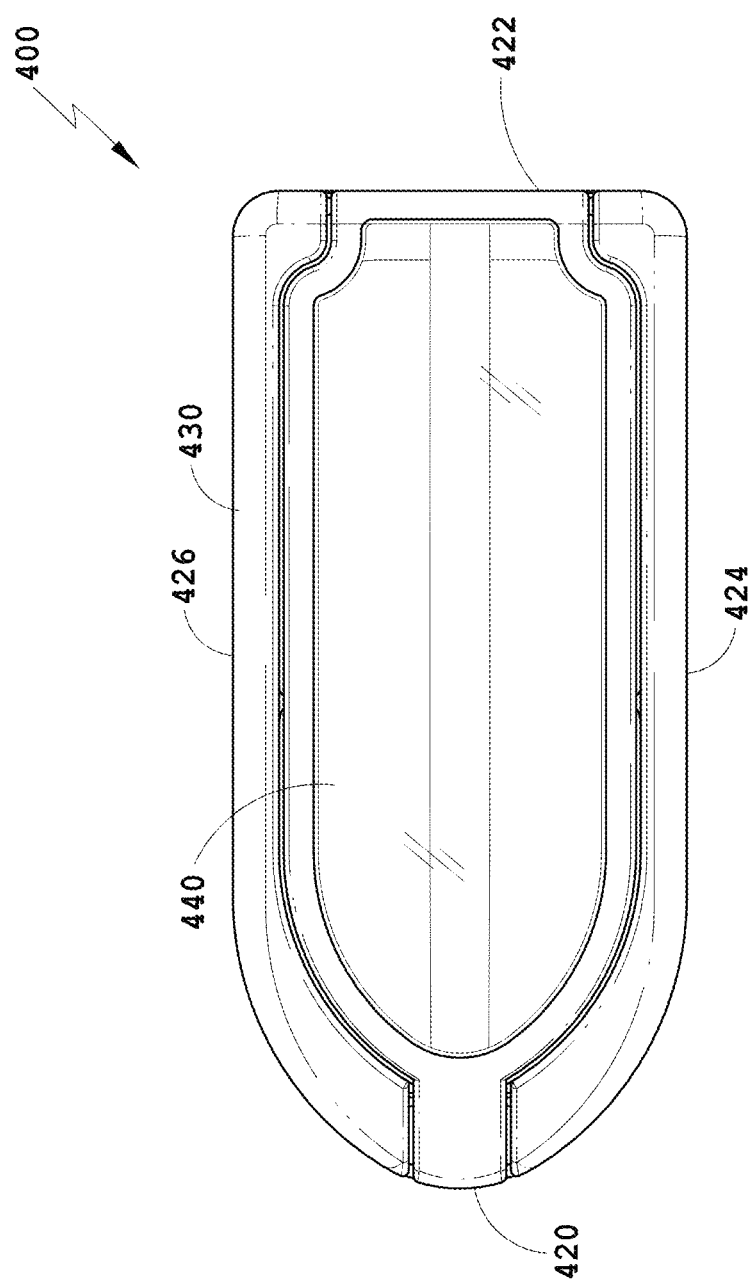
FIG. 38 is a top view of the spinal implant device of FIG. 34.

FIG. 38 is a top view of the spinal implant device 400. The two opposing side walls 424, 426 can extend between the distal end 420 and the proximal end 422. In some embodiments, the two opposing side walls 424, 426 are separated by the same width along a substantial portion of the length of the two opposing side walls 424, 426.

Figure 39:
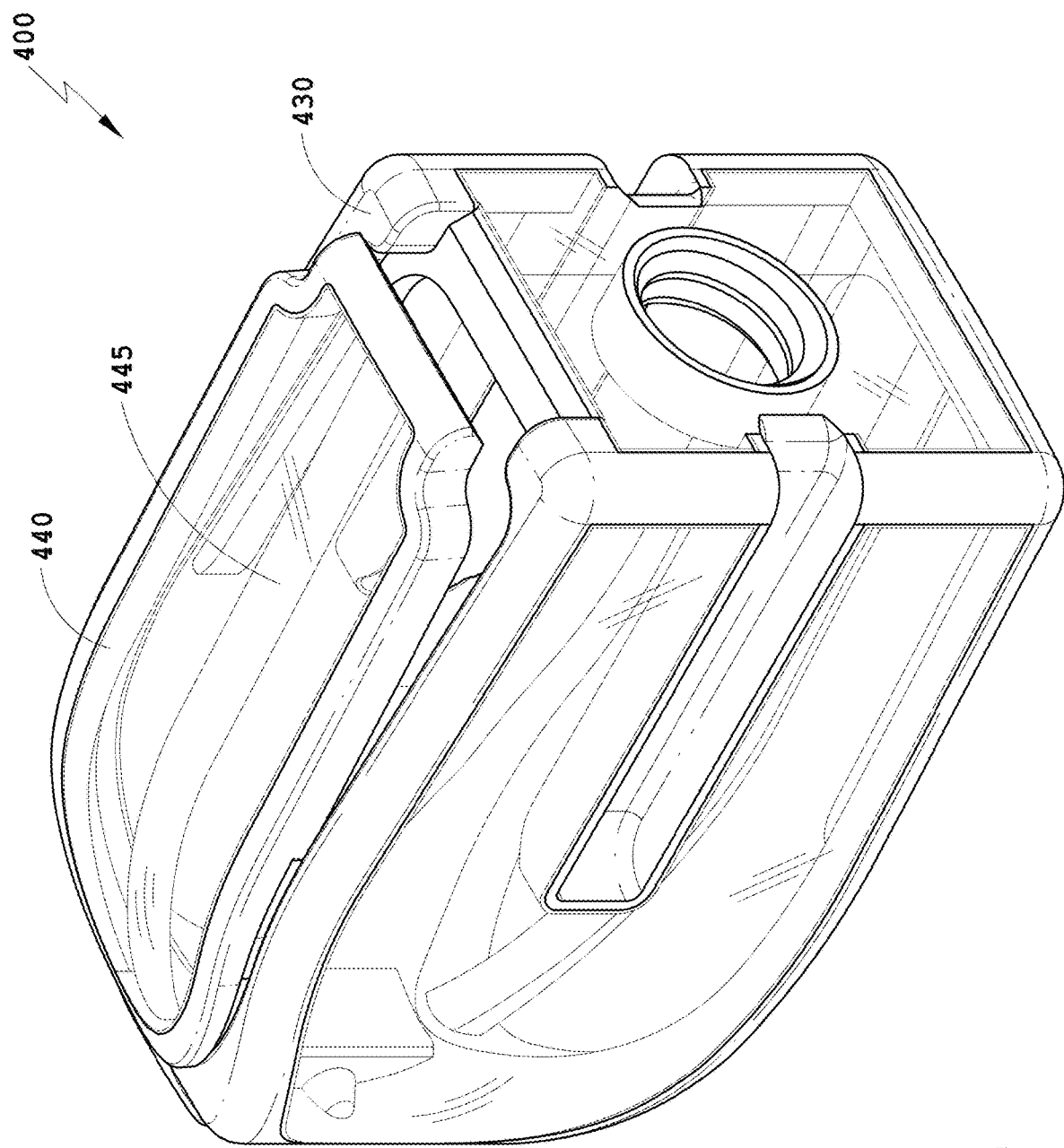
FIG. 39 is a top perspective view of the spinal implant device of FIG. 34 with the movable lid shown in an opened position.

The spinal implant device 400 can include a movable lid 440. FIG. 38 is a top view of the spinal implant device 400 with the movable lid 440 closed. FIG. 39 is a top perspective view of the spinal implant device 400 with the movable lid 440 opened.

In some embodiments, the movable lid 440 can include a thin framework supported by thicker edges. The movable lid 440 can include four thicker edges surrounding a thin framework. The thin framework can have a rounded edge near the distal end 420. The thin framework can have a flat edge near the proximal end 422. The thin framework can span the length of the spinal implant device 400 or a portion thereof. The thin framework of the movable lid 440 can support a porous body as described herein. The thicker edges of the movable lid 440 can be planar to form a top surface. The spinal implant device 400 can include a longitudinal bar 445 located on the movable lid 440. While one longitudinal bar 445 is illustrated, the movable lid 440 can include any number of longitudinal bars 445 (e.g., one, two, three, four, five, or six). In some embodiments, the movable lid 440 can include an opening. In some embodiments, the opening can extend through the movable lid 440. In some embodiments, the opening can extend through the upper wall 430. The opening can be elongate. The opening can extend along the length of the spinal implant device 400. The upper surface can include one or more openings (e.g., one, two, three, four, five, or six). In some embodiments, the spinal implant device 400 does not include a longitudinal bar 445 located on the movable lid 440.

The spinal implant device 400 can include an upper wall 430. The upper wall 430 can include thicker edges which forms the top surface of the spinal implant device 400. The upper wall 430 can extend between the distal end 420 and the proximal end 422. In some embodiments, the upper wall 430 is tapered toward the distal end 420. In some embodiments, the upper wall 430 is formed from the same material as the thicker edges.

In some embodiments, the upper wall 430 includes a lip or surface to support the movable lid 440. In some embodiments, the upper wall 430 forms a ledge along a portion of the edges of the movable lid 440. In some embodiments, the upper wall 430 forms a ledge along all of the edges of the movable lid 440. The moveable lid 440 can be supported along the sidewalls 424, 426, or a portion thereof, as illustrated in FIG. 39. In some embodiments, the moveable lid 440 can be unsupported along the sidewalls 424, 426. The moveable lid 440 can be supported at the distal end 420 via a movable hinge or a distal ledge. The moveable lid 440 can be supported at the proximal end 422 by a proximal edge. In some embodiments, the upper wall 430 allows for compression of the moveable lid 440 to a desired depth relative to the upper wall 430. The compression of the moveable lid 440 can promote fusion of the adjacent vertebrae. The compression of the moveable lid 440 can promote fusion by increasing the load on the material contained within the spinal implant device.

In some embodiments, the upper wall 430 forms an opening to accommodate the movable lid 440. In some embodiments, the movable lid 440 and the upper wall 430 together form the upper surface of the spinal implant device 400. In some embodiments, the movable lid 440 and the upper wall 430 are laterally adjacent when the lid 440 is closed. The movable lid 440 can be sized to be located within the upper wall 430. The movable lid 440 can be sized to be surrounded, at least laterally, by the upper wall 430. In some embodiments, the movable lid 440 and the upper wall 430 can provide a load supporting surface. In some methods, the movable lid 440 and the upper wall 430 can be positioned adjacent to a vertebral end plate of a superior vertebra.

Figure 40:
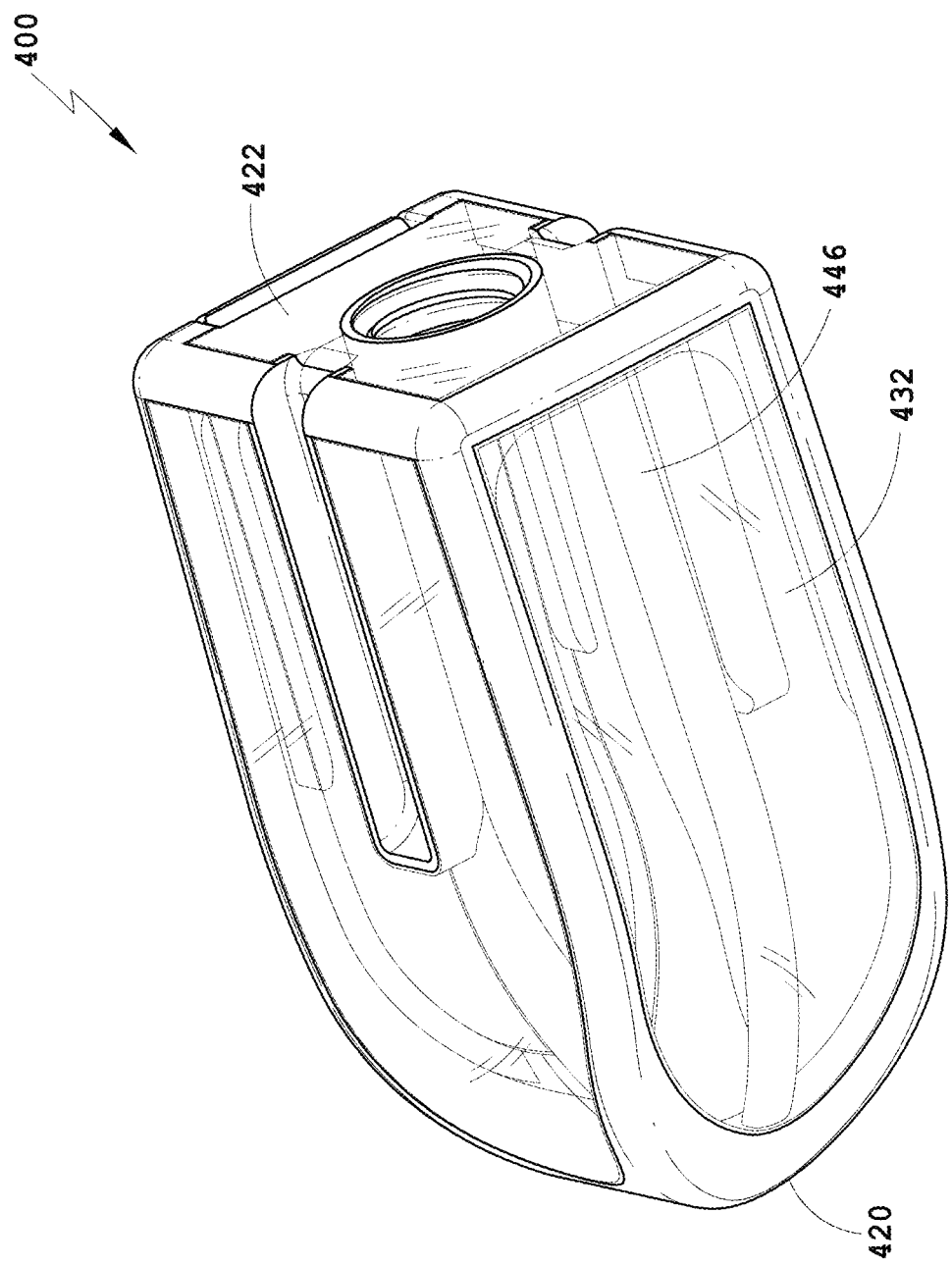
FIG. 40 is a bottom perspective view of the spinal implant device of FIG. 34.

FIG. 40 is a bottom perspective view of the spinal implant device 400. The spinal implant device 400 can include a lower wall 432. The lower wall 432 can extend between the distal end 420 and the proximal end 422. In some embodiments, the lower wall 432 is curved to mimic the shape of the vertebral endplates. The spinal implant device 400 can include a longitudinal bar 446 located on the lower wall 432. While one longitudinal bar 446 is illustrated, the lower wall 432 can include any number of longitudinal bars 446 (e.g., one, two, three, four, five, or six). In some embodiments, the one or more longitudinal bars 445, 446 extend parallel to the longitudinal axis of the spinal implant device 400. In some embodiments, the one or more longitudinal bars 445, 446 can be flat or substantially flat. In some embodiments, the one or more longitudinal bars 445, 446 can provide additional load bearing support. In some embodiments, the one or more longitudinal bars 445, 446 can support the thin framework of the moveable lid 440 and the lower wall 432.

In some embodiments, the lower wall 432 can include a thin framework supported by thicker edges. The lower wall 432 can include four thicker edges surrounding a thin framework. The thin framework can have a rounded edge near the distal end 420. The thin framework can have a flat edge near the proximal end 422. The thin framework can span the length of the spinal implant device 400 or a portion thereof. The thin framework of the lower wall 432 can support a porous body as described herein. The lower wall 432 can include thicker edges which forms the bottom surface of the spinal implant device 400. In some embodiments, the lower wall 432 is tapered toward the distal end 420. In some embodiments, the upper wall 430 and the lower wall 432 are bowed outward along a portion of the length of the spinal implant device 400. In some embodiments, the upper wall 430 and the lower wall 432 are tapered inward along a portion of the length of the spinal implant device 400.

The lower wall 432 can provide a load supporting surface. In some methods, the lower wall 432 can be positioned adjacent to a vertebral end plate of an inferior vertebra. In some embodiments, the distance between the movable lid 440 and the lower wall 432 can form the height of the spinal implant device 400.

Figure 41:
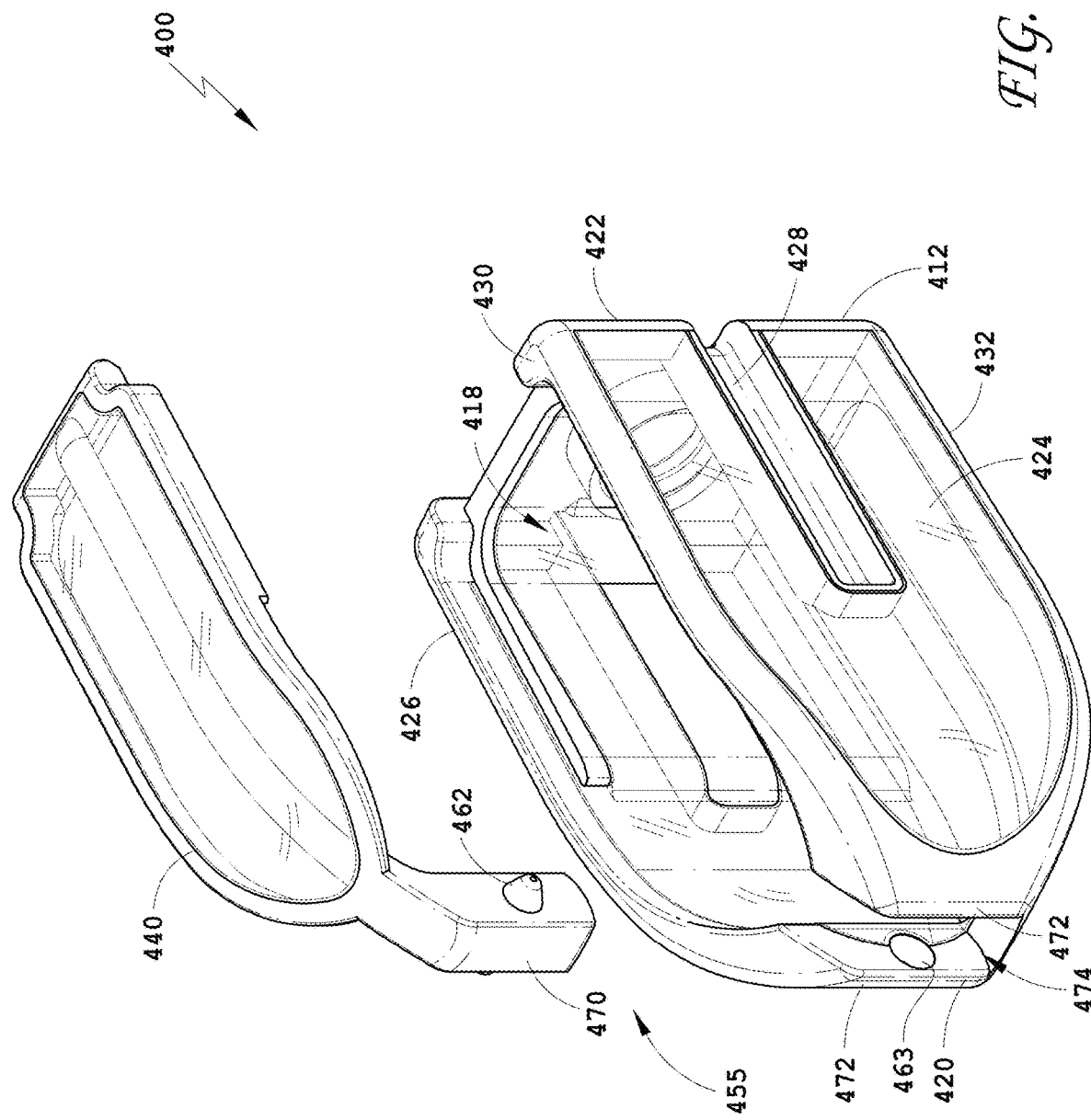
FIG. 41 is an exploded perspective view of the spinal implant device of FIG. 34.

FIG. 41 is an exploded view of the movable lid 440 and the body structure 412. In some embodiments, the movable lid 440 can be coupled to the body structure 412. In some embodiments, the movable lid 440 can be coupled to the distal end 420. The distal end 420 can include two opposing lateral posts 472. In some embodiments, the two opposing lateral posts 472 are connected with a channel 474. The recessed channel 474 can accommodate the movable lid 440. While the two opposing lateral posts 472 are illustrated bilaterally, along each side of the spinal implant device 400, other positons of the two opposing lateral posts 472 are contemplated.

In some embodiments, the spinal implant device 400 can include a movable joint 455. In some embodiments, the movable joint 455 can be positioned distally. The movable joint 455 can couple the movable lid 440 with the body structure 412. The movable joint 455 can allow for pivoting motion of the movable lid 440 relative to the body structure 412.

In some embodiments, the movable joint 455 can include one or more articulations 462. The one or more articulations 462 can be located on the movable lid 440. The one or more articulations 462 can extend from a central post 470 of the movable lid 440. The one or more articulations 462 can extend outward from the central post 470. The movable joint 455 can include hinge geometry. The movable joint 455 can include a tapered pin for the articulation 462. In some embodiments, the movable joint 455 is a hinge. In some embodiments, the one or more articulations 462 are hinge pins.

The two opposing lateral posts 472 of the distal end 420 can be sized to accommodate the central post 470 of the movable lid 440. The two opposing lateral posts 472 can allow motion with the central post 470 as described herein. The central post 470 can be truncated slightly with a flatter or blunter portion. In some embodiments, the side surfaces of the central post 470 are flat. The central post 470 can be sized to be received within the channel 474 between the two opposing lateral posts 472.

The two opposing lateral posts 472 can include one or more sockets 463 configured to engage the one or more articulations 462. In some embodiments, the movable joint 455 can include a corresponding number of articulations and sockets. The one or more sockets 463 can be perpendicular to the longitudinal axis of the spinal implant device 400. Each socket 463 can extend inward from the inside surface of a lateral post 472. In some embodiments, the orientation is reversed and one or more articulations 462 can be located on the distal end 420 and one or more sockets 463 can be located on the movable lid 440.

In some embodiments, each articulation 462 is conical, at least in part. In some embodiments, each articulation 462 forms a truncated cone. In some embodiments, each socket 463 is conical, at least in part. In some embodiments, each socket 463 forms a truncated cone shaped recess. In some embodiments, each articulation 462 is a convex frustum and each socket 463 is concave frustum.

The spinal implant device 400 can include a cavity 418. In some embodiments, the proximal end 422 can form the back inner surface of the cavity 418. In some embodiments, the distal end 420 can form the front inner surface of the cavity 418. In some embodiments, the two opposing side walls 424, 426 can form the side inner surfaces of the cavity 418. In some embodiments, the movable lid 440 can form the top inner surface of the cavity 418. In some embodiments, the lower wall 432 can form the bottom inner surface of the cavity 418. In some embodiments, the cavity 418 is partially enclosed on at least six sides. The spinal implant device 400 can have a thin framework to support porous bodies. The thin framework includes the areas where the porous body can be applied. The porous bodies can allow material to flow outwardly from the cavity 418, through the thin framework, and through the porous body. The thin framework and porous body can promote fusion by the migration of material to and from the cavity 418.

The cavity 418 can be a centrally located space within the spinal implant device 400. In some embodiments, the cavity 418 comprises a portion of the volume of the spinal implant device 400 (e.g., 50% of the volume, 60% of the volume, 70% of the volume, 80% of the volume, 90% of the volume, or 100% of the volume, or any range of the foregoing values).

Figure 42:
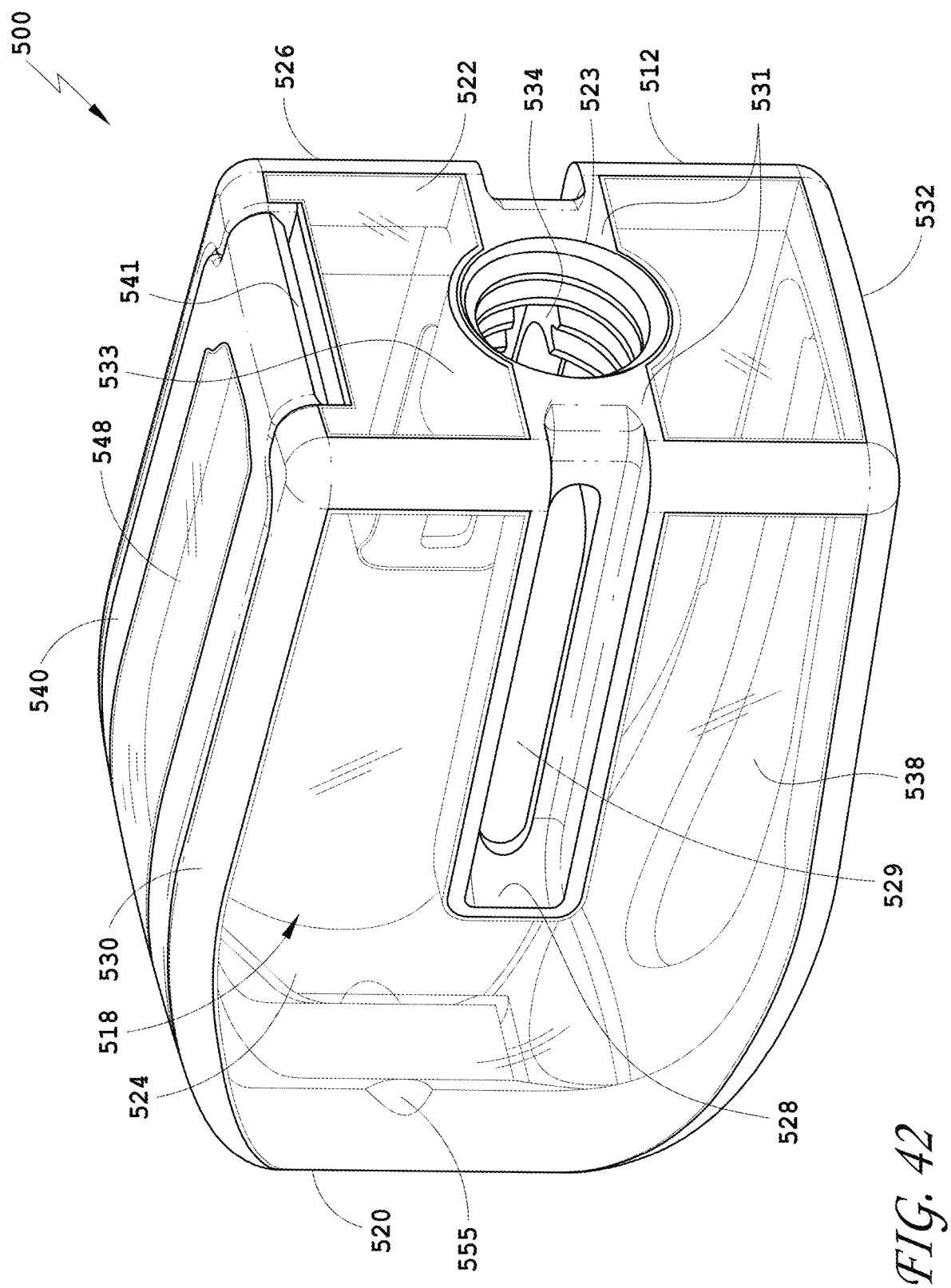
FIG. 42 is a perspective view of an embodiment of a spinal implant device with a movable lid shown in a closed position.

FIG. 42 illustrates a perspective view of a spinal implant device 500. The spinal implant device 500 can include any of the features of the spinal implant device 10, 10A, 100, 200, 300, 400 as described herein and can be used in any method or method step described herein. The spinal implant device 500 can include a body structure 512. The body structure 512 can include a framework supported by edges.

In some embodiments, the framework can be thinner than the edges. In some embodiments, the framework can support a porous body. In some embodiments, at least a portion of one surface of the spinal implant device 500 can comprise a porous body as described herein.

The spinal implant device 500 can include a distal end 520. The distal end 520 can include thicker edges which facilitates insertion of the distal end 520. The distal end 520 can be more rigid than another portion of the spinal implant device 500. The distal end 520 can be tapered. The spinal implant device 500 can include a proximal end 522. In some embodiments, the proximal end 522 can include one or more portions of a thin framework. The proximal end 522 can include thicker edges surrounding the one or more portions of the thin framework. In some embodiments, the proximal end 522 can include an opening 523. The opening 523 can be a threaded opening to couple with an insertion tool.

Figure 43:
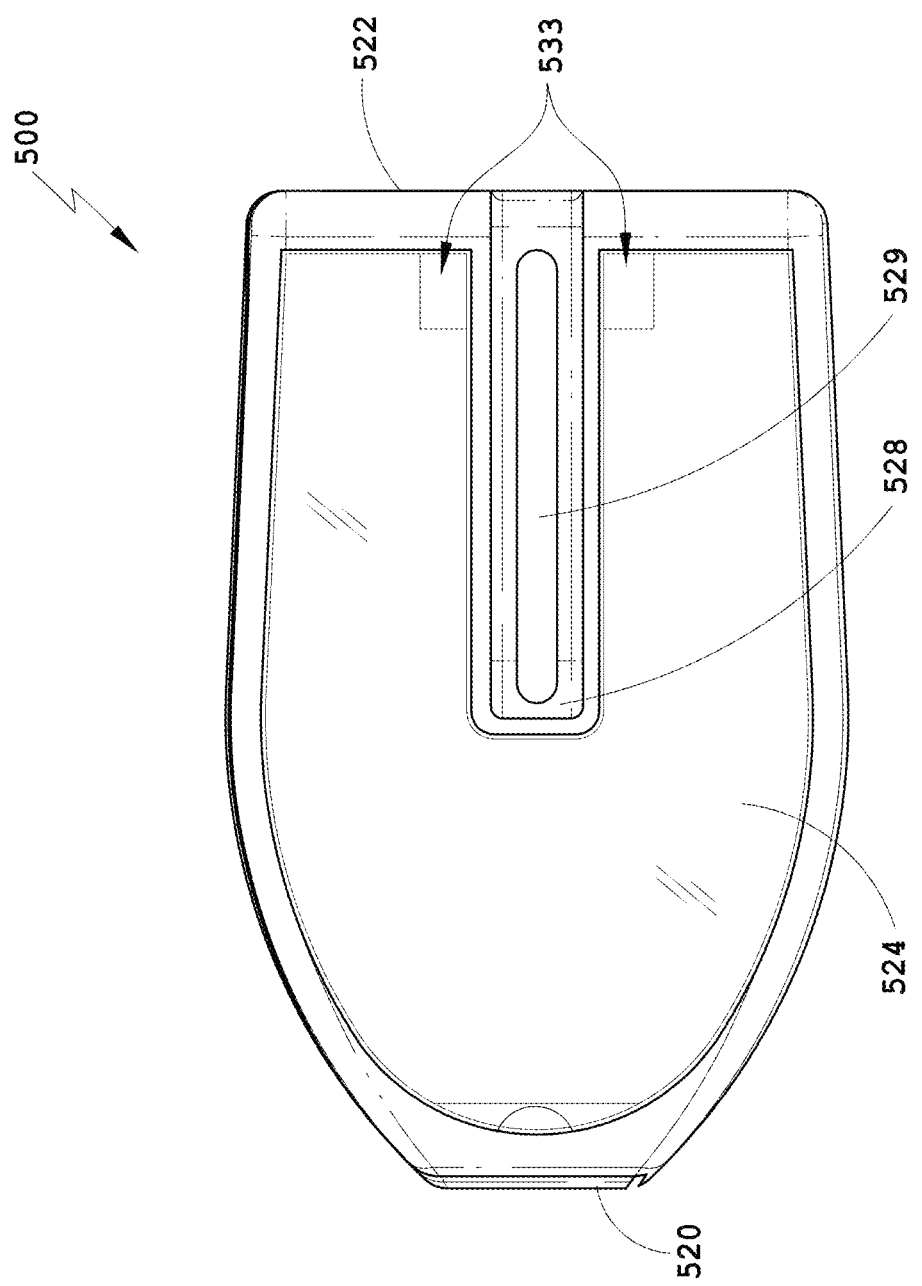
FIG. 43 is a side view of the spinal implant device of FIG. 42.

FIG. 43 is a side view of the spinal implant device 500. The spinal implant device 500 can include two opposing side walls including a first side wall 524 and a second side wall 526. FIG. 43 illustrates the first side wall 524, but the second side wall 526 can include the same or similar features. In some embodiments, each side wall 524, 526 can include a framework supported by edges. The framework can be rounded near the distal end 520. The framework can be flat or squared near the proximal end 522. In some embodiments, each of the two opposing side walls 524, 526 can include a feature 528. The feature 528 can be designed to couple with an insertion tool to facilitate insertion of the spinal implant device 500. In some embodiments, the feature 528 can include a channel or groove. In some embodiments, the feature 528 can extend from the proximal end 522 along a portion of the respective side wall 524, 526. In some embodiments, the feature 528 extends inward from one of the side walls 524, 526. The feature 528 can be considered an inserter groove. The feature 528 can include a slot 529. The slot 529 can be considered an opening. In some embodiments, the feature 528 can include one or more slots 529. The one or more slots 529 can extend through the feature 528. Each feature 528 can be the same or different shape or configuration. For instance, each feature 528 can include one slot 529. The slot 529 can act as a leaf spring, making the spinal implant device 500 more flexible. The slot 529 can allow the spinal implant device 500 to better distribute a load.

The spinal implant device 500 can include one or more lateral framework connections 531. The lateral framework connections 531 can couple the respective feature 528 to the opening 523. The lateral framework connections 531 can extend from each feature 528 to the opening 523. The opening 523 can include a thread body extension 533. The thread body extension 533 can extend into a cavity 518 of the spinal implant device. The thread body extension 533 can provide more thread engagement with inserter thread of an inserter tool. In some embodiments, the slot 529 that runs through the feature 528 partially intersects the thread body extension 533. The intersection 534 is shown between the slot 529 and the thread body extension 533 in FIG. 42.

The spinal implant device 500 can include a movable lid 540. FIG. 42 is a view of the spinal implant device 500 with the movable lid 540 closed. FIG. 39 is a view of a similar spinal implant device with a movable lid opened. In some embodiments, the movable lid 540 can include a framework supported by edges. The movable lid 540 can include thicker edges surrounding a thin framework. In some embodiments, the movable lid 540 can include an opening 548. In some embodiments, the opening 548 can be in addition to, or instead of, the framework. In some embodiments, the opening 548 can extend through the movable lid 540. The opening 548 can be elongate. The opening 548 can extend along the length of the spinal implant device 500. The upper surface can include one or more openings (e.g., one, two, three, four, five, or six). The opening 548 of the movable lid 540 can be completely open. The opening 548 of the movable lid 540 can comprise a porous material.

The spinal implant device 500 can include an upper wall 530. The upper wall 530 can include edges which forms the top surface of the spinal implant device 500. In some embodiments, the upper wall 530 includes a lip or surface to support the movable lid 540. In some embodiments, the upper wall 530 forms a ledge along a portion of the edges of the movable lid 540. In some embodiments, the upper wall 530 forms an opening to accommodate the movable lid 540 therebetween. In some embodiments, the movable lid 540 and the upper wall 530 together form the upper surface of the spinal implant device 500.

The movable lid 540 can include a chamfer 541. The chamfer 541 can be added to the movable lid 540 to assist with opening the movable lid 540. The chamfer 541 can be located near the proximal end 522.

Figure 44:
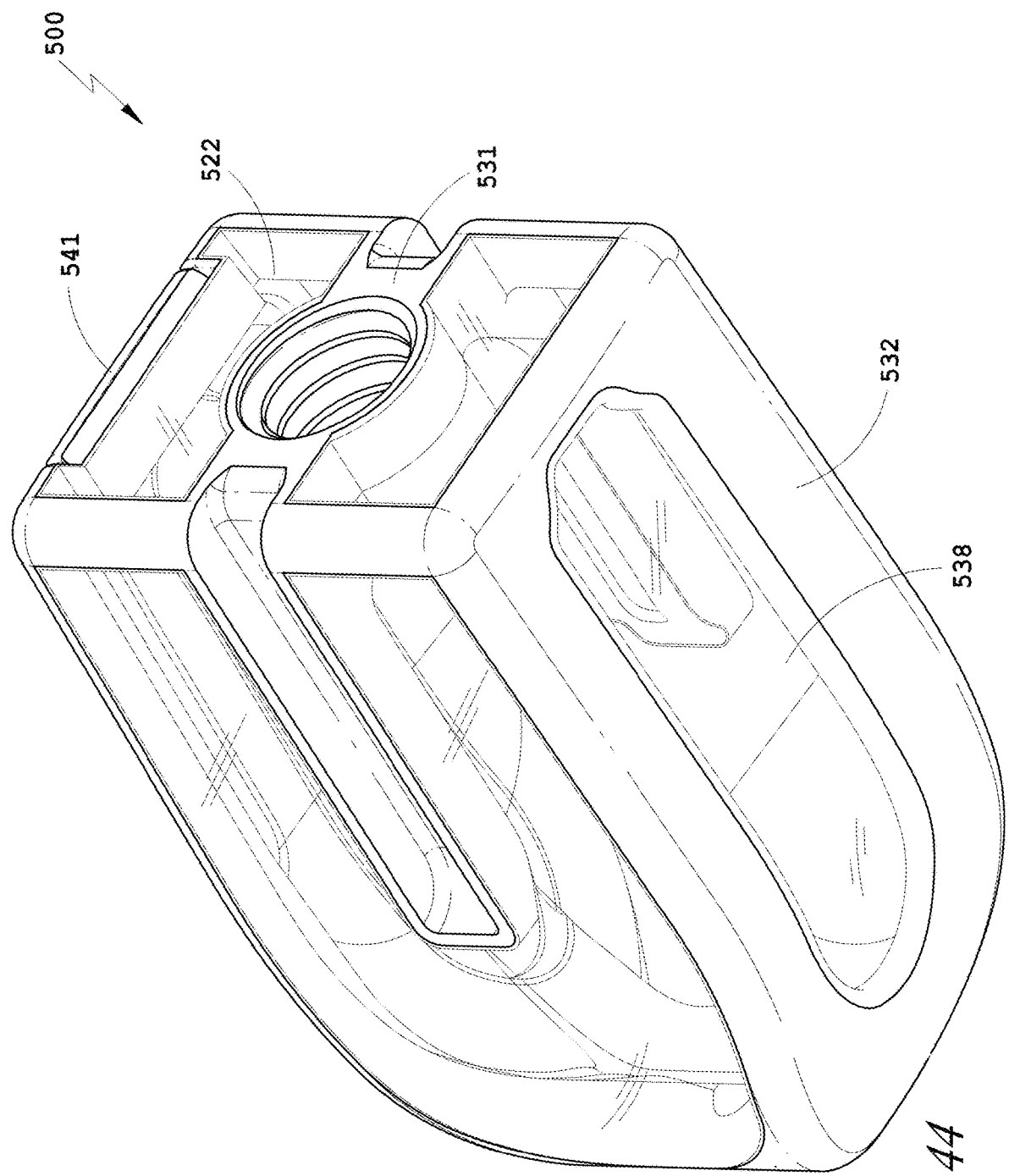
FIG. 44 is a bottom perspective view of the spinal implant device of FIG. 42.

FIG. 44 is a bottom perspective view of the spinal implant device 500. The spinal implant device 500 can include a lower wall 532. The lower wall 532 can extend between the distal end 520 and the proximal end 522. In some embodiments, the lower wall 532 can include a framework supported by edges. In some embodiments, the lower wall 532 can include an opening 538. In some embodiments, the opening 538 can be in addition to, or instead of, the framework. In some embodiments, the opening 538 can extend through the lower wall 532. The opening 538 can be elongate. The opening 538 can extend along the length of the spinal implant device 500. The lower surface can include one or more openings (e.g., one, two, three, four, five, or six). The opening 538 of the lower wall 532 can be completely open. The opening 538 of the lower wall 532 can comprise a porous material.

In some embodiments, the spinal implant device 500 can include a movable joint 555. The movable joint 555 can couple the movable lid 540 with the body structure 512. The movable joint 555 can include any of the features described herein with respect to joints. The spinal implant device 500 can include the cavity 518. The movable joint 555 can allow the movable lid 540 to pivot to provide access to the cavity 518.

The spinal implant device 500 can comprise one or more frameworks to support porous bodies. The framework includes an area where the porous body can be coupled. In some embodiments, the framework is porous itself. The porosity of the spinal implant device 500 can allow material to flow outwardly from the cavity 518, through the framework. The porosity of the spinal implant device 500 can allow material to flow outwardly from the cavity 518 and through the porous body if coupled thereto. The framework can promote fusion by the migration of material to and from the cavity 518. The cavity 518 can be a centrally located chamber within the spinal implant device 500. In some embodiments, the cavity 518 comprises a substantial portion of the volume of the spinal implant device 500.

Figure 45:
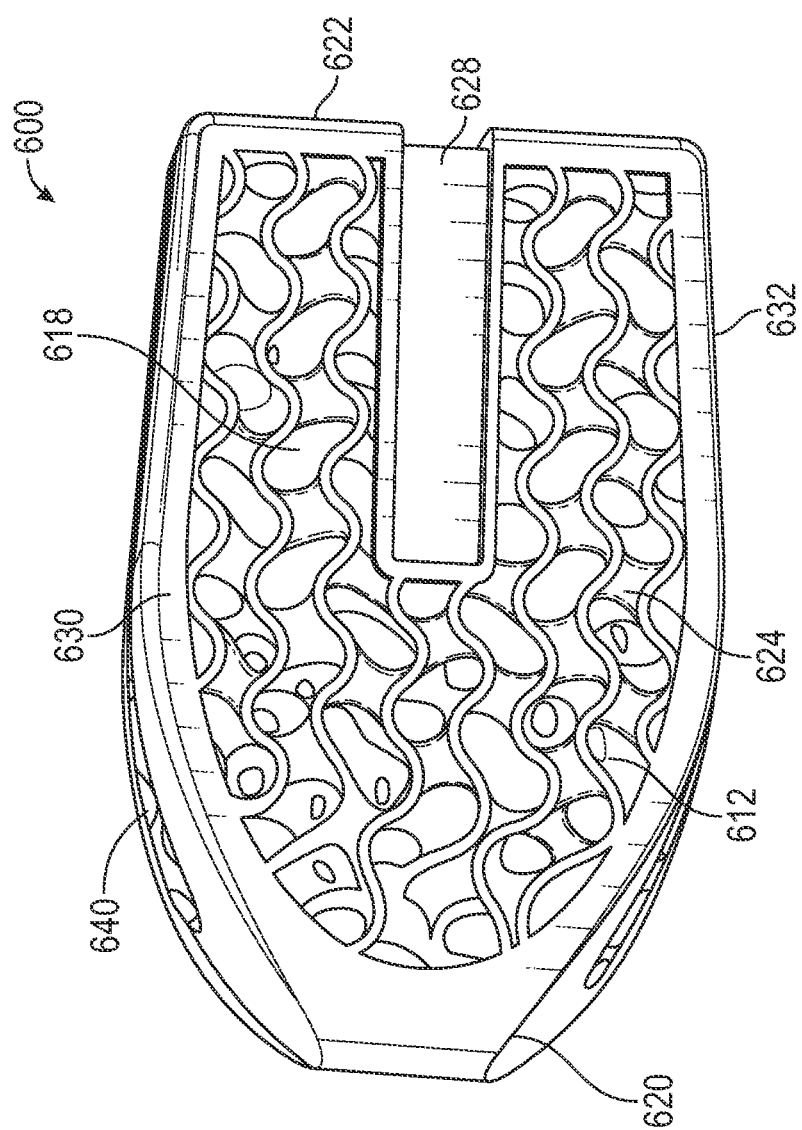
FIG. 45 is a perspective view of an embodiment of a spinal implant device with a movable lid shown in a closed position.

FIG. 45 illustrates a perspective view of a spinal implant device 600. The spinal implant device 600 can include any of the features of the spinal implant device 10, 10A, 100, 200, 200, 300, 400, 500 as described herein and can be used in any method or method step described herein. The spinal implant device 600 can include a body structure 612. The spinal implant device 600, or a portion thereof, can be formed of a porous material. In some embodiments, the porous material can be integrally formed in the body structure 612 of the spinal implant device 600. The spinal implant device 600 can include one or more porous surfaces. The porous surfaces can be surrounded, at least in part, by one or more edges. In some embodiments, the porous surface can form any surface of the spinal implant device 600 described herein.

Figure 46:
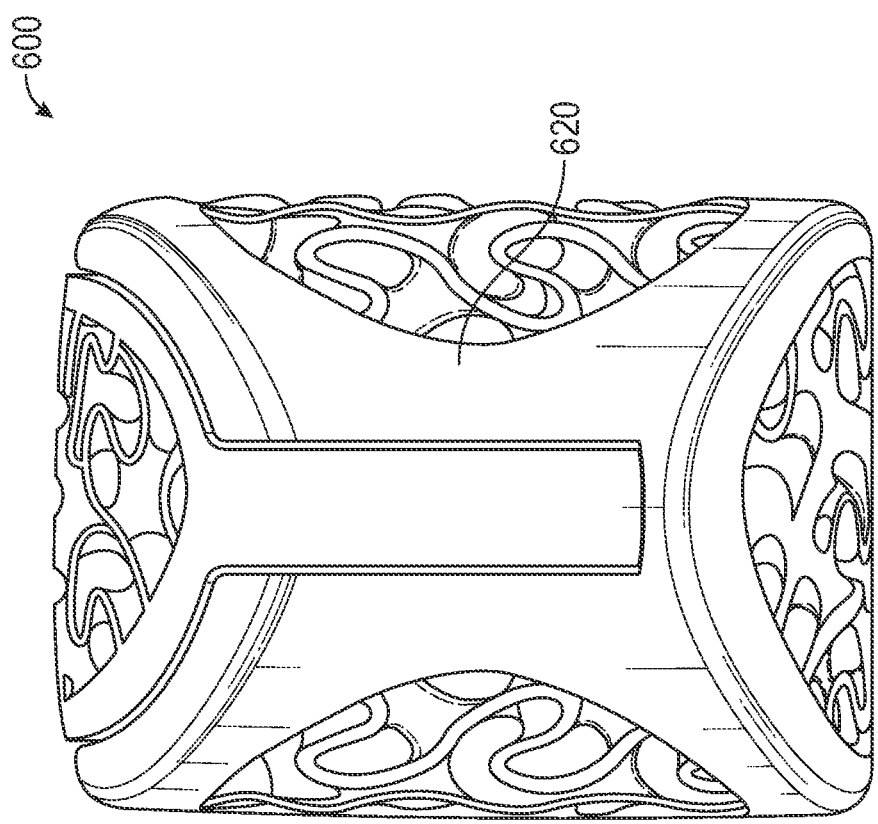
FIG. 46 is a distal view of the spinal implant device of FIG. 45.

FIG. 46 is a distal view of the spinal implant device 600. The spinal implant device 600 can include a distal end 620. In some methods of use, the distal end 620 can facilitate insertion of the spinal implant device 600. In some embodiments, the distal end 620 is tapered inward. In some embodiments, a portion of the four major surfaces of the distal end 620 can taper inward. In some embodiments, the distal end 620 can include rounded corners or edges. In some embodiments, the distal end 620 includes a solid surface. In some embodiments, the distal end 620 includes a porous surface.

Figure 47:
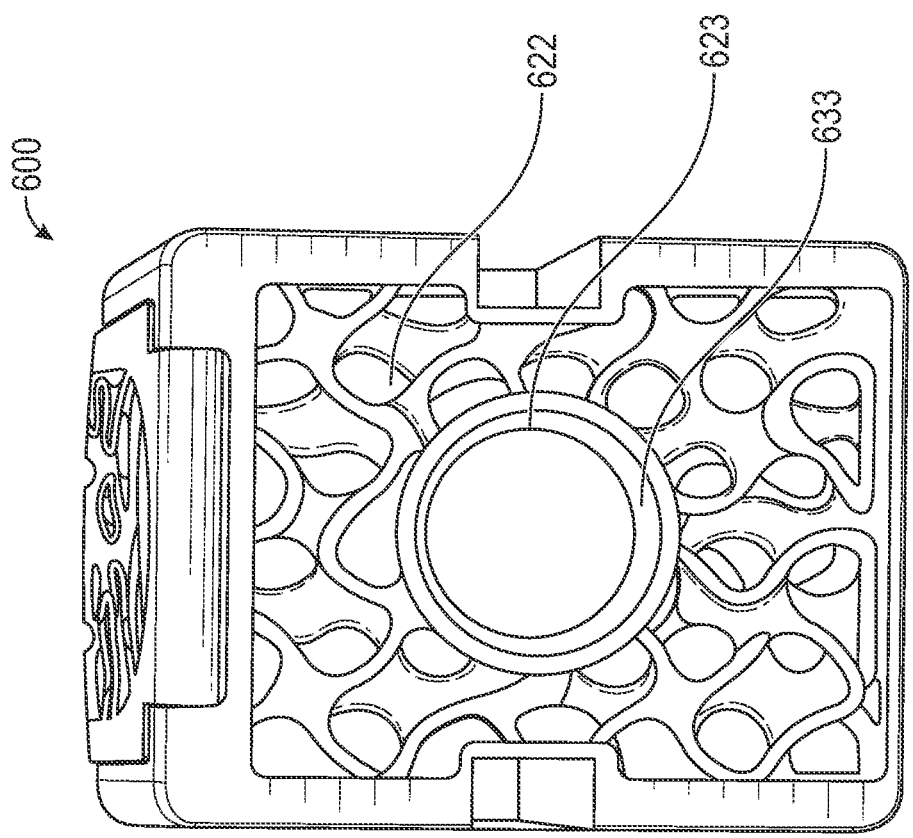
FIG. 47 is a proximal view of the spinal implant device of FIG. 45.

FIG. 47 is a proximal view of the spinal implant device 600. The spinal implant device 600 can include a proximal end 622. In some embodiments, the proximal end 622 can be planar or substantially planar. In some embodiments, the proximal end 622 can include one or more rounded corners or edges. In some embodiments, the proximal end 622 can include an opening 623. In some embodiments, the opening 623 can be threaded or have another feature to engage an insertion tool. In some embodiments, the proximal end 622 includes a solid surface. In some embodiments, the proximal end 622 includes a porous surface. In some embodiments, the proximal end 622 includes a porous framework surrounded by one or more edges. The opening 623 can include a thread body extension 633. The thread body extension 633 can extend into a cavity 618 of the spinal implant device 600. The thread body extension 633 can allow for more threaded engagement with an inserter tool. In some embodiments, the thread body extension 633 comprises the same material as the proximal end 622. In some embodiments, the thread body extension 633 comprises a different material as the proximal end 622. In some embodiments, the proximal end 622 can include a porous material and the thread body extension 633 can include a solid material.

Figure 48:
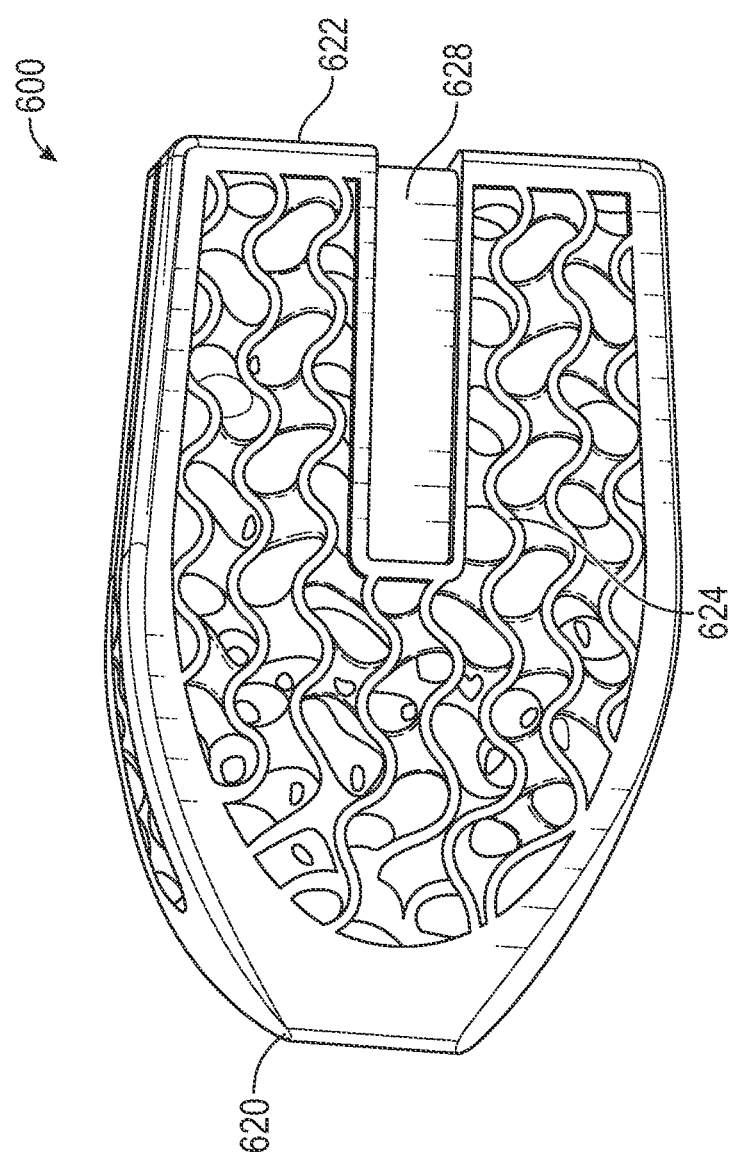
FIG. 48 is a side view of the spinal implant device of FIG. 45.

FIG. 48 is a side view of the spinal implant device 600 which illustrates the length between the distal end 620 and the proximal end 622. The spinal implant device 600 can include two opposing side walls 624, 626. FIG. 48 illustrates the first side wall 624. The second side wall 626 can include any of the features or elements described herein.

The two opposing side walls 624, 626 can span between distal end 620 and the proximal end 622. In some embodiments, the two opposing side walls 624, 626 include a solid surface. In some embodiments, the two opposing side walls 624, 626 include a porous surface. In some embodiments, each opposing side wall 624, 626 includes a porous framework surrounded by one or more edges.

The two opposing side walls 624, 626 can include a feature 628 to facilitate insertion of the spinal implant device 600. In some embodiments, the feature 628 can include a groove to accept an insertion tool. In some embodiments, the feature 628 comprises the same material as the two opposing side walls 624, 626. In some embodiments, the feature 628 comprises a different material as the two opposing side walls 624, 626. In some embodiments, the two opposing side walls 624, 626 can include a porous material and the feature 628 can include a solid material.

Figure 49:
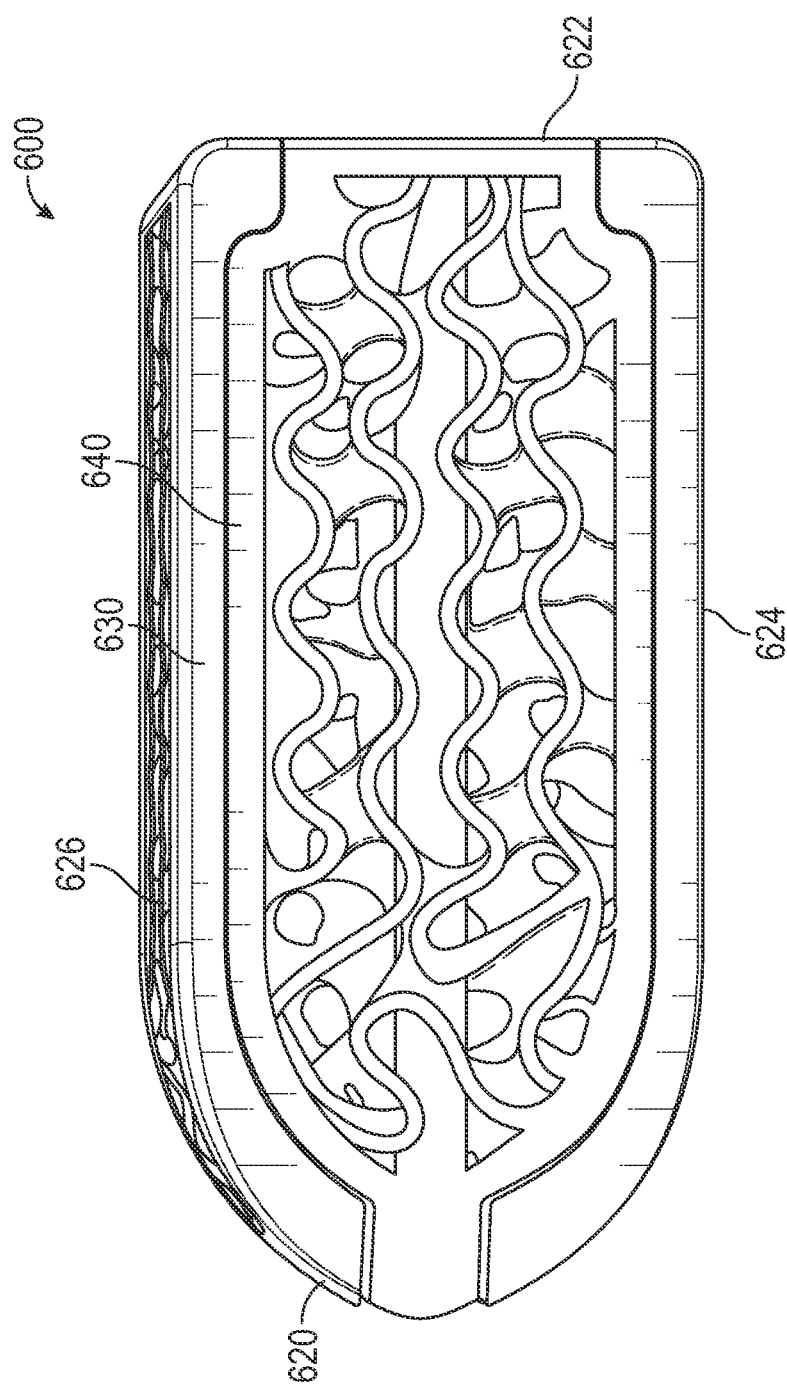
FIG. 49 is a top view of the spinal implant device of FIG. 45.
Figure 50:
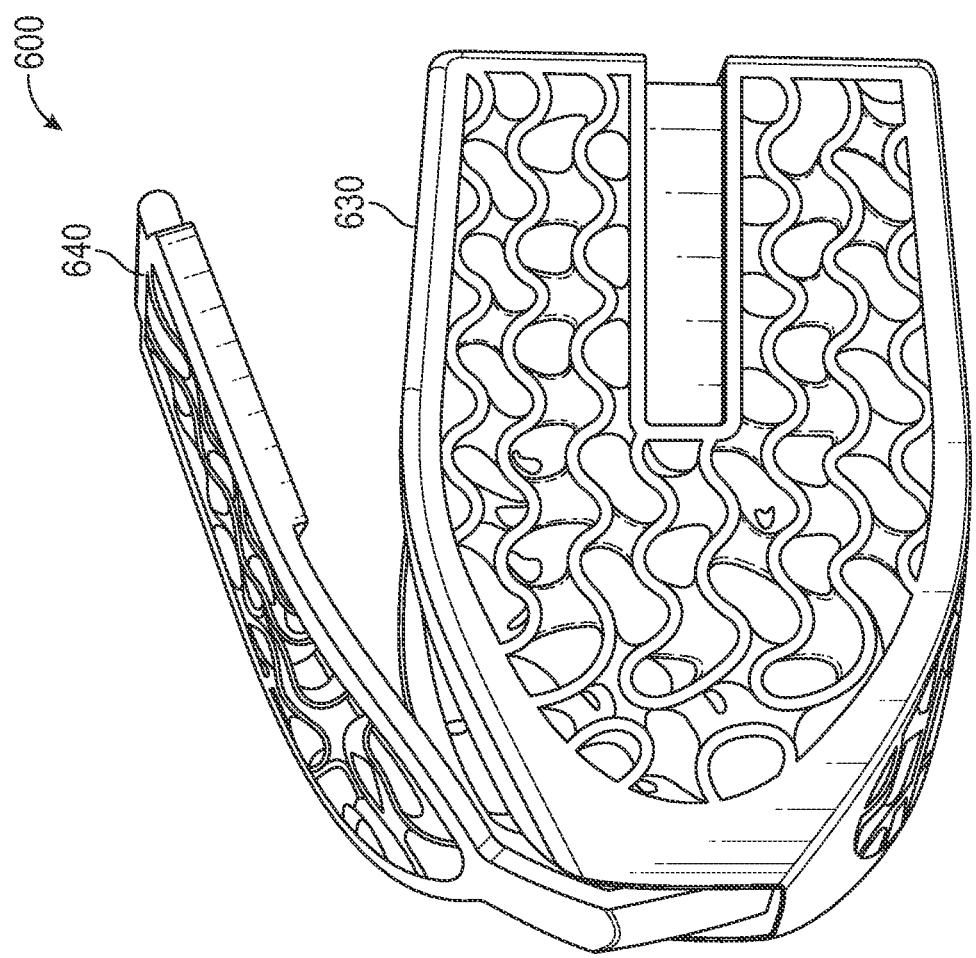
FIG. 50 is a top perspective view of the spinal implant device of FIG. 45 with the movable lid shown in an opened position.

The spinal implant device 600 can include the movable lid 640. FIG. 49 is a top view of the spinal implant device 600 with a movable lid 640 closed. FIG. 50 is a top perspective view of the spinal implant device 600 with the movable lid 640 opened.

The spinal implant device 600 can include an upper wall 630. In some embodiments, the upper wall 630 supports the movable lid 640 along the side walls 624, 626. In some embodiments, the upper wall 630 supports the movable lid 640 along the proximal end 622. In some embodiments, the upper wall 630 supports the movable lid 640 along the distal end 620. In some embodiments, the upper wall 630 comprises the same material as the movable lid 640. In some embodiments, the upper wall 630 comprises a different material as the movable lid 640. In some embodiments, the movable lid 640 can include a porous material and the upper wall 630 can include a solid material. In some embodiments, the movable lid 640 can include a thickened edge and the upper wall 630 can include a thickened edge.

Figure 51:
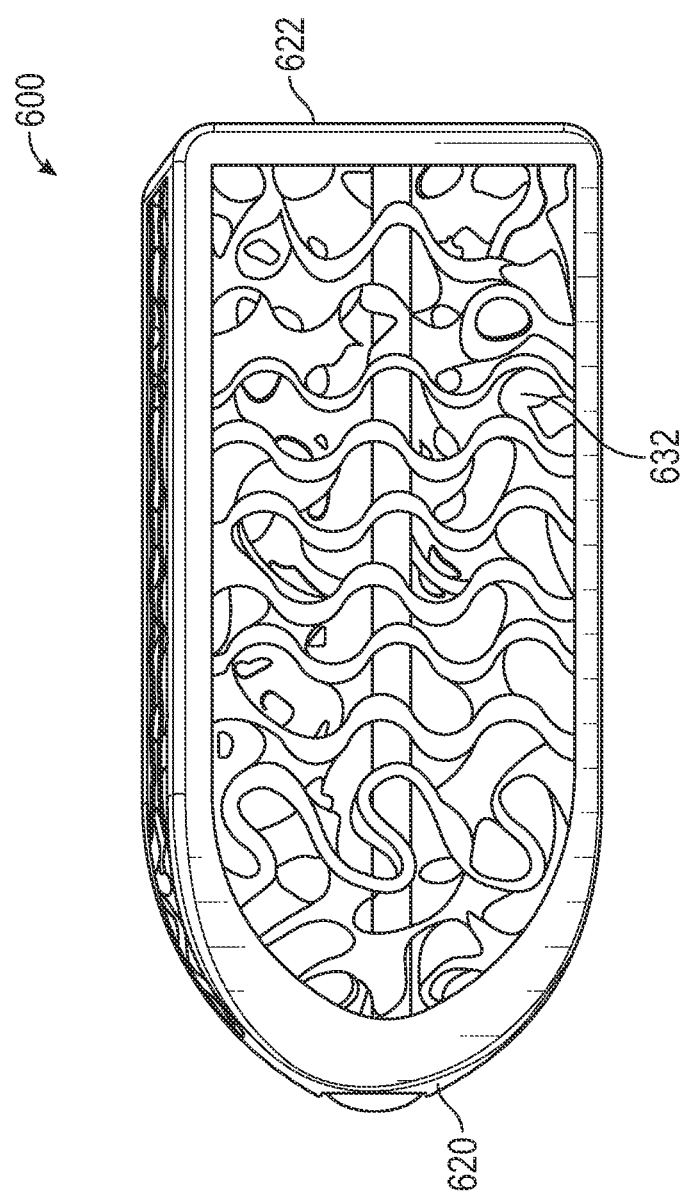
FIG. 51 is a bottom perspective view of the spinal implant device of FIG. 45.

FIG. 51 is a bottom perspective view of the spinal implant device 600. The spinal implant device 600 can include a lower wall 632. The lower wall 632 can span between the distal end 620 and the proximal end 622. In some embodiments, the lower wall 632 can include a porous surface. In some embodiments, the lower wall 632 can include a solid surface. In some embodiments, the lower wall 632 can include a porous surface enclosed by thickened edges.

Figure 52A:
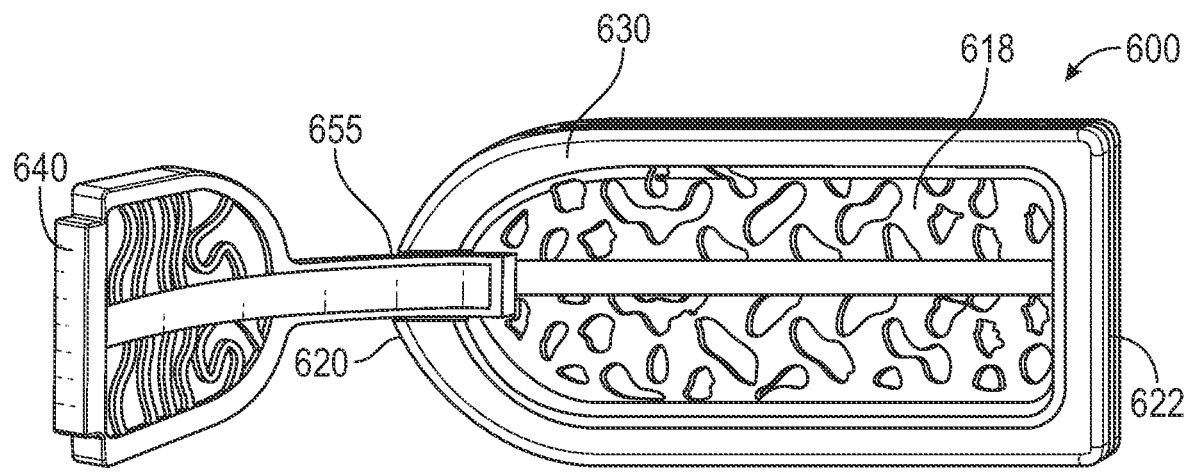
FIGS. 52A-52B are additional views of the spinal implant device of FIG. 45.
Figure 52B:
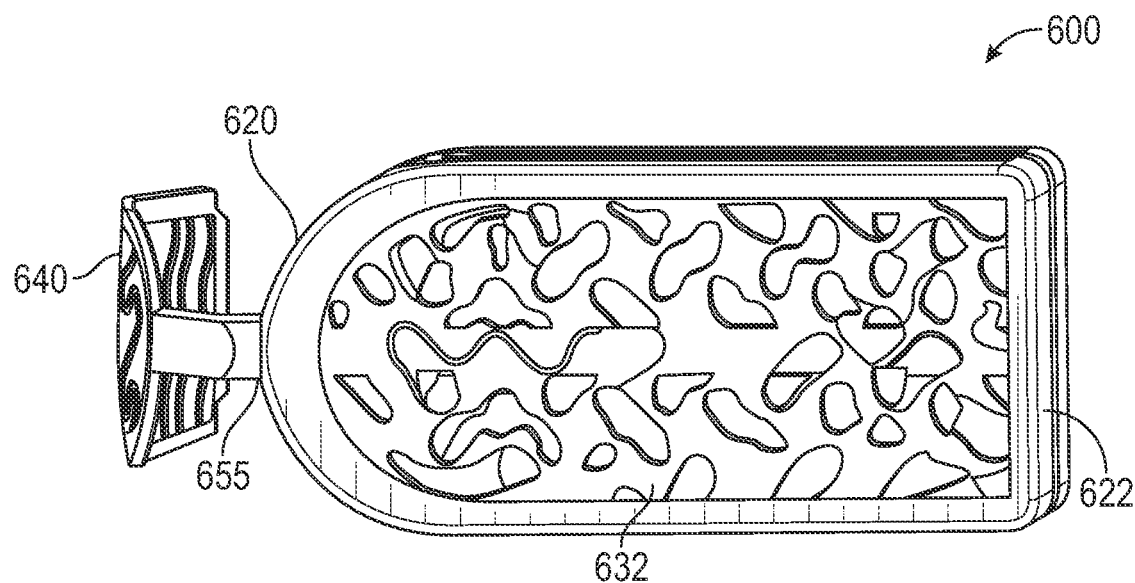

FIGS. 52A and 52B are additional views of the movable lid 640 of the spinal implant device 600. In some embodiments, the movable lid 640 can be coupled to the distal end 620. In some embodiments, the spinal implant device 600 can include a movable joint 655. The movable joint 655 can couple the movable lid 640 with any portion of the body structure 612. The movable joint 655 can allow for pivoting motion of the movable lid 640. In some embodiments, the movable joint 655 can include one axis of rotation. In some embodiments, the movable joint 655 can include more than one axis of rotation. The movable joint 655 can include any features of the joints described herein.

The spinal implant device 600 can include the cavity 618. In some embodiments, the proximal end 622 can define the back inner surface of the cavity 618. In some embodiments, the distal end 620 can define the front inner surface of the cavity 618. In some embodiments, the two opposing side walls 624, 626 can define the side inner surfaces of the cavity 618. In some embodiments, the movable lid 640 can define the top inner surface of the cavity 618. In some embodiments, the lower wall 632 can define the bottom inner surface of the cavity 618. In some embodiments, the cavity 618 is partially enclosed. In some embodiments, the cavity 618 is fully enclosed. The cavity 618 can be a contained chamber, or at least partially contained chamber, within the spinal implant device 600. In some embodiments, the cavity 618 comprises the internal volume of the spinal implant device 600.

The spinal implant device 600 can include one or more porous surfaces. Each porous surface comprises one or more openings that can facilitate fusion of adjacent vertebrae. The openings can provide adequate space for bone growth between the end plates of the vertebrae which the spinal implant device 600 is supporting. The openings can extend through the movable lid 640. The openings can allow fusion through the movable lid 640 and into the cavity 618. The openings can extend through the lower wall 632. The openings can allow fusion through the lower wall 632 and into the cavity 618. The openings can allow the material to bridge between the vertebral endplates. The openings can provide for vertical bone growth between adjacent vertebrae. The openings can facilitate bone ingrowth and fusion between end plates. In some embodiments, the openings are randomly distributed on the porous surface. In some embodiments, the openings are evenly distributed on the porous surface, for instance, through a grated framework. The one or more porous surfaces can facilitate compression of the spinal implant device 600.

In some embodiments, at least a portion of one surface of the spinal implant device 600 can have a porous body. The porous body can be created in any a variety of ways, such as by applying sintered beads or spraying plasma onto the thin framework. In some embodiments, the porous body is formed by 3D printing. The porous body can allow bone to grow into or attach to the surface of the spinal implant device 600, thus fusing the spinal implant device 600 to the adjacent bony structure. The spinal implant device 600 can be formed of a porous material. The spinal implant device 600 can be formed of a material that intrinsically participates in the growth of bone from one of adjacent vertebral bodies to the other of adjacent vertebral bodies. FIG. 53 illustrates various views of embodiments of the spinal implant device 600. The spinal implant device 600 can be sized based on the insertion approach and/or the corresponding anatomy of the patient.

Figure 54:
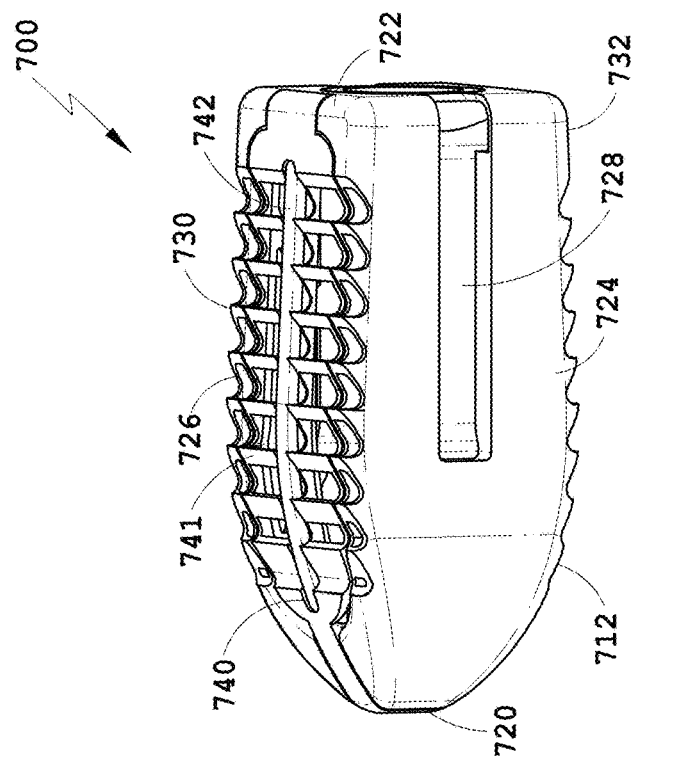
FIG. 54A-54B are views of embodiments of a spinal implant device with a movable lid shown in an opened and closed position.

FIGS. 54A-54B illustrate views of a spinal implant device 700. The spinal implant device 700 can include any of the features of the spinal implant device 10, 10A, 100, 200, 300, 400, 500, 600 as described herein and can be used in any method or method step described herein. The spinal implant device 700 can include a body structure 712, a distal end 720, a proximal end 722, two opposing side walls 724, 726, a feature 728, a movable lid 740, an upper wall 730, a lower wall 732, and the movable joint 755. FIG. 54A is a top perspective view of the spinal implant device 700 with the movable lid 740 opened. FIG. 54B is a top perspective view of the spinal implant device 700 with the movable lid 740 closed. The spinal implant device 700 can include a cavity 718. In some embodiments, the cavity 718 comprises a portion of the volume of the spinal implant device 700 (e.g., 50% of the volume, 60% of the volume, 70% of the volume, 80% of the volume, 90% of the volume, or 100% of the volume, or any range of the foregoing values).

The movable lid 740 can include one or more crossbars 741. While eight crossbars 741 are illustrated, the movable lid 740 can include any number of crossbars 741 (e.g., one, two, three, four, five, or six). In some embodiments, each crossbar 741 extends perpendicular to the longitudinal axis of the spinal implant device 700. The spinal implant device 700 can include a plurality of ridges 714. Each crossbar 741 can extend between opposed ridges 714. The spinal implant device 700 can include one or more openings 742 extending through the movable lid 740. The openings 742 can be separated by the crossbars 741.

Figure 55:
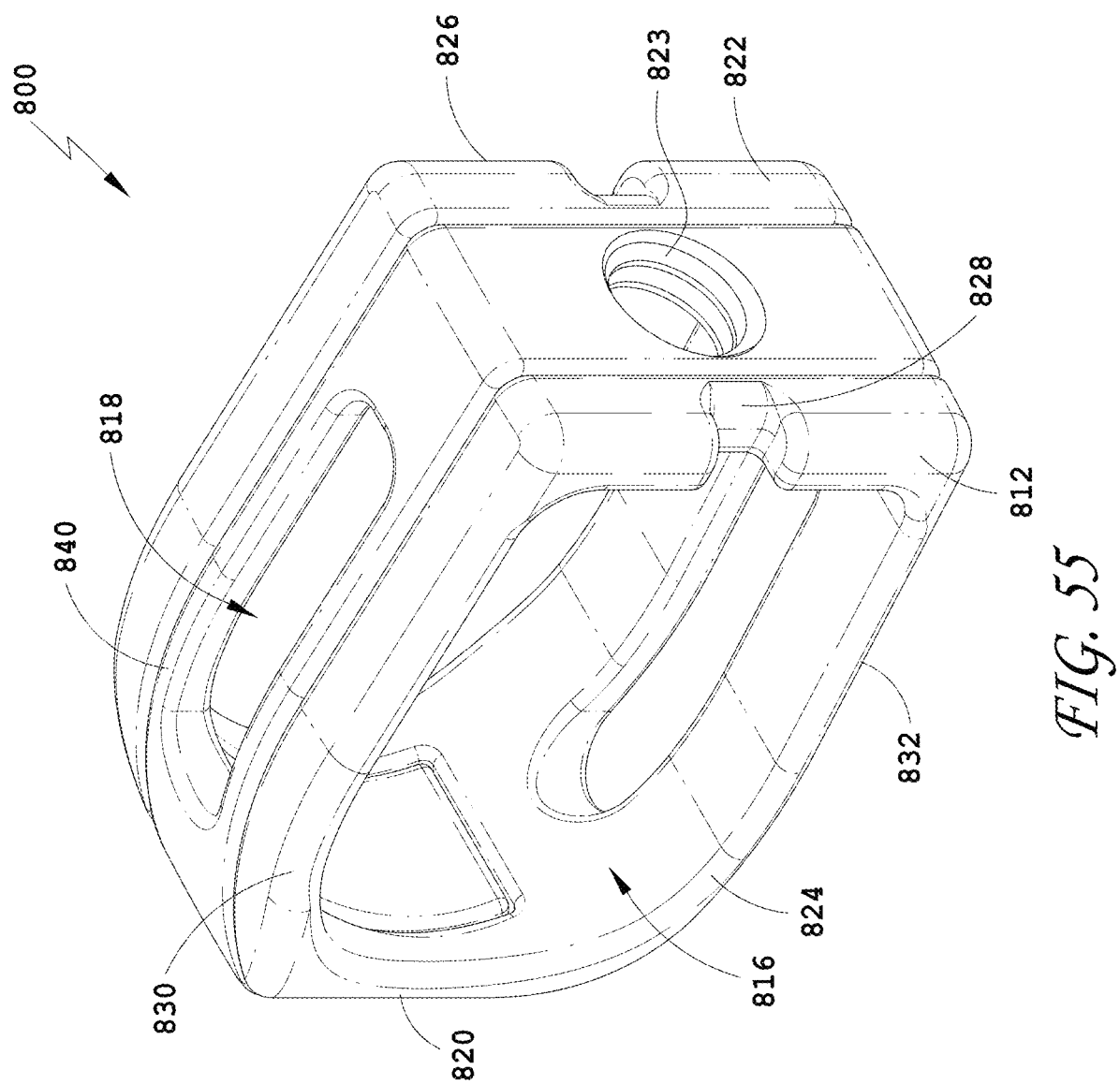
FIG. 55 is a perspective view of an embodiment of a spinal implant device with a movable lid shown in a closed position.

FIG. 55 illustrates a perspective view of a spinal implant device 800. The spinal implant device 800 can include any of the features of the spinal implant device 10, 10A, 100, 200, 300, 400, 500, 600, 700 as described herein and can be used in any method or method step described herein. The spinal implant device 800 can include a body structure 812. The body structure 812 can include thicker edges surrounding open windows 816. As described herein, the lateral sides of the body structure 812 can be open. The spinal implant device 800 can have a through lumen perpendicular to the longitudinal axis of the spinal implant device 800. As described herein, the upper and lower surface of the body structure 812 can be open, or at least partially open. The spinal implant device 800 can have a secondary through lumen perpendicular to the longitudinal axis of the spinal implant device 800. In some embodiments, the thicker edges are solid. In some embodiments, the thicker edges are porous or a mesh. In some embodiments, the open windows 816 allows bony ingrowth therethrough. In some embodiments, the open windows 816 allows the fusion of material therethrough. In some embodiments, the open windows 816 allow the spinal implant device 800 to compress.

Figure 56:
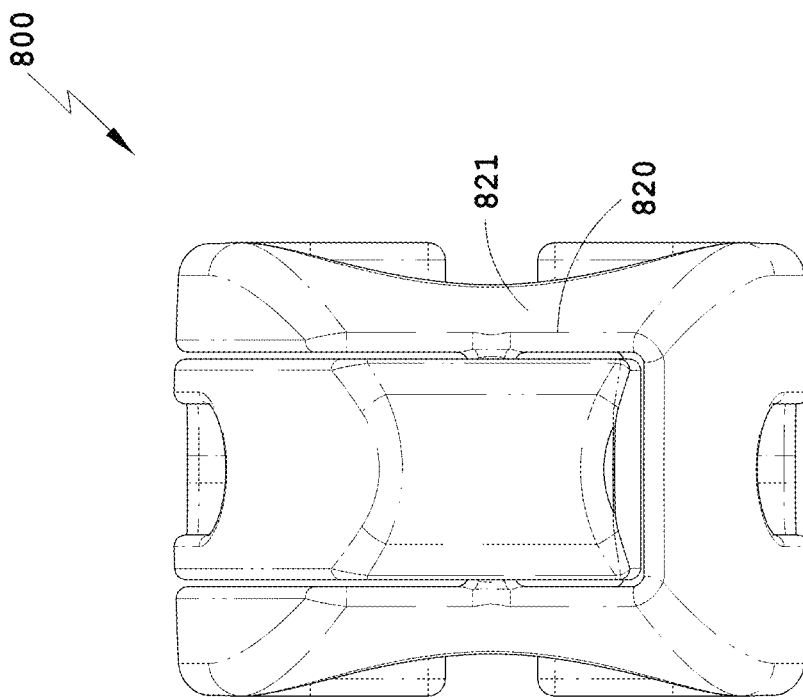
FIG. 56 is a distal view of the spinal implant device of FIG. 55.

FIG. 56 is a distal view of the spinal implant device 800. The spinal implant device 800 can include a distal end 820. The distal end 820 can include thicker edges which create a robust end to facilitate insertion of the distal end 820. The distal end 820 can be thickened to be able to be inserted or seated between vertebrae. The distal end 820 can be more rigid than another portion of the spinal implant device 800, such as the side walls. The distal end 820 can be tapered. In some embodiments, the four surfaces of the distal end 820 can taper to from a square pyramid or similar shape. The distal end 820 can form an X-shape. The distal end 820 can be formed by four thicker edges, such as the upper, lower, and side edges which come together. In some embodiments, the upper edge and the lower edge of the distal end 820 equally taper. In some embodiments, the distal end 820 can include rounded corners or edges to facilitate insertion. The distal end 820 can form a frustoconical or convex curved shape 821.

Figure 57:
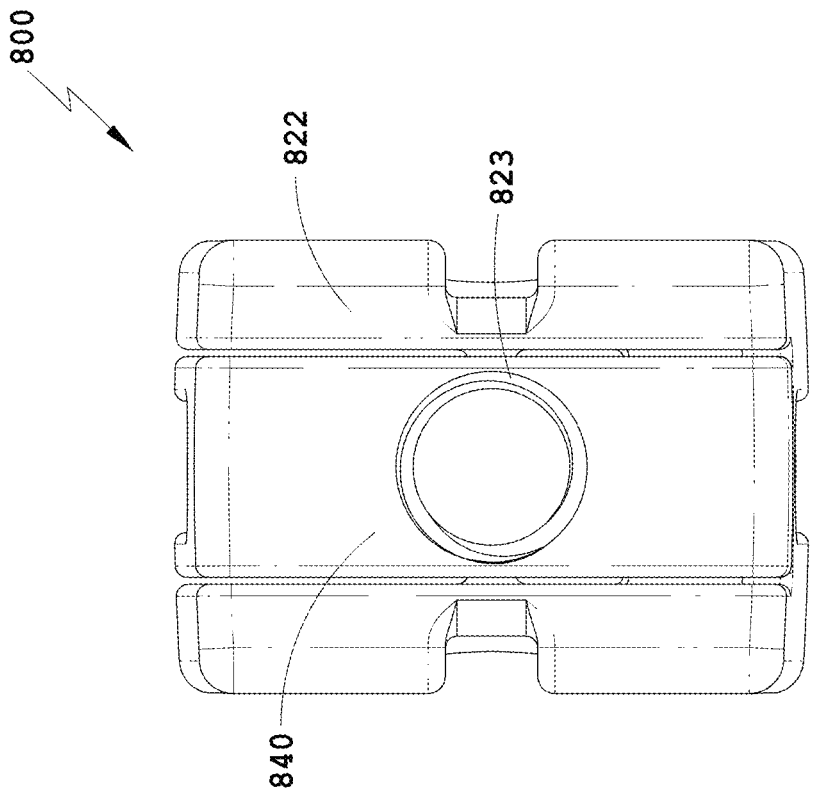
FIG. 57 is a proximal view of the spinal implant device of FIG. 55.

FIG. 57 is a proximal view of the spinal implant device 800. The spinal implant device 800 can include a proximal end 822. In some embodiments, the proximal end 822 can include at least two thicker edges. The spinal implant device 800 can include a movable lid 840. The proximal end 822 can include two lateral edges surrounding the movable lid 840, as described herein. The proximal end 822 can be square, rectangular, quadrilateral, or other polygonal shape. The proximal end 822 can be substantially square or rectangular. The thicker edges can be rounded to facilitate insertion of the spinal implant device 800. In some embodiments, the proximal end 822 can include an opening 823 such as a threaded opening to couple with an insertion tool. In some embodiments, the opening 823 can be disposed on the movable lid 840. The movable lid can include a top surface, a proximal surface, and a bottom surface when in the closed configuration, as described herein. The opening 823 can be disposed on the proximal surface of the movable lid 840.

Figure 58:
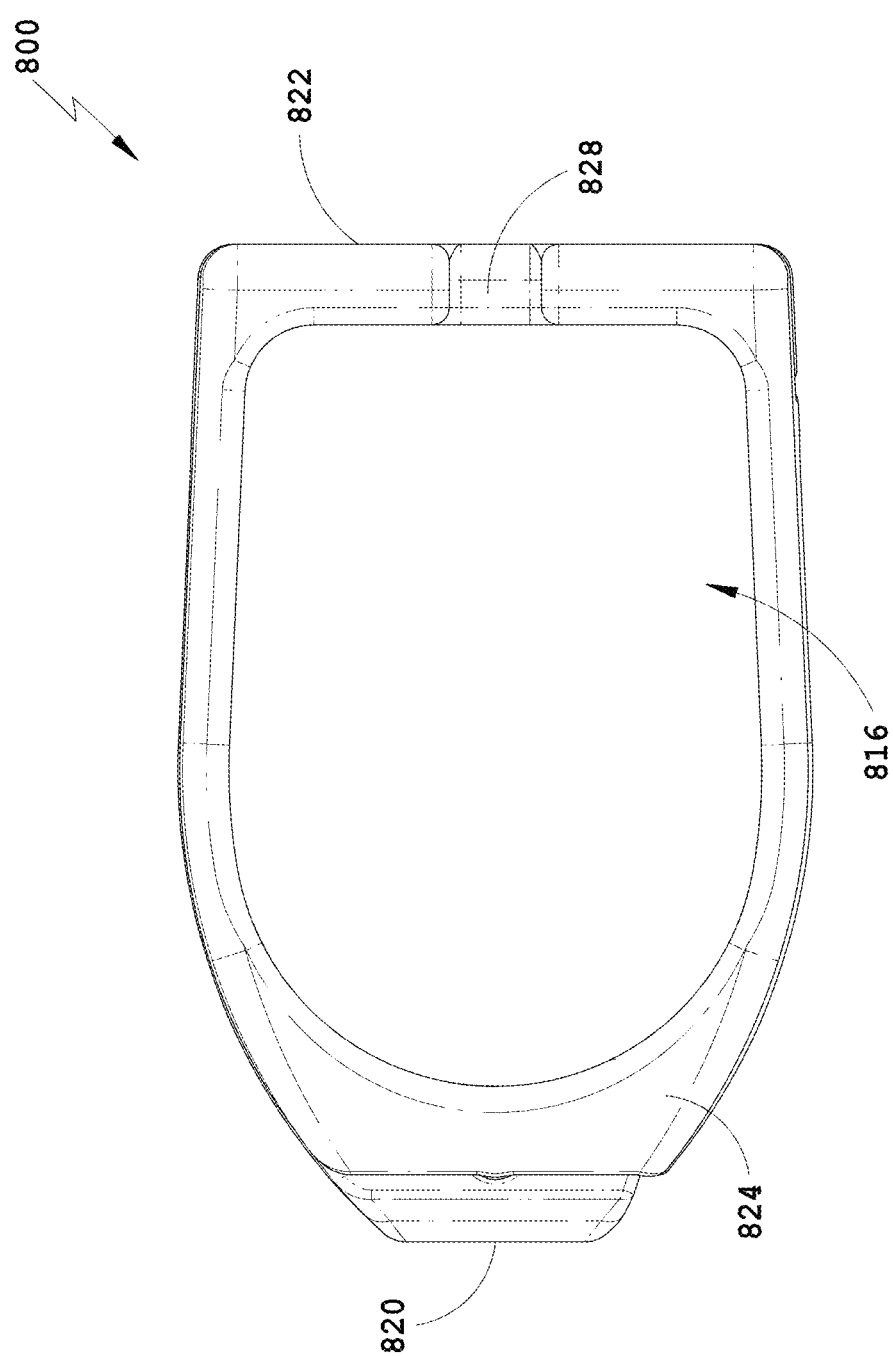
FIG. 58 is a side view of the spinal implant device of FIG. 55.

FIG. 58 is a side view of the spinal implant device 800. The length of the spinal implant device 800 can be the distance between the distal end 820 and the proximal end 822. The spinal implant device 800 can include two opposing side walls including a first side wall 824 and a second side wall 826. FIG. 58 illustrates the first side wall 824, but the second side wall 826 can include the same or similar features. In some embodiments, each side wall 824, 826 can include thicker edges surrounding an open window 816. Each side wall 824, 826 can include four thicker edges surrounding an open window 816. The thicker edges can have a rounded or tapered edge near the distal end 820. The thicker edges can have a substantially flat edge near the proximal end 822. The open window 816 can have the shape of a bullet with a rounder edge near the distal end 820 and a flatter edge near the proximal end 822. The open window 816 can span the height of the spinal implant device 800, or a portion thereof. The open window 816 can follow the shape of the side wall 824, 826.

The open window 816 can support a porous body. The porous body can be coupled to the side wall 824, 826. The open window 816 can support graft material. The open window 816 can support any fusion material. The open window 816 can allow the cavity to be packed after the spinal implant device 800 is implanted. The open window 816 can allow the cavity to compress after the spinal implant device 800 is implanted. The open window 816 can facilitate bony ingrowth.

In some embodiments, the open window 816 can allow for compression of the spinal implant device 800. The compression of the side walls 824, 826 can promote fusion of the adjacent vertebrae. The compression of the side walls 824, 826 can promote fusion by increasing the load on the material contained within the spinal implant device 800. In some embodiments, the side walls 824, 826 remain uncompressed after insertion. In some embodiments, the side walls 824, 826 remain uncompressed under normal anatomical loads.

In some embodiments, each of the two opposing side walls 824, 826 can include a feature 828. The feature 828 can be designed to facilitate placement of the spinal implant device 800 by coupling with an insertion tool. In some embodiments, the feature 828 can include a channel or groove that originates at the proximal end 822. In some embodiments, the feature 828 can extend from the proximal end 822 along a portion of one of the side walls 824, 826. In some embodiments, the feature 828 can extend from the proximal end 822 to the open window 816. In some embodiments, the feature 828 extends through the thicker edge closer to the proximal end 822. In some embodiments, the feature 828 is a groove through a thicker edge. In some embodiments, the feature 828 extends inward from one of the side walls 824, 826. In some embodiments, the feature 828 is formed from the same material as the thicker edges. In some embodiments, the feature 828 is stronger or more rigid than the adjacent thicker edge.

Figure 59:
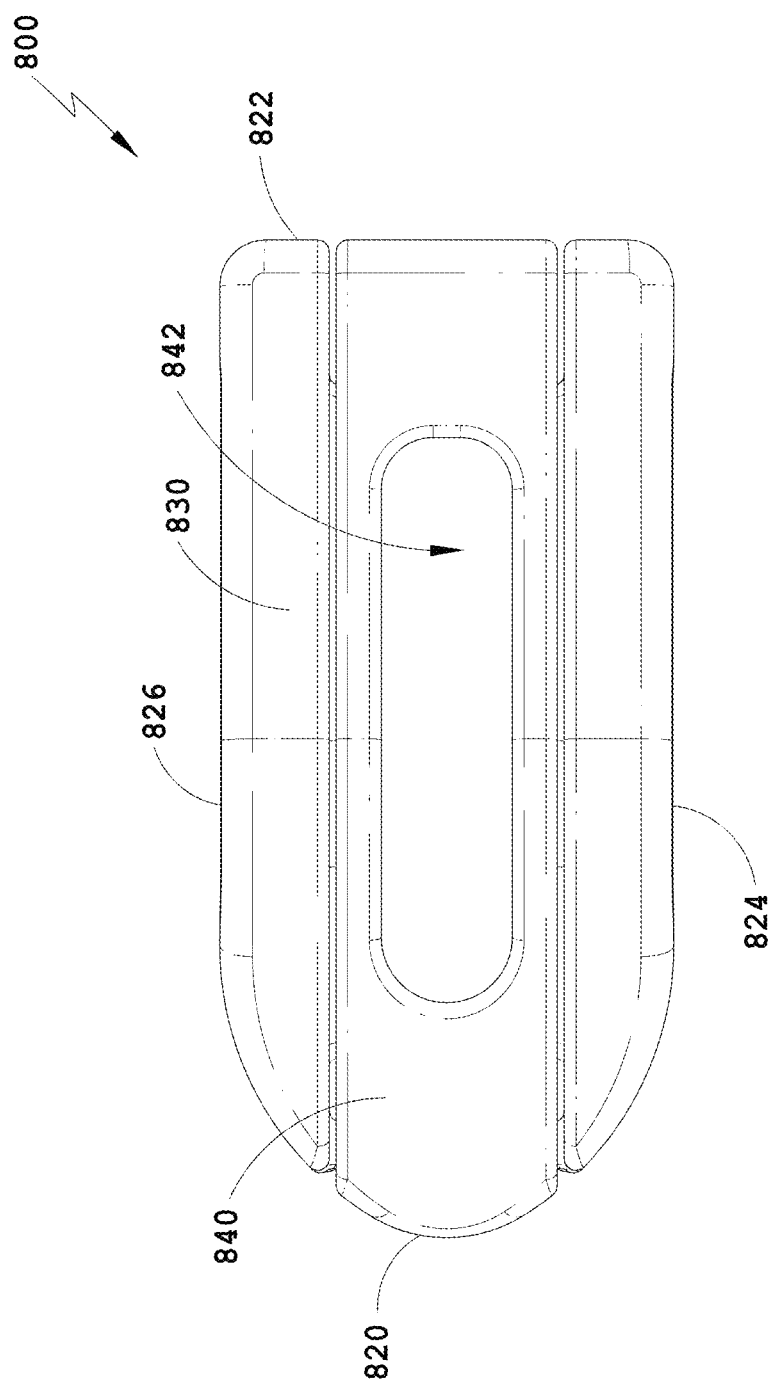
FIG. 59 is a top view of the spinal implant device of FIG. 55.

FIG. 59 is a top view of the spinal implant device 800. The two opposing side walls 824, 826 can extend between the distal end 820 and the proximal end 822. In some embodiments, the two opposing side walls 824, 826 are separated by the same width along a substantial portion of the length of the two opposing side walls 824, 826. In some embodiments, the two opposing side walls 824, 826 taper toward the distal end 820 along a substantial portion of the length of the two opposing side walls 824, 826.

Figure 60:
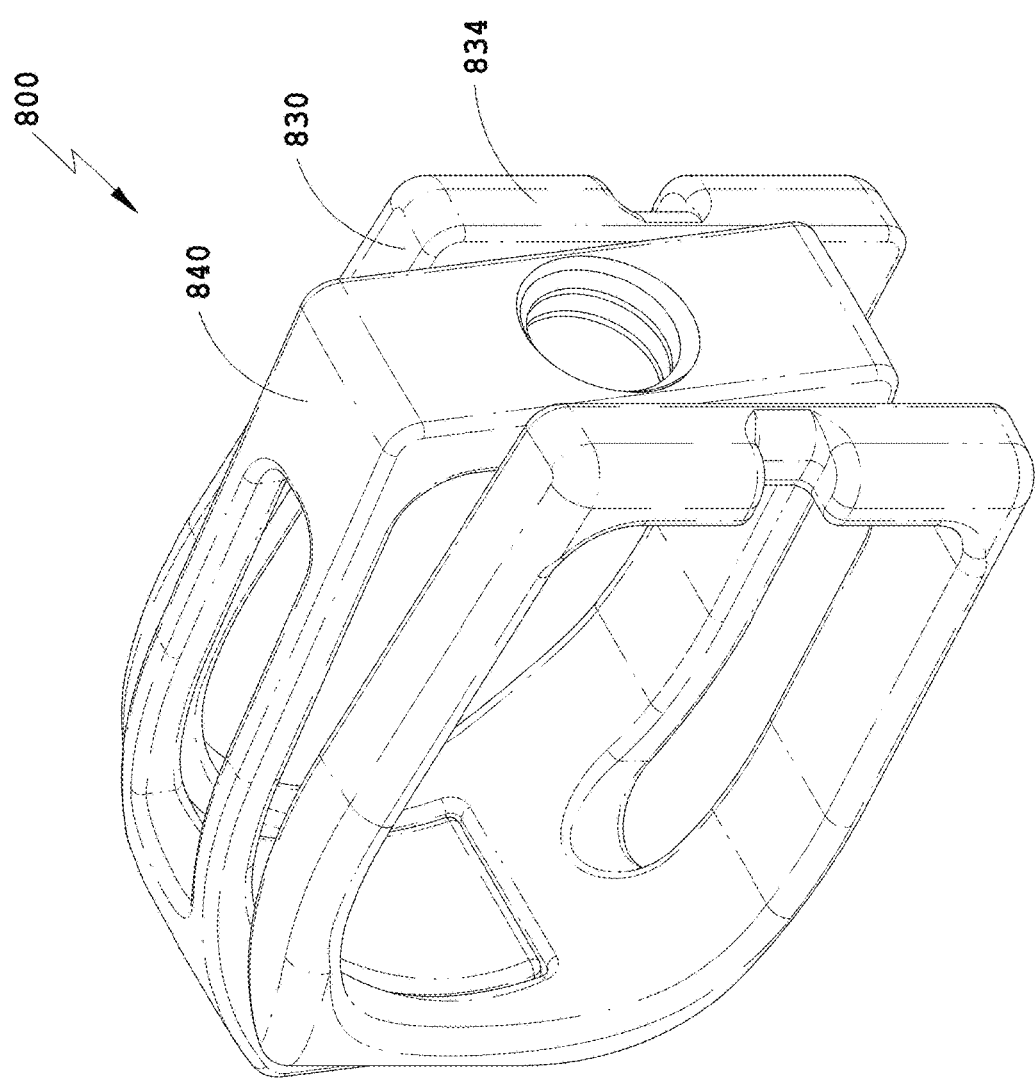
FIG. 60 is a top perspective view of the spinal implant device of FIG. 55 with the movable lid shown in an opened position.

FIG. 59 is a top view of the spinal implant device 800 with the movable lid 840 closed. FIG. 60 is a top perspective view of the spinal implant device 800 with the movable lid 840 opened. The movable lid 840 can have a width less than the width of the spinal implant device 800 between the two opposing side walls 824, 826. The movable lid 840 can have a width less than the width of the spinal implant device 800 between the thicker edges of the proximal end 822.

The spinal implant device 800 can include one or more openings 842 extending through the movable lid 840. In some embodiments, the movable lid includes one opening 842. The opening 842 can be elongate. The opening 842 can extend along a portion of the width of the movable lid 840 (e.g., 30% of the width, 40% of the width, 50% of the width, 60% of the width, 70% of the width, 80% of the width, 90% of the width, 95% of the width, or any range of the foregoing values). The opening 842 can extend along a portion of the length of the movable lid 840 (e.g., 30% of the length, 40% of the length, 50% of the length, 60% of the length, 70% of the length, 80% of the length, 90% of the length, 95% of the length, or any range of the foregoing values). In some embodiments, the one or more openings 842 cover a portion of the surface area of the movable lid 840 (e.g., 50% of the surface area, 60% of the surface area, 70% of the surface area, 80% of the surface area, 90% of the surface area, or 95% of the surface area, or any range of the foregoing values).

The one or more openings 842 of the movable lid 840 can support a porous body as described herein. The one or more openings 842 of the movable lid 840 can support graft material, as described herein. The one or more openings 842 of the movable lid 840 can promote fusion along the height of the spinal implant.

The spinal implant device 800 can include an upper wall 830. The upper wall 830 can include thicker edges which forms the top surface of the spinal implant device 800. The upper wall 830 can extend between the distal end 820 and the proximal end 822. In some embodiments, the upper wall 830 is tapered toward the distal end 820.

In some embodiments, the upper wall 830 forms an opening to accommodate the movable lid 840. In some embodiments, a top portion of the movable lid 840 and the upper wall 830 together form the upper surface of the spinal implant device 800. In some embodiments, the movable lid 840 and the upper wall 830 are laterally adjacent when the lid 840 is closed. The movable lid 840 can be sized to be located within the thicker edges of the upper wall 830. The movable lid 840 can be sized to be surrounded, at least laterally, by the thicker edges of the upper wall 830. In some embodiments, the movable lid 840 and the upper wall 830 can provide a load supporting surface. In some methods, the movable lid 840 and the upper wall 830 can be positioned adjacent to a vertebral end plate of a superior vertebra.

In some embodiments, the upper wall 830 allows for compression of the moveable lid 840 to a desired depth relative to the upper wall 830. The compression of the moveable lid 840 can promote fusion of the adjacent vertebrae. The compression of the moveable lid 840 can promote fusion by increasing the load on the material contained within the spinal implant device. In some embodiments, the upper wall 830 and the moveable lid 840 remain flush without compression. In some embodiments, the moveable lid 840 does not compress under normal anatomic loads.

Figure 61:
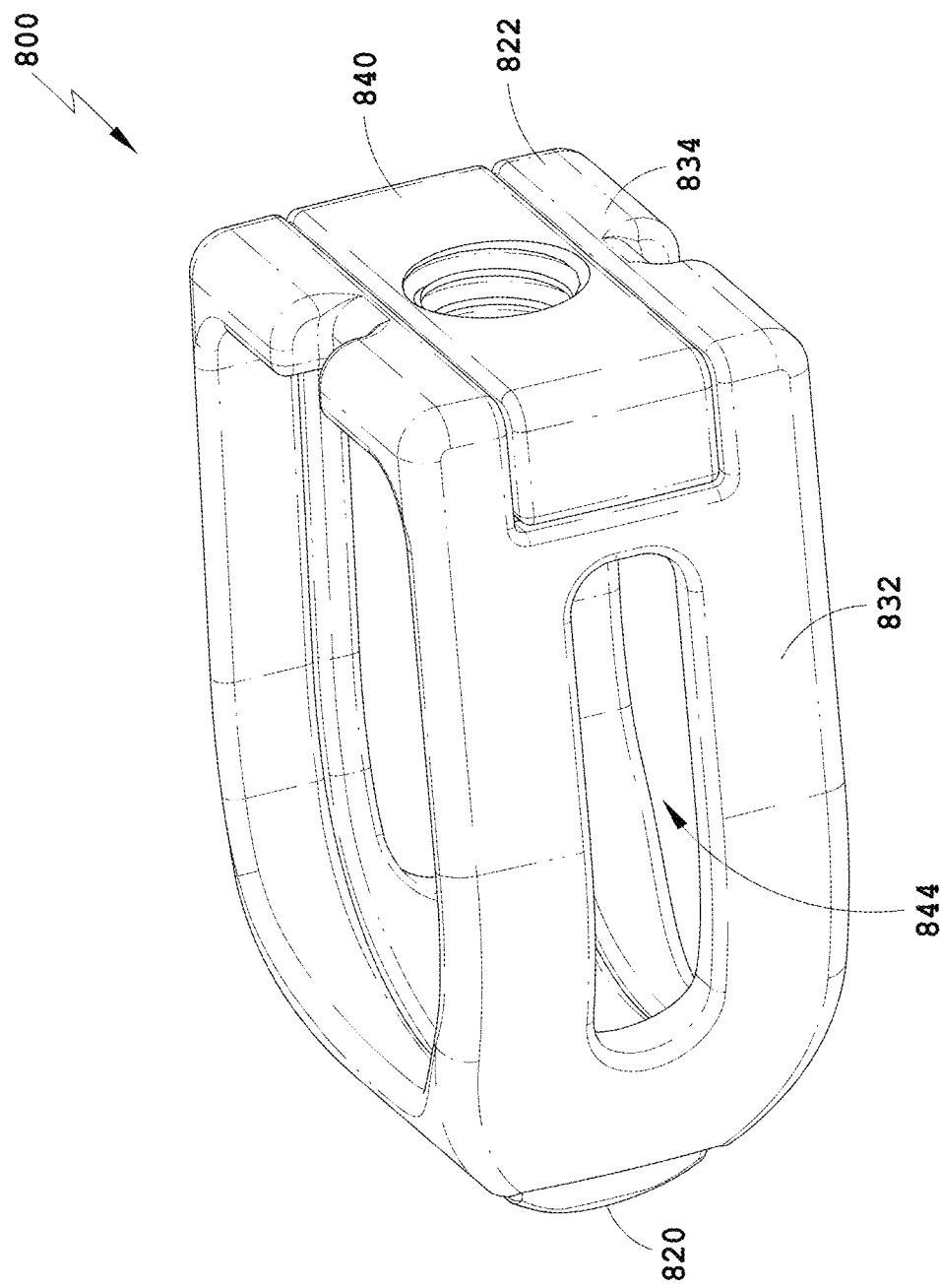
FIG. 61 is a bottom perspective view of the spinal implant device of FIG. 55.

FIG. 61 is a bottom perspective view of the spinal implant device 800. The spinal implant device 800 can include a lower wall 832. The lower wall 832 can extend between the distal end 820 and the proximal end 822. In some embodiments, the lower wall 832 is curved to mimic the shape of the vertebral endplates.

The spinal implant device 800 can include one or more openings 844 extending through the lower wall 832. The opening 844 can be elongate. The openings 842, 844 can have the same or similar shape. The openings 842, 844 can be diametrically opposed. The openings 842, 844 can have different shapes.

The opening 844 can extend along a portion of the width of the lower wall 832 (e.g., 30% of the width, 40% of the width, 50% of the width, 60% of the width, 70% of the width, 80% of the width, 90% of the width, 95% of the width, or any range of the foregoing values). The opening 844 can extend along a portion of the length of the lower wall 832 (e.g., 30% of the length, 40% of the length, 50% of the length, 60% of the length, 70% of the length, 80% of the length, 90% of the length, 95% of the length, or any range of the foregoing values). In some embodiments, the one or more openings 844 cover a portion of the surface area of the lower wall 832 (e.g., 50% of the surface area, 60% of the surface area, 70% of the surface area, 80% of the surface area, 90% of the surface area, or 100% of the surface area, or any range of the foregoing values).

In some embodiments, the lower wall 832 can include thicker edges. The lower wall 832 can include four thicker edges surrounding one or more openings 844. The opening 844 can have a rounded edge near the distal end 820. The opening 844 can have a rounded edge near the proximal end 822. The opening 844 of the lower wall 832 can support a porous body as described herein. The opening 844 of the lower wall 832 can support graft material as described herein.

The lower wall 832 can include thicker edges which forms the bottom surface of the spinal implant device 800. In some embodiments, the lower wall 832 is tapered toward the distal end 820. In some embodiments, the upper wall 830 and the lower wall 832 are bowed outward along a portion of the length of the spinal implant device 800. In some embodiments, the upper wall 830 and the lower wall 832 are tapered inward along a portion of the length of the spinal implant device 800.

In some embodiments, the lower wall 832 forms an opening to accommodate a bottom portion of the movable lid 840. In some embodiments, a bottom portion of the movable lid 840 and the lower wall 832 together form the lower surface of the spinal implant device 800. In some embodiments, the movable lid 840 and the lower wall 832 are laterally adjacent when the lid 840 is closed. The movable lid 840 can extend from the proximal end 822 and toward the distal end 820. The movable lid 840 can be sized to be located within a portion of the lower wall 832. The movable lid 840 can be sized to be surrounded, at least laterally and/or distally, by at least a portion of the thicker edges of the lower wall 832. In some embodiments, the movable lid 840 and the lower wall 832 can provide a load supporting surface. In some methods, the movable lid 840 and the lower wall 832 can be positioned adjacent to a vertebral end plate of the inferior vertebra.

Referring to FIGS. 60 and 61, the spinal implant device 800 can include a proximal wall 834. The proximal wall 834 can include thicker edges which forms the proximal surface of the spinal implant device 800. The proximal wall 834 can extend between the upper wall 830 and the lower wall 832. In some embodiments, the proximal wall 834 is flat or substantially flat. In some embodiments, the proximal wall 834 comprises rounded corners or edges.

In some embodiments, the proximal wall 834 forms an opening to accommodate the movable lid 840. In some embodiments, a proximal portion of the movable lid 840 and the proximal wall 834 together form the proximal surface of the spinal implant device 800. In some embodiments, a proximal portion of the movable lid 840 and the proximal wall 834 are laterally adjacent when the lid 840 is closed. The movable lid 840 can be sized to be located within the thicker edges of the proximal wall 834. The movable lid 840 can be sized to be surrounded, at least laterally, by the thicker edges of the proximal wall 834. In some embodiments, the movable lid 840 and the proximal wall 834 can provide a load supporting surface. In some methods, the movable lid 840 and the proximal wall 834 can be positioned adjacent to the vertebral end plates of adjacent vertebra.

In some embodiments, the movable lid 840 is generally L shaped. In some embodiments, the movable lid 840 is generally U shaped. In some embodiments, the movable lid 840 comprises the top portion, the proximal portion, and the bottom portion. In some embodiments, the top portion, the proximal portion, and the bottom portion have the same width. In some embodiments, the top portion, the proximal portion, and the bottom portion have one or more different widths.

Figure 62:
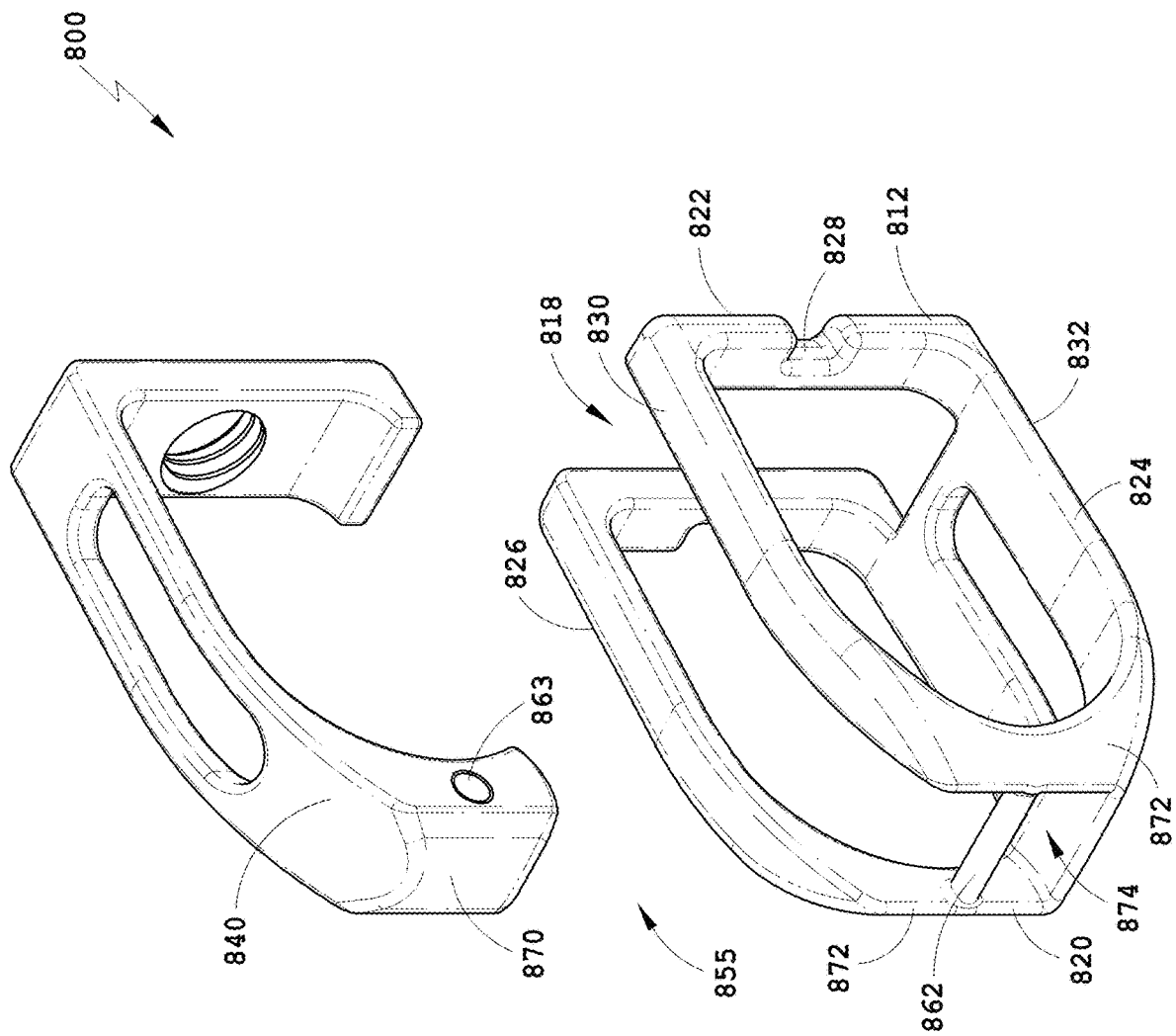
FIG. 62 is an exploded perspective view of the spinal implant device of FIG. 55.

FIG. 62 is an exploded view of the movable lid 840 and the body structure 812. In some embodiments, the movable lid 840 can be coupled to the body structure 812. In some embodiments, the movable lid 840 can be coupled to the distal end 820. The distal end 820 can include two opposing lateral posts 872. In some embodiments, the two opposing lateral posts 872 are connected with a channel 874. The recessed channel 874 can accommodate the movable lid 840. While the two opposing lateral posts 872 are illustrated bilaterally, along each side of the spinal implant device 800, other positions of the two opposing lateral posts 872 are contemplated.

In some embodiments, the spinal implant device 800 can include a movable joint 855. In some embodiments, the movable joint 855 can be positioned distally. The movable joint 855 can couple the movable lid 840 with the body structure 812. The movable joint 855 can allow for pivoting motion of the movable lid 840 relative to the body structure 812.

In some embodiments, the movable joint 855 can include one or more articulations 862. The one or more articulations 862 can extend between two opposing lateral posts 872. The articulation 862 can be an axle. The articulation 862 can be a pivot pin. The articulation 862 can be hinge pins. The articulation 862 can be any structure about which the movable lid 840 can rotate. The articulation 862 can be perpendicular to the longitudinal axis of the spinal implant device 800. The articulation 862 can extend across the width of the spinal implant device 800 or a portion thereof. The articulation 862 can extend between the two opposing side walls 824, 826.

The movable lid 840 can include one or more lumens 863 configured to engage the one or more articulations 862. The lumen 863 can be perpendicular to the longitudinal axis of the spinal implant device 800. The lumen 863 can be perpendicular to the longitudinal axis of the movable lid 840. The movable lid 840 can include the lumen 863 sized to accept the articulation 862. The movable lid 840 can include a central post 870. The one or more lumens 863 can extend through the central post 870 of the movable lid 840. The one or more articulations 862 can extend through the central post 870. The movable joint 855 can be a hinge. In some embodiments, the movable joint 855 can include a corresponding number of articulations and lumens.

The two opposing lateral posts 872 of the distal end 820 can be sized to accommodate the central post 870 of the movable lid 840. The two opposing lateral posts 872 can allow motion with the central post 870 as described herein. The central post 870 can be truncated slightly with a flatter or blunter portion. In some embodiments, the side surfaces of the central post 870 are flat. The central post 870 can be sized to be received within the channel 874 between the two opposing lateral posts 872.

The spinal implant device 800 can include a cavity 818. In some embodiments, the proximal end 822 can form the back inner surface of the cavity 818. In some embodiments, the distal end 820 can form the front inner surface of the cavity 818. In some embodiments, the two opposing side walls 824, 826 can form the side inner surfaces of the cavity 818. In some embodiments, the movable lid 840 can form a portion of the top inner surface of the cavity 818. In some embodiments, the lower wall 832 can form the bottom inner surface of the cavity 818. In some embodiments, the cavity 818 is partially enclosed on at least four sides. The spinal implant device 800 can have thicker edges with windows 816 on the two opposing side walls 824, 826. The cavity 818 can be partially open on at least two sides. The cavity 818 can be partially open laterally through the openings. The cavity 818 can include areas where the porous body or graft material can be inserted. The cavity 818 can allow material to flow outwardly or inwardly. The cavity 818 can promote fusion by the migration of material to and from the cavity 818.

The cavity 818 can be a centrally located space within the spinal implant device 800. In some embodiments, the cavity 818 comprises a portion of the volume of the spinal implant device 800 (e.g., 50% of the volume, 60% of the volume, 70% of the volume, 80% of the volume, 90% of the volume, or 95% of the volume, or any range of the foregoing values).

Figure 63:
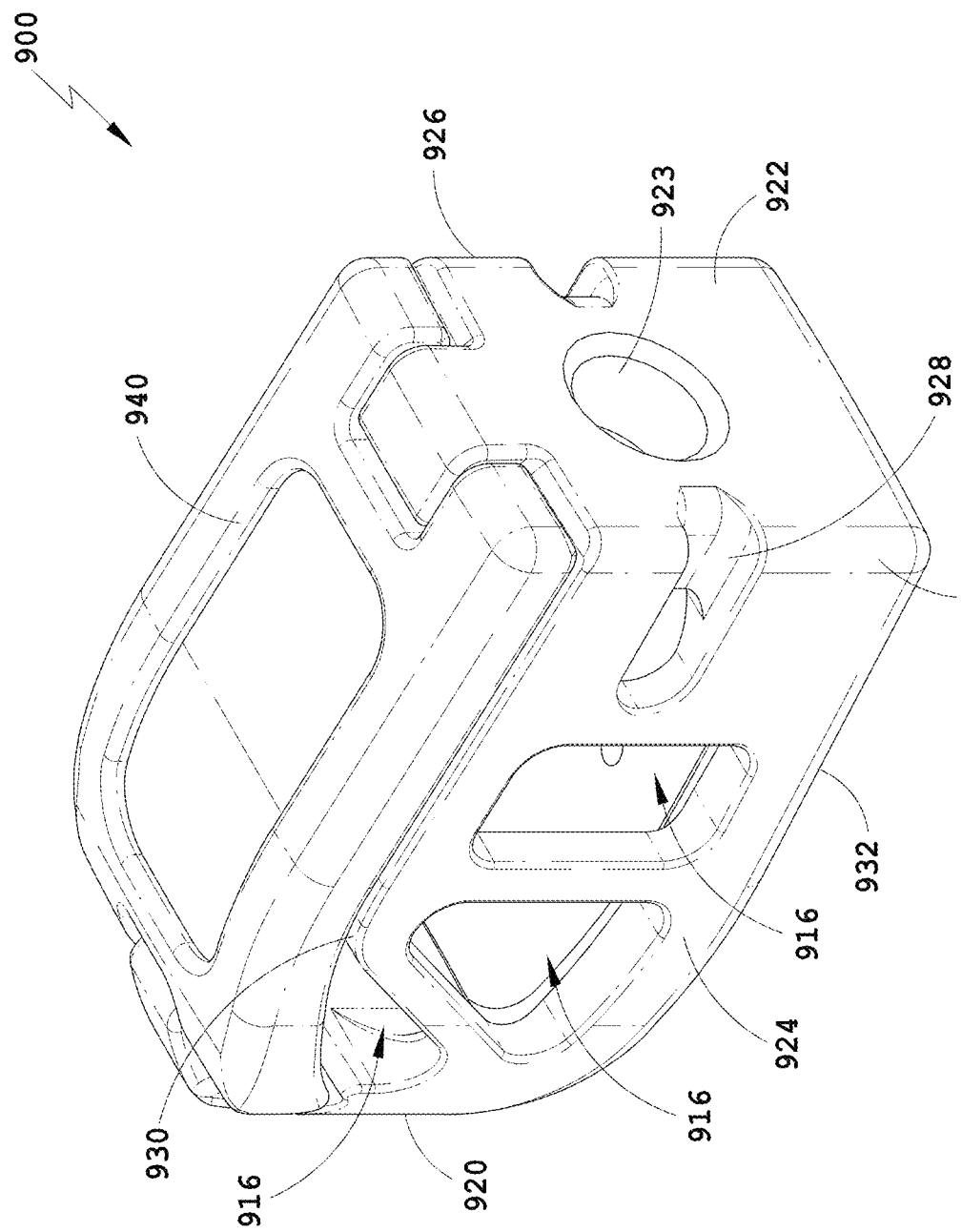
FIG. 63 is a perspective view of an embodiment of a spinal implant device with a movable lid shown in a closed position.

FIG. 63 illustrates a perspective view of a spinal implant device 900. The spinal implant device 900 can include any of the features of the spinal implant device 10, 10A, 100, 200, 300, 400, 500, 600, 700, 800 as described herein and can be used in any method or method step described herein. The spinal implant device 900 can include a body structure 912. The body structure 912 can be placed between adjacent vertebrae.

Figure 64:
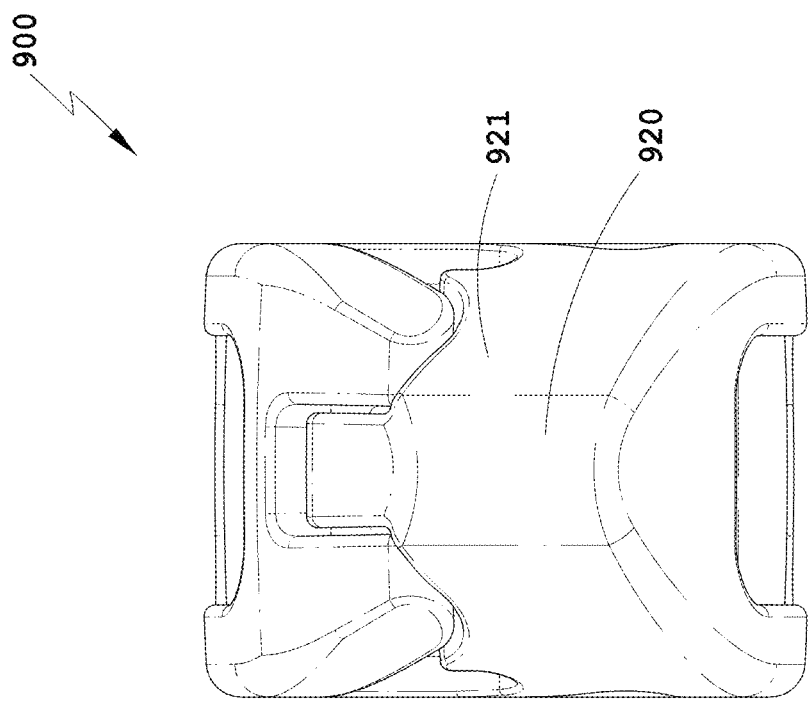
FIG. 64 is a distal view of the spinal implant device of FIG. 63.

FIG. 64 is a distal view of the spinal implant device 900. The spinal implant device 900 can include a distal end 920. In some methods of use, the distal end 920 can be the insertion end. In some embodiments, the distal end 920 is tapered inward. In some embodiments, the four surfaces of the distal end 920 can taper to from a square pyramid or similar shape. In some embodiments, the upper surface, or a portion thereof, and the lower surface of the distal end 920 equally taper. In some embodiments, the side surfaces of the distal end 920 equally taper. In some embodiments, the distal end 920 can include rounded corners or edges. The distal end 920 can form a frustoconical or convex curved shape 921.

Figure 65:
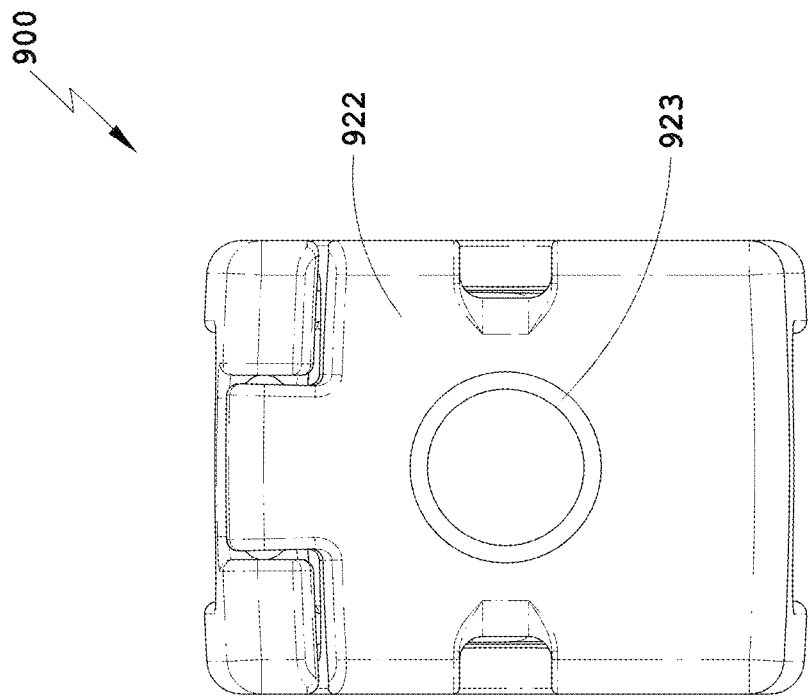
FIG. 65 is a proximal view of the spinal implant device of FIG. 63.

FIG. 65 is a proximal view of the spinal implant device 900. The spinal implant device 900 can include a proximal end 922. In some embodiments, the proximal end 922 can be flat. In some embodiments, the proximal end 922 can include one or more rounded corners or edges. The proximal end 922 can be substantially square or rectangular. In some embodiments, the proximal end 922 can include an opening 923 to couple to an insertion tool. In some embodiments, the opening 923 can be threaded.

Figure 66:
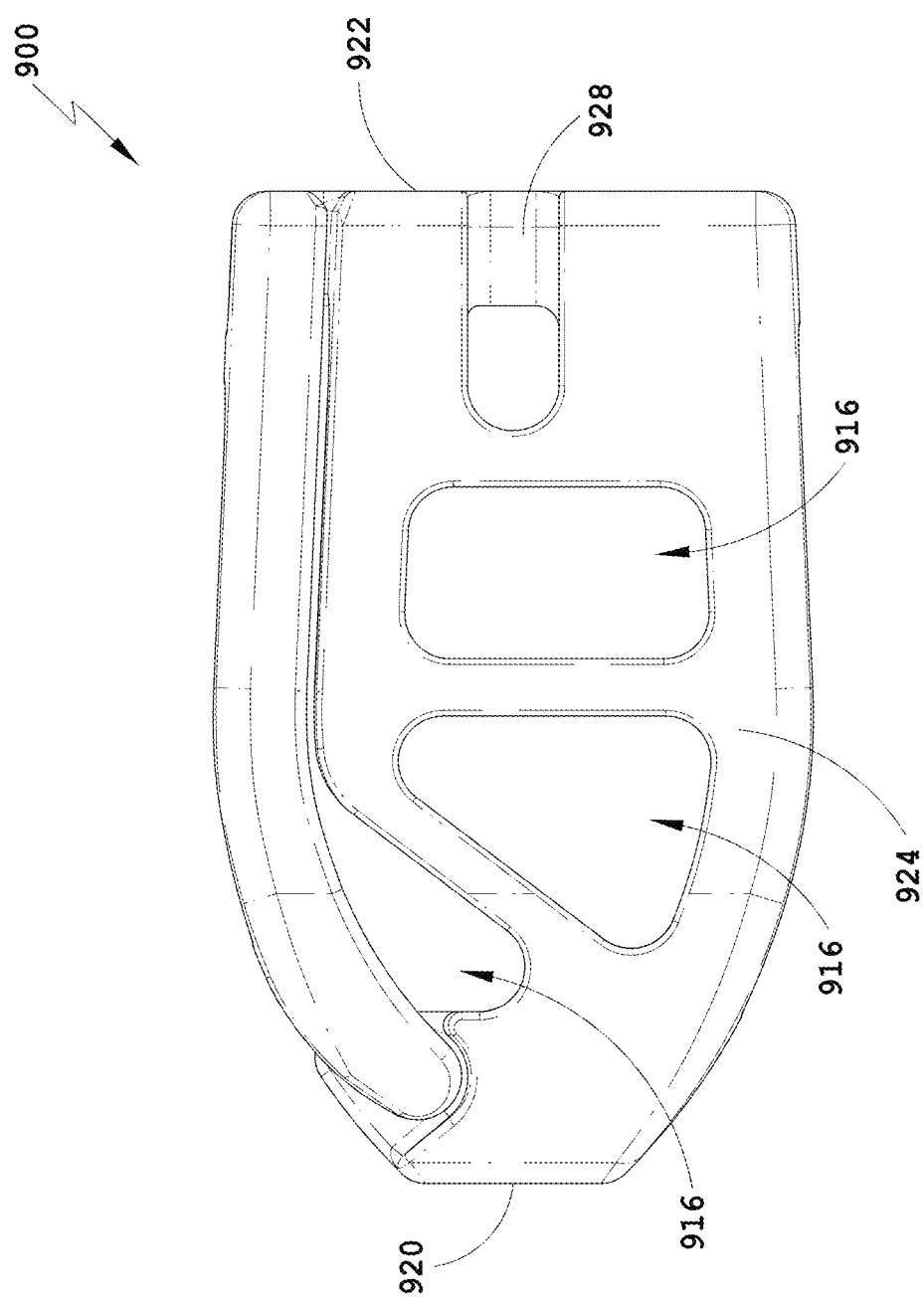
FIG. 66 is a side view of the spinal implant device of FIG. 63.

FIG. 66 is a side view of the spinal implant device 900. The length of the spinal implant device 900 can be the distance between the distal end 920 and the proximal end 922. The distal end 920 and the proximal end 922 can form the leading and trailing end, respectively. The spinal implant device 900 can include two opposing side walls including a first side wall 924 and a second side wall 926. FIG. 66 illustrates the first side wall 924, but the second side wall 926 can include the same or similar features. The first side wall 924 and the second side wall 926 can be mirror images.

In some embodiments, each of the two opposing side walls 924, 926 can include a feature 928 to facilitate placement of the spinal implant device 900. In some embodiments, the feature 928 can include a channel to accept an insertion tool. In some embodiments, the feature 928 can extend from the proximal end 922 of the spinal implant device 900 toward the distal end 920. In some embodiments, the feature 928 can form a groove in the proximal end 922. In some embodiments, the feature 928 can be partially enclosed on three sides near the proximal end 922. In some embodiments, the feature 928 can form an opening in the side walls 924, 926. In some embodiments, the feature 928 can be partially enclosed on two sides near the side walls 924, 926. In some embodiments, the feature 928 can have a greater width than the width of the side walls 924, 926. In some embodiments, the feature 928 can extend inward beyond the width of the side walls 924, 926. In some embodiments, the feature 928 can extend along a portion of the length of the spinal implant device 900 (e.g., 10% of the length, 20% of the length, 30% of the length, 40% of the length, 50% of the length, 60% of the length, 70% of the length, 80% of the length, 90% of the length, or 100% of the length, or any range of the foregoing values).

In some embodiments, each side wall 924, 926 can include thicker edges surrounding an open window 916. Each side wall 924, 926 can include four thicker edges surrounding one or more open windows 916. The one or more open windows 916 can be anywhere along the length of the side walls 924, 926. The one or more open windows 916 can be distal to the feature 928. In the illustrated embodiment, each side wall 924, 926 includes three open windows 916. The first open window 916 can be substantially rectangular. The second open window 916 can be substantially triangular. The third open window 916 can be substantially teardrop shaped. Other shapes are contemplated. One or more open windows 916 can span the height of the spinal implant device 900 or a portion thereof. One or more open windows 916 can extend to an edge of the spinal implant device 900 or a portion thereof. One or more open windows 916 can follow the shape of the side wall 924, 926. The open windows 916 can support a porous body. The porous body can be coupled to the side wall 924, 926. The open windows 916 can support graft material. The open window 916 can facilitate bony ingrowth. In some embodiments, the open windows 916 can facilitate compression of the side walls 924, 926.

Figure 67:
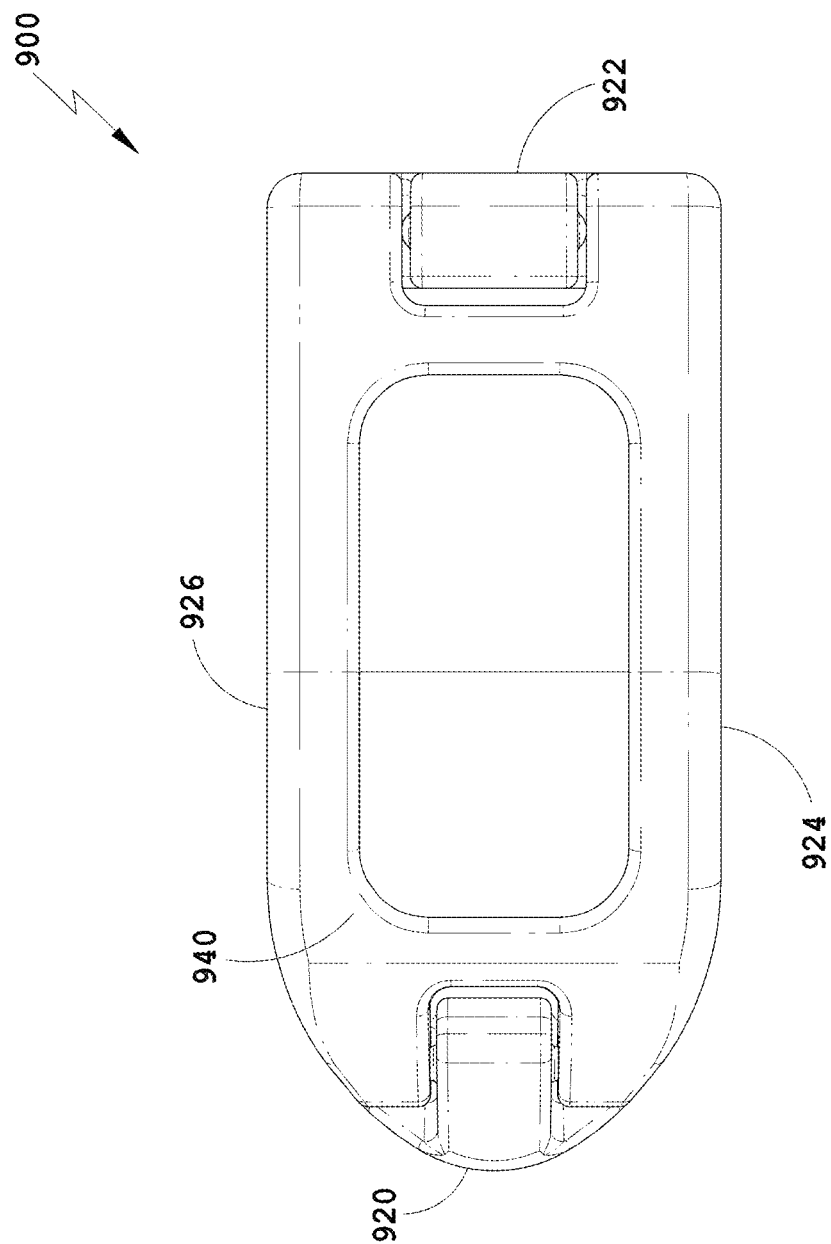
FIG. 67 is a top view of the spinal implant device of FIG. 63.
Figure 68:
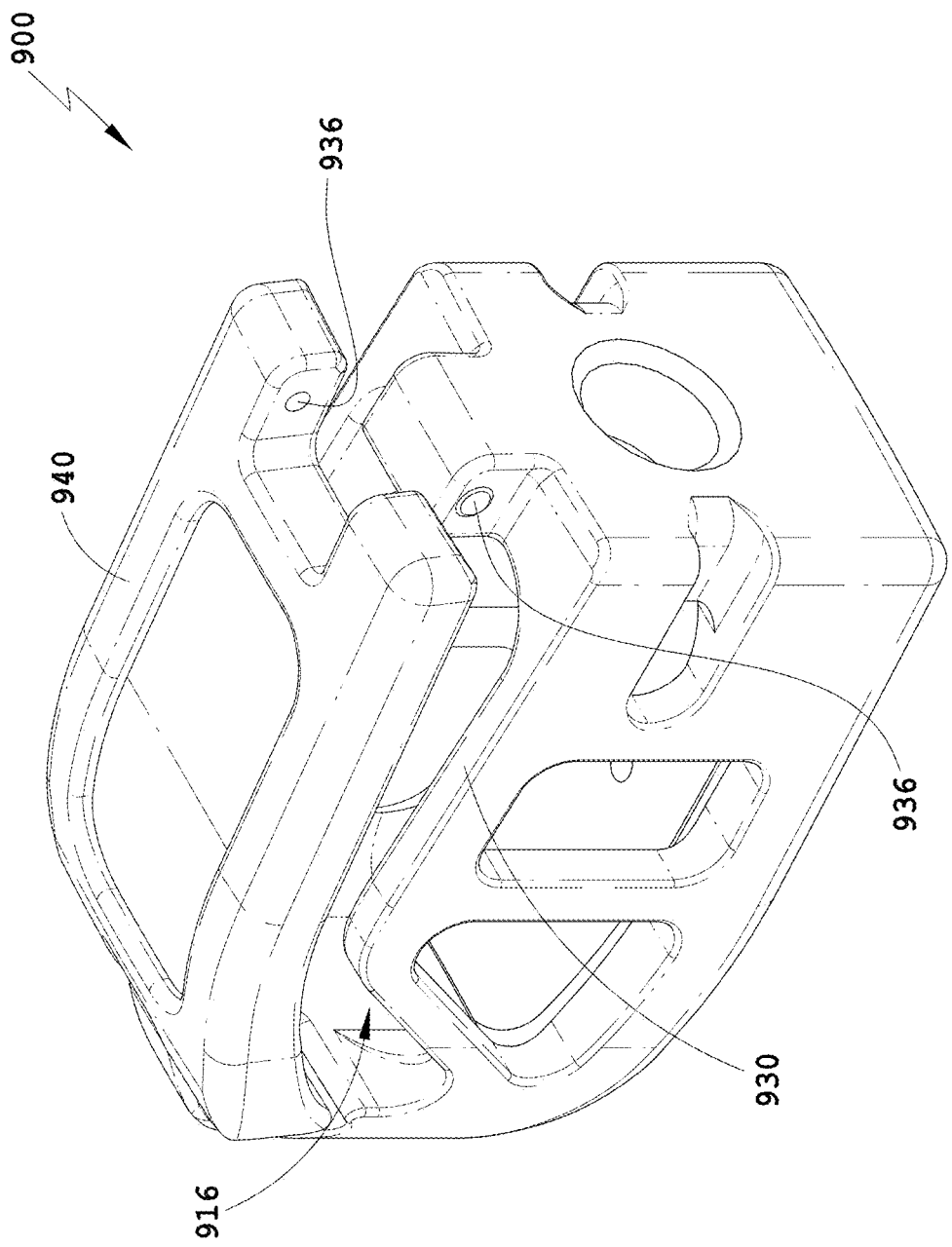
FIG. 68 is a top perspective view of the spinal implant device of FIG. 63 with the movable lid shown in an opened position.

FIG. 67 is a top view of the spinal implant device 900. The two opposing side walls 924, 926 can extend between the distal end 920 and the proximal end 922. In some embodiments, the two opposing side walls 924, 926 are separated by substantially the same width along a portion of the length of the two opposing side walls 924, 926. In some embodiments, the two opposing side walls 924, 926 are parallel or substantially parallel along a portion of the length of the side walls 924, 926. In some embodiments, the two opposing side walls 924, 926 are the same shape. In some embodiments, the distance between the two opposing side walls 924, 926 can form the width of the spinal implant The spinal implant device 900 can include a movable lid 940. FIG. 67 is a top view of the spinal implant device 900 with the movable lid 940 closed. FIG. 68 is a top perspective view of the spinal implant device 900 with the movable lid 940 opened.

The spinal implant device 900 can include an upper wall 930. The upper wall 930 can span between the distal end 920 and the proximal end 922. In some embodiments, a portion of the upper wall 930 is lower than another surface of the upper wall 930. In some embodiments, a portion of the upper wall 930 is tapered toward the distal end 920. In some embodiments, a portion of the upper wall 930 is planar or substantially planar. In some embodiments, the upper wall 930 forms a ledge to support the movable lid 940. In some embodiments, the upper wall 930 forms a support surface that mirrors the lower surface of the movable lid 940 when the movable lid 940 is closed. In some embodiments, the upper wall 930 supports the movable lid 940 along the side walls 924, 926. In some embodiments, the upper wall 930 supports the movable lid 940 along the proximal end 922. In some embodiments, the upper wall 930 supports the movable lid 940 along the distal end 920.

The upper wall 930 can include a projection near the proximal end 922. In some embodiments, a portion of the upper wall 930 is higher than another surface of the upper wall 930. In some embodiments, a portion of the upper wall 930 extends between portions of the movable lid 940. In some embodiments, a portion of the upper wall 930 is planar or substantially planar. In some embodiments, a portion of the upper wall 930 is disposed between portions of the movable lid 940. The upper wall 930 can support and align the movable lid 940. In some embodiments, a portion of the upper wall 930 extends upward from the opening 923. The upper wall 930 can form an upward tab of the proximal end 922. In some embodiments, the spinal implant device 900 can include retention features 936. The retention features 936 can include a lateral projection in a lateral recess. The projection of the upper wall can include a lateral projection and the movable lid 940 can include a lateral recess. The retention features 936 can retain the movable lid 940 relative to the body 912 near the proximal end 922.

In some embodiments, the movable lid 940 and a portion of the upper wall 930 can form the upper surface of the spinal implant device 900 configured to contact the vertebral end plate. In some embodiments, the movable lid 940 and the upper wall 930 can correspond in shape. The movable lid 940 can match the curvature of the upper wall 930. The movable lid 940 can abut the upper wall 930 when the lid 940 is closed. In some embodiments, the movable lid 940 and a portion of the upper wall 930 can provide a load supporting surface for the adjacent vertebrae. In some methods, the load can be transferred from the movable lid 940 to the upper wall 930. In some methods, the movable lid 940 can be positioned adjacent to a vertebral end plate of a superior vertebra.

The movable lid 940 can include a thin framework supported by thicker edges. The thin framework can be elongated. The thin framework can have a smaller height than another portion of the movable lid 940. The thin framework can be recessed to accept a porous body. The thin framework can be recessed to accept graft material. In some embodiments, the thin framework is solid. In some embodiments, the thin framework has the same material as the thicker edges. In some embodiments, the thin framework has a different material than the thicker edges. In some embodiments, the thin framework is porous or a mesh. In some embodiments, the thin framework allows bony ingrowth therethrough. In some embodiments, the thin framework allows the fusion of material therethrough. In some embodiments, a porous body is applied to the thin framework. The porous bodies arranged on one or more sides can allow material to flow outwardly from the spinal implant device 900 to promote fusion. The porous bodies can include any porous material. The porous bodies can be formed of any material that intrinsically participates in the growth of bone.

In some embodiments, at least a portion of one surface of the spinal implant device 900 can have a porous body. The porous body can be created in any a variety of ways, such as by applying sintered beads or spraying plasma onto the thin framework or by 3D printing. The porous body can allow bone to grow into or attach to the surface of the spinal implant device 900, thus securing the spinal implant device 900 to the bone. In some embodiments, an adhesive or sealant, such as a cyanoacrylate, polymethylmethacrylate, or other adhesive, can be used to bond the porous material to the spinal implant device 900.

Figure 69:
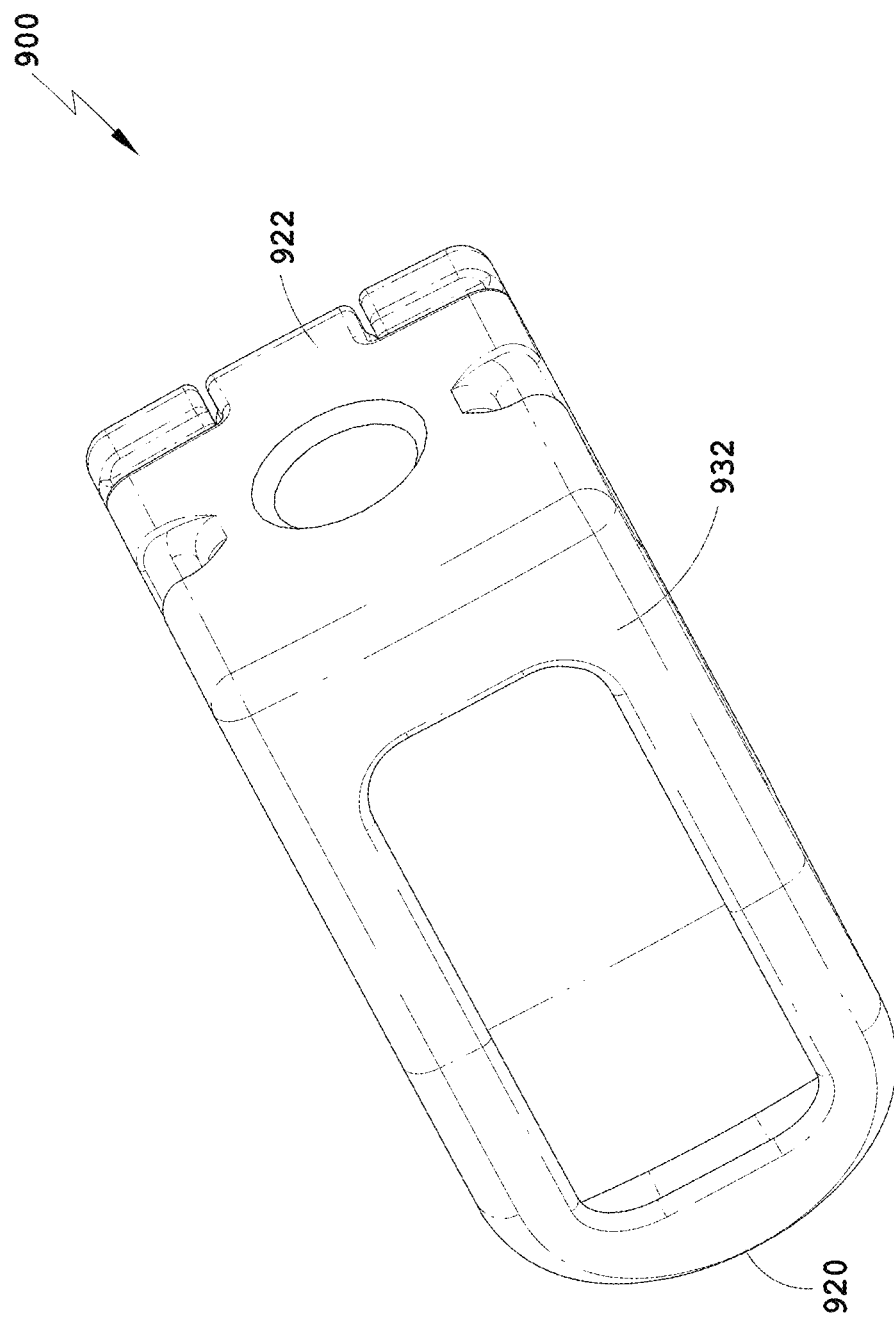
FIG. 69 is a bottom perspective view of the spinal implant device of FIG. 63.

FIG. 69 is a bottom perspective view of the spinal implant device 900. The spinal implant device 900 can include a lower wall 932. The lower wall 932 can span between the distal end 920 and the proximal end 922. In some embodiments, a portion of the lower wall 932 is tapered inward. In some embodiments, a portion of the lower wall 932 is tapered toward the distal end 920. In some embodiments, a portion of the lower wall 932 is planar or substantially planar. In some embodiments, a portion of the lower wall 932 is convex. In some embodiments, a portion of the lower wall 932 is bowed outward.

The lower wall 932 can include a thin framework supported by thicker edges. The thin framework can be elongated. The thin framework can follow the taper of the lower wall 932. The thin framework can have a smaller height than another portion of the lower wall 932. The thin framework can be recessed to accept a porous body. The thin framework can be recessed to accept graft material. The thin framework can have any features of the thin framework described herein.

The lower wall 932 can provide a load supporting surface. In some methods, the lower wall 932 can be positioned adjacent to a vertebral end plate of an inferior vertebra. In some methods, when the spinal implant device 900 is positioned between two adjacent vertebrae, the load supporting surfaces of the movable lid 940 and the lower wall 932 contact the vertebral end plates of the adjacent vertebrae. In some embodiments, the distance between the movable lid 940 and the lower wall 932 can form the height of the spinal implant device 300.

Figure 70:
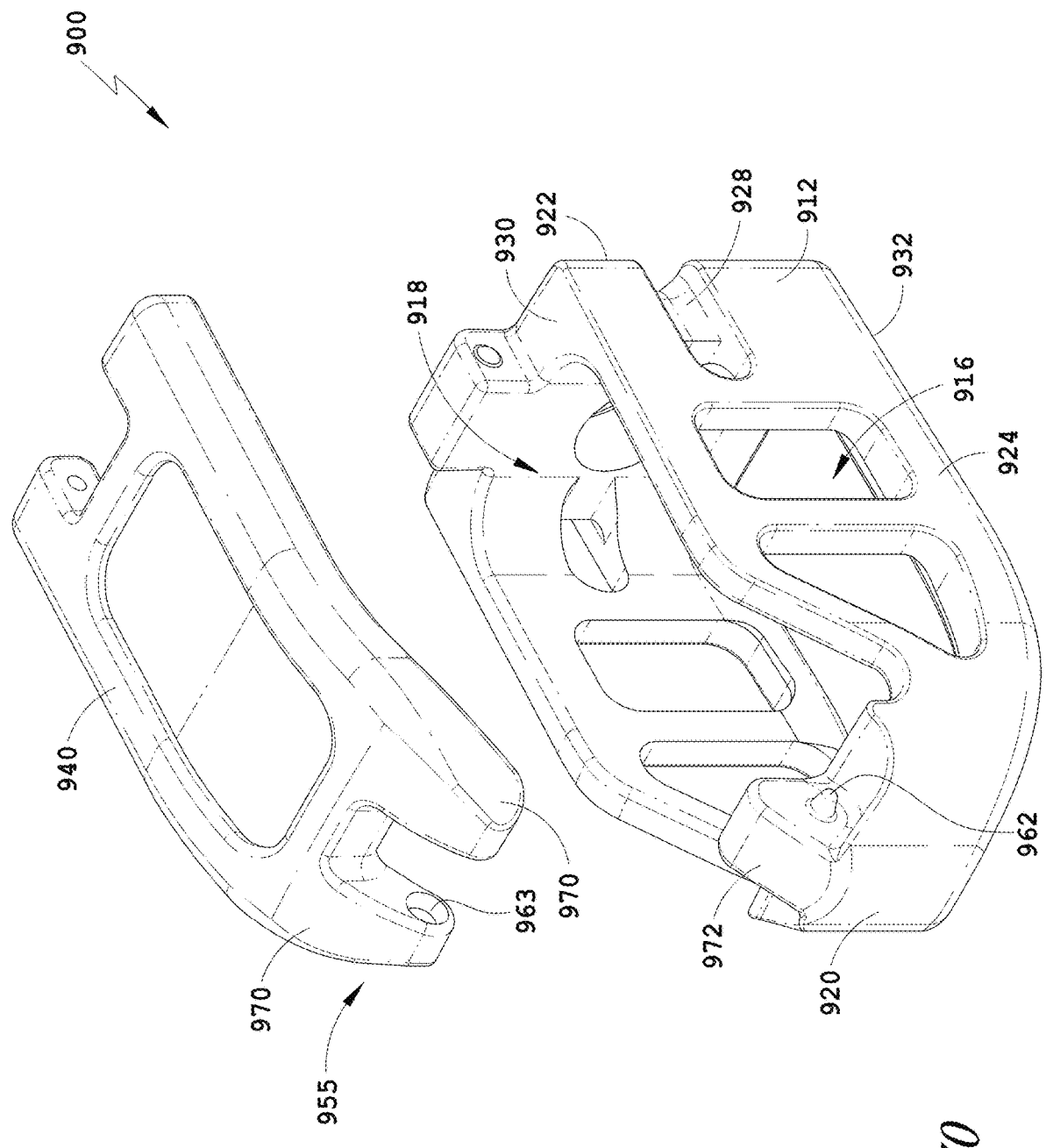
FIG. 70 is an exploded perspective view of the spinal implant device of FIG. 63.

FIG. 70 is an exploded view of the movable lid 940 of the spinal implant device 900. In some embodiments, the movable lid 940 can be coupled to the distal end 920. The distal end 920 can include a central post 972. The central post 972 can extend upward from a portion of the upper wall 930. In some embodiments, the upper wall 930 is recessed relative to the central post 972 to accommodate the movable lid 940. The central post 972 can extend along a portion of the width of the spinal implant device 900. While the central post 972 is centrally located along the longitudinal axis of the spinal implant device 900, other positions of the central post 972 are contemplated.

In some embodiments, the spinal implant device 900 can include a movable joint 955. In some embodiments, the movable joint 955 can couple the movable lid 940 to the distal end 920. The movable joint 955 can couple the movable lid 940 with any portion of the body structure 912. The movable joint 955 can allow for pivoting motion of the movable lid 940. In some embodiments, the movable joint 955 can include one axis of rotation. In some embodiments, the movable joint 955 can include more than one axis of rotation.

In some embodiments, the movable joint 955 can include a pair of articulations 962. The pair of articulations 962 can be located on the central post 972. The pair of articulations 962 can extend from the central post 972. The pair of articulations 962 can extend outward from the central post 972. The pair of articulations 962 can extend perpendicular to the longitudinal axis of the spinal implant device 900.

Each of the two opposing lateral posts 970 can include sockets 963 configured to engage an articulation 962 of the pair of articulations 962. The pair of sockets 963 can extend perpendicular to the longitudinal axis of the spinal implant device 900. The pair of sockets 963 can extend outward from the inner surfaces of the two opposing lateral posts 970. In some embodiments, the orientation is reversed and the pair of articulations 962 can be located on the movable lid 940 and the pair of sockets 963 can be located on the central post 972. The two opposing lateral posts 970 can be located near a distal end of the movable lid 940. The two opposing lateral posts 970 of the movable lid 940 can be sized to accommodate the central post 972 of the distal end 920. The two opposing lateral posts 972 of the movable lid 940 can interact with the central post 972 to allow for pivoting motion.

In some embodiments, each articulation 962 is conical and each socket 963 is conical. In some embodiments, the movable joint 955 can include one or more articulations 962 (e.g., one, two, three, four, five, or six). In some embodiments, the movable joint 955 can include a corresponding number of articulations and sockets. The moveable lid 940 can be coupled to the spinal implant device 900 at any location to facilitate packing the spinal implant device 900.

In some embodiments, the movable lid 940 is generally U shaped. In some embodiments, the movable lid 940 is generally H shaped. In some embodiments, the movable lid 940 comprises a top portion. In some embodiments, the top portion accommodates the central post 972 near the distal end of the movable lid 940. In some embodiments, the top portion accommodates the upper wall 930 near the proximal end of the movable lid 940. In some embodiments, a portion of the upper wall 930 near the proximal end and the central post 972 have the same width. In some embodiments, a portion of the upper wall 930 near the proximal end and the central post 972 have different widths.

The spinal implant device 900 can include a cavity 918. In some embodiments, the proximal end 922 can define the back inner surface of the cavity 918. In some embodiments, the distal end 920 can define the front inner surface of the cavity 918. In some embodiments, the two opposing side walls 924, 926 can define the side inner surfaces of the cavity 918. In some embodiments, the movable lid 940 can define the top inner surface of the cavity 918. In some embodiments, the lower wall 942 can define the bottom inner surface of the cavity 918. In some embodiments, the cavity 918 is partially enclosed. In some embodiments, the cavity 918 is fully enclosed. The cavity 918 can be a contained space within the spinal implant device 900. In some embodiments, the cavity 918 comprises a portion of the volume of the spinal implant device 900 (e.g., 50% of the volume, 60% of the volume, 70% of the volume, 80% of the volume, 90% of the volume, or 100% of the volume, or any range of the foregoing values).

In some embodiments, the spinal implant device 10, 10A, 100, 200, 300, 400, 500, 600, 700, 800, 900 can include a size range that accommodates the following footprints: 8×22 mm, 10×22 mm, 10×27 mm, 10×32 mm, 12×27 mm or 12×37 mm or any range of the foregoing values. In some embodiments, the spinal implant device 10, 10A, 100, 200, 300, 400, 500, 600, 700 can include a width of 8 mm, 10 mm, 12 mm, between 8 mm and 10 mm, between 10 mm and 12 mm, between 8 mm and 12 mm, or any range of the foregoing values. In some embodiments, the spinal implant device 10, 10A, 100, 200, 300, 400, 500, 600, 700 can include a length of 22 mm, 27 mm, 32 mm, 37 mm, between 22 mm and 27 mm, between 27 mm and 32 mm, between 32 mm and 37 mm, between 22 mm and 32 mm, between 27 mm and 37 mm, between 22 mm and 37 mm, or any range of the foregoing values.

In some embodiments, the spinal implant device 10, 10A, 100, 200, 300, 400, 500, 600, 700, 800, 900 can have a slight inclination, called a lordosis angle θ. In some embodiments, the lordosis angle is approximately 5°. Other configurations are contemplated, for example 1°, 2°, 3°, 4°, 5°, 6°, 7°, 8°, 9°, 10°, 11°, 12°, 13°, 14°, 15°, 16°, 17°, 18°, 19°, 20°, between 4° and 6°, between 0° and 5°, between 3° and 5°, or any range of the foregoing values. In some embodiments, the spinal implant device 10, 10A, 100, 200, 300, 400, 500, 600, 700 can have a slight inclination, called a kyphosis angle. In some embodiments, the kyphosis angle is approximately 5°. Other configurations are contemplated, for example 1°, 2°, 3°, 4°, 5°, 6°, 7°, 8°, 9°, 10°, 11°, 12°, 13°, 14°, 15°, 16°, 17°, 18°, 19°, 20°, between 4° and 6°, between 0° and 5°, between 3° and 5°, or any range of the foregoing values. In some embodiments, the spinal implant device 10, 10A, 100, 200, 300, 400, 500, 600, 700 can include an angle, for example 1°, 2°, 3°, 4°, 5°, 6°, 7°, 8°, 9°, 10°, 11°, 12°, 13°, 14°, 15°, 16°, 17°, 18°, 19°, 20°, between 4° and 6°, between 0° and 5°, between 3° and 5°, or any range of the foregoing values. In some embodiments, the spinal implant device 10, 10A, 100, 200, 300, 400, 500, 600, 700, 800, 900 does not include an angle.

Figure 71:
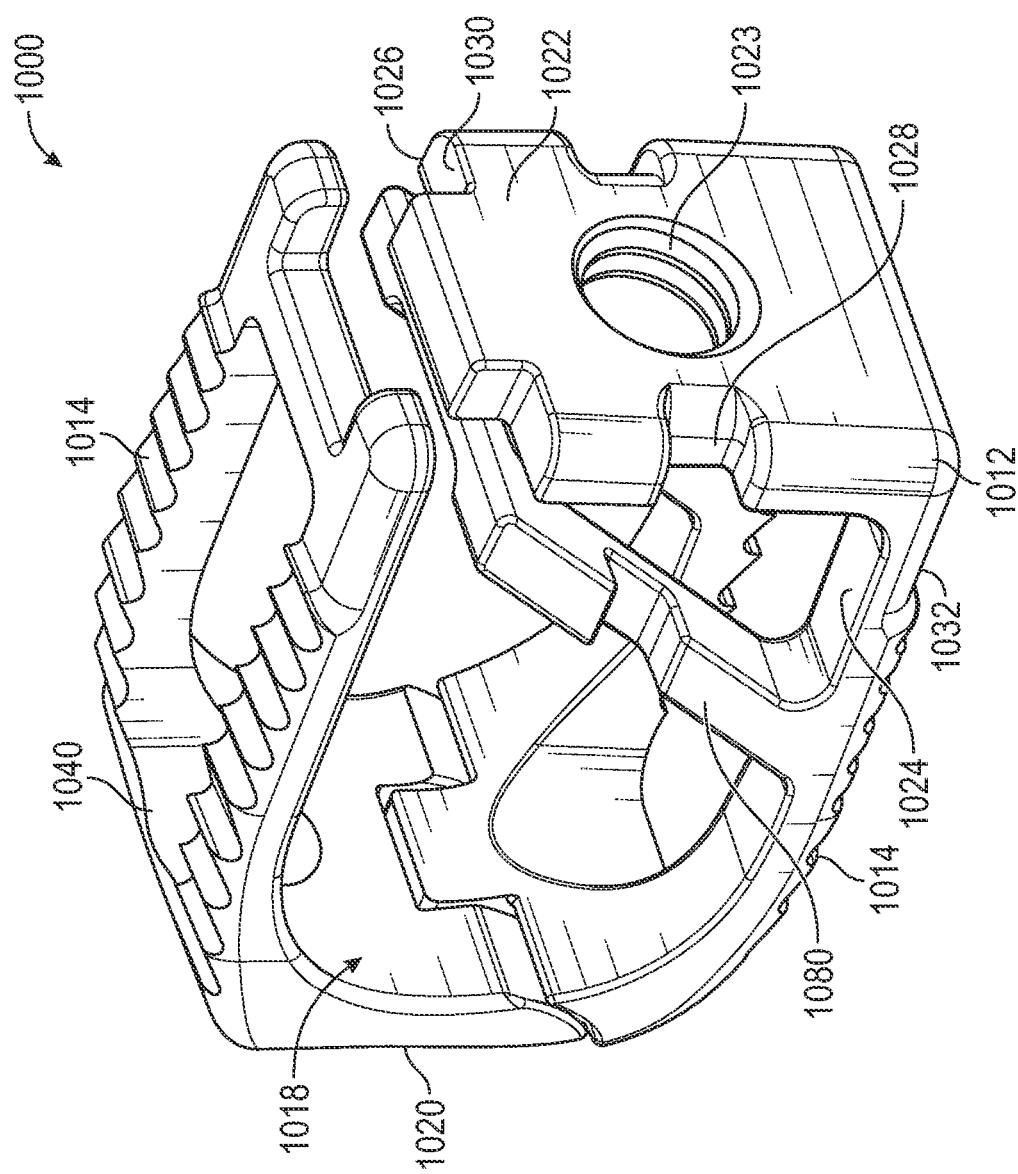
FIG. 71 is a perspective view of an embodiment of a spinal implant device with a movable lid shown in a closed position.

FIG. 71 illustrates a perspective view of a spinal implant device 1000. The spinal implant device 1000 can include any of the features of the spinal implant device 10, 10A, 100, 200, 300, 400, 500, 600, 700, 800, 900 as described herein and can be used in any method or method step described herein. The spinal implant device 1000 can include a body structure 1012. In some embodiments, the body structure 1012 can includes features to promote compression. In some methods of use, the compression of a portion of the spinal implant device 1000 can promote fusion. In some embodiments, the spinal implant device 1000 allows for compression to a desired depth. The compression of the spinal implant device 1000 can allow for increased load on the corresponding graft material or other fusion material disposed within the spinal implant device 1000. In some embodiments, the compression of the spinal implant device 1000 can promote fusion.

Figure 72:
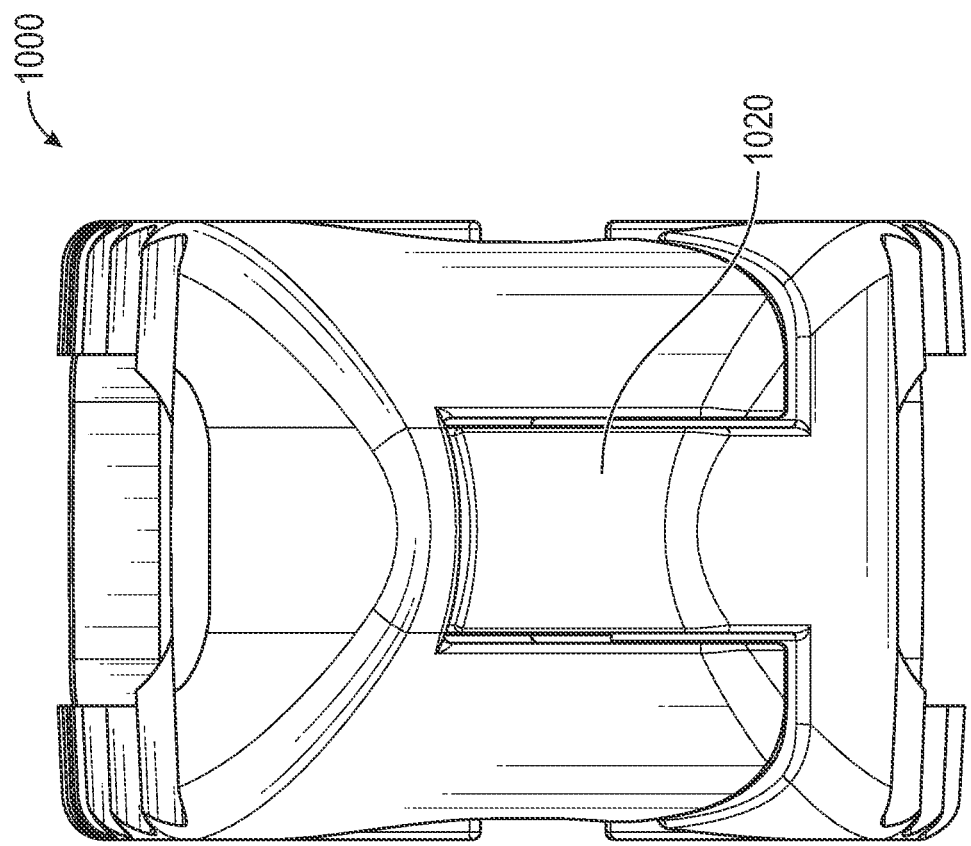
FIG. 72 is a distal view of the spinal implant device of FIG. 71.

FIG. 72 is a distal view of the spinal implant device 1000. The spinal implant device 1000 can include a distal end 1020. In some methods of use, the distal end 1020 can be the insertion end. In some embodiments, the distal end 1020 is tapered inward.

Figure 73:
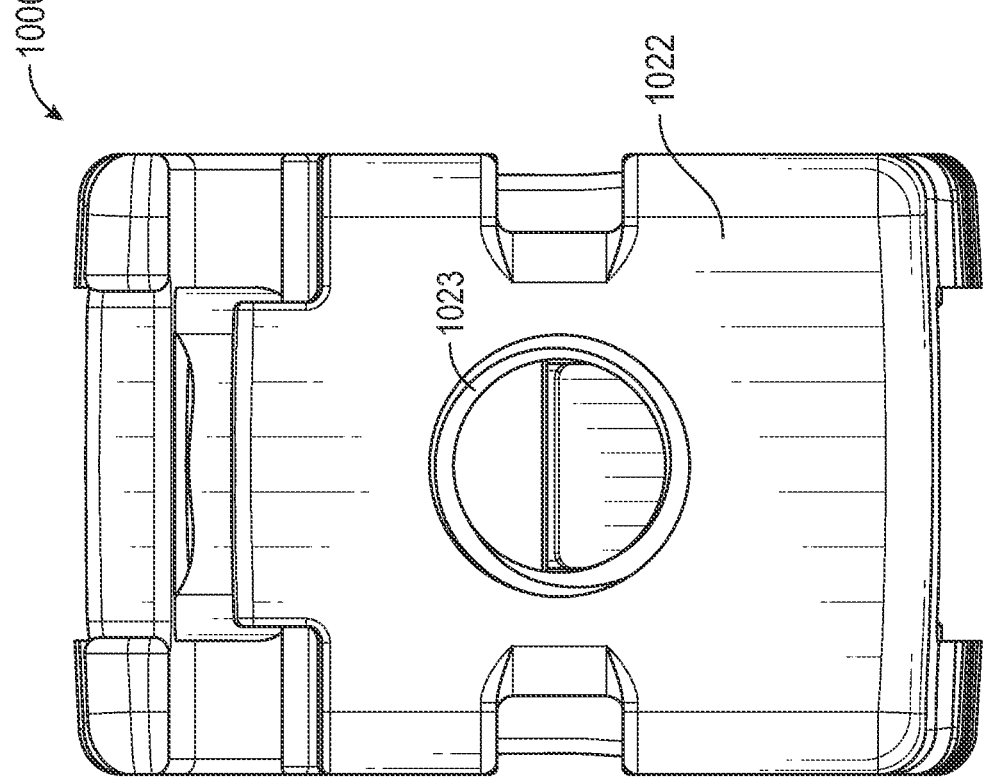
FIG. 73 is a proximal view of the spinal implant device of FIG. 71.

FIG. 73 is a proximal view of the spinal implant device 1000. The spinal implant device 1000 can include a proximal end 1022. In some embodiments, the proximal end 1022 can include an opening 1023 to couple to an insertion tool.

Figure 74:
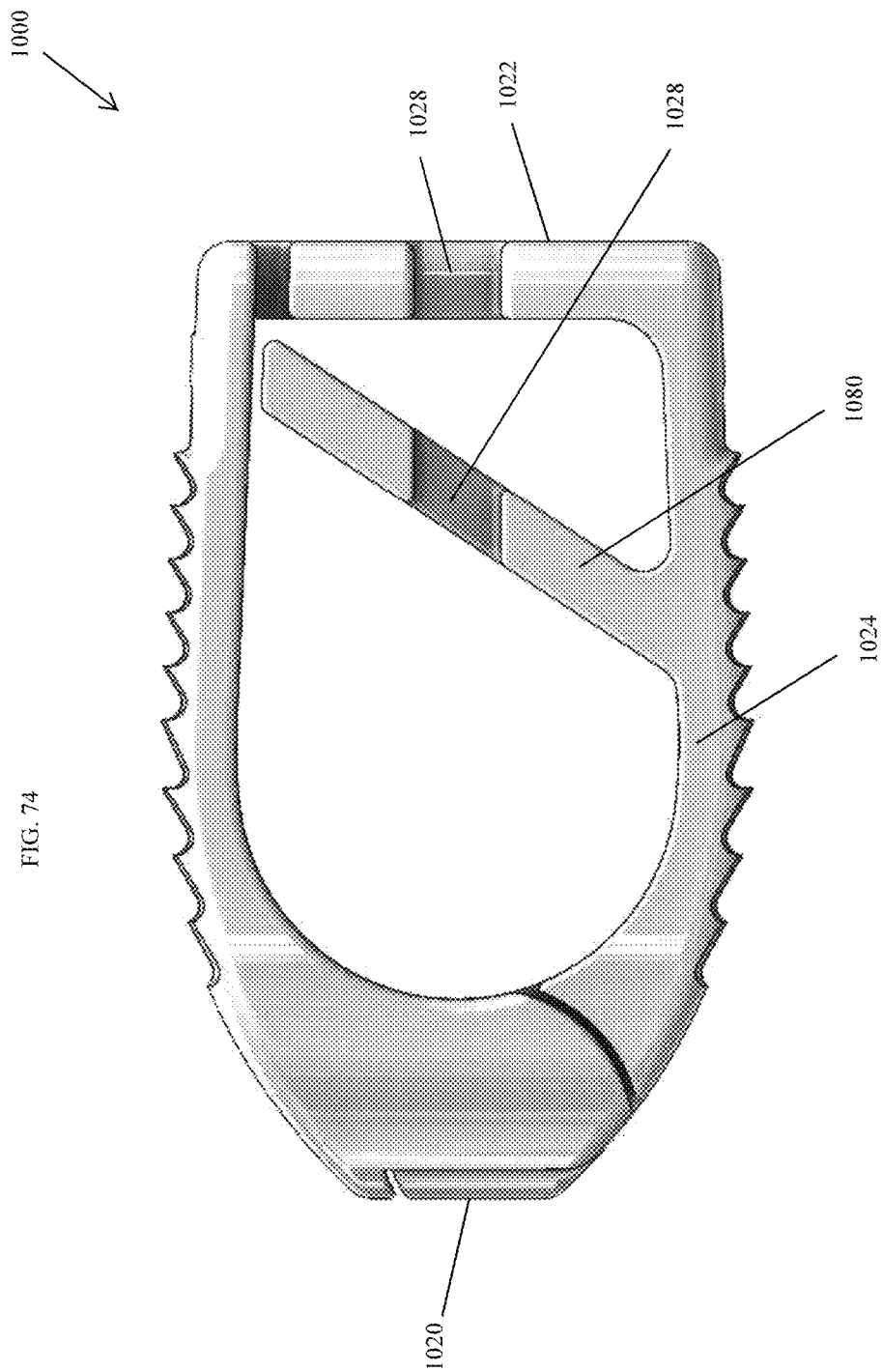
FIG. 74 is a side view of the spinal implant device of FIG. 71.

FIG. 74 is a side view of the spinal implant device 1000. The length of the spinal implant device 1000 can be the distance between the distal end 1020 and the proximal end 1022. The distal end 1020 can form the leading end and the proximal end 1022 can form the trailing end. The spinal implant device 1000 can include two opposing side walls including a first side wall 1024 and a second side wall 1026. FIG. 74 illustrates the first side wall 1024, but the second side wall 1026 can include the same or similar features. In some embodiments, each side wall 1024, 1026 can include thicker edges surrounding an open window 1016. In some embodiments, the open structure of the body 1012 can allow for compression of the body 1012.

The spinal implant device 1000 can include a connecting bar 1080. The connecting bar 1080 can include a first portion, a second portion, and third portion. The first portion of the connecting bar 1080 can extend along the first side wall 1024. The first portion of the connecting bar 1080 can have the same thickness of the first side wall 1024. The first portion of the connecting bar 1080 can be angled upward toward the proximal end 1022. The first portion of the connecting bar 1080 can be coplanar with the first side wall 1024. The second portion of the connecting bar 1080 can extend along the second side wall 1026. The second portion of the connecting bar 1080 can have the same thickness of the second side wall 1026. The second portion of the connecting bar 1080 can be angled upward toward the proximal end 1022. The second portion of the connecting bar 1080 can be coplanar with the second side wall 1026. The third portion of the connecting bar 1080 can extend between the first portion of the connecting bar 1080 and the second portion of the connecting bar 1080. The connecting bar 1080 can extend along the width of the spinal implant device 1000. The connecting bar 1080 can have a U shaped configuration. In some embodiments, the connecting bar 1080 is connected between the first side wall 1024 and the second side wall 1026. In some embodiments, the connecting bar 1080 is not connected between the first side wall 1024 and the second side wall 1026.

In some embodiments, each of the two opposing side walls 1024, 1026 can include a feature 1028 to facilitate placement of the spinal implant device 1000. In some embodiments, the feature 1028 can include a channel to accept an insertion tool. In some embodiments, the feature 1028 can extend from the proximal end 1022 of the spinal implant device 1000 toward the distal end 1020. In some embodiments, the feature 1028 can form a groove in the proximal end 1022.

In some embodiments, the connecting bar 1080 can include the feature 1028 to facilitate placement of the spinal implant device 1000. In some embodiments, the feature 1028 can include a channel to accept an insertion tool. In some embodiments, the first portion of the connecting bar 1080 can include the feature 1028. In some embodiments, the second portion of the connecting bar 1080 can include the feature 1028.

Figure 75:
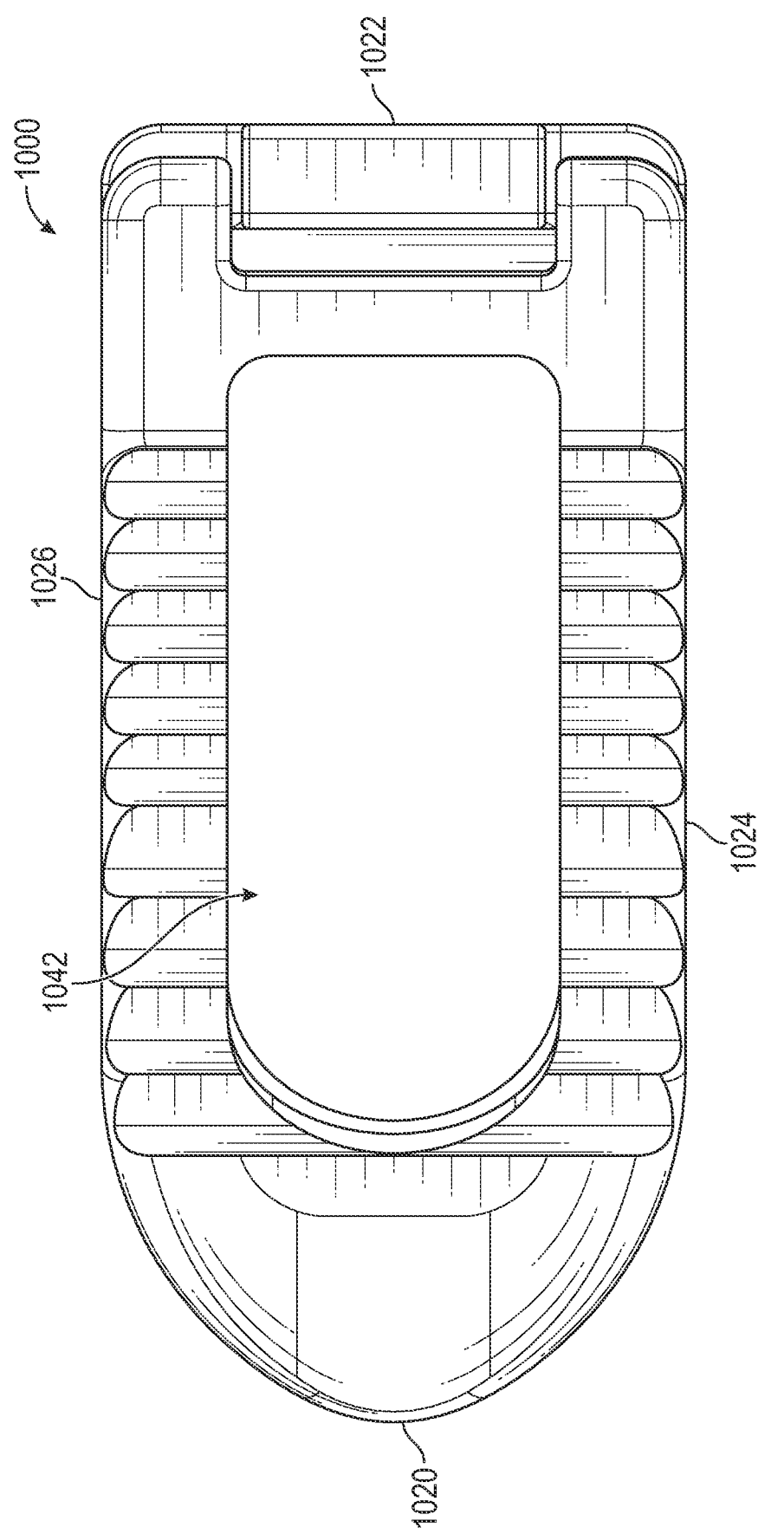
FIG. 75 is a top view of the spinal implant device of FIG. 71.
Figure 76:
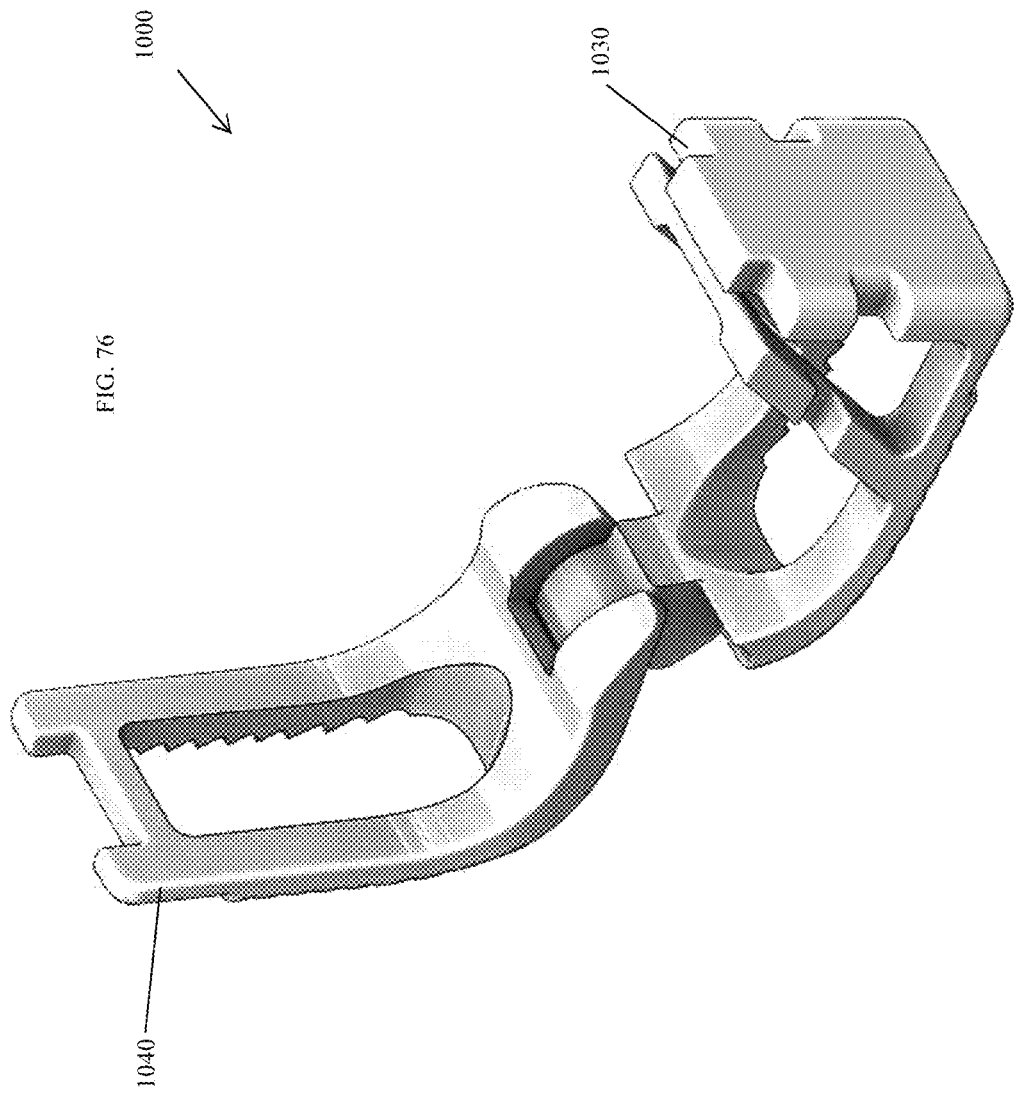
FIG. 76 is a top perspective view of the spinal implant device of FIG. 71 with the movable lid shown in an opened position.

FIG. 75 is a top view of the spinal implant device 1000. The spinal implant device 1000 can include a movable lid 1040. FIG. 75 is a top view of the spinal implant device 1000 with the movable lid 1040 in a closed position. FIG. 76 is a top perspective view of the spinal implant device 1000 with the movable lid 1040 in an opened position. The movable lid 1040 can be configured to pivot 1 degree, 2 degrees, 3 degrees, 4 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 120 degrees, 150 degrees, 180 degrees, 210 degrees, 240 degrees, 270 degrees, or any range including and between any of the foregoing values. The movable lid 1040 can be configured to pivot between 180 degrees and 210 degrees. The movable lid 1040 can pivot rest on the same horizontal surface as the bottom surface of the spinal implant device.

The spinal implant device 1000 can include one or more openings 1042 extending through the movable lid 1040. In some embodiments, the movable lid includes one elongate opening 1042.

The spinal implant device 1000 can include an upper wall 1030. The upper wall 1030 can include a portion near the distal end 1020 and a portion near the proximal end 1022. In some embodiments, a portion of the upper wall 1030 is lower than another surface of the upper wall 1030. In some embodiments, a portion of the upper wall 1030 is lower near the distal end 1020 than the proximal end 1022. In some embodiments, a portion of the upper wall 1030 near the proximal end 1022 is planar or substantially planar. In some embodiments, the upper wall 1030 forms a ledge to support the movable lid 1040 near the proximal end 1022. In some embodiments, a portion of the upper wall 1030 near the distal end 1020 is curved. In some embodiments, the upper wall 1030 forms a ledge to support the movable lid 1040 near the distal end 1020. In some embodiments, the upper wall 1030 forms a support surface or stop for the movable lid 1040 under greater than normal anatomical loads.

In some embodiments, the movable lid 1040 is separated in height from a portion of the body structure 1012 in a closed position. In some embodiments, the movable lid 1040 is separated in height from the upper wall 1030 near the proximal end 1022 in a closed position. The spinal implant device 1000 can have one or more closed positions. FIG. 74 illustrates a closed position. The spinal implant device 1000 can be packed with material and inserted in this closed position. The spinal implant device 100 can have load applied by the vertebra. In some embodiments, the application of load applied by the vertebra makes the movable lid 1040 contact the connecting bar 1080. In some embodiments, the application of load creates a second closed position. In some embodiments, the application of the normal anatomical load applied by the vertebra makes the movable lid 1040 contact the connecting bar 1080. The movable lid 1040 can hover over the connecting bar 1080 until application of a load within the ranges described herein. In some embodiments, the application of a greater than normal anatomical load applied by the vertebra makes the movable lid 1040 contact the upper wall 1030 near the proximal end 1022. In some embodiments, the application of a normal anatomical load applied by the vertebra makes the connecting bar 1080 flex. In some embodiments, the movable lid 1040 flexes. In some embodiments, until a load is applied and the movable lid 1040 is flexed, the movable lid 1040 does not contact the connecting bar 1080. In some embodiments, the flexibility of the design is what makes the movable lid 1040 contact the connecting bar 1080. In some embodiments, the connecting bar 1080 supports the movable lid 1040 along the side walls 1024, 1026 under the application of load. In some embodiments, the connecting bar 1080 supports the movable lid 1040 closer to the proximal end 1022 than the distal end 1020 under the application of load. In some embodiments, the connecting bar 1080 supports the movable lid 1040 under normal anatomical loads. In some embodiments, the connecting bar 1080 flexes such that the movable lid 1040 contacts the upper wall 1030 near the proximal end 1022 under the application of increased load. In some embodiments, the connecting bar 1080 flexes when the movable lid 1040 has contacted the connecting bar 1080. In some embodiments, the connecting bar 1080 flexes such that the movable lid 1040 moves toward the upper wall 1030 near the proximal end 1022. In some embodiments, the movable lid 1040 does not contact the upper wall 1030 near the proximal end 1022 under normal anatomical loads, only under increased loads. In some embodiments, the movable lid 1040 contacts the upper wall 1030 near the proximal end 1022 under greater than normal anatomical loads.

The upper wall 1030 can include a projection near the proximal end 1022. In some embodiments, the projection of the upper wall 1030 is higher than another surface of the upper wall 1030. In some embodiments, the projection of the upper wall 1030 extends between portions of the movable lid 1040. The projection of the upper wall 1030 can align the movable lid 1040. In some embodiments, the projection of the upper wall 1030 extends upward from the opening 1023.

In some embodiments, the movable lid 1040 can form the upper surface of the spinal implant device 1000 configured to contact the vertebral end plate. The movable lid 1040 can abut the connecting bar 1080 when the movable lid 1040 is under load. In some embodiments, the movable lid 1040 can provide a load supporting surface for the adjacent vertebrae. In some methods, the load can be transferred from the movable lid 1040 to the connecting bar 1080. In some methods, the movable lid 1040 can be positioned adjacent to a vertebral end plate of a superior vertebra.

Figure 77:
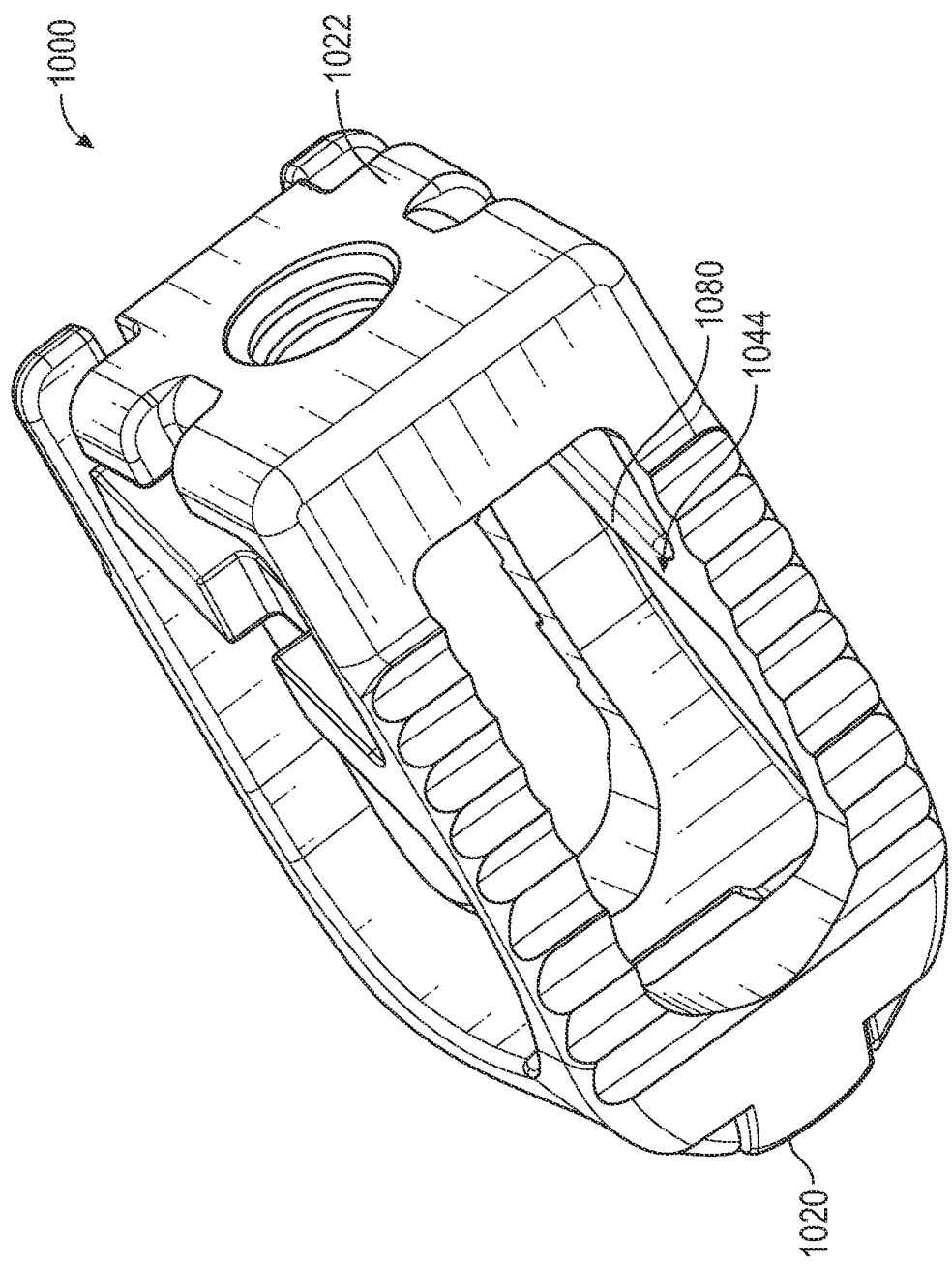
FIG. 77 is a bottom perspective view of the spinal implant device of FIG. 71.

FIG. 77 is a bottom perspective view of the spinal implant device 1000. The spinal implant device 1000 can include a lower wall 1032. The lower wall 1032 can span between the distal end 1020 and the proximal end 1022. The spinal implant device 1000 can include one or more openings 1044 extending through the lower wall 1032. The opening 1044 can be an elongate opening. The openings 1042, 1044 can have the same or similar shape. The openings 1042, 1044 can be diametrically opposed. The openings 1042, 1044 can have different shapes.

The lower wall 1032 can provide a load supporting surface. In some methods, the lower wall 1032 can be positioned adjacent to a vertebral end plate of an inferior vertebra. In some methods, when the spinal implant device 1000 is positioned between two adjacent vertebrae, the load supporting surfaces of the movable lid 1040 and the lower wall 1032 contact the vertebral end plates of the adjacent vertebrae. In some embodiments, the distance between the movable lid 1040 and the lower wall 1032 can form the height of the spinal implant device 1000.

In some embodiments, the spinal implant device 1000 can include features to limit or reduce movement of the spinal implant device 1000 between the vertebrae. The spinal implant device 1000 can include a plurality of ridges 1014. The ridges 1014 can be formed along a portion of the movable lid 1040. The ridges 1014 can be formed along a portion of the lower wall 1032. In some embodiments, the ridges 1014 are positioned on the upper surface of the spinal implant device 1000, the lower surface of the spinal implant device 1000, or both the upper surface and the lower surface of the spinal implant device 1000. In some embodiments, the ridges 1014 can be directionally oriented as described herein.

Figure 78:
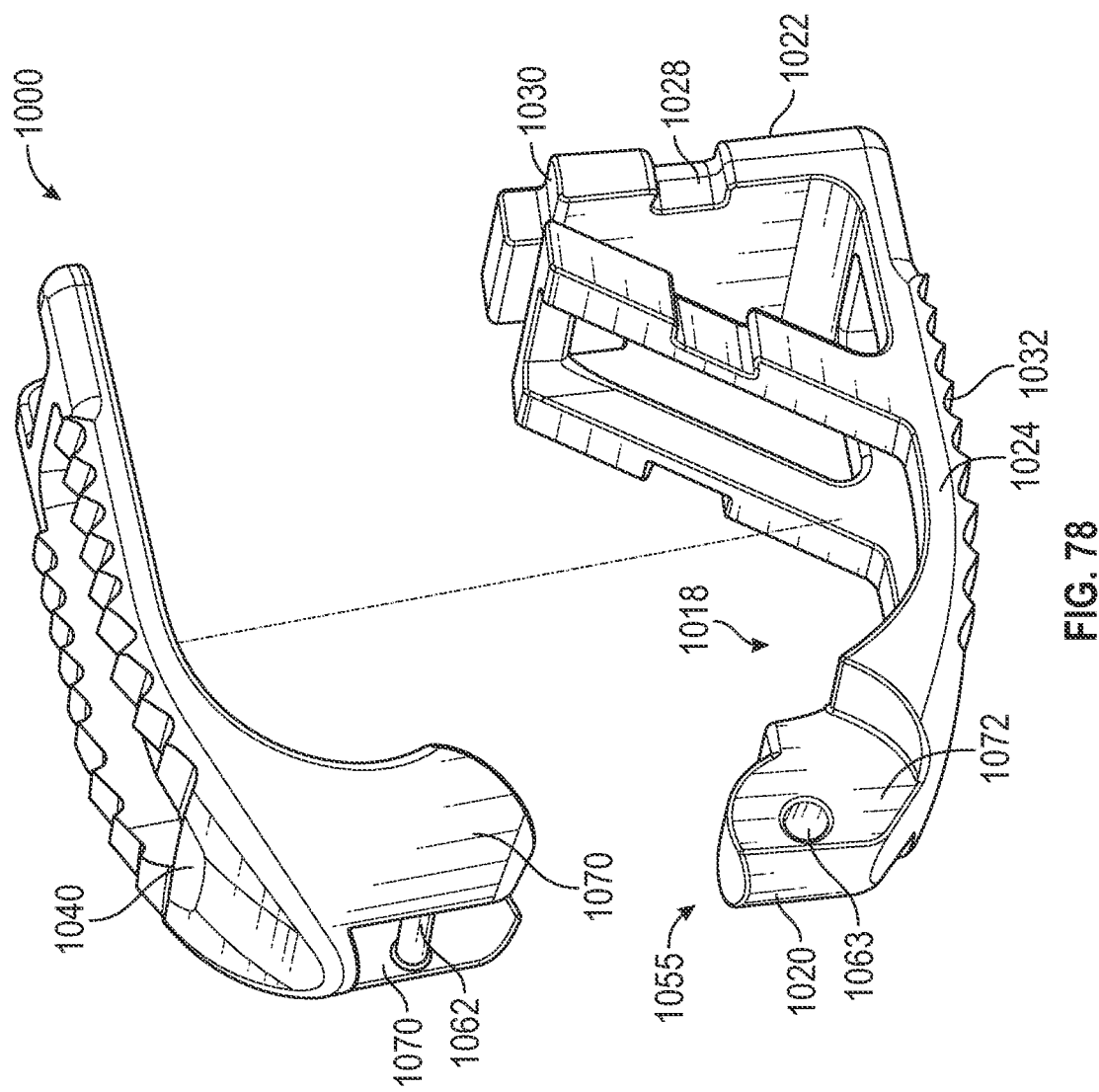
FIG. 78 is an exploded perspective view of the spinal implant device of FIG. 71.

FIG. 78 is an exploded view of the movable lid 1040 of the spinal implant device 1000. In some embodiments, the movable lid 1040 can be coupled to the distal end 1020. The distal end 1020 can include a central post 1072. The central post 1072 can extend upward from a portion of the upper wall 1030 near the distal end 1020. In some embodiments, the upper wall 1030 is recessed relative to the central post 1072 to accommodate the movable lid 1040. The central post 1072 can extend along a portion of the width of the spinal implant device 1000. The central post 1072 can be centrally located along the longitudinal axis of the spinal implant device 1000.

In some embodiments, the spinal implant device 1000 can include a movable joint 1055. In some embodiments, the movable joint 1055 can couple the movable lid 1040 to the distal end 1020. The movable joint 1055 can couple the movable lid 1040 with any portion of the body structure 1012. The movable joint 1055 can allow for pivoting motion of the movable lid 1040. In some embodiments, the movable joint 1055 can include one axis of rotation. In some embodiments, the movable joint 1055 can include more than one axis of rotation.

In some embodiments, the movable lid 1040 can include one or more articulations 1062. The one or more articulations 1062 can extend between two opposing lateral posts 1070 of the movable lid 1040. The articulation 1062 can be an axle. The articulation 1062 can be a pivot pin. The articulation 1062 can be any structure about which the movable lid 1040 can rotate. The articulation 1062 can be perpendicular to the longitudinal axis of the spinal implant device 1000. The articulation 1062 can extend across the width of the spinal implant device 1000, or a portion thereof.

The central post 1072 can include one or more lumens 1063 configured to engage the one or more articulations 1062. The lumen 1063 can be perpendicular to the longitudinal axis of the spinal implant device 1000. The central post 1072 can include the lumen 1063 sized to accept an articulation 862.

In some embodiments, the movable lid 1040 is generally U shaped. In some embodiments, the movable lid 1040 is generally H shaped. In some embodiments, the movable lid 1040 comprises a top portion. In some embodiments, the top portion accommodates the central post 1072 near the distal end of the movable lid 1040. In some embodiments, the top portion accommodates the projection of the upper wall 1030 near the proximal end of the movable lid 1040. In some embodiments, the projection and the central post 1072 have the same width. In some embodiments, the projection and the central post 1072 have different widths.

The spinal implant device 1000 can include a cavity 1018. In some embodiments, the proximal end 1022 can define the back inner surface of the cavity 1018. In some embodiments, the distal end 1020 can define the front inner surface of the cavity 1018. In some embodiments, the two opposing side walls 1024, 1026 and the first and second portions of the connecting bar 1080 can define the side inner surfaces of the cavity 1018. In some embodiments, the movable lid 1040 can define the top inner surface of the cavity 1018. In some embodiments, the lower wall 1032 can define the bottom inner surface of the cavity 1018. In some embodiments, the cavity 1018 is partially enclosed. The cavity 1018 can be a contained space within the spinal implant device 1000. In some embodiments, the cavity 1018 comprises a portion of the volume of the spinal implant device 1000 (e.g., 50% of the volume, 60% of the volume, 70% of the volume, 80% of the volume, 90% of the volume, or 100% of the volume, or any range including and between any of the foregoing values).

In some methods of use, the connecting bar 1080 supports the movable lid 1040 along the side walls 1024, 1026. The connecting bar 1080 can have a surface at a greater height than a ledge of the upper wall 1030. The movable lid 1040 can be disposed a distance from the upper wall 1030 near the proximal end 1022 during insertion of the spinal implant device 1000. The movable lid 1040 can be disposed at a distance from the upper wall 1030 near the proximal end 1022 under normal anatomic loads.

In some embodiments, the connecting bar 1080 can flex toward the proximal end 1022 after insertion of the spinal implant device 1000. In some embodiments, the connecting bar 1080 can flex under load from the vertebral end plates. In some embodiments, the connecting bar 1080 can flex when the vertebrae apply a load. The movable lid 1040 can move downward upon flexing of the connecting bar 1080. The movable lid 1040 can move toward the upper wall 1030 near the proximal end 1022. In some embodiments, the movable lid 1040 hovers over the upper wall 1030 near the proximal end 1022. In some embodiments, the movable lid 1040 can abut the upper wall 1030 near the proximal end 1022. The movable lid 1040 can compress material within the cavity 1018.

Figure 79:
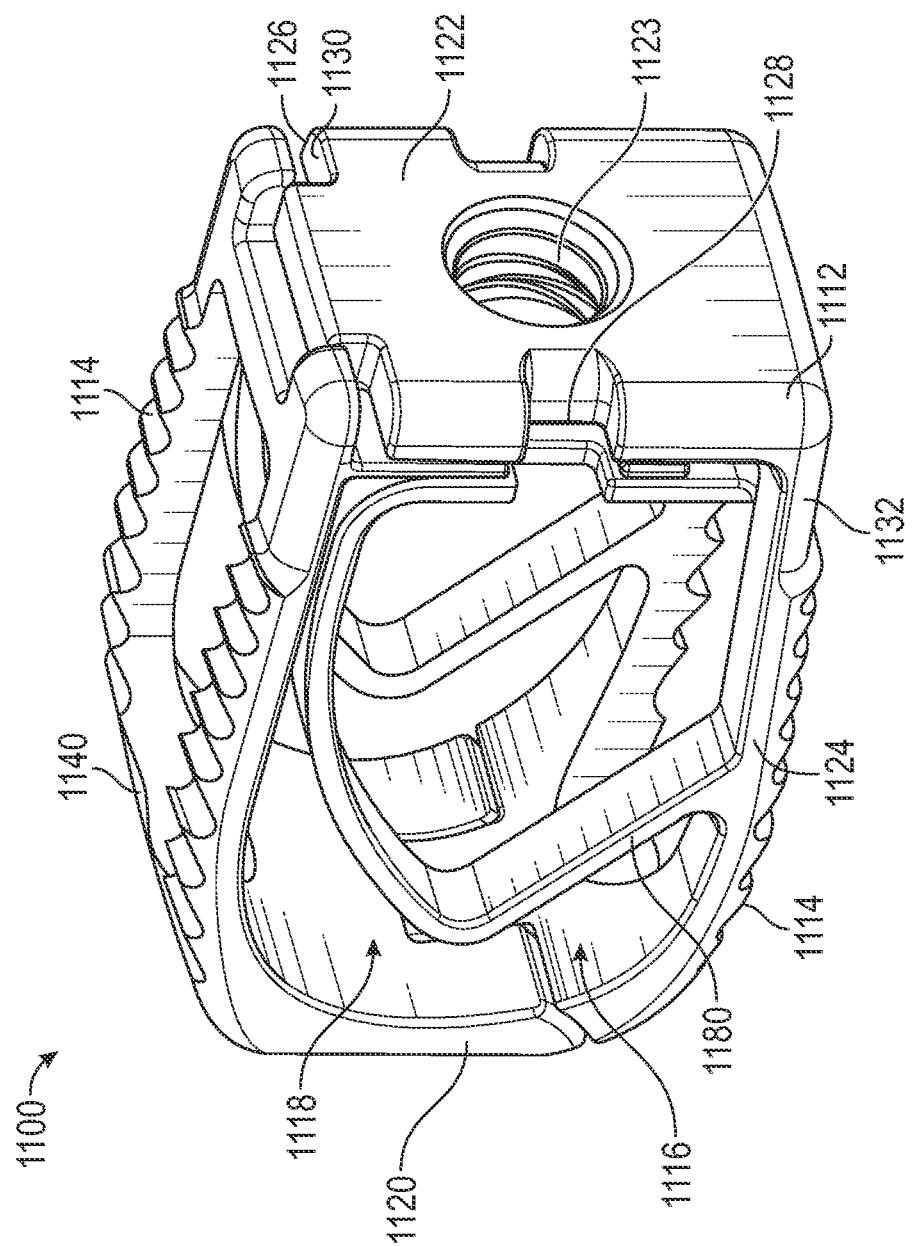
FIG. 79 is a perspective view of an embodiment of a spinal implant device with a movable lid shown in a closed position.

FIG. 79 illustrates a perspective view of a spinal implant device 1100. The spinal implant device 1100 can include any of the features of the spinal implant device 10, 10A, 100, 200, 300, 400, 500, 600, 700, 800, 900, 1000 as described herein and can be used in any method or method step described herein. The spinal implant device 1100 can include a body structure 1112. The body structure 1112 can includes features to allow a predetermined amount of compression. The body structure 1112 can includes features configured to compress a predetermined maximum distance.

As described herein, the spinal implant device 1100 can compress along the height of the spinal implant device 1100. The compression can promote fusion.

Figure 80:
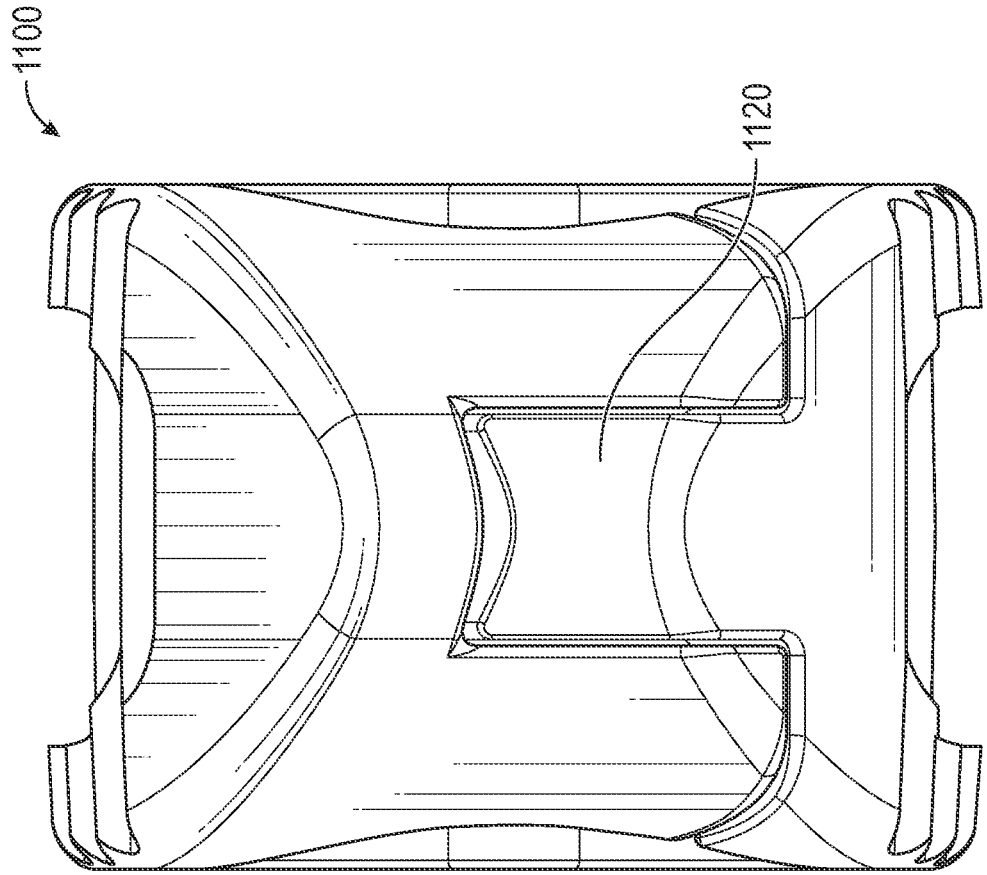
FIG. 80 is a distal view of the spinal implant device of FIG. 79.

FIG. 80 is a distal view of the spinal implant device 1100. The spinal implant device 1100 can include a distal end 1120. In some methods of use, the distal end 1120 can be the insertion end.

Figure 81:
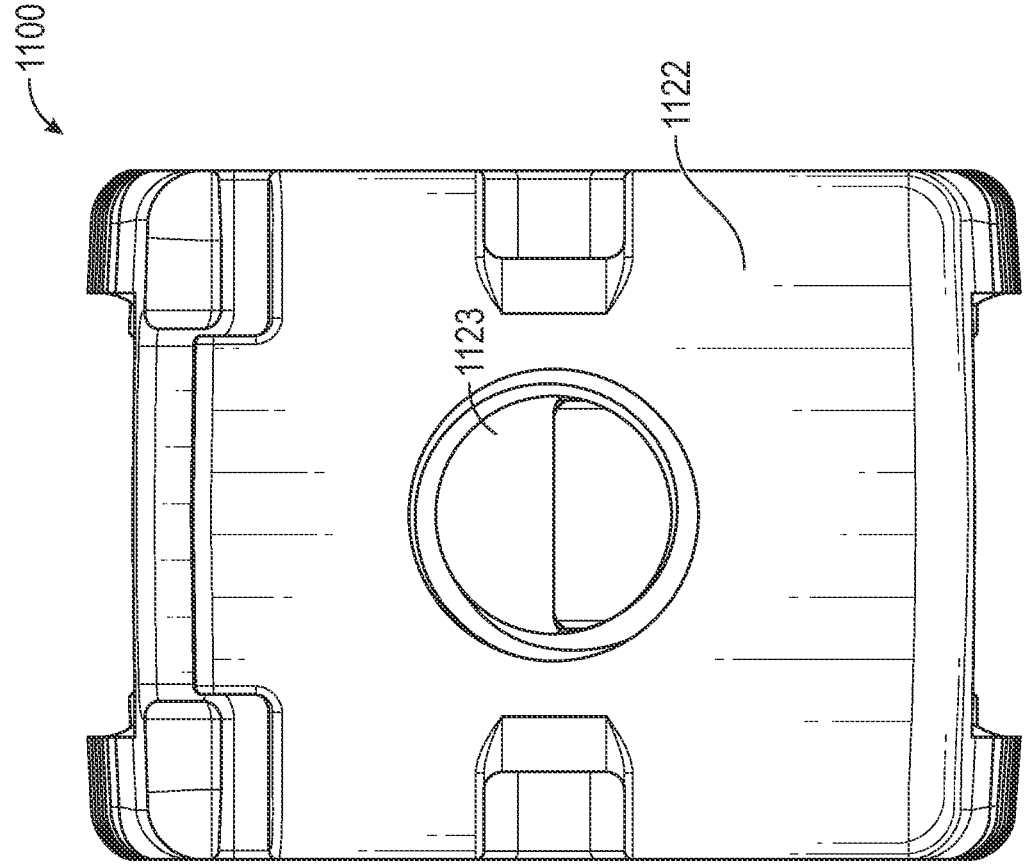
FIG. 81 is a proximal view of the spinal implant device of FIG. 79.

FIG. 81 is a proximal view of the spinal implant device 1100. The spinal implant device 1100 can include a proximal end 1122. In some embodiments, the proximal end 1122 can include an opening 1123 to couple to an insertion tool.

Figure 82:
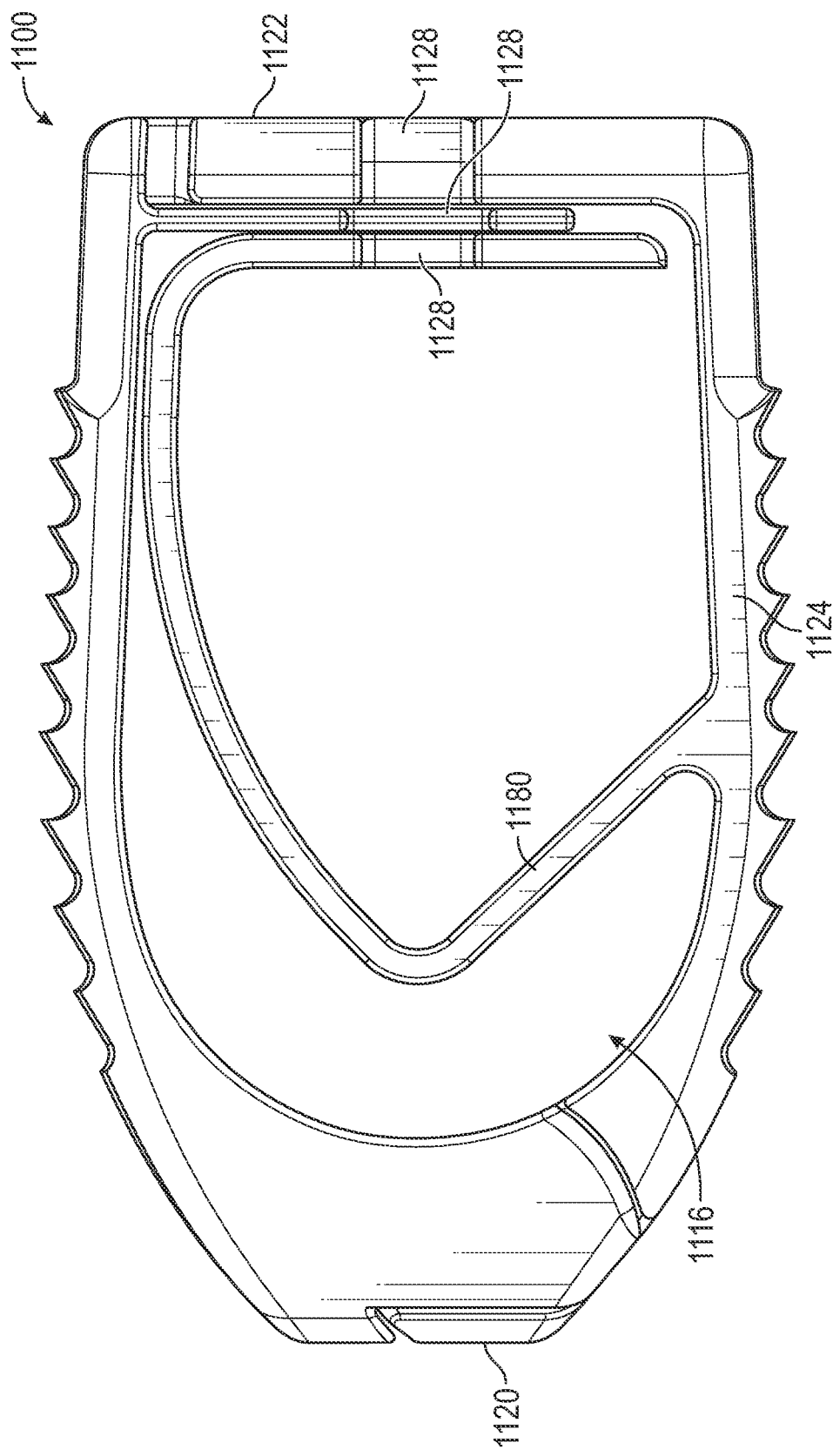
FIG. 82 is a side view of the spinal implant device of FIG. 79.

FIG. 82 is a side view of the spinal implant device 1100. The length of the spinal implant device 1100 can be the distance between the distal end 1120 and the proximal end 1122. The distal end 1120 can form the leading end and the proximal end 1122 can form the trailing end. The spinal implant device 1100 can include two opposing side walls including a first side wall 1124 and a second side wall 1126. FIG. 82 illustrates the first side wall 1124, but the second side wall 1126 can include the same or similar features. In some embodiments, each side wall 1124, 1126 can include thicker edges surrounding an open window 1116.

The spinal implant device 1100 can include a connecting bar 1180. The connecting bar 1180 can include a first portion, a second portion, a third portion, a fourth portion, and a fifth portion. The first portion of the connecting bar 1180 can extend along the first side wall 1124. The first portion of the connecting bar 1180 can have the same thickness of the first side wall 1124. The first portion of the connecting bar 1180 can be angled upward toward the distal end 1120. The connecting bar 1180 can include a bend between the first portion and the second portion. The second portion of the connecting bar 1180 can be angled upward toward the proximal end 1122. The first portion and the second portion of the connecting bar 1180 can have a generally V shape along the first side wall 1124. The first portion and the second portion of the connecting bar 1180 can be pointed toward the distal end 1120. The first portion and the second portion of the connecting bar 1180 can be coplanar with the first side wall 1124.

The third portion of the connecting bar 1180 can extend along the second side wall 1126. The third portion of the connecting bar 1180 can have the same thickness of the second side wall 1126. The third portion of the connecting bar 1180 can be angled upward toward the distal end 1120. The connecting bar 1180 can include a bend between the third portion and the fourth portion. The fourth portion of the connecting bar 1180 can be angled upward toward the proximal end 1122. The third portion and the fourth portion of the connecting bar 1180 can have a generally V shape along the second side wall 1126. The third portion and the fourth portion of the connecting bar 1180 can be pointed toward the distal end 1120. The third portion and the fourth portion of the connecting bar 1180 can be coplanar with the second side wall 1126.

The fifth portion of the connecting bar 1180 can extend between the first side wall 1124 and the second side wall 1126. The fifth portion of the connecting bar 1180 can extend along the width of the spinal implant device 1100. The fifth portion of the connecting bar 1180 can be coplanar with the proximal end 1122. The fifth portion of the connecting bar 1180 can be adjacent to the proximal end 1122. The fifth portion of the connecting bar 1180 can extend along the height of the spinal implant device 1100, or a portion thereof. The fifth portion of the connecting bar 1180 can include a predetermined distance offset from an inner surface of the spinal implant device 1100. This predetermined distance can be equal to the maximum compression of the spinal implant device 1100. In some embodiments, the connecting bar 1180 is connected between the first side wall 1124 and the second side wall 1126. In some embodiments, the connecting bar 1180 is not connected between the first side wall 1124 and the second side wall 1126.

In some embodiments, each of the two opposing side walls 1124, 1126 can include a feature 1128 to facilitate placement of the spinal implant device 1100. In some embodiments, the feature 1128 can include a channel to accept an insertion tool. In some embodiments, the feature 1128 can extend from the proximal end 1122 of the spinal implant device 1100 toward the distal end 1120. In some embodiments, the feature 1128 can form a groove in the proximal end 1122.

In some embodiments, the connecting bar 1180 can include the feature 1128 to facilitate placement of the spinal implant device 1100. In some embodiments, the fifth portion of the connecting bar 1180 can include a channel to accept an insertion tool.

Figure 83:
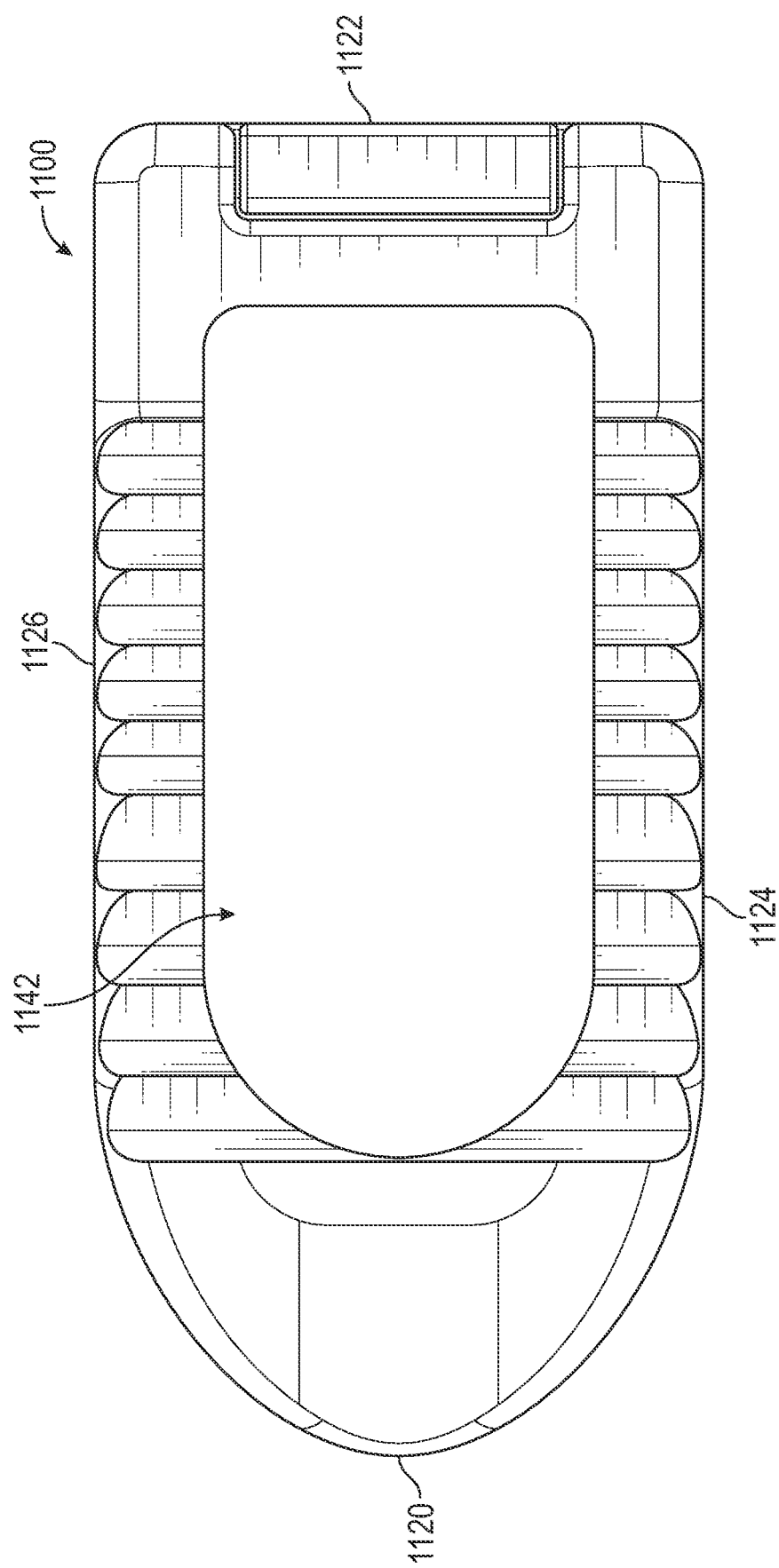
FIG. 83 is a top view of the spinal implant device of FIG. 79.
Figure 84:
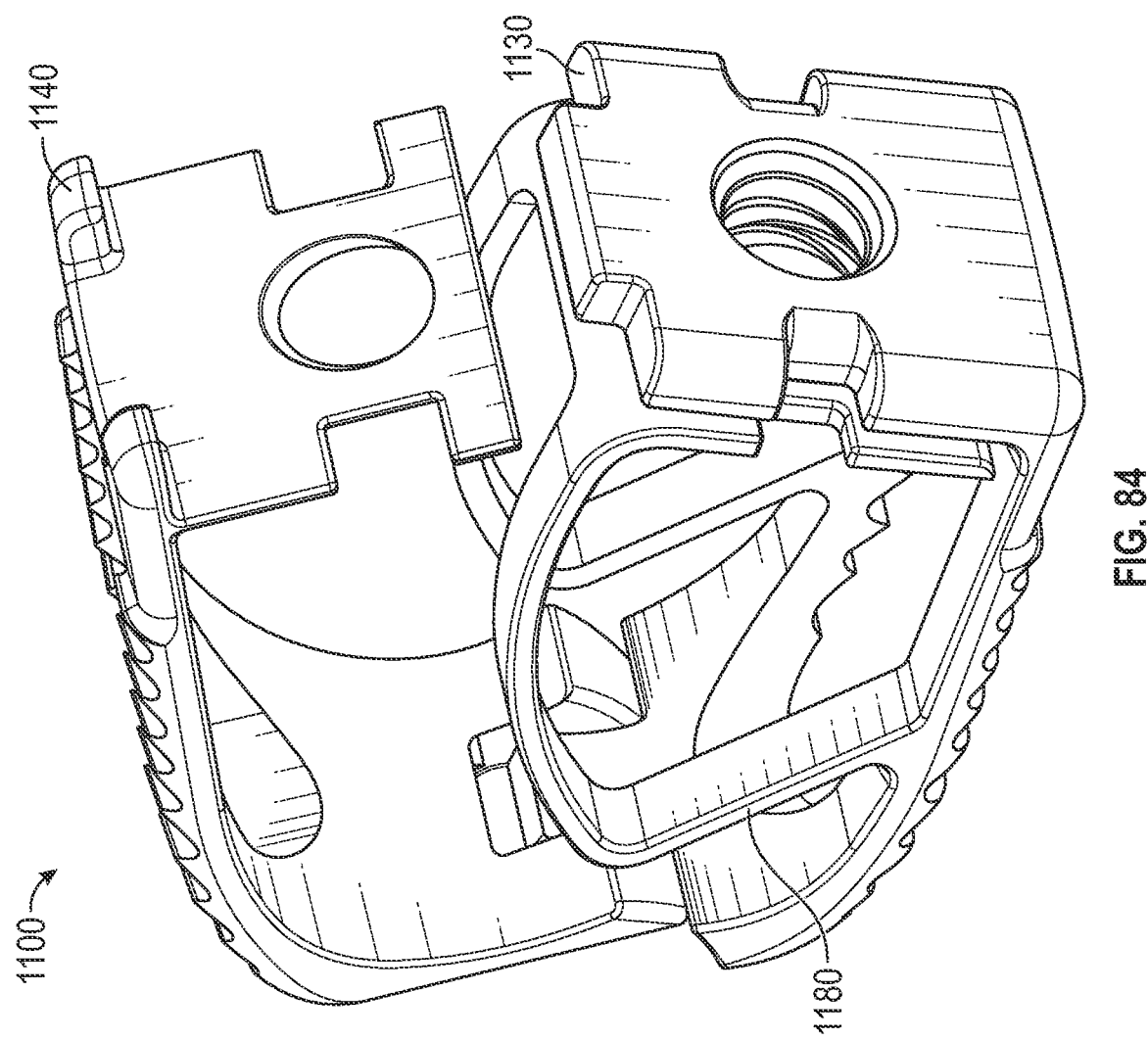
FIG. 84 is a top perspective view of the spinal implant device of FIG. 79 with the movable lid shown in an opened position.

FIG. 83 is a top view of the spinal implant device 1100. The spinal implant device 1100 can include a movable lid 1140. FIG. 83 is a top view of the spinal implant device 1100 with the movable lid 1140 closed. FIG. 84 is a top perspective view of the spinal implant device 1100 with the movable lid 1140 opened.

The spinal implant device 1100 can include one or more openings 1142 extending through the movable lid 1140. In some embodiments, the movable lid includes one elongate opening 1142.

The spinal implant device 1100 can include an upper wall 1130. The upper wall 1130 can include a portion near the distal end 1120 and a portion near the proximal end 1122. In some embodiments, the upper wall 1130 forms a ledge to prevent further compression near the proximal end 1122.

The spinal implant device 1100 can have one or more closed positions. In some embodiments, the movable lid 1140 is separated in height from the upper wall 1130 near the proximal end 1122 in a closed position. In some embodiments, the movable lid 1140 is separated in height from the connecting bar 1180 in a closed position. In some embodiments, the application of load applied by the vertebra makes the movable lid 1140 contact the connecting bar 1180. In some embodiments, the application of load creates a secondary closed position. In some embodiments, the application of a normal anatomical load applied by the vertebra makes the movable lid 1140 contact the connecting bar 1180. The movable lid 1140 can hover over the connecting bar 1180 until application of a load. In some embodiments, the application of a greater than normal anatomical load applied by the vertebra makes the movable lid 1140 move toward and, in some cases, contact the upper wall 1130 near the proximal end 1122. In some embodiments, the application of a load applied by the vertebra makes the connecting bar 1180 flex. In some embodiments, the connecting bar 1180 supports the movable lid 1140 along the side walls 1124, 1126 under the application of load. In some embodiments, the connecting bar 1180 supports the movable lid 1140 closer to the proximal end 1122 than the distal end 1120 under the application of load. In some embodiments, the connecting bar 1180 supports the movable lid 1140 under normal anatomical loads. In some embodiments, the connecting bar 1180 supports the movable lid 1140 and the movable lid 1140 hovers a distance from the upper wall 1130 near the proximal end 1120. Under larger than normal loads, the movable lid 1140 and the connecting bar 1180 can further compress until the movable lid 1140 moves towards, and in some cases, abuts the upper wall 1130 near the proximal end. In some embodiments, the connecting bar 1180 flexes if the movable lid 1140 contacts the upper wall 1130.

The upper wall 1130 can include a projection near the proximal end 1122. In some embodiments, the projection of the upper wall 1130 extends between portions of the movable lid 1140. The upper wall 1130 can help to align the movable lid 1140.

In some embodiments, at least the movable lid 1140 can form the upper surface of the spinal implant device 1100 configured to contact the vertebral end plate. In some embodiments, the movable lid 1140 can provide a load supporting surface for the adjacent vertebrae. In some methods, the load can be transferred from the movable lid 1140 to the connecting bar 1180 under normal anatomical loads. In some methods, the movable lid 1040 can be positioned adjacent to a vertebral end plate of a superior vertebra.

The movable lid 1140 can include a portion that can extend between the first side wall 1124 and the second side wall 1126. The portion of movable lid 1140 can extend along the width of the spinal implant device 1100. The portion of the movable lid 1140 can be coplanar with the proximal end 1122. The portion of the movable lid 1140 can be adjacent to the proximal end 1122 and the connecting bar 1180. The portion of the movable lid 1140 can extend along the height of the spinal implant device 1100, or a portion thereof. The portion of the movable lid 1140 can be disposed between a portion of the connecting bar 1180 and the proximal end 1122. In some embodiments, the movable lid 1140 can include a feature 1128. The portion that can extend between the first side wall 1124 and the second side wall 1126 can include the feature 1128. In some embodiments, the feature 1128 on proximal end 1122 and the feature 1128 on the movable lid 1140 can allow an insertion tool to retain the movable lid 1140 during placement or removal of spinal implant device 1100.

Figure 85:
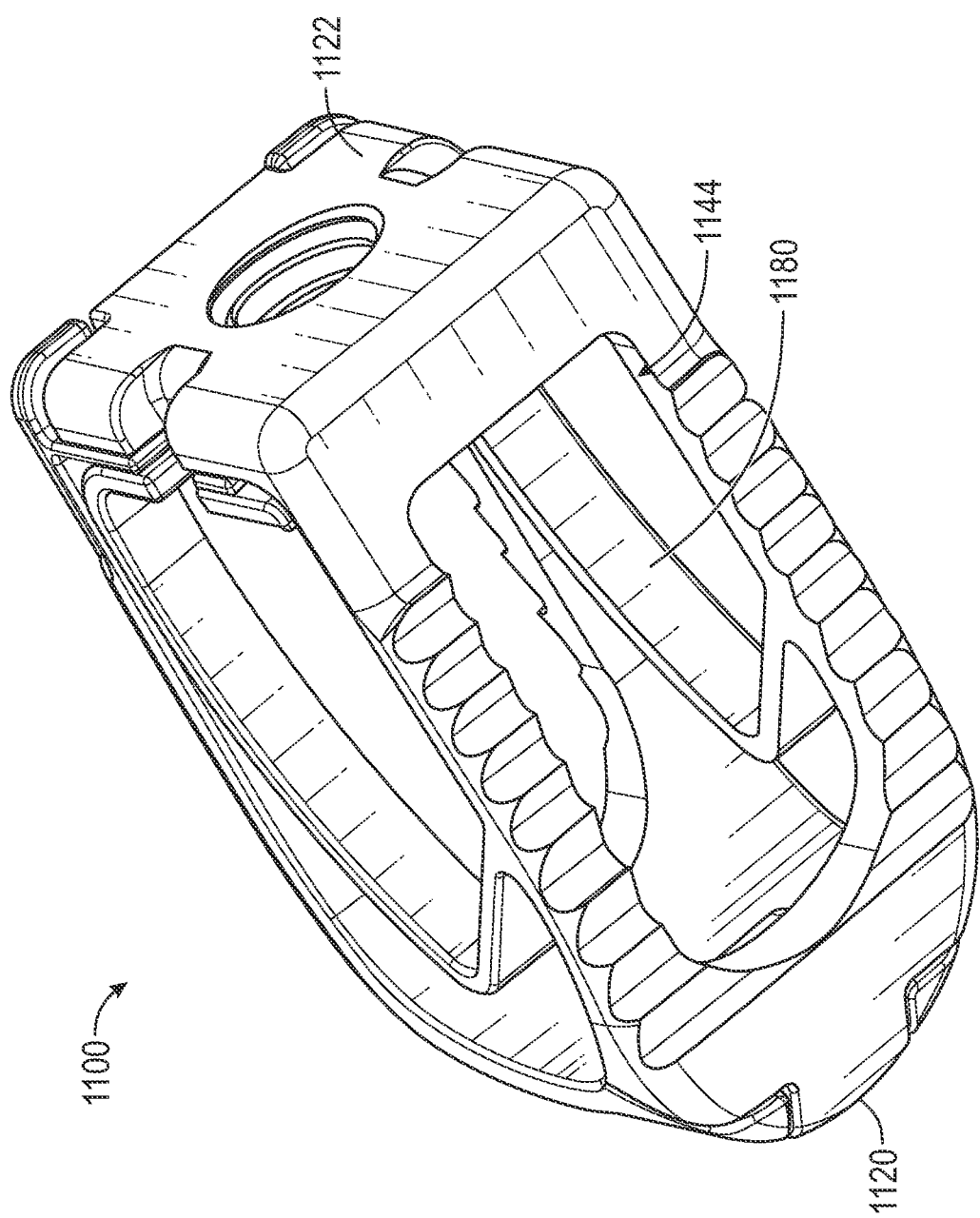
FIG. 85 is a bottom perspective view of the spinal implant device of FIG. 79.

FIG. 85 is a bottom perspective view of the spinal implant device 1100. The spinal implant device 1100 can include a lower wall 1132. The lower wall 1132 can span between the distal end 1120 and the proximal end 1122. The spinal implant device 1100 can include one or more openings 1144 extending through the lower wall 1132. The opening 1144 can be an elongate opening. The openings 1142, 1144 can have the same or similar shape. The openings 1142, 1144 can be diametrically opposed. The openings 1142, 1144 can have different shapes.

The lower wall 1132 can provide a load supporting surface. In some methods, the lower wall 1132 can be positioned adjacent to a vertebral end plate of an inferior vertebra. In some methods, when the spinal implant device 1100 is positioned between two adjacent vertebrae, the load supporting surfaces of the movable lid 1140 and the lower wall 1132 contact the vertebral end plates of the adjacent vertebrae. In some embodiments, the distance between the movable lid 1140 and the lower wall 1132 can form the height of the spinal implant device 1100.

In some embodiments, the spinal implant device 1100 can include features to limit or reduce movement of the spinal implant device 1100 between the vertebrae. The spinal implant device 1100 can include a plurality of ridges 1114. In some embodiments, the ridges 1114 are positioned on the upper surface of the spinal implant device 1100, the lower surface of the spinal implant device 1100, or both the upper surface and the lower surface of the spinal implant device 1100.

Figure 86:
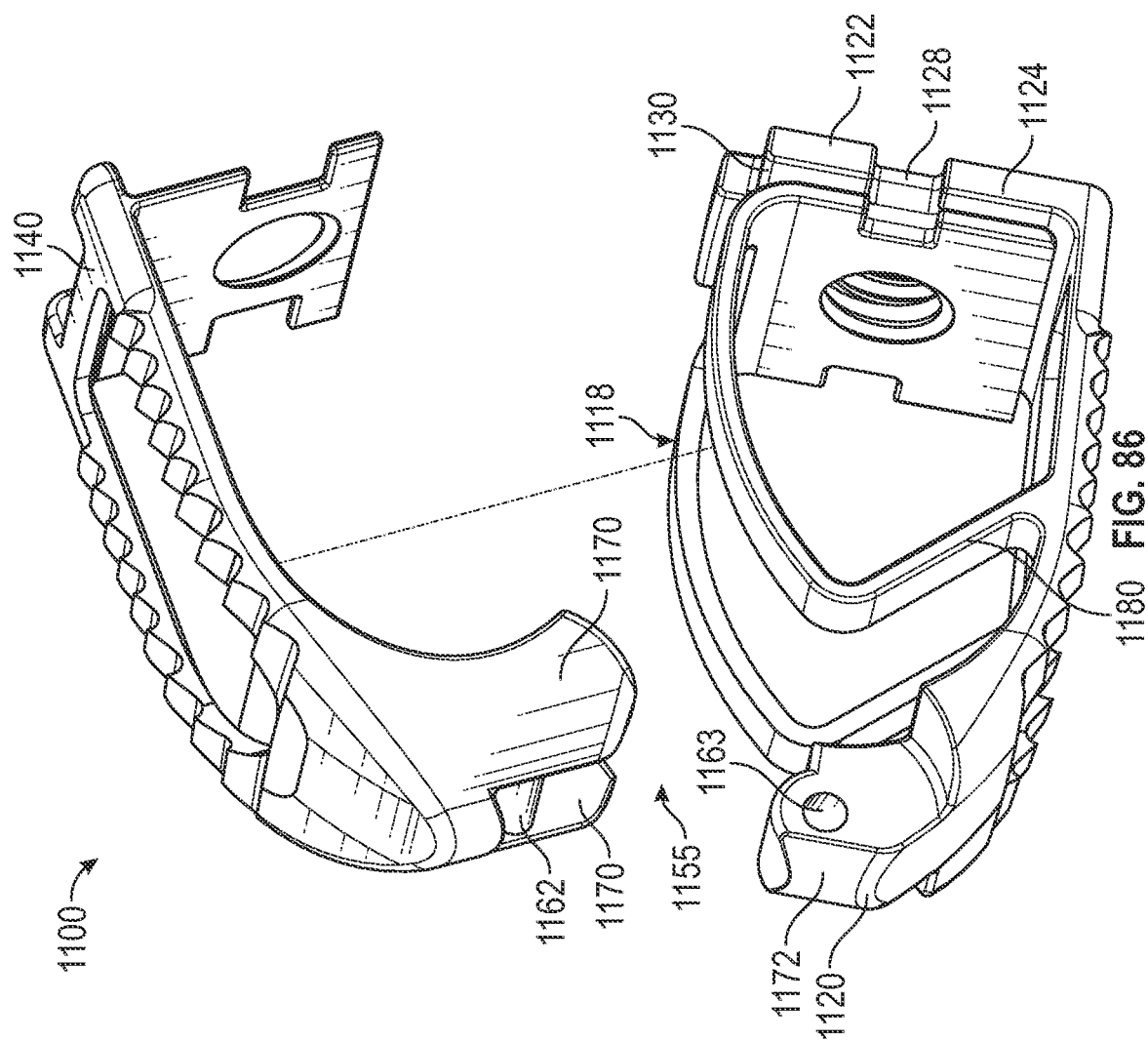
FIG. 86 is an exploded perspective view of the spinal implant device of FIG. 79.

FIG. 86 is an exploded view of the movable lid 1140 of the spinal implant device 1100. In some embodiments, the movable lid 1140 can be coupled to the distal end 1120. The distal end 1120 can include a central post 1172.

In some embodiments, the spinal implant device 1100 can include a movable joint 1155. In some embodiments, the movable joint 1155 can couple the movable lid 1140 to the distal end 1120. The movable joint 1155 can allow for pivoting motion of the movable lid 1140. The movable joint 1155 can allow for compression of the movable lid 1040.

In some embodiments, the movable lid 1140 can include one or more articulations 1162. The one or more articulations 1162 can extend between two opposing lateral posts 1170 of the movable lid 1140. The central post 1172 can include one or more lumens 1163 configured to engage the one or more articulations 1162. The lumens 1163 can be perpendicular to the longitudinal axis of the spinal implant device 1100.

The spinal implant device 1100 can include a cavity 1118. In some embodiments, the fifth portion of the connecting bar 1180 can define the back inner surface of the cavity 1118. In some embodiments, the distal end 1120 can define the front inner surface of the cavity 1118. In some embodiments, the two opposing side walls 1124, 1126, the first portion, the second portion, the third portion and the fourth portion of the connecting bar 1180 can define the side inner surfaces of the cavity 1118. In some embodiments, the movable lid 1140 can define the top inner surface of the cavity 1118. In some embodiments, the lower wall 1132 can define the bottom inner surface of the cavity 1118. In some embodiments, the cavity 1118 is partially enclosed.

The movable lid 1140 can compress under normal anatomical loads thereby decreasing the height of the spinal implant device 1100. The movable lid 1140 can move into engagement with the connecting bar 1180 near the proximal end 1122. In some methods of use, the connecting bar 1180 supports the movable lid 1140 along the side walls 1124, 1126. The connecting bar 1180 can have a surface at a greater height than a ledge of the upper wall 1130. The movable lid 1140 can be disposed a distance from the upper wall 1130 near the proximal end 1122. In some embodiments, the movable lid 1140 and the connecting bar 1180 can flex toward the lower wall 1132. In some embodiments, the movable lid 1140 and the connecting bar 1180 can flex under load from the vertebral end plates. In some embodiments, the movable lid 1140 and the connecting bar 1180 can flex when a retractor is removed. In some embodiments, the movable lid 1140 and the connecting bar 1180 can flex when the vertebrae apply a load. The movable lid 1140 can compress material within the cavity 1118 under normal anatomical loads. In some methods of use, the movable lid 1140 and the connecting bar 1180 can compress a predetermined distance. In some methods of use, the movable lid 1140 and the connecting bar 1180 can compress until the connecting bar 1180 abuts another portion of the spinal implant device 1100.

Figure 87:
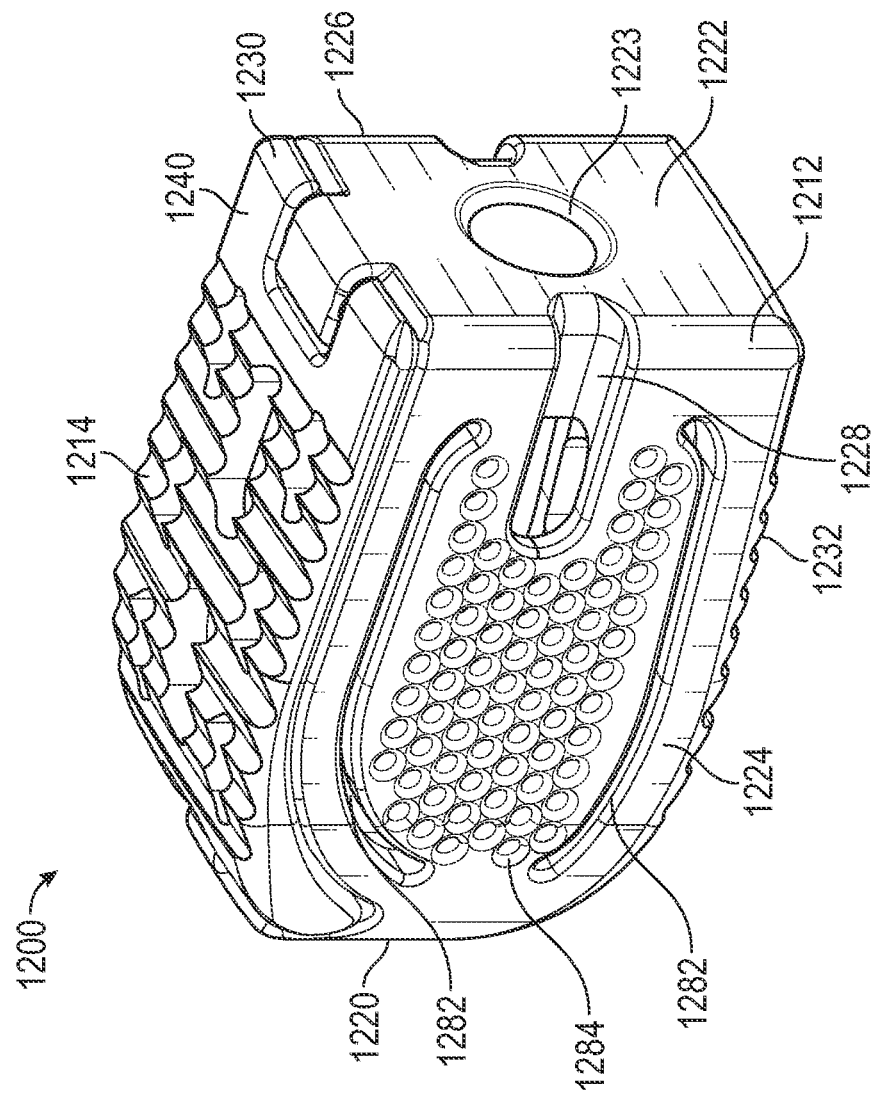
FIG. 87 is a perspective view of an embodiment of a spinal implant device with a movable lid shown in a closed position.

FIG. 87 illustrates a perspective view of a spinal implant device 1200. The spinal implant device 1200 can include any of the features of the spinal implant device 10, 10A, 100, 200, 300, 400, 500, 600, 700, 800, 900, 1000, 1100 as described herein and can be used in any method or method step described herein. The spinal implant device 1200 can include a body structure 1212. The body structure 1212 can be placed between adjacent vertebrae. The body structure 1212 can includes features to promote compression along the height of the body structure 1212. In some methods of use, the compression can promote fusion of adjacent vertebrae.

Figure 88:
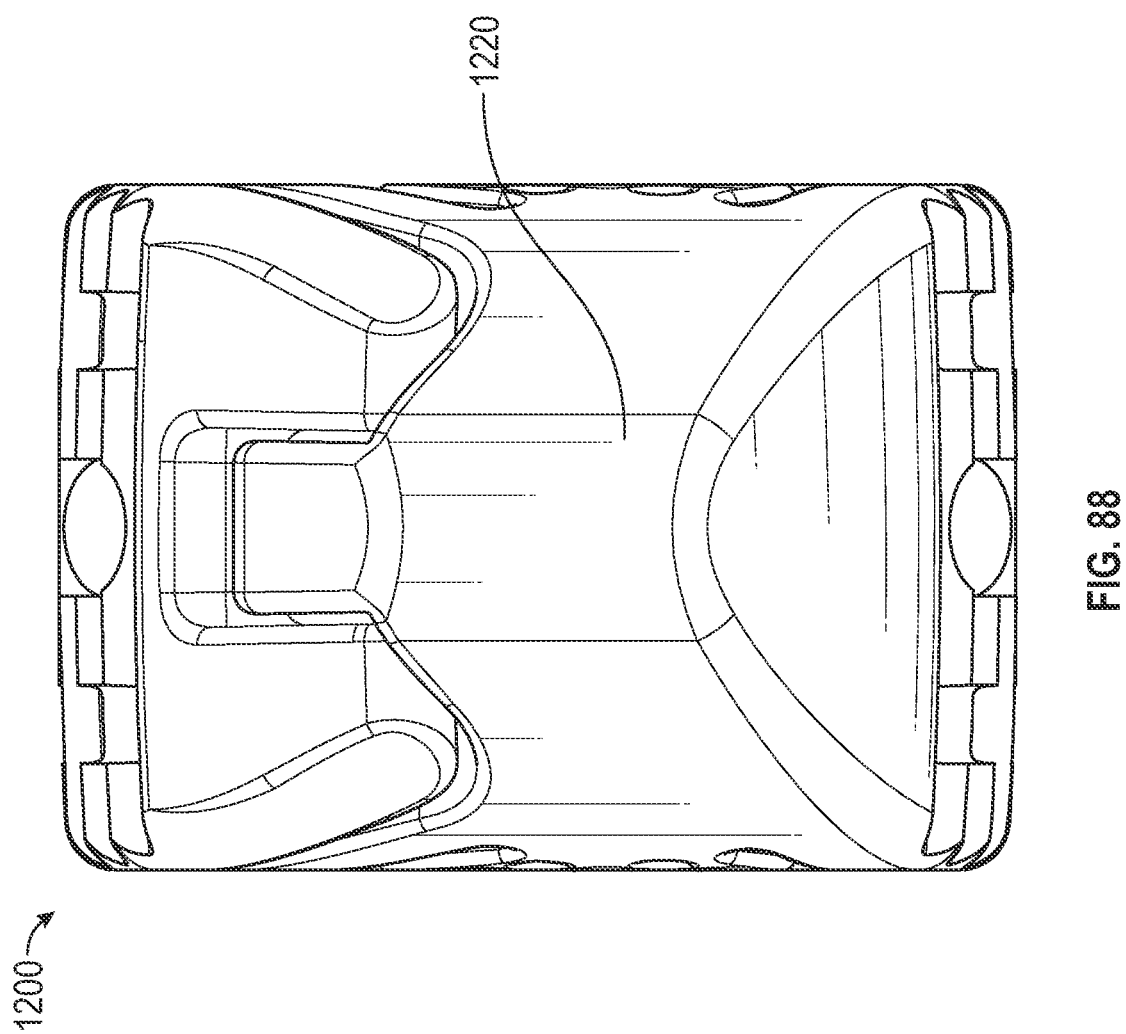
FIG. 88 is a distal view of the spinal implant device of FIG. 87.

FIG. 88 is a distal view of the spinal implant device 1200. The spinal implant device 1200 can include a distal end 1220. In some methods of use, the distal end 1220 can be the insertion end. In some embodiments, the distal end 1220 is tapered inward. The distal end 1220 can form a frustoconical or convex curved shape 1221.

Figure 89:
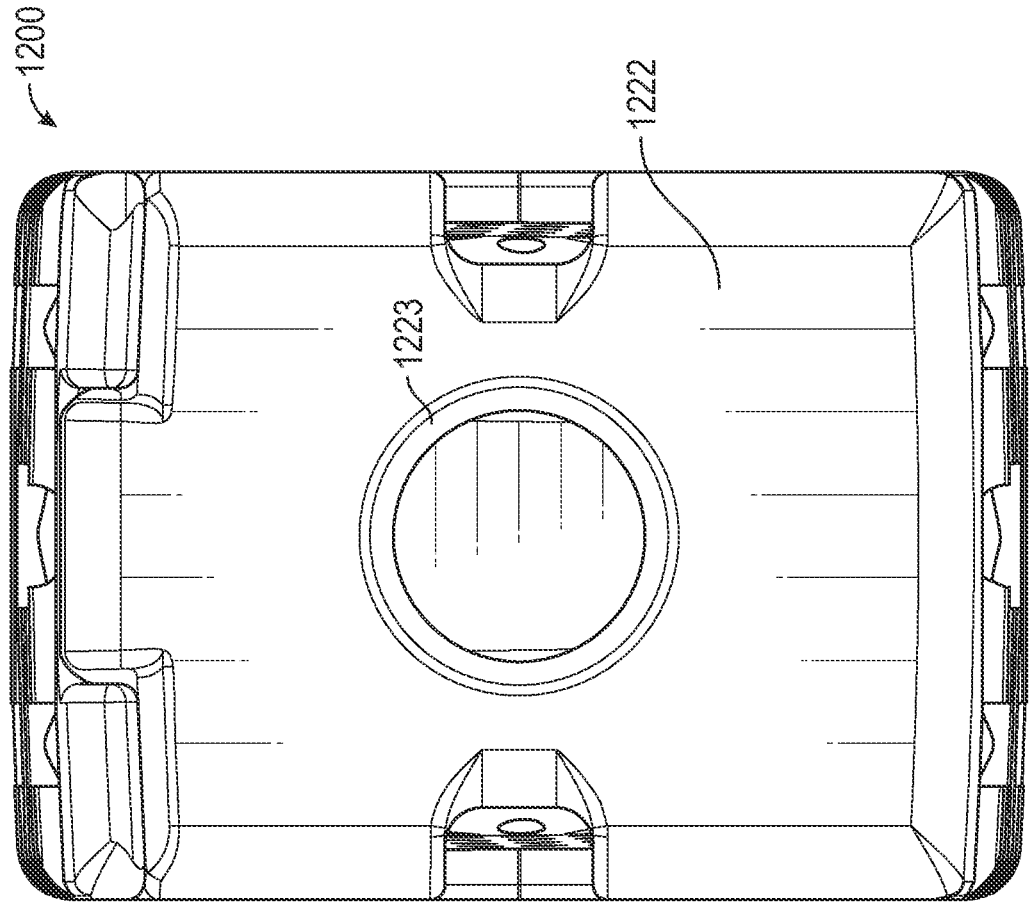
FIG. 89 is a proximal view of the spinal implant device of FIG. 87.

FIG. 89 is a proximal view of the spinal implant device 1200. The spinal implant device 1200 can include a proximal end 1222. In some embodiments, the proximal end 1222 can include an opening 1223 to couple to an insertion tool. In some embodiments, the opening 1223 can be threaded.

Figure 90:
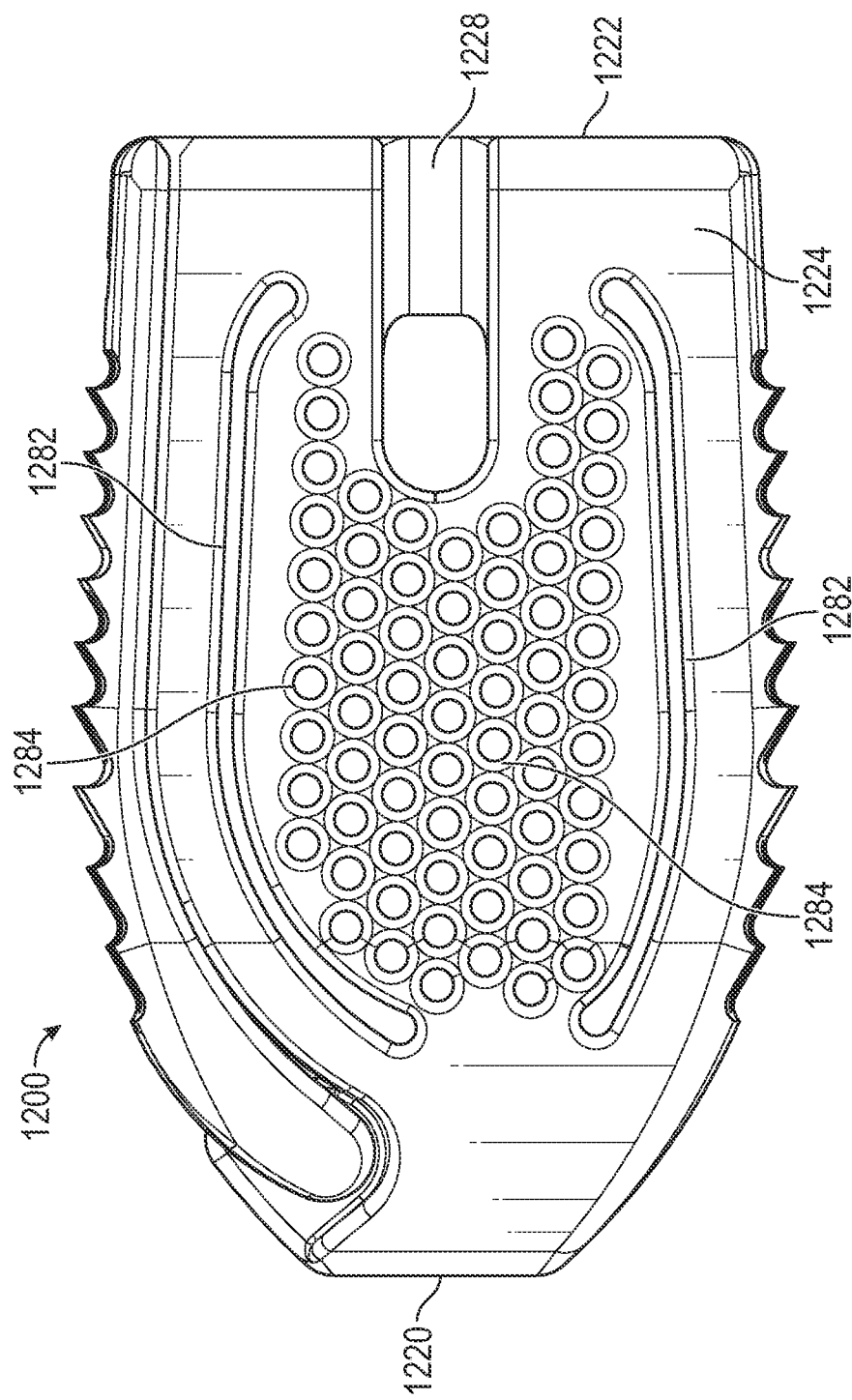
FIG. 90 is a side view of the spinal implant device of FIG. 87.

FIG. 90 is a side view of the spinal implant device 1200. The length of the spinal implant device 1200 can be the distance between the distal end 1220 and the proximal end 1222. The distal end 1220 can form the leading end and the proximal end 1222 can form the trailing end. The spinal implant device 1200 can include two opposing side walls including a first side wall 1224 and a second side wall 1226. FIG. 90 illustrates the first side wall 1224, but the second side wall 1226 can include the same or similar features.

The spinal implant device 1200 can include one or more compression openings 1282. The one or more compression openings 1282 can extend along the first side wall 1224. The one or more compression openings 1282 can extend through the first side wall 1224. The one or more compression openings 1282 can extend along the second side wall 1226. The one or more compression openings 1282 can extend through the second side wall 1226. In the illustrated embodiment, the first side wall 1224 includes a pair of compression openings 1282. In the illustrated embodiment, the second side wall 1226 includes a pair of compression openings 1282.

In some embodiments, the compression opening 1282 can be a longitudinally extending slot. In some embodiments, the compression opening 1282 can include a concave curve. In some embodiments, the compression opening 1282 can include a convex curve. In some embodiments, the compression opening 1282 can curve inward near the distal end 1220. In some embodiments, the compression opening 1282 can curve inward near the proximal end 1222. The compression opening 1282 can be shaped to allow compression along the height of the spinal implant device 1282. The compression opening 1282 can be configured to compress to decrease the height of the first side wall 1224 and the second side wall 1226.

The spinal implant device 1200 can be porous. The spinal implant device 1200 can include one or more fusion openings 1284. The one or more fusion openings 1284 can extend through the first side wall 1224. The one or more fusion openings 1284 can extend through the second side wall 1226. In some embodiments, the fusion opening 1284 can be a circular or rounded opening. In some embodiments, the fusion opening 1284 can be any shape. In some embodiments, the compression opening 1282 and the fusion opening 1284 are different shapes. In some embodiments, the compression opening 1282 and the fusion opening 1284 are different heights. In some embodiments, the compression opening 1282 and the fusion opening 1284 are disposed in different areas of the side walls 1224, 1226. In some embodiments, the compression openings 1282 are disposed closer to the upper surface and the lower surface of the spinal implant device 1200. In some embodiments, fusion openings 1284 are disposed in the middle area of the side walls 1224, 1226. In some embodiments, the one or more compression openings 1282 are configured to be compressed. In some embodiments, the one or more fusion openings 1284 are not configured to be compressed.

In some embodiments, each of the two opposing side walls 1224, 1226 can include a feature 1228 to facilitate placement of the spinal implant device 1200. In some embodiments, the feature 1228 can include a channel to accept an insertion tool. In some embodiments, the feature 1228 can extend from the proximal end 1222 of the spinal implant device 1200 toward the distal end 1220. In some embodiments, the feature 1228 can form a groove in the proximal end 1222. In some embodiments, the feature 1228 can be partially enclosed on three sides near the proximal end 1222. In some embodiments, the feature 1228 can form an opening in the side walls 1224, 1226. In some embodiments, the feature 1228 can be partially enclosed on two sides. In some embodiments, the feature 1228 can have a greater width than the width of the side walls 1224, 1226. In some embodiments, the feature 1228 can extend inward beyond the width of the side walls 1224, 1226.

Figure 91:
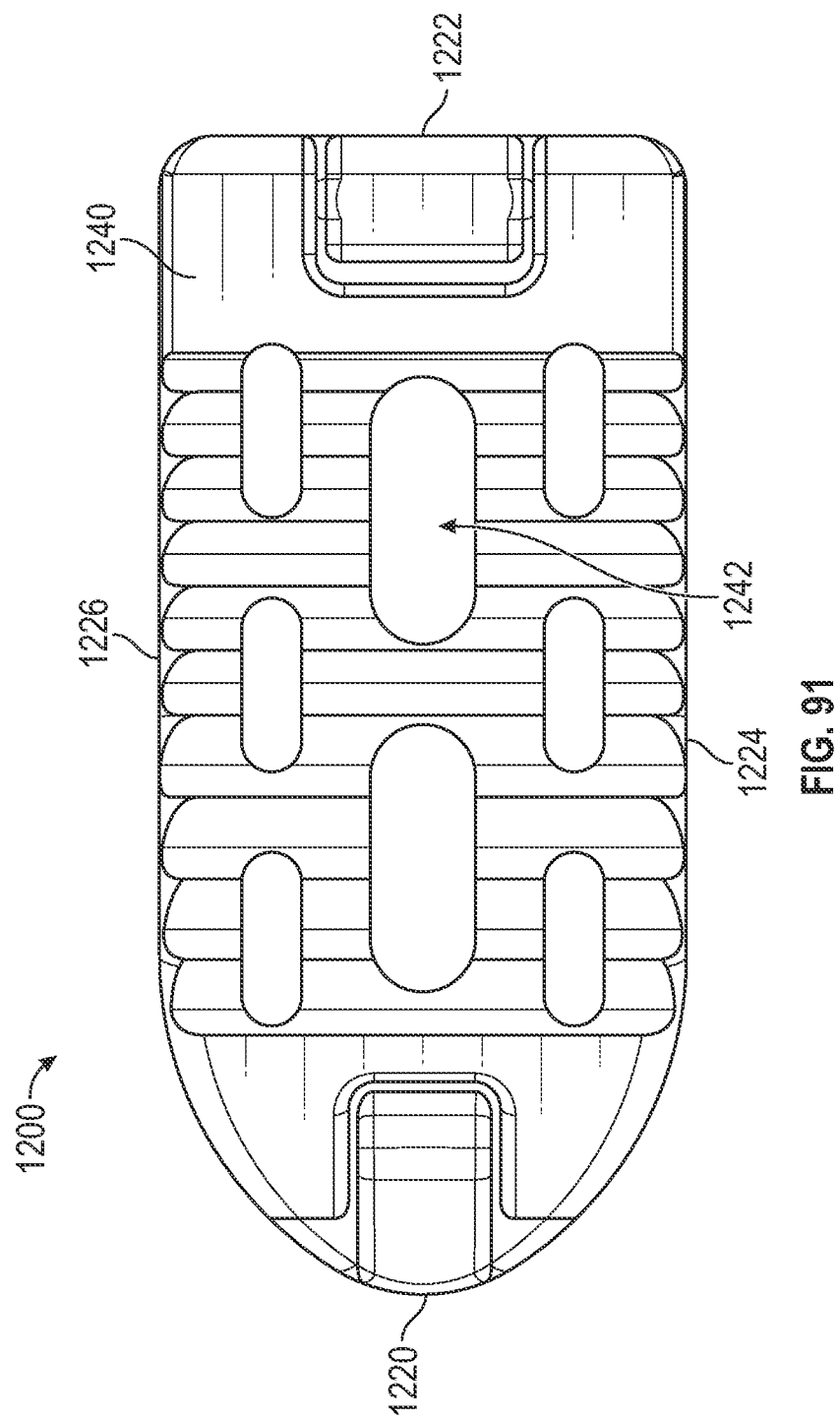
FIG. 91 is a top view of the spinal implant device of FIG. 87.
Figure 92:
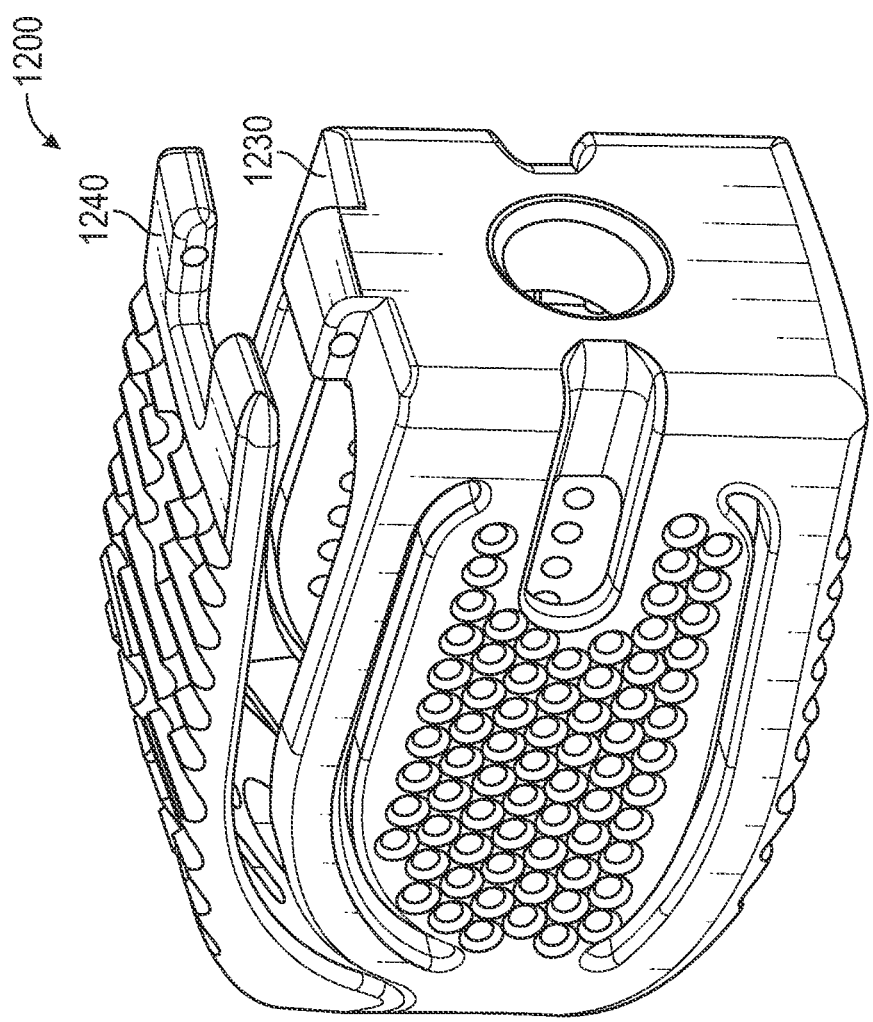
FIG. 92 is a top perspective view of the spinal implant device of FIG. 87 with the movable lid shown in an opened position.

FIG. 91 is a top view of the spinal implant device 1200. The spinal implant device 1200 can include a movable lid 1240. FIG. 91 is a top view of the spinal implant device 1200 with the movable lid 1240 closed. FIG. 92 is a top perspective view of the spinal implant device 1200 with the movable lid 1240 opened.

The spinal implant device 1200 can include one or more openings 1242 extending through the movable lid 1240. In some embodiments, the movable lid 1240 includes one or more elongate openings 1242. In some embodiments, the movable lid 1240 includes one or more openings 1242 having different widths. In some embodiments, the movable lid 1240 includes one or more openings 1242 having different lengths. In some embodiments, the movable lid 1240 includes one or more openings 1242 having different locations on the movable lid 1240.

The spinal implant device 1200 can include an upper wall 1230. In some embodiments, the upper wall 1230 forms a ledge to support the movable lid 1240 near the proximal end 1222. In some embodiments, the upper wall 1230 forms a ledge to support the movable lid 1240 during rotation near the distal end 1220.

The upper wall 1230 can include a projection near the proximal end 1222. In some embodiments, the projection of the upper wall 1230 extends between portions of the movable lid 1240. The projection of the upper wall 1230 can facilitate alignment of the movable lid 1240 with the upper wall 1230. The projection of the upper wall 1230 can reduce or limit lateral movement of the movable lid 1240.

In some embodiments, the upper wall 1230 forms a support surface for the movable lid 1240 when the movable lid 1240 is closed. In some embodiments, the movable lid 1240 rests against the upper wall 1230 during insertion.

In some embodiments, the movable lid 1240 and a portion of the upper wall 1230 can form the upper surface of the spinal implant device 1200 configured to contact the vertebral end plate. The movable lid 1240 can abut the upper wall 1230 when the lid 1240 is closed. In some embodiments, the movable lid 1240 and a portion of the upper wall 1230 can provide a load supporting surface for the adjacent vertebrae. In some methods, the load can be transferred from the movable lid 1240 to the upper wall 1230. In some methods, the movable lid 1240 and the upper wall 1230 can be positioned adjacent to a vertebral end plate of a superior vertebra.

Figure 93:
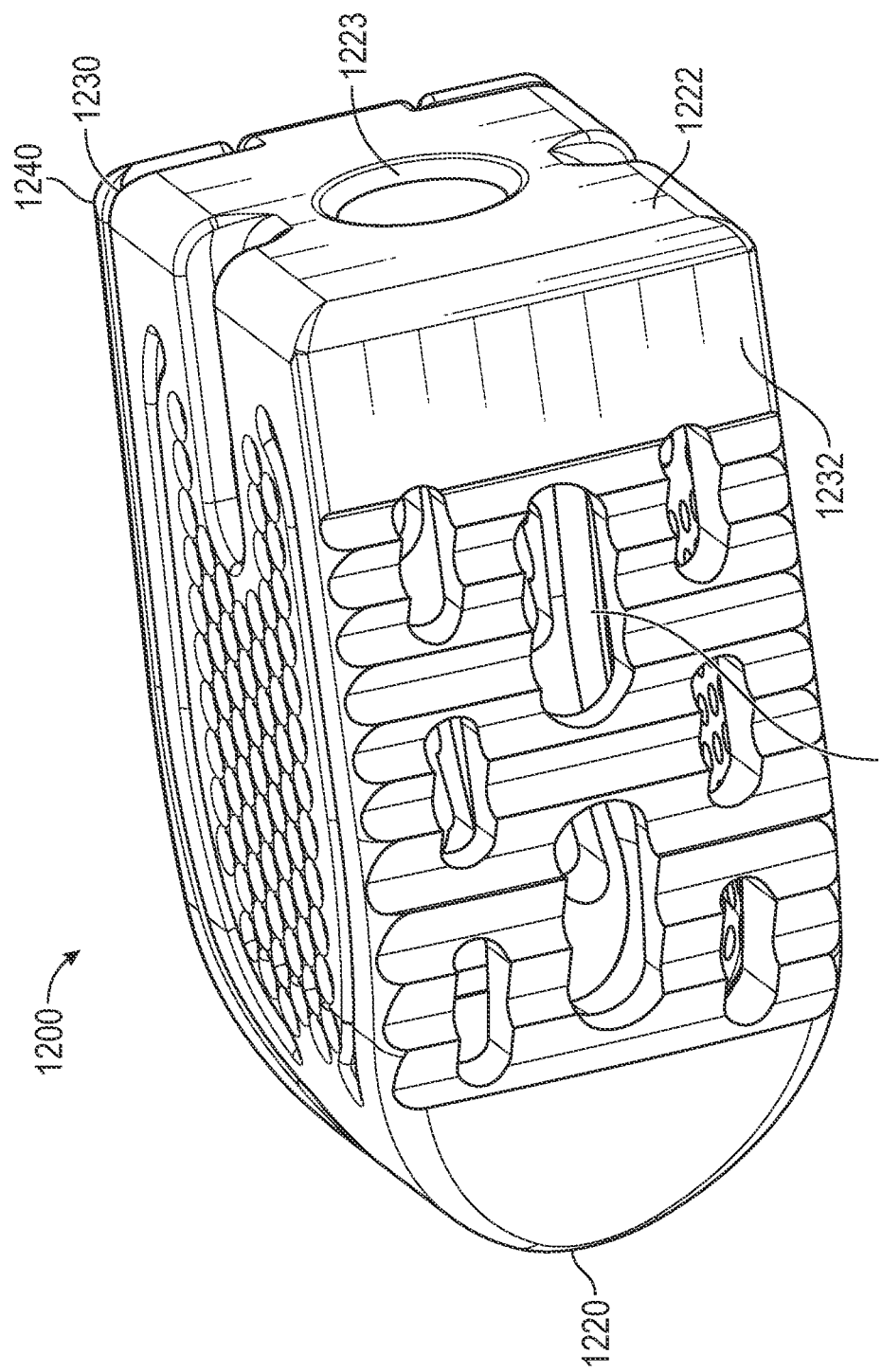
FIG. 93 is a bottom perspective view of the spinal implant device of FIG. 87.

FIG. 93 is a bottom perspective view of the spinal implant device 1200. The spinal implant device 1200 can include a lower wall 1232. The lower wall 1232 can span between the distal end 1220 and the proximal end 1222. The spinal implant device 1200 can include one or more openings 1244 extending through the lower wall 1232. In some embodiments, the lower wall 1232 includes one or more openings 1244 having different widths. In some embodiments, the lower wall 1232 includes one or more openings 1244 having different lengths. In some embodiments, the lower wall 1232 includes one or more openings 1244 having different locations on the lower wall 1232. The openings 1242, 1244 can have the same or similar shape. The openings 1242, 1244 can be diametrically opposed. The openings 1242, 1244 can have different orientations or patterns.

The lower wall 1232 can provide a load supporting surface. In some methods, the lower wall 1232 can be positioned adjacent to a vertebral end plate of an inferior vertebra. In some methods, when the spinal implant device 1200 is positioned between two adjacent vertebrae, the load supporting surfaces of the movable lid 1240 and the lower wall 1232 contact the vertebral end plates of the adjacent vertebrae. In some embodiments, the distance between the movable lid 1240 and the lower wall 1232 can form the height of the spinal implant device 300.

In some embodiments, the spinal implant device 1200 can include features to limit or reduce movement of the spinal implant device 1200 between the vertebrae. The spinal implant device 1200 can include a plurality of ridges 1214. The ridges 1214 can form a portion of the movable lid 1240. The ridges 1214 can form a portion of the lower wall 1232.

Figure 94:
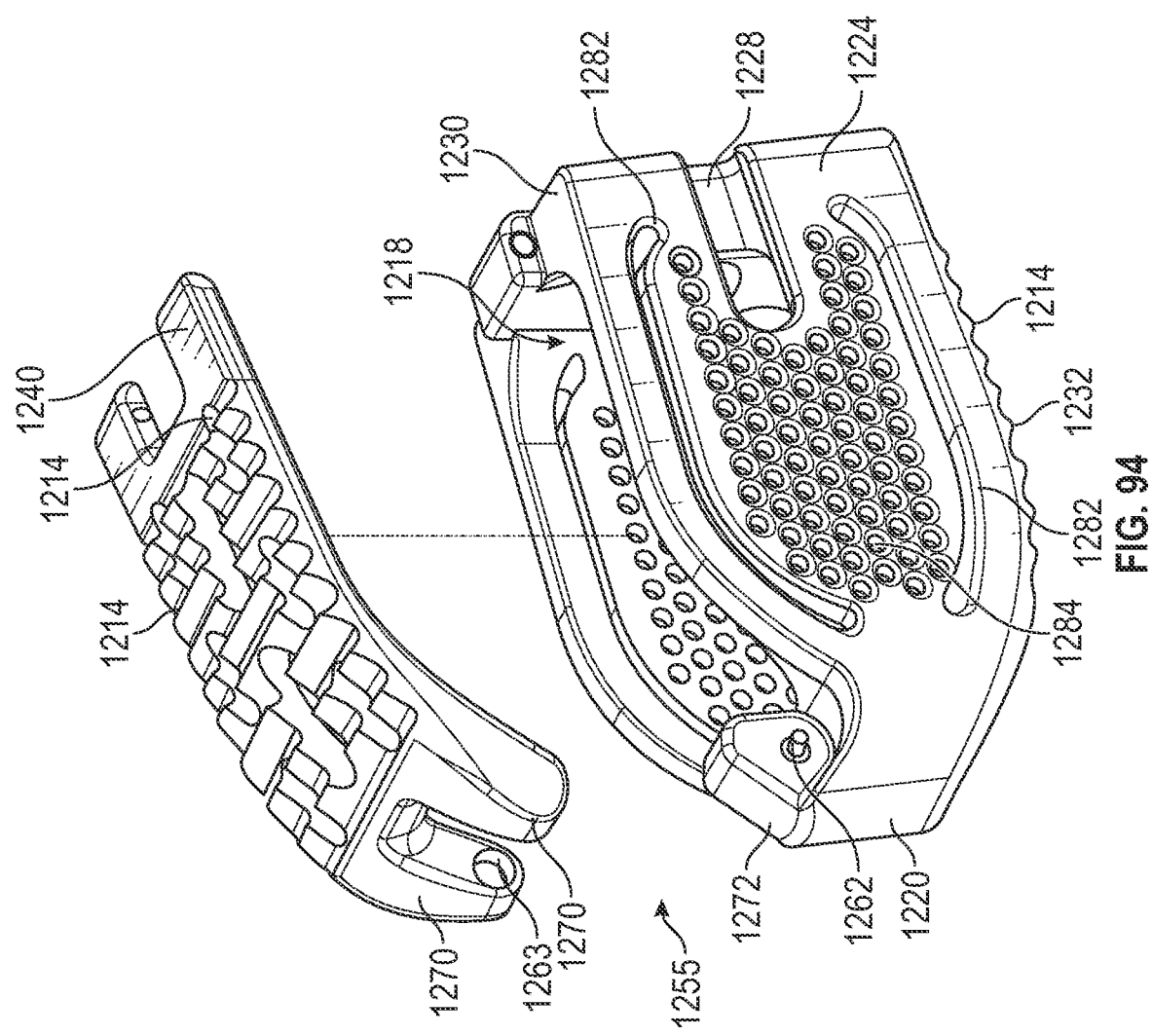
FIG. 94 is an exploded perspective view of the spinal implant device of FIG. 87.

FIG. 94 is an exploded view of the movable lid 1240 of the spinal implant device 1200. In some embodiments, the movable lid 1240 can be coupled to the distal end 1220. The distal end 1220 can include a central post 1272.

In some embodiments, the spinal implant device 1200 can include a movable joint 1255. In some embodiments, the movable joint 1255 can couple the movable lid 1240 to the distal end 1220. The movable joint 1255 can allow for pivoting motion of the movable lid 1240.

In some embodiments, the movable lid 1240 can include one or more lumens 1263 that can extend between two opposing lateral posts 1270 of the movable lid 1240. The articulation 1262 can be any structure about which the movable lid 1240 can rotate. The central post 1272 can include one or more articulation 1262 configured to be disposed in one or more lumens 1263.

The spinal implant device 1200 can include a cavity 1218. In some embodiments, the proximal end 1222 can define the back inner surface of the cavity 1218. In some embodiments, the distal end 1220 can define the front inner surface of the cavity 1218. In some embodiments, the two opposing side walls 1224, 1226 can define the side inner surfaces of the cavity 1218. In some embodiments, the movable lid 1240 can define the top inner surface of the cavity 1218. In some embodiments, the lower wall 1232 can define the bottom inner surface of the cavity 1218.

In some methods of use, the movable lid 1240 can be supported by the upper wall 1230 along the distal end 1220, the proximal end 1222, and along the side walls 1224, 1226. The movable lid 1240 can be supported when the lid is closed. The side walls 1224, 1226 can be configured to compress in height. In some embodiments, the one or more compression openings 1282 are configured to be compressed. The compression openings 1282 can be slots configured to compress in height. The compression openings 1282 can be compressed under a load from the vertebral bodies. The compression openings 1282 can compress due to the shape of the compression openings 1282. The side walls 1224, 1226 can flex to reduce the height of the side walls 1224, 1226. In some embodiments, the side walls 1224, 1226 can flex when a retractor is removed. In some embodiments, the side walls 1224, 1226 can flex when the vertebrae apply a load. The movable lid 1240 and the lower wall 1232 can compress material within the cavity 1218. In some embodiments, the movable lid 1240 moves toward the lower wall 1232. In some embodiments, the lower wall 1232 moves toward the movable lid 1240. In some embodiments, both the movable lid 1240 and the lower wall 1232 move inward.

Figure 95:
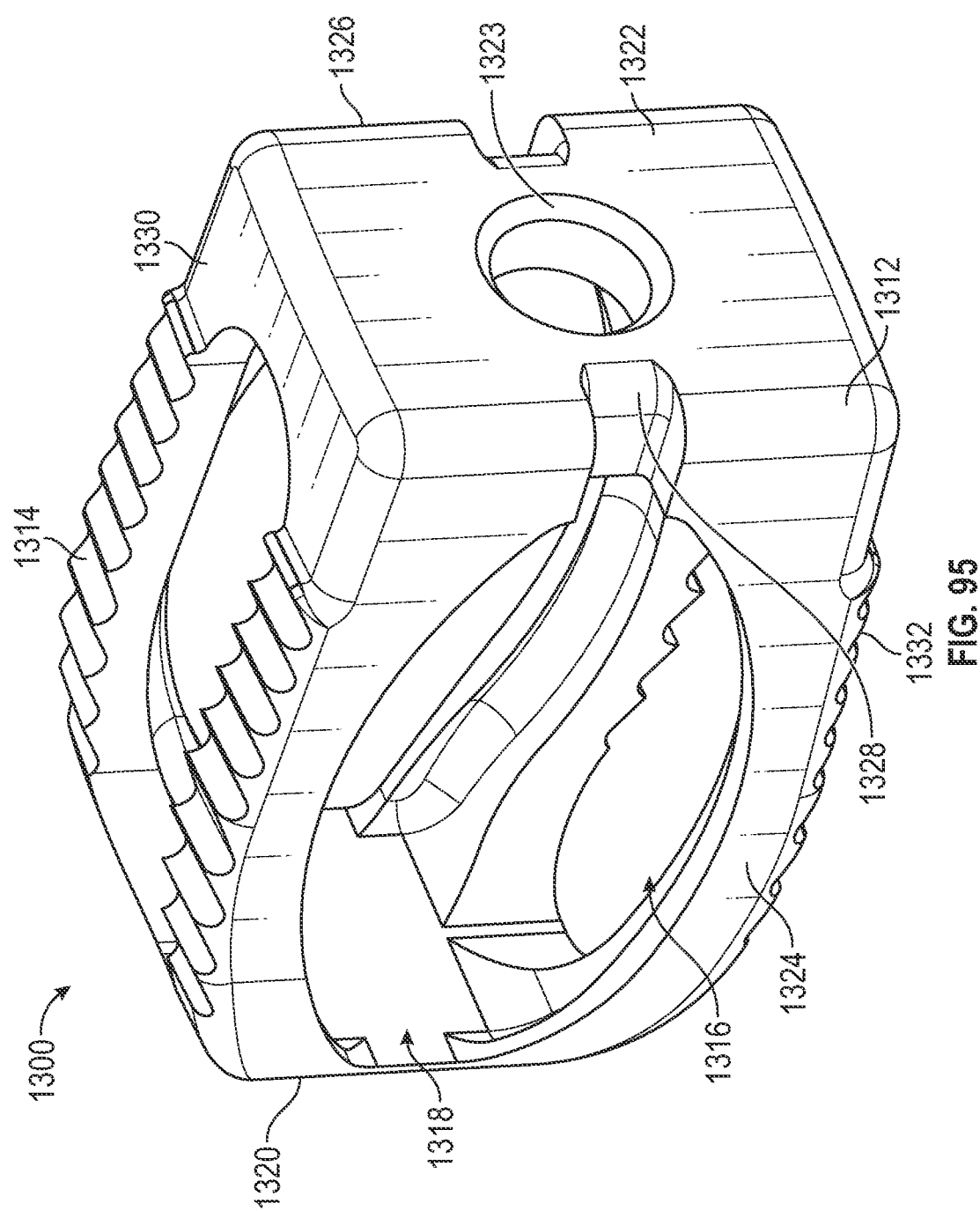
FIG. 95 is a perspective view of an embodiment of a spinal implant device.

FIG. 95 illustrates a perspective view of a spinal implant device 1300. The spinal implant device 1300 can include any of the features of the spinal implant device 10, 10A, 100, 200, 300, 400, 500, 600, 700, 800, 900, 1000, 1100, 1200 as described herein and can be used in any method or method step described herein. The spinal implant device 1300 can include a body structure 1312. The body structure 1312 can include thicker edges surrounding open windows 1316. As described herein, the lateral sides of the body structure 1312 can be open. The spinal implant device 1300 can have a through lumen perpendicular to the longitudinal axis of the spinal implant device 1300. As described herein, the upper and lower surface of the body structure 1312 can be open, or at least partially open. The spinal implant device 1300 can have a secondary through lumen perpendicular to the longitudinal axis of the spinal implant device 1300. In some embodiments, the thicker edges are solid. In some embodiments, the thicker edges are porous or a mesh. In some embodiments, the windows 1316 allow for the compression of material disposed within the spinal device 1300.

Figure 96:
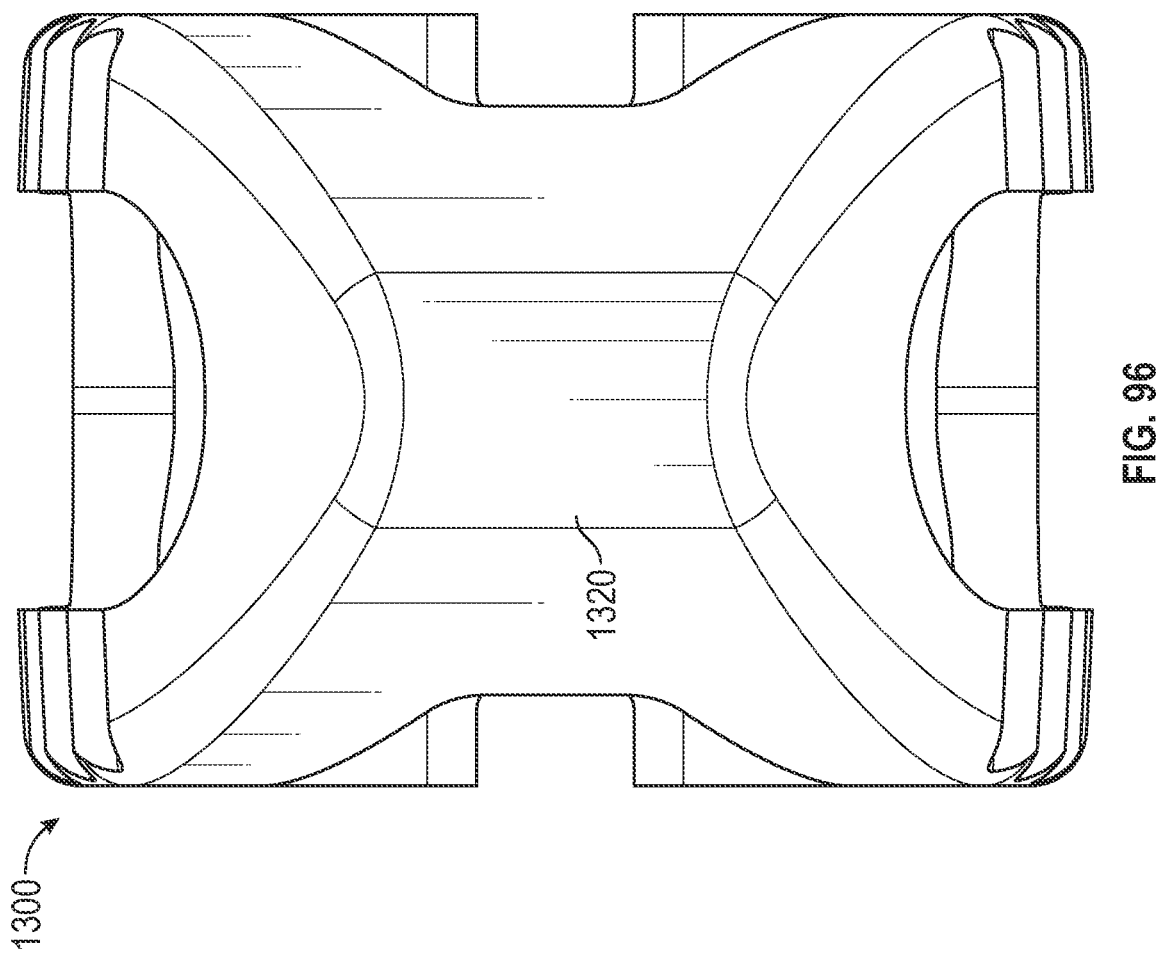
FIG. 96 is a distal view of the spinal implant device of FIG. 95.

FIG. 96 is a distal view of the spinal implant device 1300. The spinal implant device 1300 can include a distal end 1320. The distal end 1320 can include thicker edges which create a robust end to facilitate insertion of the distal end 1320. The distal end 1320 can be thickened to be able to be inserted or seated between vertebrae. The distal end 1320 can be more rigid than another portion of the spinal implant device 1300, such as the side walls. The distal end 1320 can be tapered. In some embodiments, the four surfaces of the distal end 1320 can taper to from a square pyramid or similar shape. The distal end 1320 can be formed by four thicker edges, such as the upper, lower, and side edges which come together. In some embodiments, the upper edge and the lower edge of the distal end 1320 equally taper. In some embodiments, the lateral edges of the distal end 1320 equally taper.

Figure 97:
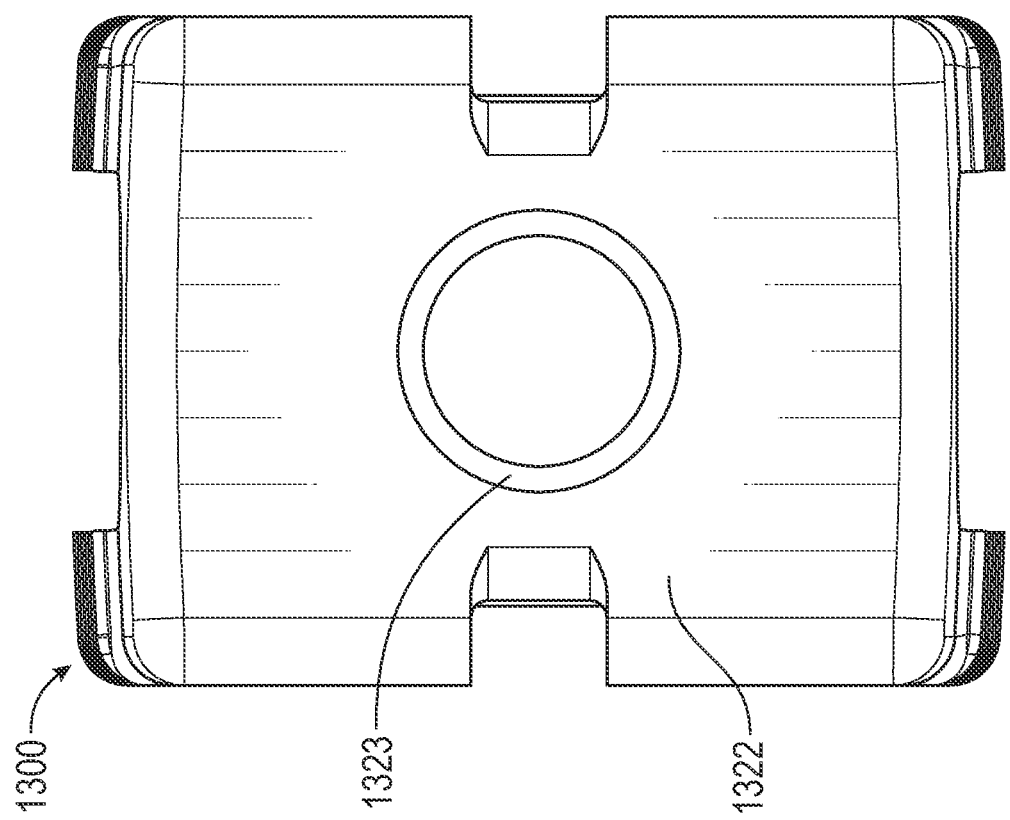
FIG. 97 is a proximal view of the spinal implant device of FIG. 95.

FIG. 97 is a proximal view of the spinal implant device 1300. The spinal implant device 1300 can include a proximal end 1322. In some embodiments, the proximal end 1322 can be flat. The proximal end 1322 can be square, rectangular, quadrilateral, or other polygonal shape. The edges or corners of the proximal end 1322 can be rounded. In some embodiments, the proximal end 1322 can include an opening 1323 such as a threaded opening to couple with an insertion tool.

Figure 98:
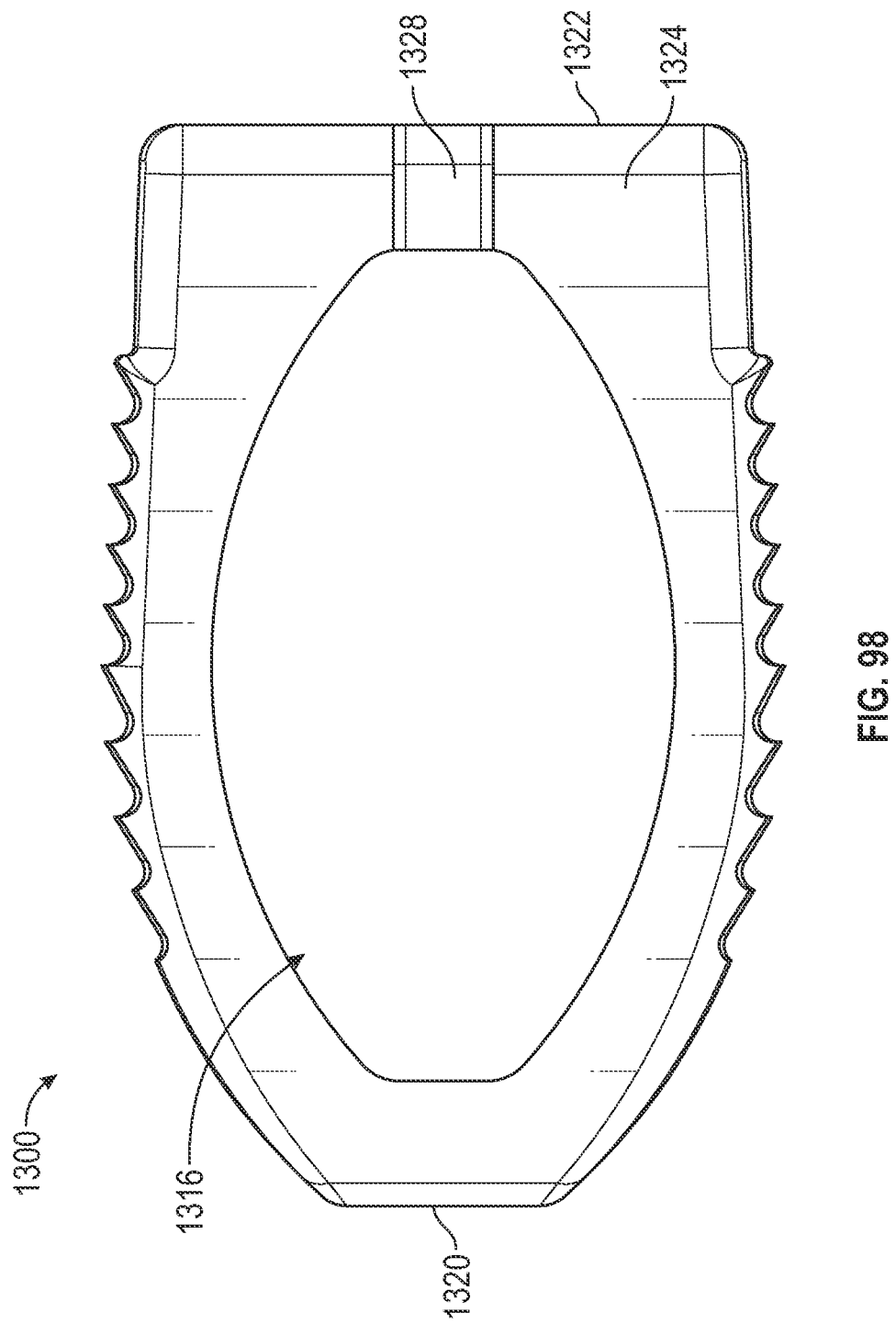
FIG. 98 is a side view of the spinal implant device of FIG. 95.

FIG. 98 is a side view of the spinal implant device 1300. The length of the spinal implant device 1300 can be the distance between the distal end 1320 and the proximal end 1322. The spinal implant device 1300 can include two opposing side walls including a first side wall 1324 and a second side wall 1326. FIG. 98 illustrates the first side wall 1324, but the second side wall 1326 can include the same or similar features. In some embodiments, each side wall 1324, 1326 can include thicker edges surrounding an open window 1316. Each side wall 1324, 1326 can include four thicker edges surrounding an open window 1316. The thicker edges can have a rounded or tapered edge near the distal end 1320. The thicker edges can have a rounded or tapered edge near the proximal end 1322. The open window 1316 can have the shape of an oval with a rounded taper near the distal end 1320 and a rounded taper near the proximal end 1322. The open window 1316 can span the height of the spinal implant device 1300, or a portion thereof. The open window 1316 can follow the shape of the side wall 1324, 1326.

The spinal implant device 1300 can include two windows 1316. Each window 1316 can extend along a portion of the width of the respective side wall 1324, 1326 (e.g., 30% of the width, 40% of the width, 50% of the width, 60% of the width, 70% of the width, 80% of the width, 90% of the width, 95% of the width, or any range including and between any of the foregoing values). Each window 1316 can extend along a portion of the length of the respective side wall 1324, 1326 (e.g., 30% of the length, 40% of the length, 50% of the length, 60% of the length, 70% of the length, 80% of the length, 90% of the length, 95% of the length, or any range including and between any of the foregoing values). Each window 1316 can extend along a portion of the surface area of the respective side wall 1324, 1326 (e.g., 50% of the surface area, 60% of the surface area, 70% of the surface area, 80% of the surface area, 90% of the surface area, or 95% of the surface area, or any range including and between any of the foregoing values).

In some embodiments, the open window 1316 can allow the side walls 1324, 1326 to flex. The open window 1316 can allow for compression of the spinal implant device 1300. The compression of the side walls 1324, 1326 can promote fusion of the adjacent vertebrae. The compression of the side walls 1324, 1326 can promote fusion by increasing the load on the material contained within the spinal implant device 1300. In some embodiments, the side walls 1324, 1326 remain uncompressed after insertion under normal anatomical loads. In some embodiments, the side walls 1324, 1326 can be compressed after insertion under normal anatomical loads In some embodiments, each of the two opposing side walls 1324, 1326 can include a feature 1328. The feature 1328 can be designed to facilitate placement of the spinal implant device 1300 by coupling with an insertion tool. In some embodiments, the feature 1328 can include a channel or groove that originates at the proximal end 1322. In some embodiments, the feature 1328 can extend from the proximal end 1322 along a portion of one of the side walls 1324, 1326. In some embodiments, the feature 1328 can extend from the proximal end 1322 to the open window 1316. In some embodiments, the feature 1328 extends through the thicker edge closer to the proximal end 1322.

Figure 99:
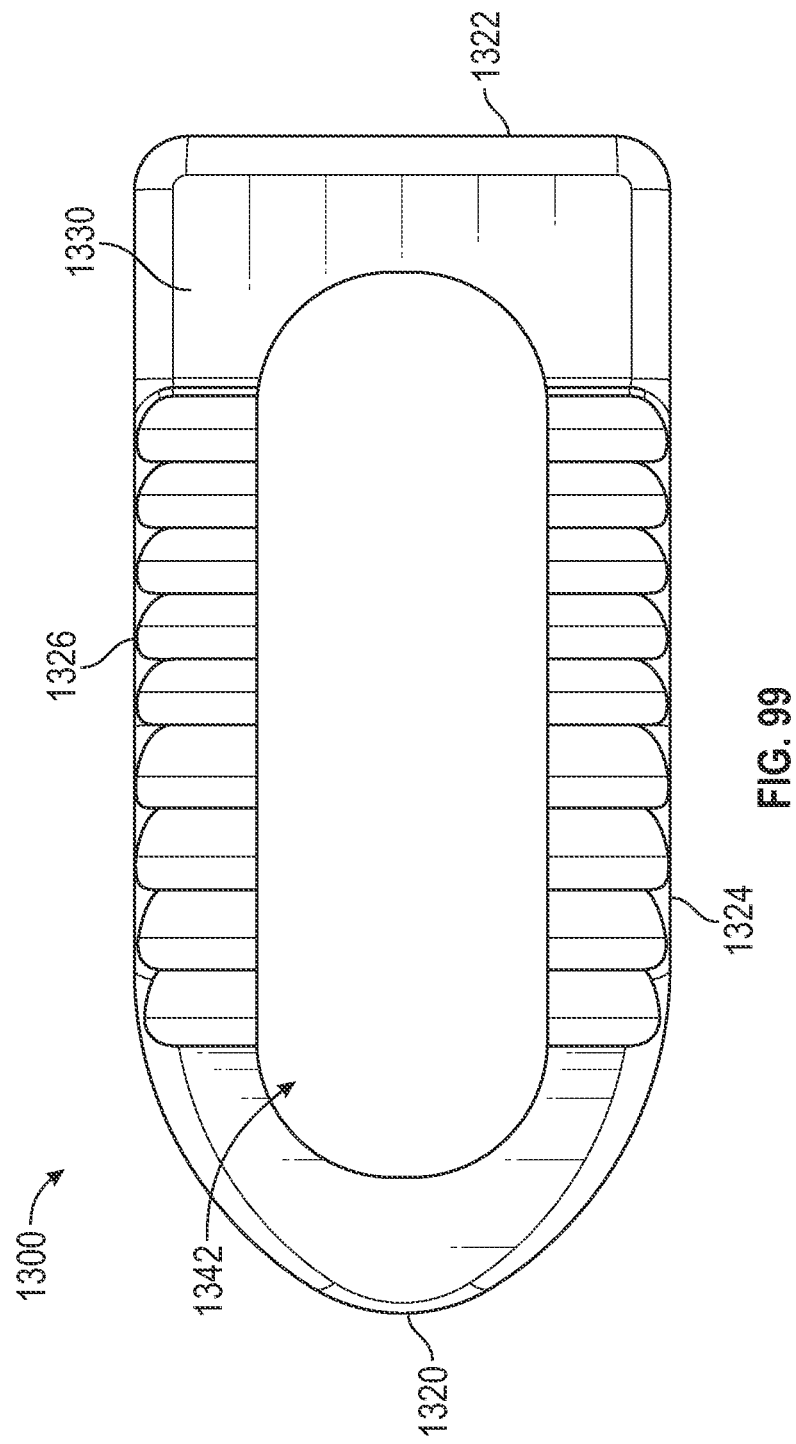
FIG. 99 is a top view of the spinal implant device of FIG. 95.

FIG. 99 is a top view of the spinal implant device 1300. The spinal implant device 1300 can include an upper wall 1330. The upper wall 1330 can include thicker edges which forms the top surface of the spinal implant device 1300. The upper wall 1330 can extend between the distal end 1320 and the proximal end 1322. In some embodiments, the upper wall 1330 is tapered toward the distal end 1320.

The spinal implant device 1300 can include one or more openings 1342. In some embodiments, the upper wall 1330 includes one opening 1342. The opening 1342 can be elongate. The opening 1342 can extend along a portion of the width of the upper wall 1330 (e.g., 30% of the width, 40% of the width, 50% of the width, 60% of the width, 70% of the width, 80% of the width, 90% of the width, 95% of the width, or any range including and between any of the foregoing values). The opening 1342 can extend along a portion of the length of the upper wall 1330 (e.g., 30% of the length, 40% of the length, 50% of the length, 60% of the length, 70% of the length, 80% of the length, 90% of the length, 95% of the length, or any range including and between any of the foregoing values). In some embodiments, the opening 1342 can cover a portion of the upper wall 1330 (e.g., 50% of the surface area, 60% of the surface area, 70% of the surface area, 80% of the surface area, 90% of the surface area, or 95% of the surface area, or any range including and between any of the foregoing values).

Figure 100:
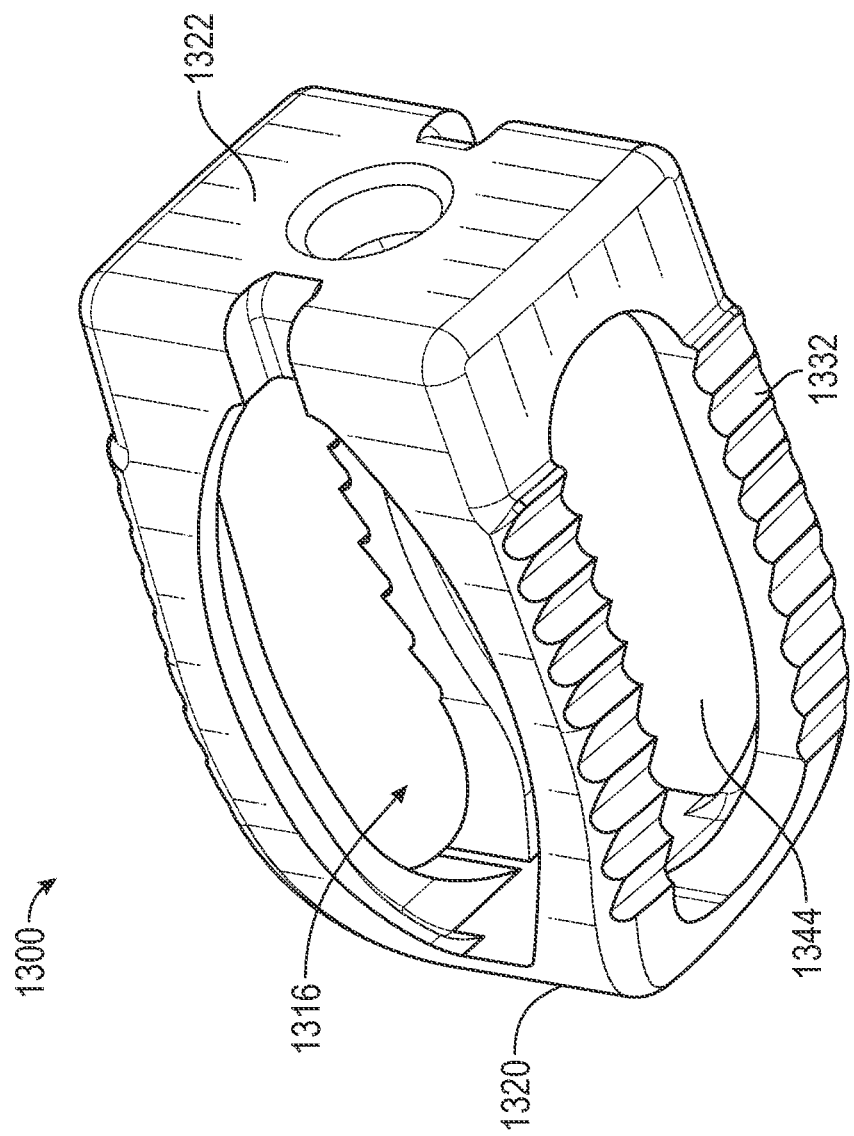
FIG. 100 is a bottom perspective view of the spinal implant device of FIG. 95.

FIG. 100 is a bottom perspective view of the spinal implant device 1300. The spinal implant device 1300 can include a lower wall 1332. The lower wall 1332 can extend between the distal end 1320 and the proximal end 1322. The spinal implant device 1300 can include one or more openings 1344 extending through the lower wall 1332. The opening 1344 can be elongate. The openings 1342, 1344 can have the same or similar shape. The openings 1342, 1344 can be diametrically opposed. The openings 1342, 1344 can have different shapes.

The opening 1344 can extend along a portion of the width of the lower wall 1332 (e.g., 30% of the width, 40% of the width, 50% of the width, 60% of the width, 70% of the width, 80% of the width, 90% of the width, 95% of the width, or any range including and between any of the foregoing values). The opening 1344 can extend along a portion of the length of the lower wall 1332 (e.g., 30% of the length, 40% of the length, 50% of the length, 60% of the length, 70% of the length, 80% of the length, 90% of the length, 95% of the length, or any range including and between any of the foregoing values). In some embodiments, the openings 1344 can cover a portion of the surface area of the lower wall 1332 (e.g., 50% of the surface area, 60% of the surface area, 70% of the surface area, 80% of the surface area, 90% of the surface area, or 100% of the surface area, or any range including and between any of the foregoing values).

In some embodiments, the spinal implant device 1300 can include features to limit or reduce movement of the spinal implant device 1300 between the vertebrae. The spinal implant device 1300 can include a plurality of ridges 1314. The ridges 1314 can form a portion of the upper wall 1330. The ridges 1314 can form a portion of the lower wall 1332. In some embodiments, the ridges 1314 can be directionally oriented as described herein.

The spinal implant device 1300 can include a cavity 1318. In some embodiments, the proximal end 1322 can form the back inner surface of the cavity 1318. In some embodiments, the distal end 1320 can form the front inner surface of the cavity 1318. In some embodiments, the two opposing side walls 1324, 1326 can form the side inner surfaces of the cavity 1318. In some embodiments, the upper wall 1330 can form the top inner surface of the cavity 1318. In some embodiments, the lower wall 1332 can form the bottom inner surface of the cavity 1318. The spinal implant device 1300 can have thicker edges with windows 1316 on the two opposing side walls 1324, 1326. The cavity 1318 can be partially open on at least two sides. The cavity 1318 can be partially open laterally through the windows 1316. The cavity 1318 can be a centrally located space within the spinal implant device 1300. In some embodiments, the cavity 1318 comprises a portion of the volume of the spinal implant device 1300 (e.g., 50% of the volume, 60% of the volume, 70% of the volume, 80% of the volume, 90% of the volume, or 95% of the volume, or any range including and between any of the foregoing values).

In some methods of use, the side walls 1324, 1326 can be configured to compress in height. In some embodiments, the one or more windows 1316 facilitates compression. The side walls 1324, 1326 can be compressed under a load from the vertebral bodies. The side walls 1324, 1326 can compress due to the shape of the windows 1316. The side walls 1324, 1326 can flex to reduce the height of the side walls 1324, 1326. The upper wall 1330 and the lower wall 1332 can compress material within the cavity 1318. In some embodiments, the upper wall 1330 moves toward the lower wall 1332. In some embodiments, the lower wall 1332 moves toward the upper wall 1330. In some embodiments, both the upper wall 1330 and the lower wall 1332 move inward.

Figure 101:
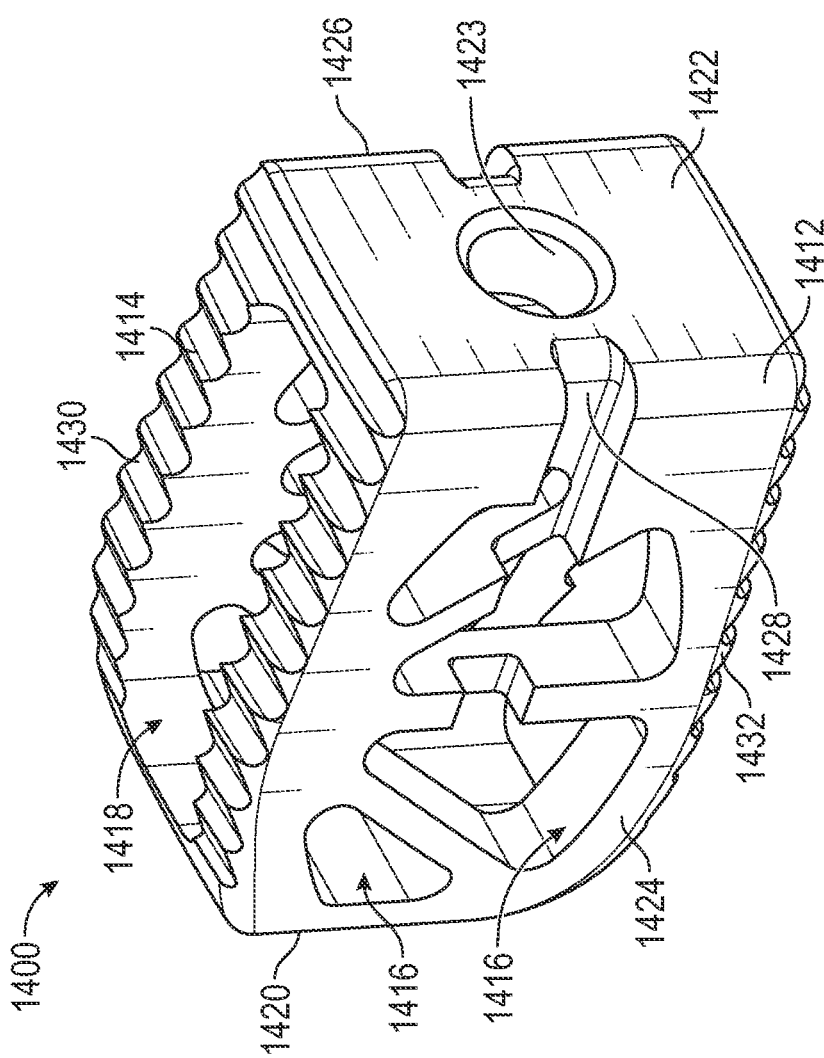
FIG. 101 is a perspective view of an embodiment of a spinal implant device.

FIG. 101 illustrates a perspective view of a spinal implant device 1400. The spinal implant device 1400 can include any of the features of the spinal implant device 10, 10A, 100, 200, 300, 400, 500, 600, 700, 800, 900, 1000, 1100, 1200, 1300 as described herein and can be used in any method or method step described herein. The spinal implant device 1400 can include a body structure 1412. In some embodiments, the body structure 1412 can allow for the compression of material disposed within the body structure 1412. In some embodiments, the shape of the body structure 1412 facilitates compression.

Figure 102:
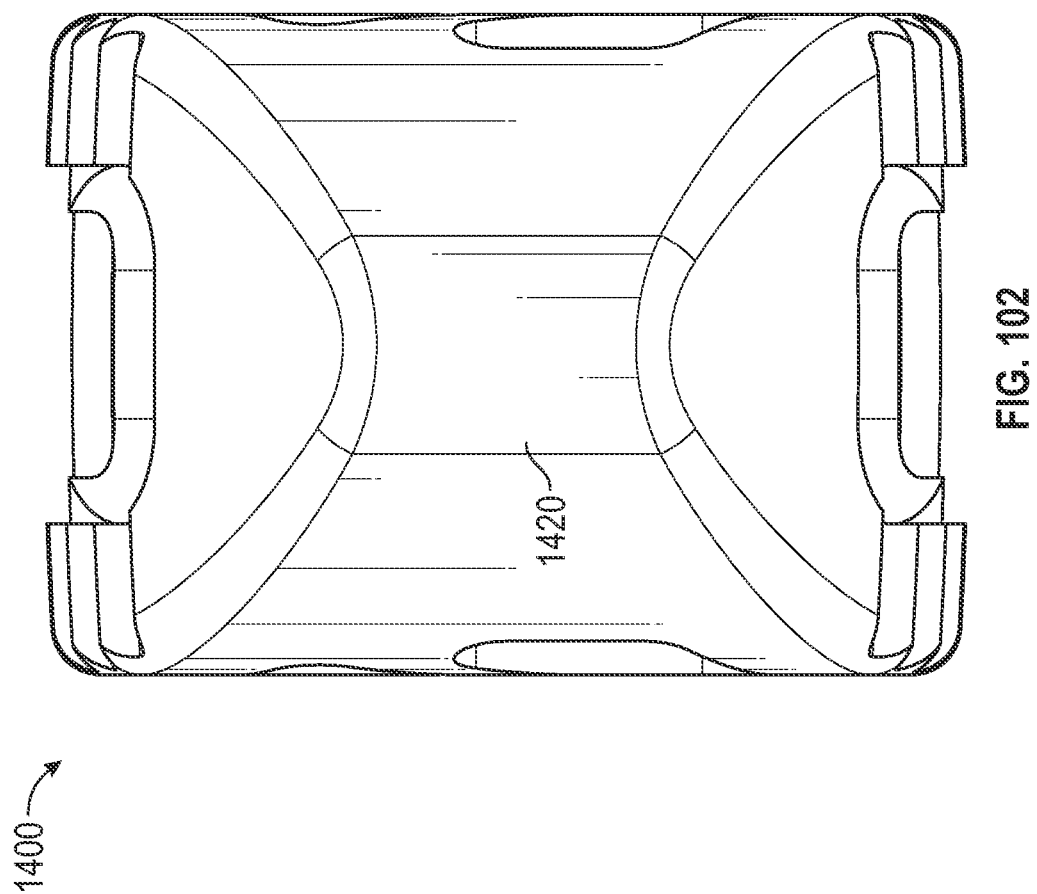
FIG. 102 is a distal view of the spinal implant device of FIG. 101.

FIG. 102 is a distal view of the spinal implant device 1400. The spinal implant device 1400 can include a distal end 1420. The distal end 1420 can be thickened to facilitate insertion of the distal end 1420. The distal end 1420 can be tapered. In some embodiments, the four surfaces of the distal end 1420 can taper to from a square pyramid or similar shape.

Figure 103:
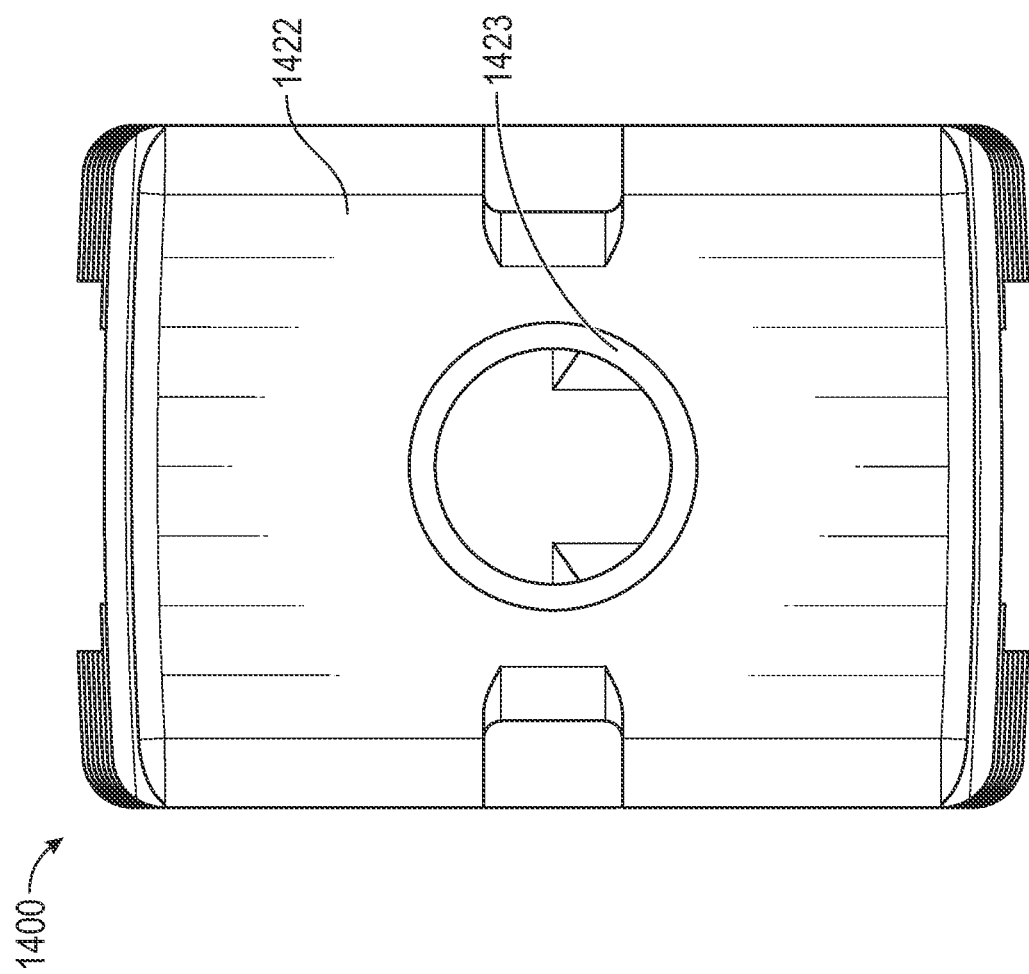
FIG. 103 is a proximal view of the spinal implant device of FIG. 101.

FIG. 103 is a proximal view of the spinal implant device 1400. The spinal implant device 1400 can include a proximal end 1422. In some embodiments, the proximal end 1422 can be flattened with rounded edges or corners. In some embodiments, the proximal end 1422 can include an opening 1423 to couple with an insertion tool.

Figure 104:
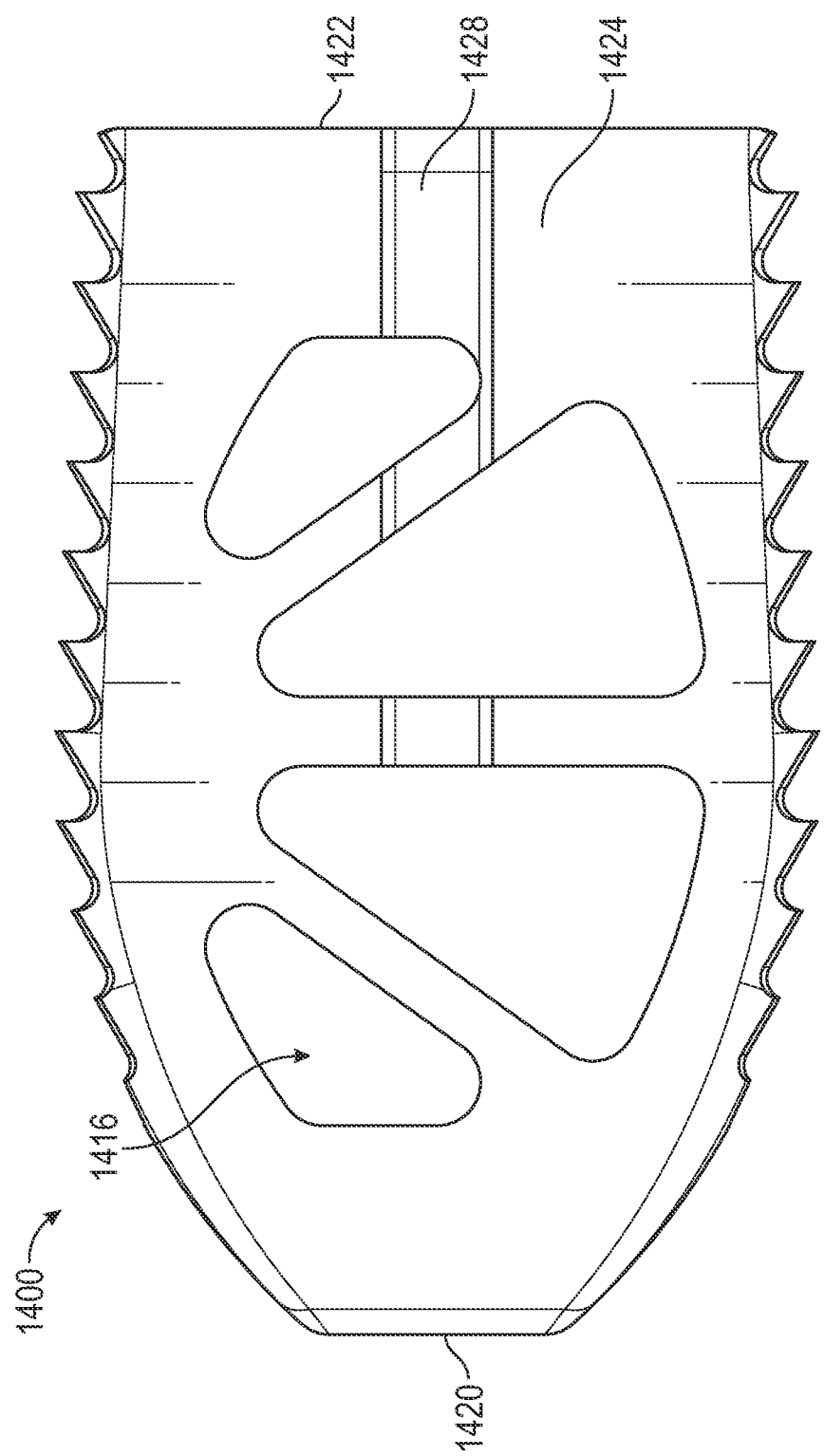
FIG. 104 is a side view of the spinal implant device of FIG. 101.

FIG. 104 is a side view of the spinal implant device 1400. The length of the spinal implant device 1400 can be the distance between the distal end 1420 and the proximal end 1422. The spinal implant device 1400 can include two opposing side walls including a first side wall 1424 and a second side wall 1426. FIG. 104 illustrates the first side wall 1424, but the second side wall 1426 can include the same or similar features.

In some embodiments, each side wall 1424, 1426 can include one or more open windows 1416. The one or more open windows 1416 can be anywhere along the length of the side walls 1424, 1426. In the illustrated embodiment, each side wall 1424, 1426 includes four open windows 1416. The first open window 1416 can be substantially triangular and near the distal end 1420. The second open window 1416 can be substantially triangular near the middle of the side wall 1424, 1426. The third open window 1416 can be substantially triangular near the middle of the side wall 1424, 1426. The fourth open window 1416 can be substantially triangular and near the proximal end 1422. The first open window 1416 and the fourth open window 1416 can be the same or similar shaped. The first open window 1416 and the fourth open window 1416 can be mirror images. The second open window 1416 and the third open window 1416 can be the same or similar shaped. The second open window 1416 and the third open window 1416 can be mirror images. Other shapes are contemplated. One or more open windows 1416 can span the height of the spinal implant device 1400, or a portion thereof. One or more open windows 1416 can follow the shape of the side wall 1424, 1426.

The one or more open windows 1416 can allow for compression of the spinal implant device 1400. In some embodiments, the one or more open windows 1416 can allow the side walls 1424, 1426 to flex. In some embodiments, the side walls 1424, 1426 can be configured to be compressed. One or more open windows 1416 can be configured to be reduced in height. One or more open windows 1416 can facilitate compression of the side walls 1424, 1426 based on the shape and placement of one or more open windows 1416. The compression of the side walls 1424, 1426 can promote fusion of the adjacent vertebrae. The compression of the side walls 1424, 1426 can promote fusion by increasing the load on the material contained within the spinal implant device 1400.

In some embodiments, each of the two opposing side walls 1424, 1426 can include a feature 1428. The feature 1428 can be designed to facilitate placement of the spinal implant device 1400 by coupling with an insertion tool. In some embodiments, the feature 1428 can include a channel or groove that originates at the proximal end 1422. In some embodiments, the feature 1428 can extend from the proximal end 1422 along a portion of one of the side walls 1424, 1426. In some embodiments, the feature 1428 can extend from the proximal end 1422 to the one or more open windows 1416. In some embodiments, the feature 1428 extends through a portion of the fourth open window 1416. In some embodiments, the feature 1428 extends through a portion of the third open window 1416.

Figure 105:
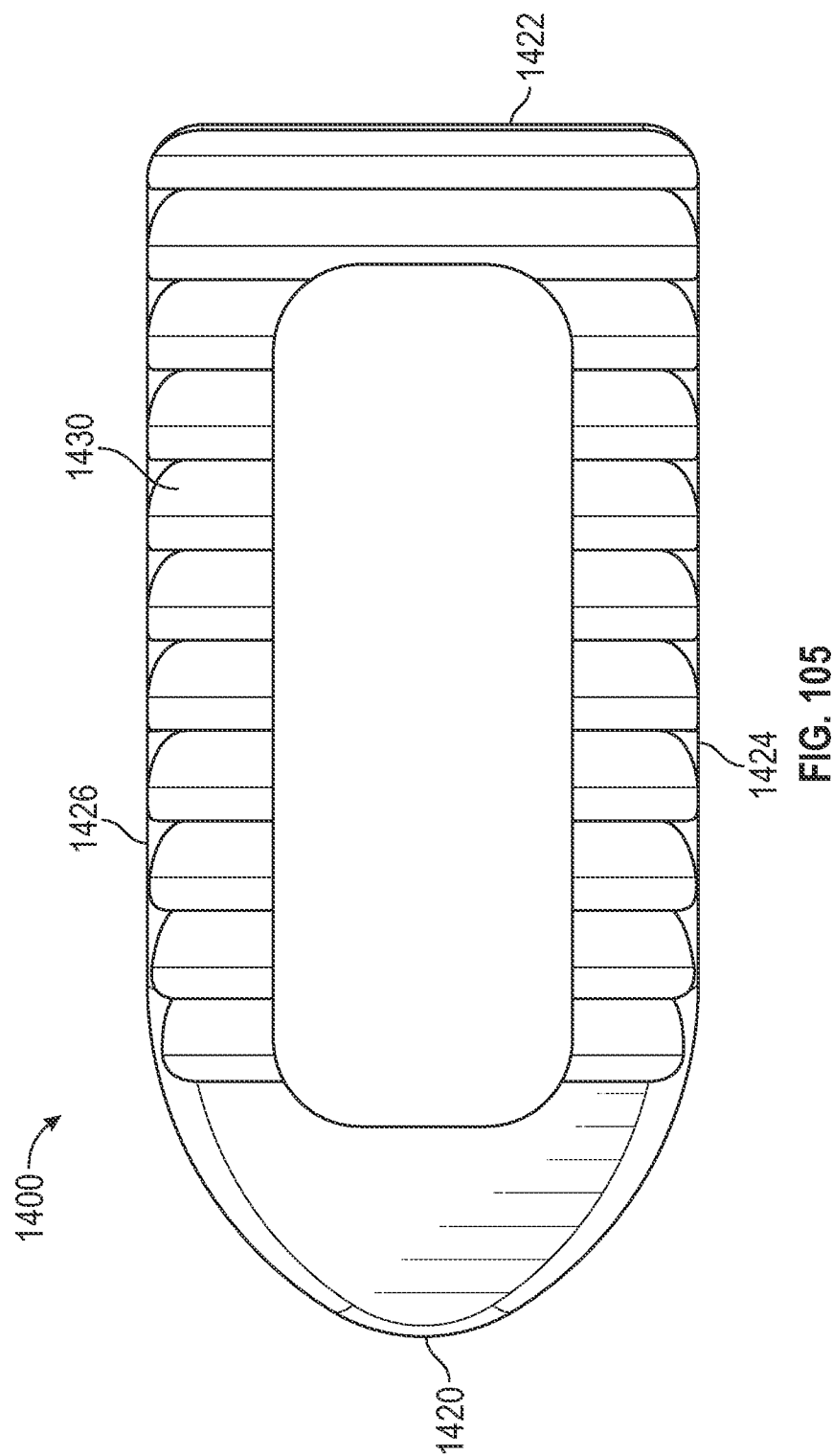
FIG. 105 is a top view of the spinal implant device of FIG. 101.

FIG. 105 is a top view of the spinal implant device 1400. The spinal implant device 1400 can include an upper wall 1430. The upper wall 1430 can include thicker edges which forms the top surface of the spinal implant device 1400. The upper wall 1430 can extend between the distal end 1420 and the proximal end 1422. In some embodiments, the upper wall 1430 is tapered toward the distal end 1420.

The spinal implant device 1400 can include one or more openings 1442. The one or more openings 1442 can extend along a portion of the width of the upper wall 1430 (e.g., 30% of the width, 40% of the width, 50% of the width, 60% of the width, 70% of the width, 80% of the width, 90% of the width, 95% of the width, or any range including and between any of the foregoing values). The one or more openings 1442 can extend along a portion of the length of the upper wall 1430 (e.g., 30% of the length, 40% of the length, 50% of the length, 60% of the length, 70% of the length, 80% of the length, 90% of the length, 95% of the length, or any range including and between any of the foregoing values). The one or more openings 1442 can cover a portion of the upper wall 1430 (e.g., 50% of the surface area, 60% of the surface area, 70% of the surface area, 80% of the surface area, 90% of the surface area, or 95% of the surface area, or any range including and between any of the foregoing values).

Figure 106:
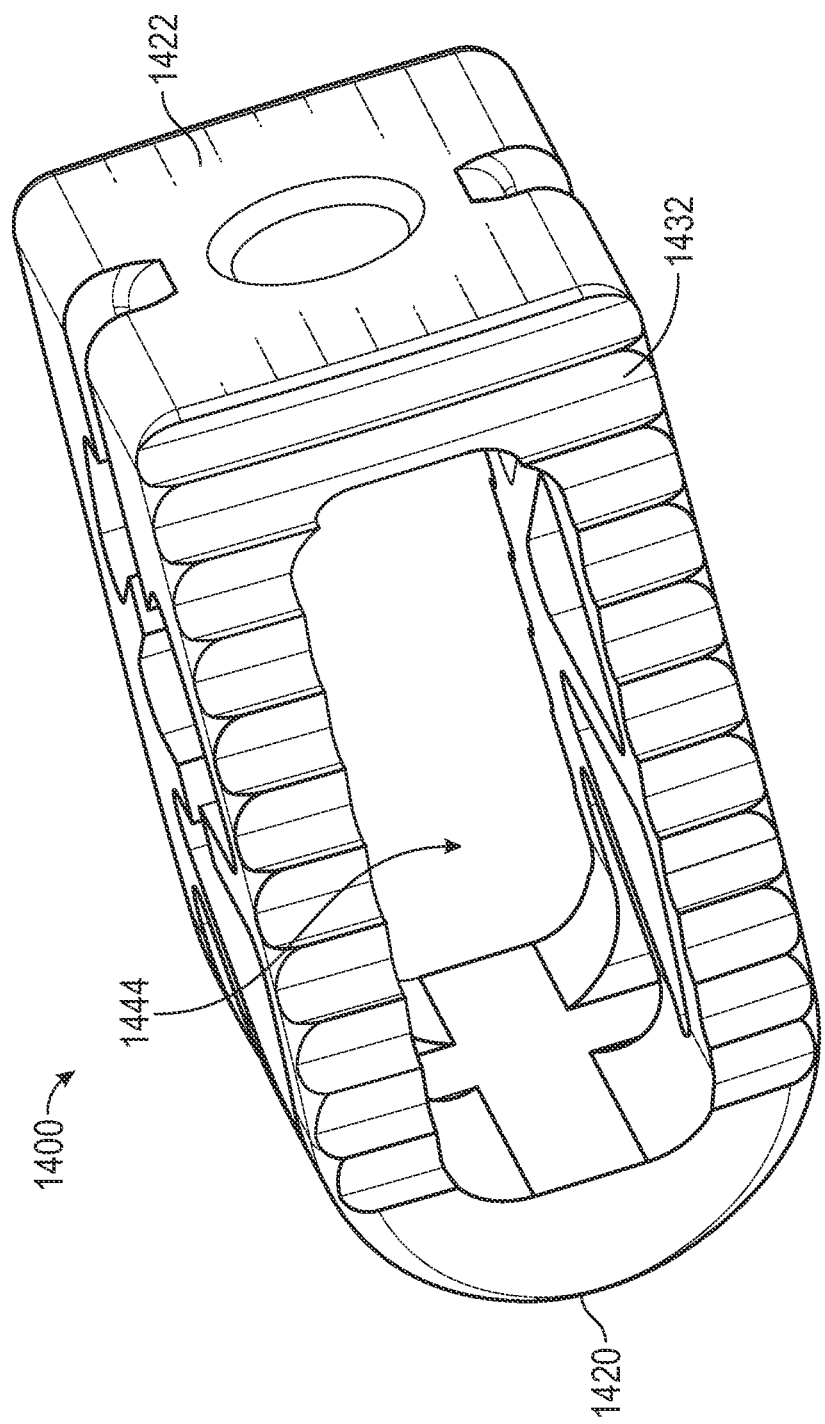
FIG. 106 is a bottom perspective view of the spinal implant device of FIG. 101.

FIG. 106 is a bottom perspective view of the spinal implant device 1400. The spinal implant device 1400 can include a lower wall 1432. The lower wall 1432 can extend between the distal end 1420 and the proximal end 1422. The spinal implant device 1400 can include one or more openings 1444 extending through the lower wall 1432. The opening 1444 can be elongate. The openings 1442, 1444 can have the same or similar shape. The openings 1442, 1444 can be diametrically opposed. The openings 1442, 1444 can have different shapes.

The one or more openings 1444 can extend along a portion of the width of the lower wall 1432 (e.g., 30% of the width, 40% of the width, 50% of the width, 60% of the width, 70% of the width, 80% of the width, 90% of the width, 95% of the width, or any range including and between any of the foregoing values). The one or more openings can extend along a portion of the length of the lower wall 1432 (e.g., 30% of the length, 40% of the length, 50% of the length, 60% of the length, 70% of the length, 80% of the length, 90% of the length, 95% of the length, or any range including and between any of the foregoing values). The one or more openings can cover a portion of the surface area of the lower wall 1432 (e.g., 50% of the surface area, 60% of the surface area, 70% of the surface area, 80% of the surface area, 90% of the surface area, or 100% of the surface area, or any range including and between any of the foregoing values).

In some embodiments, the spinal implant device 1400 can include features to limit or reduce movement of the spinal implant device 1400 between the vertebrae. The spinal implant device 1400 can include a plurality of ridges 1414. The ridges 1414 can form a portion of the upper wall 1430, a portion of the lower wall 1432, or both a portion of the upper wall 1430 and a portion of the lower wall 1432.

The spinal implant device 1400 can include a cavity 1418. In some embodiments, the proximal end 1422 can form the back inner surface of the cavity 1418. In some embodiments, the distal end 1420 can form the front inner surface of the cavity 1418. In some embodiments, the two opposing side walls 1424, 1426 can form the side inner surfaces of the cavity 1418. In some embodiments, the upper wall 1430 can form a portion of the top inner surface of the cavity 1418. In some embodiments, the lower wall 1432 can form the bottom inner surface of the cavity 1418.

In some methods of use, the side walls 1424, 1426 can be configured to reduce in height. In some embodiments, the side walls 1424, 1426 are configured to be compressed under a normal load from the vertebral bodies. The side walls 1424, 1426 can compress due to the shape of the windows 1416. The side walls 1424, 1426 can compress due to the location of the windows 1416. The side walls 1424, 1426 can compress due to the size of the windows 1416. The side walls 1424, 1426 can compress due to the number of windows 1416. The upper wall 1430 and the lower wall 1432 can compress material within the cavity 1418. In some embodiments, the upper wall 1430 moves toward the lower wall 1432. In some embodiments, the lower wall 1432 moves toward the upper wall 1430. In some embodiments, both the upper wall 1430 and the lower wall 1232 move inward.

Figure 107:
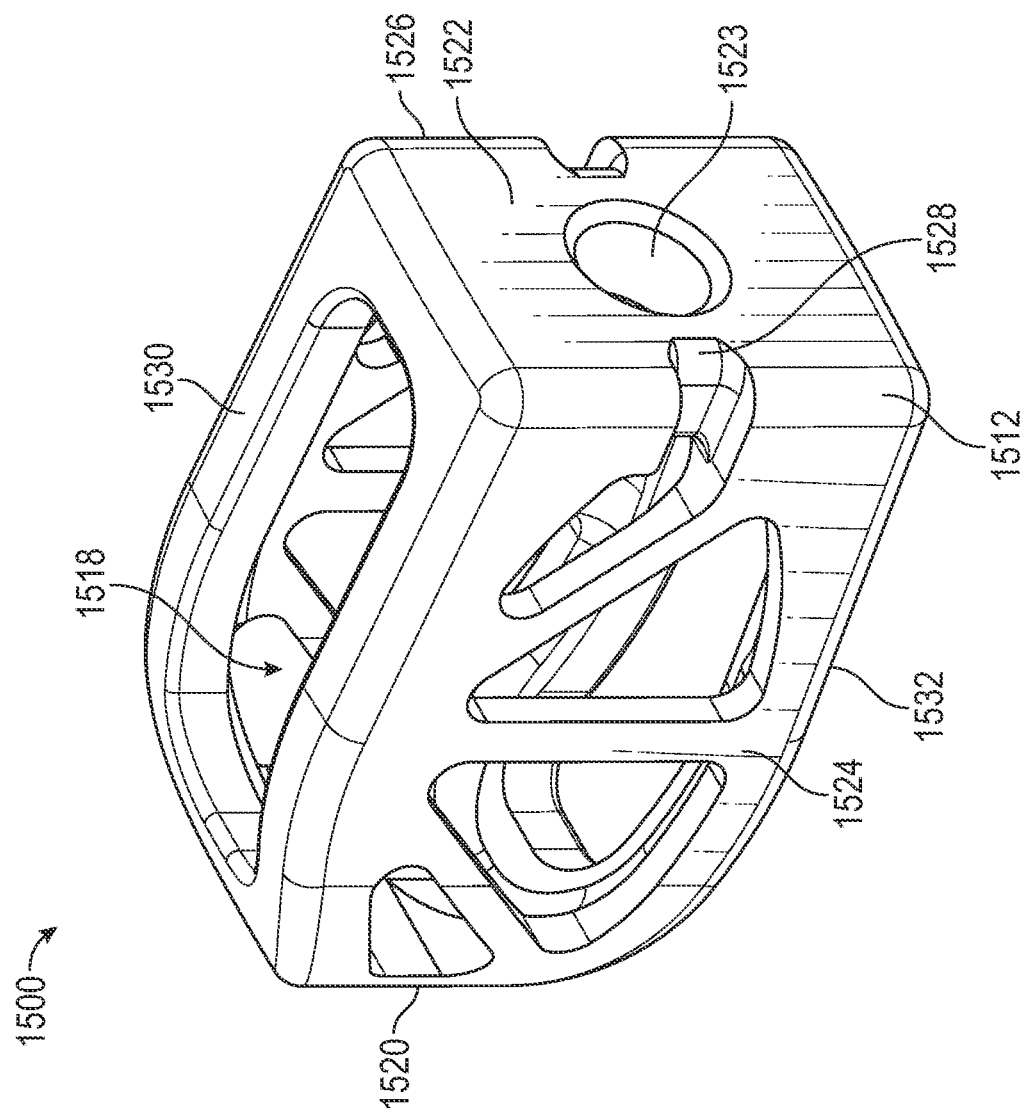
FIG. 107 is a perspective view of an embodiment of a spinal implant device.

FIG. 107 illustrates a perspective view of a spinal implant device 1500. The spinal implant device 1500 can include any of the features of the spinal implant device 10, 10A, 100, 200, 300, 400, 500, 600, 700, 800, 900, 1000, 1100, 1200, 1300, 1400 as described herein and can be used in any method or method step described herein. The spinal implant device 1500 can include a body structure 1512. The spinal implant device 1500 can be similar to the spinal implant device 1400, with certain differences described herein. Referring back to FIG. 101, in some embodiments, the spinal implant device 1400 can include ridges 1414. Referring to FIG. 107, in some embodiments, the spinal implant device 1500 does not include ridges. Referring back to FIG. 101, in some embodiments, the spinal implant device 1400 can include the feature 1428 designed to facilitate placement of the spinal implant device 1400. In some embodiments, the feature 1428 extends through a portion of the fourth open window 1416. In some embodiments, the feature 1428 extends through a portion of the third open window 1416. In some embodiments, the feature 1428 extends through a portion of the second open window 1416. Referring to FIG. 107, in some embodiments, the spinal implant device 1500 can include a feature 1528 designed to facilitate placement of the spinal implant device 1500. In some embodiments, the feature 1528 extends through only a portion of a fourth open window 1416. Any spinal implant device can have any additional feature described herein, alone or in combination. Any spinal implant device can omit any feature described herein.

Figure 108:
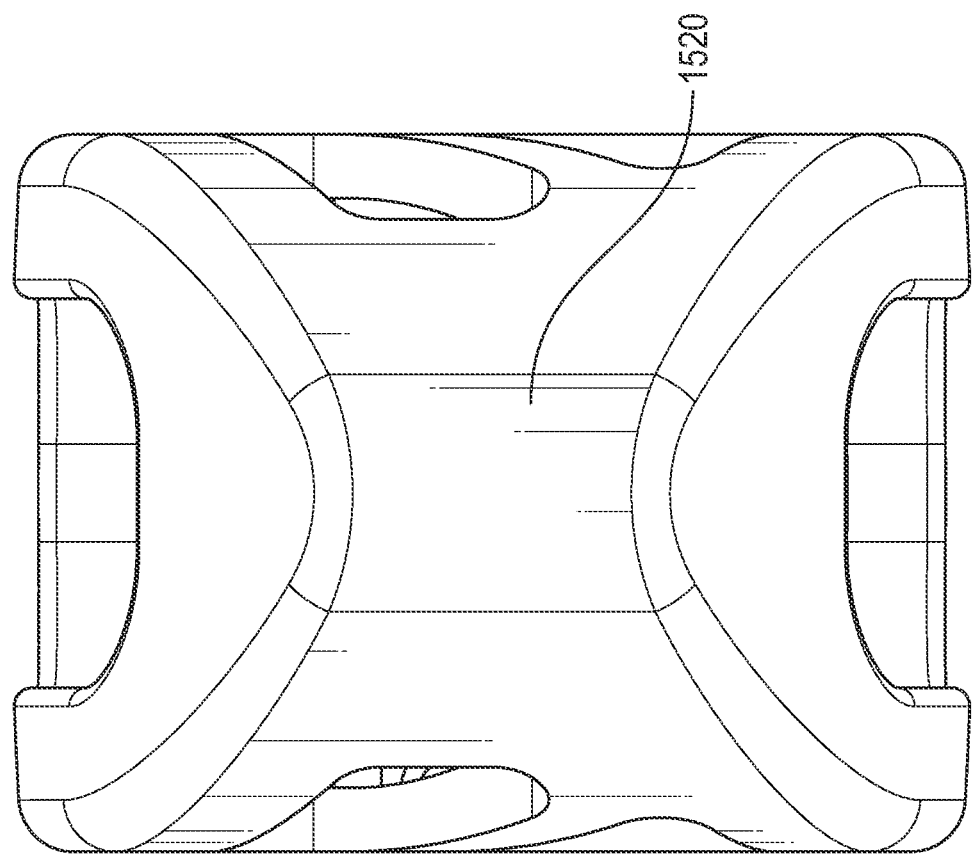
FIG. 108 is a distal view of the spinal implant device of FIG. 107.

FIG. 108 is a distal view of the spinal implant device 1500. The spinal implant device 1400 can include a distal end 1520. The distal end 1520 can be tapered to facilitate insertion.

Figure 109:
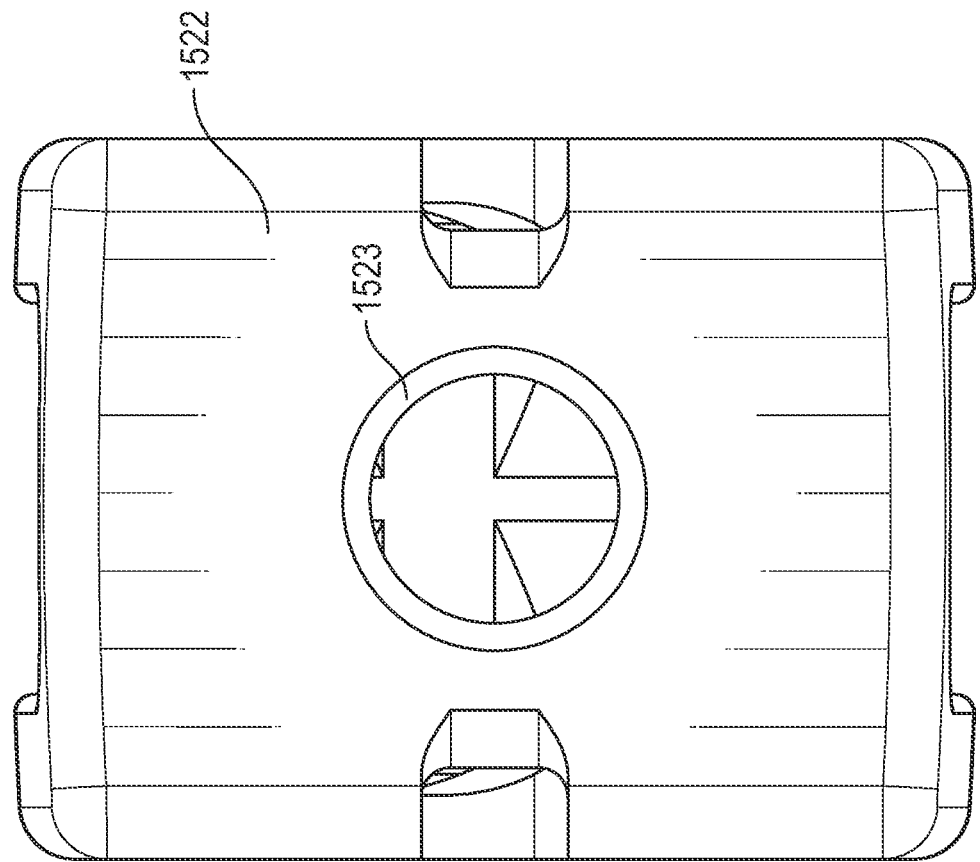
FIG. 109 is a proximal view of the spinal implant device of FIG. 107.

FIG. 109 is a proximal view of the spinal implant device 1500. The spinal implant device 1500 can include a proximal end 1522. The proximal end 1522 can be shaped to interfit with an insertion tool. In some embodiments, the proximal end 1522 can include an opening 1523.

Figure 110:
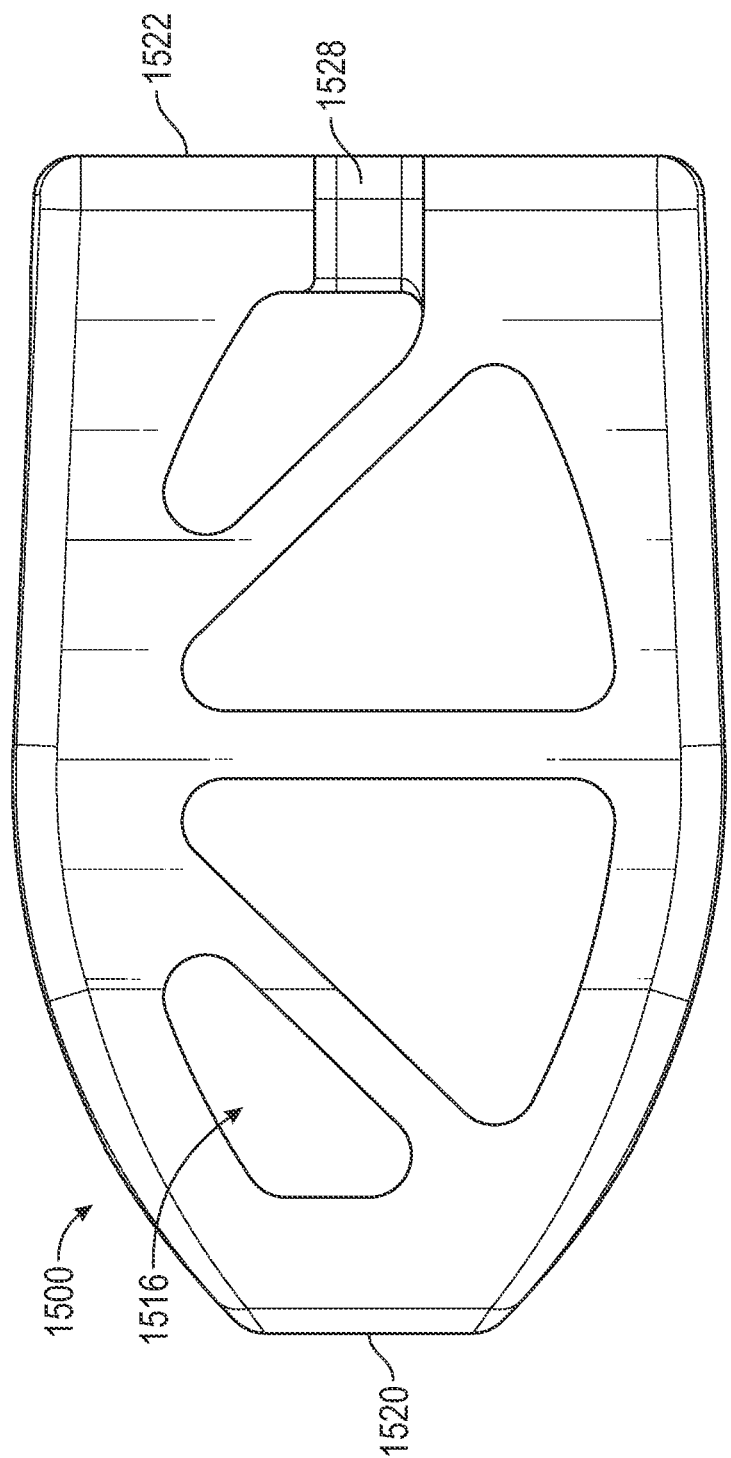
FIG. 110 is a side view of the spinal implant device of FIG. 107.

FIG. 110 is a side view of the spinal implant device 1500. The length of the spinal implant device 1500 can be the distance between the distal end 1520 and the proximal end 1522. The spinal implant device 1500 can include two opposing side walls including a first side wall 1524 and a second side wall 1526. FIG. 110 illustrates the first side wall 1524, but the second side wall 1526 can include the same or similar features.

In some embodiments, each side wall 1524, 1526 can include one or more open windows 1516. In the illustrated embodiment, each side wall 1524, 1526 includes four open windows 1516. The first open window 1516 can be substantially triangular and near the distal end 1520. The second open window 1516 can be substantially triangular near the middle of the side wall 1524, 1526. The third open window 1516 can be substantially triangular near the middle of the side wall 1524, 1526. The fourth open window 1516 can be substantially triangular and near the proximal end 1520. The first window 1516 and the fourth window 1516 can be the same or similar size. The second window 1516 and the third window 1516 can be the same or similar size.

In some embodiments, the one or more open windows 1516 can allow the side walls 1524, 1526 to flex. In some embodiments, the one or more open windows 1516 can be configured to be compressed. The compression of the side walls 1524, 1526 can promote fusion by increasing the load on the material contained within the spinal implant device 1500.

In some embodiments, each of the two opposing side walls 1524, 1526 can include the feature 1528 designed to facilitate placement of the spinal implant device 1500 by coupling with an insertion tool. In some embodiments, the feature 1528 can include a channel or groove that originates at the proximal end 1522 and can extend to the one or more open windows 1516. In some embodiments, the feature 1528 extends through a portion of the fourth open window 1516.

Figure 111:
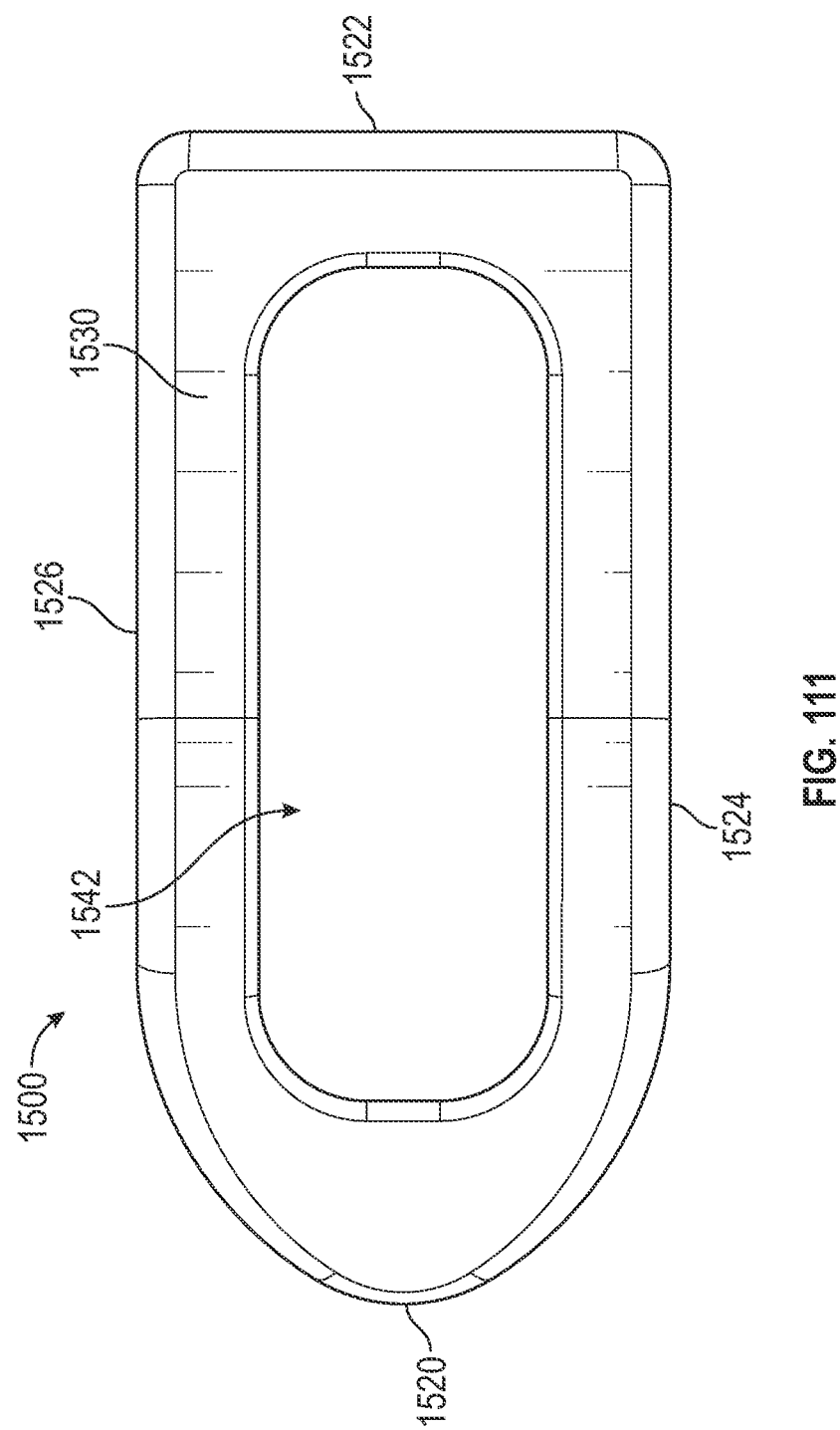
FIG. 111 is a top view of the spinal implant device of FIG. 107.

FIG. 111 is a top view of the spinal implant device 1500. The spinal implant device 1500 can include an upper wall 1530. In some embodiments, the upper wall 1530 includes one opening 1542.

Figure 112:
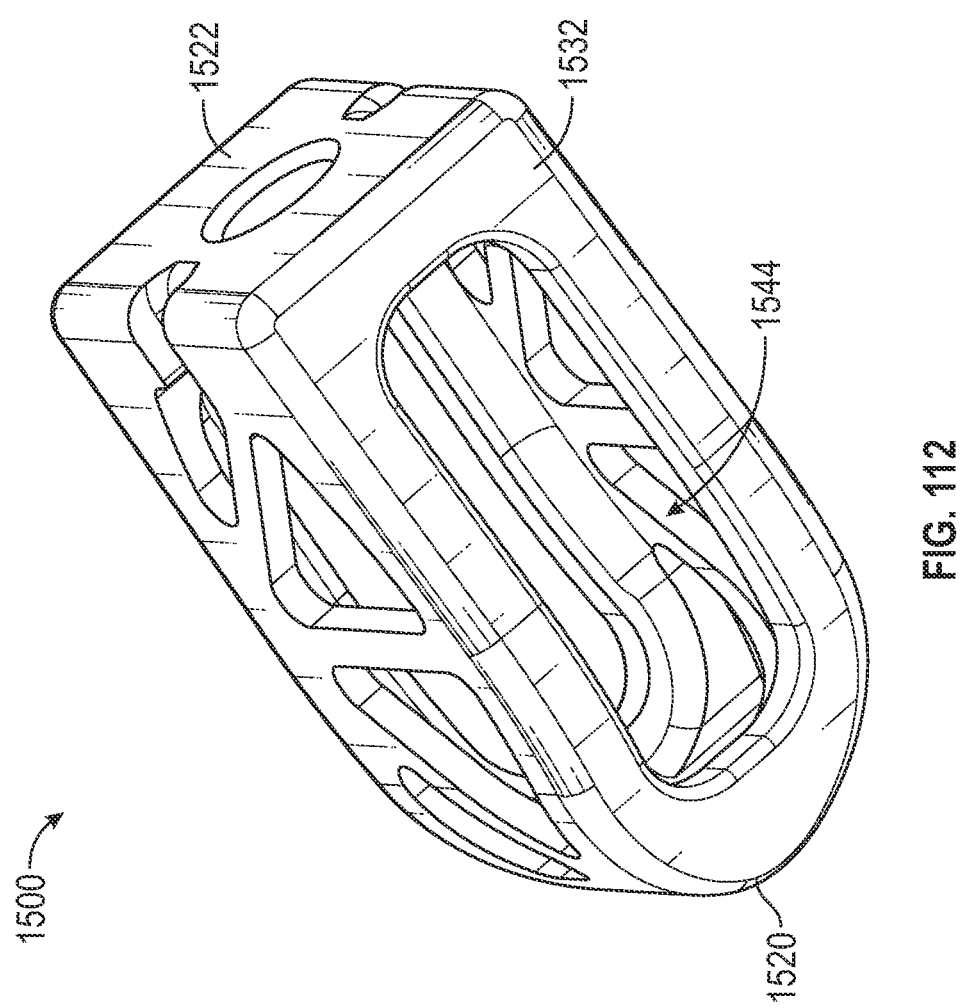
FIG. 112 is a bottom perspective view of the spinal implant device of FIG. 107.

FIG. 112 is a bottom perspective view of the spinal implant device 1500. The spinal implant device 1500 can include a lower wall 1532. In some embodiments, the lower wall 1532 can include one opening 1544.

The spinal implant device 1500 can include a cavity 1518. In some embodiments, the proximal end 1522 can form the back inner surface of the cavity 1518. In some embodiments, the distal end 1520 can form the front inner surface of the cavity 1518. In some embodiments, the two opposing side walls 1524, 1526 can form the side inner surfaces of the cavity 1518. In some embodiments, the upper wall 1530 can form a portion of the top inner surface of the cavity 1518. In some embodiments, the lower wall 1532 can form the bottom inner surface of the cavity 1518.

In some methods of use, the side walls 1524, 1526 can be configured to be compressed under a load from the vertebral bodies. The one or more windows 1516 can compress. In some embodiments, one or more of the upper wall 1530 and the lower wall 1232 move inward.

Figure 113:
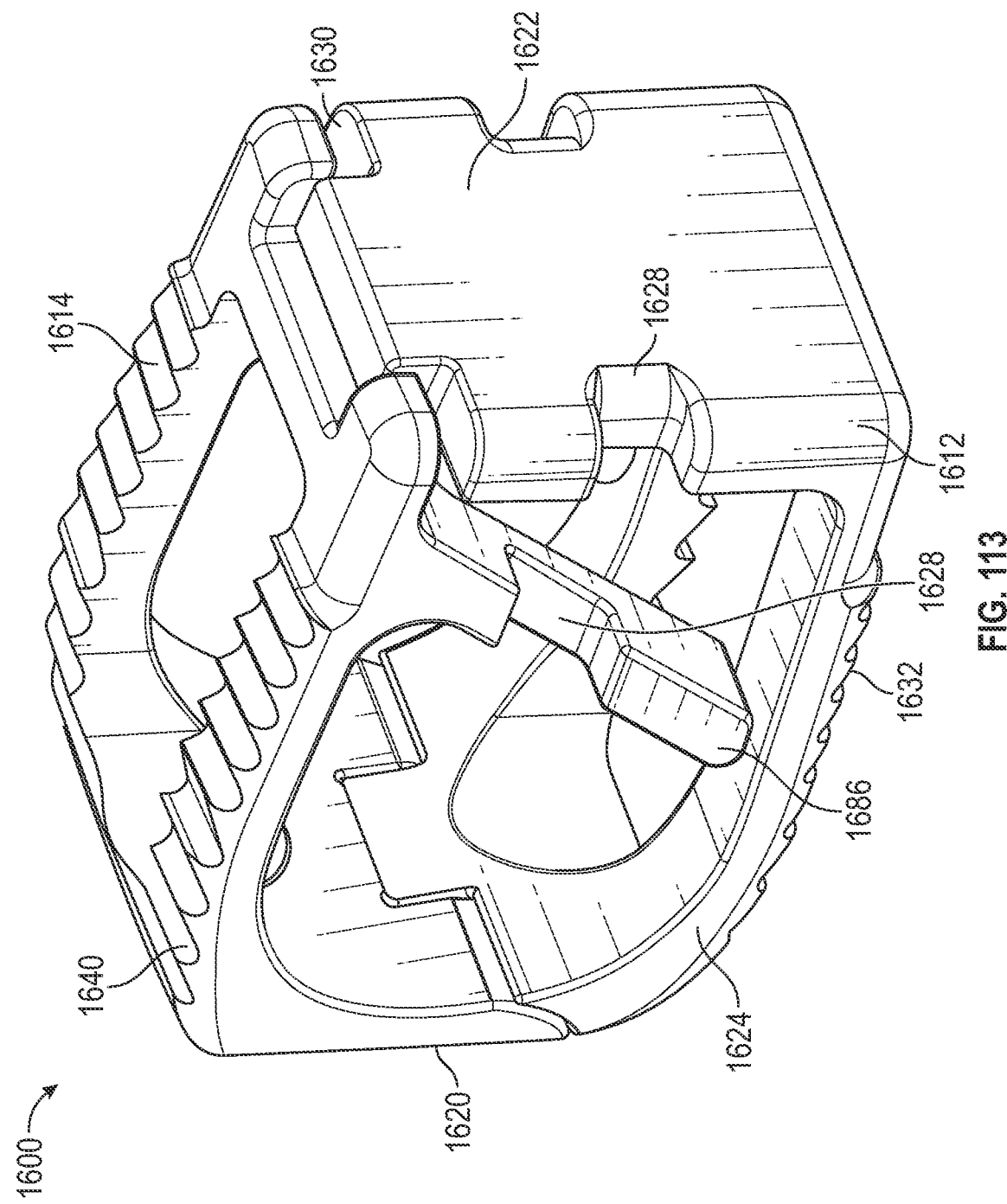
FIG. 113 is a perspective view of an embodiment of a spinal implant device with a movable lid shown in a closed position.

FIG. 113 illustrates a perspective view of a spinal implant device 1600. The spinal implant device 1600 can include any of the features of the spinal implant device 10, 10A, 100, 200, 300, 400, 500, 600, 700, 800, 900, 1000, 1100, 1200, 1300, 1400, 1500 as described herein and can be used in any method or method step described herein. The compression of the spinal implant device 1600 can allow for increased load on the material disposed within the spinal implant device 1600 as described herein. The spinal implant device 1600 can include a body structure 1612.

Figure 114:
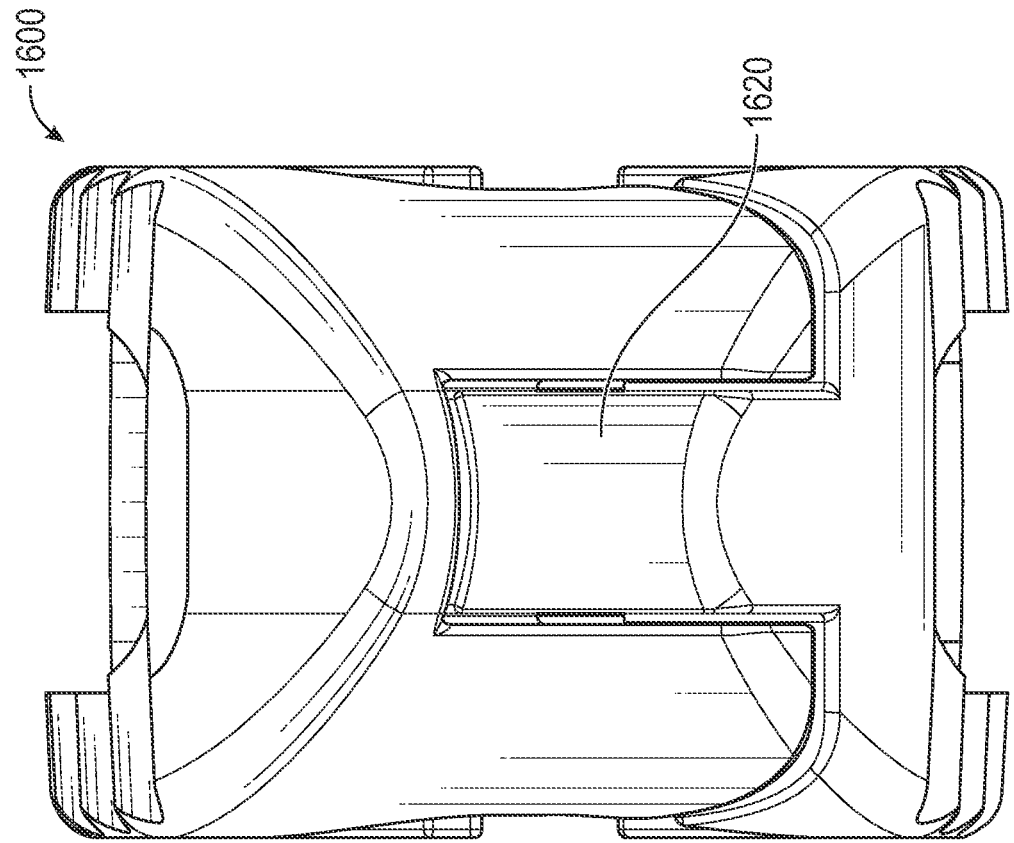
FIG. 114 is a distal view of the spinal implant device of FIG. 113.

FIG. 114 is a distal view of the spinal implant device 1600. The spinal implant device 1600 can include a distal end 1620. In some methods of use, the distal end 1620 can be the insertion end.

Figure 115:
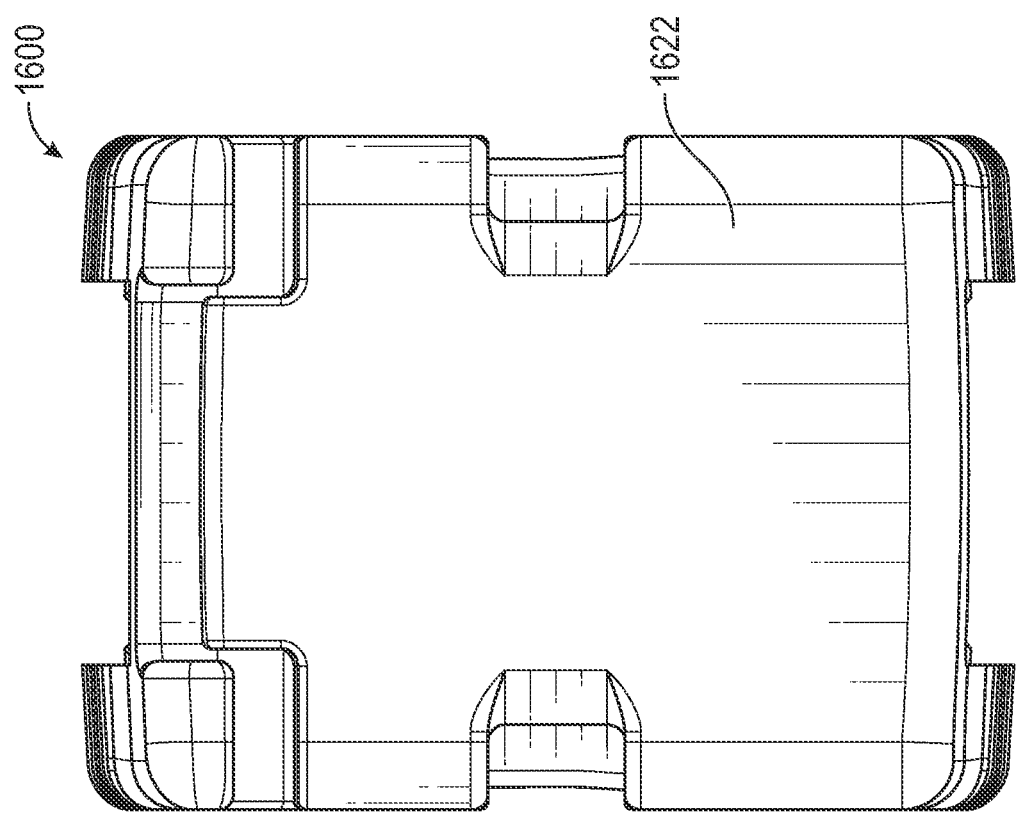
FIG. 115 is a proximal view of the spinal implant device of FIG. 113.

FIG. 115 is a proximal view of the spinal implant device 1600. The spinal implant device 1600 can include a proximal end 1622. The distal end 1620 can form the leading end and the proximal end 1622 can form the trailing end.

Figure 116:
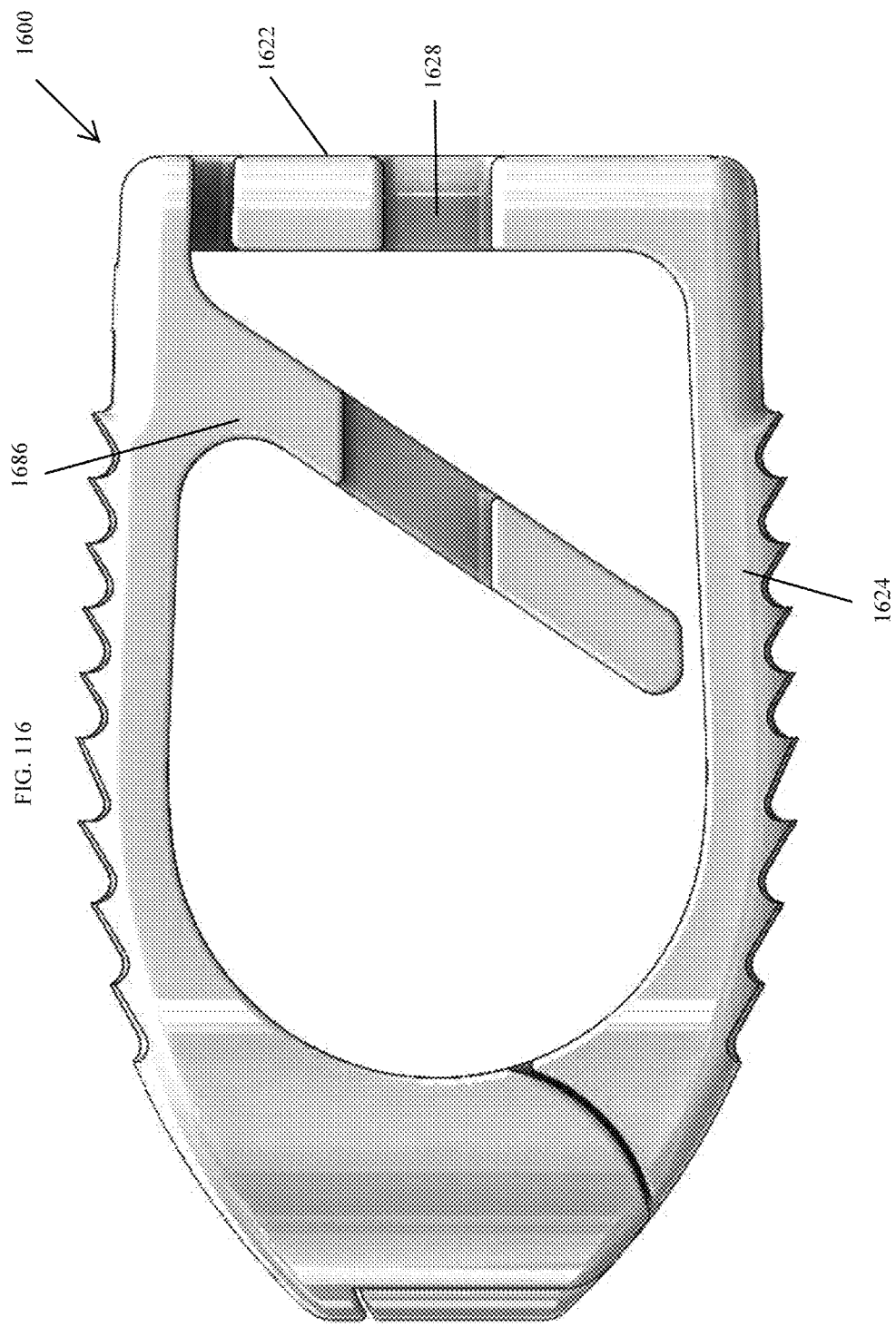
FIG. 116 is a side view of the spinal implant device of FIG. 113.
Figure 119:
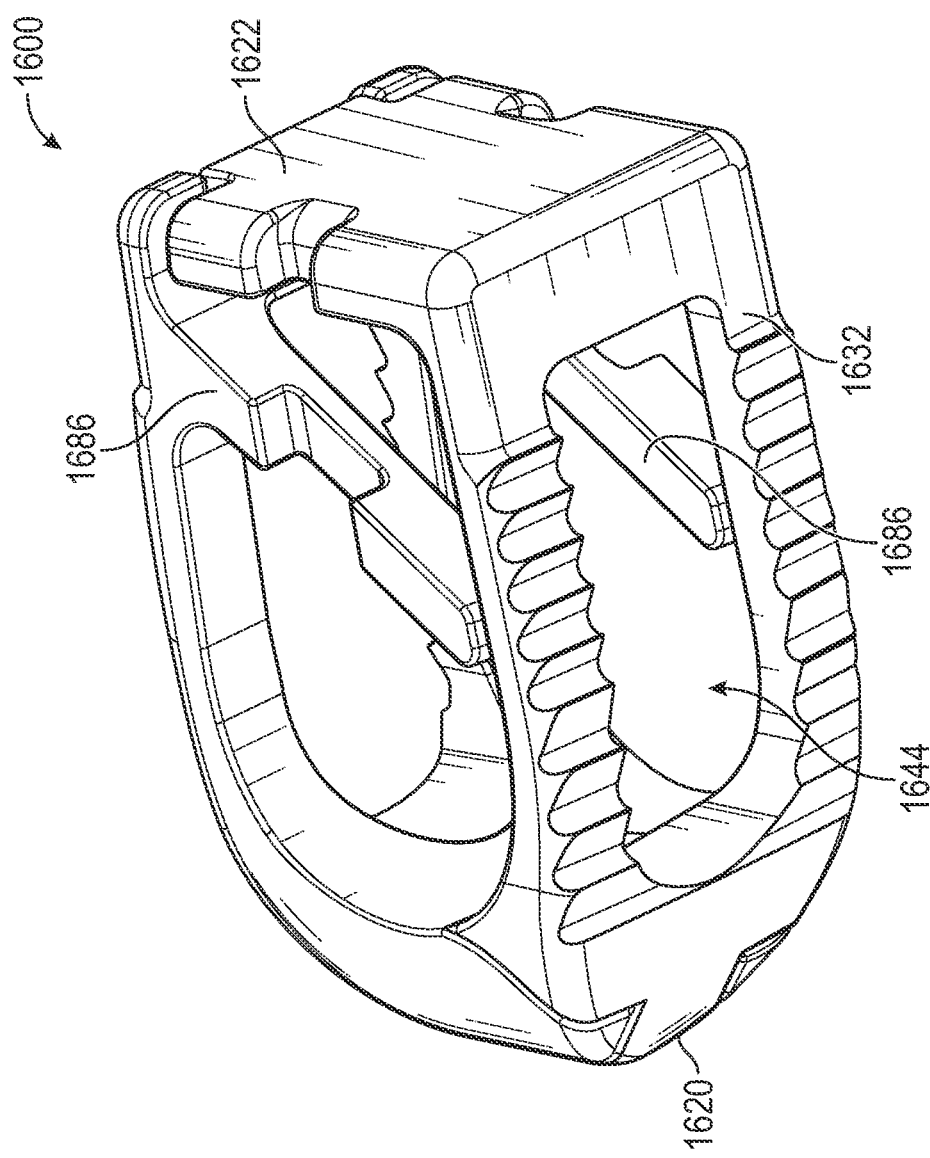

FIG. 116 is a side view of the spinal implant device 1600. The length of the spinal implant device 1600 can be the distance between the distal end 1620 and the proximal end 1622. The spinal implant device 1600 can include two opposing side walls including a first side wall 1624 and a second side wall 1626. FIG. 119 illustrates the first side wall 1624, but the second side wall 1626 can include the same or similar features. The first side wall 1624 can be substantially L shaped. The first side wall 1624 can include a proximal portion and a lower portion. The proximal portion can extend along the proximal end 1622, or a portion thereof. The lower portion can extend along a lower wall 1632, or a portion thereof.

In some embodiments, each of the two opposing side walls 1624, 1626 can include a feature 1628 to facilitate placement of the spinal implant device 1600. In some embodiments, the feature 1628 can include a channel to accept an insertion tool. In some embodiments, the feature 1628 can extend from the proximal end 1622 of the spinal implant device 1600 toward the distal end 1620. In some embodiments, the feature 1628 can form a groove in the proximal end 1622. In some embodiments, the feature 1628 can form a groove in the proximal portions of the side wall 1624, 1626.

Figure 117:
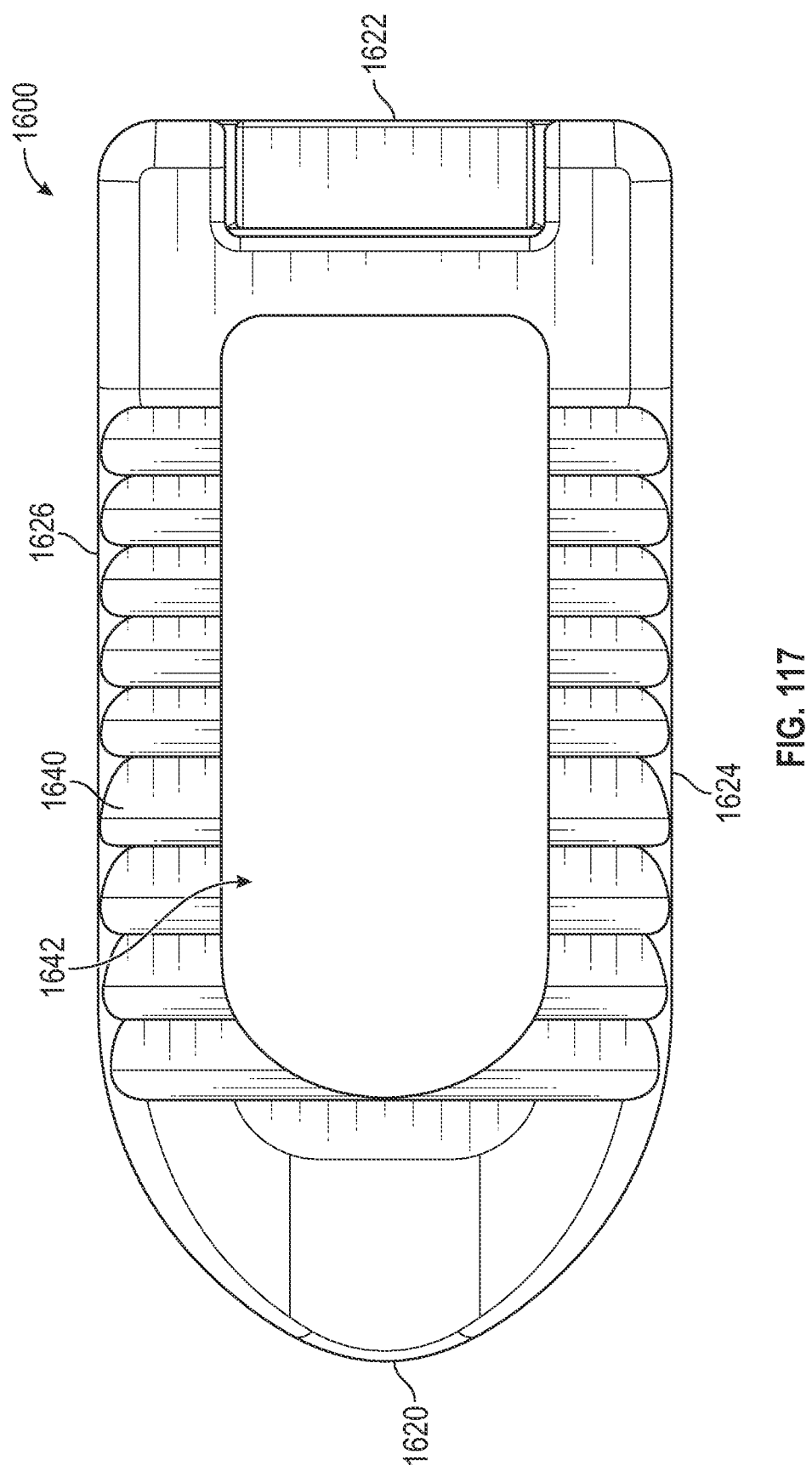
Figure 118:
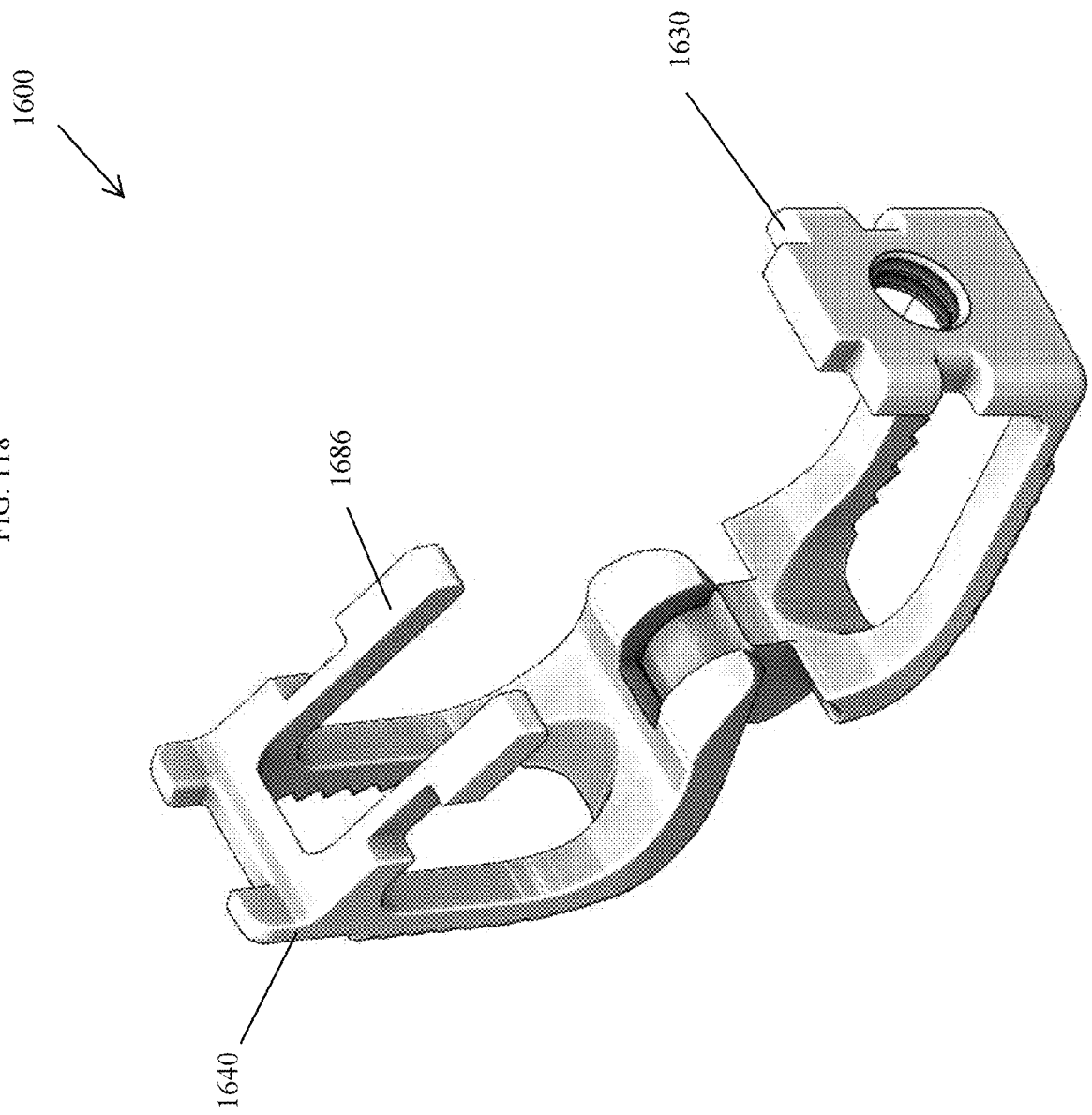

FIG. 117 is a top view of the spinal implant device 1600. The spinal implant device 1600 can include a movable lid 1640. FIG. 117 is a top view of the spinal implant device 1600 with the movable lid 1640 closed. FIG. 118 is a top perspective view of the spinal implant device 1600 with the movable lid 1640 opened.

The spinal implant device 1600 can include one or more openings 1642 extending through the movable lid 1640. In some embodiments, the movable lid includes one elongate opening 1642.

The movable lid 1640 can include one or more compression supports 1686. The first compression support 1686 can extend along the first side wall 1624. The first compression support 1686 can have the same thickness of the first side wall 1624. The first compression support 1686 can be angled downward toward the distal end 1620. The first compression support 1686 can be coplanar with the first side wall 1624. The second compression support 1686 can extend along the second side wall 1626. The second compression support 1686 can have the same thickness of the second side wall 1626. The second compression support 1686 can be angled downward toward the distal end 1620. The second compression support 1686 can be coplanar with the second side wall 1626. The movable lid 1640 can extend between the first side wall 1624 and the second side wall 1626. The movable lid 1640 can extend along the width of the spinal implant device 1600. The one or more compression supports 1686 can have a U shaped configuration with the movable lid 1640. In some embodiments, the compression supports 1686 are connected between the first side wall 1624 and the second side wall 1626. In some embodiments, the compression supports 1686 are connected between the first side wall 1624 and the second side wall 1626 by the movable lid 1640. In some embodiments, the compression supports 1686 are connected between the first side wall 1624 and the second side wall 1626 at a point below the movable lid 1640. In some embodiments, the compression supports 1686 are not connected between the first side wall 1624 and the second side wall 1626.

The spinal implant device 1600 can include an upper wall 1630. The upper wall 1630 can include a portion near the distal end 1620 and a portion near the proximal end 1622. In some embodiments, the upper wall 1630 forms a ledge to prevent further compression of the movable lid 1640 near the proximal end 1622.

In some embodiments, the movable lid 1640 can include a feature 1628. The one or more compression supports 1686 can include the feature 1628. In some embodiments, the feature 1628 on proximal end 1622 and the feature 1628 on the movable lid 1640 can allow an insertion tool to retain the movable lid 1640 during placement or removal of spinal implant device 1600. The compression supports 1686 can be offset from an inner surface of the spinal implant device 1600 during insertion. In some embodiments, the application of load applied by the vertebra makes the compression supports 1686 contact the inner surface of the spinal implant device 1600. In some embodiments, the application of load creates a secondary closed position. In some embodiments, the application of the normal anatomical load applied by the vertebra makes the compression supports 1686 contact the inner surface of the spinal implant device 1600 near the side walls 1624, 1626. The movable lid 1640 can hover over the upper wall 1630 until application of a load. In some embodiments, the application of a greater than normal anatomical load applied by the vertebra makes the movable lid 1640 move toward and, in some cases, contact the upper wall 1630 near the proximal end 1622. In some embodiments, the application of a load applied by the vertebra makes the compression supports 1686 flex. In some embodiments, the one or more compression supports 1686 support the movable lid 1640 along the side walls 1624, 1626 under application of a load. In some embodiments, the one or more compression supports 1686 support the movable lid 1640 under normal anatomical loads. In some embodiments, the one or more compression supports 1686 support the movable lid 1640 such that the movable lid 1640 is offset from contacting the upper wall 1630 under normal anatomical loads. In some embodiments, the one or more compression supports 1686 provide stability to the movable lid 1640 after compression by the vertebra.

The upper wall 1630 can include a projection near the proximal end 1622. In some embodiments, a portion of the upper wall 1630 is higher than another surface of the upper wall 1630 near the proximal end 1622. In some embodiments, a portion of the upper wall 1630 extends between portions of the movable lid 1640.

FIG. 119 is a bottom perspective view of the spinal implant device 1600. The spinal implant device 1600 can include a lower wall 1632. The lower wall 1632 can span between the distal end 1620 and the proximal end 1022. The lower wall 1632 can include one or more openings 1644.

The lower wall 1632 can provide a load supporting surface. In some methods, the lower wall 1632 can be positioned adjacent to a vertebral end plate of an inferior vertebra. In some methods, when the spinal implant device 1600 is positioned between two adjacent vertebrae, the load supporting surfaces of the movable lid 1640 and the lower wall 1632 contact the vertebral end plates of the adjacent vertebrae. In some embodiments, the distance between the movable lid 1640 and the lower wall 1632 can form the height of the spinal implant device 1600. In some embodiments, the force of the vertebral bodies reduces this height.

In some embodiments, the spinal implant device 1600 can include features to limit or reduce movement of the spinal implant device 1600 between the vertebrae. The spinal implant device 1600 can include a plurality of ridges 1614. The ridges 1614 can form a portion of the movable lid 1640. The ridges 1614 can form a portion of the lower wall 1632. In some embodiments, the ridges 1614 can be directionally oriented as described herein.

Figure 120:
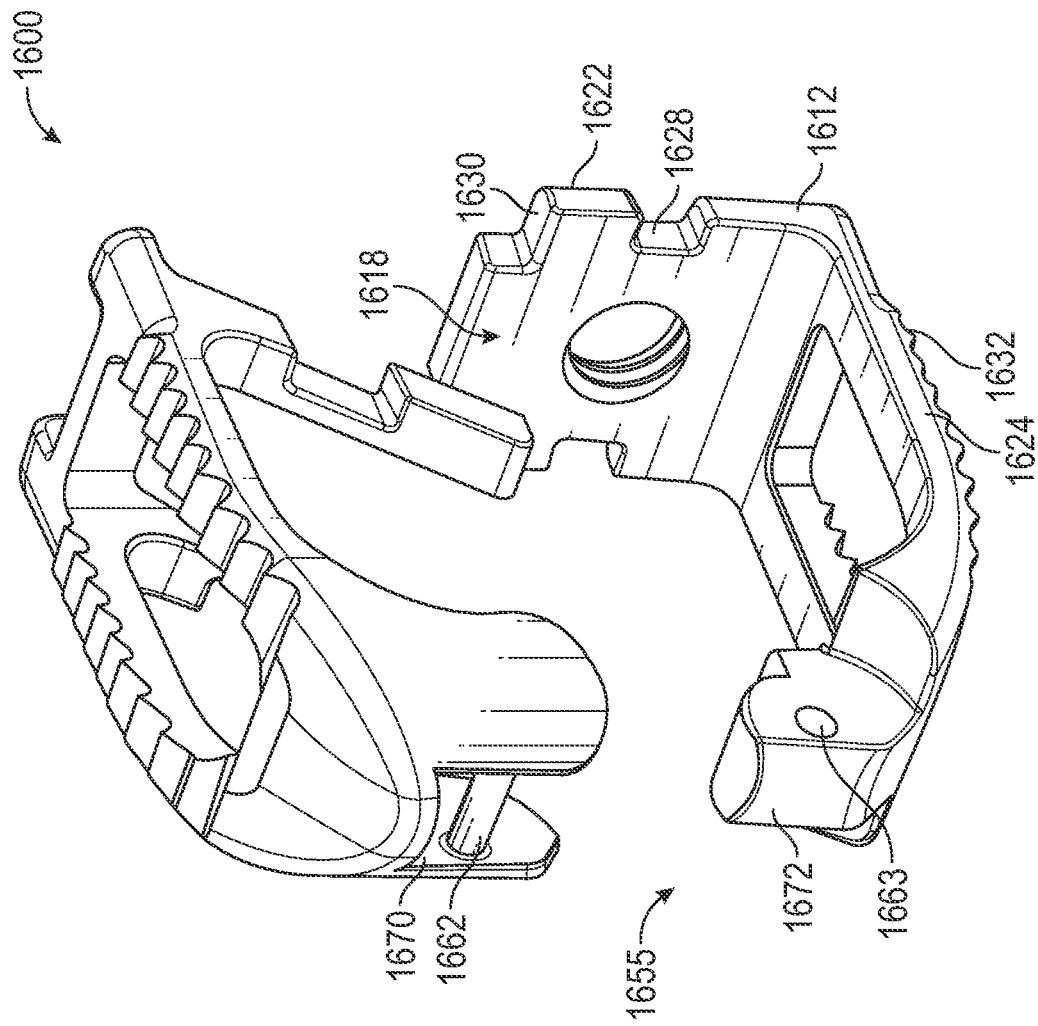

FIG. 120 is an exploded view of the movable lid 1640 of the spinal implant device 1600. In some embodiments, the spinal implant device 1600 can include a movable joint 1655. In some embodiments, the movable joint 1655 can couple the movable lid 1640 to the distal end 1620. The movable joint 1655 can allow for pivoting motion of the movable lid 1640.

In some embodiments, the movable lid 1640 can include one or more articulations 1662. The one or more articulations 1662 can extend between two opposing lateral posts 1670. The distal end 1620 can include a central post 1672. The central post 1672 can include one or more lumens 1663 configured to engage the one or more articulations 1662.

The spinal implant device 1600 can include a cavity 1618. In some embodiments, the proximal end 1622 can define the back inner surface of the cavity 1618. In some embodiments, the distal end 1620 can define the front inner surface of the cavity 1618. In some embodiments, the two opposing side walls 1624, 1626 and the one or more compression supports 1686 can define the side inner surfaces of the cavity 1618. In some embodiments, the movable lid 1640 can define the top inner surface of the cavity 1618. In some embodiments, the lower wall 1632 can define the bottom inner surface of the cavity 1618.

In some embodiments, the movable lid 1640 is configured to contact the vertebral end plate. The one or more compression supports 1686 of the movable lid 1640 can abut a portion of the body structure 1612 under normal anatomical loads thereby causing the compression supports 1686 to flex. In some embodiments, the movable lid 1640 can provide a load supporting surface for the adjacent vertebrae. In some methods, the load can be transferred from the movable lid 1640 to the one or more compression supports 1686. In some methods, the movable lid 1640 can be positioned adjacent to a vertebral end plate of a superior vertebra. The one or more compression supports 1686 of the movable lid 1640 can compress or flex when loaded. In some embodiments, the movable lid 1640 can move toward the upper wall 1630. In some embodiments, the movable lid 1640 can remain above the upper wall 1630 under normal anatomical loads. In some embodiments, the movable lid 1640 can abut the upper wall 1630 under normal anatomical loads. In some methods, the load can be transferred from the movable lid 1640 to the compression supports 1686 after compression.

Figure 121:
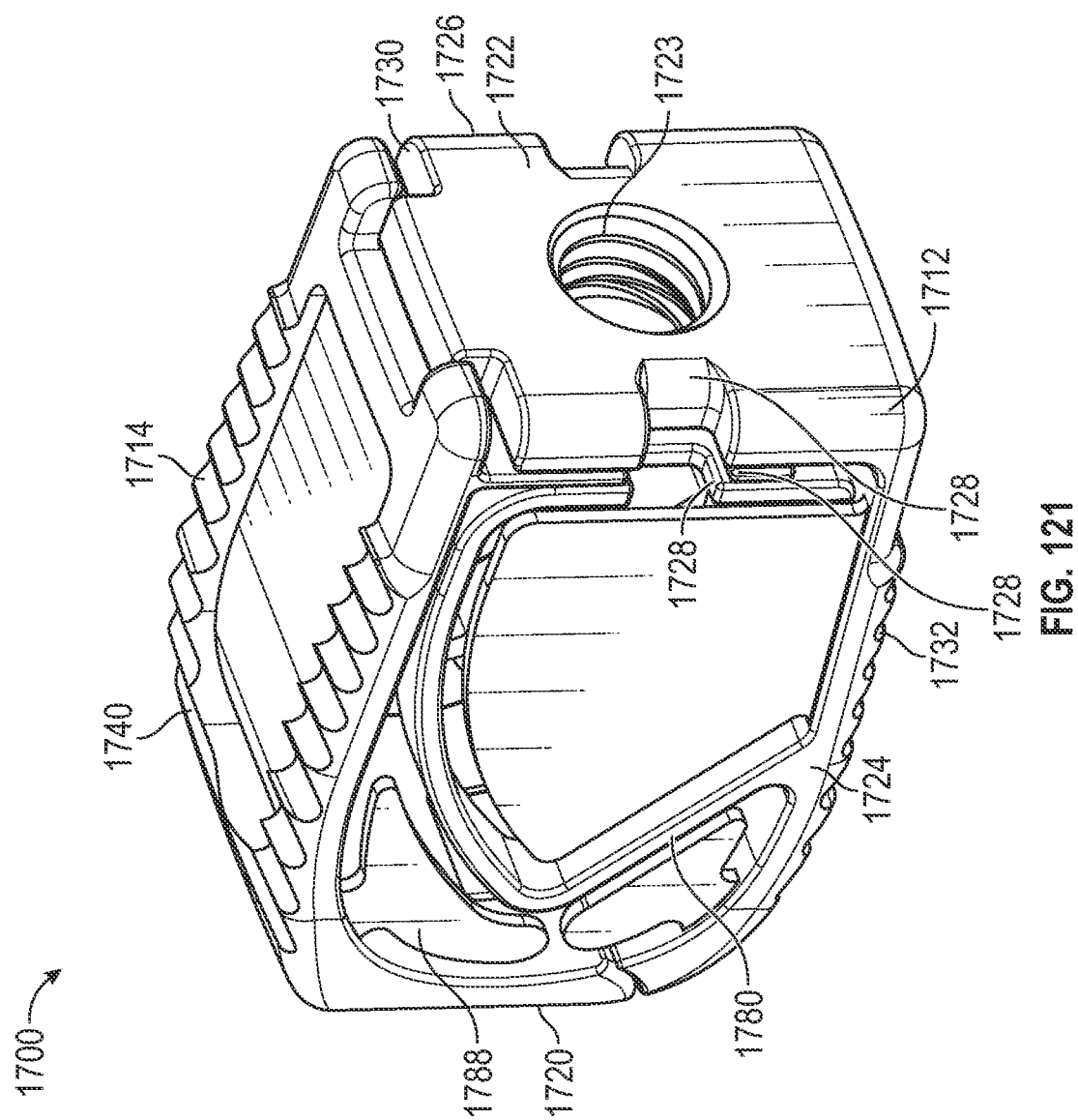

FIG. 121 illustrates a perspective view of a spinal implant device 1700. The spinal implant device 1700 can include any of the features of the spinal implant device 10, 10A, 100, 200, 300, 400, 500, 600, 700, 800, 900, 1000, 1700, 1200, 1300, 1400, 1500, 1600 as described herein and can be used in any method or method step described herein. The spinal implant device 1700 can include a body structure 1712. The spinal implant device 1700 is configured to be placed between adjacent vertebrae. The spinal implant device 1700 can includes features to allow for compression along the height of the spinal implant device 1700. The compression can promote fusion of material disposed within the spinal implant device 1700.

Figure 122:
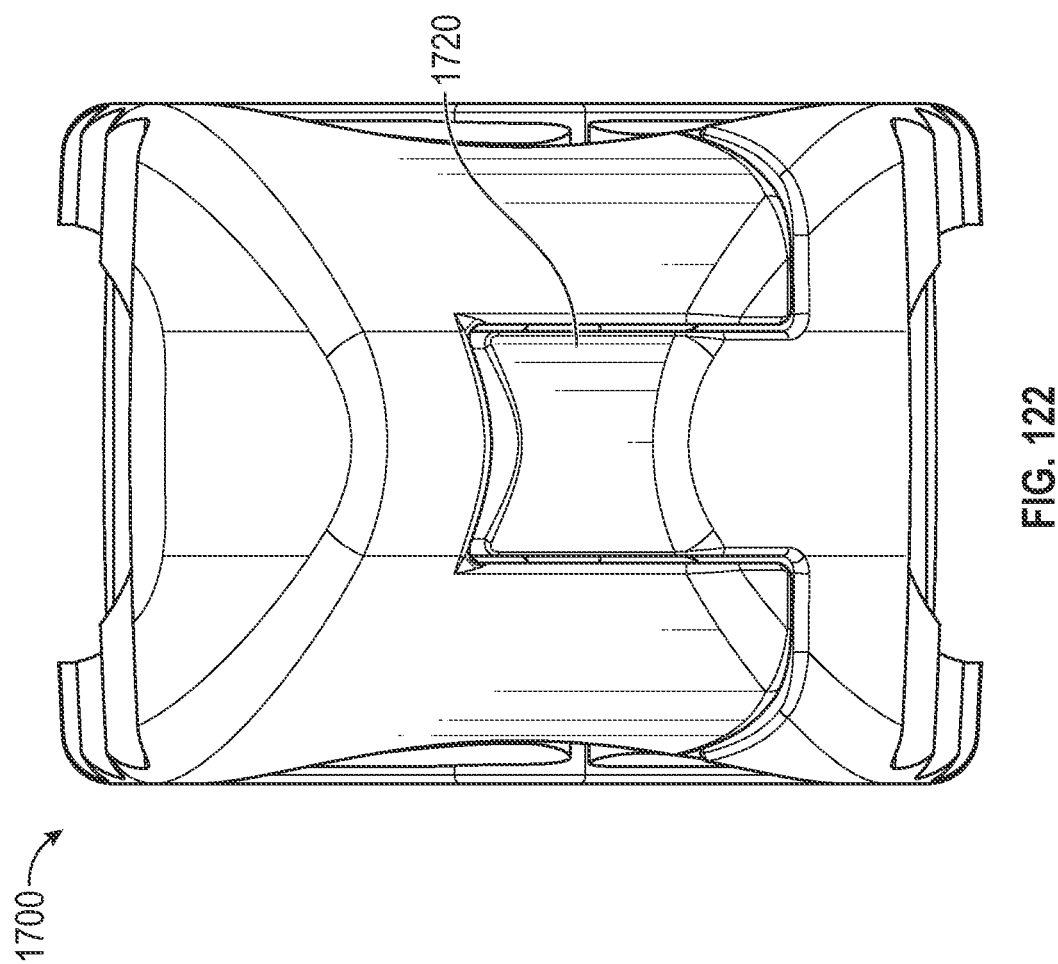

FIG. 122 is a distal view of the spinal implant device 1700. The spinal implant device 1700 can include a distal end 1720 which can be the insertion end.

Figure 123:
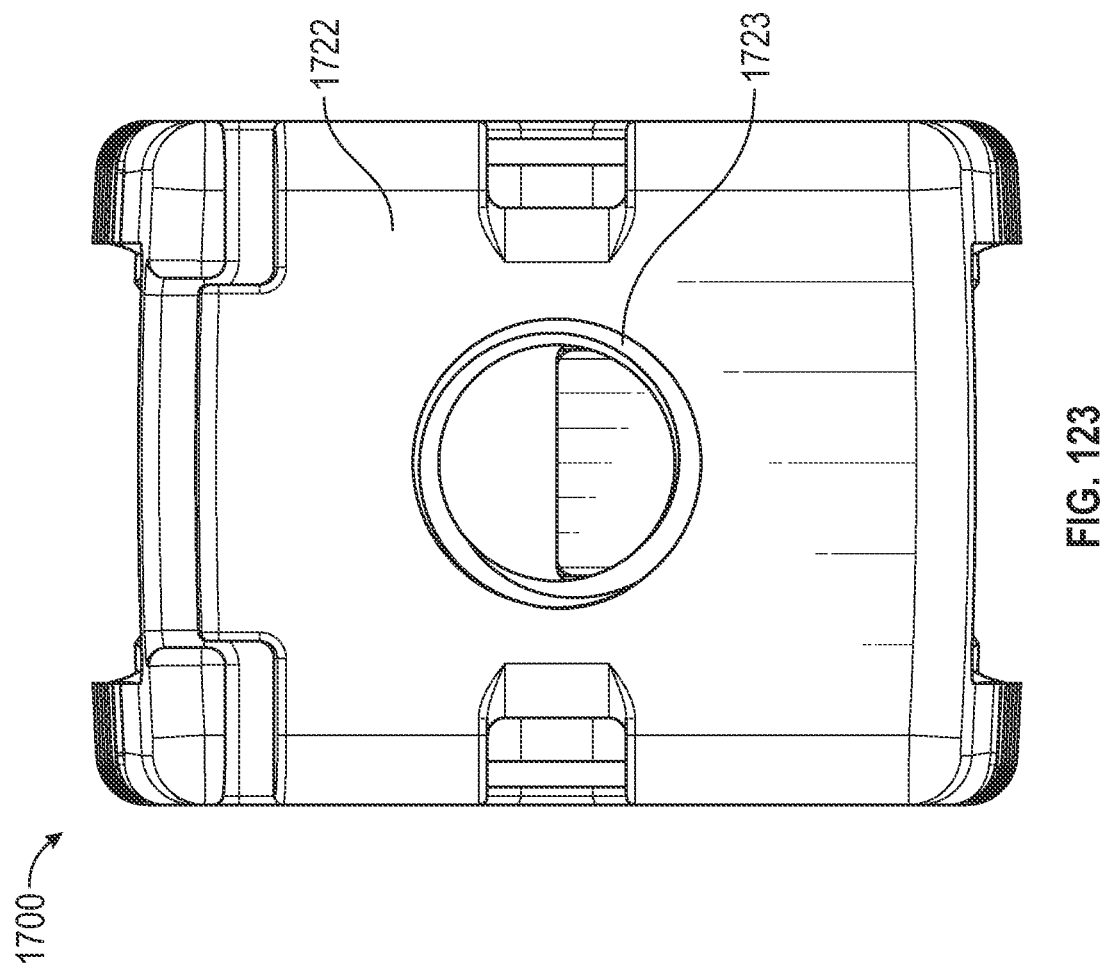

FIG. 123 is a proximal view of the spinal implant device 1700. The spinal implant device 1700 can include a proximal end 1722 which can be the trailing end. In some embodiments, the proximal end 1722 can include an opening 1723.

Figure 124:
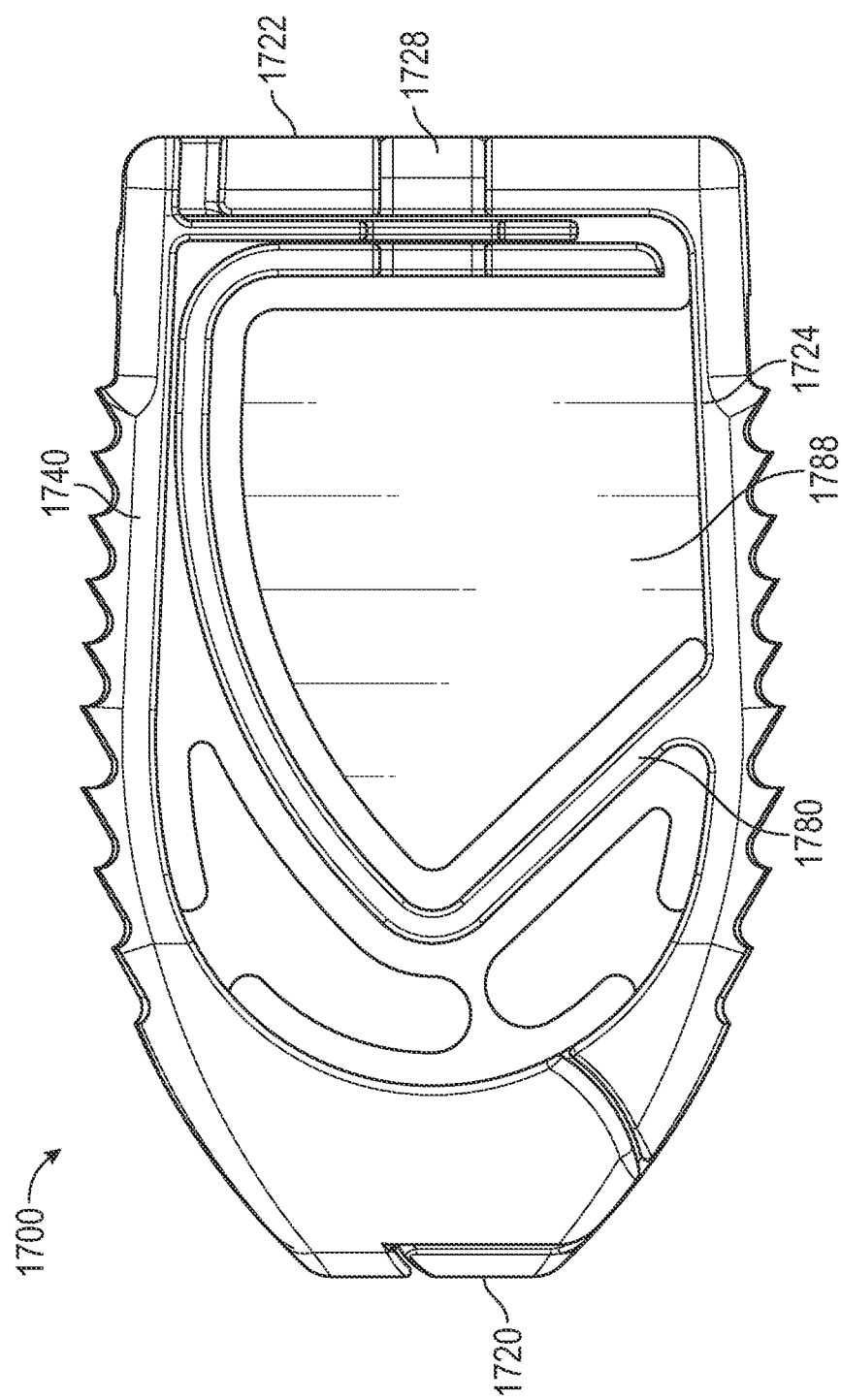

FIG. 124 is a side view of the spinal implant device 1700. The length of the spinal implant device 1700 can be the distance between the distal end 1720 and the proximal end 1722. The spinal implant device 1700 can include two opposing side walls including a first side wall 1724 and a second side wall 1726. FIG. 124 illustrates the first side wall 1724, but the second side wall 1726 can include the same or similar features. The first side wall 1724 and the second side wall 1726 can be identical.

The spinal implant device 1700 can include a connecting bar 1780. The connecting bar 1780 can include a first portion, a second portion, a third portion, a fourth portion, and a fifth portion.

The first portion of the connecting bar 1780 can be coupled to lower edge of the first side wall 1724. The first portion of the connecting bar 1780 can extend along a portion of the length of the first side wall 1724. The first portion of the connecting bar 1780 can have the same thickness of the first side wall 1724. The first portion of the connecting bar 1780 can have a different thickness as the first side wall 1724. The first portion of the connecting bar 1780 can have a variable thickness. The connecting bar 1780 can include a bend or curve. The connecting bar 1780 can form an acute angle. The connecting bar 1780 can form an obtuse angle. The connecting bar 1780 can form a right angle. The second portion of the connecting bar 1780 can extend upward from the bend toward the proximal end. The connecting bar 1780 can include another bend or curve.

The third portion of the connecting bar 1780 can be coupled to lower edge of the second side wall 1726. The third portion of the connecting bar 1780 can extend along a portion of the length of the second side wall 1726. The third portion of the connecting bar 1780 can have the same thickness of the second side wall 1726. The third portion of the connecting bar 1780 can have a different thickness as the second side wall 1726. The third portion of the connecting bar 1780 can have a variable thickness. The connecting bar 1780 can include a bend or curve. The connecting bar 1780 can form an acute angle. The connecting bar 1780 can form an obtuse angle. The connecting bar 1780 can form a right angle. The fourth portion of the connecting bar 1780 can extend upward from the bend toward the proximal end. The connecting bar 1780 can include another bend or curve.

The fifth portion of the connecting bar 1780 can extend downward from the bends toward the lower edge. The fifth portion of the connecting bar 1780 can be parallel or substantially parallel to the proximal end 1722. The fifth portion of the connecting bar 1780 can extend between the first side wall 1724 and the second side wall 1726. The fifth portion of the connecting bar 1780 can span the width of the spinal implant device 1700. The fifth portion of the connecting bar 1780 can be coplanar with the proximal end 1722. The fifth portion of the connecting bar 1780 can extend along the height of the spinal implant device 1700, or a portion thereof. The fifth portion of the connecting bar 1780 can include a predetermined distance offset from an inner surface of the spinal implant device 1700. This predetermined distance can be equal to the expected compression of the spinal implant device 1700. In some embodiments, the connecting bar 1780 is connected between the first side wall 1724 and the second side wall 1726. In some embodiments, the connecting bar 1780 is not connected between the first side wall 1724 and the second side wall 1726.

In some embodiments, the two opposing side walls 1724, 1726 can include one or more thin frameworks 1788. The first thin framework 1788 can extend below the connecting bar 1780. The second thin framework 1788 can extend proximal and below a portion of the connecting bar 1780. The third thin framework 1788 can extend proximal and above a portion of the connecting bar 1780. Other arrangements are contemplated. The one or more thin frameworks 1788 can have a smaller width than another portion of the side walls 1724, 1726. In some embodiments, the thin framework 1788 is solid. In some embodiments, the thin framework 1788 has the same material as the side walls 1724, 1726. In some embodiments, the thin framework has a different material than the side walls 1724, 1726. In some embodiments, the thin framework 1788 is porous or a mesh. In some embodiments, the thin framework 1788 allows bony ingrowth therethrough. In some embodiments, the thin framework 1788 allows the fusion of material therethrough. In some embodiments, a porous body is applied to the thin framework 1788. The porous bodies arranged on one or more side walls 1724, 1726 can allow material to flow outwardly from the spinal implant device 1700 to promote fusion.

In some embodiments, the thin framework can abut the connecting bar 1780 during compression. In some embodiments, the thin framework can limit compression by abutting the connecting bar 1780. In some embodiments, the thin framework can facilitate or control how the spinal implant device 1700 compresses.

In some embodiments, each of the two opposing side walls 1724, 1726 can include a feature 1728 to facilitate placement of the spinal implant device 1700. In some embodiments, the feature 1728 can include a channel to accept an insertion tool. In some embodiments, the feature 1728 can extend from the proximal end 1722 of the spinal implant device 1700 toward the distal end 1720. In some embodiments, the feature 1728 can form a groove in the proximal end 1722. In some embodiments, the third segment of the connecting bar 1780 can include the feature 1728 to facilitate placement of the spinal implant device 1700. In some embodiments, the connecting bar 1780 can include a channel to accept an insertion tool. In some embodiments, third segment of the connecting bar 1780 that extends between the first side wall 1724 and the second side wall 1726 can include the feature 1728. In some embodiments, the feature 1728 on proximal end 1722 and the feature 1728 on the third segment of the connecting bar 1780 can allow an insertion tool to retain the movable lid 1740 during placement or removal of spinal implant device 1700.

Figure 125:
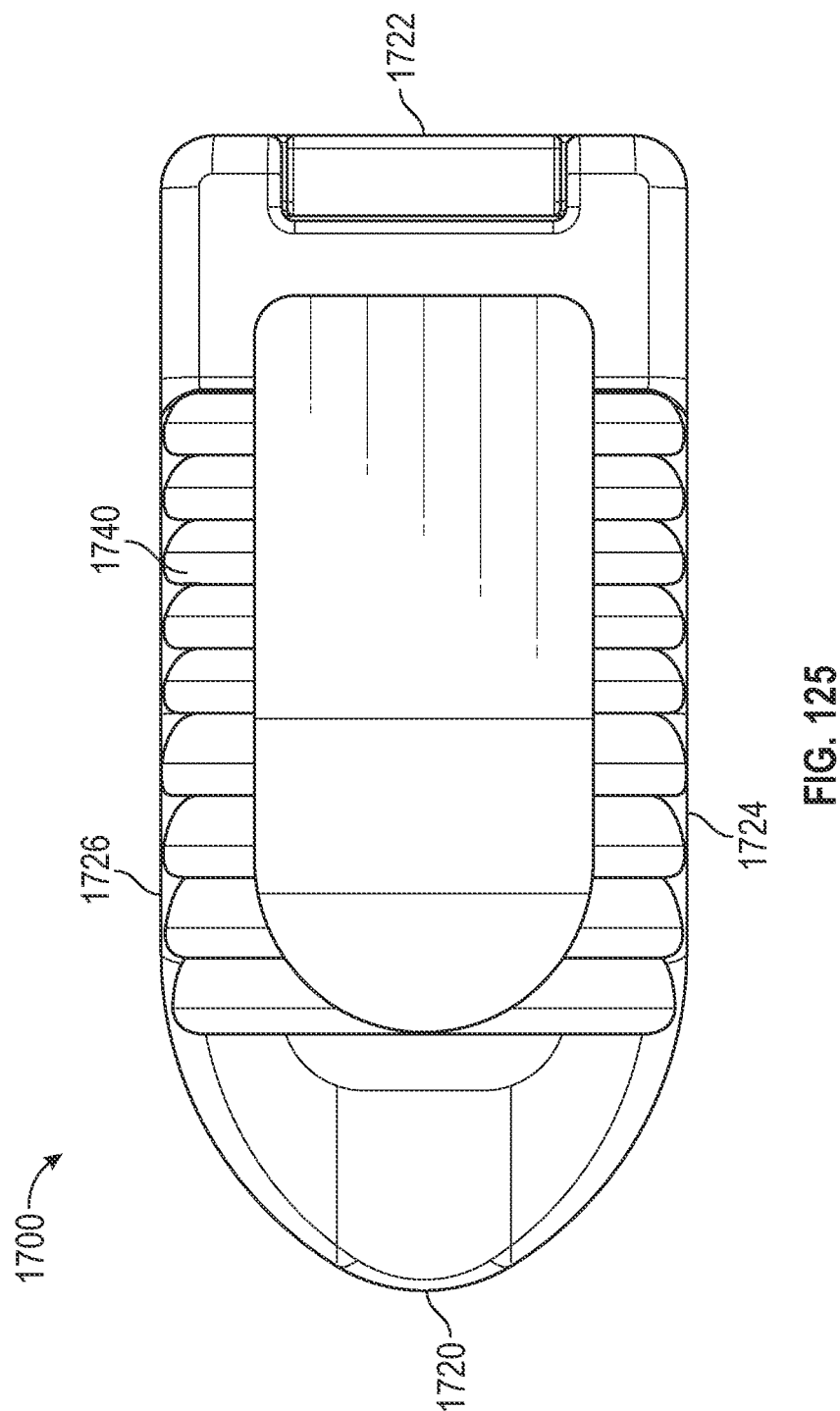
Figure 126:
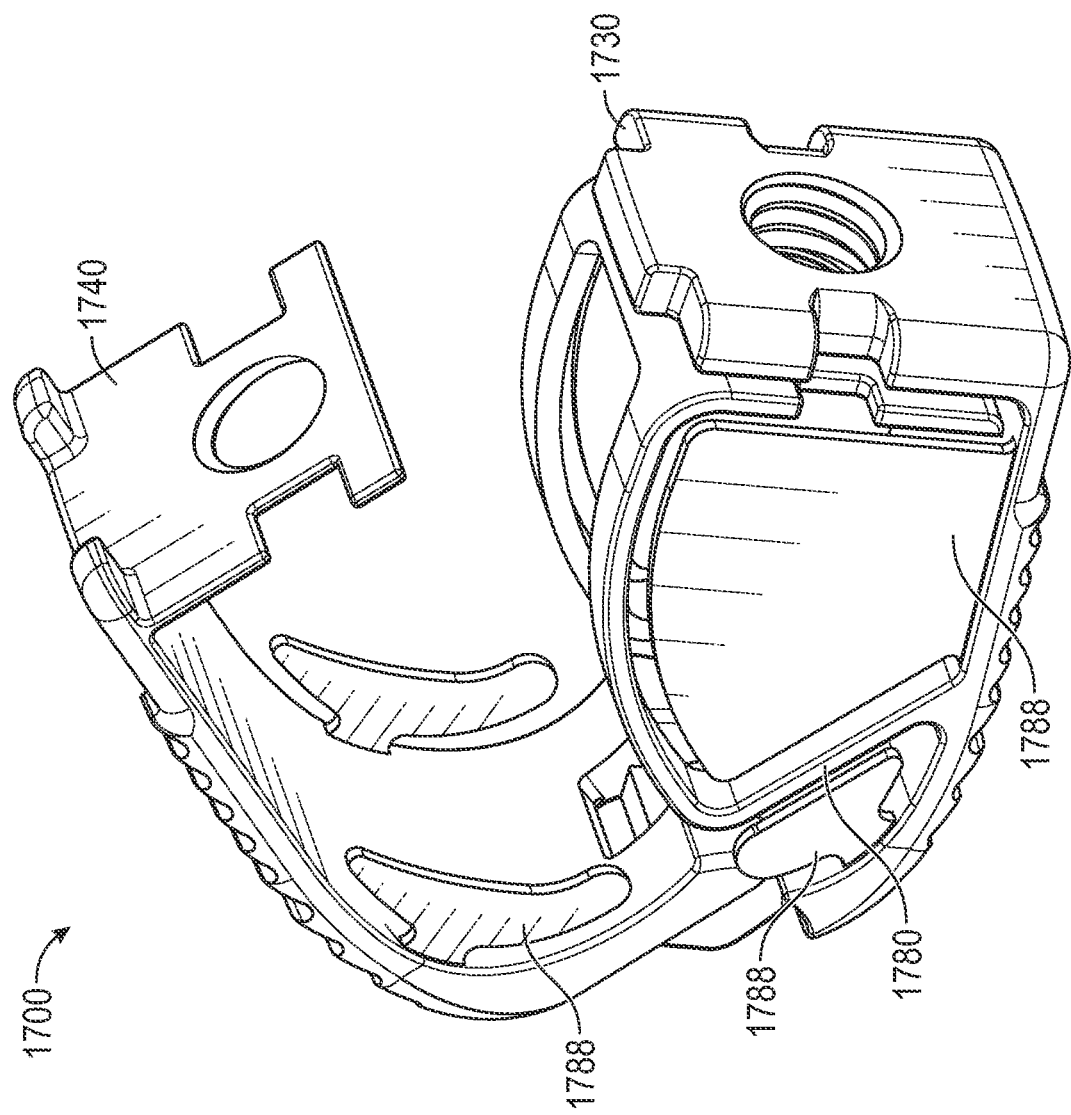

FIG. 125 is a top view of the spinal implant device 1700. The spinal implant device 1700 can include a movable lid 1740. FIG. 125 is a top view of the spinal implant device 1700 with the movable lid 1740 closed. FIG. 126 is a top perspective view of the spinal implant device 1700 with the movable lid 1740 opened. The spinal implant device 1700 can include thin frame works forming a portion of the movable lid 1740.

The spinal implant device 1700 can include an upper wall 1730. The upper wall 1730 can include a portion near the distal end 1720 and a portion near the proximal end 1722. In some embodiments, the upper wall 1730 forms a ledge near the proximal end 1722. In some embodiments, the upper wall 1730 forms a support surface for the movable lid 1740 when the movable lid 1740 is compressed. In some embodiments, the upper wall 1730 forms a support surface for the movable lid 1740 when the movable lid 1740 experiences larger than normal anatomical loads.

The spinal implant device 1700 can have an initially closed position. In some embodiments, the movable lid 1740 is separated in height from the upper wall 1730 near the proximal end 1722 in the initial position. In some embodiments, the movable lid 1740 is separated in height from the connecting bar 1780 in the initial position. The spinal implant device 1700 can be inserted between the vertebral bodies. In some embodiments, the application of load applied by the vertebral bodies makes the movable lid 1740 come in contact with or abut the connecting bar 1780. In some embodiments, the application of load causes compression of the connecting bar 1780. In some embodiments, the application of the normal anatomical load applied by the vertebra makes the connecting bar 1780 contact an inner surface of the spinal implant device 1700. In some embodiments, the application of a greater than normal anatomical load applied by the vertebra makes the connecting bar 1780 flex. This increase in load causes the movable lid 1740 to pivot toward the upper wall 1730 near the proximal end 1722. In some embodiments, the application of a greater than normal anatomical load applied by the vertebra causes the movable lid 1740 to come in contact with or abut the upper wall 1730 near the proximal end 1722. In some embodiments, the connecting bar 1780 supports the movable lid 1740 along the side walls 1724, 1726 when under a load. The connecting bar 1780 can be compressed when contacted with the movable lid 1740. In some embodiments, the movable lid 1740 abuts the connecting bar 1780 at a location or point closer to the proximal end 1722 than the distal end 1720 when under a load. In some embodiments, the connecting bar 1780 supports the movable lid 1740 when the movable lid 1740 experiences normal anatomical loads. In some embodiments, the connecting bar 1780 supports the movable lid 1740 and flexes under the load.

The upper wall 1730 can include a projection near the proximal end 1722. In some embodiments, the projection of the upper wall 1730 extends between lateral portions of the movable lid 1740. The projection of the upper wall 1730 can provide lateral support to the movable lid 1740. The projection of the upper wall 1730 can align the movable lid 1740 with the body 1712 during compression.

In some embodiments, the movable lid 1740 can form the upper surface of the spinal implant device 1700 configured to contact a vertebral end plate. In some embodiments, the movable lid 1740 can provide a load supporting surface for the adjacent vertebrae.

The movable lid 1740 can include a portion that can extend between the first side wall 1724 and the second side wall 1726. The movable lid 1740 can extend along the width of the spinal implant device 1700. The movable lid 1740 can include a portion that is coplanar with the proximal end 1722. The movable lid 1740 can include a portion that is coplanar with the third segment of the connecting bar 1780. The portion of the movable lid 1740 can be adjacent to the proximal end 1722. The portion of the movable lid 1740 can be adjacent to the third segment of the connecting bar 1780. The portion of the movable lid 1740 can be disposed between the third segment of the connecting bar 1780 and the proximal end 1722. The portion of the movable lid 1740 can extend along the height of the spinal implant device 1700, or a portion thereof. The movable lid 1740 can include a portion that aligns the movable lid 1740 during compression. The movable lid 1740 can include a portion that limits or reduces longitudinal movement of the movable lid 1740. The movable lid 1740 can include a portion that limits or reduces lateral movement of the movable lid 1740. In some embodiments, the movable lid 1740 can include a feature 1728. The portion that can extend between the first side wall 1724 and the second side wall 1726 can include the feature 1728. In some embodiments, the feature 1728 on proximal end 1722 and the feature 1728 on the movable lid 1740 can allow an insertion tool to retain the movable lid 1740 during placement or removal of spinal implant device 1700.

Figure 127:
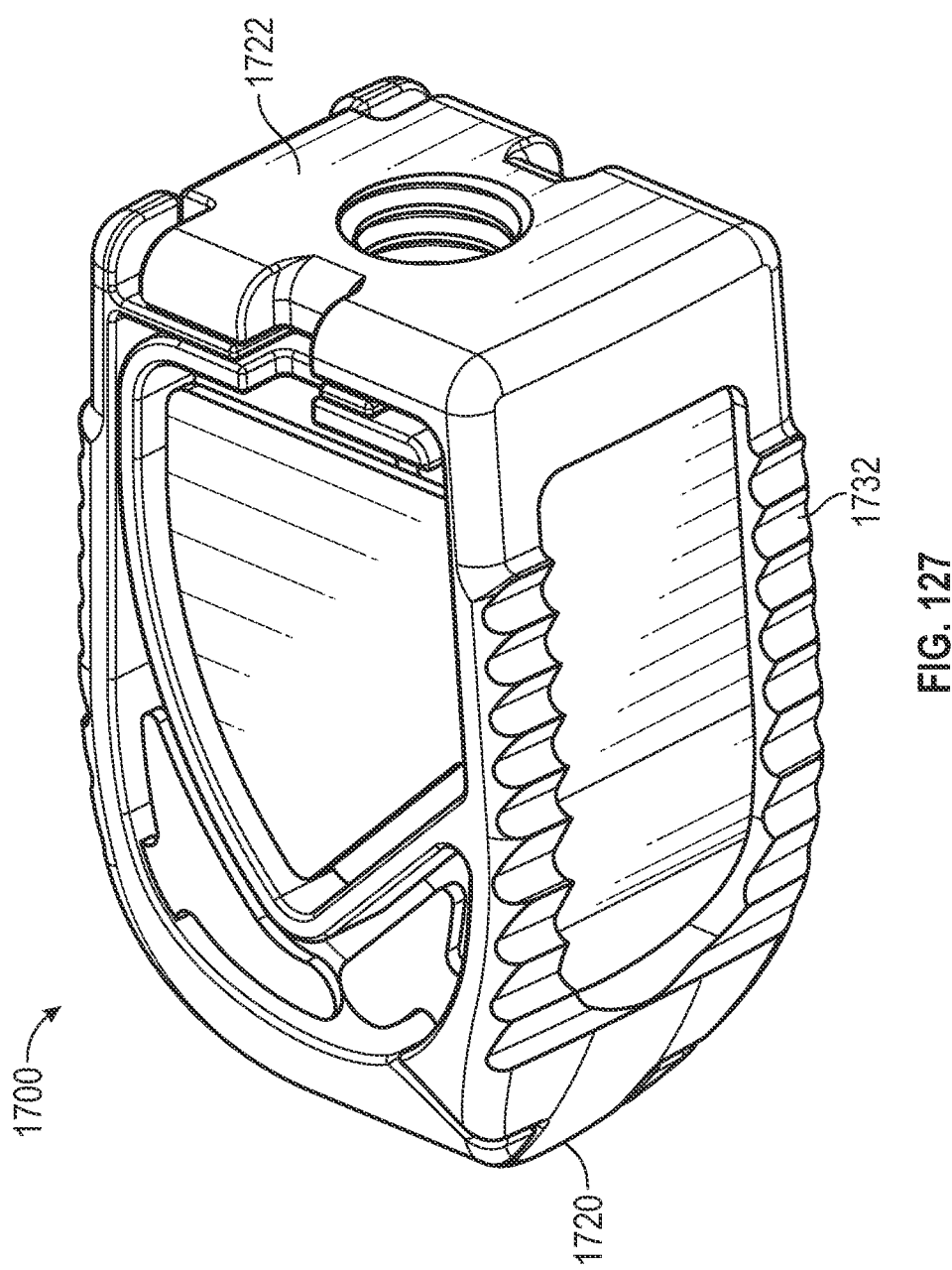

FIG. 127 is a bottom perspective view of the spinal implant device 1700. The spinal implant device 1700 can include a lower wall 1732. The lower wall 1732 can span between the distal end 1720 and the proximal end 1722. The spinal implant device 1700 can include one or more thin frameworks forming a portion of the lower wall 1732. In some embodiments, the lower wall 1732 can form the lower surface of the spinal implant device 1700 configured to contact a vertebral end plate. In some embodiments, the lower wall 1732 can provide a load supporting surface for the adjacent vertebrae.

In some embodiments, the spinal implant device 1700 can include features to limit or reduce movement of the spinal implant device 1700 between the vertebrae. The spinal implant device 1700 can include a plurality of ridges 1714.

Figure 128:
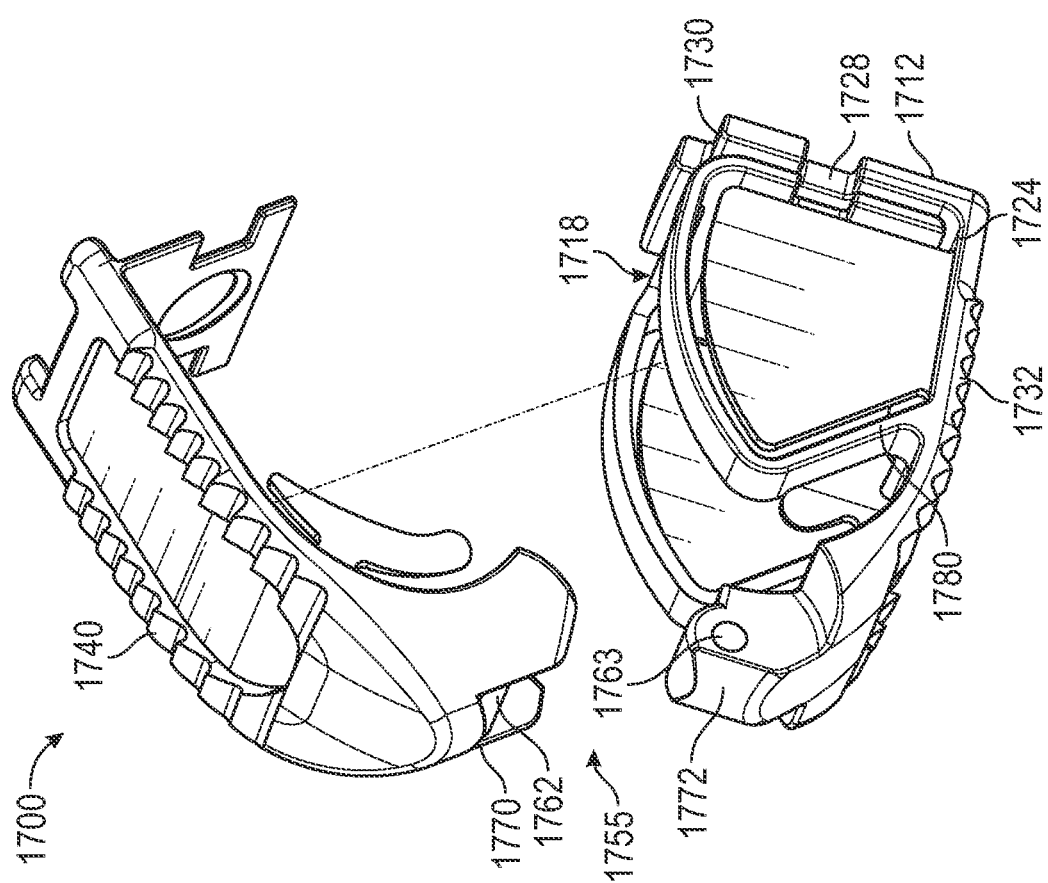

FIG. 128 is an exploded view of the movable lid 1740 of the spinal implant device 1700. In some embodiments, the spinal implant device 1700 can include a movable joint 1755. In some embodiments, the movable joint 1755 can couple the movable lid 1740 to the distal end 1720. The movable joint 1755 can allow for pivoting motion of the movable lid 1740. The movable lid 1740 can pivot via the movable joint 1755 during compression.

In some embodiments, the movable lid 1740 can include one or more articulations 1762. The one or more articulations 1762 can extend between two opposing lateral posts 1770. The distal end 1720 can include a central post 1772. The central post 1772 can include one or more lumens 1763 configured to engage the one or more articulations 1762.

The spinal implant device 1700 can include a cavity 1718. In some embodiments, the fifth portion of the connecting bar 1780 can define the back inner surface of the cavity 1718. In some embodiments, the distal end 1720 can define the front inner surface of the cavity 1718. In some embodiments, the two opposing side walls 1724, 1726, the first portion, the second portion, the third portion, and the fourth portion of the connecting bar 1780, and the thin frameworks 1788 can define the side inner surfaces of the cavity 1718. In some embodiments, the movable lid 1740 can define the top inner surface of the cavity 1718. In some embodiments, the lower wall 1732 can define the bottom inner surface of the cavity 1718.

In some methods of use, the movable lid 1740 abuts the connecting bar 1780 along the side walls 1724, 1726. The connecting bar 1780 can have a surface at a greater height than a ledge of the upper wall 1730. The movable lid 1740 can be disposed a distance from the upper wall 1730 near the proximal end 1722. In some embodiments, the connecting bar 1780 can be pushed downward toward the lower wall 1732 under normal anatomic loads. In some embodiments, the connecting bar 1780 can be pushed downward under load from the vertebral end plates. In some embodiments, the movable lid 1740 can compress under greater than normal loads and abut the upper wall 1730 near the proximal end 1722.

FIG. 129 illustrates a perspective view of a spinal implant device 1800. The spinal implant device 1800 can include any of the features of the spinal implant device 10, 10A, 100, 200, 300, 400, 500, 600, 700, 800, 900, 1000, 1100, 1200, 1300, 1400, 1500, 1600, 1700 as described herein and can be used in any method or method step described herein. The spinal implant device 1800 can include a body structure 1812. The body structure 1812 can include thicker edges surrounding open windows 1816. In some embodiments, the body structure 1812 supports thin frameworks within the open windows 1816. The thin framework can extend along the sides of the body structure 1812. The thin framework can extend along the top of the body structure 1812. The thin framework can extend along the bottom of the body structure 1812. The thin framework can extend from one or more of the thicker edges of the body structure 1812. The thin framework can extend between thicker edges, spanning a portion of an open window 1816. The thin framework can span an entire open window 1816. In some embodiments, the lateral sides of the body structure 1812 can be open. In some embodiments, the upper and lower surface of the body structure 1812 can be open, or at least partially open. In some embodiments, the body structure 1812 allows for the compression of material disposed within the spinal implant device 1800.

FIG. 130 is a distal view of the spinal implant device 1800. The spinal implant device 1800 can include a distal end 1820. The distal end 1820 can include a thickened surface to facilitate insertion of the distal end 1820. The distal end 1820 can be tapered.

FIG. 131 is a proximal view of the spinal implant device 1800. The spinal implant device 1800 can include a proximal end 1822. In some embodiments, the proximal end 1822 can be flat. The proximal end 1822 can be square, rectangular, quadrilateral, or other polygonal shape. The edges or corners of the proximal end 1822 can be rounded. In some embodiments, the proximal end 1822 can include an opening 1823 such as a threaded opening to couple with an insertion tool.

The spinal implant device 1800 can include a compression opening 1882. The compression opening 1882 can extend along the proximal end 1822. In some embodiments, the compression opening 1882 can extend along the distal end 1820. The compression opening 1882 can extend through the proximal end 1822. In some embodiments, the compression opening 1882 can extend through the distal end 1820. The compression opening 1882 can extend across the proximal end 1822. In some embodiments, the compression opening 1882 can extend across the distal end 1820. The compression opening 1882 can extend above the opening 1832. The compression opening 1882 can be closer to an upper wall 1830 than a lower wall 1832. In some embodiments, the compression opening 1882 is connected between the first side wall 1824 and the second side wall 1826. In some embodiments, the compression opening 1882 is not connected between the first side wall 1824 and the second side wall 1826.

In some embodiments, the compression opening 1882 can be a slot extending the width of the spinal implant device 1800. In some embodiments, the compression opening 1882 can include a concave curve. In some embodiments, the compression opening 1882 can include a convex curve. In some embodiments, the compression opening 1882 can curve around the opening 1823. The compression opening 1882 can be shaped to allow compression along the height of the spinal implant device 1882. The compression opening 1882 can be configured to compress to bring the upper wall 1830 toward the lower wall 1832.

FIG. 132 is a side view of the spinal implant device 1800. The length of the spinal implant device 1800 can be the distance between the distal end 1820 and the proximal end 1822. The spinal implant device 1800 can include two opposing side walls including a first side wall 1824 and a second side wall 1826. FIG. 132 illustrates the first side wall 1824, but the second side wall 1826 can include the same or similar features. In some embodiments, each side wall 1824, 1826 can include thicker edges surrounding an open window 1816. Each side wall 1824, 1826 can include four thicker edges surrounding an open window 1816. The open window 1816 can be curved or rounded. The open window 1816 can follow the shape of the side wall 1824, 1826. Each side wall 1824, 1826 can include the compression opening 1882.

In some embodiments, the compression opening 1882 can be a slot extending along a portion of the first side wall 1824 and the second side wall 1826. In some embodiments, the compression opening 1882 can include a flat slot. The compression opening 1882 can extend from the proximal end 1822 to the windows 1816. The compression opening 1882 can be shaped to allow compression of one end of the spinal implant device 1882.

In some embodiments, each of the two opposing side walls 1824, 1826 can include a feature 1828. The feature 1828 can be designed to facilitate placement of the spinal implant device 1800 by coupling with an insertion tool. In some embodiments, the feature 1828 can include a channel or groove that originates at the proximal end 1822 and extends along a portion of one of the side walls 1824, 1826. In some embodiments, the feature 1828 can extend from the proximal end 1822 to the window 1816. The compression opening 1882 can extend above the feature 1828. The compression opening 1882 can extend between the upper wall 1830 and the feature 1828.

FIG. 133 is a top view of the spinal implant device 1800. The spinal implant device 1800 can include the upper wall 1830. The upper wall 1830 can include thicker edges which forms the top surface of the spinal implant device 1800. The upper wall 1830 can extend between the distal end 1820 and the proximal end 1822. The upper wall 1830 can include one or more openings 1842. In some embodiments, the upper wall 1830 includes one opening 1842.

FIG. 134 is a bottom perspective view of the spinal implant device 1800. The spinal implant device 1800 can include the lower wall 1832. The lower wall 1832 can extend between the distal end 1820 and the proximal end 1822. The lower wall 1832 can include one or more openings 1844. In some embodiments, the lower wall 1832 can include one opening 1842.

The spinal implant device 1800 can include a cavity 1818. In some embodiments, the proximal end 1822 can form the back inner surface of the cavity 1818. In some embodiments, the distal end 1820 can form the front inner surface of the cavity 1818. In some embodiments, the two opposing side walls 1824, 1826 can form the side inner surfaces of the cavity 1818. In some embodiments, the upper wall 1830 can form a portion of the top inner surface of the cavity 1818. In some embodiments, the lower wall 1832 can form the bottom inner surface of the cavity 1818.

In some methods of use, the side walls 1824, 1826 can be configured to compress in height. The compression opening 1882 can be configured to compress in height. The compression opening 1882 can be compressed under a load from the vertebral bodies. The side walls 1824, 1826 can flex to reduce the height of the side walls 1824, 1826. The upper wall 1830 and the lower wall 1832 can compress material within the cavity 1818. In some embodiments, the upper wall 1830 moves toward the lower wall 1832. In some embodiments, the lower wall 1832 moves toward the upper wall 1830. In some embodiments, both the upper wall 1830 and the lower wall 1832 move inward.

FIG. 135 illustrates a perspective view of a spinal implant device 1900. The spinal implant device 1900 can include any of the features of the spinal implant device 10, 10A, 100, 200, 300, 400, 500, 600, 700, 800, 900, 1000, 1100, 1200, 1300, 1400, 1500, 1600, 1700, 1800 as described herein and can be used in any method or method step described herein. The spinal implant device 1900 can include a body structure 1912. The body structure 1912 can includes features to promote compression. In some methods of use, the compression of a portion of the spinal implant device 1900 can promote fusion. The compression of the spinal implant device 1900 can allow for increased load on the corresponding graft material or other fusion material disposed within the spinal implant device 1900.

FIG. 136 is a distal view of the spinal implant device 1900. The spinal implant device 1900 can include a distal end 1920. In some methods of use, the distal end 1920 can be the insertion end. In some embodiments, the distal end 1920 is tapered inward.

FIG. 137 is a proximal view of the spinal implant device 1900. The spinal implant device 1900 can include a proximal end 1922. In some embodiments, the proximal end 1922 can include an opening 1923 to couple to an insertion tool.

FIG. 138 is a side view of the spinal implant device 1900. The length of the spinal implant device 1900 can be the distance between the distal end 1920 and the proximal end 1922. The spinal implant device 1900 can include two opposing side walls including a first side wall 1924 and a second side wall 1926. FIG. 138 illustrates the first side wall 1924, but the second side wall 1926 can include the same or similar features. In some embodiments, each side wall 1924, 1926 can include thicker edges surrounding an open window 1916.

The spinal implant device 1900 can include a connecting bar 1980. The connecting bar 1980 can include a first portion, a second portion, and third portion. The first portion of the connecting bar 1980 can extend along the first side wall 1924. The first portion of the connecting bar 1980 can be angled upward toward the proximal end 1922. The first portion of the connecting bar 1980 can be angled upward at any angle including 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 45 degrees and 60 degrees, greater than 45 degrees, less than 60 degrees, or any range including and between the foregoing values.

The second portion of the connecting bar 1980 can extend along the second side wall 1926. The second portion of the connecting bar 1980 can be angled upward toward the proximal end 1922. The second portion of the connecting bar 1980 can be angled upward at any angle including 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 45 degrees and 60 degrees, greater than 45 degrees, less than 60 degrees, or any range including and between the foregoing values.

The third portion of the connecting bar 1980 can extend between the first portion of the connecting bar 1980 and the second portion of the connecting bar 1980. The third portion of the connecting bar 1980 can form a ledge for a movable lid 1940 described herein. The third portion of the connecting bar 1980 can extend along the width of the spinal implant device 1900. The connecting bar 1980 can have U shaped configuration. In some embodiments, the connecting bar 1980 is connected between the first side wall 1924 and the second side wall 1926. In some embodiments, the connecting bar 1980 is not connected between the first side wall 1924 and the second side wall 1926. In some embodiments, any connecting bars or compression bars described herein may be connected between the first side wall and the second side wall.

In some embodiments, the spinal implant device 1900 can include a feature 1928 to facilitate placement of the spinal implant device 1900. In some embodiments, the feature 1928 can include a channel to accept an insertion tool. In some embodiments, the feature 1928 can extend from the proximal end 1922 of the spinal implant device 1900 toward the distal end 1920. In some embodiments, the feature 1928 can form a groove in the proximal end 1922. In some embodiments, the connecting bar 1980 can include the feature 1928 to facilitate placement of the spinal implant device 1900. In some embodiments, the first portion of the connecting bar 1980 can include the feature 1928. In some embodiments, the second portion of the connecting bar 1980 can include the feature 1928.

FIG. 139 is a top view of the spinal implant device 1900. The spinal implant device 1900 can include the movable lid 1940. FIG. 139 is a top view of the spinal implant device 1900 with the movable lid 1940 closed. FIG. 140 is a top perspective view of the spinal implant device 1900 with the movable lid 1940 opened.

The spinal implant device 1900 can include one or more openings 1942 extending through the movable lid 1940. In some embodiments, the movable lid includes one elongate opening 1942.

The spinal implant device 1900 can include an upper wall 1930. The upper wall 1930 can include a portion near the distal end 1920 and a portion near the proximal end 1922. The portion near the distal end 1920 can include a curved surface to allow the movable lid 1940 to rotate. The portion near the distal end 1920 can include a ledge to reduce or limit further rotation of the movable lid 1940. The ledge of the upper wall 1930 near the distal end 1920 can interact with the movable lid 1940. The movable lid 1940 can include one or more features to interact with the upper wall 1930. The movable lid 1940 can include a stepped lower surface. The stepped lower surface can include a plurality of heights. The stepped lower surface can dispose the movable lid 1940 away from the upper wall 1930 under normal anatomical loads.

The portion of the upper wall near the proximal end 1922 can include a ledge to reduce or limit further rotation of the movable lid 1940. The ledge of the upper wall 1930 near the proximal end 1922 can interact with the movable lid 1940 to form a stop. In some embodiments, the portion of the upper wall 1930 near the proximal end 1922 is planar or substantially planar. In some embodiments, the movable lid 1940 hovers over the upper wall 1930 under normal anatomical loads. In some embodiments, the movable lid 1940 does not contact the upper wall 1930 near the proximal end 1922. In some embodiments, the movable lid 1940 does not contact the upper wall 1930 near the proximal end 1922 once a load is applied. In some embodiments, the upper wall near the proximal end 1922 acts as a stop for increased load. In some embodiments, the upper wall near the proximal end 1922 acts as a stop for safety.

In some embodiments, the movable lid 1940 is separated in height from the connecting bar 1980 in a closed position. The spinal implant device 1900 can be inserted in this closed position. In some embodiments, the movable lid 1940 contacts the connecting bar 1980 in a closed position. The spinal implant device 1900 can be inserted in this closed position. The spinal implant device 1900 can have a load applied by the vertebra. In some embodiments, the application of load applied by the vertebra makes the movable lid 1940 contact the connecting bar 1980. In some embodiments, the application of load applied by the vertebra makes the movable lid 1940 cause the connecting bar 1980 to flex. In some embodiments, the application of a greater load applied by the vertebra causes the movable lid 1940 to move toward the upper wall 1930 near the proximal end 1922. In some embodiments, the application of a greater than normal anatomical load applied by the vertebra causes the movable lid 1940 to contact the upper wall 1930 near the proximal end 1922. In some embodiments, the movable lid 1940 flexes as the movable lid 1940 pivots toward the upper wall 1930. In some embodiments, the connecting bar 1980 supports the movable lid 1940 along the side walls 1924, 1926. In some embodiments, the connecting bar 1980 supports the movable lid 1940 closer to the proximal end 1922 than the distal end 1920. In some embodiments, the connecting bar 1980 supports the movable lid 1940 such that the movable lid 1940 does not abut the upper wall 1930 near the proximal end 1922. In some embodiments, the connecting bar 1980 supports the movable lid 1940 under normal anatomical loads.

The upper wall 1930 can include a projection near the proximal end 1922. In some embodiments, the projection of the upper wall 1930 is higher than the surface of ledge of the upper wall 1930. In some embodiments, the projection of the upper wall 1930 extends between portions of the movable lid 1940. The projection of the upper wall 1930 can align the movable lid 1940 during rotation.

In some embodiments, the movable lid 1940 forms the upper surface of the spinal implant device 1900 configured to contact the vertebral end plate. The movable lid 1940 can hover over the ledge of the upper wall 1930 near the proximal end 1922 under normal anatomical loads. In some embodiments, the movable lid 1940 can provide a load supporting surface for the adjacent vertebrae. In some methods, the load can be transferred from the movable lid 1940 to the connecting bar 1980. In some methods, the movable lid 1940 can be positioned adjacent to a vertebral end plate of a superior vertebra.

FIG. 141 is a bottom perspective view of the spinal implant device 1900. The spinal implant device 1900 can include a lower wall 1932. The lower wall 1932 can span between the distal end 1920 and the proximal end 1922. The spinal implant device 1900 can include one or more openings 1944 extending through the lower wall 1932.

The lower wall 1932 can provide a load supporting surface. In some methods, the lower wall 1932 can be positioned adjacent to a vertebral end plate of an inferior vertebra. In some methods, when the spinal implant device 1900 is positioned between two adjacent vertebrae, the load supporting surfaces of the movable lid 1940 and the lower wall 1932 contact the vertebral end plates of the adjacent vertebrae. In some embodiments, the distance between the movable lid 1940 and the lower wall 1932 can form the height of the spinal implant device 1900.

In some embodiments, the spinal implant device 1900 can include features to limit or reduce movement of the spinal implant device 1900 between the vertebrae. The spinal implant device 1900 can include a plurality of ridges 1914.

FIG. 142 is an exploded view of the movable lid 1940 of the spinal implant device 1900. In some embodiments, the movable lid 1940 can be coupled to the distal end 1920. In some embodiments, the spinal implant device 1900 can include a movable joint 1955.

In some embodiments, the movable lid 1940 can include one or more articulations 1962. The one or more articulations 1962 can extend between two opposing lateral posts 1970 of the movable lid 1940. The articulation 1962 can be an axle. The distal end 1920 can include a central post 1972. The central post 1972 can include one or more lumens 1963 configured to engage the one or more articulations 1962.

The spinal implant device 1900 can include a cavity 1918. In some embodiments, the proximal end 1922 can define the back inner surface of the cavity 1918. In some embodiments, the distal end 1920 can define the front inner surface of the cavity 1918. In some embodiments, the two opposing side walls 1924, 1926 and the first and second portions of the connecting bar 1980 can define the side inner surfaces of the cavity 1918. In some embodiments, the movable lid 1940 can define the top inner surface of the cavity 1918. In some embodiments, the lower wall 1932 can define the bottom inner surface of the cavity 1918.

In some methods of use, the connecting bar 1980 supports the movable lid 1940 along the side walls 1924, 1926. The connecting bar 1980 can have a surface at a greater height than the ledge of the upper wall 1930 near the proximal end 1922. The movable lid 1940 can be disposed a distance from the upper wall 1930 near the proximal end 1922 during insertion of the spinal implant device 1900. The movable lid 1940 can be disposed at a distance from the upper wall 1930 near the proximal end 1922 after a load has been applied. In some methods of use, the upper wall 1930 near the proximal end 1922 is not configured to be contacted by the movable lid 1940 during normal operating conditions of the spinal implant device 1900.

In some embodiments, the implant body 1912 and the movable lid 1940 can include features to limit further rotation. The distal end of the upper wall 1930 can include a ledge and the movable lid 1940 can include a corresponding step. The step feature can be disposed toward the distal end. The connecting bar 1980 can form a ledge to support the movable lid 1940. The connecting bar 1980 can be a height that supports the movable lid 1940 under normal anatomical loads such that the movable lid 1930 hovers over the upper wall 1930. The movable lid 1940 can have a shaped lower surface to interact with the surfaces of the upper wall 1930 and the connecting bar 1980. The movable lid 1940 can have a shaped lower surface that can form a step to offset a proximal end of the movable lid 1940 from the upper wall 1930 near the proximal end 1922. The movable lid 1940 flexes on the connecting bar 1980 and the proximal portion of the movable lid 1940 hovers over the proximal end 1922 under normal anatomical loads. The connecting bar 1980 can be various angles from the lower surface, for instance 45 degrees or 60 degrees. The movable lid 1940 does not contact the ledge of the upper wall 1930 near the proximal end 1922 under normal anatomical loads. The movable lid 1940 does not contact the upper wall 1930 near the proximal end 1922 once the load is applied. The upper wall 1930 near the proximal end 1922 can act as a stop for increased load or safety. The distal and proximal outer portions of the movable lid 1940 provide lateral stability.

FIG. 143 illustrates a perspective view of a spinal implant device 2000. The spinal implant device 2000 can include any of the features of the spinal implant device 10, 10A, 100, 200, 300, 400, 500, 600, 700, 800, 900, 1000, 1100, 1200, 1300, 1400, 1500, 1600, 1700, 1800, 1900 as described herein and can be used in any method or method step described herein. The compression of the spinal implant device 2000 can allow for increased load on the material disposed within the spinal implant device 2000 as described herein. The spinal implant device 2000 can include a body structure 2012.

FIG. 144 is a distal view of the spinal implant device 2000. The spinal implant device 2000 can include a distal end 2020. In some methods of use, the distal end 2020 can be the insertion end.

FIG. 145 is a proximal view of the spinal implant device 2000. The spinal implant device 2000 can include a proximal end 2022. The distal end 2020 can form the leading end and the proximal end 2022 can form the trailing end.

FIG. 146 is a side view of the spinal implant device 2000. The length of the spinal implant device 2000 can be the distance between the distal end 2020 and the proximal end 2022. The spinal implant device 2000 can include two opposing side walls including a first side wall 2024 and a second side wall 2026. FIG. 146 illustrates the first side wall 2024, but the second side wall 2026 can include the same or similar features.

In some embodiments, the two opposing side walls 2024, 2026 can include one or more porous or network surfaces 2090. The first porous or network surface 2090 can be located on the first side wall 2024. The second porous or network surface 2090 can be located on the second side wall 2026. The porous or network surfaces 2090 can be a matrix. The porous or network surfaces 2090 can be square or rectangular. The porous or network surfaces 2090 can be planar. The porous or network surfaces 2090 can be non-planar. The porous or network surfaces 2090 can include rows extending along one plane and alternating rows extending along another plane. The porous or network surfaces 2090 can include any structure to promote bony fusion. The porous or network surfaces 2090 can include any structure. In some embodiments, the spinal implant device 2000 does not include the porous or network surfaces 2090 on the first side wall 2024 and/or the porous or network surfaces 2090 on the second side wall 2026. In some embodiments, the first side wall 2024 and/or the second side wall 2026 are open.

The one or more porous or network surfaces 2090 can have the same width than another portion of the side walls 2024, 2026. In some embodiments, the one or more porous or network surfaces 2090 can have the same material as the side walls 2024, 2026. In some embodiments, the one or more porous or network surfaces 2090 can have a different material than the side walls 2024, 2026.

In some embodiments, movable lid 2040 can include a ledge 2034 (not shown) at the distal end 2020 of the spinal implant device 2000. In some embodiments, ledge 2034 can extend from the first side wall 2024 to the second side wall 2026. In some embodiments, ledge 2034 can slope or project toward the bottom of spinal implant device 2000. In some embodiments, upper wall 2030 can include a step 2036 (not shown) at the distal end 2020 of the spinal implant device 2000. In some embodiments, step 2036 can be angled or chamfered. In some embodiments, ledge 2034 and step 2036 can have corresponding shapes configured to mate or abut one another. In some embodiments, ledge 2034 can abut step 2036. In some embodiments, ledge 2034 and step 2036 can abut one another to increase the shear strength of spinal implant device 2000.

FIG. 147 is a top view of the spinal implant device 2000. The spinal implant device 2000 can include a movable lid 2040. FIG. 147 is a top view of the spinal implant device 2000 with the movable lid 2040 closed. FIG. 148 is a top perspective view of the spinal implant device 2000 with the movable lid 2040 opened. In some embodiments, the movable lid 2040 can include one or more porous or network surfaces 2090. The one or more porous or network surfaces 2090 can be elongate. In some embodiments, the movable lid 2040 does not include one or more porous or network surfaces 2090. In some embodiments, the movable lid 2040 is open.

The movable lid 2040 can include one or more compression supports 2086. The first compression support 2086 can extend along the first side wall 2024. The first compression support 2086 can be angled downward from the movable lid 2040 toward the proximal end 2022. The first compression support 2086 can be angled downward at any angle including 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 45 degrees and 60 degrees, greater than 45 degrees, less than 60 degrees, or any range including and between the foregoing values. The first compression support 2086 can be coplanar with the first side wall 2024.

The second compression support 2086 can extend along the second side wall 2026. The second compression support 2086 can be angled downward from the movable lid 2040 toward the proximal end 2022. The second compression support 2086 can be angled downward at any angle including 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 45 degrees and 60 degrees, greater than 45 degrees, less than 60 degrees, or any range including and between the foregoing values. The first compression support 2086 can be coplanar with the first side wall 2024. The second compression support 2086 can be coplanar with the second side wall 2026. The movable lid 2040 can extend between the first side wall 2024 and the second side wall 2026. The movable lid 2040 can extend along the width of the spinal implant device 2000. The compression supports 2086 can have a U shaped configuration with the movable lid 2040. In some embodiments, the compression supports 2086 are connected between the first side wall 2024 and the second side wall 2026. In some embodiments, the compression supports 2086 are connected between the first side wall 2024 and the second side wall 2026 by the movable lid 2040. In some embodiments, the compression supports 2086 are connected between the first side wall 2024 and the second side wall 2026 at a point below the movable lid 2040. In some embodiments, the compression supports 2086 are not connected between the first side wall 2024 and the second side wall 2026.

The spinal implant device 2000 can include an upper wall 2030. The upper wall 2030 can include a portion near the distal end 2020 and a portion near the proximal end 2022. The portion near the distal end 2020 can include a curved surface to allow the movable lid 2040 to rotate. The portion near the distal end 2020 can include a ledge to reduce or limit further rotation of the movable lid 2040. The movable lid 2040 can include one or more features to interact with the upper wall 2030.

The portion of the upper wall near the proximal end 2022 can include a recess to reduce or limit further rotation of the movable lid 2040. The recess of the upper wall 2030 can interact with the movable lid 2040 to form a stop. In some embodiments, the portion of the upper wall 2030 near the proximal end 2022 is planar or substantially planar and the recess can be disposed below this planar surface. In some embodiments, the movable lid 2040 hovers within the recess of the upper wall 2030. In some embodiments, the movable lid 2040 does not contact the lower surface of the recess of the upper wall 2030 under normal anatomical loads. In some embodiments, the movable lid 2040 does not contact the lower surface of the recess once load is applied. In some embodiments, the lower surface of the recess acts as a stop for increased load. In some embodiments, the lower surface of the recess acts as a stop for safety.

In some embodiments, the compression supports 2086 can be offset from an internal, lower surface of the spinal implant device 2000 during insertion. In some embodiments, the application of load applied by the vertebra makes the compression supports 2086 contact the lower surface of the spinal implant device 2000. In some embodiments, the application of the normal anatomical load applied by the vertebra makes the compression supports 2086 of the movable lid 2040 contact the lower surface of the spinal implant device 2000 near the side walls 2024, 2026. The movable lid 2040 can hover over the proximal end 2022 until application of a load. The compression supports 2086 can hover over the lower surface of the spinal implant device 2000 under application of a load. In some embodiments, the application of a greater load causes the compression supports 2086 to contact the lower surface causing the compression supports 2086 to flex. The movable lid 2040 flexes the compression supports 2086 and pivots toward the upper wall 2030 near the proximal end 2022. In some embodiments, the application of a greater than normal anatomical load makes the movable lid 2040 contact the upper wall 2030 near the proximal end 2022. In some embodiments, the one or more compression supports 2086 support the movable lid 2040 along the side walls 2024, 2026. In some embodiments, the one or more compression supports 2086 support the movable lid 2040 under normal loads. In some embodiments, the one or more compression supports 2086 support the movable lid 2040 without the movable lid 2040 contacting the lower surface of the recess. In some embodiments, the one or more compression supports 2086 support the movable lid 2040 after compression.

FIG. 149 is a bottom perspective view of the spinal implant device 2000. The spinal implant device 2000 can include a lower wall 2032. The lower wall 2032 can span between the distal end 2020 and the proximal end 2022. In some embodiments, the lower wall 2032 can include one or more porous or network surfaces 2090. The one or more porous or network surfaces 2090 can be elongate. In some embodiments, the lower wall 2032 does not include one or more porous or network surfaces 2090. In some embodiments, the lower wall 2032 is open.

The lower wall 2032 can provide a load supporting surface. In some methods, the lower wall 2032 can be positioned adjacent to a vertebral end plate of an inferior vertebra. In some methods, when the spinal implant device 2000 is positioned between two adjacent vertebrae, the load supporting surfaces of the movable lid 2040 and the lower wall 2032 contact the vertebral end plates of the adjacent vertebrae. In some embodiments, the distance between the movable lid 2040 and the lower wall 2032 can form the height of the spinal implant device 2000. In some embodiments, the force of the vertebral bodies reduces this height.

In some embodiments, the spinal implant device 2000 can include features to limit or reduce movement of the spinal implant device 2000 between the vertebrae. The spinal implant device 2000 can include a plurality of ridges 2014. The ridges 2014 can form a portion of the movable lid 2040. The ridges 2014 can form a portion of the lower wall 2032. In some embodiments, the ridges 2014 can be directionally oriented as described herein.

FIG. 150 is an exploded view of the movable lid 2040 of the spinal implant device 2000. In some embodiments, the spinal implant device 2000 can include a movable joint 2055. In some embodiments, the movable joint 2055 can couple the movable lid 2040 to the distal end 2020. The movable joint 2055 can allow for pivoting motion of the movable lid 2040.

In some embodiments, the movable lid 2040 can include one or more articulations 2062. The one or more articulations 2062 can extend between two opposing lateral posts 2070. The distal end 2020 can include a central post 2072. The central post 2072 can include one or more lumens 2063 configured to engage the one or more articulations 2062.

The spinal implant device 2000 can include a cavity 2018. In some embodiments, the proximal end 2022 can define the back inner surface of the cavity 2018. In some embodiments, the distal end 2020 can define the front inner surface of the cavity 2018. In some embodiments, the two opposing side walls 2024, 2026 and the one or more compression supports 2086 can define the side inner surfaces of the cavity 2018. In some embodiments, the movable lid 2040 can define the top inner surface of the cavity 2018. In some embodiments, the lower wall 2032 can define the bottom inner surface of the cavity 2018.

In some embodiments, the movable lid 2040 is configured to contact the vertebral end plate. The one or more compression supports 2086 of the movable lid 2040 can abut a portion of the body structure 2012 under normal loads. In some embodiments, the movable lid 2040 can provide a load supporting surface for the adjacent vertebrae. In some methods, the load can be transferred from the movable lid 2040 to the one or more compression supports 2086. In some methods, the movable lid 2040 can be positioned adjacent to a vertebral end plate of a superior vertebra. The one or more compression supports 2086 of the movable lid 2040 can compress or flex. In some embodiments, the movable lid 2040 can rotate further downward within the recess of the upper wall 1930. In some embodiments, the movable lid 2040 does not abut the lower surface of the recess after compression. In some embodiments, the movable lid 2040 hovers above the lower surface of the recess after compression.

In some embodiments, the spinal implant device 2000 can include a feature 2028 to facilitate placement of the spinal implant device 2000. In some embodiments, the feature 2028 can include a channel to accept an insertion tool. In some embodiments, the feature 2028 can extend from the proximal end 2022 of the spinal implant device 2000 toward the distal end 2020. In some embodiments, the feature 2028 can form a groove in the proximal end 2022. In some embodiments, the one or more compression supports 2086 can include the feature 2028 to facilitate placement of the spinal implant device 2000. In some embodiments, the feature 2028 on proximal end 2022 and the feature 2028 on one or more compression supports 2086 can allow an insertion tool to retain the movable lid 2040 during placement or removal of spinal implant device 2000.

FIG. 151 illustrates a perspective view of a spinal implant device 2100. The spinal implant device 2100 can include any of the features of the spinal implant device 10, 10A, 100, 200, 300, 400, 500, 600, 700, 800, 900, 1000, 1100, 1200, 1300, 1400, 1500, 1600, 1700, 1800, 1900, 2000 as described herein and can be used in any method or method step described herein. The spinal implant device 2100 can include a body structure 2112. The spinal implant device 2100 is configured to be placed between adjacent vertebrae. The spinal implant device 2100 can includes features to allow for compression along the height of the spinal implant device 2100. The compression can promote fusion of material disposed within the spinal implant device 2100.

FIG. 152 is a distal view of the spinal implant device 2100. The spinal implant device 2100 can include a distal end 2120 which can be the insertion end.

FIG. 153 is a proximal view of the spinal implant device 2100. The spinal implant device 2100 can include a proximal end 2122 which can be the trailing end. In some embodiments, the proximal end 2122 can include an opening 2123.

FIG. 154 is a side view of the spinal implant device 2100. The length of the spinal implant device 2100 can be the distance between the distal end 2120 and the proximal end 2122. The spinal implant device 2100 can include two opposing side walls including a first side wall 2124 and a second side wall 2126. FIG. 154 illustrates the first side wall 2124, but the second side wall 2126 can include the same or similar features. The first side wall 2124 and the second side wall 2126 can be identical or mirror images.

The body structure 2112 can include thicker edges surrounding open windows 2116. As described herein, the lateral sides of the body structure 2112 can be open. The spinal implant device 2100 can have a through lumen perpendicular to the longitudinal axis of the spinal implant device 2100. Each window 2116 can extend along a portion of the respective side wall 2124, 2126. In some embodiments, the thicker edges can be porous. In some embodiments, a portion of the respective side wall 2124, 2126 can be porous. In some embodiments, a portion of the body structure 2112 surrounding the windows 2116 can be porous.

The spinal implant device 2100 can include one or more support bars 2192. The support bars 2192 can include a set extending upward from a bottom surface of the first sidewall 2124. The support bars 2192 can include a set extending upward from a bottom surface of the second sidewall 2126. The support bars 2192 can include a set extending downward from a movable lid 2140, as described herein.

In some embodiments, the one or more support bars 2192 are solid. In some embodiments, the one or more support bars 2192 are hollow. In some embodiments, the one or more support bars 2192 can include a lumen extending from the top surface of the spinal implant device 2100 to the bottom surface of the spinal implant device 2100. In some embodiments, the one or more support bars 2192 have the same material as the side walls 2124, 2126. In some embodiments, the one or more support bars 2192 have a different material than the side walls 2124, 2126. In some embodiments, the one or more support bars 2192 are porous or a mesh. In some embodiments, the one or more support bars 2192 allow bony ingrowth therethrough. In some embodiments, the one or more support bars 2192 allow the fusion of material therethrough. In some embodiments, the one or more support bars 2192 are connected between the first side wall 2124 and the second side wall 2126. In some embodiments, the one or more support bars 2192 are not connected between the first side wall 2124 and the second side wall 2126.

FIG. 155 is a top view of the spinal implant device 2100. The spinal implant device 2100 can include a movable lid 2140. FIG. 155 is a top view of the spinal implant device 2100 with the movable lid 2140 closed. FIG. 156 is a top perspective view of the spinal implant device 2100 with the movable lid 2140 opened. The spinal implant device 2100 can include one or more support bars 2192. The support bars 2192 can include a set extending downward from a bottom surface of the movable lid 2140. The support bars 2192 extending from the movable lid 1040 can abut the support bars 2192 extending along the first side wall 2124 and the second side wall 2126. In some embodiments, the support bars 2192 extending upward from a bottom surface of the first sidewall 2124 and the support bars 2192 extending upward from a bottom surface of the second sidewall 2126 do not abut the support bars 2192 extending downward from the movable lid 1040. In some embodiments, the support bars 2192 are separated by a distance to allow compression of the spinal implant device 2100. In some embodiments, the support bars 2192 extending from the movable lid 1040 can abut the support bars 2192 extending upward from a bottom surface of the first sidewall 2124 and the support bars 2192 extending upward from a bottom surface of the second sidewall 2126 under normal anatomical loads. In some embodiments, the support bars 2192 extending from the movable lid 1040 can abut the support bars 2192 extending upward from a bottom surface of the first sidewall 2124 and the support bars 2192 extending upward from a bottom surface of the second sidewall 2126 under greater than normal anatomical loads, thereby acting as a stop for further compression.

The spinal implant device 2100 can include an upper wall 2130. The upper wall 2130 can include a portion near the distal end 2120 and a portion near the proximal end 2122. In some embodiments, the upper wall 2130 forms a ledge to support the movable lid 2140 near the proximal end 2122. In some embodiments, the upper wall 2130 forms a ledge to support the movable lid 2140 near the distal end 2120. In some embodiments, the upper wall 2130 forms a support surface for the movable lid 2140.

In some embodiments, the support bars 2192 of the movable lid 2140 can be offset during insertion. In some embodiments, the application of load applied by the vertebra makes the support bars 2192 of the movable lid 2140 contact the support bars 2192 of the body structure 2112. In some embodiments, the application of an anatomical load, within a normal range, applied by the vertebra makes the support bars 2192 of the movable lid 2140 contact the support bars 2192 of the body structure 2112 near the side walls 2124, 2126. The movable lid 2140 can hover over the support bars 2192 until application of a load. In some embodiments, the application of a greater load after the support bars 2192 contact each other causes the support bars 2192 to flex. The movable lid 2140 flexes the support bars 2192 and pivots toward the upper wall 2130 near the proximal end 2122. In some embodiments, the application of a greater than normal anatomical load applied by the vertebra makes the movable lid 2140 contact the upper wall 2130 near the proximal end 2122. In some embodiments, the support bars 2192 support the movable lid 2140 along the side walls 2124, 2126. The support bars 2192 of the movable lid 2140 can abut the support bars 2192. In some embodiments, the movable lid 2140 includes one or more openings 2142.

The upper wall 2130 can include a projection near the proximal end 2122. In some embodiments, the projection of the upper wall 2130 extends between lateral portions of the movable lid 2140. The projection of the upper wall 2130 can provide lateral support to the movable lid 2140. The projection of the upper wall 2130 can align the movable lid 2140 during compression. The movable lid 2140 can be laterally adjacent to the projection 2130 at the proximal end 2122.

In some embodiments, the movable lid 2140 can form the upper surface of the spinal implant device 2100 configured to contact a vertebral end plate. In some embodiments, the movable lid 2140 can provide a load supporting surface for the adjacent vertebrae.

FIG. 157 is a bottom perspective view of the spinal implant device 2100. The spinal implant device 2100 can include the lower wall 2132. The lower wall 2132 can span between the distal end 2120 and the proximal end 2122. The lower wall 2132 can include one or more openings 2144. In some embodiments, the lower wall 2132 can provide a load supporting surface for the adjacent vertebrae.

In some embodiments, the spinal implant device 2100 can include features to limit or reduce movement of the spinal implant device 2100 between the vertebrae. The spinal implant device 2100 can include a plurality of ridges 2114.

FIG. 158 is an exploded view of the movable lid 2140 of the spinal implant device 2100. In some embodiments, the spinal implant device 2100 can include a movable joint 2155. In some embodiments, the movable joint 2155 can couple the movable lid 2140 with the distal end 2120. The movable joint 2155 can allow for pivoting motion of the movable lid 2140. The movable lid 2140 can pivot via the movable joint 2155 during compression.

In some embodiments, the movable lid 2140 can include one or more articulations 2162. The one or more articulations 2162 can extend between two opposing lateral posts 2170. The distal end 2120 can include a central post 2172. The central post 2172 can include one or more lumens 2163 configured to engage the one or more articulations 2162.

The spinal implant device 2100 can include a cavity 2118. The one or more support bars 2192 can be disposed within the cavity. The one or more support bars 2192 can retain graft material within the cavity.

In some methods of use, the one or more support bars 2192 of the movable lid 2140 abut one or more support bars 2192 along the side walls 2124, 2126. The movable lid 2140 can abut the upper wall 2130 near the proximal end 2122. In some embodiments, the one or more support bars 2192 can flex or subside during use. In some embodiments, the one or more support bars 2192 can be pushed downward under load from the vertebral end plates.

FIG. 159 illustrates a perspective view of a spinal implant device 2200. The spinal implant device 2200 can include any of the features of the spinal implant device 10, 10A, 100, 200, 300, 400, 500, 600, 700, 800, 900, 1000, 1100, 1200, 1300, 1400, 1500, 1600, 1700, 1800, 1900, 2000, 2100 as described herein and can be used in any method or method step described herein. The spinal implant device 2200 can include a body structure 2212. The body structure 2212 can be placed between adjacent vertebrae. The body structure 2212 can includes features to enhance capillary action of blood being drawn into the body structure 2212.

FIG. 160 is a distal view of the spinal implant device 2200. The spinal implant device 2200 can include a distal end 2220. In some methods of use, the distal end 2220 can be the insertion end. In some embodiments, the distal end 2220 is tapered inward.

FIG. 161 is a proximal view of the spinal implant device 2200. The spinal implant device 2200 can include a proximal end 2222. In some embodiments, the proximal end 2222 can include an opening 2223 to couple to an insertion tool. In some embodiments, the opening 2223 can be threaded.

FIG. 162 is a side view of the spinal implant device 2200. The length of the spinal implant device 2200 can be the distance between the distal end 2220 and the proximal end 2222. The distal end 2220 can form the leading end and the proximal end 2222 can form the trailing end. The spinal implant device 2200 can include two opposing side walls including a first side wall 2224 and a second side wall 2226. FIG. 162 illustrates the first side wall 2224, but the second side wall 2226 can include the same or similar features.

The first side wall 2224 can include an interior wall and an exterior wall. The interior wall and the exterior wall of the first side wall 2224 can have a stacked configuration. The interior wall and the exterior wall of the first side wall 2224 can have a nested configuration. The interior wall and the exterior wall of the first side wall 2224 can be parallel. The interior wall and the exterior wall of the first side wall 2224 can be skewed. The interior wall of the first side wall 2224 can be closer to a cavity 2118 and the exterior wall of the first side wall 2224 can be farther from the cavity 2118. The interior wall of the first side wall 2224 can be convex. The convex shape can increase the strength of the spinal implant device 2200. The interior wall of the first side wall 2224 can be concave. The concave shape can allow for greater graft volume within the cavity 2218 of the spinal implant device 2200.

The second side wall 2226 can include an interior wall and an exterior wall. The interior wall and the exterior wall of the second side wall 2226 can have a stacked configuration. The interior wall and the exterior wall of the second side wall 2226 can have a nested configuration. The interior wall and the exterior wall of the second side wall 2226 can be parallel. The interior wall and the exterior wall of the second side wall 2226 can be skewed. The interior wall of the second side wall 2226 can be closer to the cavity 2118 and the exterior wall of the second side wall 2226 can be farther from the cavity 2118. The interior wall of the second side wall 2226 can be convex. The convex shape can increase the strength of the spinal implant device 2200. The interior wall of the second side wall 2226 can be concave. The concave shape can allow for greater graft volume within the cavity 2218 of the spinal implant device 2200.

The interior wall of the second side wall 2226 can be closer to the interior wall of the first side wall 2224 than to the exterior wall of the first side wall 2224. The interior wall of the first side wall 2224 can be closer to the interior wall of the second side wall 2226 than to the exterior wall of the second side wall 2226. The interior wall and the exterior wall of the first side wall 2224 and the interior wall and the exterior wall of the second side wall 2226 can be all be parallel. The interior wall and the exterior wall of the first side wall 2224 and the interior wall and the exterior wall of the second side wall 2226 can be all be generally aligned.

The spinal implant device 2200 can be porous. The spinal implant device 2200 can include one or more fusion openings 2284. The one or more fusion openings 2284 can extend through the interior wall and the exterior wall of the first side wall 2224. In the illustrated embodiments, the one or more fusion openings 2284 of the interior wall of the first side wall 2224 can be offset from the one or more fusion openings 2284 of the exterior wall of the first side wall 2224. The one or more fusion openings 2284 of the interior wall of the first side wall 2224 can be laterally disposed between the one or more fusion openings 2284 of the exterior wall of the first side wall 2224. In some embodiments, the one or more fusion openings 2284 of the interior wall of the first side wall 2224 can be aligned with the one or more fusion openings 2284 of the exterior wall of the first side wall 2224.

The one or more fusion openings 2284 can extend through the interior wall and the exterior wall of the second side wall 2226. In the illustrated embodiments, the one or more fusion openings 2284 of the interior wall of the second side wall 2226 can be offset from the one or more fusion openings 2284 of the exterior wall of the second side wall 2226. The one or more fusion openings 2284 of the interior wall of the second side wall 2226 can be laterally disposed between the one or more fusion openings 2284 of the exterior wall of the second side wall 2226. In some embodiments, the one or more fusion openings 2284 of the interior wall of the first side wall 2224 can be aligned with the one or more fusion openings 2284 of the exterior wall of the second side wall 2226.

In some embodiments, the fusion opening 2284 can be a circular or rounded openings. In some embodiments, the fusion opening 2284 can be any shape. In some embodiments, fusion openings 2284 are disposed in the middle area of the side walls 2224, 2226. In some embodiments, the one or more fusion openings 2284 are configured to be compressed. In some embodiments, the one or more fusion openings 2284 are not configured to be compressed under normal anatomical loads.

In some embodiments, each of the two opposing side walls 2224, 2226 can include a feature 2228 to facilitate placement of the spinal implant device 2200. In some embodiments, the feature 2228 can include a channel to accept an insertion tool. In some embodiments, the feature 2228 can extend from the proximal end 2222 of the spinal implant device 2200 toward the distal end 2220. In some embodiments, the feature 2228 can form a groove in the proximal end 2222. In some embodiments, the feature 2228 can be partially enclosed near the proximal end 2222. In some embodiments, the feature 2228 can form an opening in the side walls 2224, 2226. In some embodiments, the exterior wall of the first side wall 2224 and the exterior wall of the second side wall 2226 can include an elongate opening. The opening can be U shaped in the exterior wall of the first side wall 2224 and the exterior wall of the second side wall 2226. In some embodiments, the interior wall of the first side wall 2224 and the interior wall of the second side wall 2226 can include an elongate opening. The opening can be oval or elongate in the interior wall of the first side wall 2224 and the interior wall of the second side wall 2226.

FIG. 163 is a top view of the spinal implant device 2200. The spinal implant device 2200 can include a movable lid 2240. FIG. 163 is a top view of the spinal implant device 2200 with the movable lid 2240 closed. FIG. 164 is a top perspective view of the spinal implant device 2200 with the movable lid 2240 opened.

The spinal implant device 2200 can include one or more openings 2242 extending through the movable lid 2240. In some embodiments, the movable lid 2240 includes one or more elongate openings 2242. In some embodiments, the movable lid 2240 includes one or more openings 2242 having different widths. In some embodiments, the movable lid 2240 includes one or more openings 2242 having different lengths. In some embodiments, the movable lid 2240 includes one or more openings 2242 having different locations on the movable lid 2240.

The spinal implant device 2200 can include an upper wall 2230. The upper wall 2230 of the spinal implant device 2220 can connect the interior wall and the exterior wall of the first side wall 2224. The upper wall 2230 of the spinal implant device 2220 can connect the interior wall and the exterior wall of the second side wall 2226. In some embodiments, the upper wall 2230 forms a ledge to support the movable lid 2240 along the length of the movable lid 1240. In some embodiments, the upper wall 2230 forms a ledge to support the movable lid 2240 near the proximal end. In some embodiments, the upper wall 2230 can include one or more retention features 2236 to support the movable lid 2240 near the proximal end 2222. The retention features 2236 can include a hook and recess. The upper wall 2230 can include one or more recesses near the proximal end 2222. In some embodiments, the proximal end 2222 includes one or more recesses. The recess can interact with one or more hooks of the movable lid 2240 to retain or lock the movable lid 2240 in a closed position. The retention features 2236 can retain the movable lid 2240 relative to the body 2212 near the proximal end 2222.

The upper wall 2230 can include a projection near the proximal end 2222. In some embodiments, the projection of the upper wall 2230 extends between portions of the movable lid 2240. In some embodiments, the projection of the upper wall 2230 extends between recesses of the retention features 2236. The recesses can be disposed on either side of the projection of the upper wall 2230. The projection of the upper wall 2230 can facilitate alignment of the movable lid 2240 with the upper wall 2230. The projection of the upper wall 2230 can reduce or limit lateral movement of the movable lid 2240.

In some embodiments, the upper wall 2230 forms a support surface for the movable lid 2240 when the movable lid 2240 is closed. In some embodiments, the movable lid 2240 rests against the upper wall 2230 during insertion. In some embodiments, the movable lid 2240 rests against the upper wall 2230 under normal anatomical loads. The upper wall 2230 can include one or more fusion openings 2284. The one or more fusion openings 2284 can be aligned with one or more openings 2242 of the movable lid 2240.

In some embodiments, the movable lid 2240 and the projection of the upper wall 2230 can form the upper surface of the spinal implant device 2200 configured to contact the vertebral end plate. The movable lid 2240 can abut the upper wall 2230 when the lid 2240 is closed. The retention features 2236 can hold the movable lid 2240 closed. In some embodiments, the movable lid 2240 and the projection of the upper wall 2230 can provide a load supporting surface for the adjacent vertebrae. In some methods, the load can be transferred from the movable lid 2240 to the upper wall 2230. In some methods, the movable lid 2240 and the upper wall 2230 can be positioned adjacent to a vertebral end plate of a superior vertebra.

FIG. 165 is a bottom perspective view of the spinal implant device 2200. The spinal implant device 2200 can include a lower wall 2232. The lower wall 2232 can span between the distal end 2220 and the proximal end 2222. The spinal implant device 2200 can include one or more openings 2244 extending through the lower wall 2232. In some embodiments, the lower wall 2232 includes one or more openings 2244 having different widths. In some embodiments, the lower wall 2232 includes one or more openings 2244 having different lengths. In some embodiments, the lower wall 2232 includes one or more openings 2244 having different locations on the lower wall 2232. The openings 2242, 2244 can have the same or similar shape. The openings 2242, 2244 can be diametrically opposed. The openings 2242, 2244 can have different orientations or patterns. The one or more fusion openings 2284 of the upper wall 2230 can be aligned with one or more openings 2244 of the lower wall 2232.

The lower wall 2232 can provide a load supporting surface. In some methods, the lower wall 2232 can be positioned adjacent to a vertebral end plate of an inferior vertebra. In some methods, when the spinal implant device 2200 is positioned between two adjacent vertebrae, the load supporting surfaces of the movable lid 2240 and the lower wall 2232 contact the vertebral end plates of the adjacent vertebrae. In some embodiments, the distance between the movable lid 2240 and the lower wall 2232 can form the height of the spinal implant device 300.

In some embodiments, the spinal implant device 2200 can include features to limit or reduce movement of the spinal implant device 2200 between the vertebrae. The spinal implant device 2200 can include a plurality of ridges 2214. The ridges 2214 can form a portion of the movable lid 2240. The ridges 2214 can form a portion of the lower wall 2232.

FIG. 166 is an exploded view of the movable lid 2240 of the spinal implant device 2200. In some embodiments, the movable lid 2240 can be coupled to the distal end 2220. In some embodiments, the spinal implant device 2200 can include a movable joint 2255. In some embodiments, the movable joint 2255 can couple the movable lid 2240 to the distal end 2220. The movable joint 2255 can allow for pivoting motion of the movable lid 2240.

The distal end 2220 can include a central post 2272. In some embodiments, the central post 2272 can include one or more lumens 2263 that can extend between the central post 2272. In some embodiments, the movable lid 2240 can include one or more articulation 2262 extending between two lateral posts 2270. The articulation 2262 can be any structure about which the movable lid 2240 can rotate.

The spinal implant device 2200 can include a cavity 2218. In some embodiments, the proximal end 2222 can define the back inner surface of the cavity 2218. In some embodiments, the distal end 2220 can define the front inner surface of the cavity 2218. In some embodiments, the interior wall of the two opposing side walls 2224, 2226 can define the side inner surfaces of the cavity 2218. In some embodiments, the movable lid 2240 can define the top inner surface of the cavity 2218. In some embodiments, the lower wall 2232 can define the bottom inner surface of the cavity 2218.

In some methods of use, the movable lid 2240 can be supported by the upper wall 2230. The movable lid 2240 can be retained in a closed position by engagement of the retention features 2236. The hooks on the movable lid 2240 lock on the recess on the upper wall 2230 near the posterior end 2222. The side walls 2224, 2226 can be a double walled construction. The side walls 2224, 2226 can include offset fusion openings 2284 on each of the interior and exterior wall. In some embodiments, the side walls 2224, 2226 can include aligned fusion openings 2284 on each of the interior and exterior wall. The double walled design of each side wall 2224, 2226 may enhance capillary action of blood being drawn through the one or more fusion openings 2284.

FIG. 167 illustrates a perspective view of a spinal implant device 2300. The spinal implant device 2300 can include any of the features of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200 as described herein and can be used in any method or method step described herein. The spinal implant device 2300 can include a body structure 2312. The body structure 2312 can be placed between adjacent vertebrae.

FIG. 168 is a distal view of the spinal implant device 2300. The spinal implant device 2300 can include a distal end 2320. In some methods of use, the distal end 2320 can be the insertion end. In some embodiments, the distal end 2320 is tapered.

FIG. 169 is a proximal view of the spinal implant device 2300. The spinal implant device 2300 can include a proximal end 2322. In some embodiments, the proximal end 2322 can include an opening 2223 to couple to an insertion tool. In some embodiments, the opening 2223 can be threaded.

FIG. 170 is a side view of the spinal implant device 2300. The length of the spinal implant device 2300 can be the distance between the distal end 2320 and the proximal end 2322. The distal end 2320 can form the leading end and the proximal end 2322 can form the trailing end. The spinal implant device 2300 can include two opposing side walls including a first side wall 2324 and a second side wall 2326. FIG. 170 illustrates the first side wall 2324, but the second side wall 2326 can include the same or similar features.

The first side wall 2324 can include an interior wall and an exterior wall. The interior wall and the exterior wall of the first side wall 2324 can be parallel or generally aligned. The interior wall of the first side wall 2324 can be closer to a cavity 2318 and the exterior wall of the first side wall 2324 can be farther from the cavity 2318. The interior wall of the first side wall 2324 can be convex. The interior wall of the first side wall 2324 can be concave.

The second side wall 2326 can include an interior wall and an exterior wall. The interior wall and the exterior wall of the second side wall 2326 can be parallel or generally aligned. The interior wall of the second side wall 2326 can be closer to the cavity 2318 and the exterior wall of the second side wall 2326 can be farther from the cavity 2318. The interior wall of the second side wall 2326 can be convex. The interior wall of the second side wall 2326 can be concave.

In some embodiments, interior wall and the exterior wall of the first side wall 2324 and the interior wall and the exterior wall of the second side wall 2326 can include one or more open windows 2316. In the illustrated embodiment, each side wall 2324, 2326 includes seven open windows 2316. The first open window 2316 can be substantially triangular and near the proximal end 2322. The second open window 2316 can be substantially polygonal or quadrilateral near the middle of the side wall 2324, 2326. The third open window 2316 can be substantially polygonal or quadrilateral near the middle of the side wall 2324, 2326. The fourth open window 2316 can be substantially polygonal or trapezoidal near the distal end 2320. The fifth open window 2316 can be substantially polygonal or quadrilateral near the middle of the side wall 2324, 2626. The sixth open window 2316 can be substantially polygonal or quadrilateral near the middle of the side wall 2324, 2626. The seventh open window 2316 can be substantially triangular near the proximal end 2322.

The first window 2316 and the seventh window 2316 can be the same or similar size. The first window 2316 and the seventh window 2316 can be mirror images. The second window 2316 and the sixth window 2316 can be the same or similar size. The second window 2316 and the sixth window 2316 can be mirror images. The third window 2316 and the fifth window 2316 can be the same or similar size. The third window 2316 and the fifth window 2316 can be mirror images. Other configurations of windows 2316 are contemplated.

In some embodiments, each of the two opposing side walls 2324, 2326 can include a feature 2328 to facilitate placement of the spinal implant device 2300. In some embodiments, the feature 2328 can include a channel to accept an insertion tool. The feature 2328 can be disposed between the first window 2316 and the seventh window 2316. The feature 2328 can be disposed between the second window 2316 and the sixth window 2316. The feature 2328 can be disposed between the third window 2316 and the fifth window 2316. The feature 2328 can extend to the fourth window 2316.

FIG. 171 is a top view of the spinal implant device 2300. The two opposing side walls 2324, 2326 can extend between the distal end 2320 and the proximal end 2322. In some embodiments, the interior walls of the two opposing side walls 2324, 2326 are separated the same width along the length of the two opposing side walls 2324, 2326. In some embodiments, the interior walls of the two opposing side walls 2324, 2326 are parallel or substantially parallel. In some embodiments, the exterior walls of the two opposing side walls 2324, 2326 are parallel or substantially parallel. In some embodiments, the distance between the exterior walls of two opposing side walls 2324, 2326 can form the width of the spinal implant device 2300. In some embodiments, the two opposing side walls 2324, 2326 are mirror images.

The spinal implant device 2300 can include a movable lid 2340. FIG. 171 is a top view of the spinal implant device 2300 with the movable lid 2340 closed. FIG. 172 is a top perspective view of the spinal implant device 2300 with the movable lid 2340 opened.

The spinal implant device 2300 can include an upper wall 2330. The upper wall 2330 can extend between the distal end 2320 and the proximal end 2322. In some embodiments, the upper wall 2330 is curved to mimic the shape of the vertebral endplates. In some embodiments, the upper wall 2330 forms an opening to accommodate the movable lid 2340. The moveable lid 2340 can be supported at the distal end 2320 via a movable hinge, as described herein. The moveable lid 2340 can be supported at the proximal end 2322 by a ledge of the upper wall 2330 near the proximal end 2322.

In some embodiments, the movable lid 2340 and the upper wall 2330 together form the upper surface of the spinal implant device 2300. In some embodiments, the movable lid 2340 and the upper wall 2330 are laterally adjacent when the lid 2340 is closed. The movable lid 2340 can be sized to be surrounded, at least partially, by the upper wall 2330. The movable lid 2340 can match the curvature of the upper wall 2330. In some embodiments, the movable lid 2340 and the upper wall 2330 can provide a load supporting surface. In some methods, the movable lid 2340 and the upper wall 2330 can be positioned adjacent to a vertebral end plate of a superior vertebra.

FIG. 173 is a bottom perspective view of the spinal implant device 2300. The spinal implant device 2300 can include a lower wall 2332. The lower wall 2332 can extend between the distal end 2320 and the proximal end 2322. In some embodiments, the lower wall 2332 is curved to mimic the shape of the vertebral endplates. The lower wall 2332 can provide a load supporting surface. In some methods, the lower wall 2332 can be positioned adjacent to a vertebral end plate of an inferior vertebra. In some methods, when the spinal implant device 2300 is positioned between two adjacent vertebrae, the load supporting surfaces of the movable lid 2340, the upper wall 2330, and the lower wall 2332 contact the vertebral end plates of the adjacent vertebrae. In some embodiments, the distance between the movable lid 2340 and the lower wall 2332 can form the height of the spinal implant device 2300.

FIG. 174 is an exploded view of the movable lid 2340 and the body structure 2312. In some embodiments, the movable lid 2340 can be coupled to the distal end 2320. In some embodiments, the spinal implant device 2300 can include a movable joint 2355. The movable joint 2355 can couple the movable lid 2340 with the body structure 2312. The movable joint 2355 can allow for pivoting motion of the movable lid 2340 relative to the body structure 2312.

The distal end 2320 can include two opposing lateral posts 2372. In some embodiments, the two opposing lateral posts 2372 are connected with a recessed channel 2374. The recessed channel 2374 can accommodate a distal portion of the movable lid 2340. The two opposing lateral posts 2372 can include a pair of rounded sockets 2263.

In some embodiments, the movable lid 2340 can include a ball-like articulation 2362. The articulation 2362 can extend from a central post 2370 of the movable lid 2340. The central post 2370 can be located near a distal end of the movable lid 2340. The two opposing lateral posts 2372 of the distal end 2320 can be sized to accommodate the central post 2370 of the movable lid 2340. The movable joint can be a ball and socket type joint. The movable lid 2340 can include the ball and the distal end 2320 can include the socket. In some embodiments, the movable lid 2340 can include the socket and the distal end 2320 can include the ball.

The spinal implant device 2300 can include a cavity 2318. In some embodiments, the proximal end 2322 can form the back inner surface of the cavity 2318. In some embodiments, the distal end 2320 can form the front inner surface of the cavity 2318. In some embodiments, the interior walls of the two opposing side walls 2324, 2326 can form the side inner surfaces of the cavity 2318. In some embodiments, the movable lid 2340 can form the top inner surface of the cavity 2318. In some embodiments, the lower wall 2332 can form the bottom inner surface of the cavity 2318.

In some embodiments, the spinal implant device 2300 can include features to facilitate maintaining the position of the spinal implant device 2300 between the vertebrae. The spinal implant device 2300 can include a plurality of ridges 2314.

The movable lid 2340 can include one or more crossbars 2341. In some embodiments, the one or more crossbars 2341 extend perpendicular to the longitudinal axis of the spinal implant device 2300. Each crossbar 2341 can extend along a surface of a ridge 2314. Each crossbar 2341 can extend across the width of the movable lid 2340. The spinal implant device 2300 can include one or more openings 2342 extending through the movable lid 2340. The openings 2342 can be formed by the crossbars 2341. In some embodiments, a portion of the movable lid 2340 can be porous. In some embodiments, a portion of the movable lid 2340 surrounding the openings 2342 can be porous.

The lower wall 2332 can include one or more crossbars 2343. In some embodiments, each crossbar 2343 extends perpendicular to the longitudinal axis of the spinal implant device 2300. Each crossbar 2343 can extend along a surface of a ridge 2314. Each crossbar 2343 can extend across the width of the lower wall 2332. The spinal implant device 2300 can include one or more openings 2344 extending through the lower wall 2332. The openings 2344 can be formed by the crossbars 2343. The openings 2342, 2344 can be aligned to define a vertical flow path between the upper and lower surface of the spinal implant device 2300. In some embodiments, a portion of the lower wall 2332 can be porous. In some embodiments, a portion of the body structure 2212 surrounding the openings 2344 can be porous.

In some embodiments, the spinal implant device 2300 can include one or more longitudinal bars 2345 located on the movable lid 2340. In some embodiments, the spinal implant device 2300 does not include a longitudinal bar 2345 located on the movable lid 2340. In some embodiments, the spinal implant device 2300 can include one or more longitudinal bars 2346 located on the lower wall 2332. In some embodiments, the spinal implant device 2300 does not include one or more longitudinal bars 2346 located on the lower wall 2332. In some embodiments, the one or more longitudinal bars 2345, 2346 extend parallel to the longitudinal axis of the spinal implant device 2300. In some embodiments, the longitudinal bar 2345, 2346 can extend across the ridges 2314.

In some methods of use, the movable lid 2340 can be supported by the upper wall 2330 near the proximal end 2322. The side walls 2324, 2326 can include one or more windows 2316 on each of the interior and exterior wall. In some embodiments, the side walls 2224, 2226 can include aligned windows 2316 on each of the interior and exterior wall. The double walled design of each side wall 2324, 2326 may enhance strength of the spinal implant device 2300 while allowing fusion therethrough. In some embodiments, a portion of the side walls 2324, 2326 can be porous. In some embodiments, a portion of the body structure 2212 surrounding the windows 2316 can be porous.

FIG. 175 illustrates a perspective view of a spinal implant device 2400. The spinal implant device 2400 can include any of the features of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300 as described herein and can be used in any method or method step described herein. The spinal implant device 2400 can include a body structure 2412. In some embodiments, the spinal implant device 2400, or a portion thereof, can be formed of a material configured to compress under normal anatomical loads. In some embodiments, the spinal implant device 2400, or a portion thereof, can be formed of a material that is not configured to compress under normal anatomical loads.

FIG. 176 is a distal view of the spinal implant device 2400. The spinal implant device 2400 can include a distal end 2420. In some methods of use, the distal end 2420 can facilitate insertion of the spinal implant device 2400. In some embodiments, the distal end 2420 is tapered inward. In some embodiments, a portion of the four major surfaces of the distal end 2420 can taper inward. In some embodiments, the distal end 2420 can include rounded corners or edges. In some embodiments, the distal end 2420 includes a solid surface.

FIG. 177 is a proximal view of the spinal implant device 2400. The spinal implant device 2400 can include a proximal end 2422. In some embodiments, the proximal end 2422 can be planar or substantially planar. In some embodiments, the proximal end 2422 can include one or more rounded corners or edges. In some embodiments, the proximal end 2422 can include an opening 2423. In some embodiments, the opening 2423 can be threaded or have another feature to engage an insertion tool. In some embodiments, the proximal end 2422 includes a solid surface.

FIG. 178 is a side view of the spinal implant device 2400 which illustrates the length between the distal end 2420 and the proximal end 2422. The spinal implant device 2400 can include two opposing side walls 2424, 2426. FIG. 178 illustrates the first side wall 2424. The second side wall 2426 can include any of the features or elements described herein. The two opposing side walls 2424, 2426 can span between distal end 2420 and the proximal end 2422. In some embodiments, the two opposing side walls 2424, 2426 include a solid surface.

The two opposing side walls 2424, 2426 can include a feature 2428 to facilitate insertion of the spinal implant device 2400. In some embodiments, the feature 2428 can include a groove to accept an insertion tool. In some embodiments, the feature 2428 can include a solid surface. In some embodiments, the feature 2428 can be formed in the solid surface of the proximal end 2422. In some embodiments, the feature 2428 can be formed in the solid surfaces of the side walls 2424, 2426. In some embodiments, a portion of the feature 2428 can be porous.

The spinal implant device 2400 can include the movable lid 2440. FIG. 179 is a top view of the spinal implant device 2400 with a movable lid 2440 closed. FIG. 180 is a top perspective view of the spinal implant device 2400 with the movable lid 2440 opened.

The spinal implant device 2400 can include an upper wall 2430. In some embodiments, the upper wall 2430 provides alignment for the movable lid 2440 along the side walls 2424, 2426. In some embodiments, the upper wall 2430 supports the movable lid 2440 along the proximal end 2422. In some embodiments, the upper wall 2430 includes a solid surface. In some embodiments, a portion of the upper wall 2430 can be porous.

The upper wall 2430 can include thicker edges which forms the top surface of the spinal implant device 2400. The upper wall 2430 can extend between the distal end 2420 and the proximal end 2422. In some embodiments, the upper wall 2430 is tapered toward the distal end 2420.

In some embodiments, the upper wall 2430 includes a ledge to support the movable lid 2440. In some embodiments, the upper wall 2430 forms a ledge along a portion of length of the movable lid 2440. In some embodiments, the upper wall 2430 forms a ledge from the proximal end 2422 toward the distal end 2420. The moveable lid 2440 can be supported along the sidewalls 2424, 2426, or a portion thereof. In some embodiments, the moveable lid 2440 can be unsupported along the sidewalls 2424, 2426 near the distal end 2420. The moveable lid 2440 can be supported at the distal end 2420 via a movable hinge. In some embodiments, a portion of the side walls 2324, 2326 can be porous. In some embodiments, a portion of the movable lid 2440 can be porous.

FIG. 181 is a bottom perspective view of the spinal implant device 2400. The spinal implant device 2400 can include a lower wall 2432. The lower wall 2432 can span between the distal end 2420 and the proximal end 2422. In some embodiments, the lower wall 2432 can include a solid surface. In some embodiments, a portion of the lower wall 2432 can be porous.

FIG. 182 is an exploded view of the movable lid 2440 of the spinal implant device 2400. In some embodiments, the movable lid 2440 can be coupled to the distal end 2420. In some embodiments, the spinal implant device 2400 can include a movable joint 2455. The movable joint 2455 can couple the movable lid 2440 with any portion of the body structure 2412. The movable joint 2455 can allow for pivoting motion of the movable lid 2440. In some embodiments, the body structure 2412, or a portion thereof, can be porous.

In some embodiments, the movable lid 2440 can include two articulations 2462. The distal end 2420 can include a central post 2470. The central post 2470 can include one or more sockets 2463 configured to engage the one or more articulations 2462.

In some embodiments, the movable lid 2440 can include a ball-like articulations 2462. The articulation 2462 can extend laterally from the distal end of the movable lid 2340. The ball-like sockets 2463 of the distal end 2420 can be sized to accommodate the articulation 2462 of the movable lid 2440. The movable joint 2455 can be a ball and socket type joint. The movable lid 2440 can include the ball and the distal end 2420 can include the socket. In some embodiments, the movable lid 2440 can include the socket and the distal end 2420 can include the ball.

The movable joint 2455 can be a free-floating hinge. In some embodiments, material is removed from the underside of the movable lid 2440 near the movable hinge 2455. In some embodiments, material is removed from the inside of the distal end 2420. The hinge 2455 can have a low profile design. The removal of material to create the hinge design can allow for hinge action. The removal of material to create the hinge design can allow for insertion of large graft volumes. In some embodiments, one or more stops or ledges can be included to secure the movable lid 2440 relative to the body 2412. In some embodiments, one or more stops or ledges can be included to secure the hinge within the spinal implant device 2400.

The spinal implant device 2400 can include a cavity 2418. In some embodiments, the proximal end 2422 can define the back inner surface of the cavity 2418. In some embodiments, the distal end 2420 can define the front inner surface of the cavity 2418. In some embodiments, the two opposing side walls 2424, 2426 can define the side inner surfaces of the cavity 2418. In some embodiments, the movable lid 2440 can define the top inner surface of the cavity 2418. In some embodiments, the lower wall 2432 can define the bottom inner surface of the cavity 2418. In some embodiments, the cavity 2418 is fully enclosed. The cavity 2418 can be a contained chamber, or at least partially contained chamber, within the spinal implant device 2400. In some embodiments, the cavity 2418 comprises the internal volume of the spinal implant device 2400.

As described herein, in some embodiments, the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can be designed to allow compression in some embodiments under the loads described herein and/or within the ranges disclosed herein. The bodies of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400, or a portion thereof, can compress and in some embodiments compress under the loads described herein and/or within the ranges disclosed herein. The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can compress in some embodiments under the loads described herein and/or within the ranges disclosed herein. In some embodiments, the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can be designed to allow compression under normal anatomical loads. The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can rotate to compress material within the spinal implant device. The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can rotate to compress material under the loads described herein and/or within the ranges disclosed herein. The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can hover over the proximal end or within a cavity or recess of the proximal end in a closed position. The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can flex under a normal anatomical load. The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can hover over a connecting bar in a closed position The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can cause a connecting bar or compression support to flex under a normal anatomical load. The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can hover over the proximal end or within a cavity or recess of the proximal end under a normal anatomical load. The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can include a feature such as an opening for an insertion tool that retains the movable lid during insertion. The movable lid, if present, of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can include a retention feature that retains the lid in a closed position. One or more sidewalls of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can compress. One or more sidewalls of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can compress under the loads disclosed herein and/or within the ranges disclosed herein. Any side or surface of the spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can compress under the loads described herein and/or within the ranges disclosed herein.

The spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can include any feature or features described herein to facilitate compression. The spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400, or any portion thereof, can comprise any material described herein. The spinal implant device 10, 10A, 100, 200, 300, 400, 500, 600, 700, 800, 900, 1000, 1100, 1200, 1300, 1400, 1500, 1600, 1700, 1800, 1900, 2000, 2100, 2200, 2300, 2400 can include or omit any feature or features described herein. A spinal implant device can comprise one or more features of any spinal implant device described herein.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims. Although the present invention has been described in relation to various exemplary embodiments, various additional embodiments and alterations to the described embodiments are contemplated within the scope of the invention. Thus, no part of the foregoing description should be interpreted to limit the scope of the invention as set forth in the following claims. For all of the embodiments described above, the steps of the methods need not be performed sequentially.

What is claimed is:

1. A method comprising:
    pivoting a lid of a spinal implant device, the spinal implant device comprising a distal end, a proximal end, two opposing side walls extending between the distal end and the proximal end, an upper wall configured to be positioned adjacent to a vertebral end plate of an upper vertebra, a lower wall configured to be positioned adjacent to a vertebral end plate of a lower vertebra, and a central cavity, wherein pivoting the lid relative to the upper wall provides access to the central cavity, wherein the lid extends the entire length of the spinal implant device from the distal end to the proximal end, wherein the lid and the upper wall together form an upper surface of the spinal implant device;
    packing the central cavity with a material; and
    pivoting the lid to cover the central cavity after the central cavity is packed.

2. The method of claim 1, further comprising inserting the spinal implant device between the upper vertebra and the lower vertebra.

3. The method of claim 1, further comprising inserting the spinal implant device with the distal end inserted first into an intervertebral space between the upper vertebra and the lower vertebra.

4. The method of claim 1, wherein the distance between the upper wall and the lower wall is configured to restore the spacing between the upper vertebra and the lower vertebra.

5. The method of claim 1, further comprising positioning the spinal implant device wherein the lid and the upper wall contacts the vertebral end plate of the upper vertebra and the lower wall contacts the vertebral end plate of the lower vertebra.

6. The method of claim 1, wherein the material comprises an osteoinductive material.

7. The method of claim 1, wherein the material comprises a graft material.

8. The method of claim 1, wherein the lid and the upper wall contact the vertebral end plate of the upper vertebra.

9. The method of claim 1, wherein the lid pivots relative to the upper wall in an arc.

10. The method of claim 1, wherein the lid pivots relative to the upper wall between 90° and 240°.

11. The method of claim 1, wherein the lid is coupled to the distal end by a hinge.

12. The method of claim 1, wherein pivoting the lid to cover the central cavity comprises closing the lid to be flush with the upper wall.

13. A method comprising:
   providing a spinal implant device comprising a distal end and a proximal end defining a length therebetween, two opposing side walls extending between the distal end and the proximal end, an upper surface and a lower surface defining a height therebetween, and a central cavity;
   pivoting a lid to provide access to the central cavity;
   packing the central cavity with a material;
   pivoting the lid to form at least a portion of an upper surface of spinal implant device; and
   inserting the spinal implant device between vertebrae with the upper surface positioned adjacent to a vertebral end plate of an upper vertebra and the lower surface positioned adjacent to a vertebral end plate of a lower vertebra, wherein the lid hovers above a ledge of the spinal implant device under normal anatomical loads.

14. The method of claim 13, wherein the lid and an upper wall form the upper surface of the spinal implant device.

15. The method of claim 13, wherein the lid contacts the ledge of the spinal implant device under greater than normal anatomical loads.

16. The method of claim 13, wherein a portion of an upper wall of the spinal implant device is disposed between portions of the lid.

17. A method comprising:
   pivoting a lid of a spinal implant device to provide access to a central cavity of the spinal implant device, wherein the lid comprises an upper opening, wherein the spinal implant device further comprises a distal end, a proximal end, two opposing side walls extending between the distal end and the proximal end, an upper wall, and a lower wall comprising a lower opening, wherein the lid extends the entire width of the spinal implant device, wherein the lid and the upper wall together form an upper surface of the spinal implant device;
   packing the central cavity with a material;
   pivoting the lid to cover the central cavity before inserting the spinal implant device between adjacent vertebrae; and
   inserting the spinal implant device between the adjacent vertebrae, wherein the upper opening and the lower opening provide a vertical flow path between the adjacent vertebrae.

18. The method of claim 17, wherein the lid is pivoted relative to the upper wall.

19. The method of claim 17, wherein pivoting the lid to cover the central cavity comprises pivoting the lid to be flush with the upper wall.

\* \* \* \* \*